United States Patent
Campbell et al.

(10) Patent No.: US 9,617,338 B1
(45) Date of Patent: Apr. 11, 2017

(54) ANTIBODIES AND IMMUNOCYTOKINES

(71) Applicant: Kymab Limited, Cambridge (GB)

(72) Inventors: Jamie Campbell, Cambridge (GB); Nikole Sandy, Cambridge (GB); Stephen D. Gillies, Carlisle, MA (US); Volker Germaschewski, Cambridge (GB); Cassandra van Krinks, Cambridge (GB); Ian Kirby, Cambridge (GB); Miha Kosmac, Cambridge (GB); Steve Arkinstall, Cambridge (GB); Thomas Gallagher, Cambridge (GB)

(73) Assignee: Kymab Limited, Cambridge (GB)

( * ) Notice: Subject to any disclaimer, the term of this patent is extended or adjusted under 35 U.S.C. 154(b) by 0 days.

(21) Appl. No.: 15/354,971

(22) Filed: Nov. 17, 2016

Related U.S. Application Data

(62) Division of application No. 15/211,504, filed on Jul. 15, 2016, now Pat. No. 9,567,399.

(60) Provisional application No. 62/352,291, filed on Jun. 20, 2016.

(51) Int. Cl.
| | |
|---|---|
| C07K 16/28 | (2006.01) |
| A61K 39/395 | (2006.01) |
| C07K 14/55 | (2006.01) |
| C07K 16/46 | (2006.01) |
| C07K 19/00 | (2006.01) |
| A61K 39/00 | (2006.01) |

(52) U.S. Cl.
CPC .......... *C07K 16/2803* (2013.01); *C07K 14/55* (2013.01); *C07K 16/468* (2013.01); *C07K 19/00* (2013.01); *A61K 2039/505* (2013.01); *C07K 2317/31* (2013.01); *C07K 2317/56* (2013.01); *C07K 2317/565* (2013.01); *C07K 2317/76* (2013.01); *C07K 2317/92* (2013.01); *C07K 2319/00* (2013.01); *C07K 2319/02* (2013.01)

(58) Field of Classification Search
None
See application file for complete search history.

(56) References Cited

U.S. PATENT DOCUMENTS 9,567,399 B1 * 2/2017 Campbell et al. . C07K 16/2803
424/139.1

OTHER PUBLICATIONS

Abiko et al., "PD-L1 on tumor cells is induced in ascites and promotes peritoneal dissemination of ovarian cancer through CTL dysfunction", Clin Cancer Res, 19(6):1363-74 (2013).

Blank et al., "PD-L1/B7H-1 inhibits the effector phase of tumor rejection by T cell receptor (TCR) transgenic CD8+ T cells" 64(3):1140-5 (2004).
Brahmer et al., "Phase I study of single-agent anti-programmed death-1 (MDX-1106) in refractory solid tumors: safety, clinical activity, pharmacodynamics, and immunologic correlates", J Clin Oncol, 28(19):3167-75 (2010).
Brahmer et al., "Safety and activity of anti-PD-L1 antibody in patients with advanced cancer", N Engl J Med, 366 (26):2455-65 (2012).
Brown et al., "Blockade of programmed death-1 ligands on dendritic cells enhances T cell activation and cytokine production", J Immunol, 170(3):1257-66 (2003).
Butte et al., "Programmed death-1 ligand 1 interacts specifically with the B7-1 costimulatory molecule to inhibit T cell responses", Immunity, 27(1):111-22 (2007).
Dong et al., "B7-H1, a third member of the B7 family, co-stimulates T-cell proliferation and interleukin-10 secretion" Nat Med, 5(12):1365-9 (1999).
Dong et al., "Tumor-associated B7-H1 promotes T-cell apoptosis: a potential mechanism of immune evasion", Nat Med, 8(8):793-800 (2002).
Fehrenbacher et al., "Atezolizumab versus docetaxel for patients with previously treated non-small-cell lung aancer (POPLAR): a multicentre, open-label, phase 2 randomised controlled trial", Lancet, 387(10030):1837-46 (2016).
Freeman et al., "Engagement of the PD-1 immunoinhibitory receptor by a novel B7 family member leads to negative regulation of lymphocyte activation", J Exp Med, 192(7):1027-34 (2000).
Herbst et al., "Predictive correlates of response to the anti-PD-L1 antibody MPDL3280A in cancer patients", Nature, 515(7528):563-7 (2014).
Hirano et al., "Blockade of B7-H1 and PD-1 by monoclonal antibodies potentiates cancer therapeutic immunity", Cancer Res, 65(3):1089-96 (2005).
Iwai et al., "Involvement of PD-L1 on tumor cells in the escape from host immune system and tumor immunotherapy by PD-L1 blockade", Proc Natl Acad Sci USA, 99(19):12293-7 (2002).
Kaiser et al., Reduced tumor-antigen density leads to PD-1/PD-L1-mediated impairment of partially exhausted CD8+ T cells, Eur J Immunol, 42(3):662-71 (2012).
Lin et al., "The PD-1/PD-L1 complex resembles the antigen-binding Fv domains of antibodies and T cell receptors", Proc Natl Acad Sci USA, 105(8):3011-6 (2008).
Rosenberg et al., "Atezolizumab in patients with locally advanced and metastatic urothelial carcinoma who have progressed following treatment with platinum-based chemotherapy: a single-arm, multicentre, phase 2 trial", Lancet, 387(10031):1909-20 (2016).
Rossi et al., "Optimization of multivalent bispecific antibodies and immunocytokines with improved in vivo properties", Bioconjug Chem, 24(1):63-71 (2013).
Song et al., "Overexpression of B7-H1 correlates with malignant cell proliferation in pancreatic cancer", Oncol Rep, 31(3)1191-8 (2014).

(Continued)

*Primary Examiner* — Ilia Ouspenski
(74) *Attorney, Agent, or Firm* — Nixon Peabody, LLP; David S. Resnick; Leena H. Karttunen Contarino

(57) ABSTRACT

The present invention relates to anti-PD-L1 antibodies, bispecific antibodies containing one domain with specificity to PD-L1, and to immunocytokines comprising an anti-PD-L1 antibody fused to a cytokine, such as IL-2. The present invention also provides methods of treatment, uses and pharmaceutical compositions comprising the antibodies, bispecific antibodies and immunocytokines.

20 Claims, 19 Drawing Sheets

(56) References Cited

OTHER PUBLICATIONS

Thompson et al., "Tumor B7-H1 is associated with poor prognosis in renal cell carcinoma patients with long-term follow-up", Cancer Res, 66(7):3381-5 (2006).
Topalian et al., "Safety, activity, and immune correlates of anti-PD-1 antibody in cancer", N Engl J Med, 366 (26):2443-54 (2012).
West et al., "PD-L1 blockade synergizes with IL-2 therapy in reinvigorating exhausted T cells", J Clin Invest, 123 (6):2604-15 (2013).
Yang et al., "Programmed cell death-ligand 1 expression in surgically resected stage I pulmonary adenocarcinoma and its correlation with driver mutations and clinical outcomes", Eur J Cancer, 50(7):1361-9 (2014).

\* cited by examiner

SEQUENCE LISTING

<160> NUMBER OF SEQ ID NOS: 342

<210> SEQ ID NO 1
<211> LENGTH: 290
<212> TYPE: PRT
<213> ORGANISM: Homo sapiens
<220> FEATURE:
<221> NAME/KEY: misc_feature
<223> OTHER INFORMATION: Human PD-L1, NCBI number: NP_054862.1

<400> SEQUENCE: 1

Met Arg Ile Phe Ala Val Phe Ile Phe Met Thr Tyr Trp His Leu Leu
1               5                   10                  15

Asn Ala Phe Thr Val Thr Val Pro Lys Asp Leu Tyr Val Val Glu Tyr
            20                  25                  30

Gly Ser Asn Met Thr Ile Glu Cys Lys Phe Pro Val Glu Lys Gln Leu
        35                  40                  45

Asp Leu Ala Ala Leu Ile Val Tyr Trp Glu Met Glu Asp Lys Asn Ile
    50                  55                  60

Ile Gln Phe Val His Gly Glu Glu Asp Leu Lys Val Gln His Ser Ser
65                  70                  75                  80

Tyr Arg Gln Arg Ala Arg Leu Leu Lys Asp Gln Leu Ser Leu Gly Asn
                85                  90                  95

Ala Ala Leu Gln Ile Thr Asp Val Lys Leu Gln Asp Ala Gly Val Tyr
            100                 105                 110

Arg Cys Met Ile Ser Tyr Gly Gly Ala Asp Tyr Lys Arg Ile Thr Val
        115                 120                 125

Lys Val Asn Ala Pro Tyr Asn Lys Ile Asn Gln Arg Ile Leu Val Val
    130                 135                 140

Asp Pro Val Thr Ser Glu His Glu Leu Thr Cys Gln Ala Glu Gly Tyr
145                 150                 155                 160

Pro Lys Ala Glu Val Ile Trp Thr Ser Ser Asp His Gln Val Leu Ser
                165                 170                 175

Gly Lys Thr Thr Thr Thr Asn Ser Lys Arg Glu Glu Lys Leu Phe Asn
            180                 185                 190

Val Thr Ser Thr Leu Arg Ile Asn Thr Thr Thr Asn Glu Ile Phe Tyr
        195                 200                 205

Cys Thr Phe Arg Arg Leu Asp Pro Glu Glu Asn His Thr Ala Glu Leu
    210                 215                 220

Val Ile Pro Glu Leu Pro Leu Ala His Pro Pro Asn Glu Arg Thr His
225                 230                 235                 240

Leu Val Ile Leu Gly Ala Ile Leu Leu Cys Leu Gly Val Ala Leu Thr
                245                 250                 255

Phe Ile Phe Arg Leu Arg Lys Gly Arg Met Met Asp Val Lys Lys Cys
            260                 265                 270

Gly Ile Gln Asp Thr Asn Ser Lys Lys Gln Ser Asp Thr His Leu Glu
        275                 280                 285

Glu Thr
    290

<210> SEQ ID NO 2
<211> LENGTH: 241
<212> TYPE: PRT
<213> ORGANISM: Macaca fascicularis
<220> FEATURE:
<221> NAME/KEY: misc_feature
<223> OTHER INFORMATION: Cyno PD-L1, NCBI number: XP_014973154.1

<400> SEQUENCE: 2

```
Met Gly Trp Ser Cys Ile Ile Leu Phe Leu Val Ala Thr Ala Thr Gly
1               5                   10                  15

Val His Ser Met Phe Thr Val Thr Val Pro Lys Asp Leu Tyr Val Val
            20                  25                  30

Glu Tyr Gly Ser Asn Met Thr Ile Glu Cys Lys Phe Pro Val Glu Lys
        35                  40                  45

Gln Leu Asp Leu Thr Ser Leu Ile Val Tyr Trp Glu Met Glu Asp Lys
    50                  55                  60

Asn Ile Ile Gln Phe Val His Gly Glu Glu Asp Leu Lys Val Gln His
65                  70                  75                  80

Ser Asn Tyr Arg Gln Arg Ala Gln Leu Leu Lys Asp Gln Leu Ser Leu
                85                  90                  95

Gly Asn Ala Ala Leu Arg Ile Thr Asp Val Lys Leu Gln Asp Ala Gly
            100                 105                 110

Val Tyr Arg Cys Met Ile Ser Tyr Gly Gly Ala Asp Tyr Lys Arg Ile
        115                 120                 125

Thr Val Lys Val Asn Ala Pro Tyr Asn Lys Ile Asn Gln Arg Ile Leu
    130                 135                 140

Val Val Asp Pro Val Thr Ser Glu His Glu Leu Thr Cys Gln Ala Glu
145                 150                 155                 160

Gly Tyr Pro Lys Ala Glu Val Ile Trp Thr Ser Ser Asp His Gln Val
                165                 170                 175

Leu Ser Gly Lys Thr Thr Thr Thr Asn Ser Lys Arg Glu Glu Lys Leu
            180                 185                 190

Leu Asn Val Thr Ser Thr Leu Arg Ile Asn Thr Thr Ala Asn Glu Ile
        195                 200                 205

Phe Tyr Cys Ile Phe Arg Arg Leu Asp Pro Glu Glu Asn His Thr Ala
    210                 215                 220

Glu Leu Val Ile Pro Glu Leu Pro Leu Ala Leu Pro Pro Asn Glu Arg
225                 230                 235                 240

Thr
```

<210> SEQ ID NO 3
<211> LENGTH: 245
<212> TYPE: PRT
<213> ORGANISM: Homo sapiens
<220> FEATURE:
<221> NAME/KEY: misc_feature
<223> OTHER INFORMATION: Human PD-L1 ECD with C-terminal His tag

<400> SEQUENCE: 3

```
Met Arg Ile Phe Ala Val Phe Ile Phe Met Thr Tyr Trp His Leu Leu
1               5                   10                  15

Asn Ala Phe Thr Val Thr Val Pro Lys Asp Leu Tyr Val Val Glu Tyr
            20                  25                  30

Gly Ser Asn Met Thr Ile Glu Cys Lys Phe Pro Val Glu Lys Gln Leu
        35                  40                  45

Asp Leu Ala Ala Leu Ile Val Tyr Trp Glu Met Glu Asp Lys Asn Ile
    50                  55                  60

Ile Gln Phe Val His Gly Glu Glu Asp Leu Lys Val Gln His Ser Ser
65                  70                  75                  80

Tyr Arg Gln Arg Ala Arg Leu Leu Lys Asp Gln Leu Ser Leu Gly Asn
                85                  90                  95

Ala Ala Leu Gln Ile Thr Asp Val Lys Leu Gln Asp Ala Gly Val Tyr
```

```
                    100                 105                 110
Arg Cys Met Ile Ser Tyr Gly Gly Ala Asp Tyr Lys Arg Ile Thr Val
            115                 120                 125
Lys Val Asn Ala Pro Tyr Asn Lys Ile Asn Gln Arg Ile Leu Val Val
            130                 135                 140
Asp Pro Val Thr Ser Glu His Glu Leu Thr Cys Gln Ala Glu Gly Tyr
145                 150                 155                 160
Pro Lys Ala Glu Val Ile Trp Thr Ser Ser Asp His Gln Val Leu Ser
            165                 170                 175
Gly Lys Thr Thr Thr Thr Asn Ser Lys Arg Glu Glu Lys Leu Phe Asn
            180                 185                 190
Val Thr Ser Thr Leu Arg Ile Asn Thr Thr Thr Asn Glu Ile Phe Tyr
            195                 200                 205
Cys Thr Phe Arg Arg Leu Asp Pro Glu Glu Asn His Thr Ala Glu Leu
            210                 215                 220
Val Ile Pro Glu Leu Pro Leu Ala His Pro Pro Asn Glu Arg Thr His
225                 230                 235                 240
His His His His His
            245

<210> SEQ ID NO 4
<211> LENGTH: 475
<212> TYPE: PRT
<213> ORGANISM: Homo sapiens
<220> FEATURE:
<221> NAME/KEY: misc_feature
<223> OTHER INFORMATION: Human PD-L1 ECD with C-term Fc fusion

<400> SEQUENCE: 4

Met Arg Ile Phe Ala Val Phe Ile Phe Met Thr Tyr Trp His Leu Leu
1               5                   10                  15
Asn Ala Phe Thr Val Thr Val Pro Lys Asp Leu Tyr Val Val Glu Tyr
            20                  25                  30
Gly Ser Asn Met Thr Ile Glu Cys Lys Phe Pro Val Glu Lys Gln Leu
        35                  40                  45
Asp Leu Ala Ala Leu Ile Val Tyr Trp Glu Met Glu Asp Lys Asn Ile
    50                  55                  60
Ile Gln Phe Val His Gly Glu Glu Asp Leu Lys Val Gln His Ser Ser
65                  70                  75                  80
Tyr Arg Gln Arg Ala Arg Leu Leu Lys Asp Gln Leu Ser Leu Gly Asn
                85                  90                  95
Ala Ala Leu Gln Ile Thr Asp Val Lys Leu Gln Asp Ala Gly Val Tyr
            100                 105                 110
Arg Cys Met Ile Ser Tyr Gly Gly Ala Asp Tyr Lys Arg Ile Thr Val
            115                 120                 125
Lys Val Asn Ala Pro Tyr Asn Lys Ile Asn Gln Arg Ile Leu Val Val
            130                 135                 140
Asp Pro Val Thr Ser Glu His Glu Leu Thr Cys Gln Ala Glu Gly Tyr
145                 150                 155                 160
Pro Lys Ala Glu Val Ile Trp Thr Ser Ser Asp His Gln Val Leu Ser
            165                 170                 175
Gly Lys Thr Thr Thr Thr Asn Ser Lys Arg Glu Glu Lys Leu Phe Asn
            180                 185                 190
Val Thr Ser Thr Leu Arg Ile Asn Thr Thr Thr Asn Glu Ile Phe Tyr
            195                 200                 205
```

```
Cys Thr Phe Arg Arg Leu Asp Pro Glu Glu Asn His Thr Ala Glu Leu
    210                 215                 220
Val Ile Pro Glu Leu Pro Leu Ala His Pro Pro Asn Glu Arg Thr Ile
225                 230                 235                 240
Glu Gly Arg Glu Pro Lys Ser Cys Asp Lys Thr His Thr Cys Pro Pro
                245                 250                 255
Cys Pro Ala Pro Glu Leu Leu Gly Gly Pro Ser Val Phe Leu Phe Pro
            260                 265                 270
Pro Lys Pro Lys Asp Thr Leu Met Ile Ser Arg Thr Pro Glu Val Thr
        275                 280                 285
Cys Val Val Val Asp Val Ser His Glu Asp Pro Glu Val Lys Phe Asn
    290                 295                 300
Trp Tyr Val Asp Gly Val Glu Val His Asn Ala Lys Thr Lys Pro Arg
305                 310                 315                 320
Glu Glu Gln Tyr Asn Ser Thr Tyr Arg Val Val Ser Val Leu Thr Val
                325                 330                 335
Leu His Gln Asp Trp Leu Asn Gly Lys Glu Tyr Lys Cys Lys Val Ser
            340                 345                 350
Asn Lys Ala Leu Pro Ala Pro Ile Glu Lys Thr Ile Ser Lys Ala Lys
        355                 360                 365
Gly Gln Pro Arg Glu Pro Gln Val Tyr Thr Leu Pro Pro Ser Arg Asp
    370                 375                 380
Glu Leu Thr Lys Asn Gln Val Ser Leu Thr Cys Leu Val Lys Gly Phe
385                 390                 395                 400
Tyr Pro Ser Asp Ile Ala Val Glu Trp Glu Ser Asn Gly Gln Pro Glu
                405                 410                 415
Asn Asn Tyr Lys Thr Thr Pro Pro Val Leu Asp Ser Asp Gly Ser Phe
            420                 425                 430
Phe Leu Tyr Ser Lys Leu Thr Val Asp Lys Ser Arg Trp Gln Gln Gly
        435                 440                 445
Asn Val Phe Ser Cys Ser Val Met His Glu Ala Leu His Asn His Tyr
    450                 455                 460
Thr Gln Lys Ser Leu Ser Leu Ser Pro Gly Lys
465                 470                 475

<210> SEQ ID NO 5
<211> LENGTH: 249
<212> TYPE: PRT
<213> ORGANISM: Macaca fascicularis
<220> FEATURE:
<221> NAME/KEY: misc_feature
<223> OTHER INFORMATION: Cynomolgus PD-L1 ECD with N-term FLAG tag

<400> SEQUENCE: 5

Met Gly Trp Ser Cys Ile Ile Leu Phe Leu Val Ala Thr Ala Thr Gly
1               5                   10                  15
Val His Ser Met Phe Thr Val Thr Val Pro Lys Asp Leu Tyr Val Val
            20                  25                  30
Glu Tyr Gly Ser Asn Met Thr Ile Glu Cys Lys Phe Pro Val Glu Lys
        35                  40                  45
Gln Leu Asp Leu Thr Ser Leu Ile Val Tyr Trp Glu Met Glu Asp Lys
    50                  55                  60
Asn Ile Ile Gln Phe Val His Gly Glu Glu Asp Leu Lys Val Gln His
65                  70                  75                  80
Ser Asn Tyr Arg Gln Arg Ala Gln Leu Leu Lys Asp Gln Leu Ser Leu
                85                  90                  95
```

```
Gly Asn Ala Ala Leu Arg Ile Thr Asp Val Lys Leu Gln Asp Ala Gly
            100                 105                 110

Val Tyr Arg Cys Met Ile Ser Tyr Gly Gly Ala Asp Tyr Lys Arg Ile
            115                 120                 125

Thr Val Lys Val Asn Ala Pro Tyr Asn Lys Ile Asn Gln Arg Ile Leu
            130                 135                 140

Val Val Asp Pro Val Thr Ser Glu His Glu Leu Thr Cys Gln Ala Glu
145                 150                 155                 160

Gly Tyr Pro Lys Ala Glu Val Ile Trp Thr Ser Ser Asp His Gln Val
                165                 170                 175

Leu Ser Gly Lys Thr Thr Thr Thr Asn Ser Lys Arg Glu Glu Lys Leu
            180                 185                 190

Leu Asn Val Thr Ser Thr Leu Arg Ile Asn Thr Thr Ala Asn Glu Ile
            195                 200                 205

Phe Tyr Cys Ile Phe Arg Arg Leu Asp Pro Glu Glu Asn His Thr Ala
            210                 215                 220

Glu Leu Val Ile Pro Glu Leu Pro Leu Ala Leu Pro Pro Asn Glu Arg
225                 230                 235                 240

Thr Asp Tyr Lys Asp Asp Asp Lys
                245

<210> SEQ ID NO 6
<211> LENGTH: 405
<212> TYPE: PRT
<213> ORGANISM: Homo sapiens
<220> FEATURE:
<221> NAME/KEY: misc_feature
<223> OTHER INFORMATION: Human PD-1 full length sequence as human Fc
      fusion

<400> SEQUENCE: 6

Met Gly Trp Ser Cys Ile Ile Leu Phe Leu Val Ala Thr Ala Thr Gly
1               5                   10                  15

Val His Ser Leu Asp Ser Pro Asp Arg Pro Trp Asn Pro Pro Thr Phe
            20                  25                  30

Ser Pro Ala Leu Leu Val Val Thr Glu Gly Asp Asn Ala Thr Phe Thr
            35                  40                  45

Cys Ser Phe Ser Asn Thr Ser Glu Ser Phe Val Leu Asn Trp Tyr Arg
        50                  55                  60

Met Ser Pro Ser Asn Gln Thr Asp Lys Leu Ala Ala Phe Pro Glu Asp
65                  70                  75                  80

Arg Ser Gln Pro Gly Gln Asp Cys Arg Phe Arg Val Thr Gln Leu Pro
                85                  90                  95

Asn Gly Arg Asp Phe His Met Ser Val Val Arg Ala Arg Arg Asn Asp
            100                 105                 110

Ser Gly Thr Tyr Leu Cys Gly Ala Ile Ser Leu Ala Pro Lys Ala Gln
            115                 120                 125

Ile Lys Glu Ser Leu Arg Ala Glu Leu Arg Val Thr Glu Arg Arg Ala
            130                 135                 140

Glu Val Pro Thr Ala His Pro Ser Pro Ser Pro Arg Pro Ala Gly Gln
145                 150                 155                 160

Lys Leu Glu Asn Leu Tyr Phe Gln Gly Ile Glu Gly Arg Met Asp Glu
                165                 170                 175

Pro Lys Ser Cys Asp Lys Thr His Thr Cys Pro Pro Cys Pro Ala Pro
            180                 185                 190
```

```
Glu Leu Leu Gly Gly Pro Ser Val Phe Leu Phe Pro Lys Pro Lys
            195                 200                 205

Asp Thr Leu Met Ile Ser Arg Thr Pro Glu Val Thr Cys Val Val Val
210                 215                 220

Asp Val Ser His Glu Asp Pro Glu Val Lys Phe Asn Trp Tyr Val Asp
225                 230                 235                 240

Gly Val Glu Val His Asn Ala Lys Thr Lys Pro Arg Glu Glu Gln Tyr
            245                 250                 255

Asn Ser Thr Tyr Arg Val Val Ser Val Leu Thr Val Leu His Gln Asp
            260                 265                 270

Trp Leu Asn Gly Lys Glu Tyr Lys Cys Lys Val Ser Asn Lys Ala Leu
            275                 280                 285

Pro Ala Pro Ile Glu Lys Thr Ile Ser Lys Ala Lys Gly Gln Pro Arg
            290                 295                 300

Glu Pro Gln Val Tyr Thr Leu Pro Pro Ser Arg Asp Glu Leu Thr Lys
305                 310                 315                 320

Asn Gln Val Ser Leu Thr Cys Leu Val Lys Gly Phe Tyr Pro Ser Asp
            325                 330                 335

Ile Ala Val Glu Trp Glu Ser Asn Gly Gln Pro Glu Asn Asn Tyr Lys
            340                 345                 350

Thr Thr Pro Pro Val Leu Asp Ser Asp Gly Ser Phe Phe Leu Tyr Ser
            355                 360                 365

Lys Leu Thr Val Asp Lys Ser Arg Trp Gln Gln Gly Asn Val Phe Ser
            370                 375                 380

Cys Ser Val Met His Glu Ala Leu His Asn His Tyr Thr Gln Lys Ser
385                 390                 395                 400

Leu Ser Leu Ser Pro
            405

<210> SEQ ID NO 7
<211> LENGTH: 8
<212> TYPE: PRT
<213> ORGANISM: Homo sapiens
<220> FEATURE:
<221> NAME/KEY: misc_feature
<223> OTHER INFORMATION: Amino acid sequence of CDRH1 of 84G09 using
      IMGT

<400> SEQUENCE: 7

Gly Phe Thr Phe Asp Asp Tyr Ala
1               5

<210> SEQ ID NO 8
<211> LENGTH: 8
<212> TYPE: PRT
<213> ORGANISM: Homo sapiens
<220> FEATURE:
<221> NAME/KEY: misc_feature
<223> OTHER INFORMATION: Amino acid sequence of CDRH2 of 84G09 using
      IMGT

<400> SEQUENCE: 8

Ile Ser Trp Lys Ser Asn Ile Ile
1               5

<210> SEQ ID NO 9
<211> LENGTH: 15
<212> TYPE: PRT
<213> ORGANISM: Homo sapiens
<220> FEATURE:
<221> NAME/KEY: misc_feature
```

<223> OTHER INFORMATION: Amino acid sequence of CDRH3 of 84G09 using
      IMGT

<400> SEQUENCE: 9

Ala Arg Asp Ile Thr Gly Ser Gly Ser Tyr Gly Trp Phe Asp Pro
1               5                   10                  15

<210> SEQ ID NO 10
<211> LENGTH: 5
<212> TYPE: PRT
<213> ORGANISM: Homo sapiens
<220> FEATURE:
<221> NAME/KEY: misc_feature
<223> OTHER INFORMATION: Amino acid sequence of CDRH1 of 84G09 using
      Kabat

<400> SEQUENCE: 10

Asp Tyr Ala Met His
1               5

<210> SEQ ID NO 11
<211> LENGTH: 17
<212> TYPE: PRT
<213> ORGANISM: Homo sapiens
<220> FEATURE:
<221> NAME/KEY: misc_feature
<223> OTHER INFORMATION: Amino acid sequence of CDRH2 of 84G09 using
      Kabat

<400> SEQUENCE: 11

Gly Ile Ser Trp Lys Ser Asn Ile Ile Gly Tyr Ala Asp Ser Val Lys
1               5                   10                  15

Gly

<210> SEQ ID NO 12
<211> LENGTH: 13
<212> TYPE: PRT
<213> ORGANISM: Homo sapiens
<220> FEATURE:
<221> NAME/KEY: misc_feature
<223> OTHER INFORMATION: Amino acid sequence of CDRH3 of 84G09 using
      Kabat

<400> SEQUENCE: 12

Asp Ile Thr Gly Ser Gly Ser Tyr Gly Trp Phe Asp Pro
1               5                   10

<210> SEQ ID NO 13
<211> LENGTH: 122
<212> TYPE: PRT
<213> ORGANISM: Homo sapiens
<220> FEATURE:
<221> NAME/KEY: misc_feature
<223> OTHER INFORMATION: Amino acid sequence of VH of 84G09

<400> SEQUENCE: 13

Glu Val Gln Leu Val Glu Ser Gly Gly Gly Leu Val Gln Pro Gly Arg
1               5                   10                  15

Ser Leu Arg Leu Ser Cys Ala Ala Ser Gly Phe Thr Phe Asp Asp Tyr
            20                  25                  30

Ala Met His Trp Val Arg Gln Thr Pro Gly Lys Gly Leu Glu Trp Val
        35                  40                  45

Ser Gly Ile Ser Trp Lys Ser Asn Ile Ile Gly Tyr Ala Asp Ser Val
    50                  55                  60

Lys Gly Arg Phe Thr Ile Ser Arg Asp Asn Ala Lys Asn Ser Leu Tyr

```
                65                  70                  75                  80
Leu Gln Met Asn Ser Leu Arg Ala Glu Asp Thr Ala Leu Tyr Tyr Cys
                    85                  90                  95

Ala Arg Asp Ile Thr Gly Ser Gly Ser Tyr Gly Trp Phe Asp Pro Trp
                100                 105                 110

Gly Gln Gly Thr Leu Val Thr Val Ser Ser
                115                 120

<210> SEQ ID NO 14
<211> LENGTH: 508
<212> TYPE: DNA
<213> ORGANISM: Homo sapiens
<220> FEATURE:
<221> NAME/KEY: misc_feature
<223> OTHER INFORMATION: Nucleic acid sequence of VH of 84G09

<400> SEQUENCE: 14
caagaaaaag cttgccgcca ccatggagtt tgggctgagc tggatttttcc ttttggctat      60 tttaaaaggt gtccagtgtg aagtacaatt ggtggagtcc gggggaggct tggtacagcc     120
tggcaggtcc ctgagactct cctgtgcagc ctctggattc acctttgatg attatgccat     180
gcactgggtc cgacaaactc agggaaggg cctggagtgg gtctcaggta taagttggaa     240
gagtaatatc ataggctatg cggactctgt gaagggccga ttcaccatct ccagagacaa     300
cgccaagaac tccctgtatc tgcaaatgaa cagtctgaga gctgaggaca cggccttgta     360
ttattgtgca agagatataa cggttcgggg agttatggc tggttcgacc cctggggcca     420
gggaaccctg gtcaccgtct cctcagccaa aacgacaccc ccatctgtct atccactggc     480
ccctgaatct gctaaaactc agcctccg                                         508

<210> SEQ ID NO 15
<211> LENGTH: 449
<212> TYPE: PRT
<213> ORGANISM: Homo sapiens
<220> FEATURE:
<221> NAME/KEY: misc_feature
<223> OTHER INFORMATION: Amino acid sequence of 84G09 heavy chain

<400> SEQUENCE: 15

Glu Val Gln Leu Val Glu Ser Gly Gly Gly Leu Val Gln Pro Gly Arg
1               5                   10                  15

Ser Leu Arg Leu Ser Cys Ala Ala Ser Gly Phe Thr Phe Asp Asp Tyr
                20                  25                  30

Ala Met His Trp Val Arg Gln Thr Pro Gly Lys Gly Leu Glu Trp Val
            35                  40                  45

Ser Gly Ile Ser Trp Lys Ser Asn Ile Ile Gly Tyr Ala Asp Ser Val
        50                  55                  60

Lys Gly Arg Phe Thr Ile Ser Arg Asp Asn Ala Lys Asn Ser Leu Tyr
65                  70                  75                  80

Leu Gln Met Asn Ser Leu Arg Ala Glu Asp Thr Ala Leu Tyr Tyr Cys
                85                  90                  95

Ala Arg Asp Ile Thr Gly Ser Gly Ser Tyr Gly Trp Phe Asp Pro Trp
                100                 105                 110

Gly Gln Gly Thr Leu Val Thr Val Ser Ser Ala Ser Thr Lys Gly Pro
                115                 120                 125

Ser Val Phe Pro Leu Ala Pro Cys Ser Arg Ser Thr Ser Glu Ser Thr
            130                 135                 140

Ala Ala Leu Gly Cys Leu Val Lys Asp Tyr Phe Pro Glu Pro Val Thr
```

```
            145                 150                 155                 160
        Val Ser Trp Asn Ser Gly Ala Leu Thr Ser Gly Val His Thr Phe Pro
                        165                 170                 175

Ala Val Leu Gln Ser Ser Gly Leu Tyr Ser Leu Ser Ser Val Val Thr
                    180                 185                 190

Val Pro Ser Ser Ser Leu Gly Thr Lys Thr Tyr Thr Cys Asn Val Asp
                    195                 200                 205

His Lys Pro Ser Asn Thr Lys Val Asp Lys Arg Val Glu Ser Lys Tyr
                    210                 215                 220

Gly Pro Pro Cys Pro Cys Pro Ala Pro Glu Phe Glu Gly Gly Pro
        225                 230                 235                 240

Ser Val Phe Leu Phe Pro Pro Lys Pro Lys Asp Thr Leu Met Ile Ser
                        245                 250                 255

Arg Thr Pro Glu Val Thr Cys Val Val Val Asp Val Ser Gln Glu Asp
                    260                 265                 270

Pro Glu Val Gln Phe Asn Trp Tyr Val Asp Gly Val Glu Val His Asn
                    275                 280                 285

Ala Lys Thr Lys Pro Arg Glu Glu Gln Phe Asn Ser Thr Tyr Arg Val
                290                 295                 300

Val Ser Val Leu Thr Val Leu His Gln Asp Trp Leu Asn Gly Lys Glu
        305                 310                 315                 320

Tyr Lys Cys Lys Val Ser Asn Lys Gly Leu Pro Ser Ser Ile Glu Lys
                        325                 330                 335

Thr Ile Ser Lys Ala Lys Gly Gln Pro Arg Glu Pro Gln Val Tyr Thr
                    340                 345                 350

Leu Pro Pro Ser Gln Glu Glu Met Thr Lys Asn Gln Val Ser Leu Thr
                    355                 360                 365

Cys Leu Val Lys Gly Phe Tyr Pro Ser Asp Ile Ala Val Glu Trp Glu
                370                 375                 380

Ser Asn Gly Gln Pro Glu Asn Asn Tyr Lys Thr Thr Pro Pro Val Leu
        385                 390                 395                 400

Asp Ser Asp Gly Ser Phe Phe Leu Tyr Ser Arg Leu Thr Val Asp Lys
                        405                 410                 415

Ser Arg Trp Gln Glu Gly Asn Val Phe Ser Cys Ser Val Met His Glu
                    420                 425                 430

Ala Leu His Asn His Tyr Thr Gln Lys Ser Leu Ser Leu Ser Leu Gly
                    435                 440                 445

Lys

<210> SEQ ID NO 16
<211> LENGTH: 1356
<212> TYPE: DNA
<213> ORGANISM: Homo sapiens
<220> FEATURE:
<221> NAME/KEY: misc_feature
<223> OTHER INFORMATION: Nucleic acid sequence of 84G09 heavy chain

<400> SEQUENCE: 16
gaagtgcagc tggtggaatc tggcggcgga ctggtgcagc ctggcagatc cctgagactg        60
tcttgtgccg cctccggctt caccttcgac gactacgcta tgcactgggt gcgacagacc       120
cctggcaagg gcctggaatg ggtgtccggc atctcctgga agtccaacat catcggctac       180
gccgactccg tgaagggccg gttcaccatc tcccgggaca cgccaagaa ctccctgtac       240 ctgcagatga acagcctgcg ggccgaggac accgccctgt actactgcgc cagagacatc       300
```

```
accggctccg gctcctacgg atggttcgat ccttggggcc agggcaccct cgtgaccgtg    360
tcctctgcca gcaccaaggg cccctctgtg ttccctctgg ccccttccag caagtccacc    420
tctggcggaa cagccgctct gggctgcctc gtgaaggact acttccccga gcctgtgacc    480
gtgtcctgga actctggcgc tctgaccagc ggagtgcaca ccttccctgc tgtgctgcag    540
tcctccggcc tgtactccct gtcctccgtc gtgaccgtgc cttccagctc tctgggcacc    600
cagacctaca tctgcaacgt gaaccacaag ccctccaaca ccaaggtgga caagaaggtg    660
gaacccaagt cctgcgacaa gacccacacc tgtcccccct tgtcctgccc tgaactgctg    720
ggcggacctt ccgtgttcct gttcccccca aagcccaagg acaccctgat gatctcccgg    780 accccgaag tgacctgcgt ggtggtggat gtgtcccacg aggaccctga agtgaagttc    840
aattggtacg tggacggcgt ggaagtgcac aacgccaaga ccaagcctag agaggaacag    900
tacaactcca cctaccgggt ggtgtccgtg ctgaccgtgc tgcaccagga ttggctgaac    960
ggcaaagagt acaagtgcaa ggtgtccaac aaggccctgc ctgcccccat cgaaaagacc   1020
atctccaagg ccaagggcca gccccgggaa ccccaggtgt acacactgcc cctagcagg   1080 gacgagctga ccaagaacca ggtgtccctg acctgtctcg tgaaaggctt ctaccctcc    1140 gatatcgccg tggaatggga gtccaacggc agcctgaga caactacaa gaccacccc    1200 cctgtgctgg actccgacgg ctcattcttc ctgtacagca agctgacagt ggacaagtcc   1260
cggtggcagc agggcaacgt gttctcctgc tccgtgatgc acgaggccct gcacaaccac   1320
tacacccaga gtccctgtc cctgagcccc ggcaag                              1356
```

<210> SEQ ID NO 17
<211> LENGTH: 6
<212> TYPE: PRT
<213> ORGANISM: Homo sapiens
<220> FEATURE:
<221> NAME/KEY: misc_feature
<223> OTHER INFORMATION: Amino acid sequence of CDRL1 of 84G09 using
      IMGT

<400> SEQUENCE: 17

Gln Ser Ile Ser Ser Tyr
1               5

<210> SEQ ID NO 18
<211> LENGTH: 3
<212> TYPE: PRT
<213> ORGANISM: Homo sapiens
<220> FEATURE:
<221> NAME/KEY: misc_feature
<223> OTHER INFORMATION: Amino acid sequence of CDRL2 of 84G09 using
      IMGT

<400> SEQUENCE: 18

Val Ala Ser
1

<210> SEQ ID NO 19
<211> LENGTH: 9
<212> TYPE: PRT
<213> ORGANISM: Homo sapiens
<220> FEATURE:
<221> NAME/KEY: misc_feature
<223> OTHER INFORMATION: Amino acid sequence of CDRL3 of 84G09 using
      IMGT

<400> SEQUENCE: 19

Gln Gln Ser Tyr Ser Asn Pro Ile Thr

<210> SEQ ID NO 20
<211> LENGTH: 11
<212> TYPE: PRT
<213> ORGANISM: Homo sapiens
<220> FEATURE:
<221> NAME/KEY: misc_feature
<223> OTHER INFORMATION: Amino acid sequence of CDRL1 of 84G09 using
      Kabat

<400> SEQUENCE: 20

Arg Ala Ser Gln Ser Ile Ser Ser Tyr Leu Asn
1               5                   10

<210> SEQ ID NO 21
<211> LENGTH: 7
<212> TYPE: PRT
<213> ORGANISM: Homo sapiens
<220> FEATURE:
<221> NAME/KEY: misc_feature
<223> OTHER INFORMATION: Amino acid sequence of CDRL2 of 84G09 using
      Kabat

<400> SEQUENCE: 21

Val Ala Ser Ser Leu Gln Ser
1               5

<210> SEQ ID NO 22
<211> LENGTH: 9
<212> TYPE: PRT
<213> ORGANISM: Homo sapiens
<220> FEATURE:
<221> NAME/KEY: misc_feature
<223> OTHER INFORMATION: Amino acid sequence of CDRL3 of 84G09 using
      Kabat

<400> SEQUENCE: 22

Gln Gln Ser Tyr Ser Asn Pro Ile Thr
1               5

<210> SEQ ID NO 23
<211> LENGTH: 107
<212> TYPE: PRT
<213> ORGANISM: Homo sapiens
<220> FEATURE:
<221> NAME/KEY: misc_feature
<223> OTHER INFORMATION: Amino acid sequence of VL of 84G09

<400> SEQUENCE: 23

Asp Ile Gln Met Thr Gln Ser Pro Ser Ser Leu Ser Ala Ser Val Gly
1               5                   10                  15

Asp Arg Val Thr Ile Thr Cys Arg Ala Ser Gln Ser Ile Ser Ser Tyr
            20                  25                  30

Leu Asn Trp Tyr Gln Gln Lys Pro Gly Lys Ala Pro Lys Pro Leu Ile
        35                  40                  45

Tyr Val Ala Ser Ser Leu Gln Ser Gly Val Pro Ser Ser Phe Ser Gly
    50                  55                  60

Ser Gly Ser Gly Thr Asp Phe Thr Leu Thr Ile Ser Ser Leu Gln Pro
65                  70                  75                  80

Glu Asp Phe Ala Thr Tyr Tyr Cys Gln Gln Ser Tyr Ser Asn Pro Ile
                85                  90                  95

Thr Phe Gly Gln Gly Thr Arg Leu Glu Ile Lys
            100                 105

<210> SEQ ID NO 24
<211> LENGTH: 321
<212> TYPE: DNA
<213> ORGANISM: Homo sapiens
<220> FEATURE:
<221> NAME/KEY: misc_feature
<223> OTHER INFORMATION: Nucleic acid sequence of VL of 84G09

<400> SEQUENCE: 24

```
gacatccaga tgacccagtc tccatcctcc ctgtctgcat ctgtaggaga cagagtcacc      60
atcacttgcc gggcaagtca gagcattagc agctatttaa attggtatca gcagaaacca     120
gggaaagccc ctaagcccct gatctatgtt gcatccagtt tgcaaagtgg ggtcccatca     180
agtttcagtg gcagtggatc tgggacagat ttcactctca ccatcagcag tctgcaacct     240
gaagattttg caacttacta ctgtcaacag agttacagta tccgatcac cttcggccaa     300
gggacacgac tggagatcaa a                                                321
```

<210> SEQ ID NO 25
<211> LENGTH: 214
<212> TYPE: PRT
<213> ORGANISM: Homo sapiens
<220> FEATURE:
<221> NAME/KEY: misc_feature
<223> OTHER INFORMATION: Amino acid sequence of 84G09 light chain

<400> SEQUENCE: 25

Asp Ile Gln Met Thr Gln Ser Pro Ser Ser Leu Ser Ala Ser Val Gly
1               5                   10                  15

Asp Arg Val Thr Ile Thr Cys Arg Ala Ser Gln Ser Ile Ser Ser Tyr
            20                  25                  30

Leu Asn Trp Tyr Gln Gln Lys Pro Gly Lys Ala Pro Lys Pro Leu Ile
        35                  40                  45

Tyr Val Ala Ser Ser Leu Gln Ser Gly Val Pro Ser Ser Phe Ser Gly
    50                  55                  60

Ser Gly Ser Gly Thr Asp Phe Thr Leu Thr Ile Ser Ser Leu Gln Pro
65                  70                  75                  80

Glu Asp Phe Ala Thr Tyr Tyr Cys Gln Gln Ser Tyr Ser Asn Pro Ile
                85                  90                  95

Thr Phe Gly Gln Gly Thr Arg Leu Glu Ile Lys Arg Thr Val Ala Ala
            100                 105                 110

Pro Ser Val Phe Ile Phe Pro Pro Ser Asp Glu Gln Leu Lys Ser Gly
        115                 120                 125

Thr Ala Ser Val Val Cys Leu Leu Asn Asn Phe Tyr Pro Arg Glu Ala
    130                 135                 140

Lys Val Gln Trp Lys Val Asp Asn Ala Leu Gln Ser Gly Asn Ser Gln
145                 150                 155                 160

Glu Ser Val Thr Glu Gln Asp Ser Lys Asp Ser Thr Tyr Ser Leu Ser
                165                 170                 175

Ser Thr Leu Thr Leu Ser Lys Ala Asp Tyr Glu Lys His Lys Val Tyr
            180                 185                 190

Ala Cys Glu Val Thr His Gln Gly Leu Ser Ser Pro Val Thr Lys Ser
        195                 200                 205

Phe Asn Arg Gly Glu Cys
    210

<210> SEQ ID NO 26
<211> LENGTH: 642

```
<212> TYPE: DNA
<213> ORGANISM: Homo sapiens
<220> FEATURE:
<221> NAME/KEY: misc_feature
<223> OTHER INFORMATION: Nucleic acid sequence of 84G09 light chain

<400> SEQUENCE: 26
gacatccaga tgacccagtc tccatcctcc ctgtctgcat ctgtaggaga cagagtcacc      60
atcacttgcc gggcaagtca gagcattagc agctatttaa attggtatca gcagaaacca     120
gggaaagccc ctaagcccct gatctatgtt gcatccagtt tgcaaagtgg ggtcccatca     180
agtttcagtg gcagtggatc tgggacagat tcactctca ccatcagcag tctgcaacct      240
gaagattttg caacttacta ctgtcaacag agttacagta atccgatcac cttcggccaa     300
gggacacgac tggagatcaa acgtacggtg gccgctccct ccgtgttcat cttcccacct     360
tccgacgagc agctgaagtc cggcaccgct tctgtcgtgt gcctgctgaa caacttctac     420
ccccgcgagg ccaaggtgca gtggaaggtg gacaacgccc tgcagtccgg caactcccag     480
gaatccgtga ccgagcagga ctccaaggac agcacctact ccctgtcctc caccctgacc     540
ctgtccaagg ccgactacga gaagcacaag gtgtacgcct gcgaagtgac ccaccagggc     600
ctgtctagcc ccgtgaccaa gtctttcaac cggggcgagt gt                        642

<210> SEQ ID NO 27
<211> LENGTH: 8
<212> TYPE: PRT
<213> ORGANISM: Homo sapiens
<220> FEATURE:
<221> NAME/KEY: misc_feature
<223> OTHER INFORMATION: Amino acid sequence of CDRH1 of 1D05 using IMGT

<400> SEQUENCE: 27

Gly Phe Thr Phe Asp Asp Tyr Ala
1               5

<210> SEQ ID NO 28
<211> LENGTH: 8
<212> TYPE: PRT
<213> ORGANISM: Homo sapiens
<220> FEATURE:
<221> NAME/KEY: misc_feature
<223> OTHER INFORMATION: Amino acid sequence of CDRH2 of 1D05 using IMGT

<400> SEQUENCE: 28

Ile Ser Trp Ile Arg Thr Gly Ile
1               5

<210> SEQ ID NO 29
<211> LENGTH: 16
<212> TYPE: PRT
<213> ORGANISM: Homo sapiens
<220> FEATURE:
<221> NAME/KEY: misc_feature
<223> OTHER INFORMATION: Amino acid sequence of CDRH3 of 1D05 using IMGT

<400> SEQUENCE: 29

Ala Lys Asp Met Lys Gly Ser Gly Thr Tyr Gly Gly Trp Phe Asp Thr
1               5                   10                  15

<210> SEQ ID NO 30
<211> LENGTH: 5
<212> TYPE: PRT
<213> ORGANISM: Homo sapiens
<220> FEATURE:
<221> NAME/KEY: misc_feature
```

```
<223> OTHER INFORMATION: Amino acid sequence of CDRH1 of 1D05 using
      Kabat

<400> SEQUENCE: 30

Asp Tyr Ala Met His
1               5

<210> SEQ ID NO 31
<211> LENGTH: 17
<212> TYPE: PRT
<213> ORGANISM: Homo sapiens
<220> FEATURE:
<221> NAME/KEY: misc_feature
<223> OTHER INFORMATION: Amino acid sequence of CDRH2 of 1D05 using
      Kabat

<400> SEQUENCE: 31

Gly Ile Ser Trp Ile Arg Thr Gly Ile Gly Tyr Ala Asp Ser Val Lys
1               5                   10                  15

Gly

<210> SEQ ID NO 32
<211> LENGTH: 14
<212> TYPE: PRT
<213> ORGANISM: Homo sapiens
<220> FEATURE:
<221> NAME/KEY: misc_feature
<223> OTHER INFORMATION: Amino acid sequence of CDRH3 of 1D05 using
 Kabat

<400> SEQUENCE: 32

Asp Met Lys Gly Ser Gly Thr Tyr Gly Gly Trp Phe Asp Thr
1               5                   10

<210> SEQ ID NO 33
<211> LENGTH: 123
<212> TYPE: PRT
<213> ORGANISM: Homo sapiens
<220> FEATURE:
<221> NAME/KEY: misc_feature
<223> OTHER INFORMATION: Amino acid sequence of VH of 1D05

<400> SEQUENCE: 33

Glu Val Gln Leu Val Glu Ser Gly Gly Leu Val Gln Pro Gly Arg
1               5                   10                  15

Ser Leu Arg Leu Ser Cys Ala Ala Ser Gly Phe Thr Phe Asp Asp Tyr
                20                  25                  30

Ala Met His Trp Val Arg Gln Val Pro Gly Lys Gly Leu Glu Trp Val
            35                  40                  45

Ser Gly Ile Ser Trp Ile Arg Thr Gly Ile Gly Tyr Ala Asp Ser Val
        50                  55                  60

Lys Gly Arg Phe Thr Ile Phe Arg Asp Asn Ala Lys Asn Ser Leu Tyr
65                  70                  75                  80

Leu Gln Met Asn Ser Leu Arg Ala Glu Asp Thr Ala Leu Tyr Tyr Cys
                85                  90                  95

Ala Lys Asp Met Lys Gly Ser Gly Thr Tyr Gly Gly Trp Phe Asp Thr
            100                 105                 110

Trp Gly Gln Gly Thr Leu Val Thr Val Ser Ser
            115                 120

<210> SEQ ID NO 34
<211> LENGTH: 482
<212> TYPE: DNA
```

<213> ORGANISM: Homo sapiens
<220> FEATURE:
<221> NAME/KEY: misc_feature
<223> OTHER INFORMATION: Nucleic acid sequence of VH of 1D05

<400> SEQUENCE: 34

```
aagcttgccg ccaccatgga gtttgggctg agctggattt ccttttggc tattttaaaa    60
ggtgtccagt gtgaagtgca gctggtggag tctgggggag gcttggtgca gcctggcagg   120
tccctgagac tctcctgtgc agcctctgga ttcacctttg atgattatgc catgcactgg   180
gtccggcaag ttccagggaa gggcctggaa tgggtctcag gcattagttg gattcgtact   240
ggcataggct atgcggactc tgtgaagggc cgattcacca ttttcagaga caacgccaag   300
aattccctgt atctgcaaat gaacagtctg agagctgagg acacggcctt gtattactgt   360
gcaaaagata tgaagggttc ggggacttat ggggggtggt tcgacacctg gggccaggga   420
accctggtca ccgtctcctc agccaaaaca acagcccat cggtctatcc actggcccct   480
gc                                                                  482
```

<210> SEQ ID NO 35
<211> LENGTH: 450
<212> TYPE: PRT
<213> ORGANISM: Mus musculus
<220> FEATURE:
<221> NAME/KEY: misc_feature
<223> OTHER INFORMATION: Amino acid sequence of 1D05 heavy chain

<400> SEQUENCE: 35

Glu Val Gln Leu Val Glu Ser Gly Gly Gly Leu Val Gln Pro Gly Arg
1               5                   10                  15

Ser Leu Arg Leu Ser Cys Ala Ala Ser Gly Phe Thr Phe Asp Asp Tyr
            20                  25                  30

Ala Met His Trp Val Arg Gln Val Pro Gly Lys Gly Leu Glu Trp Val
        35                  40                  45

Ser Gly Ile Ser Trp Ile Arg Thr Gly Ile Gly Tyr Ala Asp Ser Val
    50                  55                  60

Lys Gly Arg Phe Thr Ile Phe Arg Asp Asn Ala Lys Asn Ser Leu Tyr
65                  70                  75                  80

Leu Gln Met Asn Ser Leu Arg Ala Glu Asp Thr Ala Leu Tyr Tyr Cys
                85                  90                  95

Ala Lys Asp Met Lys Gly Ser Gly Thr Tyr Gly Gly Trp Phe Asp Thr
            100                 105                 110

Trp Gly Gln Gly Thr Leu Val Thr Val Ser Ser Ala Ser Thr Lys Gly
        115                 120                 125

Pro Ser Val Phe Pro Leu Ala Pro Cys Ser Arg Ser Thr Ser Glu Ser
    130                 135                 140

Thr Ala Ala Leu Gly Cys Leu Val Lys Asp Tyr Phe Pro Glu Pro Val
145                 150                 155                 160

Thr Val Ser Trp Asn Ser Gly Ala Leu Thr Ser Gly Val His Thr Phe
                165                 170                 175

Pro Ala Val Leu Gln Ser Ser Gly Leu Tyr Ser Leu Ser Ser Val Val
            180                 185                 190

Thr Val Pro Ser Ser Ser Leu Gly Thr Lys Thr Tyr Thr Cys Asn Val
        195                 200                 205

Asp His Lys Pro Ser Asn Thr Lys Val Asp Lys Arg Val Glu Ser Lys
    210                 215                 220

Tyr Gly Pro Pro Cys Pro Pro Cys Pro Ala Pro Glu Phe Glu Gly Gly

```
                225                 230                 235                 240
Pro Ser Val Phe Leu Phe Pro Lys Pro Lys Asp Thr Leu Met Ile
                245                 250                 255
Ser Arg Thr Pro Glu Val Thr Cys Val Val Val Asp Val Ser Gln Glu
                260                 265                 270
Asp Pro Glu Val Gln Phe Asn Trp Tyr Val Asp Gly Val Glu Val His
                275                 280                 285
Asn Ala Lys Thr Lys Pro Arg Glu Glu Gln Phe Asn Ser Thr Tyr Arg
                290                 295                 300
Val Val Ser Val Leu Thr Val Leu His Gln Asp Trp Leu Asn Gly Lys
305                 310                 315                 320
Glu Tyr Lys Cys Lys Val Ser Asn Lys Gly Leu Pro Ser Ser Ile Glu
                325                 330                 335
Lys Thr Ile Ser Lys Ala Lys Gly Gln Pro Arg Glu Pro Gln Val Tyr
                340                 345                 350
Thr Leu Pro Pro Ser Gln Glu Glu Met Thr Lys Asn Gln Val Ser Leu
                355                 360                 365
Thr Cys Leu Val Lys Gly Phe Tyr Pro Ser Asp Ile Ala Val Glu Trp
                370                 375                 380
Glu Ser Asn Gly Gln Pro Glu Asn Asn Tyr Lys Thr Thr Pro Pro Val
385                 390                 395                 400
Leu Asp Ser Asp Gly Ser Phe Phe Leu Tyr Ser Arg Leu Thr Val Asp
                405                 410                 415
Lys Ser Arg Trp Gln Glu Gly Asn Val Phe Ser Cys Ser Val Met His
                420                 425                 430
Glu Ala Leu His Asn His Tyr Thr Gln Lys Ser Leu Ser Leu Ser Leu
                435                 440                 445
Gly Lys
    450

<210> SEQ ID NO 36
<211> LENGTH: 1359
<212> TYPE: DNA
<213> ORGANISM: Homo sapiens
<220> FEATURE:
<221> NAME/KEY: misc_feature
<223> OTHER INFORMATION: Nucleic acid sequence of 1D05 heavy chain

<400> SEQUENCE: 36
gaagtgcagc tggtggaatc tggcggcgga ctggtgcagc ctggcagatc cctgagactg      60
tcttgtgccg cctccggctt caccttcgac gactacgcta tgcactgggt gcgacaggtg     120
ccaggcaagg gcctggaatg ggtgtccggc atctcttgga tccggaccgg catcggctac     180
gccgactctg tgaagggccg gttcaccatc ttcgggaca acgccaagaa ctccctgtac      240
ctgcagatga acagcctgcg ggccgaggac accgccctgt actactgcgc caaggacatg     300
aagggctccg gcacctacgg cggatggttc gatacttggg gccagggcac cctcgtgacc     360
gtgtcctctg ccagcaccaa gggcccctct gtgttccctc tggccccttc agcaagtcc      420
acctctggcg gaacagccgc tctgggctgc ctcgtgaagg actactcccc cgagcctgtg     480
accgtgtcct ggaactctgg cgctctgacc agcggagtgc acaccttccc tgctgtgctg     540
cagtcctccg gcctgtactc cctgtcctcc gtcgtgaccg tgccttccag ctctctgggc     600
acccagacct acatctgcaa cgtgaaccac aagccctcca caccaaggt ggacaagaag      660
gtggaaccca gtcctgcga caagacccac acctgtcccc cttgtcctgc ccctgaactg     720
```

```
ctgggcggac cttccgtgtt cctgttcccc ccaaagccca aggacaccct gatgatctcc    780 cggaccccg aagtgacctg cgtggtggtg gatgtgtccc acgaggaccc tgaagtgaag     840
ttcaattggt acgtggacgg cgtggaagtg cacaacgcca agaccaagcc tagagaggaa    900
cagtacaact ccacctaccg ggtggtgtcc gtgctgaccg tgctgcacca ggattggctg    960
aacggcaaag agtacaagtg caaggtgtcc aacaaggccc tgcctgcccc catcgaaaag   1020
accatctcca aggccaaggg ccagcccgg gaacccag tgtacacact gccccctagc     1080
agggacgagc tgaccaagaa ccaggtgtcc ctgacctgtc tcgtgaaagg cttctacccc   1140
tccgatatcg ccgtggaatg ggagtccaac ggccagcctg agaacaacta caagaccacc   1200 cccctgtgc tggactccga cggctcattc ttcctgtaca gcaagctgac agtggacaag    1260
tcccggtggc agcagggcaa cgtgttctcc tgctccgtga tgcacgaggc cctgcacaac   1320
cactacaccc agaagtccct gtccctgagc cccggcaag                           1359
```

<210> SEQ ID NO 37
<211> LENGTH: 6
<212> TYPE: PRT
<213> ORGANISM: Homo sapiens
<220> FEATURE:
<221> NAME/KEY: misc_feature
<223> OTHER INFORMATION: Amino acid sequence of CDRL1 of 1D05 using IMGT

<400> SEQUENCE: 37

Gln Ser Ile Ser Ser Tyr
1               5

<210> SEQ ID NO 38
<211> LENGTH: 3
<212> TYPE: PRT
<213> ORGANISM: Homo sapiens
<220> FEATURE:
<221> NAME/KEY: misc_feature
<223> OTHER INFORMATION: Amino acid sequence of CDRL2 of 1D05 using IMGT

<400> SEQUENCE: 38

Val Ala Ser
1

<210> SEQ ID NO 39
<211> LENGTH: 9
<212> TYPE: PRT
<213> ORGANISM: Homo sapiens
<220> FEATURE:
<221> NAME/KEY: misc_feature
<223> OTHER INFORMATION: Amino acid sequence of CDRL3 of 1D05 using IMGT

<400> SEQUENCE: 39

Gln Gln Ser Tyr Ser Thr Pro Ile Thr
1               5

<210> SEQ ID NO 40
<211> LENGTH: 11
<212> TYPE: PRT
<213> ORGANISM: Homo sapiens
<220> FEATURE:
<221> NAME/KEY: misc_feature
<223> OTHER INFORMATION: Amino acid sequence of CDRL1 of 1D05 using
      Kabat

<400> SEQUENCE: 40

Arg Ala Ser Gln Ser Ile Ser Ser Tyr Leu Asn
1               5                   10

```
<210> SEQ ID NO 41
<211> LENGTH: 7
<212> TYPE: PRT
<213> ORGANISM: Homo sapiens
<220> FEATURE:
<221> NAME/KEY: misc_feature
<223> OTHER INFORMATION: Amino acid sequence of CDRL2 of 1D05 using
      Kabat

<400> SEQUENCE: 41

Val Ala Ser Ser Leu Gln Ser
1               5

<210> SEQ ID NO 42
<211> LENGTH: 9
<212> TYPE: PRT
<213> ORGANISM: Homo sapiens
<220> FEATURE:
<221> NAME/KEY: misc_feature
<223> OTHER INFORMATION: Amino acid sequence of CDRL3 of 1D05 using
      Kabat

<400> SEQUENCE: 42

Gln Gln Ser Tyr Ser Thr Pro Ile Thr
1               5

<210> SEQ ID NO 43
<211> LENGTH: 107
<212> TYPE: PRT
<213> ORGANISM: Homo sapiens
<220> FEATURE:
<221> NAME/KEY: misc_feature
<223> OTHER INFORMATION: Amino acid sequence of VL of 1D05

<400> SEQUENCE: 43

Asp Ile Gln Met Thr Gln Ser Pro Ser Ser Leu Ser Ala Ser Val Gly
1               5                   10                  15

Asp Arg Val Thr Ile Thr Cys Arg Ala Ser Gln Ser Ile Ser Ser Tyr
            20                  25                  30

Leu Asn Trp Tyr Gln Gln Lys Pro Gly Lys Ala Pro Lys Leu Leu Ile
        35                  40                  45

Tyr Val Ala Ser Ser Leu Gln Ser Gly Val Pro Ser Arg Phe Ser Gly
    50                  55                  60

Ser Gly Ser Gly Thr Asp Phe Thr Leu Thr Ile Ser Ser Leu Gln Pro
65                  70                  75                  80

Glu Asp Phe Ala Thr Tyr Tyr Cys Gln Gln Ser Tyr Ser Thr Pro Ile
                85                  90                  95

Thr Phe Gly Gln Gly Thr Arg Leu Glu Ile Lys
            100                 105

<210> SEQ ID NO 44
<211> LENGTH: 418
<212> TYPE: DNA
<213> ORGANISM: Homo sapiens
<220> FEATURE:
<221> NAME/KEY: misc_feature
<223> OTHER INFORMATION: Nucleic acid sequence of VL of 1D05

<400> SEQUENCE: 44
aaagcttgcc gccaccatga ggctccctgc tcagcttctg ggctcctgc tactctggct      60 ccgaggtgcc agatgtgaca tccagatgac ccagtctcca tcctcccgt ctgcatctgt     120 aggagacaga gtcaccatca cttgccgggc aagtcagagc attagcagct atttaaattg    180
```

-continued

```
gtatcagcag aaaccaggga agcccctaa actcctgatc tatgttgcat ccagtttgca      240
aagtggggtc ccatcaaggt tcagtggcag tggatctggg acagatttca ctctcactat    300
cagcagtctg caacctgaag attttgcaac ttactactgt caacagagtt acagtacccc    360
gatcaccttc ggccaaggga cacgtctgga gatcaaacgt acggatgctg caccaact      418
```

<210> SEQ ID NO 45
<211> LENGTH: 214
<212> TYPE: PRT
<213> ORGANISM: Mus musculus
<220> FEATURE:
<221> NAME/KEY: misc_feature
<223> OTHER INFORMATION: Amino acid sequence of 1D05 light chain

<400> SEQUENCE: 45

```
Asp Ile Gln Met Thr Gln Ser Pro Ser Ser Leu Ser Ala Ser Val Gly
1               5                   10                  15

Asp Arg Val Thr Ile Thr Cys Arg Ala Ser Gln Ser Ile Ser Ser Tyr
            20                  25                  30

Leu Asn Trp Tyr Gln Gln Lys Pro Gly Lys Ala Pro Lys Leu Leu Ile
        35                  40                  45

Tyr Val Ala Ser Ser Leu Gln Ser Gly Val Pro Ser Arg Phe Ser Gly
    50                  55                  60

Ser Gly Ser Gly Thr Asp Phe Thr Leu Thr Ile Ser Ser Leu Gln Pro
65                  70                  75                  80

Glu Asp Phe Ala Thr Tyr Tyr Cys Gln Gln Ser Tyr Ser Thr Pro Ile
                85                  90                  95

Thr Phe Gly Gln Gly Thr Arg Leu Glu Ile Lys Arg Thr Val Ala Ala
            100                 105                 110

Pro Ser Val Phe Ile Phe Pro Pro Ser Asp Glu Gln Leu Lys Ser Gly
        115                 120                 125

Thr Ala Ser Val Val Cys Leu Leu Asn Asn Phe Tyr Pro Arg Glu Ala
    130                 135                 140

Lys Val Gln Trp Lys Val Asp Asn Ala Leu Gln Ser Gly Asn Ser Gln
145                 150                 155                 160

Glu Ser Val Thr Glu Gln Asp Ser Lys Asp Ser Thr Tyr Ser Leu Ser
                165                 170                 175

Ser Thr Leu Thr Leu Ser Lys Ala Asp Tyr Glu Lys His Lys Val Tyr
            180                 185                 190

Ala Cys Glu Val Thr His Gln Gly Leu Ser Ser Pro Val Thr Lys Ser
        195                 200                 205

Phe Asn Arg Gly Glu Cys
    210
```

<210> SEQ ID NO 46
<211> LENGTH: 642
<212> TYPE: DNA
<213> ORGANISM: Homo sapiens
<220> FEATURE:
<221> NAME/KEY: misc_feature
<223> OTHER INFORMATION: Nucleic acid sequence of 1D05 light chain

<400> SEQUENCE: 46

```
gacatccaga tgacccagtc cccctccagc ctgtctgctt ccgtgggcga cagagtgacc      60
atcacctgtc gggcctccca gtccatctcc tcctacctga actggtatca gcagaagccc    120
ggcaaggccc ccaagctgct gatctacgtg gccagctctc tgcagtccgg cgtgccctct    180
agattctccg gctctggctc tggcaccgac tttaccctga ccatcagctc cctgcagccc    240
```

```
gaggacttcg ccacctacta ctgccagcag tcctactcca ccccctatcac cttcggccag    300 ggcacccggc tggaaaatcaa acgtacggtg gccgctccct ccgtgttcat cttcccacct    360
tccgacgagc agctgaagtc cggcaccgct tctgtcgtgt gcctgctgaa caacttctac    420
ccccgcgagg ccaaggtgca gtggaaggtg gacaacgccc tgcagtccgg caactcccag    480
gaatccgtga ccgagcagga ctccaaggac agcacctact ccctgtcctc caccctgacc    540
ctgtccaagg ccgactacga gaagcacaag gtgtacgcct gcgaagtgac ccaccagggc    600
ctgtctagcc ccgtgaccaa gtctttcaac cggggcgagt gt                       642
```

<210> SEQ ID NO 47
<211> LENGTH: 450
<212> TYPE: PRT
<213> ORGANISM: Homo sapiens
<220> FEATURE:
<221> NAME/KEY: misc_feature
<223> OTHER INFORMATION: 1D05 HC V to A mutated aa sequence w/IgG1 LAGA
      constant region

<400> SEQUENCE: 47

```
Glu Val Gln Leu Val Glu Ser Gly Gly Gly Leu Val Gln Pro Gly Arg
1               5                   10                  15

Ser Leu Arg Leu Ser Cys Ala Ala Ser Gly Phe Thr Phe Asp Asp Tyr
            20                  25                  30

Ala Met His Trp Val Arg Gln Ala Pro Gly Lys Gly Leu Glu Trp Val
        35                  40                  45

Ser Gly Ile Ser Trp Ile Arg Thr Gly Ile Gly Tyr Ala Asp Ser Val
    50                  55                  60

Lys Gly Arg Phe Thr Ile Phe Arg Asp Asn Ala Lys Asn Ser Leu Tyr
65                  70                  75                  80

Leu Gln Met Asn Ser Leu Arg Ala Glu Asp Thr Ala Leu Tyr Tyr Cys
                85                  90                  95

Ala Lys Asp Met Lys Gly Ser Gly Thr Tyr Gly Gly Trp Phe Asp Thr
            100                 105                 110

Trp Gly Gln Gly Thr Leu Val Thr Val Ser Ser Ala Ser Thr Lys Gly
        115                 120                 125

Pro Ser Val Phe Pro Leu Ala Pro Cys Ser Arg Ser Thr Ser Glu Ser
    130                 135                 140

Thr Ala Ala Leu Gly Cys Leu Val Lys Asp Tyr Phe Pro Glu Pro Val
145                 150                 155                 160

Thr Val Ser Trp Asn Ser Gly Ala Leu Thr Ser Gly Val His Thr Phe
                165                 170                 175

Pro Ala Val Leu Gln Ser Ser Gly Leu Tyr Ser Leu Ser Ser Val Val
            180                 185                 190

Thr Val Pro Ser Ser Ser Leu Gly Thr Lys Thr Tyr Thr Cys Asn Val
        195                 200                 205

Asp His Lys Pro Ser Asn Thr Lys Val Asp Lys Arg Val Glu Ser Lys
    210                 215                 220

Tyr Gly Pro Pro Cys Pro Cys Pro Ala Pro Glu Phe Glu Gly Gly
225                 230                 235                 240

Pro Ser Val Phe Leu Phe Pro Pro Lys Pro Lys Asp Thr Leu Met Ile
                245                 250                 255

Ser Arg Thr Pro Glu Val Thr Cys Val Val Val Asp Val Ser Gln Glu
            260                 265                 270

Asp Pro Glu Val Gln Phe Asn Trp Tyr Val Asp Gly Val Glu Val His
```

```
                275                 280                 285

Asn Ala Lys Thr Lys Pro Arg Glu Glu Gln Phe Asn Ser Thr Tyr Arg
 290                 295                 300

Val Val Ser Val Leu Thr Val Leu His Gln Asp Trp Leu Asn Gly Lys
305                 310                 315                 320

Glu Tyr Lys Cys Lys Val Ser Asn Lys Gly Leu Pro Ser Ser Ile Glu
                325                 330                 335

Lys Thr Ile Ser Lys Ala Lys Gly Gln Pro Arg Glu Pro Gln Val Tyr
            340                 345                 350

Thr Leu Pro Pro Ser Gln Glu Glu Met Thr Lys Asn Gln Val Ser Leu
        355                 360                 365

Thr Cys Leu Val Lys Gly Phe Tyr Pro Ser Asp Ile Ala Val Glu Trp
    370                 375                 380

Glu Ser Asn Gly Gln Pro Glu Asn Asn Tyr Lys Thr Thr Pro Pro Val
385                 390                 395                 400

Leu Asp Ser Asp Gly Ser Phe Phe Leu Tyr Ser Arg Leu Thr Val Asp
                405                 410                 415

Lys Ser Arg Trp Gln Glu Gly Asn Val Phe Ser Cys Ser Val Met His
            420                 425                 430

Glu Ala Leu His Asn His Tyr Thr Gln Lys Ser Leu Ser Leu Ser Leu
        435                 440                 445

Gly Lys
    450

<210> SEQ ID NO 48
<211> LENGTH: 450
<212> TYPE: PRT
<213> ORGANISM: Homo sapiens
<220> FEATURE:
<221> NAME/KEY: misc_feature
<223> OTHER INFORMATION: 1D05 HC F to S mutated aa sequence

<400> SEQUENCE: 48

Glu Val Gln Leu Val Glu Ser Gly Gly Gly Leu Val Gln Pro Gly Arg
1               5                   10                  15

Ser Leu Arg Leu Ser Cys Ala Ala Ser Gly Phe Thr Phe Asp Asp Tyr
            20                  25                  30

Ala Met His Trp Val Arg Gln Val Pro Gly Lys Gly Leu Glu Trp Val
        35                  40                  45

Ser Gly Ile Ser Trp Ile Arg Thr Gly Ile Gly Tyr Ala Asp Ser Val
    50                  55                  60

Lys Gly Arg Phe Thr Ile Ser Arg Asp Asn Ala Lys Asn Ser Leu Tyr
65                  70                  75                  80

Leu Gln Met Asn Ser Leu Arg Ala Glu Asp Thr Ala Leu Tyr Tyr Cys
                85                  90                  95

Ala Lys Asp Met Lys Gly Ser Gly Thr Tyr Gly Gly Trp Phe Asp Thr
            100                 105                 110

Trp Gly Gln Gly Thr Leu Val Thr Val Ser Ser Ala Ser Thr Lys Gly
        115                 120                 125

Pro Ser Val Phe Pro Leu Ala Pro Cys Ser Arg Ser Thr Ser Glu Ser
    130                 135                 140

Thr Ala Ala Leu Gly Cys Leu Val Lys Asp Tyr Phe Pro Glu Pro Val
145                 150                 155                 160

Thr Val Ser Trp Asn Ser Gly Ala Leu Thr Ser Gly Val His Thr Phe
                165                 170                 175
```

-continued

```
Pro Ala Val Leu Gln Ser Ser Gly Leu Tyr Ser Leu Ser Ser Val Val
                180                 185                 190

Thr Val Pro Ser Ser Ser Leu Gly Thr Lys Thr Tyr Thr Cys Asn Val
            195                 200                 205

Asp His Lys Pro Ser Asn Thr Lys Val Asp Lys Arg Val Glu Ser Lys
        210                 215                 220

Tyr Gly Pro Pro Cys Pro Pro Cys Pro Ala Pro Glu Leu Ala Gly Ala
225                 230                 235                 240

Pro Ser Val Phe Leu Phe Pro Pro Lys Pro Lys Asp Thr Leu Met Ile
                245                 250                 255

Ser Arg Thr Pro Glu Val Thr Cys Val Val Val Asp Val Ser Gln Glu
            260                 265                 270

Asp Pro Glu Val Gln Phe Asn Trp Tyr Val Asp Gly Val Glu Val His
        275                 280                 285

Asn Ala Lys Thr Lys Pro Arg Glu Glu Gln Phe Asn Ser Thr Tyr Arg
    290                 295                 300

Val Val Ser Val Leu Thr Val Leu His Gln Asp Trp Leu Asn Gly Lys
305                 310                 315                 320

Glu Tyr Lys Cys Lys Val Ser Asn Lys Gly Leu Pro Ser Ser Ile Glu
                325                 330                 335

Lys Thr Ile Ser Lys Ala Lys Gly Gln Pro Arg Glu Pro Gln Val Tyr
            340                 345                 350

Thr Leu Pro Pro Ser Gln Glu Glu Met Thr Lys Asn Gln Val Ser Leu
        355                 360                 365

Thr Cys Leu Val Lys Gly Phe Tyr Pro Ser Asp Ile Ala Val Glu Trp
    370                 375                 380

Glu Ser Asn Gly Gln Pro Glu Asn Asn Tyr Lys Thr Thr Pro Pro Val
385                 390                 395                 400

Leu Asp Ser Asp Gly Ser Phe Phe Leu Tyr Ser Arg Leu Thr Val Asp
                405                 410                 415

Lys Ser Arg Trp Gln Gln Gly Asn Val Phe Ser Cys Ser Val Met His
            420                 425                 430

Glu Ala Leu His Asn His Tyr Thr Gln Lys Ser Leu Ser Leu Ser Leu
        435                 440                 445

Gly Lys
    450

<210> SEQ ID NO 49
<211> LENGTH: 449
<212> TYPE: PRT
<213> ORGANISM: Homo sapiens
<220> FEATURE:
<221> NAME/KEY: misc_feature
<223> OTHER INFORMATION: 1D05 HC  ELLG to -PVA mutated aa sequence

<400> SEQUENCE: 49

Glu Val Gln Leu Val Glu Ser Gly Gly Gly Leu Val Gln Pro Gly Arg
1               5                   10                  15

Ser Leu Arg Leu Ser Cys Ala Ala Ser Gly Phe Thr Phe Asp Asp Tyr
            20                  25                  30

Ala Met His Trp Val Arg Gln Val Pro Gly Lys Gly Leu Glu Trp Val
        35                  40                  45

Ser Gly Ile Ser Trp Ile Arg Thr Gly Ile Gly Tyr Ala Asp Ser Val
    50                  55                  60

Lys Gly Arg Phe Thr Ile Phe Arg Asp Asn Ala Lys Asn Ser Leu Tyr
65                  70                  75                  80
```

```
Leu Gln Met Asn Ser Leu Arg Ala Glu Asp Thr Ala Leu Tyr Tyr Cys
                 85                  90                  95

Ala Lys Asp Met Lys Gly Ser Gly Thr Tyr Gly Gly Trp Phe Asp Thr
            100                 105                 110

Trp Gly Gln Gly Thr Leu Val Thr Val Ser Ser Ala Ser Thr Lys Gly
        115                 120                 125

Pro Ser Val Phe Pro Leu Ala Pro Cys Ser Arg Ser Thr Ser Glu Ser
    130                 135                 140

Thr Ala Ala Leu Gly Cys Leu Val Lys Asp Tyr Phe Pro Glu Pro Val
145                 150                 155                 160

Thr Val Ser Trp Asn Ser Gly Ala Leu Thr Ser Gly Val His Thr Phe
                165                 170                 175

Pro Ala Val Leu Gln Ser Ser Gly Leu Tyr Ser Leu Ser Ser Val Val
            180                 185                 190

Thr Val Pro Ser Ser Ser Leu Gly Thr Lys Thr Tyr Thr Cys Asn Val
        195                 200                 205

Asp His Lys Pro Ser Asn Thr Lys Val Asp Lys Arg Val Glu Ser Lys
    210                 215                 220

Tyr Gly Pro Pro Cys Pro Pro Cys Pro Ala Pro Pro Val Ala Gly Pro
225                 230                 235                 240

Ser Val Phe Leu Phe Pro Pro Lys Pro Lys Asp Thr Leu Met Ile Ser
                245                 250                 255

Arg Thr Pro Glu Val Thr Cys Val Val Val Asp Val Ser Gln Glu Asp
            260                 265                 270

Pro Glu Val Gln Phe Asn Trp Tyr Val Asp Gly Val Glu Val His Asn
        275                 280                 285

Ala Lys Thr Lys Pro Arg Glu Glu Gln Phe Asn Ser Thr Tyr Arg Val
    290                 295                 300

Val Ser Val Leu Thr Val Leu His Gln Asp Trp Leu Asn Gly Lys Glu
305                 310                 315                 320

Tyr Lys Cys Lys Val Ser Asn Lys Gly Leu Pro Ser Ser Ile Glu Lys
                325                 330                 335

Thr Ile Ser Lys Ala Lys Gly Gln Pro Arg Glu Pro Gln Val Tyr Thr
            340                 345                 350

Leu Pro Pro Ser Gln Glu Glu Met Thr Lys Asn Gln Val Ser Leu Thr
        355                 360                 365

Cys Leu Val Lys Gly Phe Tyr Pro Ser Asp Ile Ala Val Glu Trp Glu
    370                 375                 380

Ser Asn Gly Gln Pro Glu Asn Asn Tyr Lys Thr Thr Pro Pro Val Leu
385                 390                 395                 400

Asp Ser Asp Gly Ser Phe Phe Leu Tyr Ser Arg Leu Thr Val Asp Lys
                405                 410                 415

Ser Arg Trp Gln Glu Gly Asn Val Phe Ser Cys Ser Val Met His Glu
            420                 425                 430

Ala Leu His Asn His Tyr Thr Gln Lys Ser Leu Ser Leu Ser Leu Gly
        435                 440                 445

Lys
```

<210> SEQ ID NO 50
<211> LENGTH: 214
<212> TYPE: PRT
<213> ORGANISM: Homo sapiens
<220> FEATURE:
<221> NAME/KEY: misc_feature
<223> OTHER INFORMATION: 1D05 HC V to A mutated aa sequence

<400> SEQUENCE: 50

```
Asp Ile Gln Met Thr Gln Ser Pro Ser Ser Leu Ser Ala Ser Val Gly
1               5                   10                  15

Asp Arg Val Thr Ile Thr Cys Arg Ala Ser Gln Ser Ile Ser Ser Tyr
            20                  25                  30

Leu Asn Trp Tyr Gln Gln Lys Pro Gly Lys Ala Pro Lys Leu Leu Ile
        35                  40                  45

Tyr Ala Ala Ser Ser Leu Gln Ser Gly Val Pro Ser Arg Phe Ser Gly
50                  55                  60

Ser Gly Ser Gly Thr Asp Phe Thr Leu Thr Ile Ser Ser Leu Gln Pro
65                  70                  75                  80

Glu Asp Phe Ala Thr Tyr Tyr Cys Gln Gln Ser Tyr Ser Thr Pro Ile
            85                  90                  95

Thr Phe Gly Gln Gly Thr Arg Leu Glu Ile Lys Arg Thr Val Ala Ala
            100                 105                 110

Pro Ser Val Phe Ile Phe Pro Pro Ser Asp Glu Gln Leu Lys Ser Gly
        115                 120                 125

Thr Ala Ser Val Val Cys Leu Leu Asn Asn Phe Tyr Pro Arg Glu Ala
130                 135                 140

Lys Val Gln Trp Lys Val Asp Asn Ala Leu Gln Ser Gly Asn Ser Gln
145                 150                 155                 160

Glu Ser Val Thr Glu Gln Asp Ser Lys Asp Ser Thr Tyr Ser Leu Ser
            165                 170                 175

Ser Thr Leu Thr Leu Ser Lys Ala Asp Tyr Glu Lys His Lys Val Tyr
            180                 185                 190

Ala Cys Glu Val Thr His Gln Gly Leu Ser Ser Pro Val Thr Lys Ser
            195                 200                 205

Phe Asn Arg Gly Glu Cys
    210
```

<210> SEQ ID NO 51
<211> LENGTH: 214
<212> TYPE: PRT
<213> ORGANISM: Homo sapiens
<220> FEATURE:
<221> NAME/KEY: misc_feature
<223> OTHER INFORMATION: 1D05 LC L to F mutated aa sequence

<400> SEQUENCE: 51

```
Asp Ile Gln Met Thr Gln Ser Pro Ser Ser Leu Ser Ala Ser Val Gly
1               5                   10                  15

Asp Arg Val Thr Ile Thr Cys Arg Ala Ser Gln Ser Ile Ser Ser Tyr
            20                  25                  30

Leu Asn Trp Tyr Gln Gln Lys Pro Gly Lys Ala Pro Lys Leu Phe Ile
        35                  40                  45

Tyr Val Ala Ser Ser Leu Gln Ser Gly Val Pro Ser Arg Phe Ser Gly
50                  55                  60

Ser Gly Ser Gly Thr Asp Phe Thr Leu Thr Ile Ser Ser Leu Gln Pro
65                  70                  75                  80

Glu Asp Phe Ala Thr Tyr Tyr Cys Gln Gln Ser Tyr Ser Thr Pro Ile
            85                  90                  95

Thr Phe Gly Gln Gly Thr Arg Leu Glu Ile Lys Arg Thr Val Ala Ala
            100                 105                 110

Pro Ser Val Phe Ile Phe Pro Pro Ser Asp Glu Gln Leu Lys Ser Gly
```

-continued

```
                115                 120                 125
Thr Ala Ser Val Val Cys Leu Leu Asn Asn Phe Tyr Pro Arg Glu Ala
    130                 135                 140
Lys Val Gln Trp Lys Val Asp Asn Ala Leu Gln Ser Gly Asn Ser Gln
145                 150                 155                 160
Glu Ser Val Thr Glu Gln Asp Ser Lys Asp Ser Thr Tyr Ser Leu Ser
                165                 170                 175
Ser Thr Leu Thr Leu Ser Lys Ala Asp Tyr Glu Lys His Lys Val Tyr
            180                 185                 190
Ala Cys Glu Val Thr His Gln Gly Leu Ser Ser Pro Val Thr Lys Ser
        195                 200                 205
Phe Asn Arg Gly Glu Cys
    210

<210> SEQ ID NO 52
<211> LENGTH: 8
<212> TYPE: PRT
<213> ORGANISM: Homo sapiens
<220> FEATURE:
<221> NAME/KEY: misc_feature
<223> OTHER INFORMATION: Amino acid sequence of CDRH1 of 411B08 using
      IMGT

<400> SEQUENCE: 52

Gly Phe Thr Phe Ser Ser Tyr Trp
1               5

<210> SEQ ID NO 53
<211> LENGTH: 8
<212> TYPE: PRT
<213> ORGANISM: Homo sapiens
<220> FEATURE:
<221> NAME/KEY: misc_feature
<223> OTHER INFORMATION: Amino acid sequence of CDRH2 of 411B08 using
      IMGT

<400> SEQUENCE: 53

Ile Lys Glu Asp Gly Ser Glu Lys
1               5

<210> SEQ ID NO 54
<211> LENGTH: 12
<212> TYPE: PRT
<213> ORGANISM: Homo sapiens
<220> FEATURE:
<221> NAME/KEY: misc_feature
<223> OTHER INFORMATION: Amino acid sequence of CDRH3 of 411B08 using
      IMGT

<400> SEQUENCE: 54

Ala Arg Asn Arg Leu Tyr Ser Asp Phe Leu Asp Asn
1               5                   10

<210> SEQ ID NO 55
<211> LENGTH: 5
<212> TYPE: PRT
<213> ORGANISM: Homo sapiens
<220> FEATURE:
<221> NAME/KEY: misc_feature
<223> OTHER INFORMATION: Amino acid sequence of CDRH1 of 411B08 using
      Kabat

<400> SEQUENCE: 55

Ser Tyr Trp Met Ser
1               5
```

```
<210> SEQ ID NO 56
<211> LENGTH: 17
<212> TYPE: PRT
<213> ORGANISM: Homo sapiens
<220> FEATURE:
<221> NAME/KEY: misc_feature
<223> OTHER INFORMATION: Amino acid sequence of CDRH2 of 411B08 using
      Kabat

<400> SEQUENCE: 56

Asn Ile Lys Glu Asp Gly Ser Glu Lys Tyr Tyr Val Asp Ser Val Lys
1               5                   10                  15

Gly

<210> SEQ ID NO 57
<211> LENGTH: 10
<212> TYPE: PRT
<213> ORGANISM: Homo sapiens
<220> FEATURE:
<221> NAME/KEY: misc_feature
<223> OTHER INFORMATION: Amino acid sequence of CDRH3 of 411B08 using
      Kabat

<400> SEQUENCE: 57

Asn Arg Leu Tyr Ser Asp Phe Leu Asp Asn
1               5                   10

<210> SEQ ID NO 58
<211> LENGTH: 119
<212> TYPE: PRT
<213> ORGANISM: Homo sapiens
<220> FEATURE:
<221> NAME/KEY: misc_feature
<223> OTHER INFORMATION: Amino acid sequence of VH of 411B08

<400> SEQUENCE: 58

Glu Val Gln Leu Val Glu Ser Gly Gly Gly Leu Val Gln Pro Gly Gly
1               5                   10                  15

Ser Leu Arg Leu Ser Cys Ala Ala Ser Gly Phe Thr Phe Ser Ser Tyr
            20                  25                  30

Trp Met Ser Trp Val Arg Gln Ala Pro Gly Lys Gly Leu Glu Trp Val
        35                  40                  45

Ala Asn Ile Lys Glu Asp Gly Ser Glu Lys Tyr Tyr Val Asp Ser Val
    50                  55                  60

Lys Gly Arg Phe Thr Ile Ser Arg Asp Asn Ala Lys Asn Ser Leu Tyr
65                  70                  75                  80

Leu Gln Met Asn Ser Leu Arg Ala Glu Asp Thr Ser Val Tyr Tyr Cys
                85                  90                  95

Ala Arg Asn Arg Leu Tyr Ser Asp Phe Leu Asp Asn Trp Gly Gln Gly
            100                 105                 110

Thr Leu Val Thr Val Ser Ser
        115

<210> SEQ ID NO 59
<211> LENGTH: 358
<212> TYPE: DNA
<213> ORGANISM: Homo sapiens
<220> FEATURE:
<221> NAME/KEY: misc_feature
<223> OTHER INFORMATION: Nucleic acid sequence of VH of 411B08

<400> SEQUENCE: 59
```

-continued

```
gaggtgcagc tggtggagtc tggggggaggc ttggtccagc ctggggggtc cctgagactc      60
tcctgtgcag cctctggatt cacgtttagt agctattgga tgagttgggt ccgccaggct     120
ccagggaagg ggctggagtg ggtggccaac atcaaagaag atggaagtga aaatactat     180 gtcgactctg tgaagggccg attcaccatc tccagagaca acgccaagaa ctcactgtat     240
ctgcaaatga acagcctgag agccgaggac acgtctgtgt attactgtgc gagaaatcga     300
ctctacagtg acttccttga caactggggc cagggaaccc tggtcaccgt ctcctcag      358
```

<210> SEQ ID NO 60
<211> LENGTH: 449
<212> TYPE: PRT
<213> ORGANISM: Homo sapiens
<220> FEATURE:
<221> NAME/KEY: misc_feature
<223> OTHER INFORMATION: Amino acid sequence of 411B08 heavy chain

<400> SEQUENCE: 60

```
Glu Val Gln Leu Val Glu Ser Gly Gly Gly Leu Val Gln Pro Gly Gly
1               5                   10                  15

Ser Leu Arg Leu Ser Cys Ala Ala Ser Gly Phe Thr Phe Ser Ser Tyr
            20                  25                  30

Trp Met Ser Trp Val Arg Gln Ala Pro Gly Lys Gly Leu Glu Trp Val
        35                  40                  45

Ala Asn Ile Lys Glu Asp Gly Ser Glu Lys Tyr Tyr Val Asp Ser Val
    50                  55                  60

Lys Gly Arg Phe Thr Ile Ser Arg Asp Asn Ala Lys Asn Ser Leu Tyr
65                  70                  75                  80

Leu Gln Met Asn Ser Leu Arg Ala Glu Asp Thr Ser Val Tyr Tyr Cys
                85                  90                  95

Ala Arg Asn Arg Leu Tyr Ser Asp Phe Leu Asp Asn Trp Gly Gln Gly
            100                 105                 110

Thr Leu Val Thr Val Ser Ser Ala Ser Thr Lys Gly Pro Ser Val Phe
        115                 120                 125

Pro Leu Ala Pro Ser Ser Lys Ser Thr Ser Gly Gly Thr Ala Ala Leu
    130                 135                 140

Gly Cys Leu Val Lys Asp Tyr Phe Pro Glu Pro Val Thr Val Ser Trp
145                 150                 155                 160

Asn Ser Gly Ala Leu Thr Ser Gly Val His Thr Phe Pro Ala Val Leu
                165                 170                 175

Gln Ser Ser Gly Leu Tyr Ser Leu Ser Ser Val Val Thr Val Pro Ser
            180                 185                 190

Ser Ser Leu Gly Thr Gln Thr Tyr Ile Cys Asn Val Asn His Lys Pro
        195                 200                 205

Ser Asn Thr Lys Val Asp Lys Lys Val Glu Pro Lys Ser Cys Asp Lys
    210                 215                 220

Thr His Thr Cys Pro Pro Cys Pro Ala Pro Glu Leu Leu Gly Gly Pro
225                 230                 235                 240

Ser Val Phe Leu Phe Pro Pro Lys Pro Lys Asp Thr Leu Met Ile Ser
                245                 250                 255

Arg Thr Pro Glu Val Thr Cys Val Val Val Asp Val Ser His Glu Asp
            260                 265                 270

Pro Glu Val Lys Phe Asn Trp Tyr Val Asp Gly Val Glu Val His Asn
        275                 280                 285

Ala Lys Thr Lys Pro Arg Glu Glu Gln Tyr Asn Ser Thr Tyr Arg Val
    290                 295                 300
```

```
Val Ser Val Leu Thr Val Leu His Gln Asp Trp Leu Asn Gly Lys Glu
305                 310                 315                 320

Tyr Lys Cys Lys Val Ser Asn Lys Ala Leu Pro Ala Pro Ile Glu Lys
                325                 330                 335

Thr Ile Ser Lys Ala Lys Gly Gln Pro Arg Glu Pro Gln Val Tyr Thr
            340                 345                 350

Leu Pro Pro Ser Arg Asp Glu Leu Thr Lys Asn Gln Val Ser Leu Thr
        355                 360                 365

Cys Leu Val Lys Gly Phe Tyr Pro Ser Asp Ile Ala Val Glu Trp Glu
370                 375                 380

Ser Asn Gly Gln Pro Glu Asn Asn Tyr Lys Thr Thr Pro Pro Val Leu
385                 390                 395                 400

Asp Ser Asp Gly Ser Phe Phe Leu Tyr Ser Lys Leu Thr Val Asp Lys
                405                 410                 415

Ser Arg Trp Gln Gln Gly Asn Val Phe Ser Cys Ser Val Met His Glu
            420                 425                 430

Ala Leu His Asn His Tyr Thr Gln Lys Ser Leu Ser Leu Ser Pro Gly
        435                 440                 445

Lys

<210> SEQ ID NO 61
<211> LENGTH: 1347
<212> TYPE: DNA
<213> ORGANISM: Homo sapiens
<220> FEATURE:
<221> NAME/KEY: misc_feature
<223> OTHER INFORMATION: Nucleic acid sequence of 411B08 heavy chain

<400> SEQUENCE: 61
gaggtgcagc tggtggagtc tgggggaggc ttggtccagc ctggggggtc cctgagactc      60
tcctgtgcag cctctggatt cacgtttagt agctattgga tgagttgggt ccgccaggct     120
ccagggaagg ggctggagtg ggtggccaac atcaaagaag atggaagtga aaatactat     180
gtcgactctg tgaagggccg attcaccatc tccagagaca acgccaagaa ctcactgtat     240
ctgcaaatga acagcctgag agccgaggac acgtctgtgt attactgtgc gagaaatcga     300
ctctacagtg acttccttga caactggggc cagggaaccc tggtcaccgt ctcctcagcc     360
agcaccaagg gcccctctgt gttccctctg gccccttcca gcaagtccac ctctggcgga     420
acagccgctc tgggctgcct cgtgaaggac tacttccccg agcctgtgac cgtgtcctgg     480
aactctggcg ctctgaccag cggagtgcac accttccctg ctgtgctgca gtcctccggc     540
ctgtactccc tgtcctccgt cgtgaccgtg ccttccagct ctctgggcac ccagacctac     600
atctgcaacg tgaaccacaa gcctccaac accaaggtgg acaagaaggt ggaacccaag     660
tcctgcgaca gacccacac ctgtcccct tgtcctgccc tgaactgct gggcggacct      720
tccgtgttcc tgttcccccc aaagcccaag gacaccctga tgatctcccg gacccccgaa     780
gtgacctgcg tggtggtgga tgtgtcccac gaggaccctg aagtgaagtt caattggtac     840
gtggacggcg tggaagtgca caacgccaag accaagccta gagaggaaca gtacaactcc     900
acctaccggg tggtgtccgt gctgaccgtg ctgcaccagg attggctgaa cggcaaagag     960
tacaagtgca aggtgtccaa caaggccctg cctgccccca tcgaaaagac catctccaag    1020
gccaagggcc agccccggga acccagggtg tacacactgc ccctagcag ggacgagctg    1080
accaagaacc aggtgtccct gacctgtctc gtgaaaggct ctacccctc cgatatcgcc    1140
```

-continued

```
gtggaatggg agtccaacgg ccagcctgag aacaactaca agaccacccc ccctgtgctg    1200
gactccgacg gctcattctt cctgtacagc aagctgacag tggacaagtc ccggtggcag    1260
cagggcaacg tgttctcctg ctccgtgatg cacgaggccc tgcacaacca ctacacccag    1320
aagtccctgt ccctgagccc cggcaag                                        1347
```

```
<210> SEQ ID NO 62
<211> LENGTH: 6
<212> TYPE: PRT
<213> ORGANISM: Homo sapiens
<220> FEATURE:
<221> NAME/KEY: misc_feature
<223> OTHER INFORMATION: Amino acid sequence of CDRL1 of 411B08 using
      IMGT

<400> SEQUENCE: 62

Gln Gly Val Ser Ser Trp
1               5

<210> SEQ ID NO 63
<211> LENGTH: 3
<212> TYPE: PRT
<213> ORGANISM: Homo sapiens
<220> FEATURE:
<221> NAME/KEY: misc_feature
<223> OTHER INFORMATION: Amino acid sequence of CDRL2 of 411B08 using
      IMGT

<400> SEQUENCE: 63

Gly Ala Ser
1

<210> SEQ ID NO 64
<211> LENGTH: 9
<212> TYPE: PRT
<213> ORGANISM: Homo sapiens
<220> FEATURE:
<221> NAME/KEY: misc_feature
<223> OTHER INFORMATION: Amino acid sequence of CDRL3 of 411B08 using
      IMGT

<400> SEQUENCE: 64

Gln Gln Ala Asn Ser Ile Pro Phe Thr
1               5

<210> SEQ ID NO 65
<211> LENGTH: 11
<212> TYPE: PRT
<213> ORGANISM: Homo sapiens
<220> FEATURE:
<221> NAME/KEY: misc_feature
<223> OTHER INFORMATION: Amino acid sequence of CDRL1 of 411B08 using
      Kabat

<400> SEQUENCE: 65

Arg Ala Ser Gln Gly Val Ser Ser Trp Leu Ala
1               5                   10

<210> SEQ ID NO 66
<211> LENGTH: 7
<212> TYPE: PRT
<213> ORGANISM: Homo sapiens
<220> FEATURE:
<221> NAME/KEY: misc_feature
<223> OTHER INFORMATION: Amino acid sequence of CDRL2 of 411B08 using
      Kabat

<400> SEQUENCE: 66
```

```
<210> SEQ ID NO 67
<211> LENGTH: 9
<212> TYPE: PRT
<213> ORGANISM: Homo sapiens
<220> FEATURE:
<221> NAME/KEY: misc_feature
<223> OTHER INFORMATION: Amino acid sequence of CDRL3 of 411B08 using
      Kabat

<400> SEQUENCE: 67

Gln Gln Ala Asn Ser Ile Pro Phe Thr
1               5

<210> SEQ ID NO 68
<211> LENGTH: 107
<212> TYPE: PRT
<213> ORGANISM: Homo sapiens
<220> FEATURE:
<221> NAME/KEY: misc_feature
<223> OTHER INFORMATION: Amino acid sequence of VL of 411B08

<400> SEQUENCE: 68

Asp Ile Gln Met Thr Gln Ser Pro Ser Ser Val Ser Ala Ser Val Gly
1               5                   10                  15

Asp Arg Val Thr Ile Thr Cys Arg Ala Ser Gln Gly Val Ser Ser Trp
            20                  25                  30

Leu Ala Trp Tyr Gln Gln Lys Ser Gly Lys Ala Pro Lys Leu Leu Ile
        35                  40                  45

Tyr Gly Ala Ser Ser Leu Gln Ser Gly Val Pro Ser Arg Phe Ser Gly
    50                  55                  60

Ser Gly Ser Gly Thr Glu Phe Ile Leu Thr Ile Ser Ser Leu Gln Pro
65                  70                  75                  80

Glu Asp Phe Ala Thr Tyr Tyr Cys Gln Gln Ala Asn Ser Ile Pro Phe
                85                  90                  95

Thr Phe Gly Pro Gly Thr Lys Val Asp Ile Lys
            100                 105

<210> SEQ ID NO 69
<211> LENGTH: 322
<212> TYPE: DNA
<213> ORGANISM: Homo sapiens
<220> FEATURE:
<221> NAME/KEY: misc_feature
<223> OTHER INFORMATION: Nucleic acid sequence of VL of 411B08

<400> SEQUENCE: 69
gacatccaga tgacccagtc tccatcttcc gtgtctgcat ctgtcggaga cagagtcacc     60
atcacttgtc gggcgagtca gggtgttagc agctggttag cctggtatca gcagaaatca    120
gggaaagccc ctaagctcct gatctatggt gcatccagtt tgcaaagtgg ggtcccatca    180
agattcagcg gcagtggatc tgggacagag ttcattctca ccatcagcag cctgcagcct    240
gaagattttg caacttacta ttgtcaacag gctaacagta tcccattcac tttcggccct    300
gggaccaaag tggatatcaa ac                                              322

<210> SEQ ID NO 70
<211> LENGTH: 214
<212> TYPE: PRT
<213> ORGANISM: Homo sapiens
```

<220> FEATURE:
<221> NAME/KEY: misc_feature
<223> OTHER INFORMATION: Amino acid sequence of 411B08 light chain

<400> SEQUENCE: 70

| | | | | | | | | | | | | | | | |
|---|---|---|---|---|---|---|---|---|---|---|---|---|---|---|---|
| Asp | Ile | Gln | Met | Thr | Gln | Ser | Pro | Ser | Ser | Val | Ser | Ala | Ser | Val | Gly |
| 1 | | | | 5 | | | | | 10 | | | | | 15 | |
| Asp | Arg | Val | Thr | Ile | Thr | Cys | Arg | Ala | Ser | Gln | Gly | Val | Ser | Ser | Trp |
| | | | 20 | | | | | 25 | | | | | 30 | | |
| Leu | Ala | Trp | Tyr | Gln | Gln | Lys | Ser | Gly | Lys | Ala | Pro | Lys | Leu | Leu | Ile |
| | | | 35 | | | | | 40 | | | | | 45 | | |
| Tyr | Gly | Ala | Ser | Ser | Leu | Gln | Ser | Gly | Val | Pro | Ser | Arg | Phe | Ser | Gly |
| | | 50 | | | | | 55 | | | | | 60 | | | |
| Ser | Gly | Ser | Gly | Thr | Glu | Phe | Ile | Leu | Thr | Ile | Ser | Ser | Leu | Gln | Pro |
| 65 | | | | | 70 | | | | | 75 | | | | | 80 |
| Glu | Asp | Phe | Ala | Thr | Tyr | Tyr | Cys | Gln | Gln | Ala | Asn | Ser | Ile | Pro | Phe |
| | | | | 85 | | | | | 90 | | | | | 95 | |
| Thr | Phe | Gly | Pro | Gly | Thr | Lys | Val | Asp | Ile | Lys | Arg | Thr | Val | Ala | Ala |
| | | | 100 | | | | | 105 | | | | | 110 | | |
| Pro | Ser | Val | Phe | Ile | Phe | Pro | Pro | Ser | Asp | Glu | Gln | Leu | Lys | Ser | Gly |
| | | | 115 | | | | | 120 | | | | | 125 | | |
| Thr | Ala | Ser | Val | Val | Cys | Leu | Leu | Asn | Asn | Phe | Tyr | Pro | Arg | Glu | Ala |
| | | 130 | | | | | 135 | | | | | 140 | | | |
| Lys | Val | Gln | Trp | Lys | Val | Asp | Asn | Ala | Leu | Gln | Ser | Gly | Asn | Ser | Gln |
| 145 | | | | | 150 | | | | | 155 | | | | | 160 |
| Glu | Ser | Val | Thr | Glu | Gln | Asp | Ser | Lys | Asp | Ser | Thr | Tyr | Ser | Leu | Ser |
| | | | | 165 | | | | | 170 | | | | | 175 | |
| Ser | Thr | Leu | Thr | Leu | Ser | Lys | Ala | Asp | Tyr | Glu | Lys | His | Lys | Val | Tyr |
| | | | 180 | | | | | 185 | | | | | 190 | | |
| Ala | Cys | Glu | Val | Thr | His | Gln | Gly | Leu | Ser | Ser | Pro | Val | Thr | Lys | Ser |
| | | | 195 | | | | | 200 | | | | | 205 | | |
| Phe | Asn | Arg | Gly | Glu | Cys | | | | | | | | | | |
| | | | 210 | | | | | | | | | | | | |

<210> SEQ ID NO 71
<211> LENGTH: 642
<212> TYPE: DNA
<213> ORGANISM: Homo sapiens
<220> FEATURE:
<221> NAME/KEY: misc_feature
<223> OTHER INFORMATION: Nucleic acid sequence of 411B08 light chain

<400> SEQUENCE: 71

```
gacatccaga tgacccagtc tccatcttcc gtgtctgcat ctgtcggaga cagagtcacc      60
atcacttgtc gggcgagtca gggtgttagc agctggttag cctggtatca gcagaaatca     120
gggaaagccc ctaagctcct gatctatggt gcatccagtt tgcaaagtgg ggtcccatca     180
agattcagcg gcagtggatc tgggacagag ttcattctca ccatcagcag cctgcagcct     240
gaagattttg caacttacta ttgtcaacag gctaacagta tcccattcac tttcggccct     300
gggaccaaag tggatatcaa acgtacggtg gccgctccct ccgtgttcat cttcccacct     360
tccgacgagc agctgaagtc cggcaccgct tctgtcgtgt gcctgctgaa caacttctac     420
ccccgcgagg ccaaggtgca gtggaaggtg gacaacgccc tgcagtccgg caactcccag     480
gaatccgtga ccgagcagga ctccaaggac agcacctact ccctgtcctc caccctgacc     540
ctgtccaagg ccgactacga aaagcacaag gtgtacgcct gcgaagtgac ccaccagggc     600
```
ctgtctagcc ccgtgaccaa gtctttcaac cggggcgagt gt          642

<210> SEQ ID NO 72
<211> LENGTH: 8
<212> TYPE: PRT
<213> ORGANISM: Homo sapiens
<220> FEATURE:
<221> NAME/KEY: misc_feature
<223> OTHER INFORMATION: Amino acid sequence of CDRH1 of 411C04 using
      IMGT

<400> SEQUENCE: 72

Gly Phe Thr Phe Ser Ser Tyr Trp
1               5

<210> SEQ ID NO 73
<211> LENGTH: 8
<212> TYPE: PRT
<213> ORGANISM: Homo sapiens
<220> FEATURE:
<221> NAME/KEY: misc_feature
<223> OTHER INFORMATION: Amino acid sequence of CDRH2 of 411C04 using
      IMGT

<400> SEQUENCE: 73

Ile Lys Glu Asp Gly Ser Glu Lys
1               5

<210> SEQ ID NO 74
<211> LENGTH: 12
<212> TYPE: PRT
<213> ORGANISM: Homo sapiens
<220> FEATURE:
<221> NAME/KEY: misc_feature
<223> OTHER INFORMATION: Amino acid sequence of CDRH3 of 411C04 using
      IMGT

<400> SEQUENCE: 74

Ala Arg Val Arg Leu Tyr Ser Asp Phe Leu Asp Tyr
1               5                   10

<210> SEQ ID NO 75
<211> LENGTH: 5
<212> TYPE: PRT
<213> ORGANISM: Homo sapiens
<220> FEATURE:
<221> NAME/KEY: misc_feature
<223> OTHER INFORMATION: Amino acid sequence of CDRH1 of 411C04 using
      Kabat

<400> SEQUENCE: 75

Ser Tyr Trp Met Ser
1               5

<210> SEQ ID NO 76
<211> LENGTH: 17
<212> TYPE: PRT
<213> ORGANISM: Homo sapiens
<220> FEATURE:
<221> NAME/KEY: misc_feature
<223> OTHER INFORMATION: Amino acid sequence of CDRH2 of 411C04 using
      Kabat

<400> SEQUENCE: 76

Asn Ile Lys Glu Asp Gly Ser Glu Lys Tyr Tyr Val Asp Ser Leu Lys
1               5                   10                  15

Gly

<210> SEQ ID NO 77
<211> LENGTH: 10
<212> TYPE: PRT
<213> ORGANISM: Homo sapiens
<220> FEATURE:
<221> NAME/KEY: misc_feature
<223> OTHER INFORMATION: Amino acid sequence of CDRH3 of 411C04 using
      Kabat

<400> SEQUENCE: 77

Val Arg Leu Tyr Ser Asp Phe Leu Asp Tyr
1               5                   10

<210> SEQ ID NO 78
<211> LENGTH: 119
<212> TYPE: PRT
<213> ORGANISM: Homo sapiens
<220> FEATURE:
<221> NAME/KEY: misc_feature
<223> OTHER INFORMATION: Amino acid sequence of VH of 411C04

<400> SEQUENCE: 78

Glu Val Gln Leu Val Asp Ser Gly Gly Gly Leu Val Gln Pro Gly Gly
1               5                   10                  15

Ser Leu Arg Leu Ser Cys Ala Ala Ser Gly Phe Thr Phe Ser Ser Tyr
            20                  25                  30

Trp Met Ser Trp Val Arg Gln Ala Pro Gly Lys Gly Leu Glu Trp Val
        35                  40                  45

Ala Asn Ile Lys Glu Asp Gly Ser Glu Lys Tyr Tyr Val Asp Ser Leu
    50                  55                  60

Lys Gly Arg Phe Thr Ile Ser Arg Asp Asn Ala Lys Asn Ser Leu Tyr
65                  70                  75                  80

Leu Gln Met Asn Ser Leu Arg Ala Glu Asp Thr Ser Val Tyr Tyr Cys
                85                  90                  95

Ala Arg Val Arg Leu Tyr Ser Asp Phe Leu Asp Tyr Trp Gly Gln Gly
            100                 105                 110

Thr Leu Val Thr Val Ser Ser
        115

<210> SEQ ID NO 79
<211> LENGTH: 358
<212> TYPE: DNA
<213> ORGANISM: Homo sapiens
<220> FEATURE:
<221> NAME/KEY: misc_feature
<223> OTHER INFORMATION: Nucleic acid sequence of VH of 411C04

<400> SEQUENCE: 79
gaggtgcagc tggtggactc tggggggaggc ttggtccagc ctggggggtc cctgagactc      60
tcctgtgcag cctctggatt cacgtttagt agctattgga tgagttgggt ccgccaggct     120
ccaggaaagg ggctggagtg ggtggccaac ataaagaag atggaagtga aaaatactat      180
gtagactctt tgaagggccg attcaccatc tccagagaca cgccaagaa ctcactgtat      240 ctgcaaatga acagcctgag agccgaggac acgtctgtgt attactgtgc gagagttcga     300
ctctacagtg acttccttga ctactggggc cagggaaccc tggtcaccgt ctcctcag       358

<210> SEQ ID NO 80
<211> LENGTH: 449
<212> TYPE: PRT
<213> ORGANISM: Homo sapiens
<220> FEATURE:

<221> NAME/KEY: misc_feature
<223> OTHER INFORMATION: Amino acid sequence of 411C04 heavy chain

<400> SEQUENCE: 80

```
Glu Val Gln Leu Val Asp Ser Gly Gly Gly Leu Val Gln Pro Gly Gly
1               5                   10                  15

Ser Leu Arg Leu Ser Cys Ala Ala Ser Gly Phe Thr Phe Ser Ser Tyr
            20                  25                  30

Trp Met Ser Trp Val Arg Gln Ala Pro Gly Lys Gly Leu Glu Trp Val
        35                  40                  45

Ala Asn Ile Lys Glu Asp Gly Ser Glu Lys Tyr Tyr Val Asp Ser Leu
    50                  55                  60

Lys Gly Arg Phe Thr Ile Ser Arg Asp Asn Ala Lys Asn Ser Leu Tyr
65                  70                  75                  80

Leu Gln Met Asn Ser Leu Arg Ala Glu Asp Thr Ser Val Tyr Tyr Cys
                85                  90                  95

Ala Arg Val Arg Leu Tyr Ser Asp Phe Leu Asp Tyr Trp Gly Gln Gly
            100                 105                 110

Thr Leu Val Thr Val Ser Ser Ala Ser Thr Lys Gly Pro Ser Val Phe
        115                 120                 125

Pro Leu Ala Pro Ser Ser Lys Ser Thr Ser Gly Gly Thr Ala Ala Leu
    130                 135                 140

Gly Cys Leu Val Lys Asp Tyr Phe Pro Glu Pro Val Thr Val Ser Trp
145                 150                 155                 160

Asn Ser Gly Ala Leu Thr Ser Gly Val His Thr Phe Pro Ala Val Leu
                165                 170                 175

Gln Ser Ser Gly Leu Tyr Ser Leu Ser Ser Val Val Thr Val Pro Ser
            180                 185                 190

Ser Ser Leu Gly Thr Gln Thr Tyr Ile Cys Asn Val Asn His Lys Pro
        195                 200                 205

Ser Asn Thr Lys Val Asp Lys Lys Val Glu Pro Lys Ser Cys Asp Lys
    210                 215                 220

Thr His Thr Cys Pro Pro Cys Pro Ala Pro Glu Leu Leu Gly Gly Pro
225                 230                 235                 240

Ser Val Phe Leu Phe Pro Pro Lys Pro Lys Asp Thr Leu Met Ile Ser
                245                 250                 255

Arg Thr Pro Glu Val Thr Cys Val Val Val Asp Val Ser His Glu Asp
            260                 265                 270

Pro Glu Val Lys Phe Asn Trp Tyr Val Asp Gly Val Glu Val His Asn
        275                 280                 285

Ala Lys Thr Lys Pro Arg Glu Glu Gln Tyr Asn Ser Thr Tyr Arg Val
    290                 295                 300

Val Ser Val Leu Thr Val Leu His Gln Asp Trp Leu Asn Gly Lys Glu
305                 310                 315                 320

Tyr Lys Cys Lys Val Ser Asn Lys Ala Leu Pro Ala Pro Ile Glu Lys
                325                 330                 335

Thr Ile Ser Lys Ala Lys Gly Gln Pro Arg Glu Pro Gln Val Tyr Thr
            340                 345                 350

Leu Pro Pro Ser Arg Asp Glu Leu Thr Lys Asn Gln Val Ser Leu Thr
        355                 360                 365

Cys Leu Val Lys Gly Phe Tyr Pro Ser Asp Ile Ala Val Glu Trp Glu
    370                 375                 380

Ser Asn Gly Gln Pro Glu Asn Asn Tyr Lys Thr Thr Pro Pro Val Leu
385                 390                 395                 400
```

Asp Ser Asp Gly Ser Phe Phe Leu Tyr Ser Lys Leu Thr Val Asp Lys
                405                 410                 415

Ser Arg Trp Gln Gln Gly Asn Val Phe Ser Cys Ser Val Met His Glu
        420                 425                 430

Ala Leu His Asn His Tyr Thr Gln Lys Ser Leu Ser Leu Ser Pro Gly
            435                 440                 445

Lys

<210> SEQ ID NO 81
<211> LENGTH: 1347
<212> TYPE: DNA
<213> ORGANISM: Homo sapiens
<220> FEATURE:
<221> NAME/KEY: misc_feature
<223> OTHER INFORMATION: Nucleic acid sequence of 411C04 heavy chain

<400> SEQUENCE: 81

```
gaggtgcagc tggtggactc tgggggaggc ttggtccagc ctgggggtc cctgagactc       60 tcctgtgcag cctctggatt cacgtttagt agctattgga tgagttgggt ccgccaggct      120
ccaggaaagg ggctggagtg ggtggccaac ataaaagaag atggaagtga aaatactat       180 gtagactctt tgaagggccg attcaccatc tccagagaca cgccaagaa ctcactgtat       240 ctgcaaatga acagcctgag agccgaggac acgtctgtgt attactgtgc gagagttcga      300
ctctacagtg acttccttga ctactgggc cagggaaccc tggtcaccgt ctcctcagcc       360
agcaccaagg gcccctctgt gttccctctg gccccttcca gcaagtccac ctctggcgga      420
acagccgctc tgggctgcct cgtgaaggac tacttccccg agcctgtgac cgtgtcctgg      480
aactctggcg ctctgaccag cggagtgcac accttcctg ctgtgctgca gtcctccggc      540
ctgtactccc tgtcctccgt cgtgaccgtg ccttccagct ctctgggcac ccagacctac      600
atctgcaacg tgaaccacaa gcctccaac accaaggtgg acaagaaggt ggaacccaag      660
tcctgcgaca gacccacac ctgtccccct tgtcctgccc ctgaactgct gggcggacct      720
tccgtgttcc tgttcccccc aaagcccaag gacaccctga tgatctcccg gacccccgaa      780
gtgacctgcg tggtggtgga tgtgtcccac gaggaccctg aagtgaagtt caattggtac      840
gtggacggcg tggaagtgca caacgccaag accaagccta gagaggaaca gtacaactcc      900
acctaccggg tggtgtccgt gctgaccgtg ctgcaccagg attggctgaa cggcaaagag      960
tacaagtgca aggtgtccaa caaggccctg cctgcccca tcgaaaagac catctccaag     1020
gccaagggcc agccccggga accccaggtg tacacactgc cccctagcag ggacgagctg     1080
accaagaacc aggtgtccct gacctgtctc gtgaaaggct tctacccctc cgatatcgcc     1140
gtggaatggg agtccaacgg ccagcctgag aacaactaca agaccacccc cctgtgctg      1200 gactccgacg gctcattctt cctgtacagc aagctgacag tggacaagtc ccggtggcag     1260
cagggcaacg tgttctcctg ctccgtgatg cacgaggccc tgcacaacca ctacacccag     1320
aagtccctgt ccctgagccc cggcaag                                         1347
```

<210> SEQ ID NO 82
<211> LENGTH: 6
<212> TYPE: PRT
<213> ORGANISM: Homo sapiens
<220> FEATURE:
<221> NAME/KEY: misc_feature
<223> OTHER INFORMATION: Amino acid sequence of CDRL1 of 411C04 using
      IMGT

<400> SEQUENCE: 82

Gln Gly Val Ser Ser Trp
1               5

<210> SEQ ID NO 83
<211> LENGTH: 3
<212> TYPE: PRT
<213> ORGANISM: Homo sapiens
<220> FEATURE:
<221> NAME/KEY: misc_feature
<223> OTHER INFORMATION: Amino acid sequence of CDRL2 of 411C04 using
      IMGT

<400> SEQUENCE: 83

Gly Ala Ser
1

<210> SEQ ID NO 84
<211> LENGTH: 9
<212> TYPE: PRT
<213> ORGANISM: Homo sapiens
<220> FEATURE:
<221> NAME/KEY: misc_feature
<223> OTHER INFORMATION: Amino acid sequence of CDRL3 of 411C04 using
      IMGT

<400> SEQUENCE: 84

Gln Gln Ala Asn Ser Ile Pro Phe Thr
1               5

<210> SEQ ID NO 85
<211> LENGTH: 11
<212> TYPE: PRT
<213> ORGANISM: Homo sapiens
<220> FEATURE:
<221> NAME/KEY: misc_feature
<223> OTHER INFORMATION: Amino acid sequence of CDRL1 of 411C04 using
      Kabat

<400> SEQUENCE: 85

Arg Ala Ser Gln Gly Val Ser Ser Trp Leu Ala
1               5                   10

<210> SEQ ID NO 86
<211> LENGTH: 7
<212> TYPE: PRT
<213> ORGANISM: Homo sapiens
<220> FEATURE:
<221> NAME/KEY: misc_feature
<223> OTHER INFORMATION: Amino acid sequence of CDRL2 of 411C04 using
      Kabat

<400> SEQUENCE: 86

Gly Ala Ser Ser Leu Gln Ser
1               5

<210> SEQ ID NO 87
<211> LENGTH: 9
<212> TYPE: PRT
<213> ORGANISM: Homo sapiens
<220> FEATURE:
<221> NAME/KEY: misc_feature
<223> OTHER INFORMATION: Amino acid sequence of CDRL3 of 411C04 using
      Kabat

<400> SEQUENCE: 87

Gln Gln Ala Asn Ser Ile Pro Phe Thr
1               5

<210> SEQ ID NO 88
<211> LENGTH: 107
<212> TYPE: PRT
<213> ORGANISM: Homo sapiens
<220> FEATURE:
<221> NAME/KEY: misc_feature
<223> OTHER INFORMATION: Amino acid sequence of VL of 411C04

<400> SEQUENCE: 88

```
Asp Ile Gln Met Thr Gln Ser Pro Ser Ser Val Ser Ala Ser Val Gly
1               5                   10                  15

Asp Arg Val Thr Ile Thr Cys Arg Ala Ser Gln Gly Val Ser Ser Trp
            20                  25                  30

Leu Ala Trp Tyr Gln Gln Lys Ser Gly Lys Ala Pro Lys Leu Leu Ile
        35                  40                  45

Tyr Gly Ala Ser Ser Leu Gln Ser Gly Val Pro Ser Arg Phe Ser Gly
    50                  55                  60

Ser Gly Ser Gly Thr Glu Phe Ile Leu Ser Ile Ser Leu Gln Pro
65              70                  75                  80

Glu Asp Phe Ala Thr Tyr Tyr Cys Gln Gln Ala Asn Ser Ile Pro Phe
                85                  90                  95

Thr Phe Gly Pro Gly Thr Lys Val Asp Ile Lys
            100                 105
```

<210> SEQ ID NO 89
<211> LENGTH: 322
<212> TYPE: DNA
<213> ORGANISM: Homo sapiens
<220> FEATURE:
<221> NAME/KEY: misc_feature
<223> OTHER INFORMATION: Nucleic acid sequence of VL of 411C04

<400> SEQUENCE: 89

```
gacatccaga tgacccagtc tccatcttcc gtgtctgcat ctgtcggaga cagagtcacc      60
atcacttgtc gggcgagtca gggtgttagc agttggttag cctggtatca gcagaaatca     120
gggaaagccc ctaagctcct gatctatggt gcctccagtt tgcaaagtgg ggtcccatca     180
agattcagcg gcagtggatc tgggacagag ttcattctca gcatcagcag cctgcagcct     240
gaagattttg caacttacta ttgtcaacag gctaacagta tcccattcac tttcggccct     300
gggaccaaag tggatatcaa ac                                              322
```

<210> SEQ ID NO 90
<211> LENGTH: 214
<212> TYPE: PRT
<213> ORGANISM: Homo sapiens
<220> FEATURE:
<221> NAME/KEY: misc_feature
<223> OTHER INFORMATION: Amino acid sequence of 411C04 light chain

<400> SEQUENCE: 90

```
Asp Ile Gln Met Thr Gln Ser Pro Ser Ser Val Ser Ala Ser Val Gly
1               5                   10                  15

Asp Arg Val Thr Ile Thr Cys Arg Ala Ser Gln Gly Val Ser Ser Trp
            20                  25                  30

Leu Ala Trp Tyr Gln Gln Lys Ser Gly Lys Ala Pro Lys Leu Leu Ile
        35                  40                  45

Tyr Gly Ala Ser Ser Leu Gln Ser Gly Val Pro Ser Arg Phe Ser Gly
    50                  55                  60
```

```
Ser Gly Ser Gly Thr Glu Phe Ile Leu Ser Ile Ser Leu Gln Pro
 65                  70                  75                  80

Glu Asp Phe Ala Thr Tyr Tyr Cys Gln Gln Ala Asn Ser Ile Pro Phe
                 85                  90                  95

Thr Phe Gly Pro Gly Thr Lys Val Asp Ile Lys Arg Thr Val Ala Ala
            100                 105                 110

Pro Ser Val Phe Ile Phe Pro Pro Ser Asp Glu Gln Leu Lys Ser Gly
        115                 120                 125

Thr Ala Ser Val Val Cys Leu Leu Asn Asn Phe Tyr Pro Arg Glu Ala
130                 135                 140

Lys Val Gln Trp Lys Val Asp Asn Ala Leu Gln Ser Gly Asn Ser Gln
145                 150                 155                 160

Glu Ser Val Thr Glu Gln Asp Ser Lys Asp Ser Thr Tyr Ser Leu Ser
                165                 170                 175

Ser Thr Leu Thr Leu Ser Lys Ala Asp Tyr Glu Lys His Lys Val Tyr
            180                 185                 190

Ala Cys Glu Val Thr His Gln Gly Leu Ser Ser Pro Val Thr Lys Ser
        195                 200                 205

Phe Asn Arg Gly Glu Cys
    210
```

<210> SEQ ID NO 91
<211> LENGTH: 642
<212> TYPE: DNA
<213> ORGANISM: Homo sapiens
<220> FEATURE:
<221> NAME/KEY: misc_feature
<223> OTHER INFORMATION: Nucleic acid sequence of 411C04 light chain

<400> SEQUENCE: 91

```
gacatccaga tgacccagtc tccatcttcc gtgtctgcat ctgtcggaga cagagtcacc    60
atcacttgtc gggcgagtca gggtgttagc agttggttag cctggtatca gcagaaatca   120
gggaaagccc ctaagctcct gatctatggt gcctccagtt tgcaaagtgg ggtcccatca   180
agattcagcg gcagtggatc tgggacagag ttcattctca gcatcagcag cctgcagcct   240
gaagattttg caacttacta ttgtcaacag gctaacagta tcccattcac tttcggccct   300
gggaccaaag tggatatcaa acgtacggtg gccgctccct ccgtgttcat cttcccacct   360
tccgacgagc agctgaagtc cggcaccgct tctgtcgtgt gcctgctgaa caacttctac   420
ccccgcgagg ccaaggtgca gtggaaggtg gacaacgccc tgcagtccgg caactcccag   480
gaatccgtga ccgagcagga ctccaaggac agcacctact ccctgtcctc cacccctgacc   540
ctgtccaagg ccgactacga gaagcacaag gtgtacgcct gcgaagtgac ccaccagggc   600
ctgtctagcc ccgtgaccaa gtctttcaac cggggcgagt gt                       642
```

<210> SEQ ID NO 92
<211> LENGTH: 9
<212> TYPE: PRT
<213> ORGANISM: Homo sapiens
<220> FEATURE:
<221> NAME/KEY: misc_feature
<223> OTHER INFORMATION: Amino acid sequence of CDRH1 of 411D07 using
      IMGT

<400> SEQUENCE: 92

```
Gly Gly Ser Ile Ile Ser Ser Asp Trp
1               5
```

```
<210> SEQ ID NO 93
<211> LENGTH: 7
<212> TYPE: PRT
<213> ORGANISM: Homo sapiens
<220> FEATURE:
<221> NAME/KEY: misc_feature
<223> OTHER INFORMATION: Amino acid sequence of CDRH2 of 411D07 using
      IMGT

<400> SEQUENCE: 93

Ile Phe His Ser Gly Arg Thr
1               5

<210> SEQ ID NO 94
<211> LENGTH: 8
<212> TYPE: PRT
<213> ORGANISM: Homo sapiens
<220> FEATURE:
<221> NAME/KEY: misc_feature
<223> OTHER INFORMATION: Amino acid sequence of CDRH3 of 411D07 using
      IMGT

<400> SEQUENCE: 94

Ala Arg Asp Gly Ser Gly Ser Tyr
1               5

<210> SEQ ID NO 95
<211> LENGTH: 6
<212> TYPE: PRT
<213> ORGANISM: Homo sapiens
<220> FEATURE:
<221> NAME/KEY: misc_feature
<223> OTHER INFORMATION: Amino acid sequence of CDRH1 of 411D07 using
      Kabat

<400> SEQUENCE: 95

Ser Ser Asp Trp Trp Asn
1               5

<210> SEQ ID NO 96
<211> LENGTH: 16
<212> TYPE: PRT
<213> ORGANISM: Homo sapiens
<220> FEATURE:
<221> NAME/KEY: misc_feature
<223> OTHER INFORMATION: Amino acid sequence of CDRH2 of 411D07 using
      Kabat

<400> SEQUENCE: 96

Glu Ile Phe His Ser Gly Arg Thr Asn Tyr Asn Pro Ser Leu Lys Ser
1               5                   10                  15

<210> SEQ ID NO 97
<211> LENGTH: 6
<212> TYPE: PRT
<213> ORGANISM: Homo sapiens
<220> FEATURE:
<221> NAME/KEY: misc_feature
<223> OTHER INFORMATION: Amino acid sequence of CDRH3 of 411D07 using
      Kabat

<400> SEQUENCE: 97

Asp Gly Ser Gly Ser Tyr
1               5

<210> SEQ ID NO 98
<211> LENGTH: 115
<212> TYPE: PRT
<213> ORGANISM: Homo sapiens
```

<220> FEATURE:
<221> NAME/KEY: misc_feature
<223> OTHER INFORMATION: Amino acid sequence of VH of 411D07

<400> SEQUENCE: 98

Gln Val Gln Leu Gln Glu Ser Gly Pro Gly Leu Val Lys Pro Ser Gly
1               5                   10                  15

Thr Leu Ser Leu Thr Cys Ile Val Ser Gly Gly Ser Ile Ile Ser Ser
            20                  25                  30

Asp Trp Trp Asn Trp Val Arg Gln Pro Pro Gly Lys Gly Leu Glu Trp
        35                  40                  45

Ile Gly Glu Ile Phe His Ser Gly Arg Thr Asn Tyr Asn Pro Ser Leu
    50                  55                  60

Lys Ser Arg Val Thr Ile Ser Ile Asp Lys Ser Lys Asn Gln Phe Ser
65                  70                  75                  80

Leu Arg Leu Ser Ser Val Thr Ala Ala Asp Thr Ala Val Tyr Tyr Cys
                85                  90                  95

Ala Arg Asp Gly Ser Gly Ser Tyr Trp Gly Gln Gly Thr Leu Val Thr
            100                 105                 110

Val Ser Ser
        115

<210> SEQ ID NO 99
<211> LENGTH: 346
<212> TYPE: DNA
<213> ORGANISM: Homo sapiens
<220> FEATURE:
<221> NAME/KEY: misc_feature
<223> OTHER INFORMATION: Nucleic acid sequence of VH of 411D07

<400> SEQUENCE: 99
caggtgcagc tgcaggagtc gggcccagga ctggtgaagc cttcggggac cctgtccctc      60
acctgcattg tctctggtgg ctccatcatc agtagtgact ggtggaattg ggtccgccag     120
cccccaggga aggggctgga gtggattgga gaaatctttc atagtgggag gaccaactac     180
aacccgtccc tcaagagtcg agtcaccata tcaatagaca gtccaagaa tcagttctcc      240 ctgaggctga gctctgtgac cgccgcggac acggccgtgt attactgtgc gagagatggt     300
tcggggagtt actggggcca gggaaccctg gtcaccgtct cctcag                    346

<210> SEQ ID NO 100
<211> LENGTH: 445
<212> TYPE: PRT
<213> ORGANISM: Homo sapiens
<220> FEATURE:
<221> NAME/KEY: misc_feature
<223> OTHER INFORMATION: Amino acid sequence of 411D07 heavy chain

<400> SEQUENCE: 100

Gln Val Gln Leu Gln Glu Ser Gly Pro Gly Leu Val Lys Pro Ser Gly
1               5                   10                  15

Thr Leu Ser Leu Thr Cys Ile Val Ser Gly Gly Ser Ile Ile Ser Ser
            20                  25                  30

Asp Trp Trp Asn Trp Val Arg Gln Pro Pro Gly Lys Gly Leu Glu Trp
        35                  40                  45

Ile Gly Glu Ile Phe His Ser Gly Arg Thr Asn Tyr Asn Pro Ser Leu
    50                  55                  60

Lys Ser Arg Val Thr Ile Ser Ile Asp Lys Ser Lys Asn Gln Phe Ser
65                  70                  75                  80

```
Leu Arg Leu Ser Ser Val Thr Ala Ala Asp Thr Ala Val Tyr Tyr Cys
            85                  90                  95

Ala Arg Asp Gly Ser Gly Ser Tyr Trp Gly Gln Gly Thr Leu Val Thr
        100                 105                 110

Val Ser Ser Ala Ser Thr Lys Gly Pro Ser Val Phe Pro Leu Ala Pro
        115                 120                 125

Ser Ser Lys Ser Thr Ser Gly Gly Thr Ala Ala Leu Gly Cys Leu Val
        130                 135                 140

Lys Asp Tyr Phe Pro Glu Pro Val Thr Val Ser Trp Asn Ser Gly Ala
145                 150                 155                 160

Leu Thr Ser Gly Val His Thr Phe Pro Ala Val Leu Gln Ser Ser Gly
                165                 170                 175

Leu Tyr Ser Leu Ser Ser Val Val Thr Val Pro Ser Ser Ser Leu Gly
                180                 185                 190

Thr Gln Thr Tyr Ile Cys Asn Val Asn His Lys Pro Ser Asn Thr Lys
            195                 200                 205

Val Asp Lys Lys Val Glu Pro Lys Ser Cys Asp Lys Thr His Thr Cys
210                 215                 220

Pro Pro Cys Pro Ala Pro Glu Leu Leu Gly Gly Pro Ser Val Phe Leu
225                 230                 235                 240

Phe Pro Pro Lys Pro Lys Asp Thr Leu Met Ile Ser Arg Thr Pro Glu
                245                 250                 255

Val Thr Cys Val Val Val Asp Val Ser His Glu Asp Pro Glu Val Lys
            260                 265                 270

Phe Asn Trp Tyr Val Asp Gly Val Glu Val His Asn Ala Lys Thr Lys
            275                 280                 285

Pro Arg Glu Glu Gln Tyr Asn Ser Thr Tyr Arg Val Val Ser Val Leu
290                 295                 300

Thr Val Leu His Gln Asp Trp Leu Asn Gly Lys Glu Tyr Lys Cys Lys
305                 310                 315                 320

Val Ser Asn Lys Ala Leu Pro Ala Pro Ile Glu Lys Thr Ile Ser Lys
                325                 330                 335

Ala Lys Gly Gln Pro Arg Glu Pro Gln Val Tyr Thr Leu Pro Pro Ser
            340                 345                 350

Arg Asp Glu Leu Thr Lys Asn Gln Val Ser Leu Thr Cys Leu Val Lys
            355                 360                 365

Gly Phe Tyr Pro Ser Asp Ile Ala Val Glu Trp Glu Ser Asn Gly Gln
        370                 375                 380

Pro Glu Asn Asn Tyr Lys Thr Thr Pro Pro Val Leu Asp Ser Asp Gly
385                 390                 395                 400

Ser Phe Phe Leu Tyr Ser Lys Leu Thr Val Asp Lys Ser Arg Trp Gln
                405                 410                 415

Gln Gly Asn Val Phe Ser Cys Ser Val Met His Glu Ala Leu His Asn
            420                 425                 430

His Tyr Thr Gln Lys Ser Leu Ser Leu Ser Pro Gly Lys
            435                 440                 445

<210> SEQ ID NO 101
<211> LENGTH: 1335
<212> TYPE: DNA
<213> ORGANISM: Homo sapiens
<220> FEATURE:
<221> NAME/KEY: misc_feature
<223> OTHER INFORMATION: Nucleic acid sequence of 411D07 heavy chain

<400> SEQUENCE: 101
```

```
caggtgcagc tgcaggagtc gggcccagga ctggtgaagc cttcggggac cctgtccctc      60
acctgcattg tctctggtgg ctccatcatc agtagtgact ggtggaattg ggtccgccag     120
cccccaggga aggggctgga gtggattgga gaaatctttc atagtgggag gaccaactac     180
aacccgtccc tcaagagtcg agtcaccata tcaatagaca gtccaagaa tcagttctcc      240
ctgaggctga gctctgtgac cgccgcggac acggccgtgt attactgtgc gagagatggt     300
tcggggagtt actggggcca gggaaccctg gtcaccgtct cctcagccag caccaagggc     360
ccctctgtgt tccctctggc cccttccagc aagtccacct ctgcggaaac agccgctctg     420
ggctgcctcg tgaaggacta cttccccgag cctgtgaccg tgtcctggaa ctctggcgct     480
ctgaccagcg gagtgcacac cttccctgct gtgctgcagt cctccggcct gtactccctg     540
tcctccgtcg tgaccgtgcc ttccagctct ctgggcaccc agacctacat ctgcaacgtg     600
aaccacaagc cctccaacac caaggtggac aagaaggtgg aacccaagtc ctgcgacaag     660
acccacacct gtcccccttg tcctgcccct gaactgctgg gcggaccttc cgtgttcctg     720
ttcccccaa agcccaagga caccctgatg atctcccgga ccccgaagt gacctgcgtg      780
gtggtggatg tgtcccacga ggaccctgaa gtgaagttca attggtacgt ggacggcgtg     840
gaagtgcaca cgccaagac caagcctaga gaggaacagt acaactccac ctaccgggtg      900
gtgtccgtgc tgaccgtgct gcaccaggat tggctgaacg gcaaagagta caagtgcaag     960
gtgtccaaca aggccctgcc tgcccccatc gaaaagacca tctccaaggc caagggccag    1020
ccccgggaac cccaggtgta cacactgccc cctagcaggg acgagctgac caagaaccag    1080
gtgtccctga cctgtctcgt gaaaggcttc taccctcg atatcgccgt ggaatgggag      1140
tccaacggcc agcctgagaa caactacaag accacccccc ctgtgctgga ctccgacggc    1200
tcattcttcc tgtacagcaa gctgacagtg gacaagtccc ggtggcagca gggcaacgtg    1260
ttctcctgct ccgtgatgca cgaggccctg cacaaccact acacccagaa gtccctgtcc    1320
ctgagccccg gcaag                                                    1335
```

<210> SEQ ID NO 102
<211> LENGTH: 12
<212> TYPE: PRT
<213> ORGANISM: Homo sapiens
<220> FEATURE:
<221> NAME/KEY: misc_feature
<223> OTHER INFORMATION: Amino acid sequence of CDRL1 of 411D07 using
      IMGT

<400> SEQUENCE: 102

Gln Ser Val Leu Tyr Ser Ser Asn Asn Lys Asn Tyr
1               5                   10

<210> SEQ ID NO 103
<211> LENGTH: 3
<212> TYPE: PRT
<213> ORGANISM: Homo sapiens
<220> FEATURE:
<221> NAME/KEY: misc_feature
<223> OTHER INFORMATION: Amino acid sequence of CDRL2 of 411D07 using
      IMGT

<400> SEQUENCE: 103

Trp Ala Ser
1

<210> SEQ ID NO 104

<211> LENGTH: 8
<212> TYPE: PRT
<213> ORGANISM: Homo sapiens
<220> FEATURE:
<221> NAME/KEY: misc_feature
<223> OTHER INFORMATION: Amino acid sequence of CDRL3 of 411D07 using
      IMGT

<400> SEQUENCE: 104

Gln Gln Tyr Tyr Ser Asn Arg Ser
1               5

<210> SEQ ID NO 105
<211> LENGTH: 17
<212> TYPE: PRT
<213> ORGANISM: Homo sapiens
<220> FEATURE:
<221> NAME/KEY: misc_feature
<223> OTHER INFORMATION: Amino acid sequence of CDRL1 of 411D07 using
      Kabat

<400> SEQUENCE: 105

Lys Ser Ser Gln Ser Val Leu Tyr Ser Ser Asn Asn Lys Asn Tyr Leu
1               5                   10                  15

Ala

<210> SEQ ID NO 106
<211> LENGTH: 7
<212> TYPE: PRT
<213> ORGANISM: Homo sapiens
<220> FEATURE:
<221> NAME/KEY: misc_feature
<223> OTHER INFORMATION: Amino acid sequence of CDRL2 of 411D07 using
      Kabat

<400> SEQUENCE: 106

Trp Ala Ser Thr Arg Glu Ser
1               5

<210> SEQ ID NO 107
<211> LENGTH: 8
<212> TYPE: PRT
<213> ORGANISM: Homo sapiens
<220> FEATURE:
<221> NAME/KEY: misc_feature
<223> OTHER INFORMATION: Amino acid sequence of CDRL3 of 411D07 using
      Kabat

<400> SEQUENCE: 107

Gln Gln Tyr Tyr Ser Asn Arg Ser
1               5

<210> SEQ ID NO 108
<211> LENGTH: 112
<212> TYPE: PRT
<213> ORGANISM: Homo sapiens
<220> FEATURE:
<221> NAME/KEY: misc_feature
<223> OTHER INFORMATION: Amino acid sequence of VL of 411D07

<400> SEQUENCE: 108

Asp Ile Val Met Thr Gln Ser Pro Asp Ser Leu Ala Val Ser Leu Gly
1               5                   10                  15

Glu Arg Ala Thr Ile Asn Cys Lys Ser Ser Gln Ser Val Leu Tyr Ser
            20                  25                  30

Ser Asn Asn Lys Asn Tyr Leu Ala Trp Tyr Gln Gln Lys Ser Gly Gln
        35                  40                  45

```
Pro Pro Lys Leu Leu Ile Tyr Trp Ala Ser Thr Arg Glu Ser Gly Val
    50                  55                  60

Pro Asp Arg Phe Ser Gly Ser Gly Ser Gly Thr Asp Phe Thr Leu Thr
 65              70                  75                  80

Ile Ser Ser Leu Gln Thr Glu Asp Val Ala Val Tyr Tyr Cys Gln Gln
                 85                  90                  95

Tyr Tyr Ser Asn Arg Ser Phe Gly Gln Gly Thr Lys Leu Glu Ile Lys
            100                 105                 110
```

<210> SEQ ID NO 109
<211> LENGTH: 337
<212> TYPE: DNA
<213> ORGANISM: Homo sapiens
<220> FEATURE:
<221> NAME/KEY: misc_feature
<223> OTHER INFORMATION: Nucleic acid sequence of VL of 411D07

<400> SEQUENCE: 109

```
gacatcgtga tgacccagtc tccagactcc ctggctgtgt ctctgggcga gagggccacc      60
atcaactgca gtccagccag gagtgtttta tacagctcca acaataagaa ttacttagct     120
tggtaccagc agaaatcagg acagcctcct aagttgctca tttactgggc atctacccgg     180
gaatccgggg tccctgaccg attcagtggc agcgggtctg ggacagattt cactctcacc     240
atcagcagcc tgcagactga agatgtggca gtttattact gtcagcaata ttatagtaat     300
cgcagttttg gccaggggac caagctggag atcaaac                              337
```

<210> SEQ ID NO 110
<211> LENGTH: 219
<212> TYPE: PRT
<213> ORGANISM: Homo sapiens
<220> FEATURE:
<221> NAME/KEY: misc_feature
<223> OTHER INFORMATION: Amino acid sequence of 411D07 light chain

<400> SEQUENCE: 110

```
Asp Ile Val Met Thr Gln Ser Pro Asp Ser Leu Ala Val Ser Leu Gly
 1               5                  10                  15

Glu Arg Ala Thr Ile Asn Cys Lys Ser Ser Gln Ser Val Leu Tyr Ser
            20                  25                  30

Ser Asn Asn Lys Asn Tyr Leu Ala Trp Tyr Gln Gln Lys Ser Gly Gln
        35                  40                  45

Pro Pro Lys Leu Leu Ile Tyr Trp Ala Ser Thr Arg Glu Ser Gly Val
    50                  55                  60

Pro Asp Arg Phe Ser Gly Ser Gly Ser Gly Thr Asp Phe Thr Leu Thr
 65              70                  75                  80

Ile Ser Ser Leu Gln Thr Glu Asp Val Ala Val Tyr Tyr Cys Gln Gln
                 85                  90                  95

Tyr Tyr Ser Asn Arg Ser Phe Gly Gln Gly Thr Lys Leu Glu Ile Lys
            100                 105                 110

Arg Thr Val Ala Ala Pro Ser Val Phe Ile Phe Pro Pro Ser Asp Glu
        115                 120                 125

Gln Leu Lys Ser Gly Thr Ala Ser Val Val Cys Leu Leu Asn Asn Phe
    130                 135                 140

Tyr Pro Arg Glu Ala Lys Val Gln Trp Lys Val Asp Asn Ala Leu Gln
145                 150                 155                 160

Ser Gly Asn Ser Gln Glu Ser Val Thr Glu Gln Asp Ser Lys Asp Ser
                165                 170                 175
```

Thr Tyr Ser Leu Ser Ser Thr Leu Thr Leu Ser Lys Ala Asp Tyr Glu
                180                 185                 190

Lys His Lys Val Tyr Ala Cys Glu Val Thr His Gln Gly Leu Ser Ser
            195                 200                 205

Pro Val Thr Lys Ser Phe Asn Arg Gly Glu Cys
        210                 215

<210> SEQ ID NO 111
<211> LENGTH: 657
<212> TYPE: DNA
<213> ORGANISM: Homo sapiens
<220> FEATURE:
<221> NAME/KEY: misc_feature
<223> OTHER INFORMATION: Nucleic acid sequence of 411D07 light chain

<400> SEQUENCE: 111
gacatcgtga tgacccagtc tccagactcc ctggctgtgt ctctgggcga gagggccacc    60
atcaactgca gtccagcca gagtgtttta tacagctcca acaataagaa ttacttagct   120
tggtaccagc agaaatcagg acagcctcct aagttgctca tttactgggc atctacccgg   180
gaatccgggg tccctgaccg attcagtggc agcgggtctg ggacagattt cactctcacc   240
atcagcagcc tgcagactga agatgtggca gtttattact gtcagcaata ttatagtaat   300
cgcagttttg gccaggggac caagctggag atcaaacgta cggtggccgc tcccccgtg    360 ttcatcttcc caccttccga cgagcagctg aagtccggca ccgcttctgt cgtgtgcctg   420
ctgaacaact tctacccccg cgaggccaag gtgcagtgga aggtggacaa cgccctgcag   480
tccggcaact cccaggaatc cgtgaccgag caggactcca aggacagcac ctactccctg   540
tcctccaccc tgaccctgtc caaggccgac tacgagaagc acaaggtgta cgcctgcgaa   600
gtgacccacc agggcctgtc tagccccgtg accaagtctt tcaaccgggg cgagtgt     657

<210> SEQ ID NO 112
<211> LENGTH: 8
<212> TYPE: PRT
<213> ORGANISM: Homo sapiens
<220> FEATURE:
<221> NAME/KEY: misc_feature
<223> OTHER INFORMATION: Amino acid sequence of CDRH1 of 385F01 using
      IMGT

<400> SEQUENCE: 112

Gly Phe Thr Phe Ser Ser Tyr Trp
1               5

<210> SEQ ID NO 113
<211> LENGTH: 8
<212> TYPE: PRT
<213> ORGANISM: Homo sapiens
<220> FEATURE:
<221> NAME/KEY: misc_feature
<223> OTHER INFORMATION: Amino acid sequence of CDRH2 of 385F01 using
      IMGT

<400> SEQUENCE: 113

Ile Lys Glu Asp Gly Ser Glu Lys
1               5

<210> SEQ ID NO 114
<211> LENGTH: 12
<212> TYPE: PRT
<213> ORGANISM: Homo sapiens
<220> FEATURE:

```
<221> NAME/KEY: misc_feature
<223> OTHER INFORMATION: Amino acid sequence of CDRH3 of 385F01 using
      IMGT

<400> SEQUENCE: 114

Ala Arg Asn Arg Leu Tyr Ser Asp Phe Leu Asp Asn
1               5                   10

<210> SEQ ID NO 115
<211> LENGTH: 5
<212> TYPE: PRT
<213> ORGANISM: Homo sapiens
<220> FEATURE:
<221> NAME/KEY: misc_feature
<223> OTHER INFORMATION: Amino acid sequence of CDRH1 of 385F01 using
      Kabat

<400> SEQUENCE: 115

Ser Tyr Trp Met Ser
1               5

<210> SEQ ID NO 116
<211> LENGTH: 17
<212> TYPE: PRT
<213> ORGANISM: Homo sapiens
<220> FEATURE:
<221> NAME/KEY: misc_feature
<223> OTHER INFORMATION: Amino acid sequence of CDRH2 of 385F01 using
      Kabat

<400> SEQUENCE: 116

Asn Ile Lys Glu Asp Gly Ser Glu Lys Tyr Tyr Val Asp Ser Val Lys
1               5                   10                  15

Gly

<210> SEQ ID NO 117
<211> LENGTH: 10
<212> TYPE: PRT
<213> ORGANISM: Homo sapiens
<220> FEATURE:
<221> NAME/KEY: misc_feature
<223> OTHER INFORMATION: Amino acid sequence of CDRH3 of 385F01 using
      Kabat

<400> SEQUENCE: 117

Asn Arg Leu Tyr Ser Asp Phe Leu Asp Asn
1               5                   10

<210> SEQ ID NO 118
<211> LENGTH: 119
<212> TYPE: PRT
<213> ORGANISM: Homo sapiens
<220> FEATURE:
<221> NAME/KEY: misc_feature
<223> OTHER INFORMATION: Amino acid sequence of VH of 385F01

<400> SEQUENCE: 118

Glu Val Gln Leu Val Glu Ser Gly Gly Gly Leu Val Gln Pro Gly Gly
1               5                   10                  15

Ser Leu Arg Leu Ser Cys Ala Ala Ser Gly Phe Thr Phe Ser Ser Tyr
            20                  25                  30

Trp Met Ser Trp Val Arg Gln Ala Pro Gly Lys Gly Leu Glu Trp Val
        35                  40                  45

Ala Asn Ile Lys Glu Asp Gly Ser Glu Lys Tyr Tyr Val Asp Ser Val
    50                  55                  60
```

```
Lys Gly Arg Phe Thr Ile Ser Arg Asp Asn Ala Lys Asn Ser Leu Tyr
 65                  70                  75                  80

Leu Gln Met Asn Ser Leu Arg Ala Glu Asp Thr Ser Val Tyr Tyr Cys
                 85                  90                  95

Ala Arg Asn Arg Leu Tyr Ser Asp Phe Leu Asp Asn Trp Gly Gln Gly
            100                 105                 110

Thr Leu Val Thr Val Ser Ser
            115
```

<210> SEQ ID NO 119
<211> LENGTH: 358
<212> TYPE: DNA
<213> ORGANISM: Homo sapiens
<220> FEATURE:
<221> NAME/KEY: misc_feature
<223> OTHER INFORMATION: Nucleic acid sequence of VH of 385F01

<400> SEQUENCE: 119

```
gaggtgcagc tggtggagtc tgggggaggc ttggtccagc ctggggggtc cctgagactc    60
tcctgtgcag cctctggatt cacgtttagt agctattgga tgagttgggt ccgccaggct   120
ccagggaagg gctggagtg gtggccaac atcaaagaag atggaagtga aaatactat    180
gtcgactctg tgaagggccg attcaccatc tccagagaca cgccaagaa ctcactgtat    240
ctgcaaatga acagcctgag agccgaggac acgtctgtgt attactgtgc gagaaatcga   300
ctctacagtg acttccttga caactggggc cagggaaccc tggtcaccgt ctcctcag    358
```

<210> SEQ ID NO 120
<211> LENGTH: 449
<212> TYPE: PRT
<213> ORGANISM: Homo sapiens
<220> FEATURE:
<221> NAME/KEY: misc_feature
<223> OTHER INFORMATION: Amino acid sequence of 385F01 heavy chain

<400> SEQUENCE: 120

```
Glu Val Gln Leu Val Glu Ser Gly Gly Gly Leu Val Gln Pro Gly Gly
  1               5                  10                  15

Ser Leu Arg Leu Ser Cys Ala Ala Ser Gly Phe Thr Phe Ser Ser Tyr
             20                  25                  30

Trp Met Ser Trp Val Arg Gln Ala Pro Gly Lys Gly Leu Glu Trp Val
         35                  40                  45

Ala Asn Ile Lys Glu Asp Gly Ser Glu Lys Tyr Tyr Val Asp Ser Val
 50                  55                  60

Lys Gly Arg Phe Thr Ile Ser Arg Asp Asn Ala Lys Asn Ser Leu Tyr
 65                  70                  75                  80

Leu Gln Met Asn Ser Leu Arg Ala Glu Asp Thr Ser Val Tyr Tyr Cys
                 85                  90                  95

Ala Arg Asn Arg Leu Tyr Ser Asp Phe Leu Asp Asn Trp Gly Gln Gly
            100                 105                 110

Thr Leu Val Thr Val Ser Ser Ala Ser Thr Lys Gly Pro Ser Val Phe
            115                 120                 125

Pro Leu Ala Pro Ser Ser Lys Ser Thr Ser Gly Gly Thr Ala Ala Leu
        130                 135                 140

Gly Cys Leu Val Lys Asp Tyr Phe Pro Glu Pro Val Thr Val Ser Trp
145                 150                 155                 160

Asn Ser Gly Ala Leu Thr Ser Gly Val His Thr Phe Pro Ala Val Leu
                165                 170                 175
```

Gln Ser Ser Gly Leu Tyr Ser Leu Ser Ser Val Val Thr Val Pro Ser
             180                 185                 190

Ser Ser Leu Gly Thr Gln Thr Tyr Ile Cys Asn Val Asn His Lys Pro
         195                 200                 205

Ser Asn Thr Lys Val Asp Lys Lys Val Glu Pro Lys Ser Cys Asp Lys
     210                 215                 220

Thr His Thr Cys Pro Pro Cys Pro Ala Pro Glu Leu Leu Gly Gly Pro
225                 230                 235                 240

Ser Val Phe Leu Phe Pro Pro Lys Pro Lys Asp Thr Leu Met Ile Ser
                245                 250                 255

Arg Thr Pro Glu Val Thr Cys Val Val Val Asp Val Ser His Glu Asp
            260                 265                 270

Pro Glu Val Lys Phe Asn Trp Tyr Val Asp Gly Val Glu Val His Asn
        275                 280                 285

Ala Lys Thr Lys Pro Arg Glu Glu Gln Tyr Asn Ser Thr Tyr Arg Val
    290                 295                 300

Val Ser Val Leu Thr Val Leu His Gln Asp Trp Leu Asn Gly Lys Glu
305                 310                 315                 320

Tyr Lys Cys Lys Val Ser Asn Lys Ala Leu Pro Ala Pro Ile Glu Lys
                325                 330                 335

Thr Ile Ser Lys Ala Lys Gly Gln Pro Arg Glu Pro Gln Val Tyr Thr
            340                 345                 350

Leu Pro Pro Ser Arg Asp Glu Leu Thr Lys Asn Gln Val Ser Leu Thr
        355                 360                 365

Cys Leu Val Lys Gly Phe Tyr Pro Ser Asp Ile Ala Val Glu Trp Glu
    370                 375                 380

Ser Asn Gly Gln Pro Glu Asn Asn Tyr Lys Thr Thr Pro Pro Val Leu
385                 390                 395                 400

Asp Ser Asp Gly Ser Phe Phe Leu Tyr Ser Lys Leu Thr Val Asp Lys
                405                 410                 415

Ser Arg Trp Gln Gln Gly Asn Val Phe Ser Cys Ser Val Met His Glu
            420                 425                 430

Ala Leu His Asn His Tyr Thr Gln Lys Ser Leu Ser Leu Ser Pro Gly
        435                 440                 445

Lys

<210> SEQ ID NO 121
<211> LENGTH: 1347
<212> TYPE: DNA
<213> ORGANISM: Homo sapiens
<220> FEATURE:
<221> NAME/KEY: misc_feature
<223> OTHER INFORMATION: Nucleic acid sequence of 385F01 heavy chain

<400> SEQUENCE: 121
gaggtgcagc tggtggagtc tgggggaggc ttggtccagc ctgggggtc cctgagactc      60 tcctgtgcag cctctggatt cacgtttagt agctattgga tgagttgggt ccgccaggct    120
ccagggaagg gctggagtg gtggccaac atcaaagaag atggaagtga aaatactat       180 gtcgactctg tgaagggccg attcaccatc tccagagaca acgccaagaa ctcactgtat    240
ctgcaaatga acagcctgag agccgaggac acgtctgtgt attactgtgc gagaaatcga    300
ctctacagtg acttccttga caactggggc cagggaaccc tggtcaccgt ctcctcagcc    360
agcaccaagg gcccctctgt gttccctctg gccccttcca gcaagtccac ctctggcgga    420
acagccgctc tgggctgcct cgtgaaggac tacttccccg agcctgtgac cgtgtcctgg    480

```
aactctggcg ctctgaccag cggagtgcac accttccctg ctgtgctgca gtcctccggc    540
ctgtactccc tgtcctccgt cgtgaccgtg ccttccagct ctctgggcac ccagacctac    600
atctgcaacg tgaaccacaa gccctccaac accaaggtgg acaagaaggt ggaacccaag    660
tcctgcgaca gacccacac ctgtcccct tgtcctgccc ctgaactgct gggcggacct    720
tccgtgttcc tgttcccccc aaagcccaag gacaccctga tgatctcccg gacccccgaa    780
gtgacctgcg tggtggtgga tgtgtcccac gaggaccctg aagtgaagtt caattggtac    840
gtggacggcg tggaagtgca caacgccaag accaagccta gagaggaaca gtacaactcc    900
acctaccggg tggtgtccgt gctgaccgtg ctgcaccagg attggctgaa cggcaaagag    960
tacaagtgca aggtgtccaa caaggccctg cctgccccca tcgaaaagac catctccaag   1020
gccaagggcc agccccggga accccaggtg tacacactgc ccctagcag ggacgagctg   1080 accaagaacc aggtgtccct gacctgtctc gtgaaaggct tctacccctc cgatatcgcc   1140
gtggaatggg agtccaacgg ccagcctgag aacaactaca agaccacccc ccctgtgctg   1200
gactccgacg gctcattctt cctgtacagc aagctgacag tggacaagtc ccggtggcag   1260
cagggcaacg tgttctcctg ctccgtgatg cacgaggccc tgcacaacca ctacacccag   1320
aagtccctgt ccctgagccc cggcaag                                       1347
```

<210> SEQ ID NO 122
<211> LENGTH: 6
<212> TYPE: PRT
<213> ORGANISM: Homo sapiens
<220> FEATURE:
<221> NAME/KEY: misc_feature
<223> OTHER INFORMATION: Amino acid sequence of CDRL1 of 385F01 using
      IMGT

<400> SEQUENCE: 122

Gln Gly Val Ser Ser Trp
1               5

<210> SEQ ID NO 123
<211> LENGTH: 3
<212> TYPE: PRT
<213> ORGANISM: Homo sapiens
<220> FEATURE:
<221> NAME/KEY: misc_feature
<223> OTHER INFORMATION: Amino acid sequence of CDRL2 of 385F01 using
      IMGT

<400> SEQUENCE: 123

Gly Ala Ser
1

<210> SEQ ID NO 124
<211> LENGTH: 9
<212> TYPE: PRT
<213> ORGANISM: Homo sapiens
<220> FEATURE:
<221> NAME/KEY: misc_feature
<223> OTHER INFORMATION: Amino acid sequence of CDRL3 of 385F01 using
      IMGT

<400> SEQUENCE: 124

Gln Gln Ala Asn Ser Ile Pro Phe Thr
1               5

<210> SEQ ID NO 125
<211> LENGTH: 11

```
<212> TYPE: PRT
<213> ORGANISM: Homo sapiens
<220> FEATURE:
<221> NAME/KEY: misc_feature
<223> OTHER INFORMATION: Amino acid sequence of CDRL1 of 385F01 using
      Kabat

<400> SEQUENCE: 125

Arg Ala Ser Gln Gly Val Ser Ser Trp Leu Ala
1               5                   10

<210> SEQ ID NO 126
<211> LENGTH: 7
<212> TYPE: PRT
<213> ORGANISM: Homo sapiens
<220> FEATURE:
<221> NAME/KEY: misc_feature
<223> OTHER INFORMATION: Amino acid sequence of CDRL2 of 385F01 using
      Kabat

<400> SEQUENCE: 126

Gly Ala Ser Ser Leu Gln Ser
1               5

<210> SEQ ID NO 127
<211> LENGTH: 9
<212> TYPE: PRT
<213> ORGANISM: Homo sapiens
<220> FEATURE:
<221> NAME/KEY: misc_feature
<223> OTHER INFORMATION: Amino acid sequence of CDRL3 of 385F01 using
      Kabat

<400> SEQUENCE: 127

Gln Gln Ala Asn Ser Ile Pro Phe Thr
1               5

<210> SEQ ID NO 128
<211> LENGTH: 107
<212> TYPE: PRT
<213> ORGANISM: Homo sapiens
<220> FEATURE:
<221> NAME/KEY: misc_feature
<223> OTHER INFORMATION: Amino acid sequence of VL of 385F01

<400> SEQUENCE: 128

Asp Ile Gln Met Thr Gln Ser Pro Ser Ser Val Ser Ala Ser Val Gly
1               5                   10                  15

Asp Arg Val Thr Ile Thr Cys Arg Ala Ser Gln Gly Val Ser Ser Trp
            20                  25                  30

Leu Ala Trp Tyr Gln Gln Lys Ser Gly Lys Ala Pro Lys Leu Leu Ile
        35                  40                  45

Tyr Gly Ala Ser Ser Leu Gln Ser Gly Val Pro Ser Arg Phe Ser Gly
    50                  55                  60

Ser Gly Ser Gly Thr Glu Phe Ile Leu Thr Ile Ser Ser Leu Gln Pro
65                  70                  75                  80

Glu Asp Phe Ala Thr Tyr Tyr Cys Gln Gln Ala Asn Ser Ile Pro Phe
                85                  90                  95

Thr Phe Gly Pro Gly Thr Lys Val Asp Ile Lys
            100                 105

<210> SEQ ID NO 129
<211> LENGTH: 322
<212> TYPE: DNA
<213> ORGANISM: Homo sapiens
```

<220> FEATURE:
<221> NAME/KEY: misc_feature
<223> OTHER INFORMATION: Nucleic acid sequence of VL of 385F01

<400> SEQUENCE: 129

```
gacatccaga tgacccagtc tccatcttcc gtgtctgcat ctgtcggaga cagagtcacc      60
atcacttgtc gggcgagtca gggtgttagc agctggttag cctggtatca gcagaaatca    120
gggaaagccc ctaagctcct gatctatggt gcatccagtt tgcaaagtgg ggtcccatca    180
agattcagcg gcagtggatc tgggacagag ttcattctca ccatcagcag cctgcagcct    240
gaagattttg caacttacta ttgtcaacag gctaacagta tcccattcac tttcggccct    300
gggaccaaag tggatatcaa ac                                             322
```

<210> SEQ ID NO 130
<211> LENGTH: 214
<212> TYPE: PRT
<213> ORGANISM: Homo sapiens
<220> FEATURE:
<221> NAME/KEY: misc_feature
<223> OTHER INFORMATION: Amino acid sequence of 385F01 light chain

<400> SEQUENCE: 130

```
Asp Ile Gln Met Thr Gln Ser Pro Ser Ser Val Ser Ala Ser Val Gly
1               5                   10                  15

Asp Arg Val Thr Ile Thr Cys Arg Ala Ser Gln Gly Val Ser Ser Trp
            20                  25                  30

Leu Ala Trp Tyr Gln Gln Lys Ser Gly Lys Ala Pro Lys Leu Leu Ile
        35                  40                  45

Tyr Gly Ala Ser Ser Leu Gln Ser Gly Val Pro Ser Arg Phe Ser Gly
    50                  55                  60

Ser Gly Ser Gly Thr Glu Phe Ile Leu Thr Ile Ser Ser Leu Gln Pro
65                  70                  75                  80

Glu Asp Phe Ala Thr Tyr Tyr Cys Gln Gln Ala Asn Ser Ile Pro Phe
                85                  90                  95

Thr Phe Gly Pro Gly Thr Lys Val Asp Ile Lys Arg Thr Val Ala Ala
            100                 105                 110

Pro Ser Val Phe Ile Phe Pro Pro Ser Asp Glu Gln Leu Lys Ser Gly
        115                 120                 125

Thr Ala Ser Val Val Cys Leu Leu Asn Asn Phe Tyr Pro Arg Glu Ala
    130                 135                 140

Lys Val Gln Trp Lys Val Asp Asn Ala Leu Gln Ser Gly Asn Ser Gln
145                 150                 155                 160

Glu Ser Val Thr Glu Gln Asp Ser Lys Asp Ser Thr Tyr Ser Leu Ser
                165                 170                 175

Ser Thr Leu Thr Leu Ser Lys Ala Asp Tyr Glu Lys His Lys Val Tyr
            180                 185                 190

Ala Cys Glu Val Thr His Gln Gly Leu Ser Ser Pro Val Thr Lys Ser
        195                 200                 205

Phe Asn Arg Gly Glu Cys
    210
```

<210> SEQ ID NO 131
<211> LENGTH: 642
<212> TYPE: DNA
<213> ORGANISM: Homo sapiens
<220> FEATURE:
<221> NAME/KEY: misc_feature
<223> OTHER INFORMATION: Nucleic acid sequence of 385F01 light chain

<400> SEQUENCE: 131

```
gacatccaga tgacccagtc tccatcttcc gtgtctgcat ctgtcggaga cagagtcacc    60
atcacttgtc gggcgagtca gggtgttagc agctggttag cctggtatca gcagaaatca   120
gggaaagccc ctaagctcct gatctatggt gcatccagtt tgcaaagtgg ggtcccatca   180
agattcagcg gcagtggatc tgggacagag ttcattctca ccatcagcag cctgcagcct   240
gaagattttg caacttacta ttgtcaacag gctaacagta tcccattcac tttcggccct   300
gggaccaaag tggatatcaa acgtacggtg gccgctccct ccgtgttcat cttcccacct   360
tccgacgagc agctgaagtc cggcaccgct tctgtcgtgt gcctgctgaa caacttctac   420
ccccgcgagg ccaaggtgca gtggaaggtg gacaacgccc tgcagtccgg caactcccag   480
gaatccgtga ccgagcagga ctccaaggac agcacctact ccctgtcctc caccctgacc   540
ctgtccaagg ccgactacga gaagcacaag gtgtacgcct gcgaagtgac ccaccagggc   600
ctgtctagcc ccgtgaccaa gtctttcaac cggggcgagt gt                      642
```

<210> SEQ ID NO 132
<211> LENGTH: 8
<212> TYPE: PRT
<213> ORGANISM: Homo sapiens
<220> FEATURE:
<221> NAME/KEY: misc_feature
<223> OTHER INFORMATION: Amino acid sequence of CDRH1 of 413D08 using IMGT

<400> SEQUENCE: 132

Gly Phe Thr Phe Arg Ile Tyr Gly
1               5

<210> SEQ ID NO 133
<211> LENGTH: 8
<212> TYPE: PRT
<213> ORGANISM: Homo sapiens
<220> FEATURE:
<221> NAME/KEY: misc_feature
<223> OTHER INFORMATION: Amino acid sequence of CDRH2 of 413D08 using IMGT

<400> SEQUENCE: 133

Ile Trp Tyr Asp Gly Ser Asn Lys
1               5

<210> SEQ ID NO 134
<211> LENGTH: 11
<212> TYPE: PRT
<213> ORGANISM: Homo sapiens
<220> FEATURE:
<221> NAME/KEY: misc_feature
<223> OTHER INFORMATION: Amino acid sequence of CDRH3 of 413D08 using IMGT

<400> SEQUENCE: 134

Ala Arg Asp Met Asp Tyr Phe Gly Met Asp Val
1               5                   10

<210> SEQ ID NO 135
<211> LENGTH: 5
<212> TYPE: PRT
<213> ORGANISM: Homo sapiens
<220> FEATURE:
<221> NAME/KEY: misc_feature
<223> OTHER INFORMATION: Amino acid sequence of CDRH1 of 413D08 using Kabat

```
<400> SEQUENCE: 135

Ile Tyr Gly Met His
1               5

<210> SEQ ID NO 136
<211> LENGTH: 17
<212> TYPE: PRT
<213> ORGANISM: Homo sapiens
<220> FEATURE:
<221> NAME/KEY: misc_feature
<223> OTHER INFORMATION: Amino acid sequence of CDRH2 of 413D08 using
      Kabat

<400> SEQUENCE: 136

Val Ile Trp Tyr Asp Gly Ser Asn Lys Tyr Tyr Ala Asp Ser Val Lys
1               5                   10                  15

Gly

<210> SEQ ID NO 137
<211> LENGTH: 9
<212> TYPE: PRT
<213> ORGANISM: Homo sapiens
<220> FEATURE:
<221> NAME/KEY: misc_feature
<223> OTHER INFORMATION: Amino acid sequence of CDRH3 of 413D08 using
      Kabat

<400> SEQUENCE: 137

Asp Met Asp Tyr Phe Gly Met Asp Val
1               5

<210> SEQ ID NO 138
<211> LENGTH: 118
<212> TYPE: PRT
<213> ORGANISM: Homo sapiens
<220> FEATURE:
<221> NAME/KEY: misc_feature
<223> OTHER INFORMATION: Amino acid sequence of VH of 413D08

<400> SEQUENCE: 138

Gln Val Gln Leu Val Glu Ser Gly Gly Gly Val Val Gln Pro Gly Arg
1               5                   10                  15

Ser Leu Arg Leu Ser Cys Ala Ala Ser Gly Phe Thr Phe Arg Ile Tyr
                20                  25                  30

Gly Met His Trp Val Arg Gln Ala Pro Gly Lys Gly Leu Glu Trp Val
            35                  40                  45

Ala Val Ile Trp Tyr Asp Gly Ser Asn Lys Tyr Tyr Ala Asp Ser Val
        50                  55                  60

Lys Gly Arg Phe Thr Ile Ser Arg Asp Asn Ser Asp Asn Thr Leu Tyr
65                  70                  75                  80

Leu Gln Met Asn Ser Leu Arg Ala Glu Asp Thr Ala Val Tyr Tyr Cys
                85                  90                  95

Ala Arg Asp Met Asp Tyr Phe Gly Met Asp Val Trp Gly Gln Gly Thr
            100                 105                 110

Thr Val Thr Val Ser Ser
            115

<210> SEQ ID NO 139
<211> LENGTH: 355
<212> TYPE: DNA
<213> ORGANISM: Homo sapiens
<220> FEATURE:
```

<221> NAME/KEY: misc_feature
<223> OTHER INFORMATION: Nucleic acid sequence of VH of 413D08

<400> SEQUENCE: 139

```
caggtgcagc tggtggagtc tgggggaggc gtggtccagc ctggagagtc cctgagactc      60
tcctgtgcag cgtctggatt caccttccgt atttatggca tgcactgggt ccgccaggct     120
ccaggcaagg ggctggagtg ggtggcagtt atatggtatg atggaagtaa taaatactat     180
gctgactccg tgaagggccg attcaccatc tccagagaca attccgacaa cacgctgtat     240
ctgcaaatga acagcctgag agccgaggac acggctgtgt attactgtgc gagagatatg     300
gactacttcg gtatggacgt ctggggccaa gggaccacgg tcaccgtctc ctcag          355
```

<210> SEQ ID NO 140
<211> LENGTH: 448
<212> TYPE: PRT
<213> ORGANISM: Homo sapiens
<220> FEATURE:
<221> NAME/KEY: misc_feature
<223> OTHER INFORMATION: Amino acid sequence of 413D08 heavy chain

<400> SEQUENCE: 140

```
Gln Val Gln Leu Val Glu Ser Gly Gly Gly Val Val Gln Pro Gly Arg
1               5                   10                  15

Ser Leu Arg Leu Ser Cys Ala Ala Ser Gly Phe Thr Phe Arg Ile Tyr
            20                  25                  30

Gly Met His Trp Val Arg Gln Ala Pro Gly Lys Gly Leu Glu Trp Val
        35                  40                  45

Ala Val Ile Trp Tyr Asp Gly Ser Asn Lys Tyr Tyr Ala Asp Ser Val
    50                  55                  60

Lys Gly Arg Phe Thr Ile Ser Arg Asp Asn Ser Asp Asn Thr Leu Tyr
65                  70                  75                  80

Leu Gln Met Asn Ser Leu Arg Ala Glu Asp Thr Ala Val Tyr Tyr Cys
                85                  90                  95

Ala Arg Asp Met Asp Tyr Phe Gly Met Asp Val Trp Gly Gln Gly Thr
            100                 105                 110

Thr Val Thr Val Ser Ser Ala Ser Thr Lys Gly Pro Ser Val Phe Pro
        115                 120                 125

Leu Ala Pro Ser Ser Lys Ser Thr Ser Gly Gly Thr Ala Ala Leu Gly
    130                 135                 140

Cys Leu Val Lys Asp Tyr Phe Pro Glu Pro Val Thr Val Ser Trp Asn
145                 150                 155                 160

Ser Gly Ala Leu Thr Ser Gly Val His Thr Phe Pro Ala Val Leu Gln
                165                 170                 175

Ser Ser Gly Leu Tyr Ser Leu Ser Ser Val Val Thr Val Pro Ser Ser
            180                 185                 190

Ser Leu Gly Thr Gln Thr Tyr Ile Cys Asn Val Asn His Lys Pro Ser
        195                 200                 205

Asn Thr Lys Val Asp Lys Lys Val Glu Pro Lys Ser Cys Asp Lys Thr
    210                 215                 220

His Thr Cys Pro Pro Cys Pro Ala Pro Glu Leu Leu Gly Gly Pro Ser
225                 230                 235                 240

Val Phe Leu Phe Pro Pro Lys Pro Lys Asp Thr Leu Met Ile Ser Arg
                245                 250                 255

Thr Pro Glu Val Thr Cys Val Val Val Asp Val Ser His Glu Asp Pro
            260                 265                 270
```

```
Glu Val Lys Phe Asn Trp Tyr Val Asp Gly Val Glu Val His Asn Ala
            275                 280                 285

Lys Thr Lys Pro Arg Glu Glu Gln Tyr Asn Ser Thr Tyr Arg Val Val
    290                 295                 300

Ser Val Leu Thr Val Leu His Gln Asp Trp Leu Asn Gly Lys Glu Tyr
305                 310                 315                 320

Lys Cys Lys Val Ser Asn Lys Ala Leu Pro Ala Pro Ile Glu Lys Thr
                325                 330                 335

Ile Ser Lys Ala Lys Gly Gln Pro Arg Glu Pro Gln Val Tyr Thr Leu
            340                 345                 350

Pro Pro Ser Arg Asp Glu Leu Thr Lys Asn Gln Val Ser Leu Thr Cys
        355                 360                 365

Leu Val Lys Gly Phe Tyr Pro Ser Asp Ile Ala Val Glu Trp Glu Ser
370                 375                 380

Asn Gly Gln Pro Glu Asn Asn Tyr Lys Thr Thr Pro Pro Val Leu Asp
385                 390                 395                 400

Ser Asp Gly Ser Phe Phe Leu Tyr Ser Lys Leu Thr Val Asp Lys Ser
                405                 410                 415

Arg Trp Gln Gln Gly Asn Val Phe Ser Cys Ser Val Met His Glu Ala
            420                 425                 430

Leu His Asn His Tyr Thr Gln Lys Ser Leu Ser Leu Ser Pro Gly Lys
        435                 440                 445

<210> SEQ ID NO 141
<211> LENGTH: 1344
<212> TYPE: DNA
<213> ORGANISM: Homo sapiens
<220> FEATURE:
<221> NAME/KEY: misc_feature
<223> OTHER INFORMATION: Nucleic acid sequence of 413D08 heavy chain

<400> SEQUENCE: 141
caggtgcagc tggtggagtc tgggggaggc gtggtccagc ctgggaggtc cctgagactc      60
tcctgtgcag cgtctggatt caccttccgt atttatggca tgcactgggt ccgccaggct     120
ccaggcaagg ggctggagtg ggtggcagtt atatggtatg atggaagtaa taaatactat     180
gctgactccg tgaagggccg attcaccatc tccagagaca attccgacaa cacgctgtat     240
ctgcaaatga acagcctgag agccgaggac acggctgtgt attactgtgc gagagatatg     300
gactacttcg gtatggacgt ctggggccaa gggaccacgg tcaccgtctc ctcagccagc     360
accaagggcc cctctgtgtt ccctctggcc cttccagcaa gtccacctc tggcggaaca     420 gccgctctgg gctgcctcgt gaaggactac ttccccgagc ctgtgaccgt gtcctggaac     480
tctggcgctc tgaccagcgg agtgcacacc ttccctgctg tgctgcagtc ctccggcctg     540
tactccctgt cctccgtcgt gaccgtgcct tccagctctc tgggcaccca gacctacatc     600
tgcaacgtga accacaagcc ctccaacacc aaggtggaca gaaggtgga acccaagtcc     660 tgcgacaaga cccacacctg tccccctgt cctgccctg aactgctggg cggaccttcc     720
gtgttcctgt tcccccaaa gcccaaggac accctgatga tctcccggac cccgaagtg      780 acctgcgtgg tggtggatgt gtcccacgag accctgaag tgaagttcaa ttggtacgtg     840
gacggcgtgg aagtgcacaa cgccaagacc aagcctagag aggaacagta caactccacc     900
taccgggtgg tgtccgtgct gaccgtgctg caccaggatt ggctgaacgg caaagagtac     960
aagtgcaagg tgtccaacaa ggccctgcct gcccccatcg aaaagaccat ctccaaggcc    1020
aagggccagc ccgggaacc ccaggtgtac acactgcccc ctagcaggga cgagctgacc    1080
```

-continued

```
aagaaccagg tgtccctgac ctgtctcgtg aaaggcttct acccctccga tatcgccgtg    1140
gaatgggagt ccaacggcca gcctgagaac aactacaaga ccaccccccc tgtgctggac    1200
tccgacggct cattcttcct gtacagcaag ctgacagtgg acaagtcccg gtggcagcag    1260
ggcaacgtgt tctcctgctc cgtgatgcac gaggccctgc acaaccacta cacccagaag    1320
tccctgtccc tgagccccgg caag                                           1344
```

<210> SEQ ID NO 142
<211> LENGTH: 6
<212> TYPE: PRT
<213> ORGANISM: Homo sapiens
<220> FEATURE:
<221> NAME/KEY: misc_feature
<223> OTHER INFORMATION: Amino acid sequence of CDRL1 of 413D08 using
      IMGT

<400> SEQUENCE: 142

Gln Gly Ile Arg Asn Asp
1               5

<210> SEQ ID NO 143
<211> LENGTH: 3
<212> TYPE: PRT
<213> ORGANISM: Homo sapiens
<220> FEATURE:
<221> NAME/KEY: misc_feature
<223> OTHER INFORMATION: Amino acid sequence of CDRL2 of 413D08 using
      IMGT

<400> SEQUENCE: 143

Ala Ala Ser
1

<210> SEQ ID NO 144
<211> LENGTH: 9
<212> TYPE: PRT
<213> ORGANISM: Homo sapiens
<220> FEATURE:
<221> NAME/KEY: misc_feature
<223> OTHER INFORMATION: Amino acid sequence of CDRL3 of 413D08 using
      IMGT

<400> SEQUENCE: 144

Leu Gln His Asn Ser Tyr Pro Arg Thr
1               5

<210> SEQ ID NO 145
<211> LENGTH: 11
<212> TYPE: PRT
<213> ORGANISM: Homo sapiens
<220> FEATURE:
<221> NAME/KEY: misc_feature
<223> OTHER INFORMATION: Amino acid sequence of CDRL1 of 413D08 using
      Kabat

<400> SEQUENCE: 145

Arg Ala Ser Gln Gly Ile Arg Asn Asp Leu Gly
1               5                   10

<210> SEQ ID NO 146
<211> LENGTH: 7
<212> TYPE: PRT
<213> ORGANISM: Homo sapiens
<220> FEATURE:
<221> NAME/KEY: misc_feature
<223> OTHER INFORMATION: Amino acid sequence of CDRL2 of 413D08 using Kabat

<400> SEQUENCE: 146

Ala Ala Ser Ser Leu Gln Ser
1               5

<210> SEQ ID NO 147
<211> LENGTH: 9
<212> TYPE: PRT
<213> ORGANISM: Homo sapiens
<220> FEATURE:
<221> NAME/KEY: misc_feature
<223> OTHER INFORMATION: Amino acid sequence of CDRL3 of 413D08 using
      Kabat

<400> SEQUENCE: 147

Leu Gln His Asn Ser Tyr Pro Arg Thr
1               5

<210> SEQ ID NO 148
<211> LENGTH: 107
<212> TYPE: PRT
<213> ORGANISM: Homo sapiens
<220> FEATURE:
<221> NAME/KEY: misc_feature
<223> OTHER INFORMATION: Amino acid sequence of VL of 413D08

<400> SEQUENCE: 148

Asp Leu Gln Met Thr Gln Ser Pro Ser Ser Leu Ser Ala Ser Val Gly
1               5                   10                  15

Asp Arg Val Thr Ile Thr Cys Arg Ala Ser Gln Gly Ile Arg Asn Asp
            20                  25                  30

Leu Gly Trp Tyr Gln Gln Lys Pro Gly Lys Ala Pro Lys Arg Leu Ile
        35                  40                  45

Tyr Ala Ala Ser Ser Leu Gln Ser Gly Val Pro Ser Arg Phe Ser Gly
    50                  55                  60

Ser Gly Ser Gly Thr Glu Phe Thr Leu Thr Ile Ser Ser Leu Gln Pro
65                  70                  75                  80

Glu Asp Phe Ala Thr Tyr Tyr Cys Leu Gln His Asn Ser Tyr Pro Arg
                85                  90                  95

Thr Phe Gly Gln Gly Thr Lys Val Glu Ile Lys
            100                 105

<210> SEQ ID NO 149
<211> LENGTH: 322
<212> TYPE: DNA
<213> ORGANISM: Homo sapiens
<220> FEATURE:
<221> NAME/KEY: misc_feature
<223> OTHER INFORMATION: Nucleic acid sequence of VL of 413D08

<400> SEQUENCE: 149
gacctccaga tgacccagtc tccatcctcc ctgtctgcat ctgtaggaga cagagtcacc    60
atcacttgcc gggcaagtca gggcattaga aatgatttag gctggtatca gcagaaacca   120
gggaaagccc ctaagcgcct gatctatgct gcatccagtt tgcaaagtgg ggtcccatca   180
aggttcagcg gcagtggatc tgggacagaa ttcactctca caatcagcag cctgcagcct   240
gaagattttg caacttatta ctgtctacag cataatagtt accctcggac gttcggccaa   300
gggaccaagg tggaaatcaa ac                                            322

<210> SEQ ID NO 150

<211> LENGTH: 214
<212> TYPE: PRT
<213> ORGANISM: Homo sapiens
<220> FEATURE:
<221> NAME/KEY: misc_feature
<223> OTHER INFORMATION: Amino acid sequence of 413D08 light chain

<400> SEQUENCE: 150

Asp Leu Gln Met Thr Gln Ser Pro Ser Ser Leu Ser Ala Ser Val Gly
1               5                   10                  15
Asp Arg Val Thr Ile Thr Cys Arg Ala Ser Gln Gly Ile Arg Asn Asp
            20                  25                  30
Leu Gly Trp Tyr Gln Gln Lys Pro Gly Lys Ala Pro Lys Arg Leu Ile
        35                  40                  45
Tyr Ala Ala Ser Ser Leu Gln Ser Gly Val Pro Ser Arg Phe Ser Gly
    50                  55                  60
Ser Gly Ser Gly Thr Glu Phe Thr Leu Thr Ile Ser Ser Leu Gln Pro
65                  70                  75                  80
Glu Asp Phe Ala Thr Tyr Tyr Cys Leu Gln His Asn Ser Tyr Pro Arg
                85                  90                  95
Thr Phe Gly Gln Gly Thr Lys Val Glu Ile Lys Arg Thr Val Ala Ala
            100                 105                 110
Pro Ser Val Phe Ile Phe Pro Pro Ser Asp Glu Gln Leu Lys Ser Gly
        115                 120                 125
Thr Ala Ser Val Val Cys Leu Leu Asn Asn Phe Tyr Pro Arg Glu Ala
    130                 135                 140
Lys Val Gln Trp Lys Val Asp Asn Ala Leu Gln Ser Gly Asn Ser Gln
145                 150                 155                 160
Glu Ser Val Thr Glu Gln Asp Ser Lys Asp Ser Thr Tyr Ser Leu Ser
                165                 170                 175
Ser Thr Leu Thr Leu Ser Lys Ala Asp Tyr Glu Lys His Lys Val Tyr
            180                 185                 190
Ala Cys Glu Val Thr His Gln Gly Leu Ser Ser Pro Val Thr Lys Ser
        195                 200                 205
Phe Asn Arg Gly Glu Cys
    210

<210> SEQ ID NO 151
<211> LENGTH: 642
<212> TYPE: DNA
<213> ORGANISM: Homo sapiens
<220> FEATURE:
<221> NAME/KEY: misc_feature
<223> OTHER INFORMATION: Nucleic acid sequence of 413D08 light chain

<400> SEQUENCE: 151
gacctccaga tgacccagtc tccatcctcc ctgtctgcat ctgtaggaga cagagtcacc        60
atcacttgcc gggcaagtca gggcattaga aatgatttag ctggtatcag cagaaacca       120 gggaaagccc ctaagcgcct gatctatgct gcatccagtt tgcaaagtgg ggtcccatca      180
aggttcagcg gcagtggatc tgggacagaa ttcactctca caatcagcag cctgcagcct      240
gaagattttg caacttatta ctgtctacag cataatagtt accctcggac gttcggccaa      300
gggaccaagg tggaaatcaa acgtacggtg gccgctccct ccgtgttcat cttcccacct      360
tccgacgagc agctgaagtc cggcaccgct tctgtcgtgt gctgctgaa caacttctac       420 ccccgcgagg ccaaggtgca gtggaaggtg gacaacgccc tgcagtccgg caactcccag      480
gaatccgtga ccgagcagga ctccaaggac agcacctact ccctgtcctc caccctgacc      540

```
ctgtccaagg ccgactacga gaagcacaag gtgtacgcct gcgaagtgac ccaccagggc    600
ctgtctagcc ccgtgaccaa gtctttcaac cggggcgagt gt                      642
```

<210> SEQ ID NO 152
<211> LENGTH: 9
<212> TYPE: PRT
<213> ORGANISM: Homo sapiens
<220> FEATURE:
<221> NAME/KEY: misc_feature
<223> OTHER INFORMATION: Amino acid sequence of CDRH1 of 386H03 using
      IMGT

<400> SEQUENCE: 152

Gly Gly Ser Ile Ser Ser Ser Asp Trp
1               5

<210> SEQ ID NO 153
<211> LENGTH: 7
<212> TYPE: PRT
<213> ORGANISM: Homo sapiens
<220> FEATURE:
<221> NAME/KEY: misc_feature
<223> OTHER INFORMATION: Amino acid sequence of CDRH2 of 386H03 using
      IMGT

<400> SEQUENCE: 153

Ile Phe His Ser Gly Asn Thr
1               5

<210> SEQ ID NO 154
<211> LENGTH: 8
<212> TYPE: PRT
<213> ORGANISM: Homo sapiens
<220> FEATURE:
<221> NAME/KEY: misc_feature
<223> OTHER INFORMATION: Amino acid sequence of CDRH3 of 386H03 using
      IMGT

<400> SEQUENCE: 154

Val Arg Asp Gly Ser Gly Ser Tyr
1               5

<210> SEQ ID NO 155
<211> LENGTH: 6
<212> TYPE: PRT
<213> ORGANISM: Homo sapiens
<220> FEATURE:
<221> NAME/KEY: misc_feature
<223> OTHER INFORMATION: Amino acid sequence of CDRH1 of 386H03 using
      Kabat

<400> SEQUENCE: 155

Ser Ser Asp Trp Trp Ser
1               5

<210> SEQ ID NO 156
<211> LENGTH: 16
<212> TYPE: PRT
<213> ORGANISM: Homo sapiens
<220> FEATURE:
<221> NAME/KEY: misc_feature
<223> OTHER INFORMATION: Amino acid sequence of CDRH2 of 386H03 using
      Kabat

<400> SEQUENCE: 156

Glu Ile Phe His Ser Gly Asn Thr Asn Tyr Asn Pro Ser Leu Lys Ser
1               5                   10                  15

<210> SEQ ID NO 157
<211> LENGTH: 6
<212> TYPE: PRT
<213> ORGANISM: Homo sapiens
<220> FEATURE:
<221> NAME/KEY: misc_feature
<223> OTHER INFORMATION: Amino acid sequence of CDRH3 of 386H03 using
      Kabat

<400> SEQUENCE: 157

Asp Gly Ser Gly Ser Tyr
1               5

<210> SEQ ID NO 158
<211> LENGTH: 115
<212> TYPE: PRT
<213> ORGANISM: Homo sapiens
<220> FEATURE:
<221> NAME/KEY: misc_feature
<223> OTHER INFORMATION: Amino acid sequence of VH of 386H03

<400> SEQUENCE: 158

Gln Val Gln Leu Gln Glu Ser Gly Pro Gly Leu Val Lys Pro Ser Gly
1               5                   10                  15

Thr Leu Ser Leu Thr Cys Ala Val Ser Gly Gly Ser Ile Ser Ser Ser
            20                  25                  30

Asp Trp Trp Ser Trp Val Arg Gln Pro Pro Gly Lys Gly Leu Glu Trp
        35                  40                  45

Ile Gly Glu Ile Phe His Ser Gly Asn Thr Asn Tyr Asn Pro Ser Leu
    50                  55                  60

Lys Ser Arg Val Thr Ile Ser Val Asp Lys Ser Lys Asn Gln Ile Ser
65                  70                  75                  80

Leu Arg Leu Asn Ser Val Thr Ala Ala Asp Thr Ala Val Tyr Tyr Cys
                85                  90                  95

Val Arg Asp Gly Ser Gly Ser Tyr Trp Gly Gln Gly Thr Leu Val Thr
            100                 105                 110

Val Ser Ser
        115

<210> SEQ ID NO 159
<211> LENGTH: 346
<212> TYPE: DNA
<213> ORGANISM: Homo sapiens
<220> FEATURE:
<221> NAME/KEY: misc_feature
<223> OTHER INFORMATION: Nucleic acid sequence of VH of 386H03

<400> SEQUENCE: 159
caggtgcagc tgcaggagtc gggcccagga ctggtgaagc cttcggggac cctgtccctc      60
acctgcgctg tctctggtgg ctccatcagc agtagtgact ggtggagttg ggtccgccag     120
cccccaggga aggggctgga gtggattggg gaaatctttc atagtgggaa caccaactac     180
aacccgtccc tcaagagtcg agtcaccata tcagtagaca gtccaagaa ccagatctcc      240 ctgaggctga actctgtgac cgccgcggac acggccgtgt attactgtgt gagagatggt     300
tcggggagtt actggggcca gggaaccctg gtcaccgtct cctcag                    346

<210> SEQ ID NO 160
<211> LENGTH: 445
<212> TYPE: PRT
<213> ORGANISM: Homo sapiens

```
<220> FEATURE:
<221> NAME/KEY: misc_feature
<223> OTHER INFORMATION: Amino acid sequence of 386H03 heavy chain

<400> SEQUENCE: 160

Gln Val Gln Leu Gln Glu Ser Gly Pro Gly Leu Val Lys Pro Ser Gly
1               5                   10                  15

Thr Leu Ser Leu Thr Cys Ala Val Ser Gly Gly Ser Ile Ser Ser Ser
            20                  25                  30

Asp Trp Trp Ser Trp Val Arg Gln Pro Pro Gly Lys Gly Leu Glu Trp
        35                  40                  45

Ile Gly Glu Ile Phe His Ser Gly Asn Thr Asn Tyr Asn Pro Ser Leu
50                  55                  60

Lys Ser Arg Val Thr Ile Ser Val Asp Lys Ser Lys Asn Gln Ile Ser
65                  70                  75                  80

Leu Arg Leu Asn Ser Val Thr Ala Ala Asp Thr Ala Val Tyr Tyr Cys
                85                  90                  95

Val Arg Asp Gly Ser Gly Ser Tyr Trp Gly Gln Gly Thr Leu Val Thr
            100                 105                 110

Val Ser Ser Ala Ser Thr Lys Gly Pro Ser Val Phe Pro Leu Ala Pro
        115                 120                 125

Ser Ser Lys Ser Thr Ser Gly Gly Thr Ala Ala Leu Gly Cys Leu Val
130                 135                 140

Lys Asp Tyr Phe Pro Glu Pro Val Thr Val Ser Trp Asn Ser Gly Ala
145                 150                 155                 160

Leu Thr Ser Gly Val His Thr Phe Pro Ala Val Leu Gln Ser Ser Gly
                165                 170                 175

Leu Tyr Ser Leu Ser Ser Val Val Thr Val Pro Ser Ser Ser Leu Gly
            180                 185                 190

Thr Gln Thr Tyr Ile Cys Asn Val Asn His Lys Pro Ser Asn Thr Lys
        195                 200                 205

Val Asp Lys Lys Val Glu Pro Lys Ser Cys Asp Lys Thr His Thr Cys
210                 215                 220

Pro Pro Cys Pro Ala Pro Glu Leu Leu Gly Gly Pro Ser Val Phe Leu
225                 230                 235                 240

Phe Pro Pro Lys Pro Lys Asp Thr Leu Met Ile Ser Arg Thr Pro Glu
                245                 250                 255

Val Thr Cys Val Val Val Asp Val Ser His Glu Asp Pro Glu Val Lys
            260                 265                 270

Phe Asn Trp Tyr Val Asp Gly Val Glu Val His Asn Ala Lys Thr Lys
        275                 280                 285

Pro Arg Glu Glu Gln Tyr Asn Ser Thr Tyr Arg Val Val Ser Val Leu
290                 295                 300

Thr Val Leu His Gln Asp Trp Leu Asn Gly Lys Glu Tyr Lys Cys Lys
305                 310                 315                 320

Val Ser Asn Lys Ala Leu Pro Ala Pro Ile Glu Lys Thr Ile Ser Lys
                325                 330                 335

Ala Lys Gly Gln Pro Arg Glu Pro Gln Val Tyr Thr Leu Pro Pro Ser
            340                 345                 350

Arg Asp Glu Leu Thr Lys Asn Gln Val Ser Leu Thr Cys Leu Val Lys
        355                 360                 365

Gly Phe Tyr Pro Ser Asp Ile Ala Val Glu Trp Glu Ser Asn Gly Gln
370                 375                 380

Pro Glu Asn Asn Tyr Lys Thr Thr Pro Pro Val Leu Asp Ser Asp Gly
```

```
                385              390              395              400
Ser Phe Phe Leu Tyr Ser Lys Leu Thr Val Asp Lys Ser Arg Trp Gln
                    405              410              415

Gln Gly Asn Val Phe Ser Cys Ser Val Met His Glu Ala Leu His Asn
                420              425              430

His Tyr Thr Gln Lys Ser Leu Ser Leu Ser Pro Gly Lys
                435              440              445

<210> SEQ ID NO 161
<211> LENGTH: 1335
<212> TYPE: DNA
<213> ORGANISM: Homo sapiens
<220> FEATURE:
<221> NAME/KEY: misc_feature
<223> OTHER INFORMATION: Nucleic acid sequence of 386H03 heavy chain

<400> SEQUENCE: 161
caggtgcagc tgcaggagtc gggcccagga ctggtgaagc cttcggggac cctgtccctc      60
acctgcgctg tctctggtgg ctccatcagc agtagtgact ggtggagttg ggtccgccag     120
cccccaggga aggggctgga gtggattggg gaaatctttc atagtgggaa caccaactac     180
aacccgtccc tcaagagtcg agtcaccata tcagtagaca gtccaagaa ccagatctcc      240 ctgaggctga actctgtgac cgccgcggac acggccgtgt attactgtgt gagagatggt     300
tcggggagtt actggggcca gggaaccctg gtcaccgtct cctcagccag caccaagggc     360
ccctctgtgt tccctctggc cccttccagc aagtccacct ctgcggaac agccgctctg      420 ggctgcctcg tgaaggacta cttccccgag cctgtgaccg tgtcctggaa ctctggcgct     480
ctgaccagcg gagtgcacac cttccctgct gtgctgcagt cctccggcct gtactccctg     540
tcctccgtcg tgaccgtgcc ttccagctct ctgggcaccc agacctacat ctgcaacgtg     600
aaccacaagc cctccaacac caaggtggac aagaaggtgg aacccaagtc ctgcgacaag     660
acccacacct gtcccccttg tcctgcccct gaactgctgg gcggaccttc cgtgttcctg     720
ttccccccaa agcccaagga caccctgatg atctcccgga ccccgaagt gacctgcgtg      780 gtggtggatg tgtcccacga ggaccctgaa gtgaagttca attggtacgt ggacggcgtg     840
gaagtgcaca cgccaagac caagcctaga gaggaacagt acaactccac ctaccgggtg     900
gtgtccgtgc tgaccgtgct gcaccaggat tggctgaacg gcaaagagta caagtgcaag     960
gtgtccaaca aggccctgcc tgcccccatc gaaaagacca tctccaaggc caagggccag    1020
ccccgggaac cccaggtgta cacactgccc cctagcaggg acgagctgac caagaaccag    1080
gtgtccctga cctgtctcgt gaaaggcttc taccctcccg atatcgccgt ggaatgggag    1140
tccaacggcc agcctgagaa caactacaag accaccccc ctgtgctgga ctccgacggc    1200
tcattcttcc tgtacagcaa gctgacagtg gacaagtccc ggtggcagca gggcaacgtg    1260
ttctcctgct ccgtgatgca cgaggccctg cacaaccact acacccagaa gtccctgtcc    1320
ctgagccccg gcaag                                                     1335

<210> SEQ ID NO 162
<211> LENGTH: 12
<212> TYPE: PRT
<213> ORGANISM: Homo sapiens
<220> FEATURE:
<221> NAME/KEY: misc_feature
<223> OTHER INFORMATION: Amino acid sequence of CDRL1 of 386H03 using
      IMGT

<400> SEQUENCE: 162
```

```
Gln Ser Val Leu Tyr Ser Ser Asn Asn Lys Asn Tyr
1               5                   10
```

<210> SEQ ID NO 163
<211> LENGTH: 3
<212> TYPE: PRT
<213> ORGANISM: Homo sapiens
<220> FEATURE:
<221> NAME/KEY: misc_feature
<223> OTHER INFORMATION: Amino acid sequence of CDRL2 of 386H03 using
      IMGT

<400> SEQUENCE: 163

```
Trp Ala Ser
1
```

<210> SEQ ID NO 164
<211> LENGTH: 8
<212> TYPE: PRT
<213> ORGANISM: Homo sapiens
<220> FEATURE:
<221> NAME/KEY: misc_feature
<223> OTHER INFORMATION: Amino acid sequence of CDRL3 of 386H03 using
      IMGT

<400> SEQUENCE: 164

```
Gln Gln Tyr Tyr Ser Thr Arg Ser
1               5
```

<210> SEQ ID NO 165
<211> LENGTH: 17
<212> TYPE: PRT
<213> ORGANISM: Homo sapiens
<220> FEATURE:
<221> NAME/KEY: misc_feature
<223> OTHER INFORMATION: Amino acid sequence of CDRL1 of 386H03 using
      Kabat

<400> SEQUENCE: 165

```
Lys Ser Ser Gln Ser Val Leu Tyr Ser Ser Asn Asn Lys Asn Tyr Leu
1               5                   10                  15

Ala
```

<210> SEQ ID NO 166
<211> LENGTH: 7
<212> TYPE: PRT
<213> ORGANISM: Homo sapiens
<220> FEATURE:
<221> NAME/KEY: misc_feature
<223> OTHER INFORMATION: Amino acid sequence of CDRL2 of 386H03 using
      Kabat

<400> SEQUENCE: 166

```
Trp Ala Ser Thr Arg Glu Ser
1               5
```

<210> SEQ ID NO 167
<211> LENGTH: 8
<212> TYPE: PRT
<213> ORGANISM: Homo sapiens
<220> FEATURE:
<221> NAME/KEY: misc_feature
<223> OTHER INFORMATION: Amino acid sequence of CDRL3 of 386H03 using
      Kabat

<400> SEQUENCE: 167

```
Gln Gln Tyr Tyr Ser Thr Arg Ser
```

<210> SEQ ID NO 168
<211> LENGTH: 112
<212> TYPE: PRT
<213> ORGANISM: Homo sapiens
<220> FEATURE:
<221> NAME/KEY: misc_feature
<223> OTHER INFORMATION: Amino acid sequence of VL of 386H03

<400> SEQUENCE: 168

Asp Ile Val Met Thr Gln Ser Pro Asp Ser Leu Ala Val Ser Leu Gly
1               5                   10                  15
Glu Arg Ala Thr Ile Asn Cys Lys Ser Ser Gln Ser Val Leu Tyr Ser
            20                  25                  30
Ser Asn Asn Lys Asn Tyr Leu Ala Trp Tyr Gln Gln Lys Pro Gly Gln
        35                  40                  45
Pro Pro Lys Leu Leu Ile Tyr Trp Ala Ser Thr Arg Glu Ser Gly Val
    50                  55                  60
Pro Asp Arg Phe Ser Gly Ser Gly Ser Gly Thr Asp Phe Thr Leu Thr
65                  70                  75                  80
Ile Ser Ser Leu Gln Ala Glu Asp Val Ala Val Tyr Tyr Cys Gln Gln
                85                  90                  95
Tyr Tyr Ser Thr Arg Ser Phe Gly Gln Gly Thr Lys Leu Glu Ile Lys
            100                 105                 110

<210> SEQ ID NO 169
<211> LENGTH: 337
<212> TYPE: DNA
<213> ORGANISM: Homo sapiens
<220> FEATURE:
<221> NAME/KEY: misc_feature
<223> OTHER INFORMATION: Nucleic acid sequence of VL of 386H03

<400> SEQUENCE: 169
gacatcgtga tgacccagtc tccagactcc ctggctgtgt ctctgggcga gagggccacc      60
atcaactgca gtccagcca gagtgtttta tacagctcca acaataagaa ctacttagct      120
tggtaccagc agaaaccagg acagcctcct aaactgctca tttactgggc atctacccgg     180
gaatccgggg tccctgaccg attcagtggc agcgggtctg ggacagattt cactctcacc     240
atcagcagcc tgcaggctga agatgtggca gtttattact gtcagcaata ttatagtact     300
cgcagttttg gccaggggac caagctggag atcaaac                              337

<210> SEQ ID NO 170
<211> LENGTH: 219
<212> TYPE: PRT
<213> ORGANISM: Homo sapiens
<220> FEATURE:
<221> NAME/KEY: misc_feature
<223> OTHER INFORMATION: Amino acid sequence of 386H03 light chain

<400> SEQUENCE: 170

Asp Ile Val Met Thr Gln Ser Pro Asp Ser Leu Ala Val Ser Leu Gly
1               5                   10                  15
Glu Arg Ala Thr Ile Asn Cys Lys Ser Ser Gln Ser Val Leu Tyr Ser
            20                  25                  30
Ser Asn Asn Lys Asn Tyr Leu Ala Trp Tyr Gln Gln Lys Pro Gly Gln
        35                  40                  45
Pro Pro Lys Leu Leu Ile Tyr Trp Ala Ser Thr Arg Glu Ser Gly Val
    50                  55                  60

```
Pro Asp Arg Phe Ser Gly Ser Gly Ser Gly Thr Asp Phe Thr Leu Thr
 65                  70                  75                  80

Ile Ser Ser Leu Gln Ala Glu Asp Val Ala Val Tyr Tyr Cys Gln Gln
                 85                  90                  95

Tyr Tyr Ser Thr Arg Ser Phe Gly Gln Gly Thr Lys Leu Glu Ile Lys
            100                 105                 110

Arg Thr Val Ala Ala Pro Ser Val Phe Ile Phe Pro Pro Ser Asp Glu
        115                 120                 125

Gln Leu Lys Ser Gly Thr Ala Ser Val Val Cys Leu Leu Asn Asn Phe
    130                 135                 140

Tyr Pro Arg Glu Ala Lys Val Gln Trp Lys Val Asp Asn Ala Leu Gln
145                 150                 155                 160

Ser Gly Asn Ser Gln Glu Ser Val Thr Glu Gln Asp Ser Lys Asp Ser
                165                 170                 175

Thr Tyr Ser Leu Ser Ser Thr Leu Thr Leu Ser Lys Ala Asp Tyr Glu
            180                 185                 190

Lys His Lys Val Tyr Ala Cys Glu Val Thr His Gln Gly Leu Ser Ser
        195                 200                 205

Pro Val Thr Lys Ser Phe Asn Arg Gly Glu Cys
    210                 215

<210> SEQ ID NO 171
<211> LENGTH: 657
<212> TYPE: DNA
<213> ORGANISM: Homo sapiens
<220> FEATURE:
<221> NAME/KEY: misc_feature
<223> OTHER INFORMATION: Nucleic acid sequence of 386H03 light chain

<400> SEQUENCE: 171
gacatcgtga tgacccagtc tccagactcc ctggctgtgt ctctgggcga gagggccacc      60
atcaactgca gtccagcca gagtgtttta tacagctcca acaataagaa ctacttagct      120
tggtaccagc agaaaccagg acagcctcct aaactgctca tttactgggc atctacccgg     180
gaatccgggg tccctgaccg attcagtggc agcgggtctg ggacagattt cactctcacc     240
atcagcagcc tgcaggctga agatgtggca gtttattact gtcagcaata ttatagtact    300
cgcagttttg gccaggggac caagctggag atcaaacgta cggtggccgc tcccctccgtg    360 ttcatcttcc caccttccga cgagcagctg aagtccggca ccgcttctgt cgtgtgcctg    420
ctgaacaact ctacccccg cgaggccaag gtgcagtgga aggtggacaa cgccctgcag    480
tccggcaact cccaggaatc cgtgaccgag caggactcca aggacagcac ctactccctg     540
tcctccaccc tgaccctgtc caaggccgac tacgagaagc acaaggtgta cgcctgcgaa     600
gtgacccacc agggcctgtc tagccccgtg accaagtctt tcaaccgggg cgagtgt       657

<210> SEQ ID NO 172
<211> LENGTH: 10
<212> TYPE: PRT
<213> ORGANISM: Homo sapiens
<220> FEATURE:
<221> NAME/KEY: misc_feature
<223> OTHER INFORMATION: Amino acid sequence of CDRH1 of 389A03 using
      IMGT

<400> SEQUENCE: 172

Gly Gly Ser Ile Ser Ser Ser Ser Tyr Tyr
1               5                   10
```

```
<210> SEQ ID NO 173
<211> LENGTH: 7
<212> TYPE: PRT
<213> ORGANISM: Homo sapiens
<220> FEATURE:
<221> NAME/KEY: misc_feature
<223> OTHER INFORMATION: Amino acid sequence of CDRH2 of 389A03 using
      IMGT

<400> SEQUENCE: 173

Ile Tyr Ser Thr Gly Tyr Thr
1               5

<210> SEQ ID NO 174
<211> LENGTH: 13
<212> TYPE: PRT
<213> ORGANISM: Homo sapiens
<220> FEATURE:
<221> NAME/KEY: misc_feature
<223> OTHER INFORMATION: Amino acid sequence of CDRH3 of 389A03 using
      IMGT

<400> SEQUENCE: 174

Ala Ile Ser Thr Ala Ala Gly Pro Glu Tyr Phe His Arg
1               5                   10

<210> SEQ ID NO 175
<211> LENGTH: 7
<212> TYPE: PRT
<213> ORGANISM: Homo sapiens
<220> FEATURE:
<221> NAME/KEY: misc_feature
<223> OTHER INFORMATION: Amino acid sequence of CDRH1 of 389A03 using
      Kabat

<400> SEQUENCE: 175

Ser Ser Ser Tyr Tyr Cys Gly
1               5

<210> SEQ ID NO 176
<211> LENGTH: 16
<212> TYPE: PRT
<213> ORGANISM: Homo sapiens
<220> FEATURE:
<221> NAME/KEY: misc_feature
<223> OTHER INFORMATION: Amino acid sequence of CDRH2 of 389A03 using
      Kabat

<400> SEQUENCE: 176

Ser Ile Tyr Ser Thr Gly Tyr Thr Tyr Tyr Asn Pro Ser Leu Lys Ser
1               5                   10                  15

<210> SEQ ID NO 177
<211> LENGTH: 11
<212> TYPE: PRT
<213> ORGANISM: Homo sapiens
<220> FEATURE:
<221> NAME/KEY: misc_feature
<223> OTHER INFORMATION: Amino acid sequence of CDRH3 of 389A03 using
      Kabat

<400> SEQUENCE: 177

Ser Thr Ala Ala Gly Pro Glu Tyr Phe His Arg
1               5                   10

<210> SEQ ID NO 178
<211> LENGTH: 120
<212> TYPE: PRT
```

<213> ORGANISM: Homo sapiens
<220> FEATURE:
<221> NAME/KEY: misc_feature
<223> OTHER INFORMATION: Amino acid sequence of VH of 389A03

<400> SEQUENCE: 178

```
Gln Leu Gln Glu Ser Gly Pro Gly Leu Val Lys Pro Ser Glu Thr Leu
1               5                   10                  15

Ser Leu Thr Cys Thr Val Ser Gly Gly Ser Ile Ser Ser Ser Ser Tyr
            20                  25                  30

Tyr Cys Gly Trp Ile Arg Gln Pro Pro Gly Lys Gly Leu Asp Trp Ile
        35                  40                  45

Gly Ser Ile Tyr Ser Thr Gly Tyr Thr Tyr Tyr Asn Pro Ser Leu Lys
    50                  55                  60

Ser Arg Val Thr Ile Ser Ile Asp Thr Ser Lys Asn Gln Phe Ser Cys
65                  70                  75                  80

Leu Ile Leu Thr Ser Val Thr Ala Ala Asp Thr Ala Val Tyr Tyr Cys
                85                  90                  95

Ala Ile Ser Thr Ala Ala Gly Pro Glu Tyr Phe His Arg Trp Gly Gln
            100                 105                 110

Gly Thr Leu Val Thr Val Ser Ser
        115                 120
```

<210> SEQ ID NO 179
<211> LENGTH: 361
<212> TYPE: DNA
<213> ORGANISM: Homo sapiens
<220> FEATURE:
<221> NAME/KEY: misc_feature
<223> OTHER INFORMATION: Nucleic acid sequence of VH of 389A03

<400> SEQUENCE: 179

```
cagctgcagg agtcgggccc aggcctggtg aagccttcgg agaccctgtc cctcacctgc      60
actgtctctg gtggctccat cagcagtagt agttattact gcggctggat ccgccagccc     120
cctgggaagg ggctggactg gattgggagt atctattcta ctgggtacac ctactacaac     180
ccgtccctca gagtcgagt caccatttcc atagacacgt ccaagaacca gttctcatgc     240
ctgatactga cctctgtgac cgccgcagac acggctgtgt attactgtgc gataagtaca     300
gcagctggcc ctgaatactt ccatcgctgg ggccagggca ccctggtcac cgtctcctca     360
g                                                                    361
```

<210> SEQ ID NO 180
<211> LENGTH: 450
<212> TYPE: PRT
<213> ORGANISM: Homo sapiens
<220> FEATURE:
<221> NAME/KEY: misc_feature
<223> OTHER INFORMATION: Amino acid sequence of 389A03 heavy chain

<400> SEQUENCE: 180

```
Gln Leu Gln Glu Ser Gly Pro Gly Leu Val Lys Pro Ser Glu Thr Leu
1               5                   10                  15

Ser Leu Thr Cys Thr Val Ser Gly Gly Ser Ile Ser Ser Ser Ser Tyr
            20                  25                  30

Tyr Cys Gly Trp Ile Arg Gln Pro Pro Gly Lys Gly Leu Asp Trp Ile
        35                  40                  45

Gly Ser Ile Tyr Ser Thr Gly Tyr Thr Tyr Tyr Asn Pro Ser Leu Lys
    50                  55                  60
```

```
Ser Arg Val Thr Ile Ser Ile Asp Thr Ser Lys Asn Gln Phe Ser Cys
 65                  70                  75                  80

Leu Ile Leu Thr Ser Val Thr Ala Ala Asp Thr Ala Val Tyr Tyr Cys
                 85                  90                  95

Ala Ile Ser Thr Ala Ala Gly Pro Glu Tyr Phe His Arg Trp Gly Gln
            100                 105                 110

Gly Thr Leu Val Thr Val Ser Ser Ala Ser Thr Lys Gly Pro Ser Val
        115                 120                 125

Phe Pro Leu Ala Pro Ser Ser Lys Ser Thr Ser Gly Gly Thr Ala Ala
    130                 135                 140

Leu Gly Cys Leu Val Lys Asp Tyr Phe Pro Glu Pro Val Thr Val Ser
145                 150                 155                 160

Trp Asn Ser Gly Ala Leu Thr Ser Gly Val His Thr Phe Pro Ala Val
                165                 170                 175

Leu Gln Ser Ser Gly Leu Tyr Ser Leu Ser Ser Val Val Thr Val Pro
            180                 185                 190

Ser Ser Ser Leu Gly Thr Gln Thr Tyr Ile Cys Asn Val Asn His Lys
        195                 200                 205

Pro Ser Asn Thr Lys Val Asp Lys Lys Val Glu Pro Lys Ser Cys Asp
    210                 215                 220

Lys Thr His Thr Cys Pro Pro Cys Pro Ala Pro Glu Leu Leu Gly Gly
225                 230                 235                 240

Pro Ser Val Phe Leu Phe Pro Pro Lys Pro Lys Asp Thr Leu Met Ile
                245                 250                 255

Ser Arg Thr Pro Glu Val Thr Cys Val Val Val Asp Val Ser His Glu
            260                 265                 270

Asp Pro Glu Val Lys Phe Asn Trp Tyr Val Asp Gly Val Glu Val His
        275                 280                 285

Asn Ala Lys Thr Lys Pro Arg Glu Glu Gln Tyr Asn Ser Thr Tyr Arg
    290                 295                 300

Val Val Ser Val Leu Thr Val Leu His Gln Asp Trp Leu Asn Gly Lys
305                 310                 315                 320

Glu Tyr Lys Cys Lys Val Ser Asn Lys Ala Leu Pro Ala Pro Ile Glu
                325                 330                 335

Lys Thr Ile Ser Lys Ala Lys Gly Gln Pro Arg Glu Pro Gln Val Tyr
            340                 345                 350

Thr Leu Pro Pro Ser Arg Asp Glu Leu Thr Lys Asn Gln Val Ser Leu
        355                 360                 365

Thr Cys Leu Val Lys Gly Phe Tyr Pro Ser Asp Ile Ala Val Glu Trp
    370                 375                 380

Glu Ser Asn Gly Gln Pro Glu Asn Asn Tyr Lys Thr Thr Pro Pro Val
385                 390                 395                 400

Leu Asp Ser Asp Gly Ser Phe Phe Leu Tyr Ser Lys Leu Thr Val Asp
                405                 410                 415

Lys Ser Arg Trp Gln Gln Gly Asn Val Phe Ser Cys Ser Val Met His
            420                 425                 430

Glu Ala Leu His Asn His Tyr Thr Gln Lys Ser Leu Ser Leu Ser Pro
        435                 440                 445

Gly Lys
    450

<210> SEQ ID NO 181
<211> LENGTH: 1350
<212> TYPE: DNA
```

<213> ORGANISM: Homo sapiens
<220> FEATURE:
<221> NAME/KEY: misc_feature
<223> OTHER INFORMATION: Nucleic acid sequence of 389A03 heavy chain

<400> SEQUENCE: 181

```
cagctgcagg agtcgggccc aggcctggtg aagccttcgg agaccctgtc cctcacctgc    60
actgtctctg gtggctccat cagcagtagt agttattact gcggctggat ccgccagccc   120
cctgggaagg gctggactg gattgggagt atctattcta ctgggtacac ctactacaac   180
ccgtccctca agagtcgagt caccatttcc atagacacgt ccaagaacca gttctcatgc   240
ctgatactga cctctgtgac cgccgcagac acggctgtgt attactgtgc gataagtaca   300
gcagctggcc ctgaatactt ccatcgctgg ggccagggca ccctggtcac cgtctcctca   360
gccagcacca agggcccctc tgtgttccct ggccccctt ccagcaagtc cacctctggc   420
ggaacagccg ctctgggctg cctcgtgaag gactacttcc ccgagcctgt gaccgtgtcc   480
tggaactctg gcgctctgac cagcggagtg cacaccttcc ctgctgtgct gcagtcctcc   540
ggcctgtact ccctgtcctc cgtcgtgacc gtgccttcca gctctctggg cacccagacc   600
tacatctgca acgtgaacca caagccctcc aacaccaagg tggacaagaa ggtggaaccc   660
aagtcctgcg acaagaccca cacctgtccc ccttgtcctg cccctgaact gctgggcgga   720
ccttccgtgt tcctgttccc cccaaagccc aaggacaccc tgatgatctc ccggaccccc   780
gaagtgacct gcgtggtggt ggatgtgtcc cacgaggacc ctgaagtgaa gttcaattgg   840
tacgtggacg gcgtggaagt gcacaacgcc aagaccaagc ctagagagga acagtacaac   900
tccacctacc gggtggtgtc cgtgctgacc gtgctgcacc aggattggct gaacggcaaa   960
gagtacaagt gcaaggtgtc caacaaggcc ctgcctgccc catcgaaaa gaccatctcc  1020
aaggccaagg ccagccccg gaaccccag gtgtacacac tgcccctag cagggacgag  1080
ctgaccaaga accaggtgtc cctgacctgt ctcgtgaaag cttctaccc ctccgatatc  1140
gccgtggaat gggagtccaa cggccagcct gagaacaact acaagaccac cccccctgtg  1200
ctggactccg acggctcatt cttcctgtac agcaagctga cagtggacaa gtcccggtgg  1260
cagcagggca acgtgttctc ctgctccgtg atgcacgagg ccctgcacaa ccactacacc  1320
cagaagtccc tgtccctgag ccccggcaag                                   1350
```

<210> SEQ ID NO 182
<211> LENGTH: 12
<212> TYPE: PRT
<213> ORGANISM: Homo sapiens
<220> FEATURE:
<221> NAME/KEY: misc_feature
<223> OTHER INFORMATION: Amino acid sequence of CDRL1 of 389A03 using
      IMGT

<400> SEQUENCE: 182

Gln Ser Val Leu Tyr Ser Ser Asn Ser Lys Asn Phe
1               5                   10

<210> SEQ ID NO 183
<211> LENGTH: 3
<212> TYPE: PRT
<213> ORGANISM: Homo sapiens
<220> FEATURE:
<221> NAME/KEY: misc_feature
<223> OTHER INFORMATION: Amino acid sequence of CDRL2 of 389A03 using
      IMGT

<400> SEQUENCE: 183

Trp Ala Ser
1

<210> SEQ ID NO 184
<211> LENGTH: 9
<212> TYPE: PRT
<213> ORGANISM: Homo sapiens
<220> FEATURE:
<221> NAME/KEY: misc_feature
<223> OTHER INFORMATION: Amino acid sequence of CDRL3 of 389A03 using
      IMGT

<400> SEQUENCE: 184

Gln Gln Tyr Tyr Ser Thr Pro Arg Thr
1               5

<210> SEQ ID NO 185
<211> LENGTH: 17
<212> TYPE: PRT
<213> ORGANISM: Homo sapiens
<220> FEATURE:
<221> NAME/KEY: misc_feature
<223> OTHER INFORMATION: Amino acid sequence of CDRL1 of 389A03 using
      Kabat

<400> SEQUENCE: 185

Lys Ser Ser Gln Ser Val Leu Tyr Ser Ser Asn Ser Lys Asn Phe Leu
1               5                   10                  15

Ala

<210> SEQ ID NO 186
<211> LENGTH: 7
<212> TYPE: PRT
<213> ORGANISM: Homo sapiens
<220> FEATURE:
<221> NAME/KEY: misc_feature
<223> OTHER INFORMATION: Amino acid sequence of CDRL2 of 389A03 using
      Kabat

<400> SEQUENCE: 186

Trp Ala Ser Thr Arg Gly Ser
1               5

<210> SEQ ID NO 187
<211> LENGTH: 9
<212> TYPE: PRT
<213> ORGANISM: Homo sapiens
<220> FEATURE:
<221> NAME/KEY: misc_feature
<223> OTHER INFORMATION: Amino acid sequence of CDRL3 of 389A03 using
      Kabat

<400> SEQUENCE: 187

Gln Gln Tyr Tyr Ser Thr Pro Arg Thr
1               5

<210> SEQ ID NO 188
<211> LENGTH: 113
<212> TYPE: PRT
<213> ORGANISM: Homo sapiens
<220> FEATURE:
<221> NAME/KEY: misc_feature
<223> OTHER INFORMATION: Amino acid sequence of VL of 389A03

<400> SEQUENCE: 188

Asp Ile Val Met Thr Gln Ser Pro Asp Ser Leu Ala Val Ser Leu Gly
1               5                   10                  15

```
Glu Arg Ala Thr Ile Asn Cys Lys Ser Ser Gln Ser Val Leu Tyr Ser
            20                  25                  30

Ser Asn Ser Lys Asn Phe Leu Ala Trp Tyr Gln Gln Lys Pro Gly Gln
            35                  40                  45

Pro Pro Lys Leu Phe Ile Tyr Trp Ala Ser Thr Arg Gly Ser Gly Val
 50                  55                  60

Pro Asp Arg Ile Ser Gly Ser Gly Ser Gly Thr Asp Phe Asn Leu Thr
 65                  70                  75                  80

Ile Ser Ser Leu Gln Ala Glu Asp Val Ala Val Tyr Tyr Cys Gln Gln
                85                  90                  95

Tyr Tyr Ser Thr Pro Arg Thr Phe Gly Gln Gly Thr Lys Val Glu Ile
            100                 105                 110

Lys

<210> SEQ ID NO 189
<211> LENGTH: 340
<212> TYPE: DNA
<213> ORGANISM: Homo sapiens
<220> FEATURE:
<221> NAME/KEY: misc_feature
<223> OTHER INFORMATION: Nucleic acid sequence of VL of 389A03

<400> SEQUENCE: 189
gacatcgtga tgacccagtc tccagactcc ctggctgtgt ctctgggcga gagggccacc      60
atcaactgca agtccagcca gagtgtttta tacagctcca acagtaagaa cttcttagct     120
tggtaccagc agaaaccggg acagcctcct aagctgttca tttactgggc atctacccgg     180
ggatccgggg tccctgaccg aatcagtggc agcgggtctg ggacagattt caatctcacc     240
atcagcagcc tgcaggctga agatgtggca gtttattact gtcaacaata ttatagtact     300
cctcggacgt tcggccaagg gaccaaggtg gagatcaaac                           340

<210> SEQ ID NO 190
<211> LENGTH: 220
<212> TYPE: PRT
<213> ORGANISM: Homo sapiens
<220> FEATURE:
<221> NAME/KEY: misc_feature
<223> OTHER INFORMATION: Amino acid sequence of 389A03 light chain

<400> SEQUENCE: 190

Asp Ile Val Met Thr Gln Ser Pro Asp Ser Leu Ala Val Ser Leu Gly
1               5                   10                  15

Glu Arg Ala Thr Ile Asn Cys Lys Ser Ser Gln Ser Val Leu Tyr Ser
            20                  25                  30

Ser Asn Ser Lys Asn Phe Leu Ala Trp Tyr Gln Gln Lys Pro Gly Gln
            35                  40                  45

Pro Pro Lys Leu Phe Ile Tyr Trp Ala Ser Thr Arg Gly Ser Gly Val
 50                  55                  60

Pro Asp Arg Ile Ser Gly Ser Gly Ser Gly Thr Asp Phe Asn Leu Thr
 65                  70                  75                  80

Ile Ser Ser Leu Gln Ala Glu Asp Val Ala Val Tyr Tyr Cys Gln Gln
                85                  90                  95

Tyr Tyr Ser Thr Pro Arg Thr Phe Gly Gln Gly Thr Lys Val Glu Ile
            100                 105                 110

Lys Arg Thr Val Ala Ala Pro Ser Val Phe Ile Phe Pro Pro Ser Asp
            115                 120                 125
```

| Glu | Gln | Leu | Lys | Ser | Gly | Thr | Ala | Ser | Val | Val | Cys | Leu | Leu | Asn | Asn |
| --- | --- | --- | --- | --- | --- | --- | --- | --- | --- | --- | --- | --- | --- | --- | --- |
| 130 | | | | | 135 | | | | | 140 | | | | | |

| Phe | Tyr | Pro | Arg | Glu | Ala | Lys | Val | Gln | Trp | Lys | Val | Asp | Asn | Ala | Leu |
| --- | --- | --- | --- | --- | --- | --- | --- | --- | --- | --- | --- | --- | --- | --- | --- |
| 145 | | | | | 150 | | | | | 155 | | | | | 160 |

| Gln | Ser | Gly | Asn | Ser | Gln | Glu | Ser | Val | Thr | Glu | Gln | Asp | Ser | Lys | Asp |
| --- | --- | --- | --- | --- | --- | --- | --- | --- | --- | --- | --- | --- | --- | --- | --- |
| | | | 165 | | | | | 170 | | | | | 175 | | |

| Ser | Thr | Tyr | Ser | Leu | Ser | Ser | Thr | Leu | Thr | Leu | Ser | Lys | Ala | Asp | Tyr |
| --- | --- | --- | --- | --- | --- | --- | --- | --- | --- | --- | --- | --- | --- | --- | --- |
| | | | 180 | | | | | 185 | | | | | 190 | | |

| Glu | Lys | His | Lys | Val | Tyr | Ala | Cys | Glu | Val | Thr | His | Gln | Gly | Leu | Ser |
| --- | --- | --- | --- | --- | --- | --- | --- | --- | --- | --- | --- | --- | --- | --- | --- |
| | | | 195 | | | | | 200 | | | | | 205 | | |

| Ser | Pro | Val | Thr | Lys | Ser | Phe | Asn | Arg | Gly | Glu | Cys |
| --- | --- | --- | --- | --- | --- | --- | --- | --- | --- | --- | --- |
| 210 | | | | | 215 | | | | | 220 | |

<210> SEQ ID NO 191
<211> LENGTH: 660
<212> TYPE: DNA
<213> ORGANISM: Homo sapiens
<220> FEATURE:
<221> NAME/KEY: misc_feature
<223> OTHER INFORMATION: Nucleic acid sequence of 389A03 light chain

<400> SEQUENCE: 191

```
gacatcgtga tgacccagtc tccagactcc ctggctgtgt ctctgggcga gagggccacc     60
atcaactgca gtccagccga gtgttttta tacagctcca acagtaagaa cttcttagct    120
tggtaccagc agaaaccggg acagcctcct aagctgttca tttactgggc atctacccgg    180
ggatccgggg tccctgaccg aatcagtggc agcgggtctg ggacagattt caatctcacc    240
atcagcagcc tgcaggctga agatgtggca gtttattact gtcaacaata ttatagtact    300
cctcggacgt tcggccaagg gaccaaggtg gagatcaaac gtacggtggc cgctcccctcc   360
gtgttcatct tcccaccttc cgacgagcag ctgaagtccg gcaccgcttc tgtcgtgtgc    420
ctgctgaaca acttctaccc cgcgaggcc aaggtgcagt ggaaggtgga caacgccctg     480
cagtccggca actcccagga atccgtgacc gagcaggact ccaaggacag cacctactcc    540
ctgtcctcca ccctgaccct gtccaaggcc gactacgaga agcacaaggt gtacgcctgc    600
gaagtgaccc accagggcct gtctagcccc gtgaccaagt ctttcaaccg gggcgagtgt    660
```

<210> SEQ ID NO 192
<211> LENGTH: 981
<212> TYPE: DNA
<213> ORGANISM: Homo sapiens
<220> FEATURE:
<221> NAME/KEY: misc_feature
<223> OTHER INFORMATION: Heavy Chain Constant Region Nucleotide Sequence
    IGHG*01

<400> SEQUENCE: 192

```
gcttccacca agggcccatc cgtcttcccc ctggcgccct gctccaggag cacctccgag     60
agcacagccg ccctgggctg cctggtcaag gactacttcc ccgaaccggt gacggtgtcg    120
tggaactcag gcgccctgac cagcggcgtg cacaccttcc cggctgtcct acagtcctca    180
ggactctact ccctcagcag cgtggtgacc gtgccctcca gcagcttggg cacgaagacc    240
tacacctgca acgtagatca caagcccagc aacaccaagg tggacaagag agttgagtcc    300
aaatatggtc cccatgccc atcatgccca gcacctgagt tcctggggg accatcagtc     360
ttcctgttcc cccaaaaacc caaggacact ctcatgatct cccggacccc tgaggtcacg    420
tgcgtggtgg tggacgtgag ccaggaagac cccgaggtcc agttcaactg gtacgtggat    480
```

```
ggcgtggagg tgcataatgc caagacaaag ccgcgggagg agcagttcaa cagcacgtac    540
cgtgtggtca gcgtcctcac cgtcctgcac caggactggc tgaacggcaa ggagtacaag    600
tgcaaggtct ccaacaaagg cctcccgtcc tccatcgaga aaaccatctc caaagccaaa    660
gggcagcccc gagagccaca ggtgtacacc ctgcccccat cccaggagga gatgaccaag    720
aaccaggtca gcctgacctg cctggtcaaa ggcttctacc ccagcgacat cgccgtggag    780
tgggagagca atgggcagcc ggagaacaac tacaagacca cgcctcccgt gctggactcc    840
gacggctcct tcttcctcta cagcaggcta accgtggaca agagcaggtg gcaggagggg    900
aatgtcttct catgctccgt gatgcatgag gctctgcaca accactacac acagaagagc    960
ctctccctgt ctctgggtaa a    981
```

<210> SEQ ID NO 193
<211> LENGTH: 327
<212> TYPE: PRT
<213> ORGANISM: Homo sapiens
<220> FEATURE:
<221> NAME/KEY: misc_feature
<223> OTHER INFORMATION: Heavy Chain Constant Region Amino Acid Sequence IGHG*01

<400> SEQUENCE: 193

```
Ala Ser Thr Lys Gly Pro Ser Val Phe Pro Leu Ala Pro Cys Ser Arg
1               5                   10                  15

Ser Thr Ser Glu Ser Thr Ala Ala Leu Gly Cys Leu Val Lys Asp Tyr
            20                  25                  30

Phe Pro Glu Pro Val Thr Val Ser Trp Asn Ser Gly Ala Leu Thr Ser
        35                  40                  45

Gly Val His Thr Phe Pro Ala Val Leu Gln Ser Ser Gly Leu Tyr Ser
    50                  55                  60

Leu Ser Ser Val Val Thr Val Pro Ser Ser Ser Leu Gly Thr Lys Thr
65                  70                  75                  80

Tyr Thr Cys Asn Val Asp His Lys Pro Ser Asn Thr Lys Val Asp Lys
                85                  90                  95

Arg Val Glu Ser Lys Tyr Gly Pro Pro Cys Pro Ser Cys Pro Ala Pro
            100                 105                 110

Glu Phe Leu Gly Gly Pro Ser Val Phe Leu Phe Pro Pro Lys Pro Lys
        115                 120                 125

Asp Thr Leu Met Ile Ser Arg Thr Pro Glu Val Thr Cys Val Val Val
    130                 135                 140

Asp Val Ser Gln Glu Asp Pro Glu Val Gln Phe Asn Trp Tyr Val Asp
145                 150                 155                 160

Gly Val Glu Val His Asn Ala Lys Thr Lys Pro Arg Glu Glu Gln Phe
                165                 170                 175

Asn Ser Thr Tyr Arg Val Val Ser Val Leu Thr Val Leu His Gln Asp
            180                 185                 190

Trp Leu Asn Gly Lys Glu Tyr Lys Cys Lys Val Ser Asn Lys Gly Leu
        195                 200                 205

Pro Ser Ser Ile Glu Lys Thr Ile Ser Lys Ala Lys Gly Gln Pro Arg
    210                 215                 220

Glu Pro Gln Val Tyr Thr Leu Pro Pro Ser Gln Glu Glu Met Thr Lys
225                 230                 235                 240

Asn Gln Val Ser Leu Thr Cys Leu Val Lys Gly Phe Tyr Pro Ser Asp
                245                 250                 255

Ile Ala Val Glu Trp Glu Ser Asn Gly Gln Pro Glu Asn Asn Tyr Lys
```

```
              260                 265                 270
Thr Thr Pro Pro Val Leu Asp Ser Asp Gly Ser Phe Phe Leu Tyr Ser
            275                 280                 285

Arg Leu Thr Val Asp Lys Ser Arg Trp Gln Glu Gly Asn Val Phe Ser
            290                 295                 300

Cys Ser Val Met His Glu Ala Leu His Asn His Tyr Thr Gln Lys Ser
305                 310                 315                 320

Leu Ser Leu Ser Leu Gly Lys
                325
```

<210> SEQ ID NO 194
<211> LENGTH: 981
<212> TYPE: DNA
<213> ORGANISM: Homo sapiens
<220> FEATURE:
<221> NAME/KEY: misc_feature
<223> OTHER INFORMATION: Heavy Chain Constant Region Nucleotide Sequence
      IGHG*02

<400> SEQUENCE: 194

```
gcttccacca agggcccatc cgtcttcccc ctggcgccct gctccaggag cacctccgag      60
agcacagccg ccctgggctg cctggtcaag gactacttcc ccgaaccggt gacggtgtcg     120
tggaactcag gcgccctgac cagcggcgtg cacaccttcc cggctgtcct acagtcctca     180
ggactctact ccctcagcag cgtggtgacc gtgccctcca gcagcttggg cacgaagacc     240
tacacctgca acgtagatca caagcccagc aacaccaagg tggacaagag agttgagtcc     300
aaatatggtc cccgtgccc atcatgccca gcacctgagt tcctggggggg accatcagtc     360
ttcctgttcc ccccaaaacc caaggacact ctcatgatct cccggacccc tgaggtcacg     420
tgcgtggtgg tggacgtgag ccaggaagac cccgaggtcc agttcaactg gtacgtggat     480
ggcgtggagg tgcataatgc caagacaaag ccgcgggagg agcagttcaa cagcacgtac     540
cgtgtggtca gcgtcctcac cgtcgtgcac caggactggc tgaacggcaa ggagtacaag     600
tgcaaggtct ccaacaaagg cctcccgtcc tccatcgaga aaaccatctc caaagccaaa     660
gggcagcccc gagagccaca ggtgtacacc ctgcccccat cccaggagga gatgaccaag     720
aaccaggtca gcctgacctg cctggtcaaa ggcttctacc ccagcgacat cgccgtggag     780
tgggagagca atgggcagcc ggagaacaac tacaagacca cgcctcccgt gctggactcc     840
gacggctcct tcttcctcta cagcaggcta accgtggaca agagcaggtg gcaggagggg     900
aatgtcttct catgctccgt gatgcatgag gctctgcaca accactacac gcagaagagc     960
ctctccctgt ctctgggtaa a                                               981
```

<210> SEQ ID NO 195
<211> LENGTH: 327
<212> TYPE: PRT
<213> ORGANISM: Homo sapiens
<220> FEATURE:
<221> NAME/KEY: misc_feature
<223> OTHER INFORMATION: Heavy Chain Constant Region Amino Acid Sequence
      IGHG*02

<400> SEQUENCE: 195

```
Ala Ser Thr Lys Gly Pro Ser Val Phe Pro Leu Ala Pro Cys Ser Arg
1               5                  10                  15

Ser Thr Ser Glu Ser Thr Ala Ala Leu Gly Cys Leu Val Lys Asp Tyr
            20                  25                  30

Phe Pro Glu Pro Val Thr Val Ser Trp Asn Ser Gly Ala Leu Thr Ser
```

-continued

```
                35                  40                  45
Gly Val His Thr Phe Pro Ala Val Leu Gln Ser Ser Gly Leu Tyr Ser
 50                  55                  60
Leu Ser Ser Val Val Thr Val Pro Ser Ser Leu Gly Thr Lys Thr
 65                  70                  75                  80
Tyr Thr Cys Asn Val Asp His Lys Pro Ser Asn Thr Lys Val Asp Lys
                 85                  90                  95
Arg Val Glu Ser Lys Tyr Gly Pro Pro Cys Pro Ser Cys Pro Ala Pro
                100                 105                 110
Glu Phe Leu Gly Gly Pro Ser Val Phe Leu Phe Pro Pro Lys Pro Lys
            115                 120                 125
Asp Thr Leu Met Ile Ser Arg Thr Pro Glu Val Thr Cys Val Val Val
        130                 135                 140
Asp Val Ser Gln Glu Asp Pro Glu Val Gln Phe Asn Trp Tyr Val Asp
145                 150                 155                 160
Gly Val Glu Val His Asn Ala Lys Thr Lys Pro Arg Glu Glu Gln Phe
                165                 170                 175
Asn Ser Thr Tyr Arg Val Val Ser Val Leu Thr Val Val His Gln Asp
            180                 185                 190
Trp Leu Asn Gly Lys Glu Tyr Lys Cys Lys Val Ser Asn Lys Gly Leu
        195                 200                 205
Pro Ser Ser Ile Glu Lys Thr Ile Ser Lys Ala Lys Gly Gln Pro Arg
210                 215                 220
Glu Pro Gln Val Tyr Thr Leu Pro Pro Ser Gln Glu Glu Met Thr Lys
225                 230                 235                 240
Asn Gln Val Ser Leu Thr Cys Leu Val Lys Gly Phe Tyr Pro Ser Asp
                245                 250                 255
Ile Ala Val Glu Trp Glu Ser Asn Gly Gln Pro Glu Asn Asn Tyr Lys
            260                 265                 270
Thr Thr Pro Pro Val Leu Asp Ser Asp Gly Ser Phe Phe Leu Tyr Ser
        275                 280                 285
Arg Leu Thr Val Asp Lys Ser Arg Trp Gln Glu Gly Asn Val Phe Ser
290                 295                 300
Cys Ser Val Met His Glu Ala Leu His Asn His Tyr Thr Gln Lys Ser
305                 310                 315                 320
Leu Ser Leu Ser Leu Gly Lys
                325

<210> SEQ ID NO 196
<211> LENGTH: 981
<212> TYPE: DNA
<213> ORGANISM: Homo sapiens
<220> FEATURE:
<221> NAME/KEY: misc_feature
<223> OTHER INFORMATION: Heavy Chain Constant Region Nucleotide Sequence
      IGHG*03

<400> SEQUENCE: 196
gcttccacca agggcccatc cgtcttcccc ctggcgccct gctccaggag cacctccgag      60
agcacagccg ccctgggctg cctggtcaag gactacttcc ccgaaccggt gacggtgtcg     120
tggaactcag gcgccctgac cagcggcgtg cacaccttcc cggctgtcct acagtcctca     180
ggactctact ccctcagcag cgtggtgacc gtgccctcca gcagcttggg cacgaagacc     240
tacacctgca acgtagatca caagcccagc aacaccaagg tggacaagag agttgagtcc     300
aaatatggtc ccccatgccc atcatgccca gcacctgagt tcctgggggg accatcagtc     360
```

```
ttcctgttcc ccccaaaacc caaggacact ctcatgatct cccggacccc tgaggtcacg    420
tgcgtggtgg tggacgtgag ccaggaagac cccgaggtcc agttcaactg gtacgtggat    480
ggcgtggagg tgcataatgc caagacaaag ccgcgggagg agcagttcaa cagcacgtac    540
cgtgtggtca gcgtcctcac cgtcctgcac caggactggc tgaacggcaa ggagtacaag    600
tgcaaggtct ccaacaaagg cctcccgtcc tccatcgaga aaaccatctc caaagccaaa    660
gggcagcccc gagagccaca ggtgtacacc ctgcccccat cccaggagga gatgaccaag    720
aaccaggtca gcctgacctg cctggtcaaa ggcttctacc ccagcgacat cgccgtggag    780
tgggagagca atgggcagcc ggagaacaac tacaagacca cgcctcccgt gctggactcc    840
gacggctcct tcttcctcta cagcaagctc accgtggaca agagcaggtg gcaggagggg    900
aacgtcttct catgctccgt gatgcatgag gctctgcaca accactacac gcagaagagc    960
ctctccctgt ctctgggtaa a    981
```

<210> SEQ ID NO 197
<211> LENGTH: 327
<212> TYPE: PRT
<213> ORGANISM: Homo sapiens
<220> FEATURE:
<221> NAME/KEY: misc_feature
<223> OTHER INFORMATION: Heavy Chain Constant Region Amino Acid Sequence IGHG*03

<400> SEQUENCE: 197

```
Ala Ser Thr Lys Gly Pro Ser Val Phe Pro Leu Ala Pro Cys Ser Arg
1               5                   10                  15

Ser Thr Ser Glu Ser Thr Ala Ala Leu Gly Cys Leu Val Lys Asp Tyr
            20                  25                  30

Phe Pro Glu Pro Val Thr Val Ser Trp Asn Ser Gly Ala Leu Thr Ser
        35                  40                  45

Gly Val His Thr Phe Pro Ala Val Leu Gln Ser Ser Gly Leu Tyr Ser
    50                  55                  60

Leu Ser Ser Val Val Thr Val Pro Ser Ser Leu Gly Thr Lys Thr
65                  70                  75                  80

Tyr Thr Cys Asn Val Asp His Lys Pro Ser Asn Thr Lys Val Asp Lys
                85                  90                  95

Arg Val Glu Ser Lys Tyr Gly Pro Pro Cys Pro Ser Cys Pro Ala Pro
            100                 105                 110

Glu Phe Leu Gly Gly Pro Ser Val Phe Leu Phe Pro Pro Lys Pro Lys
        115                 120                 125

Asp Thr Leu Met Ile Ser Arg Thr Pro Glu Val Thr Cys Val Val Val
    130                 135                 140

Asp Val Ser Gln Glu Asp Pro Glu Val Gln Phe Asn Trp Tyr Val Asp
145                 150                 155                 160

Gly Val Glu Val His Asn Ala Lys Thr Lys Pro Arg Glu Glu Gln Phe
                165                 170                 175

Asn Ser Thr Tyr Arg Val Val Ser Val Leu Thr Val Leu His Gln Asp
            180                 185                 190

Trp Leu Asn Gly Lys Glu Tyr Lys Cys Lys Val Ser Asn Lys Gly Leu
        195                 200                 205

Pro Ser Ser Ile Glu Lys Thr Ile Ser Lys Ala Lys Gly Gln Pro Arg
    210                 215                 220

Glu Pro Gln Val Tyr Thr Leu Pro Pro Ser Gln Glu Glu Met Thr Lys
225                 230                 235                 240
```

```
Asn Gln Val Ser Leu Thr Cys Leu Val Lys Gly Phe Tyr Pro Ser Asp
                245                 250                 255

Ile Ala Val Glu Trp Glu Ser Asn Gly Gln Pro Glu Asn Asn Tyr Lys
            260                 265                 270

Thr Thr Pro Pro Val Leu Asp Ser Asp Gly Ser Phe Phe Leu Tyr Ser
        275                 280                 285

Lys Leu Thr Val Asp Lys Ser Arg Trp Gln Glu Gly Asn Val Phe Ser
    290                 295                 300

Cys Ser Val Met His Glu Ala Leu His Asn His Tyr Thr Gln Lys Ser
305                 310                 315                 320

Leu Ser Leu Ser Leu Gly Lys
                325

<210> SEQ ID NO 198
<211> LENGTH: 981
<212> TYPE: DNA
<213> ORGANISM: Homo sapiens
<220> FEATURE:
<221> NAME/KEY: misc_feature
<223> OTHER INFORMATION: HC Constant Region NT Sequence Synthetic
      Version A

<400> SEQUENCE: 198
gcctccacca agggcccatc cgtcttcccc ctggcgccct gctccaggag cacctccgag      60
agcacggccg ccctgggctg cctggtcaag gactacttcc ccgaaccagt gacggtgtcg     120
tggaactcag gcgccctgac cagcggcgtg cacaccttcc cggctgtcct acagtcctca     180
ggactctact ccctcagcag cgtggtgacc gtgccctcca gcagcttggg cacgaagacc     240
tacacctgca acgtagatca caagcccagc aacaccaagg tggacaagag agttgagtcc     300
aaatatggtc ccccatgccc accatgccca gcgcctgaat tgaggggggg accatcagtc     360
ttcctgttcc ccccaaaacc caaggacact ctcatgatct cccggacccc tgaggtcacg     420
tgcgtggtgg tggacgtgag ccaggaagac cccgaggtcc agttcaactg gtacgtggat     480
ggcgtggagg tgcataatgc caagacaaag ccgcggagg agcagttcaa cagcacgtac     540
cgtgtggtca gcgtcctcac cgtcctgcac caggactggc tgaacggcaa ggagtacaag     600
tgcaaggtct ccaacaaagg cctcccgtca tcgatcgaga aaaccatctc caaagccaaa     660
gggcagcccc gagagccaca ggtgtacacc ctgcccccat cccaggagga tgaccaag      720 aaccaggtca gcctgacctg cctggtcaaa ggcttctacc ccagcgacat cgccgtggag     780
tgggagagca atgggcagcc ggagaacaac tacaagacca cgcctcccgt gctggactcc     840
gacggatcct tcttcctcta cagcaggcta accgtggaca gagcaggtg gcaggagggg     900 aatgtcttct catgctccgt gatgcatgag gctctgcaca accactacac acagaagagc     960
ctctccctgt ctctgggtaa a                                               981

<210> SEQ ID NO 199
<211> LENGTH: 327
<212> TYPE: PRT
<213> ORGANISM: Homo sapiens
<220> FEATURE:
<221> NAME/KEY: misc_feature
<223> OTHER INFORMATION: HC Constant Region AA Sequence Encoded by
      Synthetic A, B & C

<400> SEQUENCE: 199

Ala Ser Thr Lys Gly Pro Ser Val Phe Pro Leu Ala Pro Cys Ser Arg
1               5                   10                  15
```

Ser Thr Ser Glu Ser Thr Ala Ala Leu Gly Cys Leu Val Lys Asp Tyr
            20                  25                  30

Phe Pro Glu Pro Val Thr Val Ser Trp Asn Ser Gly Ala Leu Thr Ser
        35                  40                  45

Gly Val His Thr Phe Pro Ala Val Leu Gln Ser Ser Gly Leu Tyr Ser
    50                  55                  60

Leu Ser Ser Val Val Thr Val Pro Ser Ser Leu Gly Thr Lys Thr
65                  70                  75                  80

Tyr Thr Cys Asn Val Asp His Lys Pro Ser Asn Thr Lys Val Asp Lys
                85                  90                  95

Arg Val Glu Ser Lys Tyr Gly Pro Pro Cys Pro Pro Cys Pro Ala Pro
            100                 105                 110

Glu Phe Glu Gly Gly Pro Ser Val Phe Leu Phe Pro Pro Lys Pro Lys
        115                 120                 125

Asp Thr Leu Met Ile Ser Arg Thr Pro Glu Val Thr Cys Val Val Val
    130                 135                 140

Asp Val Ser Gln Glu Asp Pro Glu Val Gln Phe Asn Trp Tyr Val Asp
145                 150                 155                 160

Gly Val Glu Val His Asn Ala Lys Thr Lys Pro Arg Glu Glu Gln Phe
                165                 170                 175

Asn Ser Thr Tyr Arg Val Val Ser Val Leu Thr Val Leu His Gln Asp
            180                 185                 190

Trp Leu Asn Gly Lys Glu Tyr Lys Cys Lys Val Ser Asn Lys Gly Leu
        195                 200                 205

Pro Ser Ser Ile Glu Lys Thr Ile Ser Lys Ala Lys Gly Gln Pro Arg
    210                 215                 220

Glu Pro Gln Val Tyr Thr Leu Pro Pro Ser Gln Glu Glu Met Thr Lys
225                 230                 235                 240

Asn Gln Val Ser Leu Thr Cys Leu Val Lys Gly Phe Tyr Pro Ser Asp
                245                 250                 255

Ile Ala Val Glu Trp Glu Ser Asn Gly Gln Pro Glu Asn Asn Tyr Lys
            260                 265                 270

Thr Thr Pro Pro Val Leu Asp Ser Asp Gly Ser Phe Phe Leu Tyr Ser
        275                 280                 285

Arg Leu Thr Val Asp Lys Ser Arg Trp Gln Glu Gly Asn Val Phe Ser
    290                 295                 300

Cys Ser Val Met His Glu Ala Leu His Asn His Tyr Thr Gln Lys Ser
305                 310                 315                 320

Leu Ser Leu Ser Leu Gly Lys
                325

<210> SEQ ID NO 200
<211> LENGTH: 981
<212> TYPE: DNA
<213> ORGANISM: Homo sapiens
<220> FEATURE:
<221> NAME/KEY: misc_feature
<223> OTHER INFORMATION: HC Constant Region NT Sequence Synthetic
      Version B

<400> SEQUENCE: 200
gcctccacca agggacctag cgtgttccct ctcgcccct gttccaggtc cacaagcgag     60
tccaccgctg ccctcggctg tctggtgaaa gactactttc ccgagcccgt gaccgtctcc    120
tggaatagcg gagccctgac ctccggcgtg cacacatttc ccgccgtgct gcagagcagc    180

| | |
|---|---|
| ggactgtata gcctgagcag cgtggtgacc gtgcccagct ccagcctcgg caccaaaacc | 240 |
| tacacctgca acgtggacca caagcccctcc aacaccaagg tggacaagcg ggtggagagc | 300 |
| aagtacggcc ccccttgccc tccttgtcct gcccctgagt tcgagggagg accctccgtg | 360 |
| ttcctgtttc cccccaaacc caaggacacc ctgatgatct cccggacacc cgaggtgacc | 420 |
| tgtgtggtcg tggacgtcag ccaggaggac cccgaggtgc agttcaactg gtatgtggac | 480 |
| ggcgtggagg tgcacaatgc caaaaccaag cccaggggag agcagttcaa ttccacctac | 540 |
| agggtggtga gcgtgctgac cgtcctgcat caggattggc tgaacggcaa ggagtacaag | 600 |
| tgcaaggtgt ccaacaaggg actgcccagc tccatcgaga agaccatcag caaggctaag | 660 |
| ggccagccga gggagcccca ggtgtatacc ctgcctccta gccaggaaga gatgaccaag | 720 |
| aaccaagtgt ccctgacctg cctggtgaag ggattctacc cctccgacat cgccgtggag | 780 |
| tgggagagca atggccagcc cgagaacaac tacaaaacaa cccctcccgt gctcgatagc | 840 |
| gacggcagct tctttctcta cagccggctg acagtggaca agagcaggtg gcaggagggc | 900 |
| aacgtgttct cctgttccgt gatgcacgag gccctgcaca tcactacac ccagaagagc | 960 |
| ctctccctgt ccctgggcaa g | 981 |

<210> SEQ ID NO 201
<211> LENGTH: 981
<212> TYPE: DNA
<213> ORGANISM: Homo sapiens
<220> FEATURE:
<221> NAME/KEY: misc_feature
<223> OTHER INFORMATION: HC Constant Region NT Sequence Synthetic Version C

<400> SEQUENCE: 201

| | |
|---|---|
| gccagcacca agggcccttc cgtgttcccc ctggcccctt gcagcaggag cacctccgaa | 60 |
| tccacagctg ccctgggctg tctggtgaag gactactttc ccgagcccgt gaccgtgagc | 120 |
| tggaacagcg gcgctctgac atccggcgtc cacacctttc ctgccgtcct gcagtcctcc | 180 |
| ggcctctact ccctgtcctc cgtggtgacc gtgcctagct cctccctcgg caccaagacc | 240 |
| tacacctgta acgtggacca caaaccctcc aacaccaagg tggacaaacg ggtcgagagc | 300 |
| aagtacggcc ctcccctgccc tccttgtcct gcccccgagt tcgaaggcgg acccagcgtg | 360 |
| ttcctgttcc ctcctaagcc caaggacacc ctcatgatca gccggacacc cgaggtgacc | 420 |
| tgcgtggtgg tggatgtgag ccaggaggac cctgaggtcc agttcaactg gtatgtggat | 480 |
| ggcgtggagg tgcacaacgc caagacaaag ccccgggaag agcagttcaa ctccacctac | 540 |
| agggtggtca gcgtgctgac cgtgctgcat caggactggc tgaacggcaa ggagtacaag | 600 |
| tgcaaggtca gcaataaggg actgcccagc agcatcgaga agaccatctc caaggctaaa | 660 |
| ggccagcccc gggaacctca ggtgtacacc ctgcctccca gcaggagga gatgaccaag | 720 |
| aaccaggtga gcctgacctg cctggtgaag ggattctacc cttccgacat cgccgtggag | 780 |
| tgggagtcca acgccagcc cgagaacaat tataagacca cccctcccgt cctcgacagc | 840 |
| gacggatcct tctttctgta ctccaggctg accgtggata gtccaggtg gcaggaaggc | 900 |
| aacgtgttca gctgctccgt gatgcacgag gccctgcaca tcactacac ccagaagtcc | 960 |
| ctgagcctgt ccctgggaaa g | 981 |

<210> SEQ ID NO 202
<211> LENGTH: 981
<212> TYPE: DNA
<213> ORGANISM: Homo sapiens
<220> FEATURE:
<221> NAME/KEY: misc_feature
<223> OTHER INFORMATION: HC Constant Region NT Sequence Synthetic
      Version D

<400> SEQUENCE: 202

```
gcctccacca agggcccatc cgtcttcccc ctggcgccct gctccaggag cacctccgag      60
agcacggccg ccctgggctg cctggtcaag gactacttcc ccgaaccagt gacggtgtcg     120
tggaactcag gcgccctgac cagcggcgtg cacaccttcc cggctgtcct acagtcctca     180
ggactctact ccctcagcag cgtggtgacc gtgccctcca gcagcttggg cacgaagacc     240
tacacctgca acgtagatca caagcccagc aacaccaagg tggacaagag agttgagtcc     300
aaatatggtc ccccatgccc accatgccca gcgcctccag ttgcgggggg accatcagtc     360
ttcctgttcc ccccaaaacc caaggacact ctcatgatct cccggacccc tgaggtcacg     420
tgcgtggtgg tggacgtgag ccaggaagac cccgaggtcc agttcaactg gtacgtggat     480
ggcgtggagg tgcataatgc caagacaaag ccgcgggagg agcagttcaa cagcacgtac     540
cgtgtggtca gcgtcctcac cgtcctgcac caggactggc tgaacggcaa ggagtacaag     600
tgcaaggtct ccaacaaagg cctcccgtca tcgatcgaga aaaccatctc aaaagccaaa     660
gggcagcccc gagagccaca ggtgtacacc ctgcccccat cccaggagga gatgaccaag     720
aaccaggtca gcctgacctg cctggtcaaa ggcttctacc ccagcgacat cgccgtggag     780
tgggagagca atgggcagcc ggagaacaac tacaagacca cgcctcccgt gctggactcc     840
gacggatcct tcttcctcta cagcaggcta accgtggaca gagcaggtg gcaggagggg     900 aatgtcttct catgctccgt gatgcatgag gctctgcaca accactacac acagaagagc     960
ctctccctgt ctctgggtaa a                                                981
```

<210> SEQ ID NO 203
<211> LENGTH: 327
<212> TYPE: PRT
<213> ORGANISM: Homo sapiens
<220> FEATURE:
<221> NAME/KEY: misc_feature
<223> OTHER INFORMATION: HC Constant Region AA Sequence encoded by
      Synthetic D

<400> SEQUENCE: 203

```
Ala Ser Thr Lys Gly Pro Ser Val Phe Pro Leu Ala Pro Cys Ser Arg
1               5                   10                  15

Ser Thr Ser Glu Ser Thr Ala Ala Leu Gly Cys Leu Val Lys Asp Tyr
            20                  25                  30

Phe Pro Glu Pro Val Thr Val Ser Trp Asn Ser Gly Ala Leu Thr Ser
        35                  40                  45

Gly Val His Thr Phe Pro Ala Val Leu Gln Ser Ser Gly Leu Tyr Ser
    50                  55                  60

Leu Ser Ser Val Val Thr Val Pro Ser Ser Ser Leu Gly Thr Lys Thr
65                  70                  75                  80

Tyr Thr Cys Asn Val Asp His Lys Pro Ser Asn Thr Lys Val Asp Lys
                85                  90                  95

Arg Val Glu Ser Lys Tyr Gly Pro Pro Cys Pro Pro Cys Pro Ala Pro
            100                 105                 110

Pro Val Ala Gly Gly Pro Ser Val Phe Leu Phe Pro Pro Lys Pro Lys
        115                 120                 125

Asp Thr Leu Met Ile Ser Arg Thr Pro Glu Val Thr Cys Val Val Val
    130                 135                 140
```

```
Asp Val Ser Gln Glu Asp Pro Glu Val Gln Phe Asn Trp Tyr Val Asp
145                 150                 155                 160

Gly Val Glu Val His Asn Ala Lys Thr Lys Pro Arg Glu Glu Gln Phe
                165                 170                 175

Asn Ser Thr Tyr Arg Val Val Ser Val Leu Thr Val Leu His Gln Asp
            180                 185                 190

Trp Leu Asn Gly Lys Glu Tyr Lys Cys Lys Val Ser Asn Lys Gly Leu
        195                 200                 205

Pro Ser Ser Ile Glu Lys Thr Ile Ser Lys Ala Lys Gly Gln Pro Arg
210                 215                 220

Glu Pro Gln Val Tyr Thr Leu Pro Pro Ser Gln Glu Glu Met Thr Lys
225                 230                 235                 240

Asn Gln Val Ser Leu Thr Cys Leu Val Lys Gly Phe Tyr Pro Ser Asp
                245                 250                 255

Ile Ala Val Glu Trp Glu Ser Asn Gly Gln Pro Glu Asn Asn Tyr Lys
            260                 265                 270

Thr Thr Pro Pro Val Leu Asp Ser Asp Gly Ser Phe Phe Leu Tyr Ser
        275                 280                 285

Arg Leu Thr Val Asp Lys Ser Arg Trp Gln Gln Gly Asn Val Phe Ser
290                 295                 300

Cys Ser Val Met His Glu Ala Leu His Asn His Tyr Thr Gln Lys Ser
305                 310                 315                 320

Leu Ser Leu Ser Leu Gly Lys
                325
```

<210> SEQ ID NO 204
<211> LENGTH: 990
<212> TYPE: DNA
<213> ORGANISM: Homo sapiens
<220> FEATURE:
<221> NAME/KEY: misc_feature
<223> OTHER INFORMATION: Heavy Chain Constant Region Nucleotide Sequence

<400> SEQUENCE: 204

```
gcctccacca agggcccatc ggtcttcccc ctggcaccct cctccaagag cacctctggg    60
ggcacagcgg ccctgggctg cctggtcaag gactacttcc ccgaaccggt gacggtgtcg   120
tggaactcag gcgccctgac cagcggcgtg cacaccttcc cggctgtcct acagtcctca   180
ggactctact ccctcagcag cgtggtgacc gtgccctcca gcagcttggg cacccagacc   240
tacatctgca acgtgaatca caagcccagc aacaccaagg tggacaagaa agttgagccc   300
aaatcttgtg acaaaactca cacatgccca ccgtgcccag cacctgaact cgcggggggca   360
ccgtcagtct tcctcttccc cccaaaaccc aaggacaccc tcatgatctc ccggacccct   420
gaggtcacat gcgtggtggt ggacgtgagc cacgaagacc ctgaggtcaa gttcaactgg   480
tacgtggacg gcgtggaggt gcataatgcc aagacaaagc cgcgggagga gcagtacaac   540
agcacgtacc gtgtggtcag cgtcctcacc gtcctgcacc aggactggct gaatggcaag   600
gagtacaagt gcaaggtctc caacaaagcc ctcccagccc ccatcgagaa aaccatctcc   660
aaagccaaag gcagccccg agaaccacag gtgtacaccc tgcccccatc ccgggatgag   720
ctgaccaaga accaggtcag cctgacctgc ctggtcaaag gcttctatcc cagcgacatc   780
gccgtggagt gggagagcaa tgggcagccg gagaacaact acaagaccac gcctcccgtg   840
ctggactccg acggctcctt cttcctctac agcaagctca ccgtggacaa gagcaggtgg   900
cagcagggga acgtcttctc atgctccgtg atgcatgagg ctctgcacaa ccactacacg   960
```
cagaagagcc tctccctgtc tccgggtaaa                                        990

<210> SEQ ID NO 205
<211> LENGTH: 330
<212> TYPE: PRT
<213> ORGANISM: Homo sapiens
<220> FEATURE:
<221> NAME/KEY: misc_feature
<223> OTHER INFORMATION: Heavy Chain Constant Region Amino Acid Sequence

<400> SEQUENCE: 205

Ala Ser Thr Lys Gly Pro Ser Val Phe Pro Leu Ala Pro Ser Ser Lys
1               5                   10                  15

Ser Thr Ser Gly Gly Thr Ala Ala Leu Gly Cys Leu Val Lys Asp Tyr
            20                  25                  30

Phe Pro Glu Pro Val Thr Val Ser Trp Asn Ser Gly Ala Leu Thr Ser
        35                  40                  45

Gly Val His Thr Phe Pro Ala Val Leu Gln Ser Ser Gly Leu Tyr Ser
    50                  55                  60

Leu Ser Ser Val Val Thr Val Pro Ser Ser Leu Gly Thr Gln Thr
65                  70                  75                  80

Tyr Ile Cys Asn Val Asn His Lys Pro Ser Asn Thr Lys Val Asp Lys
                85                  90                  95

Lys Val Glu Pro Lys Ser Cys Asp Lys Thr His Thr Cys Pro Pro Cys
            100                 105                 110

Pro Ala Pro Glu Leu Ala Gly Ala Pro Ser Val Phe Leu Phe Pro Pro
        115                 120                 125

Lys Pro Lys Asp Thr Leu Met Ile Ser Arg Thr Pro Glu Val Thr Cys
    130                 135                 140

Val Val Val Asp Val Ser His Glu Asp Pro Glu Val Lys Phe Asn Trp
145                 150                 155                 160

Tyr Val Asp Gly Val Glu Val His Asn Ala Lys Thr Lys Pro Arg Glu
                165                 170                 175

Glu Gln Tyr Asn Ser Thr Tyr Arg Val Val Ser Val Leu Thr Val Leu
            180                 185                 190

His Gln Asp Trp Leu Asn Gly Lys Glu Tyr Lys Cys Lys Val Ser Asn
        195                 200                 205

Lys Ala Leu Pro Ala Pro Ile Glu Lys Thr Ile Ser Lys Ala Lys Gly
    210                 215                 220

Gln Pro Arg Glu Pro Gln Val Tyr Thr Leu Pro Pro Ser Arg Asp Glu
225                 230                 235                 240

Leu Thr Lys Asn Gln Val Ser Leu Thr Cys Leu Val Lys Gly Phe Tyr
                245                 250                 255

Pro Ser Asp Ile Ala Val Glu Trp Glu Ser Asn Gly Gln Pro Glu Asn
            260                 265                 270

Asn Tyr Lys Thr Thr Pro Pro Val Leu Asp Ser Asp Gly Ser Phe Phe
        275                 280                 285

Leu Tyr Ser Lys Leu Thr Val Asp Lys Ser Arg Trp Gln Gln Gly Asn
    290                 295                 300

Val Phe Ser Cys Ser Val Met His Glu Ala Leu His Asn His Tyr Thr
305                 310                 315                 320

Gln Lys Ser Leu Ser Leu Ser Pro Gly Lys
                325                 330

<210> SEQ ID NO 206

<211> LENGTH: 321
<212> TYPE: DNA
<213> ORGANISM: Homo sapiens
<220> FEATURE:
<221> NAME/KEY: misc_feature
<223> OTHER INFORMATION: Ck Light Chain Constant Region Nucleotide
      Sequence  IGKC*01

<400> SEQUENCE: 206
cgtacggtgg ccgctccctc cgtgttcatc ttcccacctt ccgacgagca gctgaagtcc    60
ggcaccgctt ctgtcgtgtg cctgctgaac aacttctacc ccgcgaggc caaggtgcag   120 tggaaggtgg acaacgccct gcagtccggc aactcccagg aatccgtgac cgagcaggac   180
tccaaggaca gcacctactc cctgtcctcc accctgaccc tgtccaaggc cgactacgag   240
aagcacaagg tgtacgcctg cgaagtgacc caccagggcc tgtctagccc cgtgaccaag   300
tctttcaacc ggggcgagtg t                                             321

<210> SEQ ID NO 207
<211> LENGTH: 107
<212> TYPE: PRT
<213> ORGANISM: Homo sapiens
<220> FEATURE:
<221> NAME/KEY: misc_feature
<223> OTHER INFORMATION: Ck Light Chain Constant Region Amino Acid
      Sequence IGKC*01

<400> SEQUENCE: 207

Arg Thr Val Ala Ala Pro Ser Val Phe Ile Phe Pro Pro Ser Asp Glu
1               5                   10                  15

Gln Leu Lys Ser Gly Thr Ala Ser Val Val Cys Leu Leu Asn Asn Phe
            20                  25                  30

Tyr Pro Arg Glu Ala Lys Val Gln Trp Lys Val Asp Asn Ala Leu Gln
        35                  40                  45

Ser Gly Asn Ser Gln Glu Ser Val Thr Glu Gln Asp Ser Lys Asp Ser
    50                  55                  60

Thr Tyr Ser Leu Ser Ser Thr Leu Thr Leu Ser Lys Ala Asp Tyr Glu
65                  70                  75                  80

Lys His Lys Val Tyr Ala Cys Glu Val Thr His Gln Gly Leu Ser Ser
                85                  90                  95

Pro Val Thr Lys Ser Phe Asn Arg Gly Glu Cys
            100                 105

<210> SEQ ID NO 208
<211> LENGTH: 321
<212> TYPE: DNA
<213> ORGANISM: Homo sapiens
<220> FEATURE:
<221> NAME/KEY: misc_feature
<223> OTHER INFORMATION: Ck Light Chain Constant Region Nucleotide
      Sequence  IGKC*02

<400> SEQUENCE: 208
cgaactgtgg ctgcaccatc tgtcttcatc ttcccgccat ctgatgagca gttgaaatct    60
ggaactgcct ctgttgtgtg cctgctgaat aacttctatc ccagagaggc caaagtacag   120
tggaaggtgg ataacgccct ccaatcgggt aactcccagg agagtgtcac agagcaggag   180
agcaaggaca gcacctacag cctcagcagc accctgacgc tgagcaaagc agactacgag   240
aaacacaaag tctacgccgg cgaagtcacc catcagggcc tgagctcgcc cgtcacaaag   300
agcttcaaca ggggagagtg t                                             321

<210> SEQ ID NO 209
<211> LENGTH: 107
<212> TYPE: PRT
<213> ORGANISM: Homo sapiens
<220> FEATURE:
<221> NAME/KEY: misc_feature
<223> OTHER INFORMATION: Ck Light Chain Constant Region Amino Acid
      Sequence  IGKC*02

<400> SEQUENCE: 209

Arg Thr Val Ala Ala Pro Ser Val Phe Ile Phe Pro Pro Ser Asp Glu
1               5                   10                  15

Gln Leu Lys Ser Gly Thr Ala Ser Val Val Cys Leu Leu Asn Asn Phe
            20                  25                  30

Tyr Pro Arg Glu Ala Lys Val Gln Trp Lys Val Asp Asn Ala Leu Gln
        35                  40                  45

Ser Gly Asn Ser Gln Glu Ser Val Thr Glu Gln Ser Lys Asp Ser
    50                  55                  60

Thr Tyr Ser Leu Ser Ser Thr Leu Thr Leu Ser Lys Ala Asp Tyr Glu
65                  70                  75                  80

Lys His Lys Val Tyr Ala Gly Glu Val Thr His Gln Gly Leu Ser Ser
                85                  90                  95

Pro Val Thr Lys Ser Phe Asn Arg Gly Glu Cys
            100                 105

<210> SEQ ID NO 210
<211> LENGTH: 321
<212> TYPE: DNA
<213> ORGANISM: Homo sapiens
<220> FEATURE:
<221> NAME/KEY: misc_feature
<223> OTHER INFORMATION: Ck Light Chain Constant Region Nucleotide
      Sequence  IGKC*03

<400> SEQUENCE: 210
cgaactgtgg ctgcaccatc tgtcttcatc ttcccgccat ctgatgagca gttgaaatct     60
ggaactgcct ctgttgtgtg cctgctgaat aacttctatc ccagagaggc caaagtacag    120
cggaaggtgg ataacgccct ccaatcgggt aactcccagg agagtgtcac agagcaggag    180
agcaaggaca gcacctacag cctcagcagc accctgacgc tgagcaaagc agactacgag    240
aaacacaaag tctacgcctg cgaagtcacc catcagggcc tgagctcgcc cgtcacaaag    300
agcttcaaca ggggagagtg t                                              321

<210> SEQ ID NO 211
<211> LENGTH: 107
<212> TYPE: PRT
<213> ORGANISM: Homo sapiens
<220> FEATURE:
<221> NAME/KEY: misc_feature
<223> OTHER INFORMATION: Ck Light Chain Constant Region Amino Acid
      Sequence  IGKC*03

<400> SEQUENCE: 211

Arg Thr Val Ala Ala Pro Ser Val Phe Ile Phe Pro Pro Ser Asp Glu
1               5                   10                  15

Gln Leu Lys Ser Gly Thr Ala Ser Val Val Cys Leu Leu Asn Asn Phe
            20                  25                  30

Tyr Pro Arg Glu Ala Lys Val Gln Arg Lys Val Asp Asn Ala Leu Gln
        35                  40                  45

Ser Gly Asn Ser Gln Glu Ser Val Thr Glu Gln Glu Ser Lys Asp Ser

```
                50                  55                  60
Thr Tyr Ser Leu Ser Ser Thr Leu Thr Leu Ser Lys Ala Asp Tyr Glu
 65                  70                  75                  80

Lys His Lys Val Tyr Ala Cys Glu Val Thr His Gln Gly Leu Ser Ser
                 85                  90                  95

Pro Val Thr Lys Ser Phe Asn Arg Gly Glu Cys
                100                 105
```

```
<210> SEQ ID NO 212
<211> LENGTH: 321
<212> TYPE: DNA
<213> ORGANISM: Homo sapiens
<220> FEATURE:
<221> NAME/KEY: misc_feature
<223> OTHER INFORMATION: Ck Light Chain Constant Region Nucleotide
      Sequence  IGKC*04

<400> SEQUENCE: 212
```

```
cgaactgtgg ctgcaccatc tgtcttcatc ttcccgccat ctgatgagca gttgaaatct      60
ggaactgcct ctgttgtgtg cctgctgaat aacttctatc ccagagaggc caaagtacag     120
tggaaggtgg ataacgccct ccaatcgggt aactcccagg agagtgtcac agagcaggac     180
agcaaggaca gcacctacag cctcagcagc accctgacgc tgagcaaagc agactacgag     240
aaacacaaac tctacgcctg cgaagtcacc catcagggcc tgagctcgcc cgtcacaaag     300
agcttcaaca ggggagagtg t                                               321
```

```
<210> SEQ ID NO 213
<211> LENGTH: 107
<212> TYPE: PRT
<213> ORGANISM: Homo sapiens
<220> FEATURE:
<221> NAME/KEY: misc_feature
<223> OTHER INFORMATION: Ck Light Chain Constant Region Amino Acid
      Sequence  IGKC*04

<400> SEQUENCE: 213
```

```
Arg Thr Val Ala Ala Pro Ser Val Phe Ile Phe Pro Pro Ser Asp Glu
 1               5                  10                  15

Gln Leu Lys Ser Gly Thr Ala Ser Val Val Cys Leu Leu Asn Asn Phe
                20                  25                  30

Tyr Pro Arg Glu Ala Lys Val Gln Trp Lys Val Asp Asn Ala Leu Gln
             35                  40                  45

Ser Gly Asn Ser Gln Glu Ser Val Thr Glu Gln Asp Ser Lys Asp Ser
 50                  55                  60

Thr Tyr Ser Leu Ser Ser Thr Leu Thr Leu Ser Lys Ala Asp Tyr Glu
 65                  70                  75                  80

Lys His Lys Leu Tyr Ala Cys Glu Val Thr His Gln Gly Leu Ser Ser
                 85                  90                  95

Pro Val Thr Lys Ser Phe Asn Arg Gly Glu Cys
                100                 105
```

```
<210> SEQ ID NO 214
<211> LENGTH: 321
<212> TYPE: DNA
<213> ORGANISM: Homo sapiens
<220> FEATURE:
<221> NAME/KEY: misc_feature
<223> OTHER INFORMATION: Ck Light Chain Constant Region Nucleotide
      Sequence  IGKC*05

<400> SEQUENCE: 214
```

```
cgaactgtgg ctgcaccatc tgtcttcatc ttcccgccat ctgatgagca gttgaaatct    60
ggaactgcct ctgttgtgtg cctgctgaat aacttctatc ccagagaggc caaagtacag   120
tggaaggtgg ataacgccct ccaatcgggt aactcccagg agagtgtcac agagcaggac   180
agcaaggaca gcacctacag cctcagcaac accctgacgc tgagcaaagc agactacgag   240
aaacacaaag tctacgcctg cgaagtcacc catcagggcc tgagctcgcc cgtcacaaag   300
agcttcaaca ggggagagtg c                                             321
```

<210> SEQ ID NO 215
<211> LENGTH: 107
<212> TYPE: PRT
<213> ORGANISM: Homo sapiens
<220> FEATURE:
<221> NAME/KEY: misc_feature
<223> OTHER INFORMATION: Ck Light Chain Constant Region Amino Acid
      Sequence IGKC*05

<400> SEQUENCE: 215

```
Arg Thr Val Ala Ala Pro Ser Val Phe Ile Phe Pro Pro Ser Asp Glu
 1               5                  10                  15

Gln Leu Lys Ser Gly Thr Ala Ser Val Val Cys Leu Leu Asn Asn Phe
            20                  25                  30

Tyr Pro Arg Glu Ala Lys Val Gln Trp Lys Val Asp Asn Ala Leu Gln
        35                  40                  45

Ser Gly Asn Ser Gln Glu Ser Val Thr Glu Gln Asp Ser Lys Asp Ser
    50                  55                  60

Thr Tyr Ser Leu Ser Asn Thr Leu Thr Leu Ser Lys Ala Asp Tyr Glu
65                  70                  75                  80

Lys His Lys Val Tyr Ala Cys Glu Val Thr His Gln Gly Leu Ser Ser
                85                  90                  95

Pro Val Thr Lys Ser Phe Asn Arg Gly Glu Cys
            100                 105
```

<210> SEQ ID NO 216
<211> LENGTH: 312
<212> TYPE: DNA
<213> ORGANISM: Homo sapiens
<220> FEATURE:
<221> NAME/KEY: misc_feature
<223> OTHER INFORMATION: CL Light Chain Constant Region Nucleotide
      Sequence IGCL1*01

<400> SEQUENCE: 216

```
cccaaggcca accccacggt cactctgttc ccgccctcct ctgaggagct ccaagccaac    60
aaggccacac tagtgtgtct gatcagtgac ttctacccgg gagctgtgac agtggcttgg   120
aaggcagatg gcagccccgt caaggcggga gtggagacga ccaaaccctc caaacagagc   180
aacaacaagt acgcggccag cagctacctg agcctgacgc cgagcagtg gaagtcccac   240 agaagctaca gctgccaggt cacgcatgaa gggagcaccg tggagaagac agtggcccct   300
acagaatgtt ca                                                      312
```

<210> SEQ ID NO 217
<211> LENGTH: 104
<212> TYPE: PRT
<213> ORGANISM: Homo sapiens
<220> FEATURE:
<221> NAME/KEY: misc_feature
<223> OTHER INFORMATION: CL Light Chain Constant Region Amino Acid
      Sequence IGCL1*01

<400> SEQUENCE: 217

Pro Lys Ala Asn Pro Thr Val Thr Leu Phe Pro Pro Ser Ser Glu Glu
1               5                   10                  15

Leu Gln Ala Asn Lys Ala Thr Leu Val Cys Leu Ile Ser Asp Phe Tyr
            20                  25                  30

Pro Gly Ala Val Thr Val Ala Trp Lys Ala Asp Gly Ser Pro Val Lys
        35                  40                  45

Ala Gly Val Glu Thr Thr Lys Pro Ser Lys Gln Ser Asn Asn Lys Tyr
50                  55                  60

Ala Ala Ser Ser Tyr Leu Ser Leu Thr Pro Glu Gln Trp Lys Ser His
65                  70                  75                  80

Arg Ser Tyr Ser Cys Gln Val Thr His Glu Gly Ser Thr Val Glu Lys
                85                  90                  95

Thr Val Ala Pro Thr Glu Cys Ser
            100

<210> SEQ ID NO 218
<211> LENGTH: 318
<212> TYPE: DNA
<213> ORGANISM: Homo sapiens
<220> FEATURE:
<221> NAME/KEY: misc_feature
<223> OTHER INFORMATION: CL Light Chain Constant Region Nucleotide
      Sequence IGCL1*02

<400> SEQUENCE: 218
ggtcagccca aggccaaccc cactgtcact ctgttcccgc cctcctctga ggagctccaa     60
gccaacaagg ccacactagt gtgtctgatc agtgacttct acccgggagc tgtgacagtg    120
gcctggaagg cagatggcag ccccgtcaag gcgggagtgg agaccaccaa accctccaaa    180
cagagcaaca acaagtacgc ggccagcagc tacctgagcc tgacgcccga gcagtggaag    240
tcccacagaa gctacagctg ccaggtcacg catgaaggga gcaccgtgga agacagtg     300 gcccctacag aatgttca                                                 318

<210> SEQ ID NO 219
<211> LENGTH: 106
<212> TYPE: PRT
<213> ORGANISM: Homo sapiens
<220> FEATURE:
<221> NAME/KEY: misc_feature
<223> OTHER INFORMATION: CL Light Chain Constant Region Amino Acid
      Sequence IGCL1*02

<400> SEQUENCE: 219

Gly Gln Pro Lys Ala Asn Pro Thr Val Thr Leu Phe Pro Pro Ser Ser
1               5                   10                  15

Glu Glu Leu Gln Ala Asn Lys Ala Thr Leu Val Cys Leu Ile Ser Asp
            20                  25                  30

Phe Tyr Pro Gly Ala Val Thr Val Ala Trp Lys Ala Asp Gly Ser Pro
        35                  40                  45

Val Lys Ala Gly Val Glu Thr Thr Lys Pro Ser Lys Gln Ser Asn Asn
    50                  55                  60

Lys Tyr Ala Ala Ser Ser Tyr Leu Ser Leu Thr Pro Glu Gln Trp Lys
65                  70                  75                  80

Ser His Arg Ser Tyr Ser Cys Gln Val Thr His Glu Gly Ser Thr Val
                85                  90                  95

Glu Lys Thr Val Ala Pro Thr Glu Cys Ser
            100

<210> SEQ ID NO 220
<211> LENGTH: 318
<212> TYPE: DNA
<213> ORGANISM: Homo sapiens
<220> FEATURE:
<221> NAME/KEY: misc_feature
<223> OTHER INFORMATION: CL LC Constant Region NT Sequence Version A
      IGCL2*01

<400> SEQUENCE: 220

```
ggtcagccca aggccaaccc cactgtcact ctgttcccgc cctcctctga ggagctccaa    60
gccaacaagg ccacactagt gtgtctgatc agtgacttct acccgggagc tgtgacagtg   120
gcctggaagg cagatggcag ccccgtcaag gcgggagtgg agaccaccaa accctccaaa   180
cagagcaaca acaagtacgc ggccagcagc tacctgagcc tgacgcccga gcagtggaag   240
tcccacagaa gctacagctg ccaggtcacg catgaaggga gcaccgtgga agacagtg     300 gcccctacag aatgttca                                                 318
```

<210> SEQ ID NO 221
<211> LENGTH: 318
<212> TYPE: DNA
<213> ORGANISM: Homo sapiens
<220> FEATURE:
<221> NAME/KEY: misc_feature
<223> OTHER INFORMATION: CL LC Constant Region NT Sequence Version B
      IGCL2*01

<400> SEQUENCE: 221

```
ggccagccta aggccgctcc ttctgtgacc ctgttccccc catcctccga ggaactgcag    60
gctaacaagg ccaccctcgt gtgcctgatc agcgacttct accctggcgc cgtgaccgtg   120
gcctggaagg ctgatagctc tcctgtgaag gccggcgtgg aaaccaccac cccttccaag   180
cagtccaaca caaatacgc cgcctcctcc tacctgtccc tgaccctga gcagtggaag     240 tcccaccggt cctacagctg ccaagtgacc cacgagggct ccaccgtgga aagaccgtg    300 gctcctaccg agtgctcc                                                 318
```

<210> SEQ ID NO 222
<211> LENGTH: 318
<212> TYPE: DNA
<213> ORGANISM: Homo sapiens
<220> FEATURE:
<221> NAME/KEY: misc_feature
<223> OTHER INFORMATION: CL LC Constant Region NT Sequence Version C
      IGCL2*01

<400> SEQUENCE: 222

```
ggccagccta aagctgcccc cagcgtcacc ctgtttcctc cctccagcga ggagctccag    60
gccaacaagg ccaccctcgt gtgcctgatc tccgacttct atcccggcgc tgtgaccgtg   120
gcttggaaag ccgactccag ccctgtcaaa gccggcgtgg agaccaccac accctccaag   180
cagtccaaca caagtacgc cgcctccagc tatctctccc tgaccctga gcagtggaag     240 tcccaccggt cctactcctg tcaggtgacc cacgagggct ccaccgtgga aagaccgtc    300 gcccccaccg agtgctcc                                                 318
```

<210> SEQ ID NO 223
<211> LENGTH: 106
<212> TYPE: PRT
<213> ORGANISM: Homo sapiens
<220> FEATURE:
<221> NAME/KEY: misc_feature
<223> OTHER INFORMATION: CL LC Constant Region AA Sequence Encoded by
      A, B & C IGCL2*01

<400> SEQUENCE: 223

Gly Gln Pro Lys Ala Asn Pro Thr Val Thr Leu Phe Pro Pro Ser Ser
1               5                   10                  15

Glu Glu Leu Gln Ala Asn Lys Ala Thr Leu Val Cys Leu Ile Ser Asp
            20                  25                  30

Phe Tyr Pro Gly Ala Val Thr Val Ala Trp Lys Ala Asp Gly Ser Pro
        35                  40                  45

Val Lys Ala Gly Val Glu Thr Thr Lys Pro Ser Lys Gln Ser Asn Asn
    50                  55                  60

Lys Tyr Ala Ala Ser Ser Tyr Leu Ser Leu Thr Pro Glu Gln Trp Lys
65                  70                  75                  80

Ser His Arg Ser Tyr Ser Cys Gln Val Thr His Glu Gly Ser Thr Val
                85                  90                  95

Glu Lys Thr Val Ala Pro Thr Glu Cys Ser
            100                 105

<210> SEQ ID NO 224
<211> LENGTH: 318
<212> TYPE: DNA
<213> ORGANISM: Homo sapiens
<220> FEATURE:
<221> NAME/KEY: misc_feature
<223> OTHER INFORMATION: CL Light Chain Constant Region Nucleotide
      Sequence IGCL2*02

<400> SEQUENCE: 224
ggtcagccca aggctgcccc ctcggtcact ctgttcccgc cctcctctga ggagcttcaa      60
gccaacaagg ccacactggt gtgtctcata agtgacttct acccgggagc cgtgacagtg     120
gcctggaagg cagatagcag ccccgtcaag gcgggagtgg agaccaccac accctccaaa     180
caaagcaaca acaagtacgc ggccagcagc tatctgagcc tgacgcctga gcagtggaag     240
tcccacagaa gctacagctg ccaggtcacg catgaaggga gcaccgtgga agacagtg      300 gcccctacag aatgttca                                                  318

<210> SEQ ID NO 225
<211> LENGTH: 106
<212> TYPE: PRT
<213> ORGANISM: Homo sapiens
<220> FEATURE:
<221> NAME/KEY: misc_feature
<223> OTHER INFORMATION: CL Light Chain Constant Region Amino Acid
      Sequence IGCL2*02

<400> SEQUENCE: 225

Gly Gln Pro Lys Ala Ala Pro Ser Val Thr Leu Phe Pro Pro Ser Ser
1               5                   10                  15

Glu Glu Leu Gln Ala Asn Lys Ala Thr Leu Val Cys Leu Ile Ser Asp
            20                  25                  30

Phe Tyr Pro Gly Ala Val Thr Val Ala Trp Lys Ala Asp Ser Ser Pro
        35                  40                  45

Val Lys Ala Gly Val Glu Thr Thr Thr Pro Ser Lys Gln Ser Asn Asn
    50                  55                  60

Lys Tyr Ala Ala Ser Ser Tyr Leu Ser Leu Thr Pro Glu Gln Trp Lys
65                  70                  75                  80

Ser His Arg Ser Tyr Ser Cys Gln Val Thr His Glu Gly Ser Thr Val
                85                  90                  95

Glu Lys Thr Val Ala Pro Thr Glu Cys Ser
        100                 105

<210> SEQ ID NO 226
<211> LENGTH: 312
<212> TYPE: DNA
<213> ORGANISM: Homo sapiens
<220> FEATURE:
<221> NAME/KEY: misc_feature
<223> OTHER INFORMATION: CL Light Chain Constant Region Nucleotide
      Sequence IGCL3*01

<400> SEQUENCE: 226
cccaaggctg ccccctcggt cactctgttc ccaccctcct ctgaggagct tcaagccaac      60
aaggccacac tggtgtgtct cataagtgac ttctacccgg gagccgtgac agttgcctgg     120
aaggcagata gcagccccgt caaggcgggg gtggagacca ccacaccctc caaacaaagc     180
aacaacaagt acgcggccag cagctacctg agcctgacgc ctgagcagtg gaagtcccac     240
aaaagctaca gctgccaggt cacgcatgaa gggagcaccg tggagaagac agttgcccct     300
acggaatgtt ca                                                        312

<210> SEQ ID NO 227
<211> LENGTH: 104
<212> TYPE: PRT
<213> ORGANISM: Homo sapiens
<220> FEATURE:
<221> NAME/KEY: misc_feature
<223> OTHER INFORMATION: CL Light Chain Constant Region Amino Acid
      Sequence IGCL3*01

<400> SEQUENCE: 227

Pro Lys Ala Ala Pro Ser Val Thr Leu Phe Pro Pro Ser Ser Glu Glu
1               5                   10                  15

Leu Gln Ala Asn Lys Ala Thr Leu Val Cys Leu Ile Ser Asp Phe Tyr
            20                  25                  30

Pro Gly Ala Val Thr Val Ala Trp Lys Ala Asp Ser Ser Pro Val Lys
        35                  40                  45

Ala Gly Val Glu Thr Thr Thr Pro Ser Lys Gln Ser Asn Asn Lys Tyr
    50                  55                  60

Ala Ala Ser Ser Tyr Leu Ser Leu Thr Pro Glu Gln Trp Lys Ser His
65                  70                  75                  80

Lys Ser Tyr Ser Cys Gln Val Thr His Glu Gly Ser Thr Val Glu Lys
                85                  90                  95

Thr Val Ala Pro Thr Glu Cys Ser
            100

<210> SEQ ID NO 228
<211> LENGTH: 318
<212> TYPE: DNA
<213> ORGANISM: Homo sapiens
<220> FEATURE:
<221> NAME/KEY: misc_feature
<223> OTHER INFORMATION: CL Light Chain Constant Region Nucleotide
      Sequence IGCL3*02

<400> SEQUENCE: 228
ggtcagccca aggctgcccc ctcggtcact ctgttcccac cctcctctga ggagcttcaa      60
gccaacaagg ccacactggt gtgtctcata agtgacttct acccggggcc agtgacagtt     120

```
gcctggaagg cagatagcag ccccgtcaag gcggggtgg agaccaccac accctccaaa    180
caaagcaaca acaagtacgc ggccagcagc tacctgagcc tgacgcctga gcagtggaag    240
tcccacaaaa gctacagctg ccaggtcacg catgaaggga gcaccgtgga agagacagtg    300 gccctacgg aatgttca                                                   318
```

<210> SEQ ID NO 229
<211> LENGTH: 106
<212> TYPE: PRT
<213> ORGANISM: Homo sapiens
<220> FEATURE:
<221> NAME/KEY: misc_feature
<223> OTHER INFORMATION: CL Light Chain Constant Region Amino Acid
      Sequence IGCL3*02

<400> SEQUENCE: 229

```
Gly Gln Pro Lys Ala Ala Pro Ser Val Thr Leu Phe Pro Pro Ser Ser
1               5                   10                  15

Glu Glu Leu Gln Ala Asn Lys Ala Thr Leu Val Cys Leu Ile Ser Asp
            20                  25                  30

Phe Tyr Pro Gly Pro Val Thr Val Ala Trp Lys Ala Asp Ser Ser Pro
        35                  40                  45

Val Lys Ala Gly Val Glu Thr Thr Thr Pro Ser Lys Gln Ser Asn Asn
    50                  55                  60

Lys Tyr Ala Ala Ser Ser Tyr Leu Ser Leu Thr Pro Glu Gln Trp Lys
65                  70                  75                  80

Ser His Lys Ser Tyr Ser Cys Gln Val Thr His Glu Gly Ser Thr Val
                85                  90                  95

Glu Lys Thr Val Ala Pro Thr Glu Cys Ser
            100                 105
```

<210> SEQ ID NO 230
<211> LENGTH: 318
<212> TYPE: DNA
<213> ORGANISM: Homo sapiens
<220> FEATURE:
<221> NAME/KEY: misc_feature
<223> OTHER INFORMATION: CL Light Chain Constant Region Nucleotide
      Sequence IGCL3*03

<400> SEQUENCE: 230

```
ggtcagccca aggctgcccc ctcggtcact ctgttcccac cctcctctga ggagcttcaa    60
gccaacaagg ccacactggt gtgtctcata agtgacttct acccgggagc cgtgacagtg    120
gcctggaagg cagatagcag ccccgtcaag gcgggagtgg agaccaccac accctccaaa    180
caaagcaaca acaagtacgc ggccagcagc tacctgagcc tgacgcctga gcagtggaag    240
tcccacaaaa gctacagctg ccaggtcacg catgaaggga gcaccgtgga agagacagtg    300 gccctacag aatgttca                                                   318
```

<210> SEQ ID NO 231
<211> LENGTH: 106
<212> TYPE: PRT
<213> ORGANISM: Homo sapiens
<220> FEATURE:
<221> NAME/KEY: misc_feature
<223> OTHER INFORMATION: CL Light Chain Constant Region Amino Acid
      Sequence IGCL3*03

<400> SEQUENCE: 231

```
Gly Gln Pro Lys Ala Ala Pro Ser Val Thr Leu Phe Pro Pro Ser Ser
1               5                   10                  15
```

Glu Glu Leu Gln Ala Asn Lys Ala Thr Leu Val Cys Leu Ile Ser Asp
                20                  25                  30

Phe Tyr Pro Gly Ala Val Thr Val Ala Trp Lys Ala Asp Ser Ser Pro
            35                  40                  45

Val Lys Ala Gly Val Glu Thr Thr Thr Pro Ser Lys Gln Ser Asn Asn
 50                  55                  60

Lys Tyr Ala Ala Ser Ser Tyr Leu Ser Leu Thr Pro Glu Gln Trp Lys
 65                  70                  75                  80

Ser His Lys Ser Tyr Ser Cys Gln Val Thr His Glu Gly Ser Thr Val
                85                  90                  95

Glu Lys Thr Val Ala Pro Thr Glu Cys Ser
            100                 105

<210> SEQ ID NO 232
<211> LENGTH: 318
<212> TYPE: DNA
<213> ORGANISM: Homo sapiens
<220> FEATURE:
<221> NAME/KEY: misc_feature
<223> OTHER INFORMATION: CL Light Chain Constant Region Nucleotide
      Sequence IGCL3*04

<400> SEQUENCE: 232
ggtcagccca aggctgcccc ctcggtcact ctgttcccgc cctcctctga ggagcttcaa      60
gccaacaagg ccacactggt gtgtctcata agtgacttct acccgggagc cgtgacagtg     120
gcctggaagg cagatagcag ccccgtcaag gcgggagtgg agaccaccac accctccaaa     180
caaagcaaca acaagtacgc ggccagcagc tacctgagcc tgacgcctga gcagtggaag     240
tcccacagaa gctacagctg ccaggtcacg catgaaggga gcaccgtgga agacagtg       300 gcccctacag aatgttca                                                   318

<210> SEQ ID NO 233
<211> LENGTH: 106
<212> TYPE: PRT
<213> ORGANISM: Homo sapiens
<220> FEATURE:
<221> NAME/KEY: misc_feature
<223> OTHER INFORMATION: CL Light Chain Constant Region Amino Acid
      Sequence IGCL3*04

<400> SEQUENCE: 233

Gly Gln Pro Lys Ala Ala Pro Ser Val Thr Leu Phe Pro Pro Ser Ser
 1               5                  10                  15

Glu Glu Leu Gln Ala Asn Lys Ala Thr Leu Val Cys Leu Ile Ser Asp
                20                  25                  30

Phe Tyr Pro Gly Ala Val Thr Val Ala Trp Lys Ala Asp Ser Ser Pro
            35                  40                  45

Val Lys Ala Gly Val Glu Thr Thr Thr Pro Ser Lys Gln Ser Asn Asn
 50                  55                  60

Lys Tyr Ala Ala Ser Ser Tyr Leu Ser Leu Thr Pro Glu Gln Trp Lys
 65                  70                  75                  80

Ser His Arg Ser Tyr Ser Cys Gln Val Thr His Glu Gly Ser Thr Val
                85                  90                  95

Glu Lys Thr Val Ala Pro Thr Glu Cys Ser
            100                 105

<210> SEQ ID NO 234
<211> LENGTH: 318

```
<212> TYPE: DNA
<213> ORGANISM: Homo sapiens
<220> FEATURE:
<221> NAME/KEY: misc_feature
<223> OTHER INFORMATION: CL Light Chain Constant Region Nucleotide
      Sequence IGCL6*01

<400> SEQUENCE: 234
ggtcagccca aggctgcccc atcggtcact ctgttcccgc cctcctctga ggagcttcaa      60
gccaacaagg ccacactggt gtgcctgatc agtgacttct acccgggagc tgtgaaagtg     120
gcctggaagg cagatggcag ccccgtcaac acgggagtgg agaccaccac accctccaaa     180
cagagcaaca caagtacgc ggccagcagc tacctgagcc tgacgcctga gcagtggaag      240
tcccacagaa gctacagctg ccaggtcacg catgaaggga gcaccgtgga agacagtg       300 gcccctgcag aatgttca                                                   318

<210> SEQ ID NO 235
<211> LENGTH: 106
<212> TYPE: PRT
<213> ORGANISM: Homo sapiens
<220> FEATURE:
<221> NAME/KEY: misc_feature
<223> OTHER INFORMATION: CL Light Chain Constant Region Amino Acid
      Sequence IGCL6*01

<400> SEQUENCE: 235

Gly Gln Pro Lys Ala Ala Pro Ser Val Thr Leu Phe Pro Pro Ser Ser
1               5                   10                  15

Glu Glu Leu Gln Ala Asn Lys Ala Thr Leu Val Cys Leu Ile Ser Asp
            20                  25                  30

Phe Tyr Pro Gly Ala Val Lys Val Ala Trp Lys Ala Asp Gly Ser Pro
        35                  40                  45

Val Asn Thr Gly Val Glu Thr Thr Thr Pro Ser Lys Gln Ser Asn Asn
    50                  55                  60

Lys Tyr Ala Ala Ser Ser Tyr Leu Ser Leu Thr Pro Glu Gln Trp Lys
65                  70                  75                  80

Ser His Arg Ser Tyr Ser Cys Gln Val Thr His Glu Gly Ser Thr Val
                85                  90                  95

Glu Lys Thr Val Ala Pro Ala Glu Cys Ser
            100                 105

<210> SEQ ID NO 236
<211> LENGTH: 318
<212> TYPE: DNA
<213> ORGANISM: Homo sapiens
<220> FEATURE:
<221> NAME/KEY: misc_feature
<223> OTHER INFORMATION: CL Light Chain Constant Region Nucleotide
      Sequence IGCL7*02

<400> SEQUENCE: 236
ggtcagccca aggctgcccc atcggtcact ctgttcccac cctcctctga ggagcttcaa      60
gccaacaagg ccacactggt gtgtctcgta agtgacttct acccgggagc cgtgacagtg     120
gcctggaagg cagatggcag ccccgtcaag gtgggagtgg agaccaccaa accctccaaa     180
caaagcaaca caagtatgc ggccagcagc tacctgagcc tgacgcccga gcagtggaag      240
tcccacagaa gctacagctg ccgggtcacg catgaaggga gcaccgtgga agacagtg       300 gcccctgcag aatgctct                                                   318
```

```
<210> SEQ ID NO 237
<211> LENGTH: 106
<212> TYPE: PRT
<213> ORGANISM: Homo sapiens
<220> FEATURE:
<221> NAME/KEY: misc_feature
<223> OTHER INFORMATION: CL Light Chain Constant Region Amino Acid
      Sequence IGCL7*02

<400> SEQUENCE: 237

Gly Gln Pro Lys Ala Ala Pro Ser Val Thr Leu Phe Pro Pro Ser Ser
1               5                   10                  15

Glu Glu Leu Gln Ala Asn Lys Ala Thr Leu Val Cys Leu Val Ser Asp
            20                  25                  30

Phe Tyr Pro Gly Ala Val Thr Val Ala Trp Lys Ala Asp Gly Ser Pro
        35                  40                  45

Val Lys Val Gly Val Glu Thr Thr Lys Pro Ser Lys Gln Ser Asn Asn
    50                  55                  60

Lys Tyr Ala Ala Ser Ser Tyr Leu Ser Leu Thr Pro Glu Gln Trp Lys
65                  70                  75                  80

Ser His Arg Ser Tyr Ser Cys Arg Val Thr His Glu Gly Ser Thr Val
                85                  90                  95

Glu Lys Thr Val Ala Pro Ala Glu Cys Ser
            100                 105

<210> SEQ ID NO 238
<211> LENGTH: 8
<212> TYPE: PRT
<213> ORGANISM: Homo sapiens
<220> FEATURE:
<221> NAME/KEY: misc_feature
<223> OTHER INFORMATION: Amino acid sequence of CDRH1 of 413G05 using
      IMGT

<400> SEQUENCE: 238

Gly Phe Thr Phe Ser Asp Tyr Tyr
1               5

<210> SEQ ID NO 239
<211> LENGTH: 8
<212> TYPE: PRT
<213> ORGANISM: Homo sapiens
<220> FEATURE:
<221> NAME/KEY: misc_feature
<223> OTHER INFORMATION: Amino acid sequence of CDRH2 of 413G05 using
      IMGT

<400> SEQUENCE: 239

Ile Ser Thr Ser Gly Ser Thr Ile
1               5

<210> SEQ ID NO 240
<211> LENGTH: 16
<212> TYPE: PRT
<213> ORGANISM: Homo sapiens
<220> FEATURE:
<221> NAME/KEY: misc_feature
<223> OTHER INFORMATION: Amino acid sequence of CDRH3 of 413G05 using
      IMGT

<400> SEQUENCE: 240

Ala Arg Gly Ile Thr Gly Thr Asn Phe Tyr His Tyr Gly Leu Gly Val
1               5                   10                  15

<210> SEQ ID NO 241
```

```
<211> LENGTH: 5
<212> TYPE: PRT
<213> ORGANISM: Homo sapiens
<220> FEATURE:
<221> NAME/KEY: misc_feature
<223> OTHER INFORMATION: Amino acid sequence of CDRH1 of 413G05 using
      Kabat

<400> SEQUENCE: 241

Asp Tyr Tyr Met Ser
1               5

<210> SEQ ID NO 242
<211> LENGTH: 17
<212> TYPE: PRT
<213> ORGANISM: Homo sapiens
<220> FEATURE:
<221> NAME/KEY: misc_feature
<223> OTHER INFORMATION: Amino acid sequence of CDRH2 of 413G05 using
      Kabat

<400> SEQUENCE: 242

Tyr Ile Ser Thr Ser Gly Ser Thr Ile Tyr Tyr Ala Asp Ser Val Lys
1               5                   10                  15

Gly

<210> SEQ ID NO 243
<211> LENGTH: 14
<212> TYPE: PRT
<213> ORGANISM: Homo sapiens
<220> FEATURE:
<221> NAME/KEY: misc_feature
<223> OTHER INFORMATION: Amino acid sequence of CDRH3 of 413G05 using
      Kabat

<400> SEQUENCE: 243

Gly Ile Thr Gly Thr Asn Phe Tyr His Tyr Gly Leu Gly Val
1               5                   10

<210> SEQ ID NO 244
<211> LENGTH: 123
<212> TYPE: PRT
<213> ORGANISM: Homo sapiens
<220> FEATURE:
<221> NAME/KEY: misc_feature
<223> OTHER INFORMATION: Amino acid sequence of VH of 413G05

<400> SEQUENCE: 244

Gln Val Gln Leu Val Glu Ser Gly Gly Gly Leu Val Lys Pro Gly Gly
1               5                   10                  15

Ser Leu Arg Leu Ser Cys Ala Ala Ser Gly Phe Thr Phe Ser Asp Tyr
                20                  25                  30

Tyr Met Ser Trp Ile Arg Gln Val Pro Gly Lys Gly Leu Glu Trp Val
            35                  40                  45

Ser Tyr Ile Ser Thr Ser Gly Ser Thr Ile Tyr Tyr Ala Asp Ser Val
        50                  55                  60

Lys Gly Arg Phe Thr Ile Ser Arg Asp Asn Ala Lys Asn Ser Leu Tyr
65                  70                  75                  80

Leu Gln Met Asn Ser Leu Arg Ala Glu Asp Ala Ala Val Tyr His Cys
                85                  90                  95

Ala Arg Gly Ile Thr Gly Thr Asn Phe Tyr His Tyr Gly Leu Gly Val
            100                 105                 110

Trp Gly Gln Gly Thr Thr Val Thr Val Ser Ser
        115                 120
```

<210> SEQ ID NO 245
<211> LENGTH: 370
<212> TYPE: DNA
<213> ORGANISM: Homo sapiens
<220> FEATURE:
<221> NAME/KEY: misc_feature
<223> OTHER INFORMATION: Nucleic acid sequence of VH of 413G05

<400> SEQUENCE: 245

```
caggtgcagc tggtggagtc tgggggaggc ttggtcaagc ctggagggtc cctgagactc      60
tcctgtgcag cctctggatt caccttcagt gactactaca tgagctggat ccgccaggtt     120
ccagggaagg ggctggagtg ggtttcatac attagtacta gtggtagtac catatactac     180
gcagactctg tgaagggccg attcaccatc tccagggaca cgccaagaa ctcactgtat      240
ctacaaatga acagcctgag agccgaggac gcggccgtgt atcactgtgc gagaggtata     300
actggaacta acttctacca ctacggtttg ggcgtctggg gccaagggac cacggtcacc     360
gtctcctcag                                                            370
```

<210> SEQ ID NO 246
<211> LENGTH: 453
<212> TYPE: PRT
<213> ORGANISM: Homo sapiens
<220> FEATURE:
<221> NAME/KEY: misc_feature
<223> OTHER INFORMATION: Amino acid sequence of 413G05 heavy chain

<400> SEQUENCE: 246

```
Gln Val Gln Leu Val Glu Ser Gly Gly Gly Leu Val Lys Pro Gly Gly
1               5                   10                  15

Ser Leu Arg Leu Ser Cys Ala Ala Ser Gly Phe Thr Phe Ser Asp Tyr
            20                  25                  30

Tyr Met Ser Trp Ile Arg Gln Val Pro Gly Lys Gly Leu Glu Trp Val
        35                  40                  45

Ser Tyr Ile Ser Thr Ser Gly Ser Thr Ile Tyr Tyr Ala Asp Ser Val
    50                  55                  60

Lys Gly Arg Phe Thr Ile Ser Arg Asp Asn Ala Lys Asn Ser Leu Tyr
65                  70                  75                  80

Leu Gln Met Asn Ser Leu Arg Ala Glu Asp Ala Ala Val Tyr His Cys
                85                  90                  95

Ala Arg Gly Ile Thr Gly Thr Asn Phe Tyr His Tyr Gly Leu Gly Val
            100                 105                 110

Trp Gly Gln Gly Thr Thr Val Thr Val Ser Ser Ala Ser Thr Lys Gly
        115                 120                 125

Pro Ser Val Phe Pro Leu Ala Pro Ser Ser Lys Ser Thr Ser Gly Gly
    130                 135                 140

Thr Ala Ala Leu Gly Cys Leu Val Lys Asp Tyr Phe Pro Glu Pro Val
145                 150                 155                 160

Thr Val Ser Trp Asn Ser Gly Ala Leu Thr Ser Gly Val His Thr Phe
                165                 170                 175

Pro Ala Val Leu Gln Ser Ser Gly Leu Tyr Ser Leu Ser Ser Val Val
            180                 185                 190

Thr Val Pro Ser Ser Ser Leu Gly Thr Gln Thr Tyr Ile Cys Asn Val
        195                 200                 205

Asn His Lys Pro Ser Asn Thr Lys Val Asp Lys Lys Val Glu Pro Lys
    210                 215                 220
```

Ser Cys Asp Lys Thr His Thr Cys Pro Pro Cys Pro Ala Pro Glu Leu
225                 230                 235                 240

Leu Gly Gly Pro Ser Val Phe Leu Phe Pro Pro Lys Pro Lys Asp Thr
            245                 250                 255

Leu Met Ile Ser Arg Thr Pro Glu Val Thr Cys Val Val Val Asp Val
            260                 265                 270

Ser His Glu Asp Pro Glu Val Lys Phe Asn Trp Tyr Val Asp Gly Val
275                 280                 285

Glu Val His Asn Ala Lys Thr Lys Pro Arg Glu Glu Gln Tyr Asn Ser
        290                 295                 300

Thr Tyr Arg Val Val Ser Val Leu Thr Val Leu His Gln Asp Trp Leu
305                 310                 315                 320

Asn Gly Lys Glu Tyr Lys Cys Lys Val Ser Asn Lys Ala Leu Pro Ala
            325                 330                 335

Pro Ile Glu Lys Thr Ile Ser Lys Ala Lys Gly Gln Pro Arg Glu Pro
            340                 345                 350

Gln Val Tyr Thr Leu Pro Pro Ser Arg Asp Glu Leu Thr Lys Asn Gln
        355                 360                 365

Val Ser Leu Thr Cys Leu Val Lys Gly Phe Tyr Pro Ser Asp Ile Ala
370                 375                 380

Val Glu Trp Glu Ser Asn Gly Gln Pro Glu Asn Asn Tyr Lys Thr Thr
385                 390                 395                 400

Pro Pro Val Leu Asp Ser Asp Gly Ser Phe Phe Leu Tyr Ser Lys Leu
            405                 410                 415

Thr Val Asp Lys Ser Arg Trp Gln Gln Gly Asn Val Phe Ser Cys Ser
            420                 425                 430

Val Met His Glu Ala Leu His Asn His Tyr Thr Gln Lys Ser Leu Ser
435                 440                 445

Leu Ser Pro Gly Lys
450

<210> SEQ ID NO 247
<211> LENGTH: 1359
<212> TYPE: DNA
<213> ORGANISM: Homo sapiens
<220> FEATURE:
<221> NAME/KEY: misc_feature
<223> OTHER INFORMATION: Nucleic acid sequence of 413G05 heavy chain

<400> SEQUENCE: 247
caggtgcagc tggtggagtc tgggggaggc ttggtcaagc ctggagggtc cctgagactc      60
tcctgtgcag cctctggatt caccttcagt gactactaca tgagctggat ccgccaggtt     120
ccagggaagg ggctggagtg ggtttcatac attagtacta gtggtagtac catatactac     180
gcagactctg tgaagggccg attcaccatc tccagggaca cgccaagaa ctcactgtat      240 ctacaaatga acagcctgag agccgaggac gcggccgtgt atcactgtgc gagaggtata     300
actggaacta acttctacca ctacggtttg gcgtctgggg ccaagggac cacggtcacc      360 gtctcctcag ccagcaccaa gggcccctct gtgttccctc tggccccttc agcaagtcc     420 acctctggcg aacagccgc tctgggctgc ctcgtgaagg actacttccc cgagcctgtg     480
accgtgtcct ggaactctgg cgctctgacc agcggagtgc acaccttccc tgctgtgctg     540
cagtcctccg gcctgtactc cctgtcctcc gtcgtgaccg tgccttccag ctctctgggc     600
acccagacct acatctgcaa cgtgaaccac aagccctcca caccaaggt ggacaagaag      660 gtggaaccca gtcctgcga caagacccac acctgtcccc cttgtcctgc ccctgaactg      720

```
ctgggcggac cttccgtgtt cctgttcccc ccaaagccca aggacaccct gatgatctcc    780 cggaccccg aagtgacctg cgtggtggtg gatgtgtccc acgaggaccc tgaagtgaag    840
ttcaattggt acgtggacgg cgtggaagtg cacaacgcca agaccaagcc tagagaggaa    900
cagtacaact ccacctaccg ggtggtgtcc gtgctgaccg tgctgcacca ggattggctg    960
aacggcaaag agtacaagtg caaggtgtcc aacaaggccc tgcctgcccc catcgaaaag   1020
accatctcca aggccaaggg ccagcccgg gaacccagg tgtacacact gcccctagc     1080 agggacgagc tgaccaagaa ccaggtgtcc ctgacctgtc tcgtgaaagg cttctacccc   1140
tccgatatcg ccgtggaatg ggagtccaac ggccagcctg agaacaacta caagaccacc   1200 cccctgtgc tggactccga cggctcattc ttcctgtaca gcaagctgac agtggacaag   1260
tcccggtggc agcagggcaa cgtgttctcc tgctccgtga tgcacgaggc cctgcacaac   1320
cactacaccc agaagtccct gtccctgagc cccggcaag                         1359
```

```
<210> SEQ ID NO 248
<211> LENGTH: 6
<212> TYPE: PRT
<213> ORGANISM: Homo sapiens
<220> FEATURE:
<221> NAME/KEY: misc_feature
<223> OTHER INFORMATION: Amino acid sequence of CDRL1 of 413G05 using
      IMGT

<400> SEQUENCE: 248

Gln Gly Ile Asn Ser Trp
1               5

<210> SEQ ID NO 249
<211> LENGTH: 3
<212> TYPE: PRT
<213> ORGANISM: Homo sapiens
<220> FEATURE:
<221> NAME/KEY: misc_feature
<223> OTHER INFORMATION: Amino acid sequence of CDRL2 of 413G05 using
      IMGT

<400> SEQUENCE: 249

Ala Ala Ser
1

<210> SEQ ID NO 250
<211> LENGTH: 9
<212> TYPE: PRT
<213> ORGANISM: Homo sapiens
<220> FEATURE:
<221> NAME/KEY: misc_feature
<223> OTHER INFORMATION: Amino acid sequence of CDRL3 of 413G05 using
      IMGT

<400> SEQUENCE: 250

Gln Gln Val Asn Ser Phe Pro Leu Thr
1               5

<210> SEQ ID NO 251
<211> LENGTH: 11
<212> TYPE: PRT
<213> ORGANISM: Homo sapiens
<220> FEATURE:
<221> NAME/KEY: misc_feature
<223> OTHER INFORMATION: Amino acid sequence of CDRL1 of 413G05 using
      Kabat

<400> SEQUENCE: 251
```

Arg Ala Ser Gln Gly Ile Asn Ser Trp Leu Ala
1               5                   10

<210> SEQ ID NO 252
<211> LENGTH: 7
<212> TYPE: PRT
<213> ORGANISM: Homo sapiens
<220> FEATURE:
<221> NAME/KEY: misc_feature
<223> OTHER INFORMATION: Amino acid sequence of CDRL2 of 413G05 using
      Kabat

<400> SEQUENCE: 252

Ala Ala Ser Thr Leu Gln Ser
1               5

<210> SEQ ID NO 253
<211> LENGTH: 9
<212> TYPE: PRT
<213> ORGANISM: Homo sapiens
<220> FEATURE:
<221> NAME/KEY: misc_feature
<223> OTHER INFORMATION: Amino acid sequence of CDRL3 of 413G05 using
      Kabat

<400> SEQUENCE: 253

Gln Gln Val Asn Ser Phe Pro Leu Thr
1               5

<210> SEQ ID NO 254
<211> LENGTH: 107
<212> TYPE: PRT
<213> ORGANISM: Homo sapiens
<220> FEATURE:
<221> NAME/KEY: misc_feature
<223> OTHER INFORMATION: Amino acid sequence of VL of 413G05

<400> SEQUENCE: 254

Asp Ile Gln Met Thr Gln Ser Pro Ser Ser Val Ser Ala Ser Val Gly
1               5                   10                  15

Asp Arg Val Thr Ile Thr Cys Arg Ala Ser Gln Gly Ile Asn Ser Trp
            20                  25                  30

Leu Ala Trp Tyr Gln Gln Lys Pro Gly Lys Ala Pro Lys Leu Leu Ile
        35                  40                  45

Tyr Ala Ala Ser Thr Leu Gln Ser Gly Val Pro Ser Arg Phe Ser Gly
    50                  55                  60

Ser Gly Ser Gly Ala Asp Phe Thr Leu Thr Ile Ser Ser Leu Gln Pro
65                  70                  75                  80

Glu Asp Phe Ala Thr Tyr Tyr Cys Gln Gln Val Asn Ser Phe Pro Leu
                85                  90                  95

Thr Phe Gly Gly Gly Thr Lys Val Glu Ile Lys
            100                 105

<210> SEQ ID NO 255
<211> LENGTH: 322
<212> TYPE: DNA
<213> ORGANISM: Homo sapiens
<220> FEATURE:
<221> NAME/KEY: misc_feature
<223> OTHER INFORMATION: Nucleic acid sequence of VL of 413G05

<400> SEQUENCE: 255
gacatccaga tgacccagtc tccatcttcc gtgtctgcat ctgtaggaga cagagtcacc      60

-continued

| | |
|---|---|
| atcacttgtc gggcgagtca gggtattaac agctggttag cctggtatca gcagaaacca | 120 |
| gggaaagccc ctaagctcct gatctatgct gcatccactt tgcaaagtgg ggtcccatca | 180 |
| aggttcagcg gcagtgggtc tggggcagat ttcactctca ccatcagcag cctgcagcct | 240 |
| gaagattttg caacttacta ttgtcaacag gttaacagtt tcccgctcac tttcggcgga | 300 |
| gggaccaagg tggagatcaa ac | 322 |

<210> SEQ ID NO 256
<211> LENGTH: 214
<212> TYPE: PRT
<213> ORGANISM: Homo sapiens
<220> FEATURE:
<221> NAME/KEY: misc_feature
<223> OTHER INFORMATION: Amino acid sequence of 413G05 light chain

<400> SEQUENCE: 256

Asp Ile Gln Met Thr Gln Ser Pro Ser Ser Val Ser Ala Ser Val Gly
1               5                   10                  15

Asp Arg Val Thr Ile Thr Cys Arg Ala Ser Gln Gly Ile Asn Ser Trp
            20                  25                  30

Leu Ala Trp Tyr Gln Gln Lys Pro Gly Lys Ala Pro Lys Leu Leu Ile
        35                  40                  45

Tyr Ala Ala Ser Thr Leu Gln Ser Gly Val Pro Ser Arg Phe Ser Gly
    50                  55                  60

Ser Gly Ser Gly Ala Asp Phe Thr Leu Thr Ile Ser Ser Leu Gln Pro
65                  70                  75                  80

Glu Asp Phe Ala Thr Tyr Tyr Cys Gln Gln Val Asn Ser Phe Pro Leu
                85                  90                  95

Thr Phe Gly Gly Gly Thr Lys Val Glu Ile Lys Arg Thr Val Ala Ala
            100                 105                 110

Pro Ser Val Phe Ile Phe Pro Pro Ser Asp Glu Gln Leu Lys Ser Gly
        115                 120                 125

Thr Ala Ser Val Val Cys Leu Leu Asn Asn Phe Tyr Pro Arg Glu Ala
    130                 135                 140

Lys Val Gln Trp Lys Val Asp Asn Ala Leu Gln Ser Gly Asn Ser Gln
145                 150                 155                 160

Glu Ser Val Thr Glu Gln Asp Ser Lys Asp Ser Thr Tyr Ser Leu Ser
                165                 170                 175

Ser Thr Leu Thr Leu Ser Lys Ala Asp Tyr Glu Lys His Lys Val Tyr
            180                 185                 190

Ala Cys Glu Val Thr His Gln Gly Leu Ser Ser Pro Val Thr Lys Ser
        195                 200                 205

Phe Asn Arg Gly Glu Cys
    210

<210> SEQ ID NO 257
<211> LENGTH: 642
<212> TYPE: DNA
<213> ORGANISM: Homo sapiens
<220> FEATURE:
<221> NAME/KEY: misc_feature
<223> OTHER INFORMATION: Nucleic acid sequence of 413G05 light chain

<400> SEQUENCE: 257

| | |
|---|---|
| gacatccaga tgacccagtc tccatcttcc gtgtctgcat ctgtaggaga cagagtcacc | 60 |
| atcacttgtc gggcgagtca gggtattaac agctggttag cctggtatca gcagaaacca | 120 |
| gggaaagccc ctaagctcct gatctatgct gcatccactt tgcaaagtgg ggtcccatca | 180 |

```
aggttcagcg gcagtgggtc tggggcagat ttcactctca ccatcagcag cctgcagcct    240
gaagattttg caacttacta ttgtcaacag gttaacagtt tcccgctcac tttcggcgga    300
gggaccaagg tggagatcaa acgtacggtg gccgctccct ccgtgttcat cttcccacct    360
tccgacgagc agctgaagtc cggcaccgct tctgtcgtgt gcctgctgaa caacttctac    420
ccccgcgagg ccaaggtgca gtggaaggtg acaacgccc tgcagtccgg caactcccag    480
gaatccgtga ccgagcagga ctccaaggac agcacctact ccctgtcctc acccctgacc    540
ctgtccaagg ccgactacga aagcacaag gtgtacgcct gcgaagtgac caccagggc    600 ctgtctagcc ccgtgaccaa gtctttcaac cggggcgagt gt    642
```

<210> SEQ ID NO 258
<211> LENGTH: 8
<212> TYPE: PRT
<213> ORGANISM: Homo sapiens
<220> FEATURE:
<221> NAME/KEY: misc_feature
<223> OTHER INFORMATION: Amino acid sequence of CDRH1 of 413F09 using IMGT

<400> SEQUENCE: 258

Gly Phe Thr Phe Ser Tyr Tyr Ala
1               5

<210> SEQ ID NO 259
<211> LENGTH: 8
<212> TYPE: PRT
<213> ORGANISM: Homo sapiens
<220> FEATURE:
<221> NAME/KEY: misc_feature
<223> OTHER INFORMATION: Amino acid sequence of CDRH2 of 413F09 using IMGT

<400> SEQUENCE: 259

Ile Ser Gly Gly Gly Gly Asn Thr
1               5

<210> SEQ ID NO 260
<211> LENGTH: 16
<212> TYPE: PRT
<213> ORGANISM: Homo sapiens
<220> FEATURE:
<221> NAME/KEY: misc_feature
<223> OTHER INFORMATION: Amino acid sequence of CDRH3 of 413F09 using IMGT

<400> SEQUENCE: 260

Ala Lys Asp Arg Met Lys Gln Leu Val Arg Ala Tyr Tyr Phe Asp Tyr
1               5                   10                  15

<210> SEQ ID NO 261
<211> LENGTH: 5
<212> TYPE: PRT
<213> ORGANISM: Homo sapiens
<220> FEATURE:
<221> NAME/KEY: misc_feature
<223> OTHER INFORMATION: Amino acid sequence of CDRH1 of 413F09 using Kabat

<400> SEQUENCE: 261

Tyr Tyr Ala Met Ser
1               5

<210> SEQ ID NO 262

```
<211> LENGTH: 17
<212> TYPE: PRT
<213> ORGANISM: Homo sapiens
<220> FEATURE:
<221> NAME/KEY: misc_feature
<223> OTHER INFORMATION: Amino acid sequence of CDRH2 of 413F09 using
      Kabat

<400> SEQUENCE: 262

Thr Ile Ser Gly Gly Gly Gly Asn Thr His Tyr Ala Asp Ser Val Lys
1               5                   10                  15

Gly

<210> SEQ ID NO 263
<211> LENGTH: 14
<212> TYPE: PRT
<213> ORGANISM: Homo sapiens
<220> FEATURE:
<221> NAME/KEY: misc_feature
<223> OTHER INFORMATION: Amino acid sequence of CDRH3 of 413F09 using
      Kabat

<400> SEQUENCE: 263

Asp Arg Met Lys Gln Leu Val Arg Ala Tyr Tyr Phe Asp Tyr
1               5                   10

<210> SEQ ID NO 264
<211> LENGTH: 123
<212> TYPE: PRT
<213> ORGANISM: Homo sapiens
<220> FEATURE:
<221> NAME/KEY: misc_feature
<223> OTHER INFORMATION: Amino acid sequence of VH of 413F09

<400> SEQUENCE: 264

Glu Val Pro Leu Val Glu Ser Gly Gly Gly Leu Val Gln Pro Gly Gly
1               5                   10                  15

Ser Leu Arg Leu Ser Cys Ala Ala Ser Gly Phe Thr Phe Ser Tyr Tyr
            20                  25                  30

Ala Met Ser Trp Val Arg Gln Ala Pro Gly Lys Gly Leu Asp Trp Val
        35                  40                  45

Ser Thr Ile Ser Gly Gly Gly Gly Asn Thr His Tyr Ala Asp Ser Val
    50                  55                  60

Lys Gly Arg Phe Thr Ile Ser Arg Asp Asn Ser Lys Asn Thr Leu Tyr
65                  70                  75                  80

Leu His Met Asn Ser Leu Arg Ala Glu Asp Thr Ala Val Tyr Tyr Cys
                85                  90                  95

Ala Lys Asp Arg Met Lys Gln Leu Val Arg Ala Tyr Tyr Phe Asp Tyr
            100                 105                 110

Trp Gly Gln Gly Thr Leu Val Thr Val Ser Ser
        115                 120

<210> SEQ ID NO 265
<211> LENGTH: 370
<212> TYPE: DNA
<213> ORGANISM: Homo sapiens
<220> FEATURE:
<221> NAME/KEY: misc_feature
<223> OTHER INFORMATION: Nucleic acid sequence of VH of 413F09

<400> SEQUENCE: 265
gaggtgccgc tggtggagtc tgggggaggc ttggtacagc ctggggggtc cctgagactc      60
tcctgtgcag cctctggatt cacgtttagc tactatgcca tgagctgggt ccgtcaggct     120
```

-continued

```
ccagggaagg ggctggactg ggtctcaact attagtggtg gtggtggtaa cacacactac    180
gcagactccg tgaagggccg attcactata tccagagaca attccaagaa cacgctgtat    240
ctgcacatga acagcctgag agccgaagac acggccgtct attactgtgc gaaggatcgg    300
atgaaacagc tcgtccgggc ctactacttt gactactggg ccagggaac cctggtcacc    360 gtctcctcag                                                            370
```

<210> SEQ ID NO 266
<211> LENGTH: 453
<212> TYPE: PRT
<213> ORGANISM: Homo sapiens
<220> FEATURE:
<221> NAME/KEY: misc_feature
<223> OTHER INFORMATION: Amino acid sequence of 413F09 heavy chain

<400> SEQUENCE: 266

```
Glu Val Pro Leu Val Glu Ser Gly Gly Gly Leu Val Gln Pro Gly Gly
1               5                   10                  15

Ser Leu Arg Leu Ser Cys Ala Ala Ser Gly Phe Thr Phe Ser Tyr Tyr
            20                  25                  30

Ala Met Ser Trp Val Arg Gln Ala Pro Gly Lys Gly Leu Asp Trp Val
        35                  40                  45

Ser Thr Ile Ser Gly Gly Gly Asn Thr His Tyr Ala Asp Ser Val
    50                  55                  60

Lys Gly Arg Phe Thr Ile Ser Arg Asp Asn Ser Lys Asn Thr Leu Tyr
65                  70                  75                  80

Leu His Met Asn Ser Leu Arg Ala Glu Asp Thr Ala Val Tyr Tyr Cys
                85                  90                  95

Ala Lys Asp Arg Met Lys Gln Leu Val Arg Ala Tyr Tyr Phe Asp Tyr
            100                 105                 110

Trp Gly Gln Gly Thr Leu Val Thr Val Ser Ser Ala Ser Thr Lys Gly
        115                 120                 125

Pro Ser Val Phe Pro Leu Ala Pro Ser Ser Lys Ser Thr Ser Gly Gly
    130                 135                 140

Thr Ala Ala Leu Gly Cys Leu Val Lys Asp Tyr Phe Pro Glu Pro Val
145                 150                 155                 160

Thr Val Ser Trp Asn Ser Gly Ala Leu Thr Ser Gly Val His Thr Phe
                165                 170                 175

Pro Ala Val Leu Gln Ser Ser Gly Leu Tyr Ser Leu Ser Ser Val Val
            180                 185                 190

Thr Val Pro Ser Ser Ser Leu Gly Thr Gln Thr Tyr Ile Cys Asn Val
        195                 200                 205

Asn His Lys Pro Ser Asn Thr Lys Val Asp Lys Val Glu Pro Lys
    210                 215                 220

Ser Cys Asp Lys Thr His Thr Cys Pro Pro Cys Pro Ala Pro Glu Leu
225                 230                 235                 240

Leu Gly Gly Pro Ser Val Phe Leu Phe Pro Pro Lys Pro Lys Asp Thr
                245                 250                 255

Leu Met Ile Ser Arg Thr Pro Glu Val Thr Cys Val Val Val Asp Val
            260                 265                 270

Ser His Glu Asp Pro Glu Val Lys Phe Asn Trp Tyr Val Asp Gly Val
        275                 280                 285

Glu Val His Asn Ala Lys Thr Lys Pro Arg Glu Glu Gln Tyr Asn Ser
    290                 295                 300
```

```
Thr Tyr Arg Val Val Ser Val Leu Thr Val Leu His Gln Asp Trp Leu
305                 310                 315                 320

Asn Gly Lys Glu Tyr Lys Cys Lys Val Ser Asn Lys Ala Leu Pro Ala
            325                 330                 335

Pro Ile Glu Lys Thr Ile Ser Lys Ala Lys Gly Gln Pro Arg Glu Pro
            340                 345                 350

Gln Val Tyr Thr Leu Pro Pro Ser Arg Asp Glu Leu Thr Lys Asn Gln
            355                 360                 365

Val Ser Leu Thr Cys Leu Val Lys Gly Phe Tyr Pro Ser Asp Ile Ala
370                 375                 380

Val Glu Trp Glu Ser Asn Gly Gln Pro Glu Asn Asn Tyr Lys Thr Thr
385                 390                 395                 400

Pro Pro Val Leu Asp Ser Asp Gly Ser Phe Phe Leu Tyr Ser Lys Leu
                405                 410                 415

Thr Val Asp Lys Ser Arg Trp Gln Gln Gly Asn Val Phe Ser Cys Ser
                420                 425                 430

Val Met His Glu Ala Leu His Asn His Tyr Thr Gln Lys Ser Leu Ser
            435                 440                 445

Leu Ser Pro Gly Lys
    450
```

<210> SEQ ID NO 267
<211> LENGTH: 1359
<212> TYPE: DNA
<213> ORGANISM: Homo sapiens
<220> FEATURE:
<221> NAME/KEY: misc_feature
<223> OTHER INFORMATION: Nucleic acid sequence of 413F09 heavy chain

<400> SEQUENCE: 267

```
gaggtgccgc tggtggagtc tgggggaggc ttggtacagc ctggggggtc cctgagactc      60
tcctgtgcag cctctggatt cacgtttagc tactatgcca tgagctgggt ccgtcaggct     120
ccagggaagg ggctggactg ggtctcaact attagtggtg gtggtggtaa cacacactac     180
gcagactccg tgaagggccg attcactata tccagagaca attccaagaa cacgctgtat     240
ctgcacatga acagcctgag agccgaagac acggccgtct attactgtgc gaaggatcgg     300
atgaaacagc tcgtccgggc ctactacttt gactactggg gccagggaac cctggtcacc     360
gtctcctcag ccagcaccaa gggcccctct gtgttccctc tggcccctcc agcaagtcc      420
acctctggcg gaacagccgc tctgggctgc ctcgtgaagg actacttccc cgagcctgtg     480
accgtgtcct ggaactctgg cgctctgacc agcggagtgc acaccttccc tgctgtgctg     540
cagtcctccg gcctgtactc cctgtcctcc gtcgtgaccg tgccttccag ctctctgggc     600
acccagacct acatctgcaa cgtgaaccac aagccctcca caccaaggt ggacaagaag      660
gtggaaccca gtcctgcga caagacccac acctgtcccc cttgtcctgc ccctgaactg      720
ctgggcggac cttccgtgtt cctgttcccc caaagcccca ggacaccct gatgatctcc      780
cggaccccccg aagtgacctg cgtggtggtg gatgtgtccc acgaggaccc tgaagtgaag     840
ttcaattggt acgtggacgg cgtggaagtg cacaacgcca agaccaagcc tagagaggaa     900
cagtacaact ccacctaccg ggtggtgtcc gtgctgaccg tgctgcacca ggattggctg     960
aacggcaaag agtacaagtg caaggtgtcc aacaaggccc tgcctgcccc catcgaaaag    1020
accatctcca aggccaaggg ccagccccgg gaacccagg tgtacacact gccccctagc     1080
agggacgagc tgaccaagaa ccaggtgtcc ctgacctgtc tcgtgaaagg cttctacccc    1140
```

```
tccgatatcg ccgtggaatg ggagtccaac ggccagcctg agaacaacta caagaccacc      1200 cccctgtgc  tggactccga cggctcattc ttcctgtaca gcaagctgac agtggacaag      1260
tcccggtggc agcagggcaa cgtgttctcc tgctccgtga tgcacgaggc cctgcacaac      1320
cactacaccc agaagtccct gtccctgagc cccggcaag                             1359
```

<210> SEQ ID NO 268
<211> LENGTH: 6
<212> TYPE: PRT
<213> ORGANISM: Homo sapiens
<220> FEATURE:
<221> NAME/KEY: misc_feature
<223> OTHER INFORMATION: Amino acid sequence of CDRL1 of 413F09 using
      IMGT

<400> SEQUENCE: 268

Gln Asp Ile Ser Thr Tyr
1               5

<210> SEQ ID NO 269
<211> LENGTH: 3
<212> TYPE: PRT
<213> ORGANISM: Homo sapiens
<220> FEATURE:
<221> NAME/KEY: misc_feature
<223> OTHER INFORMATION: Amino acid sequence of CDRL2 of 413F09 using
      IMGT

<400> SEQUENCE: 269

Gly Thr Ser
1

<210> SEQ ID NO 270
<211> LENGTH: 9
<212> TYPE: PRT
<213> ORGANISM: Homo sapiens
<220> FEATURE:
<221> NAME/KEY: misc_feature
<223> OTHER INFORMATION: Amino acid sequence of CDRL3 of 413F09 using
      IMGT

<400> SEQUENCE: 270

Gln Gln Leu His Thr Asp Pro Ile Thr
1               5

<210> SEQ ID NO 271
<211> LENGTH: 11
<212> TYPE: PRT
<213> ORGANISM: Homo sapiens
<220> FEATURE:
<221> NAME/KEY: misc_feature
<223> OTHER INFORMATION: Amino acid sequence of CDRL1 of 413F09 using
      Kabat

<400> SEQUENCE: 271

Trp Ala Ser Gln Asp Ile Ser Thr Tyr Leu Gly
1               5                   10

<210> SEQ ID NO 272
<211> LENGTH: 7
<212> TYPE: PRT
<213> ORGANISM: Homo sapiens
<220> FEATURE:
<221> NAME/KEY: misc_feature
<223> OTHER INFORMATION: Amino acid sequence of CDRL2 of 413F09 using
      Kabat

<400> SEQUENCE: 272

Gly Thr Ser Ser Leu Gln Ser
1               5

<210> SEQ ID NO 273
<211> LENGTH: 9
<212> TYPE: PRT
<213> ORGANISM: Homo sapiens
<220> FEATURE:
<221> NAME/KEY: misc_feature
<223> OTHER INFORMATION: Amino acid sequence of CDRL3 of 413F09 using
      Kabat

<400> SEQUENCE: 273

Gln Gln Leu His Thr Asp Pro Ile Thr
1               5

<210> SEQ ID NO 274
<211> LENGTH: 107
<212> TYPE: PRT
<213> ORGANISM: Homo sapiens
<220> FEATURE:
<221> NAME/KEY: misc_feature
<223> OTHER INFORMATION: Amino acid sequence of VL of 413F09

<400> SEQUENCE: 274

Asp Ile Gln Leu Thr Gln Ser Pro Ser Phe Leu Ser Ala Ser Val Gly
1               5                   10                  15

Asp Arg Val Thr Ile Thr Cys Trp Ala Ser Gln Asp Ile Ser Thr Tyr
            20                  25                  30

Leu Gly Trp Tyr Gln Gln Lys Pro Gly Lys Ala Pro Lys Leu Leu Ile
        35                  40                  45

Tyr Gly Thr Ser Ser Leu Gln Ser Gly Val Pro Ser Arg Phe Ser Gly
50                  55                  60

Ser Gly Ser Gly Thr Glu Phe Thr Leu Thr Ile Ser Ser Leu Gln Pro
65                  70                  75                  80

Glu Asp Phe Ala Thr Tyr Tyr Cys Gln Gln Leu His Thr Asp Pro Ile
                85                  90                  95

Thr Phe Gly Gln Gly Thr Arg Leu Glu Ile Lys
            100                 105

<210> SEQ ID NO 275
<211> LENGTH: 322
<212> TYPE: DNA
<213> ORGANISM: Homo sapiens
<220> FEATURE:
<221> NAME/KEY: misc_feature
<223> OTHER INFORMATION: Nucleic acid sequence of VL of 413F09

<400> SEQUENCE: 275
gacatccagt tgacccagtc tccatccttc ctgtctgcat ctgtaggaga cagagtcacc      60
atcacttgct gggccagtca ggacattagc acttatttag ctggtatca gcaaaaacca     120 gggaaagccc ctaagctcct gatctatggt acatccagtt tgcaaagtgg ggtcccatca    180
aggttcagcg gcagtggatc tgggacagaa ttcactctca caatcagcag cctgcagcct    240
gaagattttg caacttatta ctgtcaacag cttcatactg acccgatcac cttcggccaa    300
gggacacgac tggagatcaa ac                                             322

<210> SEQ ID NO 276
<211> LENGTH: 214
<212> TYPE: PRT
<213> ORGANISM: Homo sapiens
<220> FEATURE:
<221> NAME/KEY: misc_feature
<223> OTHER INFORMATION: Amino acid sequence of 413F09 light chain

<400> SEQUENCE: 276

Asp Ile Gln Leu Thr Gln Ser Pro Ser Phe Leu Ser Ala Ser Val Gly
1               5                   10                  15

Asp Arg Val Thr Ile Thr Cys Trp Ala Ser Gln Asp Ile Ser Thr Tyr
            20                  25                  30

Leu Gly Trp Tyr Gln Gln Lys Pro Gly Lys Ala Pro Lys Leu Leu Ile
        35                  40                  45

Tyr Gly Thr Ser Ser Leu Gln Ser Gly Val Pro Ser Arg Phe Ser Gly
    50                  55                  60

Ser Gly Ser Gly Thr Glu Phe Thr Leu Thr Ile Ser Ser Leu Gln Pro
65                  70                  75                  80

Glu Asp Phe Ala Thr Tyr Tyr Cys Gln Gln Leu His Thr Asp Pro Ile
                85                  90                  95

Thr Phe Gly Gln Gly Thr Arg Leu Glu Ile Lys Arg Thr Val Ala Ala
            100                 105                 110

Pro Ser Val Phe Ile Phe Pro Pro Ser Asp Glu Gln Leu Lys Ser Gly
        115                 120                 125

Thr Ala Ser Val Val Cys Leu Leu Asn Asn Phe Tyr Pro Arg Glu Ala
    130                 135                 140

Lys Val Gln Trp Lys Val Asp Asn Ala Leu Gln Ser Gly Asn Ser Gln
145                 150                 155                 160

Glu Ser Val Thr Glu Gln Asp Ser Lys Asp Ser Thr Tyr Ser Leu Ser
                165                 170                 175

Ser Thr Leu Thr Leu Ser Lys Ala Asp Tyr Glu Lys His Lys Val Tyr
            180                 185                 190

Ala Cys Glu Val Thr His Gln Gly Leu Ser Ser Pro Val Thr Lys Ser
        195                 200                 205

Phe Asn Arg Gly Glu Cys
    210

<210> SEQ ID NO 277
<211> LENGTH: 642
<212> TYPE: DNA
<213> ORGANISM: Homo sapiens
<220> FEATURE:
<221> NAME/KEY: misc_feature
<223> OTHER INFORMATION: Nucleic acid sequence of 413F09 light chain

<400> SEQUENCE: 277
gacatccagt tgacccagtc tccatccttc ctgtctgcat ctgtaggaga cagagtcacc      60
atcacttgct gggccagtca ggacattagc acttatttag ctggtatcag caaaaaacca    120
gggaaagccc ctaagctcct gatctatggt acatccagtt tgcaaagtgg ggtcccatca    180
aggttcagcg gcagtggatc tgggacagaa ttcactctca caatcagcag cctgcagcct    240
gaagattttg caacttatta ctgtcaacag cttcatactg acccgatcac cttcggccaa    300
gggacacgac tggagatcaa acgtacggtg gccgctccct ccgtgttcat cttcccacct    360
tccgacgagc agctgaagtc cggcaccgct tctgtcgtgt gcctgctgaa caacttctac    420 cccgcgagg ccaaggtgca gtggaaggtg gacaacgccc tgcagtccgg caactcccag    480
gaatccgtga ccgagcagga ctccaaggac agcacctact ccctgtcctc caccctgacc    540
ctgtccaagg ccgactacga gaagcacaag gtgtacgcct gcgaagtgac ccaccagggc    600
ctgtctagcc ccgtgaccaa gtctttcaac cggggcgagt gt 642

<210> SEQ ID NO 278
<211> LENGTH: 8
<212> TYPE: PRT
<213> ORGANISM: Homo sapiens
<220> FEATURE:
<221> NAME/KEY: misc_feature
<223> OTHER INFORMATION: Amino acid sequence of CDRH1 of 414B06 using IMGT

<400> SEQUENCE: 278

Gly Phe Thr Phe Ser Ser Tyr Trp
1               5

<210> SEQ ID NO 279
<211> LENGTH: 8
<212> TYPE: PRT
<213> ORGANISM: Homo sapiens
<220> FEATURE:
<221> NAME/KEY: misc_feature
<223> OTHER INFORMATION: Amino acid sequence of CDRH2 of 414B06 using IMGT

<400> SEQUENCE: 279

Ile Lys Gln Asp Gly Ser Glu Lys
1               5

<210> SEQ ID NO 280
<211> LENGTH: 12
<212> TYPE: PRT
<213> ORGANISM: Homo sapiens
<220> FEATURE:
<221> NAME/KEY: misc_feature
<223> OTHER INFORMATION: Amino acid sequence of CDRH3 of 414B06 using IMGT

<400> SEQUENCE: 280

Ala Arg Val Arg Gln Trp Ser Asp Tyr Ser Asp Tyr
1               5                   10

<210> SEQ ID NO 281
<211> LENGTH: 5
<212> TYPE: PRT
<213> ORGANISM: Homo sapiens
<220> FEATURE:
<221> NAME/KEY: misc_feature
<223> OTHER INFORMATION: Amino acid sequence of CDRH1 of 414B06 using Kabat

<400> SEQUENCE: 281

Ser Tyr Trp Met Asn
1               5

<210> SEQ ID NO 282
<211> LENGTH: 17
<212> TYPE: PRT
<213> ORGANISM: Homo sapiens
<220> FEATURE:
<221> NAME/KEY: misc_feature
<223> OTHER INFORMATION: Amino acid sequence of CDRH2 of 414B06 using Kabat

<400> SEQUENCE: 282

Asn Ile Lys Gln Asp Gly Ser Glu Lys Tyr Tyr Val Asp Ser Val Lys
1               5                   10                  15

Gly

<210> SEQ ID NO 283
<211> LENGTH: 10
<212> TYPE: PRT
<213> ORGANISM: Homo sapiens
<220> FEATURE:
<221> NAME/KEY: misc_feature
<223> OTHER INFORMATION: Amino acid sequence of CDRH3 of 414B06 using
      Kabat

<400> SEQUENCE: 283

Val Arg Gln Trp Ser Asp Tyr Ser Asp Tyr
1               5                   10

<210> SEQ ID NO 284
<211> LENGTH: 119
<212> TYPE: PRT
<213> ORGANISM: Homo sapiens
<220> FEATURE:
<221> NAME/KEY: misc_feature
<223> OTHER INFORMATION: Amino acid sequence of VH of 414B06

<400> SEQUENCE: 284

Glu Val His Leu Val Glu Ser Gly Gly Gly Leu Val Gln Pro Gly Gly
1               5                   10                  15

Ser Leu Arg Leu Ser Cys Ala Ala Ser Gly Phe Thr Phe Ser Ser Tyr
            20                  25                  30

Trp Met Asn Trp Val Arg Gln Ala Pro Gly Lys Gly Leu Glu Trp Val
        35                  40                  45

Ala Asn Ile Lys Gln Asp Gly Ser Glu Lys Tyr Tyr Val Asp Ser Val
    50                  55                  60

Lys Gly Arg Phe Thr Val Ser Arg Asp Asn Ala Lys Asn Ser Leu Tyr
65                  70                  75                  80

Leu Gln Met Asn Ser Leu Arg Ala Glu Asp Thr Ala Val Tyr Tyr Cys
                85                  90                  95

Ala Arg Val Arg Gln Trp Ser Asp Tyr Ser Asp Tyr Trp Gly Gln Gly
            100                 105                 110

Thr Pro Val Thr Val Ser Ser
        115

<210> SEQ ID NO 285
<211> LENGTH: 358
<212> TYPE: DNA
<213> ORGANISM: Homo sapiens
<220> FEATURE:
<221> NAME/KEY: misc_feature
<223> OTHER INFORMATION: Nucleic acid sequence of VH of 414B06

<400> SEQUENCE: 285
gaggtgcacc tggtggagtc tgggggaggc ttggtccagc ctggggggtc cctgagactc      60
tcctgtgcag cctctggatt cacctttagt agctattgga tgaactgggt ccgccaggct     120
ccagggaagg gctggagtg gtggccaac ataaagcaag atggaagtga aaatactat        180 gtggactctg tgaagggccg cttcaccgtc tccagagaca acgccaagaa ctcactgtat     240
ctgcaaatga acagcctgag agccgaggac acggctgtgt attactgtgc gagagttcga    300
caatggtccg actactctga ctactggggc cagggaaccc cggtcaccgt ctcctcag      358

<210> SEQ ID NO 286
<211> LENGTH: 449
<212> TYPE: PRT
<213> ORGANISM: Homo sapiens
<220> FEATURE:

<221> NAME/KEY: misc_feature
<223> OTHER INFORMATION: Amino acid sequence of 414B06 heavy chain

<400> SEQUENCE: 286

```
Glu Val His Leu Val Glu Ser Gly Gly Leu Val Gln Pro Gly Gly
 1               5                  10                  15

Ser Leu Arg Leu Ser Cys Ala Ala Ser Gly Phe Thr Phe Ser Ser Tyr
            20                  25                  30

Trp Met Asn Trp Val Arg Gln Ala Pro Gly Lys Gly Leu Glu Trp Val
        35                  40                  45

Ala Asn Ile Lys Gln Asp Gly Ser Glu Lys Tyr Tyr Val Asp Ser Val
 50                  55                  60

Lys Gly Arg Phe Thr Val Ser Arg Asp Asn Ala Lys Asn Ser Leu Tyr
 65                  70                  75                  80

Leu Gln Met Asn Ser Leu Arg Ala Glu Asp Thr Ala Val Tyr Tyr Cys
                85                  90                  95

Ala Arg Val Arg Gln Trp Ser Asp Tyr Ser Asp Tyr Trp Gly Gln Gly
            100                 105                 110

Thr Pro Val Thr Val Ser Ser Ala Ser Thr Lys Gly Pro Ser Val Phe
        115                 120                 125

Pro Leu Ala Pro Ser Ser Lys Ser Thr Ser Gly Gly Thr Ala Ala Leu
130                 135                 140

Gly Cys Leu Val Lys Asp Tyr Phe Pro Glu Pro Val Thr Val Ser Trp
145                 150                 155                 160

Asn Ser Gly Ala Leu Thr Ser Gly Val His Thr Phe Pro Ala Val Leu
                165                 170                 175

Gln Ser Ser Gly Leu Tyr Ser Leu Ser Ser Val Val Thr Val Pro Ser
            180                 185                 190

Ser Ser Leu Gly Thr Gln Thr Tyr Ile Cys Asn Val Asn His Lys Pro
        195                 200                 205

Ser Asn Thr Lys Val Asp Lys Lys Val Glu Pro Lys Ser Cys Asp Lys
210                 215                 220

Thr His Thr Cys Pro Pro Cys Pro Ala Pro Glu Leu Leu Gly Gly Pro
225                 230                 235                 240

Ser Val Phe Leu Phe Pro Pro Lys Pro Lys Asp Thr Leu Met Ile Ser
                245                 250                 255

Arg Thr Pro Glu Val Thr Cys Val Val Val Asp Val Ser His Glu Asp
            260                 265                 270

Pro Glu Val Lys Phe Asn Trp Tyr Val Asp Gly Val Glu Val His Asn
        275                 280                 285

Ala Lys Thr Lys Pro Arg Glu Glu Gln Tyr Asn Ser Thr Tyr Arg Val
290                 295                 300

Val Ser Val Leu Thr Val Leu His Gln Asp Trp Leu Asn Gly Lys Glu
305                 310                 315                 320

Tyr Lys Cys Lys Val Ser Asn Lys Ala Leu Pro Ala Pro Ile Glu Lys
                325                 330                 335

Thr Ile Ser Lys Ala Lys Gly Gln Pro Arg Glu Pro Gln Val Tyr Thr
            340                 345                 350

Leu Pro Pro Ser Arg Asp Glu Leu Thr Lys Asn Gln Val Ser Leu Thr
        355                 360                 365

Cys Leu Val Lys Gly Phe Tyr Pro Ser Asp Ile Ala Val Glu Trp Glu
370                 375                 380

Ser Asn Gly Gln Pro Glu Asn Asn Tyr Lys Thr Thr Pro Pro Val Leu
385                 390                 395                 400
```

Asp Ser Asp Gly Ser Phe Phe Leu Tyr Ser Lys Leu Thr Val Asp Lys
                405                 410                 415

Ser Arg Trp Gln Gln Gly Asn Val Phe Ser Cys Ser Val Met His Glu
            420                 425                 430

Ala Leu His Asn His Tyr Thr Gln Lys Ser Leu Ser Leu Ser Pro Gly
        435                 440                 445

Lys

<210> SEQ ID NO 287
<211> LENGTH: 1347
<212> TYPE: DNA
<213> ORGANISM: Homo sapiens
<220> FEATURE:
<221> NAME/KEY: misc_feature
<223> OTHER INFORMATION: Nucleic acid sequence of 414B06 heavy chain

<400> SEQUENCE: 287

```
gaggtgcacc tggtggagtc tgggggaggc ttggtccagc ctgggggtc cctgagactc    60
tcctgtgcag cctctggatt cacctttagt agctattgga tgaactgggt ccgccaggct   120
ccagggaagg gctggagtg gtggccaac ataaagcaag atggaagtga aaatactat    180
gtggactctg tgaagggccg cttcaccgtc tccagagaca cgccaagaa ctcactgtat   240
ctgcaaatga acagcctgag agccgaggac acggctgtgt attactgtgc gagagttcga   300
caatggtccg actactctga ctactgggc cagggaaccc cggtcaccgt ctcctcagcc   360
agcaccaagg gcccctctgt gttccctctg gccccttcca gcaagtccac ctctggcgga   420
acagccgctc tgggctgcct cgtgaaggac tacttcccg agcctgtgac cgtgtcctgg   480
aactctggcg ctctgaccag cggagtgcac accttcctg ctgtgctgca gtcctccggc   540
ctgtactccc tgtcctccgt cgtgaccgtg ccttccagct ctctgggcac ccagacctac   600
atctgcaacg tgaaccacaa gccctccaac accaaggtgg acaagaaggt ggaacccaag   660
tcctgcgaca gacccacac ctgtcccct tgtcctgccc ctgaactgct gggcggacct    720
tccgtgttcc tgttccccc aaagcccaag acaccctga tgatctcccg gacccccgaa   780
gtgacctgcg tggtggtgga tgtgtcccac gaggaccctg aagtgaagtt caattggtac   840
gtggacggcg tggaagtgca caacgccaag accaagccta gagaggaaca gtacaactcc   900
acctaccggg tggtgtccgt gctgaccgtg ctgcaccagg attggctgaa cggcaaagag   960
tacaagtgca aggtgtccaa caaggccctg cctgccccca tcgaaaagac catctccaag  1020
gccaagggcc agccccggga acccaggtg tacacactgc ccctagcag ggacgagctg   1080
accaagaacc aggtgtccct gacctgtctc gtgaaaggct tctaccctc cgatatcgcc  1140
gtggaatggg agtccaacgg ccagcctgag aacaactaca agaccacccc cctgtgctg  1200
gactccgacg gctcattctt cctgtacagc aagctgacag tggacaagtc ccggtggcag  1260
cagggcaacg tgttctcctg ctccgtgatg cacgaggccc tgcacaacca ctacacccag  1320
aagtccctgt ccctgagccc cggcaag                                      1347
```

<210> SEQ ID NO 288
<211> LENGTH: 6
<212> TYPE: PRT
<213> ORGANISM: Homo sapiens
<220> FEATURE:
<221> NAME/KEY: misc_feature
<223> OTHER INFORMATION: Amino acid sequence of CDRL1 of 414B06 using
      IMGT

```
<400> SEQUENCE: 288

Gln Gly Ile Ser Ser Trp
1               5

<210> SEQ ID NO 289
<211> LENGTH: 3
<212> TYPE: PRT
<213> ORGANISM: Homo sapiens
<220> FEATURE:
<221> NAME/KEY: misc_feature
<223> OTHER INFORMATION: Amino acid sequence of CDRL2 of 414B06 using
      IMGT

<400> SEQUENCE: 289

Ala Ala Ser
1

<210> SEQ ID NO 290
<211> LENGTH: 9
<212> TYPE: PRT
<213> ORGANISM: Homo sapiens
<220> FEATURE:
<221> NAME/KEY: misc_feature
<223> OTHER INFORMATION: Amino acid sequence of CDRL3 of 414B06 using
      IMGT

<400> SEQUENCE: 290

Gln Gln Ala Asn Ser Phe Pro Phe Thr
1               5

<210> SEQ ID NO 291
<211> LENGTH: 11
<212> TYPE: PRT
<213> ORGANISM: Homo sapiens
<220> FEATURE:
<221> NAME/KEY: misc_feature
<223> OTHER INFORMATION: Amino acid sequence of CDRL1 of 414B06 using
      Kabat

<400> SEQUENCE: 291

Arg Ala Ser Gln Gly Ile Ser Ser Trp Leu Ala
1               5                   10

<210> SEQ ID NO 292
<211> LENGTH: 7
<212> TYPE: PRT
<213> ORGANISM: Homo sapiens
<220> FEATURE:
<221> NAME/KEY: misc_feature
<223> OTHER INFORMATION: Amino acid sequence of CDRL2 of 414B06 using
      Kabat

<400> SEQUENCE: 292

Ala Ala Ser Ser Leu Gln Ser
1               5

<210> SEQ ID NO 293
<211> LENGTH: 9
<212> TYPE: PRT
<213> ORGANISM: Homo sapiens
<220> FEATURE:
<221> NAME/KEY: misc_feature
<223> OTHER INFORMATION: Amino acid sequence of CDRL3 of 414B06 using
      Kabat

<400> SEQUENCE: 293

Gln Gln Ala Asn Ser Phe Pro Phe Thr
1               5
```

<210> SEQ ID NO 294
<211> LENGTH: 107
<212> TYPE: PRT
<213> ORGANISM: Homo sapiens
<220> FEATURE:
<221> NAME/KEY: misc_feature
<223> OTHER INFORMATION: Amino acid sequence of VL of 414B06

<400> SEQUENCE: 294

Asp Ile Gln Met Thr Gln Ser Pro Ser Ser Val Ser Ala Ser Val Gly
1               5                   10                  15

Asp Arg Val Thr Ile Thr Cys Arg Ala Ser Gln Gly Ile Ser Ser Trp
            20                  25                  30

Leu Ala Trp Tyr Gln Gln Lys Pro Gly Lys Ala Pro Lys Leu Leu Ile
        35                  40                  45

Tyr Ala Ala Ser Ser Leu Gln Ser Gly Val Pro Ser Arg Phe Ser Gly
    50                  55                  60

Ser Gly Ser Gly Thr Asp Phe Thr Leu Thr Ile Ser Ser Leu Gln Pro
65                  70                  75                  80

Glu Asp Phe Ala Thr Tyr Tyr Cys Gln Gln Ala Asn Ser Phe Pro Phe
                85                  90                  95

Thr Phe Gly Pro Gly Thr Lys Val Asp Ile Lys
            100                 105

<210> SEQ ID NO 295
<211> LENGTH: 322
<212> TYPE: DNA
<213> ORGANISM: Homo sapiens
<220> FEATURE:
<221> NAME/KEY: misc_feature
<223> OTHER INFORMATION: Nucleic acid sequence of VL of 414B06

<400> SEQUENCE: 295
gacatccaga tgacccagtc tccatcttcc gtgtctgcat ctgtaggaga cagagtcacc    60
atcacttgtc gggcgagtca gggtattagc agctggttag cctggtatca gcagaaacca   120
gggaaagccc ctaagctcct gatctatgct gcatccagtt tgcaaagtgg ggtcccatca   180
aggttcagcg gcagtggatc tgggacagat tcactctca ccatcagcag cctgcagcct    240
gaagattttg caacttacta ttgtcaacag gctaacagtt tcccattcac tttcggccct   300
gggaccaaag tggatatcaa ac                                            322

<210> SEQ ID NO 296
<211> LENGTH: 214
<212> TYPE: PRT
<213> ORGANISM: Homo sapiens
<220> FEATURE:
<221> NAME/KEY: misc_feature
<223> OTHER INFORMATION: Amino acid sequence of 414B06 light chain

<400> SEQUENCE: 296

Asp Ile Gln Met Thr Gln Ser Pro Ser Ser Val Ser Ala Ser Val Gly
1               5                   10                  15

Asp Arg Val Thr Ile Thr Cys Arg Ala Ser Gln Gly Ile Ser Ser Trp
            20                  25                  30

Leu Ala Trp Tyr Gln Gln Lys Pro Gly Lys Ala Pro Lys Leu Leu Ile
        35                  40                  45

Tyr Ala Ala Ser Ser Leu Gln Ser Gly Val Pro Ser Arg Phe Ser Gly
    50                  55                  60

Ser Gly Ser Gly Thr Asp Phe Thr Leu Thr Ile Ser Ser Leu Gln Pro
65                  70                  75                  80

Glu Asp Phe Ala Thr Tyr Tyr Cys Gln Gln Ala Asn Ser Phe Pro Phe
                85                  90                  95

Thr Phe Gly Pro Gly Thr Lys Val Asp Ile Lys Arg Thr Val Ala Ala
            100                 105                 110

Pro Ser Val Phe Ile Phe Pro Pro Ser Asp Glu Gln Leu Lys Ser Gly
        115                 120                 125

Thr Ala Ser Val Val Cys Leu Leu Asn Asn Phe Tyr Pro Arg Glu Ala
    130                 135                 140

Lys Val Gln Trp Lys Val Asp Asn Ala Leu Gln Ser Gly Asn Ser Gln
145                 150                 155                 160

Glu Ser Val Thr Glu Gln Asp Ser Lys Asp Ser Thr Tyr Ser Leu Ser
                165                 170                 175

Ser Thr Leu Thr Leu Ser Lys Ala Asp Tyr Glu Lys His Lys Val Tyr
            180                 185                 190

Ala Cys Glu Val Thr His Gln Gly Leu Ser Ser Pro Val Thr Lys Ser
        195                 200                 205

Phe Asn Arg Gly Glu Cys
    210

<210> SEQ ID NO 297
<211> LENGTH: 642
<212> TYPE: DNA
<213> ORGANISM: Homo sapiens
<220> FEATURE:
<221> NAME/KEY: misc_feature
<223> OTHER INFORMATION: Nucleic acid sequence of 414B06 light chain

<400> SEQUENCE: 297
gacatccaga tgacccagtc tccatcttcc gtgtctgcat ctgtaggaga cagagtcacc      60
atcacttgtc gggcgagtca gggtattagc agctggttag cctggtatca gcagaaacca     120
gggaaagccc ctaagctcct gatctatgct gcatccagtt tgcaaagtgg ggtcccatca     180
aggttcagcg gcagtggatc tgggacagat ttcactctca ccatcagcag cctgcagcct     240
gaagattttg caacttacta ttgtcaacag gctaacagtt tcccattcac tttcggccct     300
gggaccaaag tggatatcaa acgtacggtg gccgctccct ccgtgttcat cttcccacct     360
tccgacgagc agctgaagtc cggcaccgct tctgtcgtgt gcctgctgaa caacttctac     420
ccccgcgagg ccaaggtgca gtggaaggtg gacaacgccc tgcagtccgg caactcccag     480
gaatccgtga ccgagcagga ctccaaggac agcacctact ccctgtcctc cacccctgacc    540 ctgtccaagg ccgactacga gaagcacaag gtgtacgcct gcgaagtgac ccaccagggc     600
ctgtctagcc ccgtgaccaa gtctttcaac cggggcgagt gt                        642

<210> SEQ ID NO 298
<211> LENGTH: 214
<212> TYPE: PRT
<213> ORGANISM: Homo sapiens
<220> FEATURE:
<221> NAME/KEY: misc_feature
<223> OTHER INFORMATION: V to Y mutation 1D05 LC AA sequence

<400> SEQUENCE: 298

Asp Ile Gln Met Thr Gln Ser Pro Ser Ser Leu Ser Ala Ser Val Gly
1               5                   10                  15

Asp Arg Val Thr Ile Thr Cys Arg Ala Ser Gln Ser Ile Ser Ser Tyr
            20                  25                  30

-continued

```
Leu Asn Trp Tyr Gln Gln Lys Pro Gly Lys Ala Pro Lys Leu Leu Ile
            35                  40                  45

Tyr Tyr Ala Ser Ser Leu Gln Ser Gly Val Pro Ser Arg Phe Ser Gly
    50                  55                  60

Ser Gly Ser Gly Thr Asp Phe Thr Leu Thr Ile Ser Ser Leu Gln Pro
65                  70                  75                  80

Glu Asp Phe Ala Thr Tyr Tyr Cys Gln Gln Ser Tyr Ser Thr Pro Ile
                85                  90                  95

Thr Phe Gly Gln Gly Thr Arg Leu Glu Ile Lys Arg Thr Val Ala Ala
            100                 105                 110

Pro Ser Val Phe Ile Phe Pro Pro Ser Asp Glu Gln Leu Lys Ser Gly
            115                 120                 125

Thr Ala Ser Val Val Cys Leu Leu Asn Asn Phe Tyr Pro Arg Glu Ala
            130                 135                 140

Lys Val Gln Trp Lys Val Asp Asn Ala Leu Gln Ser Gly Asn Ser Gln
145                 150                 155                 160

Glu Ser Val Thr Glu Gln Asp Ser Lys Asp Ser Thr Tyr Ser Leu Ser
                165                 170                 175

Ser Thr Leu Thr Leu Ser Lys Ala Asp Tyr Glu Lys His Lys Val Tyr
            180                 185                 190

Ala Cys Glu Val Thr His Gln Gly Leu Ser Ser Pro Val Thr Lys Ser
            195                 200                 205

Phe Asn Arg Gly Glu Cys
            210

<210> SEQ ID NO 299
<211> LENGTH: 453
<212> TYPE: PRT
<213> ORGANISM: Homo sapiens
<220> FEATURE:
<221> NAME/KEY: misc_feature
<223> OTHER INFORMATION: Amino acid sequence of IgG1 disabled variant
      of 1D05

<400> SEQUENCE: 299

Glu Val Gln Leu Val Glu Ser Gly Gly Gly Leu Val Gln Pro Gly Arg
1               5                   10                  15

Ser Leu Arg Leu Ser Cys Ala Ala Ser Gly Phe Thr Phe Asp Asp Tyr
            20                  25                  30

Ala Met His Trp Val Arg Gln Val Pro Gly Lys Gly Leu Glu Trp Val
            35                  40                  45

Ser Gly Ile Ser Trp Ile Arg Thr Gly Ile Gly Tyr Ala Asp Ser Val
    50                  55                  60

Lys Gly Arg Phe Thr Ile Phe Arg Asp Asn Ala Lys Asn Ser Leu Tyr
65                  70                  75                  80

Leu Gln Met Asn Ser Leu Arg Ala Glu Asp Thr Ala Leu Tyr Tyr Cys
                85                  90                  95

Ala Lys Asp Met Lys Gly Ser Gly Thr Tyr Gly Gly Trp Phe Asp Thr
            100                 105                 110

Trp Gly Gln Gly Thr Leu Val Thr Val Ser Ser Ala Ser Thr Lys Gly
            115                 120                 125

Pro Ser Val Phe Pro Leu Ala Pro Ser Ser Lys Ser Thr Ser Gly Gly
            130                 135                 140

Thr Ala Ala Leu Gly Cys Leu Val Lys Asp Tyr Phe Pro Glu Pro Val
145                 150                 155                 160
```

```
Thr Val Ser Trp Asn Ser Gly Ala Leu Thr Ser Gly Val His Thr Phe
                    165                 170                 175
Pro Ala Val Leu Gln Ser Ser Gly Leu Tyr Ser Leu Ser Ser Val Val
            180                 185                 190
Thr Val Pro Ser Ser Ser Leu Gly Thr Gln Thr Tyr Ile Cys Asn Val
        195                 200                 205
Asn His Lys Pro Ser Asn Thr Lys Val Asp Lys Lys Val Glu Pro Lys
    210                 215                 220
Ser Cys Asp Lys Thr His Thr Cys Pro Pro Cys Pro Ala Pro Glu Leu
225                 230                 235                 240
Ala Gly Ala Pro Ser Val Phe Leu Phe Pro Pro Lys Pro Lys Asp Thr
                245                 250                 255
Leu Met Ile Ser Arg Thr Pro Glu Val Thr Cys Val Val Val Asp Val
            260                 265                 270
Ser His Glu Asp Pro Glu Val Lys Phe Asn Trp Tyr Val Asp Gly Val
        275                 280                 285
Glu Val His Asn Ala Lys Thr Lys Pro Arg Glu Glu Gln Tyr Asn Ser
    290                 295                 300
Thr Tyr Arg Val Val Ser Val Leu Thr Val Leu His Gln Asp Trp Leu
305                 310                 315                 320
Asn Gly Lys Glu Tyr Lys Cys Lys Val Ser Asn Lys Ala Leu Pro Ala
                325                 330                 335
Pro Ile Glu Lys Thr Ile Ser Lys Ala Lys Gly Gln Pro Arg Glu Pro
            340                 345                 350
Gln Val Tyr Thr Leu Pro Pro Ser Arg Asp Glu Leu Thr Lys Asn Gln
        355                 360                 365
Val Ser Leu Thr Cys Leu Val Lys Gly Phe Tyr Pro Ser Asp Ile Ala
    370                 375                 380
Val Glu Trp Glu Ser Asn Gly Gln Pro Glu Asn Asn Tyr Lys Thr Thr
385                 390                 395                 400
Pro Pro Val Leu Asp Ser Asp Gly Ser Phe Phe Leu Tyr Ser Lys Leu
                405                 410                 415
Thr Val Asp Lys Ser Arg Trp Gln Gln Gly Asn Val Phe Ser Cys Ser
            420                 425                 430
Val Met His Glu Ala Leu His Asn His Tyr Thr Gln Lys Ser Leu Ser
        435                 440                 445
Leu Ser Pro Gly Lys
    450

<210> SEQ ID NO 300
<211> LENGTH: 347
<212> TYPE: PRT
<213> ORGANISM: Homo sapiens
<220> FEATURE:
<221> NAME/KEY: misc_feature
<223> OTHER INFORMATION: 1D05 Light chain sequence fused to wild-type
      human IL-2 sequence

<400> SEQUENCE: 300

Asp Ile Gln Met Thr Gln Ser Pro Ser Ser Leu Ser Ala Ser Val Gly
1               5                   10                  15
Asp Arg Val Thr Ile Thr Cys Arg Ala Ser Gln Ser Ile Ser Ser Tyr
            20                  25                  30
Leu Asn Trp Tyr Gln Gln Lys Pro Gly Lys Ala Pro Lys Leu Leu Ile
        35                  40                  45
Tyr Val Ala Ser Ser Leu Gln Ser Gly Val Pro Ser Arg Phe Ser Gly
```

```
                50                  55                  60
Ser Gly Ser Gly Thr Asp Phe Thr Leu Thr Ile Ser Ser Leu Gln Pro
 65                  70                  75                  80

Glu Asp Phe Ala Thr Tyr Tyr Cys Gln Gln Ser Tyr Ser Thr Pro Ile
                 85                  90                  95

Thr Phe Gly Gln Gly Thr Arg Leu Glu Ile Lys Arg Thr Val Ala Ala
                100                 105                 110

Pro Ser Val Phe Ile Phe Pro Pro Ser Asp Glu Gln Leu Lys Ser Gly
            115                 120                 125

Thr Ala Ser Val Val Cys Leu Leu Asn Asn Phe Tyr Pro Arg Glu Ala
        130                 135                 140

Lys Val Gln Trp Lys Val Asp Asn Ala Leu Gln Ser Gly Asn Ser Gln
145                 150                 155                 160

Glu Ser Val Thr Glu Gln Asp Ser Lys Asp Ser Thr Tyr Ser Leu Ser
                165                 170                 175

Ser Thr Leu Thr Leu Ser Lys Ala Asp Tyr Glu Lys His Lys Val Tyr
            180                 185                 190

Ala Cys Glu Val Thr His Gln Gly Leu Ser Ser Pro Val Thr Lys Ser
        195                 200                 205

Phe Asn Arg Gly Glu Cys Ala Pro Thr Ser Ser Ser Thr Lys Lys Thr
210                 215                 220

Gln Leu Gln Leu Glu His Leu Leu Leu Asp Leu Gln Met Ile Leu Asn
225                 230                 235                 240

Gly Ile Asn Asn Tyr Lys Asn Pro Lys Leu Thr Arg Met Leu Thr Phe
                245                 250                 255

Lys Phe Tyr Met Pro Lys Lys Ala Thr Glu Leu Lys His Leu Gln Cys
            260                 265                 270

Leu Glu Glu Glu Leu Lys Pro Leu Glu Glu Val Leu Asn Leu Ala Gln
        275                 280                 285

Ser Lys Asn Phe His Leu Arg Pro Arg Asp Leu Ile Ser Asn Ile Asn
    290                 295                 300

Val Ile Val Leu Glu Leu Lys Gly Ser Glu Thr Thr Phe Met Cys Glu
305                 310                 315                 320

Tyr Ala Asp Glu Thr Ala Thr Ile Val Glu Phe Leu Asn Arg Trp Ile
                325                 330                 335

Thr Phe Cys Gln Ser Ile Ile Ser Thr Leu Thr
            340                 345

<210> SEQ ID NO 301
<211> LENGTH: 133
<212> TYPE: PRT
<213> ORGANISM: Homo sapiens
<220> FEATURE:
<221> NAME/KEY: misc_feature
<223> OTHER INFORMATION: Human IL-2, Uniprot number: P60568

<400> SEQUENCE: 301

Ala Pro Thr Ser Ser Ser Thr Lys Lys Thr Gln Leu Gln Leu Glu His
 1               5                  10                  15

Leu Leu Leu Asp Leu Gln Met Ile Leu Asn Gly Ile Asn Asn Tyr Lys
            20                  25                  30

Asn Pro Lys Leu Thr Arg Met Leu Thr Phe Lys Phe Tyr Met Pro Lys
        35                  40                  45

Lys Ala Thr Glu Leu Lys His Leu Gln Cys Leu Glu Glu Glu Leu Lys
    50                  55                  60
```

```
Pro Leu Glu Glu Val Leu Asn Leu Ala Gln Ser Lys Asn Phe His Leu
65                  70                  75                  80

Arg Pro Arg Asp Leu Ile Ser Asn Ile Asn Val Ile Val Leu Glu Leu
                85                  90                  95

Lys Gly Ser Glu Thr Thr Phe Met Cys Glu Tyr Ala Asp Glu Thr Ala
            100                 105                 110

Thr Ile Val Glu Phe Leu Asn Arg Trp Ile Thr Phe Cys Gln Ser Ile
        115                 120                 125

Ile Ser Thr Leu Thr
        130

<210> SEQ ID NO 302
<211> LENGTH: 586
<212> TYPE: PRT
<213> ORGANISM: Homo sapiens
<220> FEATURE:
<221> NAME/KEY: misc_feature
<223> OTHER INFORMATION: HC 1D05 IgG1 variant fused at the N-terminus
      to WT hIL2

<400> SEQUENCE: 302

Glu Val Gln Leu Val Glu Ser Gly Gly Gly Leu Val Gln Pro Gly Arg
1               5                   10                  15

Ser Leu Arg Leu Ser Cys Ala Ala Ser Gly Phe Thr Phe Asp Asp Tyr
            20                  25                  30

Ala Met His Trp Val Arg Gln Pro Gly Lys Gly Leu Glu Trp Val
        35                  40                  45

Ser Gly Ile Ser Trp Ile Arg Thr Gly Ile Gly Tyr Ala Asp Ser Val
50                  55                  60

Lys Gly Arg Phe Thr Ile Phe Arg Asp Asn Ala Lys Asn Ser Leu Tyr
65                  70                  75                  80

Leu Gln Met Asn Ser Leu Arg Ala Glu Asp Thr Ala Leu Tyr Tyr Cys
            85                  90                  95

Ala Lys Asp Met Lys Gly Ser Gly Thr Tyr Gly Gly Trp Phe Asp Thr
            100                 105                 110

Trp Gly Gln Gly Thr Leu Val Thr Val Ser Ser Ala Ser Thr Lys Gly
        115                 120                 125

Pro Ser Val Phe Pro Leu Ala Pro Ser Ser Lys Ser Thr Ser Gly Gly
        130                 135                 140

Thr Ala Ala Leu Gly Cys Leu Val Lys Asp Tyr Phe Pro Glu Pro Val
145                 150                 155                 160

Thr Val Ser Trp Asn Ser Gly Ala Leu Thr Ser Gly Val His Thr Phe
                165                 170                 175

Pro Ala Val Leu Gln Ser Ser Gly Leu Tyr Ser Leu Ser Ser Val Val
            180                 185                 190

Thr Val Pro Ser Ser Ser Leu Gly Thr Gln Thr Tyr Ile Cys Asn Val
        195                 200                 205

Asn His Lys Pro Ser Asn Thr Lys Val Asp Lys Lys Val Glu Pro Lys
    210                 215                 220

Ser Cys Asp Lys Thr His Thr Cys Pro Pro Cys Pro Ala Pro Glu Leu
225                 230                 235                 240

Ala Gly Ala Pro Ser Val Phe Leu Phe Pro Pro Lys Pro Lys Asp Thr
                245                 250                 255

Leu Met Ile Ser Arg Thr Pro Glu Val Thr Cys Val Val Val Asp Val
            260                 265                 270

Ser His Glu Asp Pro Glu Val Lys Phe Asn Trp Tyr Val Asp Gly Val
```

```
                275                 280                 285
Glu Val His Asn Ala Lys Thr Lys Pro Arg Glu Glu Gln Tyr Asn Ser
        290                 295                 300

Thr Tyr Arg Val Val Ser Val Leu Thr Val Leu His Gln Asp Trp Leu
305                 310                 315                 320

Asn Gly Lys Glu Tyr Lys Cys Lys Val Ser Asn Lys Ala Leu Pro Ala
                325                 330                 335

Pro Ile Glu Lys Thr Ile Ser Lys Ala Lys Gly Gln Pro Arg Glu Pro
            340                 345                 350

Gln Val Tyr Thr Leu Pro Pro Ser Arg Asp Glu Leu Thr Lys Asn Gln
        355                 360                 365

Val Ser Leu Thr Cys Leu Val Lys Gly Phe Tyr Pro Ser Asp Ile Ala
370                 375                 380

Val Glu Trp Glu Ser Asn Gly Gln Pro Glu Asn Asn Tyr Lys Thr Thr
385                 390                 395                 400

Pro Pro Val Leu Asp Ser Asp Gly Ser Phe Phe Leu Tyr Ser Lys Leu
                405                 410                 415

Thr Val Asp Lys Ser Arg Trp Gln Gln Gly Asn Val Phe Ser Cys Ser
            420                 425                 430

Val Met His Glu Ala Leu His Asn His Tyr Thr Gln Lys Ser Leu Ser
        435                 440                 445

Leu Ser Pro Gly Lys Ala Pro Thr Ser Ser Ser Thr Lys Lys Thr Gln
450                 455                 460

Leu Gln Leu Glu His Leu Leu Leu Asp Leu Gln Met Ile Leu Asn Gly
465                 470                 475                 480

Ile Asn Asn Tyr Lys Asn Pro Lys Leu Thr Arg Met Leu Thr Phe Lys
                485                 490                 495

Phe Tyr Met Pro Lys Lys Ala Thr Glu Leu Lys His Leu Gln Cys Leu
            500                 505                 510

Glu Glu Glu Leu Lys Pro Leu Glu Glu Val Leu Asn Leu Ala Gln Ser
        515                 520                 525

Lys Asn Phe His Leu Arg Pro Arg Asp Leu Ile Ser Asn Ile Asn Val
530                 535                 540

Ile Val Leu Glu Leu Lys Gly Ser Glu Thr Thr Phe Met Cys Glu Tyr
545                 550                 555                 560

Ala Asp Glu Thr Ala Thr Ile Val Glu Phe Leu Asn Arg Trp Ile Thr
                565                 570                 575

Phe Cys Gln Ser Ile Ile Ser Thr Leu Thr
            580                 585

<210> SEQ ID NO 303
<211> LENGTH: 14
<212> TYPE: PRT
<213> ORGANISM: Homo sapiens
<220> FEATURE:
<221> NAME/KEY: misc_feature
<223> OTHER INFORMATION: IL-2 IC45 (Del 5-9) N terminal IL-2 sequence

<400> SEQUENCE: 303

Ala Pro Thr Ser Thr Gln Leu Gln Leu Glu Leu Leu Leu Asp
1               5                   10

<210> SEQ ID NO 304
<211> LENGTH: 11
<212> TYPE: PRT
<213> ORGANISM: Homo sapiens
<220> FEATURE:
```

```
<221> NAME/KEY: misc_feature
<223> OTHER INFORMATION: IL-2 IC46  (Del 1-9) N terminal IL-2 sequence

<400> SEQUENCE: 304

Thr Gln Leu Gln Leu Glu His Leu Leu Leu Asp
1               5                   10

<210> SEQ ID NO 305
<211> LENGTH: 17
<212> TYPE: PRT
<213> ORGANISM: Homo sapiens
<220> FEATURE:
<221> NAME/KEY: misc_feature
<223> OTHER INFORMATION: IL-2 IC64 (Del 5-7) N terminal IL-2 sequence

<400> SEQUENCE: 305

Ala Pro Thr Ser Lys Lys Thr Gln Leu Gln Leu Glu His Leu Leu Leu
1               5                   10                  15

Asp

<210> SEQ ID NO 306
<211> LENGTH: 19
<212> TYPE: PRT
<213> ORGANISM: Homo sapiens
<220> FEATURE:
<221> NAME/KEY: misc_feature
<223> OTHER INFORMATION: IL-2 D1 N terminal IL-2 sequence

<400> SEQUENCE: 306

Pro Thr Ser Ser Ser Thr Lys Lys Thr Gln Leu Gln Leu Glu His Leu
1               5                   10                  15

Leu Leu Asp

<210> SEQ ID NO 307
<211> LENGTH: 18
<212> TYPE: PRT
<213> ORGANISM: Homo sapiens
<220> FEATURE:
<221> NAME/KEY: misc_feature
<223> OTHER INFORMATION: IL-2 D1-2 N terminal IL-2 sequence

<400> SEQUENCE: 307

Thr Ser Ser Ser Thr Lys Lys Thr Gln Leu Gln Leu Glu His Leu Leu
1               5                   10                  15

Leu Asp

<210> SEQ ID NO 308
<211> LENGTH: 17
<212> TYPE: PRT
<213> ORGANISM: Homo sapiens
<220> FEATURE:
<221> NAME/KEY: misc_feature
<223> OTHER INFORMATION: IL-2 D1-3 N terminal IL-2 sequence

<400> SEQUENCE: 308

Ser Ser Ser Thr Lys Lys Thr Gln Leu Gln Leu Glu His Leu Leu Leu
1               5                   10                  15

Asp

<210> SEQ ID NO 309
<211> LENGTH: 16
<212> TYPE: PRT
<213> ORGANISM: Homo sapiens
<220> FEATURE:
<221> NAME/KEY: misc_feature
```

<223> OTHER INFORMATION: IL-2 D1-4 N terminal IL-2 sequence

<400> SEQUENCE: 309

Ser Ser Thr Lys Lys Thr Gln Leu Gln Leu Glu His Leu Leu Leu Asp
1               5                   10                  15

<210> SEQ ID NO 310
<211> LENGTH: 15
<212> TYPE: PRT
<213> ORGANISM: Homo sapiens
<220> FEATURE:
<221> NAME/KEY: misc_feature
<223> OTHER INFORMATION: IL-2 D1-5 N terminal IL-2 sequence

<400> SEQUENCE: 310

Ser Thr Lys Lys Thr Gln Leu Gln Leu Glu His Leu Leu Leu Asp
1               5                   10                  15

<210> SEQ ID NO 311
<211> LENGTH: 14
<212> TYPE: PRT
<213> ORGANISM: Homo sapiens
<220> FEATURE:
<221> NAME/KEY: misc_feature
<223> OTHER INFORMATION: IL-2 D1-6 N terminal IL-2 sequence

<400> SEQUENCE: 311

Thr Lys Lys Thr Gln Leu Gln Leu Glu His Leu Leu Leu Asp
1               5                   10

<210> SEQ ID NO 312
<211> LENGTH: 13
<212> TYPE: PRT
<213> ORGANISM: Homo sapiens
<220> FEATURE:
<221> NAME/KEY: misc_feature
<223> OTHER INFORMATION: IL-2 D1-7 N terminal IL-2 sequence

<400> SEQUENCE: 312

Lys Lys Thr Gln Leu Gln Leu Glu His Leu Leu Leu Asp
1               5                   10

<210> SEQ ID NO 313
<211> LENGTH: 12
<212> TYPE: PRT
<213> ORGANISM: Homo sapiens
<220> FEATURE:
<221> NAME/KEY: misc_feature
<223> OTHER INFORMATION: IL-2 D1-8 N terminal IL-2 sequence

<400> SEQUENCE: 313

Lys Thr Gln Leu Gln Leu Glu His Leu Leu Leu Asp
1               5                   10

<210> SEQ ID NO 314
<211> LENGTH: 19
<212> TYPE: PRT
<213> ORGANISM: Homo sapiens
<220> FEATURE:
<221> NAME/KEY: misc_feature
<223> OTHER INFORMATION: IL-2 D9 N terminal IL-2 sequence

<400> SEQUENCE: 314

Ala Pro Thr Ser Ser Ser Thr Lys Thr Gln Leu Gln Leu Glu His Leu
1               5                   10                  15

Leu Leu Asp

<210> SEQ ID NO 315
<211> LENGTH: 18
<212> TYPE: PRT
<213> ORGANISM: Homo sapiens
<220> FEATURE:
<221> NAME/KEY: misc_feature
<223> OTHER INFORMATION: IL-2 D9-8 N terminal IL-2 sequence

<400> SEQUENCE: 315

Ala Pro Thr Ser Ser Ser Thr Thr Gln Leu Gln Leu Glu His Leu Leu
1               5                   10                  15

Leu Asp

<210> SEQ ID NO 316
<211> LENGTH: 17
<212> TYPE: PRT
<213> ORGANISM: Homo sapiens
<220> FEATURE:
<221> NAME/KEY: misc_feature
<223> OTHER INFORMATION: IL-2 D9-7 N terminal IL-2 sequence

<400> SEQUENCE: 316

Ala Pro Thr Ser Ser Ser Thr Gln Leu Gln Leu Glu His Leu Leu Leu
1               5                   10                  15

Asp

<210> SEQ ID NO 317
<211> LENGTH: 16
<212> TYPE: PRT
<213> ORGANISM: Homo sapiens
<220> FEATURE:
<221> NAME/KEY: misc_feature
<223> OTHER INFORMATION: IL-2 D9-6 N terminal IL-2 sequence

<400> SEQUENCE: 317

Ala Pro Thr Ser Ser Thr Gln Leu Gln Leu Glu His Leu Leu Leu Asp
1               5                   10                  15

<210> SEQ ID NO 318
<211> LENGTH: 14
<212> TYPE: PRT
<213> ORGANISM: Homo sapiens
<220> FEATURE:
<221> NAME/KEY: misc_feature
<223> OTHER INFORMATION: IL-2 D9-4 N terminal IL-2 sequence

<400> SEQUENCE: 318

Ala Pro Thr Thr Gln Leu Gln Leu Glu His Leu Leu Leu Asp
1               5                   10

<210> SEQ ID NO 319
<211> LENGTH: 13
<212> TYPE: PRT
<213> ORGANISM: Homo sapiens
<220> FEATURE:
<221> NAME/KEY: misc_feature
<223> OTHER INFORMATION: IL-2 D9-3 N terminal IL-2 sequence

<400> SEQUENCE: 319

Ala Pro Thr Gln Leu Gln Leu Glu His Leu Leu Leu Asp
1               5                   10

<210> SEQ ID NO 320
<211> LENGTH: 12
<212> TYPE: PRT
<213> ORGANISM: Homo sapiens

```
<220> FEATURE:
<221> NAME/KEY: misc_feature
<223> OTHER INFORMATION: IL-2 D9-2 N terminal IL-2 sequence

<400> SEQUENCE: 320

Ala Thr Gln Leu Gln Leu Glu His Leu Leu Asp
1               5                   10

<210> SEQ ID NO 321
<211> LENGTH: 15
<212> TYPE: PRT
<213> ORGANISM: Homo sapiens
<220> FEATURE:
<221> NAME/KEY: misc_feature
<223> OTHER INFORMATION: IL-2 D2-6 N terminal IL-2 sequence

<400> SEQUENCE: 321

Ala Thr Lys Lys Thr Gln Leu Gln Leu Glu His Leu Leu Leu Asp
1               5                   10                  15

<210> SEQ ID NO 322
<211> LENGTH: 15
<212> TYPE: PRT
<213> ORGANISM: Homo sapiens
<220> FEATURE:
<221> NAME/KEY: misc_feature
<223> OTHER INFORMATION: IL-2 D3-7 N terminal IL-2 sequence

<400> SEQUENCE: 322

Ala Pro Lys Lys Thr Gln Leu Gln Leu Glu His Leu Leu Leu Asp
1               5                   10                  15

<210> SEQ ID NO 323
<211> LENGTH: 15
<212> TYPE: PRT
<213> ORGANISM: Homo sapiens
<220> FEATURE:
<221> NAME/KEY: misc_feature
<223> OTHER INFORMATION: IL-2 D4-8 N terminal IL-2 sequence

<400> SEQUENCE: 323

Ala Pro Thr Lys Thr Gln Leu Gln Leu Glu His Leu Leu Leu Asp
1               5                   10                  15

<210> SEQ ID NO 324
<211> LENGTH: 113
<212> TYPE: PRT
<213> ORGANISM: Homo sapiens
<220> FEATURE:
<221> NAME/KEY: misc_feature
<223> OTHER INFORMATION: Amino acids 21 to 133 of hIL-2

<400> SEQUENCE: 324

Leu Gln Met Ile Leu Asn Gly Ile Asn Asn Tyr Lys Asn Pro Lys Leu
1               5                   10                  15

Thr Arg Met Leu Thr Phe Lys Phe Tyr Met Pro Lys Lys Ala Thr Glu
                20                  25                  30

Leu Lys His Leu Gln Cys Leu Glu Glu Glu Leu Lys Pro Leu Glu Glu
            35                  40                  45

Val Leu Asn Leu Ala Gln Ser Lys Asn Phe His Leu Arg Pro Arg Asp
        50                  55                  60

Leu Ile Ser Asn Ile Asn Val Ile Val Leu Glu Leu Lys Gly Ser Glu
65                  70                  75                  80

Thr Thr Phe Met Cys Glu Tyr Ala Asp Glu Thr Ala Thr Ile Val Glu
                85                  90                  95
```

```
Phe Leu Asn Arg Trp Ile Thr Phe Cys Gln Ser Ile Ile Ser Thr Leu
            100                 105                 110
Thr

<210> SEQ ID NO 325
<211> LENGTH: 290
<212> TYPE: PRT
<213> ORGANISM: Mus musculus
<220> FEATURE:
<221> NAME/KEY: misc_feature
<223> OTHER INFORMATION: Mouse PD-L1, Uniprot number: Q9EP73

<400> SEQUENCE: 325

Met Arg Ile Phe Ala Gly Ile Ile Phe Thr Ala Cys Cys His Leu Leu
1               5                   10                  15

Arg Ala Phe Thr Ile Thr Ala Pro Lys Asp Leu Tyr Val Val Glu Tyr
            20                  25                  30

Gly Ser Asn Val Thr Met Glu Cys Arg Phe Pro Val Glu Arg Glu Leu
        35                  40                  45

Asp Leu Leu Ala Leu Val Val Tyr Trp Glu Lys Glu Asp Glu Gln Val
    50                  55                  60

Ile Gln Phe Val Ala Gly Glu Glu Asp Leu Lys Pro Gln His Ser Asn
65                  70                  75                  80

Phe Arg Gly Arg Ala Ser Leu Pro Lys Asp Gln Leu Leu Lys Gly Asn
                85                  90                  95

Ala Ala Leu Gln Ile Thr Asp Val Lys Leu Gln Asp Ala Gly Val Tyr
            100                 105                 110

Cys Cys Ile Ile Ser Tyr Gly Gly Ala Asp Tyr Lys Arg Ile Thr Leu
        115                 120                 125

Lys Val Asn Ala Pro Tyr Arg Lys Ile Asn Gln Arg Ile Ser Val Asp
    130                 135                 140

Pro Ala Thr Ser Glu His Glu Leu Ile Cys Gln Ala Glu Gly Tyr Pro
145                 150                 155                 160

Glu Ala Glu Val Ile Trp Thr Asn Ser Asp His Gln Pro Val Ser Gly
                165                 170                 175

Lys Arg Ser Val Thr Thr Ser Arg Thr Glu Gly Met Leu Leu Asn Val
            180                 185                 190

Thr Ser Ser Leu Arg Val Asn Ala Thr Ala Asn Asp Val Phe Tyr Cys
        195                 200                 205

Thr Phe Trp Arg Ser Gln Pro Gly Gln Asn His Thr Ala Glu Leu Ile
    210                 215                 220

Ile Pro Glu Leu Pro Ala Thr His Pro Pro Gln Asn Arg Thr His Trp
225                 230                 235                 240

Val Leu Leu Gly Ser Ile Leu Leu Phe Leu Ile Val Val Ser Thr Val
                245                 250                 255

Leu Leu Phe Leu Arg Lys Gln Val Arg Met Leu Asp Val Glu Lys Cys
            260                 265                 270

Gly Val Glu Asp Thr Ser Ser Lys Asn Arg Asn Asp Thr Gln Phe Glu
        275                 280                 285

Glu Thr
    290

<210> SEQ ID NO 326
<211> LENGTH: 226
<212> TYPE: PRT
<213> ORGANISM: Mus musculus
```

```
<220> FEATURE:
<221> NAME/KEY: misc_feature
<223> OTHER INFORMATION: Mouse PD-L1 extracellular domain with his tag

<400> SEQUENCE: 326

Phe Thr Ile Thr Ala Pro Lys Asp Leu Tyr Val Val Glu Tyr Gly Ser
1               5                   10                  15

Asn Val Thr Met Glu Cys Arg Phe Pro Val Glu Arg Glu Leu Asp Leu
            20                  25                  30

Leu Ala Leu Val Val Tyr Trp Glu Lys Glu Asp Glu Gln Val Ile Gln
        35                  40                  45

Phe Val Ala Gly Glu Glu Asp Leu Lys Pro Gln His Ser Asn Phe Arg
    50                  55                  60

Gly Arg Ala Ser Leu Pro Lys Asp Gln Leu Leu Lys Gly Asn Ala Ala
65                  70                  75                  80

Leu Gln Ile Thr Asp Val Lys Leu Gln Asp Ala Gly Val Tyr Cys Cys
                85                  90                  95

Ile Ile Ser Tyr Gly Gly Ala Asp Tyr Lys Arg Ile Thr Leu Lys Val
            100                 105                 110

Asn Ala Pro Tyr Arg Lys Ile Asn Gln Arg Ile Ser Val Asp Pro Ala
        115                 120                 125

Thr Ser Glu His Glu Leu Ile Cys Gln Ala Glu Gly Tyr Pro Glu Ala
    130                 135                 140

Glu Val Ile Trp Thr Asn Ser Asp His Gln Pro Val Ser Gly Lys Arg
145                 150                 155                 160

Ser Val Thr Thr Ser Arg Thr Glu Gly Met Leu Leu Asn Val Thr Ser
                165                 170                 175

Ser Leu Arg Val Asn Ala Thr Ala Asn Asp Val Phe Tyr Cys Thr Phe
            180                 185                 190

Trp Arg Ser Gln Pro Gly Gln Asn His Thr Ala Glu Leu Ile Ile Pro
        195                 200                 205

Glu Leu Pro Ala Thr His Pro Pro Gln Asn Arg Thr His His His His
    210                 215                 220

His His
225

<210> SEQ ID NO 327
<211> LENGTH: 251
<212> TYPE: PRT
<213> ORGANISM: Homo sapiens
<220> FEATURE:
<221> NAME/KEY: misc_feature
<223> OTHER INFORMATION: Human IL-2 receptor alpha chain

<400> SEQUENCE: 327

Glu Leu Cys Asp Asp Asp Pro Pro Glu Ile Pro His Ala Thr Phe Lys
1               5                   10                  15

Ala Met Ala Tyr Lys Glu Gly Thr Met Leu Asn Cys Glu Cys Lys Arg
            20                  25                  30

Gly Phe Arg Arg Ile Lys Ser Gly Ser Leu Tyr Met Leu Cys Thr Gly
        35                  40                  45

Asn Ser Ser His Ser Ser Trp Asp Asn Gln Cys Gln Cys Thr Ser Ser
    50                  55                  60

Ala Thr Arg Asn Thr Thr Lys Gln Val Thr Pro Gln Pro Glu Glu Gln
65                  70                  75                  80

Lys Glu Arg Lys Thr Thr Glu Met Gln Ser Pro Met Gln Pro Val Asp
                85                  90                  95
```

```
Gln Ala Ser Leu Pro Gly His Cys Arg Glu Pro Pro Trp Glu Asn
            100                 105                 110
Glu Ala Thr Glu Arg Ile Tyr His Phe Val Val Gly Gln Met Val Tyr
            115                 120                 125
Tyr Gln Cys Val Gln Gly Tyr Arg Ala Leu His Arg Gly Pro Ala Glu
        130                 135                 140
Ser Val Cys Lys Met Thr His Gly Lys Thr Arg Trp Thr Gln Pro Gln
145                 150                 155                 160
Leu Ile Cys Thr Gly Glu Met Glu Thr Ser Gln Phe Pro Gly Glu Glu
                165                 170                 175
Lys Pro Gln Ala Ser Pro Glu Gly Arg Pro Glu Ser Glu Thr Ser Cys
            180                 185                 190
Leu Val Thr Thr Thr Asp Phe Gln Ile Gln Thr Glu Met Ala Ala Thr
        195                 200                 205
Met Glu Thr Ser Ile Phe Thr Thr Glu Tyr Gln Val Ala Val Ala Gly
    210                 215                 220
Cys Val Phe Leu Leu Ile Ser Val Leu Leu Leu Ser Gly Leu Thr Trp
225                 230                 235                 240
Gln Arg Arg Gln Arg Lys Ser Arg Arg Thr Ile
                245                 250

<210> SEQ ID NO 328
<211> LENGTH: 525
<212> TYPE: PRT
<213> ORGANISM: Homo sapiens
<220> FEATURE:
<221> NAME/KEY: misc_feature
<223> OTHER INFORMATION: Human IL-2 receptor beta chain

<400> SEQUENCE: 328

Ala Val Asn Gly Thr Ser Gln Phe Thr Cys Phe Tyr Asn Ser Arg Ala
1               5                   10                  15
Asn Ile Ser Cys Val Trp Ser Gln Asp Gly Ala Leu Gln Asp Thr Ser
            20                  25                  30
Cys Gln Val His Ala Trp Pro Asp Arg Arg Arg Trp Asn Gln Thr Cys
        35                  40                  45
Glu Leu Leu Pro Val Ser Gln Ala Ser Trp Ala Cys Asn Leu Ile Leu
    50                  55                  60
Gly Ala Pro Asp Ser Gln Lys Leu Thr Thr Val Asp Ile Val Thr Leu
65                  70                  75                  80
Arg Val Leu Cys Arg Glu Gly Val Arg Trp Arg Val Met Ala Ile Gln
                85                  90                  95
Asp Phe Lys Pro Phe Glu Asn Leu Arg Leu Met Ala Pro Ile Ser Leu
            100                 105                 110
Gln Val Val His Val Glu Thr His Arg Cys Asn Ile Ser Trp Glu Ile
        115                 120                 125
Ser Gln Ala Ser His Tyr Phe Glu Arg His Leu Glu Phe Glu Ala Arg
    130                 135                 140
Thr Leu Ser Pro Gly His Thr Trp Glu Glu Ala Pro Leu Leu Thr Leu
145                 150                 155                 160
Lys Gln Lys Gln Glu Trp Ile Cys Leu Glu Thr Leu Thr Pro Asp Thr
                165                 170                 175
Gln Tyr Glu Phe Gln Val Arg Val Lys Pro Leu Gln Gly Glu Phe Thr
            180                 185                 190
Thr Trp Ser Pro Trp Ser Gln Pro Leu Ala Phe Arg Thr Lys Pro Ala
```

-continued

```
                195                 200                 205
Ala Leu Gly Lys Asp Thr Ile Pro Trp Leu Gly His Leu Leu Val Gly
    210                 215                 220

Leu Ser Gly Ala Phe Gly Phe Ile Ile Leu Val Tyr Leu Leu Ile Asn
225                 230                 235                 240

Cys Arg Asn Thr Gly Pro Trp Leu Lys Lys Val Leu Lys Cys Asn Thr
                245                 250                 255

Pro Asp Pro Ser Lys Phe Phe Ser Gln Leu Ser Ser Glu His Gly Gly
            260                 265                 270

Asp Val Gln Lys Trp Leu Ser Ser Pro Phe Pro Ser Ser Ser Phe Ser
        275                 280                 285

Pro Gly Gly Leu Ala Pro Glu Ile Ser Pro Leu Glu Val Leu Glu Arg
    290                 295                 300

Asp Lys Val Thr Gln Leu Leu Leu Gln Gln Asp Lys Val Pro Glu Pro
305                 310                 315                 320

Ala Ser Leu Ser Ser Asn His Ser Leu Thr Ser Cys Phe Thr Asn Gln
                325                 330                 335

Gly Tyr Phe Phe Phe His Leu Pro Asp Ala Leu Glu Ile Glu Ala Cys
            340                 345                 350

Gln Val Tyr Phe Thr Tyr Asp Pro Tyr Ser Glu Glu Asp Pro Asp Glu
        355                 360                 365

Gly Val Ala Gly Ala Pro Thr Gly Ser Ser Pro Gln Pro Leu Gln Pro
    370                 375                 380

Leu Ser Gly Glu Asp Asp Ala Tyr Cys Thr Phe Pro Ser Arg Asp Asp
385                 390                 395                 400

Leu Leu Leu Phe Ser Pro Ser Leu Leu Gly Gly Pro Ser Pro Pro Ser
                405                 410                 415

Thr Ala Pro Gly Gly Ser Gly Ala Gly Glu Glu Arg Met Pro Pro Ser
            420                 425                 430

Leu Gln Glu Arg Val Pro Arg Asp Trp Asp Pro Gln Pro Leu Gly Pro
        435                 440                 445

Pro Thr Pro Gly Val Pro Asp Leu Val Asp Phe Gln Pro Pro Pro Glu
    450                 455                 460

Leu Val Leu Arg Glu Ala Gly Glu Glu Val Pro Asp Ala Gly Pro Arg
465                 470                 475                 480

Glu Gly Val Ser Phe Pro Trp Ser Arg Pro Pro Gly Gln Gly Glu Phe
                485                 490                 495

Arg Ala Leu Asn Ala Arg Leu Pro Leu Asn Thr Asp Ala Tyr Leu Ser
            500                 505                 510

Leu Gln Glu Leu Gln Gly Gln Asp Pro Thr His Leu Val
        515                 520                 525

<210> SEQ ID NO 329
<211> LENGTH: 347
<212> TYPE: PRT
<213> ORGANISM: Homo sapiens
<220> FEATURE:
<221> NAME/KEY: misc_feature
<223> OTHER INFORMATION: Human IL-2 receptor common gamma chain

<400> SEQUENCE: 329

Leu Asn Thr Thr Ile Leu Thr Pro Asn Gly Asn Glu Asp Thr Thr Ala
1               5                   10                  15

Asp Phe Phe Leu Thr Thr Met Pro Thr Asp Ser Leu Ser Val Ser Thr
                20                  25                  30
```

```
Leu Pro Leu Pro Glu Val Gln Cys Phe Val Phe Asn Val Glu Tyr Met
            35                  40                  45

Asn Cys Thr Trp Asn Ser Ser Glu Pro Gln Pro Thr Asn Leu Thr
 50                  55                  60

Leu His Tyr Trp Tyr Lys Asn Ser Asp Asn Asp Lys Val Gln Lys Cys
 65                  70                  75                  80

Ser His Tyr Leu Phe Ser Glu Glu Ile Thr Ser Gly Cys Gln Leu Gln
                 85                  90                  95

Lys Lys Glu Ile His Leu Tyr Gln Thr Phe Val Val Gln Leu Gln Asp
            100                 105                 110

Pro Arg Glu Pro Arg Arg Gln Ala Thr Gln Met Leu Lys Leu Gln Asn
            115                 120                 125

Leu Val Ile Pro Trp Ala Pro Glu Asn Leu Thr Leu His Lys Leu Ser
130                 135                 140

Glu Ser Gln Leu Glu Leu Asn Trp Asn Asn Arg Phe Leu Asn His Cys
145                 150                 155                 160

Leu Glu His Leu Val Gln Tyr Arg Thr Asp Trp Asp His Ser Trp Thr
                165                 170                 175

Glu Gln Ser Val Asp Tyr Arg His Lys Phe Ser Leu Pro Ser Val Asp
            180                 185                 190

Gly Gln Lys Arg Tyr Thr Phe Arg Val Arg Ser Arg Phe Asn Pro Leu
            195                 200                 205

Cys Gly Ser Ala Gln His Trp Ser Glu Trp Ser His Pro Ile His Trp
            210                 215                 220

Gly Ser Asn Thr Ser Lys Glu Asn Pro Phe Leu Phe Ala Leu Glu Ala
225                 230                 235                 240

Val Val Ile Ser Val Gly Ser Met Gly Leu Ile Ile Ser Leu Leu Cys
                245                 250                 255

Val Tyr Phe Trp Leu Glu Arg Thr Met Pro Arg Ile Pro Thr Leu Lys
            260                 265                 270

Asn Leu Glu Asp Leu Val Thr Glu Tyr His Gly Asn Phe Ser Ala Trp
            275                 280                 285

Ser Gly Val Ser Lys Gly Leu Ala Glu Ser Leu Gln Pro Asp Tyr Ser
290                 295                 300

Glu Arg Leu Cys Leu Val Ser Glu Ile Pro Pro Lys Gly Gly Ala Leu
305                 310                 315                 320

Gly Glu Gly Pro Gly Ala Ser Pro Cys Asn Gln His Ser Pro Tyr Trp
                325                 330                 335

Ala Pro Pro Cys Tyr Thr Leu Lys Pro Glu Thr
            340                 345

<210> SEQ ID NO 330
<211> LENGTH: 152
<212> TYPE: PRT
<213> ORGANISM: Homo sapiens
<220> FEATURE:
<221> NAME/KEY: misc_feature
<223> OTHER INFORMATION: Human IL-7 amino acid sequence

<400> SEQUENCE: 330

Asp Cys Asp Ile Glu Gly Lys Asp Gly Lys Gln Tyr Glu Ser Val Leu
1               5                   10                  15

Met Val Ser Ile Asp Gln Leu Leu Asp Ser Met Lys Glu Ile Gly Ser
            20                  25                  30

Asn Cys Leu Asn Asn Glu Phe Asn Phe Phe Lys Arg His Ile Cys Asp
        35                  40                  45
```

```
Ala Asn Lys Glu Gly Met Phe Leu Phe Arg Ala Ala Arg Lys Leu Arg
 50                  55                  60

Gln Phe Leu Lys Met Asn Ser Thr Gly Asp Phe Asp Leu His Leu Leu
 65                  70                  75                  80

Lys Val Ser Glu Gly Thr Thr Ile Leu Leu Asn Cys Thr Gly Gln Val
                 85                  90                  95

Lys Gly Arg Lys Pro Ala Ala Leu Gly Glu Ala Gln Pro Thr Lys Ser
                100                 105                 110

Leu Glu Glu Asn Lys Ser Leu Lys Glu Gln Lys Lys Leu Asn Asp Leu
                115                 120                 125

Cys Phe Leu Lys Arg Leu Leu Gln Glu Ile Lys Thr Cys Trp Asn Lys
                130                 135                 140

Ile Leu Met Gly Thr Lys Glu His
145                 150

<210> SEQ ID NO 331
<211> LENGTH: 133
<212> TYPE: PRT
<213> ORGANISM: Homo sapiens
<220> FEATURE:
<221> NAME/KEY: misc_feature
<223> OTHER INFORMATION: Human IL-15 amino acid sequence

<400> SEQUENCE: 331

Gly Ile His Val Phe Ile Leu Gly Cys Phe Ser Ala Gly Leu Pro Lys
 1               5                  10                  15

Thr Glu Ala Asn Trp Val Asn Val Ile Ser Asp Leu Lys Lys Ile Glu
                20                  25                  30

Asp Leu Ile Gln Ser Met His Ile Asp Ala Thr Leu Tyr Thr Glu Ser
             35                  40                  45

Asp Val His Pro Ser Cys Lys Val Thr Ala Met Lys Cys Phe Leu Leu
 50                  55                  60

Glu Leu Gln Val Ile Ser Leu Glu Ser Gly Asp Ala Ser Ile His Asp
 65                  70                  75                  80

Thr Val Glu Asn Leu Ile Ile Leu Ala Asn Asn Ser Leu Ser Ser Asn
                 85                  90                  95

Gly Asn Val Thr Glu Ser Gly Cys Lys Glu Cys Glu Glu Leu Glu Glu
                100                 105                 110

Lys Asn Ile Lys Glu Phe Leu Gln Ser Phe Val His Ile Val Gln Met
                115                 120                 125

Phe Ile Asn Thr Ser
       130

<210> SEQ ID NO 332
<211> LENGTH: 133
<212> TYPE: PRT
<213> ORGANISM: Homo sapiens
<220> FEATURE:
<221> NAME/KEY: misc_feature
<223> OTHER INFORMATION: Human IL-21 amino acid sequence

<400> SEQUENCE: 332

Gln Gly Gln Asp Arg His Met Ile Arg Met Arg Gln Leu Ile Asp Ile
 1               5                  10                  15

Val Asp Gln Leu Lys Asn Tyr Val Asn Asp Leu Val Pro Glu Phe Leu
                20                  25                  30

Pro Ala Pro Glu Asp Val Glu Thr Asn Cys Glu Trp Ser Ala Phe Ser
             35                  40                  45
```

```
Cys Phe Gln Lys Ala Gln Leu Lys Ser Ala Asn Thr Gly Asn Asn Glu
         50                  55                  60

Arg Ile Ile Asn Val Ser Ile Lys Leu Lys Arg Lys Pro Pro Ser
 65                  70                  75                  80

Thr Asn Ala Gly Arg Arg Gln Lys His Arg Leu Thr Cys Pro Ser Cys
                 85                  90                  95

Asp Ser Tyr Glu Lys Lys Pro Pro Lys Glu Phe Leu Glu Arg Phe Lys
                100                 105                 110

Ser Leu Leu Gln Lys Met Ile His Gln His Leu Ser Ser Arg Thr His
            115                 120                 125

Gly Ser Glu Asp Ser
        130
```

<210> SEQ ID NO 333
<211> LENGTH: 127
<212> TYPE: PRT
<213> ORGANISM: Homo sapiens
<220> FEATURE:
<221> NAME/KEY: misc_feature
<223> OTHER INFORMATION: Human GM-CSF amino acid sequence

<400> SEQUENCE: 333

```
Ala Pro Ala Arg Ser Pro Ser Pro Ser Thr Gln Pro Trp Glu His Val
 1               5                  10                  15

Asn Ala Ile Gln Glu Ala Arg Arg Leu Leu Asn Leu Ser Arg Asp Thr
             20                  25                  30

Ala Ala Glu Met Asn Glu Thr Val Glu Val Ile Ser Glu Met Phe Asp
         35                  40                  45

Leu Gln Glu Pro Thr Cys Leu Gln Thr Arg Leu Glu Leu Tyr Lys Gln
 50                  55                  60

Gly Leu Arg Gly Ser Leu Thr Lys Leu Lys Gly Pro Leu Thr Met Met
 65                  70                  75                  80

Ala Ser His Tyr Lys Gln His Cys Pro Pro Thr Pro Glu Thr Ser Cys
                 85                  90                  95

Ala Thr Gln Ile Ile Thr Phe Glu Ser Phe Lys Glu Asn Leu Lys Asp
                100                 105                 110

Phe Leu Leu Val Ile Pro Phe Asp Cys Trp Glu Pro Val Gln Glu
            115                 120                 125
```

<210> SEQ ID NO 334
<211> LENGTH: 171
<212> TYPE: PRT
<213> ORGANISM: Homo sapiens
<220> FEATURE:
<221> NAME/KEY: misc_feature
<223> OTHER INFORMATION: Human IFN-a amino acid sequence

<400> SEQUENCE: 334

```
Cys Asp Leu Pro Gln Asn His Gly Leu Leu Ser Arg Asn Thr Leu Val
 1               5                  10                  15

Leu Leu His Gln Met Arg Arg Ile Ser Pro Phe Leu Cys Leu Lys Asp
             20                  25                  30

Arg Arg Asp Phe Arg Phe Pro Gln Glu Met Val Lys Gly Ser Gln Leu
         35                  40                  45

Gln Lys Ala His Val Met Ser Val Leu His Glu Met Leu Gln Gln Ile
 50                  55                  60

Phe Ser Leu Phe His Thr Glu Arg Ser Ser Ala Ala Trp Asn Met Thr
 65                  70                  75                  80
```

```
Leu Leu Asp Gln Leu His Thr Glu Leu His Gln Gln Leu Gln His Leu
                85                  90                  95

Glu Thr Cys Leu Leu Gln Val Val Gly Gly Glu Ser Ala Gly Ala
            100                 105                 110

Ile Ser Ser Pro Ala Leu Thr Leu Arg Arg Tyr Phe Gln Gly Ile Arg
        115                 120                 125

Val Tyr Leu Lys Glu Lys Lys Tyr Ser Asp Cys Ala Trp Glu Val Val
    130                 135                 140

Arg Met Glu Ile Met Lys Ser Leu Phe Leu Ser Thr Asn Met Gln Glu
145                 150                 155                 160

Arg Leu Arg Ser Lys Asp Arg Asp Leu Gly Ser
                165                 170

<210> SEQ ID NO 335
<211> LENGTH: 177
<212> TYPE: PRT
<213> ORGANISM: Homo sapiens
<220> FEATURE:
<221> NAME/KEY: misc_feature
<223> OTHER INFORMATION: Extracellular portion of human TNF-a amino
      acid sequence

<400> SEQUENCE: 335

Gly Pro Gln Arg Glu Glu Phe Pro Arg Asp Leu Ser Leu Ile Ser Pro
1               5                   10                  15

Leu Ala Gln Ala Val Arg Ser Ser Ser Arg Thr Pro Ser Asp Lys Pro
            20                  25                  30

Val Ala His Val Val Ala Asn Pro Gln Ala Glu Gly Gln Leu Gln Trp
        35                  40                  45

Leu Asn Arg Arg Ala Asn Ala Leu Leu Ala Asn Gly Val Glu Leu Arg
    50                  55                  60

Asp Asn Gln Leu Val Val Pro Ser Glu Gly Leu Tyr Leu Ile Tyr Ser
65                  70                  75                  80

Gln Val Leu Phe Lys Gly Gln Gly Cys Pro Ser Thr His Val Leu Leu
                85                  90                  95

Thr His Thr Ile Ser Arg Ile Ala Val Ser Tyr Gln Thr Lys Val Asn
            100                 105                 110

Leu Leu Ser Ala Ile Lys Ser Pro Cys Gln Arg Glu Thr Pro Glu Gly
        115                 120                 125

Ala Glu Ala Lys Pro Trp Tyr Glu Pro Ile Tyr Leu Gly Gly Val Phe
    130                 135                 140

Gln Leu Glu Lys Gly Asp Arg Leu Ser Ala Glu Ile Asn Arg Pro Asp
145                 150                 155                 160

Tyr Leu Asp Phe Ala Glu Ser Gly Gln Val Tyr Phe Gly Ile Ile Ala
                165                 170                 175

Leu

<210> SEQ ID NO 336
<211> LENGTH: 197
<212> TYPE: PRT
<213> ORGANISM: Homo sapiens
<220> FEATURE:
<221> NAME/KEY: misc_feature
<223> OTHER INFORMATION: Alpha chain of human IL-12 amino acid sequence

<400> SEQUENCE: 336

Arg Asn Leu Pro Val Ala Thr Pro Asp Pro Gly Met Phe Pro Cys Leu
1               5                   10                  15
```

His His Ser Gln Asn Leu Leu Arg Ala Val Ser Asn Met Leu Gln Lys
                20                  25                  30

Ala Arg Gln Thr Leu Glu Phe Tyr Pro Cys Thr Ser Glu Glu Ile Asp
            35                  40                  45

His Glu Asp Ile Thr Lys Asp Lys Thr Ser Thr Val Glu Ala Cys Leu
50                  55                  60

Pro Leu Glu Leu Thr Lys Asn Glu Ser Cys Leu Asn Ser Arg Glu Thr
65                  70                  75                  80

Ser Phe Ile Thr Asn Gly Ser Cys Leu Ala Ser Arg Lys Thr Ser Phe
                85                  90                  95

Met Met Ala Leu Cys Leu Ser Ser Ile Tyr Glu Asp Leu Lys Met Tyr
            100                 105                 110

Gln Val Glu Phe Lys Thr Met Asn Ala Lys Leu Leu Met Asp Pro Lys
        115                 120                 125

Arg Gln Ile Phe Leu Asp Gln Asn Met Leu Ala Val Ile Asp Glu Leu
130                 135                 140

Met Gln Ala Leu Asn Phe Asn Ser Glu Thr Val Pro Gln Lys Ser Ser
145                 150                 155                 160

Leu Glu Glu Pro Asp Phe Tyr Lys Thr Lys Ile Lys Leu Cys Ile Leu
                165                 170                 175

Leu His Ala Phe Arg Ile Arg Ala Val Thr Ile Asp Arg Val Met Ser
            180                 185                 190

Tyr Leu Asn Ala Ser
        195

<210> SEQ ID NO 337
<211> LENGTH: 306
<212> TYPE: PRT
<213> ORGANISM: Homo sapiens
<220> FEATURE:
<221> NAME/KEY: misc_feature
<223> OTHER INFORMATION: Beta chain of human IL-12 amino acid sequence

<400> SEQUENCE: 337

Ile Trp Glu Leu Lys Lys Asp Val Tyr Val Val Glu Leu Asp Trp Tyr
1               5                   10                  15

Pro Asp Ala Pro Gly Glu Met Val Val Leu Thr Cys Asp Thr Pro Glu
            20                  25                  30

Glu Asp Gly Ile Thr Trp Thr Leu Asp Gln Ser Ser Glu Val Leu Gly
        35                  40                  45

Ser Gly Lys Thr Leu Thr Ile Gln Val Lys Glu Phe Gly Asp Ala Gly
    50                  55                  60

Gln Tyr Thr Cys His Lys Gly Gly Glu Val Leu Ser His Ser Leu Leu
65                  70                  75                  80

Leu Leu His Lys Lys Glu Asp Gly Ile Trp Ser Thr Asp Ile Leu Lys
                85                  90                  95

Asp Gln Lys Glu Pro Lys Asn Lys Thr Phe Leu Arg Cys Glu Ala Lys
            100                 105                 110

Asn Tyr Ser Gly Arg Phe Thr Cys Trp Trp Leu Thr Thr Ile Ser Thr
        115                 120                 125

Asp Leu Thr Phe Ser Val Lys Ser Ser Arg Gly Ser Ser Asp Pro Gln
    130                 135                 140

Gly Val Thr Cys Gly Ala Ala Thr Leu Ser Ala Glu Arg Val Arg Gly
145                 150                 155                 160

Asp Asn Lys Glu Tyr Glu Tyr Ser Val Glu Cys Gln Glu Asp Ser Ala

```
                    165                 170                 175
Cys Pro Ala Ala Glu Glu Ser Leu Pro Ile Glu Val Met Val Asp Ala
        180                 185                 190

Val His Lys Leu Lys Tyr Glu Asn Tyr Thr Ser Ser Phe Phe Ile Arg
    195                 200                 205

Asp Ile Ile Lys Pro Asp Pro Pro Lys Asn Leu Gln Leu Lys Pro Leu
210                 215                 220

Lys Asn Ser Arg Gln Val Glu Val Ser Trp Glu Tyr Pro Asp Thr Trp
225                 230                 235                 240

Ser Thr Pro His Ser Tyr Phe Ser Leu Thr Phe Cys Val Gln Val Gln
                245                 250                 255

Gly Lys Ser Lys Arg Glu Lys Lys Asp Arg Val Phe Thr Asp Lys Thr
                260                 265                 270

Ser Ala Thr Val Ile Cys Arg Lys Asn Ala Ser Ile Ser Val Arg Ala
                275                 280                 285

Gln Asp Arg Tyr Tyr Ser Ser Ser Trp Ser Glu Trp Ala Ser Val Pro
            290                 295                 300

Cys Ser
305

<210> SEQ ID NO 338
<211> LENGTH: 103
<212> TYPE: PRT
<213> ORGANISM: Homo sapiens
<220> FEATURE:
<221> NAME/KEY: misc_feature
<223> OTHER INFORMATION: Human CXCL-9 amino acid sequence

<400> SEQUENCE: 338

Thr Pro Val Val Arg Lys Gly Arg Cys Ser Cys Ile Ser Thr Asn Gln
1               5                   10                  15

Gly Thr Ile His Leu Gln Ser Leu Lys Asp Leu Lys Gln Phe Ala Pro
            20                  25                  30

Ser Pro Ser Cys Glu Lys Ile Glu Ile Ile Ala Thr Leu Lys Asn Gly
        35                  40                  45

Val Gln Thr Cys Leu Asn Pro Asp Ser Ala Asp Val Lys Glu Leu Ile
    50                  55                  60

Lys Lys Trp Glu Lys Gln Val Ser Gln Lys Lys Lys Gln Lys Asn Gly
65                  70                  75                  80

Lys Lys His Gln Lys Lys Lys Val Leu Lys Val Arg Lys Ser Gln Arg
                85                  90                  95

Ser Arg Gln Lys Lys Thr Thr
            100

<210> SEQ ID NO 339
<211> LENGTH: 77
<212> TYPE: PRT
<213> ORGANISM: Homo sapiens
<220> FEATURE:
<221> NAME/KEY: misc_feature
<223> OTHER INFORMATION: Human CXCL-10 amino acid sequence

<400> SEQUENCE: 339

Val Pro Leu Ser Arg Thr Val Arg Cys Thr Cys Ile Ser Ile Ser Asn
1               5                   10                  15

Gln Pro Val Asn Pro Arg Ser Leu Glu Lys Leu Glu Ile Ile Pro Ala
            20                  25                  30

Ser Gln Phe Cys Pro Arg Val Glu Ile Ile Ala Thr Met Lys Lys Lys
```

```
                35                  40                  45
Gly Glu Lys Arg Cys Leu Asn Pro Glu Ser Lys Ala Ile Lys Asn Leu
         50                  55                  60

Leu Lys Ala Val Ser Lys Glu Arg Ser Lys Arg Ser Pro
65                  70                  75
```

<210> SEQ ID NO 340
<211> LENGTH: 330
<212> TYPE: PRT
<213> ORGANISM: Homo sapiens
<220> FEATURE:
<221> NAME/KEY: misc_feature
<223> OTHER INFORMATION: WT human IgG1 amino acid sequence IgG1

<400> SEQUENCE: 340

```
Ala Ser Thr Lys Gly Pro Ser Val Phe Pro Leu Ala Pro Ser Ser Lys
1               5                   10                  15

Ser Thr Ser Gly Gly Thr Ala Ala Leu Gly Cys Leu Val Lys Asp Tyr
                20                  25                  30

Phe Pro Glu Pro Val Thr Val Ser Trp Asn Ser Gly Ala Leu Thr Ser
            35                  40                  45

Gly Val His Thr Phe Pro Ala Val Leu Gln Ser Ser Gly Leu Tyr Ser
        50                  55                  60

Leu Ser Ser Val Val Thr Val Pro Ser Ser Ser Leu Gly Thr Gln Thr
65                  70                  75                  80

Tyr Ile Cys Asn Val Asn His Lys Pro Ser Asn Thr Lys Val Asp Lys
                85                  90                  95

Lys Val Glu Pro Lys Ser Cys Asp Lys Thr His Thr Cys Pro Pro Cys
            100                 105                 110

Pro Ala Pro Glu Leu Leu Gly Gly Pro Ser Val Phe Leu Phe Pro Pro
        115                 120                 125

Lys Pro Lys Asp Thr Leu Met Ile Ser Arg Thr Pro Glu Val Thr Cys
130                 135                 140

Val Val Val Asp Val Ser His Glu Asp Pro Glu Val Lys Phe Asn Trp
145                 150                 155                 160

Tyr Val Asp Gly Val Glu Val His Asn Ala Lys Thr Lys Pro Arg Glu
                165                 170                 175

Glu Gln Tyr Asn Ser Thr Tyr Arg Val Val Ser Val Leu Thr Val Leu
            180                 185                 190

His Gln Asp Trp Leu Asn Gly Lys Glu Tyr Lys Cys Lys Val Ser Asn
        195                 200                 205

Lys Ala Leu Pro Ala Pro Ile Glu Lys Thr Ile Ser Lys Ala Lys Gly
    210                 215                 220

Gln Pro Arg Glu Pro Gln Val Tyr Thr Leu Pro Pro Ser Arg Asp Glu
225                 230                 235                 240

Leu Thr Lys Asn Gln Val Ser Leu Thr Cys Leu Val Lys Gly Phe Tyr
                245                 250                 255

Pro Ser Asp Ile Ala Val Glu Trp Glu Ser Asn Gly Gln Pro Glu Asn
            260                 265                 270

Asn Tyr Lys Thr Thr Pro Pro Val Leu Asp Ser Asp Gly Ser Phe Phe
        275                 280                 285

Leu Tyr Ser Lys Leu Thr Val Asp Lys Ser Arg Trp Gln Gln Gly Asn
    290                 295                 300

Val Phe Ser Cys Ser Val Met His Glu Ala Leu His Asn His Tyr Thr
305                 310                 315                 320
```

Gln Lys Ser Leu Ser Leu Ser Pro Gly Lys
           325                 330

<210> SEQ ID NO 341
<211> LENGTH: 996
<212> TYPE: DNA
<213> ORGANISM: Homo sapiens
<220> FEATURE:
<221> NAME/KEY: misc_feature
<223> OTHER INFORMATION: WT human IgG1 nucleic acid sequence IgG1

<400> SEQUENCE: 341

| gccagcacca | agggcccctc | tgtgttccct | ctggcccctt | ccagcaagtc | cacctctggc | 60 |
| ggaacagccg | ctctgggctg | cctcgtgaag | gactacttcc | ccgagcctgt | gaccgtgtcc | 120 |
| tggaactctg | gcgctctgac | cagcggagtg | cacaccttcc | ctgctgtgct | gcagtcctcc | 180 |
| ggcctgtact | ccctgtcctc | cgtcgtgacc | gtgccttcca | gctctctggg | cacccagacc | 240 |
| tacatctgca | acgtgaacca | caagccctcc | aacaccaagg | tggacaagaa | ggtggaaccc | 300 |
| aagtcctgcg | acaagaccca | cacctgtccc | ccttgtcctg | ccctgaact | gctgggcgga | 360 |
| ccttccgtgt | tcctgttccc | cccaaagccc | aaggacaccc | tgatgatctc | ccggaccccc | 420 |
| gaagtgacct | gcgtggtggt | ggatgtgtcc | cacgaggacc | ctgaagtgaa | gttcaattgg | 480 |
| tacgtggacg | gcgtggaagt | gcacaacgcc | aagaccaagc | ctagagagga | acagtacaac | 540 |
| tccacctacc | gggtggtgtc | cgtgctgacc | gtgctgcacc | aggattggct | gaacggcaaa | 600 |
| gagtacaagt | gcaaggtgtc | caacaaggcc | ctgcctgccc | ccatcgaaaa | gaccatctcc | 660 |
| aaggccaagg | gccagccccg | ggaaccccag | gtgtacacac | tgcccctag | cagggacgag | 720 |
| ctgaccaaga | accaggtgtc | cctgacctgt | ctcgtgaaag | gcttctaccc | ctccgatatc | 780 |
| gccgtggaat | gggagtccaa | cggccagcct | gagaacaact | acaagaccac | ccccctgtg | 840 |
| ctggactccg | acggctcatt | cttcctgtac | agcaagctga | cagtggacaa | gtcccggtgg | 900 |
| cagcagggca | acgtgttctc | ctgctccgtg | atgcacgagg | ccctgcacaa | ccactacacc | 960 |
| cagaagtccc | tgtccctgag | ccccggcaag | tgatga |  |  | 996 |

<210> SEQ ID NO 342
<211> LENGTH: 450
<212> TYPE: PRT
<213> ORGANISM: Homo sapiens
<220> FEATURE:
<221> NAME/KEY: misc_feature
<223> OTHER INFORMATION: V to A mutated 1D05 HC AA sequence

<400> SEQUENCE: 342

Glu Val Gln Leu Val Glu Ser Gly Gly Gly Leu Val Gln Pro Gly Arg
1               5                   10                  15

Ser Leu Arg Leu Ser Cys Ala Ala Ser Gly Phe Thr Phe Asp Asp Tyr
            20                  25                  30

Ala Met His Trp Val Arg Gln Ala Pro Gly Lys Gly Leu Glu Trp Val
        35                  40                  45

Ser Gly Ile Ser Trp Ile Arg Thr Gly Ile Gly Tyr Ala Asp Ser Val
    50                  55                  60

Lys Gly Arg Phe Thr Ile Ser Arg Asp Asn Ala Lys Asn Ser Leu Tyr
65                  70                  75                  80

-continued

```
Leu Gln Met Asn Ser Leu Arg Ala Glu Asp Thr Ala Leu Tyr Tyr Cys
                85                  90                  95

Ala Lys Asp Met Lys Gly Ser Gly Thr Tyr Gly Gly Trp Phe Asp Thr
            100                 105                 110

Trp Gly Gln Gly Thr Leu Val Thr Val Ser Ser Ala Ser Thr Lys Gly
            115                 120                 125

Pro Ser Val Phe Pro Leu Ala Pro Cys Ser Arg Ser Thr Ser Glu Ser
        130                 135                 140

Thr Ala Ala Leu Gly Cys Leu Val Lys Asp Tyr Phe Pro Glu Pro Val
145                 150                 155                 160

Thr Val Ser Trp Asn Ser Gly Ala Leu Thr Ser Gly Val His Thr Phe
                165                 170                 175

Pro Ala Val Leu Gln Ser Ser Gly Leu Tyr Ser Leu Ser Ser Val Val
            180                 185                 190

Thr Val Pro Ser Ser Ser Leu Gly Thr Lys Thr Tyr Thr Cys Asn Val
            195                 200                 205

Asp His Lys Pro Ser Asn Thr Lys Val Asp Lys Arg Val Glu Ser Lys
        210                 215                 220

Tyr Gly Pro Pro Cys Pro Pro Cys Pro Ala Pro Glu Leu Ala Gly Ala
225                 230                 235                 240

Pro Ser Val Phe Leu Phe Pro Pro Lys Pro Lys Asp Thr Leu Met Ile
                245                 250                 255

Ser Arg Thr Pro Glu Val Thr Cys Val Val Val Asp Val Ser Gln Glu
            260                 265                 270

Asp Pro Glu Val Gln Phe Asn Trp Tyr Val Asp Gly Val Glu Val His
            275                 280                 285

Asn Ala Lys Thr Lys Pro Arg Glu Glu Gln Phe Asn Ser Thr Tyr Arg
        290                 295                 300

Val Val Ser Val Leu Thr Val Leu His Gln Asp Trp Leu Asn Gly Lys
305                 310                 315                 320

Glu Tyr Lys Cys Lys Val Ser Asn Lys Gly Leu Pro Ser Ser Ile Glu
                325                 330                 335

Lys Thr Ile Ser Lys Ala Lys Gly Gln Pro Arg Glu Pro Gln Val Tyr
            340                 345                 350

Thr Leu Pro Pro Ser Gln Glu Glu Met Thr Lys Asn Gln Val Ser Leu
        355                 360                 365

Thr Cys Leu Val Lys Gly Phe Tyr Pro Ser Asp Ile Ala Val Glu Trp
370                 375                 380

Glu Ser Asn Gly Gln Pro Glu Asn Asn Tyr Lys Thr Thr Pro Pro Val
385                 390                 395                 400

Leu Asp Ser Asp Gly Ser Phe Phe Leu Tyr Ser Arg Leu Thr Val Asp
            405                 410                 415

Lys Ser Arg Trp Gln Glu Gly Asn Val Phe Ser Cys Ser Val Met His
            420                 425                 430

Glu Ala Leu His Asn His Tyr Thr Gln Lys Ser Leu Ser Leu Ser Leu
        435                 440                 445

Gly Lys
    450
```

ANTIBODIES AND IMMUNOCYTOKINES

CROSS-REFERENCE TO RELATED APPLICATIONS

This application is a divisional application under 35 USC 1.121 of U.S. Ser. No. 15/211,504, filed on Jul. 15, 2016, which claims benefit under 35 U.S.C. §119(e) of U.S. Provisional Application No. 62/352,291 filed Jun. 20, 2016, the contents of which are incorporated herein by reference in their entirety.

SEQUENCE LISTING

The instant application contains a Sequence Listing which has been submitted in ASCII format via EFS-Web and is hereby incorporated by reference in its entirety. Said ASCII copy, created on Nov. 14, 2016, is named 2016-11-15-Sequence_Listing_069496-086962.txt and is 335,137 bytes in size.

FIELD OF THE INVENTION

Antibodies and methods of using the antibodies are described. In particular, antibodies that specifically bind human PD-L1 antigen and their use in treating various diseases are described. In some embodiments, described herein are PD-L1 specific antibodies and PD-L1 specific immunocytokines.

BACKGROUND

Immunocytokines (antibody-cytokine fusion proteins) were first reported in the literature in the early 1990s and consisted of whole antibody fusions with cytokines such as lymphotoxin (TNF-α) or interleukin 2 (IL-2). Subsequent studies in GD2-expressing tumour models in mice indicated that the ch 14.18 antibody and ch 14.18-IL2 immunocytokine both had anti-tumour activity but that the immunocytokine was far more potent than the antibody, even when combined with free IL-2, (see Sabzevari H et al., Proc. Natl. Acad. Sci. USA, 1994, 91:9626-30; Pancook J D, et al., Cancer Immunol. Immunother., 1996, 42:88-92; Becker J C, et al., Proc. Natl. Acad. Sci. USA, 1996, 93:2702-7). In addition, immune-competent mice treated with the immunocytokine, but not the antibody plus IL-2, developed an adaptive immune response dependent on CD8$^+$ T-cells that prevented subsequent tumour challenge (Becker J C, et al., J. Exp. Med., 1996, 183:2361-6; Becker J C, et al., Proc. Natl. Acad. Sci. USA, 1996, 93:7826-31). Thus, the targeting of IL-2 to the tumour microenvironment induces an anti-tumour vaccine effect that is not possible with the antibody, either alone or together with the free cytokine. A related humanized immunocytokine, hu 14.18-IL2, achieved clinical proof of concept in relapsed non-bulky neuroblastoma as monotherapy where it induced a significant number of complete responses in patients with no other treatment options (see Shusterman et al., Journal of Clinical Oncology, 2010, 28(33), 4969-4975). A number of publications describe the ability of this molecule to activate several components of the immune system to kill tumour cells (particularly NK cells and CD8$^+$ T-cells), and develop T-cell memory in order to resist subsequent tumour challenge (Yamane et al. 2009; Expert Opi, Investig. Drugs, 18(7): 991-1000; Neal et al., 2004, Clin. Cancer Res., 1010, 4839-4847).

As IL-2 based immunocytokines can have significant side effects, recent efforts have focused on the reduction of toxicity whilst maintaining efficacy. One example is Selectikine (EMD 521873), which has a substitution of aspartic acid for threonine at position 20 of IL-2, a key residue in the binding of IL-2R13 (Gillies et al., Clinical Cancer Research, 2011, 17(11), 3673-3685). Selectikine, which binds necrotic tissue, has been shown to have good anti-tumour activity, despite its selectivity for the high affinity IL-2R, over the intermediate IL-2R and good tolerability in Phase I studies (Laurent et al., Journal of Translational Medicine, 2013, 11(1), 5. Available on the World Wide Web at doi.org/10.1186/1479-5876-11-5)

WO2012/178137 (Gillies) describes light chain immunocytokine fusions with tumour targeting antibodies.

An adaptive immune response involves activation, selection, and clonal proliferation of two major classes of lymphocytes termed T-cells and B-cells. After encountering an antigen, T-cells proliferate and differentiate into antigen-specific effector cells, while B-cells proliferate and differentiate into antibody-secreting cells. T-cell activation is a multi-step process requiring several signalling events between the T-cell and an antigen-presenting cell (APC). For T-cell activation to occur, two types of signals must be delivered to a resting T-cell. The first type is mediated by the antigen-specific T-cell receptor (TcR), and confers specificity to the immune response. The second signal, a costimulatory type signal, regulates the magnitude of the response and is delivered through accessory receptors on the T-cell.

A primary costimulatory signal is delivered through the activating CD28 receptor upon engagement of its ligands B7-1 or B7-2. In contrast, engagement of the inhibitory CTLA-4 receptor by the same B7-1 or B7-2 ligands results in attenuation of a T cell response. Thus, CTLA-4 signals antagonize costimulation mediated by CD28. At high antigen concentrations, CD28 costimulation overrides the CTLA-4 inhibitory effect. Temporal regulation of the CD28 and CTLA-4 expression maintains a balance between activating and inhibitory signals and ensures the development of an effective immune response, while safeguarding against the development of autoimmunity.

Programmed death-1 (PD-1) is a 50-55 kDa type I transmembrane receptor that is a member of the CD28 family. PD-1 is involved in the regulation of T-cell activation and is expressed on T cells, B cells, and myeloid cells. Two ligands for PD-1, PD ligand 1 (PD-L1) and ligand 2 (PD-L2) have been identified and have co-stimulatory features.

Programmed cell death 1 ligand 1 (PD-L1), also known as cluster of differentiation (CD274) or B7 homolog 1 (B7-H1), is a member of the B7 family that modulates activation or inhibition of the PD-1 receptor. The open reading frame of PD-L1 encodes a putative type 1 transmembrane protein of 290 amino acids, which includes two extracellular Ig domains (a N-terminal V-like domain and a Ig C-like domain), a hydrophobic transmembrane domain and a cytoplasmic tail of 30 amino acids. The 30 amino acid intracellular (cytoplasmic) domain contains no obvious signalling motifs, but does have a potential site for protein kinase C phosphorylation.

The complete amino acid sequence for PD-L1 can be found in NCBI Reference Sequence: NP_054862.1 (SEQ ID NO: 1), which refers to many journal articles, including, for example, Dong, H., et al. (1999), "PD-L1, a third member of the B7 family, co-stimulates T-cell proliferation and interleukin-10 secretion," Nat. Med. 5 (12), 1365-1369. The PD-L1 gene is conserved in chimpanzee, Rhesus monkey, dog, cow, mouse, rat, chicken, and zebrafish. The murine form of PD-L1 bears 69% amino acid identity with the human form of PD-L1, and also shares a conserved structure.

In humans, PD-L1 is expressed on a number of immune cell types including activated and anergic/exhausted T-cells, on naive and activated B-cells, as well as on myeloid dendritic cells (DC), monocytes and mast cells. It is also expressed on non-immune cells including islets of the pancreas, Kupffer cells of the liver, vascular endothelium and selected epithelia, for example airway epithelia and renal tubule epithelia, where its expression is enhanced during inflammatory episodes. PD-L1 expression is also found at increased levels on a number of tumours including, but not limited to breast (including but not limited to triple negative breast cancer), ovarian, cervical, colon, colorectal, lung, including non-small cell lung cancer, renal, including renal cell carcinoma, gastric, oesophageal, bladder, hepatocellular cancer, squamous cell carcinoma of the head and neck (SCCHN) and pancreatic cancer, melanoma and uveal melanoma.

PD-1/PD-L1 signalling is believed to serve a critical non-redundant function within the immune system by negatively regulating T cell responses. This regulation is involved in T cell development in the thymus, in regulation of chronic inflammatory responses and in maintenance of both peripheral tolerance and immune privilege. It appears that upregulation of PD-L1 may allow cancers to evade the host immune system and, in many cancers, the expression of PD-L1 is associated with reduced survival and an unfavourable prognosis. Therapeutic monoclonal antibodies that are able to block the PD-1/PD-L1 pathway may enhance antitumoural immune responses in patients with cancer. Published clinical data suggest a correlation between clinical responses with tumoural membranous expression of PD-L1 (Brahmer et al., Journal of Clinical Oncology, 2010, Topalian et al., NEJM, 2012) and a stronger correlation between lack of clinical responses and a lack of PD-L1 protein localized to the membrane (Brahmer et al., Journal of Clinical Oncology, 2010, Topalian et al., NEJM, 2012). Thus, PD-L1 expression in tumours or tumour-infiltrating leukocytes (Herbst R S, et al., "Predictive correlates of response to the anti-PD-L1 antibody MPDL3280A in cancer patients", Nature, 2014, Nov. 27, 515(7528):563-7, doi: 10.1038/nature14011) is a candidate molecular marker for use in selecting patients for immunotherapy, for example, immunotherapy using anti-PD-L1 antibodies. Patient enrichment based on surface expression of PD-L1 may significantly enhance the clinical success of treatment with drugs targeting the PD-1/PD-L1 pathway.

Further evidence of PD-L1 expression and correlation to disease will emerge from the numerous ongoing clinical trials. Atezolizumab is the most advanced, and recent data from Phase II trials shows therapeutic effects in metastatic urothelial carcinoma and NSCLC, particularly in patients with PD-L1$^+$ immune cells in the tumour microenvironment (see Fehrenbacher et al., 2016, The Lancet, http://doi.org/10.1016/S0140-6736(16)00587-0; Rosenberg et al., 2016, The Lancet, http://doi.org/10.1016/S0140-6736(16)00561-4).

SUMMARY OF THE INVENTION

Disclosed herein are antibodies and antigen binding fragment thereof that specifically binds to PD-L1. In one embodiment, the antibody or antigen binding fragment thereof specifically binds to surface expressed PD-L1.

In a first configuration, there is provided an antibody or a fragment thereof, that specifically binds to hPD-L1 as defined by Seq ID No:1, and competes for binding to said hPD-L1 with the antibody 1D05, wherein the antibody or fragment comprises a $V_H$ domain which comprises a CDRH3 comprising the motif $X_1GSGX_2YGX_3X_4FD$, wherein $X_1$, $X_2$ and $X_3$ are independently any amino acid, and $X_4$ is either present or absent, and if present, may be any amino acid.

In a second configuration, there is provided an antibody or a fragment thereof which specifically binds to hPD-L1, and competes for binding to said hPD-L1 with the antibody 1D05, wherein the antibody or fragment comprises a $V_H$ domain which comprises the CDRH3 sequence of SEQ ID NO:29 or 32, or the CDRH3 sequence of SEQ ID NO:29 or 32 comprising 6 or fewer amino acid substitutions.

In a third configuration, there is provided an antibody or fragment thereof which specifically binds to an epitope that is identical to an epitope to which the antibody 1D05 specifically binds.

In a fourth configuration, there is provided an antibody or fragment thereof which competes for binding to hPD-L1 with the antibody 1D05.

In a fifth configuration, there is provided a bispecific antibody or fusion protein comprising an antibody or fragment thereof as defined in any other configuration, embodiment or concept.

In a sixth configuration, there is provided an antibody or fragment as defined in any other configuration, embodiment or concept for use in treating or preventing a hPD-L1-mediated disease or condition.

In a seventh configuration, there is provided the use of an antibody or fragment as defined in any other configuration, embodiment or concept in the manufacture of a medicament for administration to a human for treating or preventing a hPD-L1 mediated disease or condition in the human.

In an eighth configuration, there is provided a method of treating or preventing a hPD-L1 mediated disease or condition in a human, comprising administering to said human a therapeutically effective amount of an antibody or fragment as defined in any other configuration, embodiment or concept, wherein the hPD-L1 mediated disease or condition is thereby treated or prevented.

In a ninth configuration, there is provided a pharmaceutical composition comprising an antibody of fragment as defined in any other configuration, embodiment or concept and a pharmaceutically acceptable excipient, diluent or carrier.

In a tenth configuration, there is provided a kit comprising a pharmaceutical composition comprising an antibody of fragment as defined in any other configuration, embodiment or concept and a pharmaceutically acceptable excipient, diluent or carrier.

In an eleventh configuration, there is provided a method of modulating PD-1/PD-L1 interaction in a patient, comprising administering an effective amount of an antibody or fragment as defined in any other configuration, embodiment or concept to said patient.

In a twelfth configuration, there is provided a method of inhibiting PD-L1 activity in a patient, comprising administering an effective amount of an antibody or fragment as defined in any other configuration, embodiment or concept to said patient.

In a thirteenth configuration, there is provided a method of treating a proliferative disease in an animal (e.g. a human), comprising administering an effective amount of an antibody or fragment as defined in any other configuration, embodiment or concept to said patient.

In a fourteenth configuration, there is provided a method of detecting PD-L1 expression in a sample, comprising contacting the sample with an antibody or fragment as defined in any other configuration, embodiment or concept.

In a fifteenth configuration, there is provided a method comprising contacting a biological sample with an antibody or fragment as defined in any other configuration, embodiment or concept to form a complex with PD-L1 present in the sample and measuring the presence, absence or level of the complex in the biological sample.

In a sixteenth configuration, there is provided a method of detecting PD-L1 expression in a sample, comprising contacting the sample with an antibody or fragment as defined in any other configuration, embodiment or concept.

In a seventeenth configuration, there is provided a method comprising contacting a biological sample with an antibody or fragment as defined in any other configuration, embodiment or concept to form a complex with PD-L1 present in the sample and measuring the presence, absence or level of the complex in the biological sample.

In a eighteenth configuration, there is provided a method for identifying binding partners for PD-L1, the method comprising immunoprecipitating an intact protein complex comprising PD-L1 using an antibody or fragment as defined in any other configuration, embodiment or concept.

In a nineteenth configuration, there is provided a method of diagnosing a disease in a human subject associated with altered PD-L1 expression comprising the steps of contacting a biological sample from the human subject with an antibody as defined in other configuration, embodiment or concept to form a complex between the antibody and PD-L1 present in the sample; and detecting the amount of the complex.

In a twentieth configuration, there is provided a nucleic acid that encodes the CDRH3 of an antibody or fragment as defined in any other configuration, embodiment or concept.

In a twenty-first configuration, there is provided a nucleic acid that encodes a VH domain and/or a VL domain of an antibody or fragment as defined in any other configuration, embodiment or concept.

In a twenty-second configuration, there is provided a vector comprising the nucleic acid of any other configuration, embodiment or concept; optionally wherein the vector is a CHO or HEK293 vector.

In a twenty-third configuration, there is provided a host comprising the nucleic acid of any other configuration, embodiment or concept or the vector of any other configuration, embodiment or concept.

In a first configuration, there is provided an immunocytokine comprising an immunoglobulin heavy chain and an immunoglobulin light chain, wherein the heavy chain comprises in N- to C-terminal direction:
  a) A $V_H$ domain comprising CDRH1, CDRH2 and CDRH3; and
  b) A heavy chain constant region;
  and wherein the light chain comprises in N- to C-terminal direction:
  c) A $V_L$ domain comprising CDRL1, CDRL2 and CDRL3;
  d) A light chain constant region, ($C_L$);
  e) Optionally, a linker, (L); and
  f) An IL-2 cytokine;
  wherein the $V_H$ domain and $V_L$ domain are comprised by an antigen-binding site that specifically binds to hPD-L1 as defined by Seq ID No:1, and competes for binding to said hPD-L1 with the antibody 1D05; and
  wherein the immunocytokine comprises a $V_H$ domain which comprises a CDRH3 comprising the motif $X_1GSGX_2YGX_3X_4FD$, wherein $X_1$, $X_2$ and $X_3$ are independently any amino acid, and $X_4$ is either present or absent, and if present, may be any amino acid.

In a second configuration, there is provided an immunocytokine comprising an immunoglobulin heavy chain and an immunoglobulin light chain, wherein the heavy chain comprises in N- to C-terminal direction:
  a) A $V_H$ domain comprising CDRH1, CDRH2 and CDRH3; and
  b) A heavy chain constant region;
  and wherein the light chain comprises in N- to C-terminal direction:
  c) A $V_L$ domain comprising CDRL1, CDRL2 and CDRL3;
  d) A light chain constant region, ($C_L$);
  e) Optionally, a linker, (L); and
  f) An IL-2 cytokine;
  wherein the $V_H$ domain and $V_L$ domain are comprised by an antigen-binding site that specifically binds to hPD-L1, and competes for binding to said hPD-L1 with the antibody 1D05, wherein the antibody or fragment comprises a $V_H$ domain which comprises the CDRH3 sequence of SEQ ID NO:29 or 32, or the CDRH3 sequence of SEQ ID NO:29 or 32 comprising 6 or fewer amino acid substitutions.

In a third configuration, there is provided an immunocytokine comprising an immunoglobulin heavy chain and an immunoglobulin light chain, wherein the heavy chain comprises in N- to C-terminal direction:
  a) A $V_H$ domain comprising CDRH1, CDRH2 and CDRH3; and
  b) A heavy chain constant region;
  and wherein the light chain comprises in N- to C-terminal direction:
  c) A $V_L$ domain comprising CDRL1, CDRL2 and CDRL3;
  d) A light chain constant region, ($C_L$);
  e) Optionally, a linker, (L); and
  f) An IL-2 cytokine;
  wherein the $V_H$ domain and $V_L$ domain are comprised by an antigen-binding site that specifically binds to hPD-L1; and
  wherein the $V_H$ domain comprises a CDRH3 of from 12 to 20 amino acids and which is derived from the recombination of a human $V_H$ gene segment, a human D gene segment and a human $J_H$ gene segment, wherein the human $J_H$ gene segment is IGHJ5 (e.g. IGHJ5*02).

In a fourth configuration, there is provided an immunocytokine comprising an immunoglobulin heavy chain and an immunoglobulin light chain, wherein the heavy chain comprises in N- to C-terminal direction:
  a) A $V_H$ domain comprising CDRH1, CDRH2 and CDRH3; and
  b) A heavy chain constant region;
  and wherein the light chain comprises in N- to C-terminal direction:
  c) A $V_L$ domain comprising CDRL1, CDRL2 and CDRL3;
  d) A light chain constant region, (CO;
  e) Optionally, a linker, (L); and
  f) An IL-2 cytokine;

wherein the $V_H$ domain and $V_L$ domain are comprised by an antigen-binding site that specifically binds to an epitope that is identical to an epitope to which the antibody 1D05 specifically binds.

In a fifth configuration, there is provided an immunocytokine comprising an immunoglobulin heavy chain and an immunoglobulin light chain, wherein the heavy chain comprises in N- to C-terminal direction:
 a) A $V_H$ domain comprising CDRH1, CDRH2 and CDRH3; and
 b) A heavy chain constant region;
and wherein the light chain comprises in N- to C-terminal direction:
 c) A $V_L$ domain comprising CDRL1, CDRL2 and CDRL3;
 d) A light chain constant region, ($C_L$);
 e) Optionally, a linker, (L); and
 f) An IL-2 cytokine;
wherein the $V_H$ domain and $V_L$ domain are comprised by an antigen-binding site which competes for binding to hPD-L1 with the antibody 1D05.

In a sixth configuration, there is provided an immunocytokine as defined in any other configuration, embodiment or aspect for use in treating or preventing a hPD-L1-mediated disease or condition.

In a seventh configuration, there is provided the use of an immunocytokine as defined in any other configuration, embodiment or aspect in the manufacture of a medicament for administration to a human for treating or preventing a hPD-L1 mediated disease or condition in the human.

In an eighth configuration, there is provided a method of treating or preventing a hPD-L1 mediated disease or condition in a human, comprising administering to said human a therapeutically effective amount of an immunocytokine as defined in any other configuration, embodiment or aspect, wherein the hPD-L1 mediated disease or condition is thereby treated or prevented.

In a ninth configuration, there is provided a pharmaceutical composition comprising an immunocytokine as defined in any other configuration, embodiment or aspect, and a pharmaceutically acceptable excipient, diluent or carrier.

In a tenth configuration, there is provided a kit comprising a pharmaceutical composition comprising an immunocytokine as defined in any other configuration, embodiment or aspect, and a pharmaceutically acceptable excipient, diluent or carrier.

In an eleventh configuration, there is provided a nucleic acid that encodes a heavy chain and/or a light chain of an immunocytokine as defined in any other configuration, embodiment or aspect.

In a twelfth configuration, there is provided a vector comprising the nucleic acid that encodes a heavy chain and/or a light chain of an immunocytokine as defined in any other configuration, embodiment or aspect.

In a thirteenth configuration, there is provided a host comprising the nucleic acid of any other configuration, embodiment or aspect or the vector as defined in any other configuration, embodiment or aspect.

DESCRIPTION OF THE FIGURES

FIG. 10A) Bispecific 1, FIG. 10B) Bispecific 2, FIG. 10C) Bispecific 3, FIG. 10D) Bispecific 4. For detailed construction information of each Bispecific construct, see Table 4.

FIG. 11A) Bispecific 1, FIG. 11B) Bispecific 2, FIG. 11C) Bispecific 3, FIG. 11D) Bispecific 4. For detailed construction information of each Bispecific construct, see Table 4.

DETAILED DESCRIPTION

Figure 1:
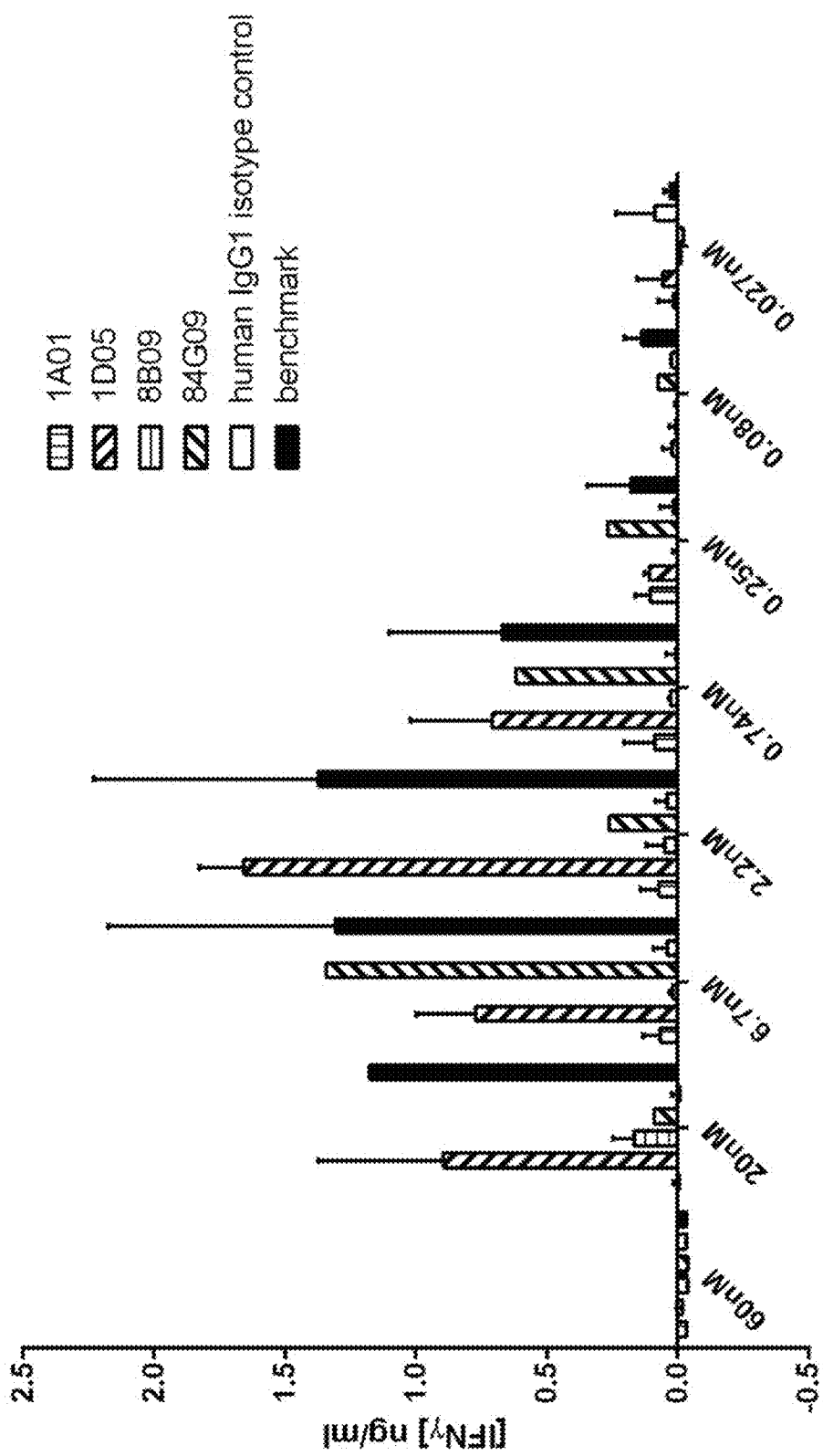
FIG. 1: Analysis of selected antibodies in a dendritic cell—T-cell mixed lymphocyte reaction. Monocytes were cultured with GM-CSF and IL-4 for seven days, before addition of allogeneic purified CD3$^+$ T cells and titrations of antibodies. Supernatants were taken at day 5 for analysis of IFNγ production. Data is shown from one experiment. Note that for 84G09, there is a single point per concentration, as one replicate failed.

Unless otherwise defined herein, scientific and technical terms shall have the meanings that are commonly understood by those of ordinary skill in the art. Further, unless otherwise required by context, singular terms shall include pluralities and plural terms shall include the singular.

The singular terms "a," "an," and "the" include plural referents unless context clearly indicates otherwise. Similarly, the word "or" is intended to include "and" unless the context clearly indicates otherwise. Although methods and materials similar or equivalent to those described herein can be used in the practice or testing of this disclosure, suitable methods and materials are described below. The abbreviation, "e.g." is derived from the Latin exempli gratia, and is used herein to indicate a non-limiting example. Thus, the abbreviation "e.g." is synonymous with the term "for example."

In the specification and claims, the term "about" is used to modify, for example, the quantity of an ingredient in a composition, concentration, volume, process temperature, process time, yield, flow rate, pressure, and like values, and ranges thereof, employed in describing the embodiments of the disclosure. The term "about" refers to variation in the numerical quantity that can occur, for example, through typical measuring and handling procedures used for making compounds, compositions, concentrates or use formulations; through inadvertent error in these procedures; through differences in the manufacture, source, or purity of starting materials or ingredients used to carry out the methods, and like proximate considerations. The term "about" also encompasses amounts that differ due to aging of a formulation with a particular initial concentration or mixture, and amounts that differ due to mixing or processing a formulation with a particular initial concentration or mixture. Where modified by the term "about" the claims appended hereto include equivalents to these quantities.

As used herein, "administer" or "administration" refers to the act of injecting or otherwise physically delivering a substance as it exists outside the body (e.g., an anti-hPD-L1 antibody provided herein) into a patient, such as by mucosal, intradermal, intravenous, intramuscular delivery and/or any other method of physical delivery described herein or known in the art. When a disease, or a symptom thereof, is being treated, administration of the substance typically occurs after the onset of the disease or symptoms thereof. When a disease, or symptoms thereof, are being prevented, administration of the substance typically occurs before the onset of the disease or symptoms thereof.

The term "antibody", "immunoglobulin" or "Ig" may be used interchangeably herein and means an immunoglobulin molecule that recognizes and specifically binds to a target, such as a protein, polypeptide, peptide, carbohydrate, polynucleotide, lipid, or combinations of the foregoing through at least one antigen recognition site within the variable region of the immunoglobulin molecule. As used herein, the term "antibody" encompasses intact polyclonal antibodies, intact monoclonal antibodies, antibody fragments (such as Fab, Fab', F(ab')$_2$, and Fμ fragments), single chain Fμ (scFμ) mutants, multispecific antibodies such as bispecific antibodies (including dual binding antibodies), chimeric antibodies, humanized antibodies, human antibodies, fusion proteins comprising an antigen determination portion of an antibody, and any other modified immunoglobulin molecule comprising an antigen recognition site so long as the antibodies exhibit the desired biological activity. The term "antibody" can also refer to a Y-shaped glycoprotein with a molecular weight of approximately 150 kDa that is made up of four polypeptide chains: two light (L) chains and two heavy (H) chains. There are five types of mammalian Ig heavy chain isotypes denoted by the Greek letters alpha ($\alpha$), delta ($\delta$), epsilon ($\epsilon$), gamma ($\gamma$), and mu ($\mu$). The type of heavy chain defines the class of antibody, i.e., IgA, IgD, IgE, IgG, and IgM, respectively. The $\gamma$ and $\alpha$ classes are further divided into subclasses on the basis of differences in the constant domain sequence and function, e.g., IgG1, IgG2A, IgG2B, IgG3, IgG4, IgA1 and IgA2. In mammals there are two types of immunoglobulin light chains, $\lambda$ and $\kappa$. The "variable region" or "variable domain" of an antibody refers to the amino-terminal domains of the heavy or light chain of the antibody. The variable domains of the heavy chain and light chain may be referred to as "VH" and "VL", respectively. These domains are generally the most variable parts of the antibody (relative to other antibodies of the same class) and contain the antigen binding sites.

The antibodies described herein may be oligoclonal, polyclonal, monoclonal (including full-length monoclonal antibodies), camelised, chimeric, CDR-grafted, multi-specific, bi-specific (including dual-binding antibodies), catalytic, chimeric, humanized, fully human, anti-idiotypic, including antibodies that can be labelled in soluble or bound form as well as fragments, variants or derivatives thereof, either alone or in combination with other amino acid sequences provided by known techniques. An antibody may be from any species. Antibodies described herein can be naked or conjugated to other molecules such as toxins, radioisotopes, etc.

The term "antigen binding domain," "antigen binding region," "antigen binding fragment," and similar terms refer to that portion of an antibody which comprises the amino acid residues that interact with an antigen and confer on the binding agent its specificity and affinity for the antigen (e.g., the complementarity determining regions (CDRs)). The antigen binding region can be derived from any animal species, such as rodents (e.g., rabbit, rat or hamster) and humans. Preferably, the antigen binding region will be of human origin.

Antigen binding fragments described herein can include single-chain Fvs (scFv), single-chain antibodies, single domain antibodies, domain antibodies, Fv fragments, Fab fragments, F(ab') fragments, F(ab')$_2$ fragments, antibody fragments that exhibit the desired biological activity, disulfide-stabilised variable region (dsFv), dimeric variable region (diabody), anti-idiotypic (anti-Id) antibodies (including, e.g., anti-Id antibodies to antibodies), intrabodies, linear antibodies, single-chain antibody molecules and multispecific antibodies formed from antibody fragments and epitope-binding fragments of any of the above. In particular, antibodies and antibody fragments described herein can include immunoglobulin molecules and immunologically active fragments of immunoglobulin molecules, i.e., molecules that contain an antigen-binding site. Digestion of antibodies with the enzyme, papain, results in two identical antigen-binding fragments, known also as "Fab" fragments, and a "Fc" fragment, having no antigen-binding activity but having the ability to crystallize. "Fab" when used herein refers to a fragment of an antibody that includes one constant and one variable domain of each of the heavy and light chains. The term "Fc region" herein is used to define a C-terminal region of an immunoglobulin heavy chain, including native-sequence Fc regions and variant Fc regions. The "Fc fragment" refers to the carboxy-terminal portions of both H chains held together by disulfides. The effector functions of antibodies are determined by sequences in the Fc region, the region which is also recognized by Fc receptors (FcR) found on certain types of cells. Digestion of antibodies with the enzyme, pepsin, results in the a F(ab')$_2$ fragment in which the two arms of the antibody molecule remain linked and comprise two-antigen binding sites. The F(ab')$_2$ fragment has the ability to crosslink antigen.

"Fv" when used herein refers to the minimum fragment of an antibody that retains both antigen-recognition and antigen-binding sites. This region consists of a dimer of one heavy and one light chain variable domain in tight, non-covalent or covalent association. It is in this configuration that the three CDRs of each variable domain interact to define an antigen-binding site on the surface of the VH-VL dimer. Collectively, the six CDRs confer antigen-binding specificity to the antibody. However, even a single variable domain (or half of an Fv comprising only three CDRs specific for an antigen) has the ability to recognize and bind antigen, although at a lower affinity than the entire binding site.

The term "monoclonal antibody" as used herein refers to an antibody obtained from a population of substantially homogeneous antibodies, i.e., the individual antibodies comprising the population are identical except for possible naturally occurring mutations and/or post-translation modifications (e.g., isomerizations, amidations) that may be present in minor amounts. Monoclonal antibodies are highly specific, and are directed against a single antigentic determinant or epitope. In contrast, polyclonal antibody preparations typically include different antibodies directed against different antigenic determinants (or epitopes). The term "monoclonal antibody" as used herein encompasses both intact and full-length monoclonal antibodies as well as antibody fragments (such as Fab, Fab', F(ab')$_2$, Fv), single chain (scFv) mutants, fusion proteins comprising an antibody portion, and any other modified immunoglobulin molecule comprising an antigen recognition site. Furthermore, "monoclonal antibody" refers to such antibodies made in any number of ways including, but not limited to, hybridoma, phage selection, recombinant expression, and transgenic animals.

The monoclonal antibodies herein can include "chimeric" antibodies (immunoglobulins) in which a portion of the heavy and/or light chain is identical with or homologous to corresponding sequences in antibodies derived from a particular species or belonging to a particular antibody class or subclass, while the remainder of the chain(s) is(are) identical with or homologous to corresponding sequences in antibodies derived from another species or belonging to another antibody class or subclass, as well as fragments of such antibodies that exhibit the desired biological activity.

The term "humanized antibody" refers to a subset of chimeric antibodies in which a "hypervariable region" from a non-human immunoglobulin (the donor antibody) replaces residues from a hypervariable region in a human immunoglobulin (recipient antibody). In general, a humanized antibody will include substantially all of at least one, and typically two, variable domains, in which all or substantially all of the hypervariable loops correspond to those of a non-human immunoglobulin sequence, and all or substantially all of the framework regions are those of a human immunoglobulin sequence, although the framework regions may include one or more substitutions that improve antibody performance, such as binding affinity, isomerization, immunogenicity, etc.

The term "bispecific antibody" means an antibody which comprises specificity for two target molecules, and includes formats such as DVD-Ig (see DiGiammarino et al., "Design and generation of DVD-Ig™ molecules for dual-specific targeting", Meth. Mo. Biol., 2012, 889, 145-156), mAb$^2$ (see WO2008/003103), FIT-Ig (see WO2015/103072), mAb-dAb, dock and lock, Fab-arm exchange, SEEDbody, Triomab, LUZ-Y, Fcab, κλ-body, orthogonal Fab, scDiabody-Fc, diabody-Fc, tandem scFv-Fc, Fab-scFv-Fc, Fab-scFv, intrabody, BiTE, diabody, DART, TandAb, scDiabody, scDiabody-CH3, Diabody-CH3, Triple body, Miniantibody, minibody, TriBi minibody, scFv-CH3 KIH, scFv-CH-CL-scFv, F(ab')2-scFv, scFv-KIH, Fab-scFv-Fc, tetravalent HCab, ImmTAC, knobs-in-holes, knobs-in-holes with common light chain, knobs-in-holes with common light chain and charge pairs, charge pairs, charge pairs with common light chain, DT-IgG, DutaMab, IgG(H)-scFv, scFv-(H)IgG, IgG(L)-scFv, scFv-(L)IgG, IgG(L,H)-Fv, IgG(H)-V, V(H)-IgG, IgG(L)-V, V(L)-IgG, KIH IgG-scFab, 2scFv-IgG, IgG-2scFv, scFv4-Ig and zybody. For a review of bispecific formats, see Spiess, C., et al., Mol. Immunol. (2015). In another embodiment, the bispecific molecule comprises an antibody which is fused to another non-Ig format, for example a T-cell receptor binding domain; an immunoglobulin superfamily domain; an agnathan variable lymphocyte receptor; a fibronectin domain (e.g., an Adnectin™); an antibody constant domain (e.g., a CH3 domain, e.g., a CH2 and/or CH3 of an Fcab™) wherein the constant domain is not a functional CH1 domain; an scFv; an (scFv)2; an sc-diabody; an scFab; a centyrin and an epitope binding domain derived from a scaffold selected from CTLA-4 (Evibody™); a lipocalin domain; Protein A such as Z-domain of Protein A (e.g., an Affibody™ or SpA); an A-domain (e.g., an Avimer™ or Maxibody™); a heat shock protein (such as and epitope binding domain derived from GroEI and GroES); a transferrin domain (e.g., a trans-body); ankyrin repeat protein (e.g., a DARPin™); peptide aptamer; C-type lectin domain (e.g., Tetranectin™); human γ-crystallin or human ubiquitin (an affilin); a PDZ domain; scorpion toxin; and a kunitz type domain of a human protease inhibitor.

In one embodiment, a "bispecific antibody" does not include a FIT-Ig format. In one embodiment, a "bispecific antibody" does not include a mAb$^2$ format. In one embodiment, a "bispecific antibody" does not include either a FIT-Ig format or a mAb$^2$ format.

In another embodiment, the bispecific antibody is a "dual binding antibody". As used herein, the term "dual binding antibody" is a bispecific antibody wherein both antigen-binding domains are formed by a $V_H/V_L$ pair, and includes FIT-Ig (see WO2015/103072), mAb-dAb, dock and lock, Fab-arm exchange, SEEDbody, Triomab, LUZ-Y, Fcab, κλ-body, orthogonal Fab, scDiabody-Fc, diabody-Fc, tandem scFv-Fc, Fab-scFv-Fc, Fab-scFv, intrabody, BiTE, diabody, DART, TandAb, scDiabody, scDiabody-CH3, Diabody-CH3, Triple body, Miniantibody, minibody, scFv-CH3 KIH, scFv-CH-CL-scFv, F(ab')2-scFv, scFv-KIH, Fab-scFv-Fc, tetravalent HCab, ImmTAC, knobs-in-holes, knobs-in-holes with common light chain, knobs-in-holes with common light chain and charge pairs, charge pairs, charge pairs with common light chain, DT-IgG, DutaMab, IgG(H)-scFv, scFv-(H)IgG, IgG(L)-scFv, scFv-(L)IgG, IgG (L,H)-Fv, IgG(H)-V, V(H)-IgG, IgG(L)-V, V(L)-IgG, KIH IgG-scFab, 2scFv-IgG, IgG-2scFv and scFv4-Ig.

The term "hypervariable region", "CDR region" or "CDR" refers to the regions of an antibody variable domain which are hypervariable in sequence and/or form structurally defined loops. Generally, antigen binding sites of an antibody include six hypervariable regions: three in the VH (CDRH1, CDRH2, CDRH3), and three in the VL (CDRL1, CDRL2, CDRL3). These regions of the heavy and light chains of an antibody confer antigen-binding specificity to the antibody. CDRs may be defined according to the Kabat system (see Kabat, E. A. et al., 1991, "Sequences of Proteins of Immunological Interest", 5th edit., NIH Publication no. 91-3242, U.S. Department of Health and Human Services). Other systems may be used to define CDRs, which as the system devised by Chothia et al (see Chothia, C. & Lesk, A. M., 1987, "Canonical structures for the hypervariable regions of immunoglobulins", J. Mol. Biol., 196, 901-917) and the IMGT system (see Lefranc, M. P., 1997, "Unique database numbering system for immunogenetic analysis", Immunol. Today, 18, 50). An antibody typically contains 3 heavy chain CDRs and 3 light chain CDRs. The term CDR or CDRs is used here to indicate one or several of these regions. A person skilled in the art is able to readily compare the different systems of nomenclature and determine whether a particular sequence may be defined as a CDR.

A "human antibody" is an antibody that possesses an amino-acid sequence corresponding to that of an antibody produced by a human and/or has been made using any of the techniques for making human antibodies and specifically excludes a humanized antibody comprising non-human antigen-binding residues. The term "specifically binds to" refers to measurable and reproducible interactions such as binding between a target and an antibody, which is determinative of the presence of the target in the presence of a heterogeneous population of molecules including biological molecules. For example, an antibody that specifically binds to a target (which can be an epitope) is an antibody that binds this target with greater affinity, avidity, more readily, and/or with greater duration than it binds to other targets. In one embodiment, the extent of binding of an antibody to an unrelated target is less than about 10% of the binding of the antibody to the target as measured, e.g., by a radioimmunoassay (RIA).

An antibody or a fragment thereof that specifically binds to a hPD-L1 antigen may be cross-reactive with related antigens. Preferably, an antibody or a fragment thereof that specifically binds to a hPD-L1 antigen does not cross-react with other antigens (but may optionally cross-react with PD-L1 of a different species, e.g., rhesus, or murine). An antibody or a fragment thereof that specifically binds to a hPD-L1 antigen can be identified, for example, by immunoassays, BIAcore™ or other techniques known to those of skill in the art. An antibody or a fragment thereof binds specifically to a PD-L1 antigen when it binds to a hPD-L1 antigen with higher affinity than to any cross-reactive antigen as determined using experimental techniques, such as radioimmunoassays (RIA) and enzyme-linked immunosorbent assays (ELISAs). Typically, a specific or selective reaction will be at least twice background signal or noise and more typically more than 10 times (such as more than 15 times, more than 20 times, more than 50 times or more than 100 times) background. See, e.g., Paul, ed., 1989, Fundamental Immunology Second Edition, Raven Press, New York at pages 332-336 for a discussion regarding antibody specificity The term "aliphatic amino acid" means that the amino acid R groups are nonpolar and hydrophobic. Hydrophobicity increases with increasing number of C atoms in the hydrocarbon chain. Glycine, Alanine, Valine, Leucine and Isoleucine are aliphatic amino acids.

The term "aromatic amino acid" means that the amino acid R groups contain an aromatic ring system. Phenylalanine, Tyrosine and Tryptophan are aromatic amino acids.

The term "hydroxyl-containing amino acid" means that the amino acid R groups contain a hydroxyl group, and are hydrophilic. Serine, Cysteine, Threonine and Methionine are hydroxyl-containing amino acids.

The term "basic amino acid" means that the amino acid R groups are nitrogen containing and are basic at neutral pH. Histidine, Lysine and Arginine are basic amino acids.

The term "cyclic amino acid" means that the amino acid R groups have an aliphatic cyclic structure. Proline is the only cyclic aliphatic amino acid.

The term "acidic amino acid" means that the amino acid R groups are polar and are negatively charged at physiological pH. Aspartate and Glutamate are acidic amino acids.

The term "amide amino acid" means that the amino acid R groups contain an amide group. Asparagine and Glutamine are amide amino acids.

As used herein, "authorization number" or "marketing authorization number" refers to a number issued by a regulatory agency upon that agency determining that a particular medical product and/or composition may be marketed and/or offered for sale in the area under the agency's jurisdiction. As used herein "regulatory agency" refers to one of the agencies responsible for evaluating, e.g., the safety and efficacy of a medical product and/or composition and controlling the sales/marketing of such products and/or compositions in a given area. The Food and Drug Administration (FDA) in the US and the European Medicines Agency (EPA) in Europe are but two examples of such regulatory agencies. Other non-limiting examples can include SDA, MPA, MHPRA, IMA, ANMAT, Hong Kong Department of Health-Drug Office, CDSCO, Medsafe, and KFDA.

As used herein, the term "biomarker" refers to a gene that is differentially expressed in individuals having a disease of interest, for example, a gene that is differentially expressed in individuals having cancer. In one embodiment, PD-L1 is a biomarker whose expression in tumours may be indicative as to whether or not a patient would respond to a particular type of treatment, in particular, whether a patient would response to treatment targeting PD-L1, for example, immunotherapy using anti-PD-L1 antibodies. In one embodiment, PD-L1 is a biomarker whose expression in tumours may be indicative as to whether or not a patient would respond to a particular type of treatment, in particular, whether a patient would response to treatment targeting PD-1, for example, immunotherapy using anti-PD-1 antibodies. In another embodiment, PD-L1 may be free or membrane bound. In another embodiment, PD-L1 may be fixed or unfixed.

As used herein, a "buffer" refers to a chemical agent that is able to absorb a certain quantity of acid or base without undergoing a strong variation in pH.

As used herein, the term "carrier" refers to a diluent, adjuvant (e.g., Freund's adjuvant (complete and incomplete)), excipient, or vehicle with which the therapeutic is administered. Such pharmaceutical carriers can be sterile liquids, such as water and oils, including those of petroleum, animal, vegetable or synthetic origin, such as peanut oil, soybean oil, mineral oil, sesame oil and the like. Water is a preferred carrier when the pharmaceutical composition is administered intravenously. Saline solutions and aqueous dextrose and glycerol solutions can also be employed as liquid carriers, particularly for injectable solutions.

The term "chemotherapeutic agent" or "chemotherapy" refers to a therapeutic agent whose primary purpose is to destroy cancer cells, typically by interfering with the tumour cell's ability to grow or multiply. There are many different types of chemotherapeutic agents, with more than 50 approved chemotherapy drugs available. Chemotherapeutic drugs can be classified based on how they work. Alkylating drugs kill cancer cells by directly attacking DNA, the genetic material of the genes. Cyclophosphamide is an alkylating drug. Antimetabolites interfere with the production of DNA and keep cells from growing and multiplying. An example of an antimetabolite is 5-fluorouracil (5-FU). Anti-tumour antibiotics are made from natural substances such as fungi in the soil. They interfere with important cell functions, including production of DNA and cell proteins. Doxorubicin and bleomycin belong to this group of chemotherapy drugs. Plant alkaloids prevent cells from dividing normally. Vinblastine and vincristine are plant alkaloids obtained from the periwinkle plant. Steroid hormones slow the growth of some cancers that depend on hormones. For example, tamoxifen is used to treat breast cancers that depend on the hormone estrogen for growth. DNA damage response (DDR) inhibitors, such as PARP inhibitors, block DNA repair mechanisms following single or double stranded breaks.

Examples of chemotherapeutic agents include Adriamycin, Doxorubicin, 5-Fluorouracil, Cytosine arabinoside (Ara-C), Cyclophosphamide, Thiotepa, Taxotere (docetaxel), Busulfan, Cytoxin, Taxol, Methotrexate, Cisplatin, Melphalan, Vinblastine, Bleomycin, Etoposide, Ifosfamide, Mitomycin C, Mitoxantrone, Vincreistine, Vinorelbine, Carboplatin, Teniposide, Daunomycin, Carminomycin, Aminopterin, Dactinomycin, Mitomycins, Esperamicins (see, U.S. Pat. No. 4,675,187), Melphalan, and other related nitrogen mustards. Suitable toxins and chemotherapeutic agents are described in Remington's Pharmaceutical Sciences, 19th Ed. (Mack Publishing Co. 1995), and in Goodman and Gilman's The Pharmacological Basis of Therapeutics, 7th Ed. (MacMillan Publishing Co. 1985). Other suitable toxins and/or chemotherapeutic agents are known to those of skill in the art.

As used herein, the term "composition" is intended to encompass a product containing the specified ingredients (e.g., an antibody of the invention) in, optionally, the specified amounts, as well as any product which results, directly or indirectly, from combination of the specified ingredients in, optionally, the specified amounts.

As used herein the term "comprising" or "comprises" is used in reference to antibodies, fragments, uses, compositions, methods, and respective component(s) thereof, that are essential to the method or composition, yet open to the inclusion of unspecified elements, whether essential or not.

The term "consisting of" refers to antibodies, fragments, uses, compositions, methods, and respective components thereof as described herein, which are exclusive of any element not recited in that description of the embodiment.

As used herein the term "consisting essentially of" refers to those elements required for a given embodiment. The term permits the presence of elements that do not materially affect the basic and novel or functional characteristic(s) of that embodiment.

In the context of a polypeptide, the term "derivative" as used herein refers to a polypeptide that comprises an amino acid sequence of a hPD-L1 polypeptide, a fragment of a hPD-L1 polypeptide, or an antibody that specifically binds to a hPD-L1 polypeptide which has been altered by the introduction of amino acid residue substitutions, deletions or additions. The term "derivative" as used herein also refers to a hPD-L1 polypeptide, a fragment of a hPD-L1 polypeptide, or an antibody that specifically binds to a hPD-L1 polypeptide which has been chemically modified, e.g., by the covalent attachment of any type of molecule to the polypeptide. For example, but not by way of limitation, a hPD-L1 polypeptide, a fragment of a hPD-L1 polypeptide, or a hPD-L1 antibody may be chemically modified, e.g., by glycosylation, acetylation, pegylation, phosphorylation, amidation, derivatization by known protecting/blocking groups, proteolytic cleavage, linkage to a cellular ligand or other protein, etc. The derivatives are modified in a manner that is different from naturally occurring or starting peptide or polypeptides, either in the type or location of the molecules attached. Derivatives further include deletion of one or more chemical groups which are naturally present on the peptide or polypeptide. A derivative of a hPD-L1 polypeptide, a fragment of a hPD-L1 polypeptide, or a hPD-L1 antibody may be chemically modified by chemical modifications using techniques known to those of skill in the art, including, but not limited to specific chemical cleavage, acetylation, formulation, metabolic synthesis of tunicamycin, etc. Further, a derivative of a hPD-L1 polypeptide, a fragment of a hPD-L1 polypeptide, or a hPD-L1 antibody may contain one or more non-classical amino acids. A polypeptide derivative possesses a similar or identical function as a hPD-L1 polypeptide, a fragment of a hPD-L1 polypeptide, or a hPD-L1 antibody described herein.

An "effective amount" refers to an amount effective, at dosages and for periods of time necessary, to achieve the desired effect, including a therapeutic or prophylactic result. A "therapeutically effective amount" refers to the minimum concentration required to effect a measurable improvement or prevention of a particular disorder. A therapeutically effective amount herein may vary according to factors such as the disease state, age, sex, and weight of the patient, and the ability of the antibody to elicit a desired response in the individual. A therapeutically effective amount is also one in which toxic or detrimental effects of the antibody are outweighed by the therapeutically beneficial effects. A "prophylactically effective amount" refers to an amount effective, at the dosages and for periods of time necessary, to achieve the desired prophylactic result. In some embodiments, the effective amount of an antibody of the invention is from about 0.1 mg/kg (mg of antibody per kg weight of the subject) to about 100 mg/kg. In certain embodiments, an effective amount of an antibody provided therein is about 0.1 mg/kg, about 0.5 mg/kg, about 1 mg/kg, 3 mg/kg, 5 mg/kg, about 10 mg/kg, about 15 mg/kg, about 20 mg/kg, about 25 mg/kg, about 30 mg/kg, about 35 mg/kg, about 40 mg/kg, about 45 mg/kg, about 50 mg/kg, about 60 mg/kg, about 70 mg/kg, about 80 mg/kg about 90 mg/kg or about 100 mg/kg (or a range therein). In some embodiments, "effective amount" as used herein also refers to the amount of an antibody of the invention to achieve a specified result (e.g., inhibition of a hPD-L1 biological activity of a cell).

The term "epitope" as used herein refers to a localized region on the surface of an antigen, such as hPD-L1 polypeptide or hPD-L1 polypeptide fragment, that is capable of being bound to one or more antigen binding regions of an antibody, and that has antigenic or immunogenic activity in an animal, preferably a mammal, and most preferably in a human, that is capable of eliciting an immune response. An epitope having immunogenic activity is a portion of a polypeptide that elicits an antibody response in an animal. An epitope having antigenic activity is a portion of a polypeptide to which an antibody specifically binds as determined by any method well known in the art, for example, by the immunoassays described herein. Antigenic epitopes need not necessarily be immunogenic. Epitopes usually consist of chemically active surface groupings of molecules such as amino acids or sugar side chains and have specific three dimensional structural characteristics as well as specific charge characteristics. A region of a polypeptide contributing to an epitope may be contiguous amino acids of the polypeptide or the epitope may come together from two or more non-contiguous regions of the polypeptide. The epitope may or may not be a three-dimensional surface feature of the antigen. In certain embodiments, a hPD-L1 epitope is a three-dimensional surface feature of a hPD-L1 polypeptide (e.g., in a trimeric form of a hPD-L1 polypeptide). In other embodiments, a hPD-L1 epitope is linear feature of a hPD-L1 polypeptide (e.g., in a trimeric form or monomeric form of the hPD-L1 polypeptide). Antibodies provided herein may specifically bind to an epitope of the monomeric (denatured) form of hPD-L1, an epitope of the trimeric (native) form of hPD-L1, or both the monomeric (denatured) form and the trimeric (native) form of hPD-L1. In specific embodiments, the antibodies provided herein specifically bind to an epitope of the trimeric form of hPD-L1 but do not specifically bind the monomeric form of hPD-L1.

The term "excipients" as used herein refers to inert substances which are commonly used as a diluent, vehicle, preservatives, binders, or stabilizing agent for drugs and includes, but not limited to, proteins (e.g., serum albumin, etc.), amino acids (e.g., aspartic acid, glutamic acid, lysine, arginine, glycine, histidine, etc.), fatty acids and phospholipids (e.g., alkyl sulfonates, caprylate, etc.), surfactants (e.g., SDS, polysorbate, nonionic surfactant, etc.), saccharides (e.g., sucrose, maltose, trehalose, etc.) and polyols (e.g., mannitol, sorbitol, etc.). See, also, Remington's Pharmaceutical Sciences (1990) Mack Publishing Co., Easton, Pa., which is hereby incorporated by reference in its entirety.

As used herein, the term "fixed" or "fixation" refers to a chemical process by which biological tissues are preserved from decay, to prevent autolysis or putrefaction. In general, fixation involves exposing the tissue to chemical compounds such as alcohols or aldehydes such as formaldehyde to terminate ongoing biochemical reactions. In some instances, fixation may also increase the mechanical strength or stability of the treated tissues. The term "unfixed" refers to a tissue that has not been subjected to a chemical process to prevent tissue decay. As used herein, the term "surface expressed" means that the protein is embedded in or spans a cell membrane or is associated with a protein that is embedded in or spans a cell membrane (i.e., a membrane associated protein). In one embodiment, a surface expressed protein includes one or more transmembrane domains. In another embodiment, the protein is associated with the exterior or interior surface of a cell membrane indirectly via association with another membrane spanning protein (i.e., the surface expressed protein is not spanning the cell membrane itself). In general, surface expressed proteins that are integrated into a cell membrane or expressed endogenously within a cell are more likely to fold in the correct conformation than recombinantly produced free forms of the same protein.

In the context of a peptide or polypeptide, the term "fragment" as used herein refers to a peptide or polypeptide that comprises less than the full length amino acid sequence. Such a fragment may arise, for example, from a truncation at the amino terminus, a truncation at the carboxy terminus, and/or an internal deletion of a residue(s) from the amino acid sequence. Fragments may, for example, result from alternative RNA splicing or from in vivo protease activity. In certain embodiments, PD-L1 fragments include polypeptides comprising an amino acid sequence of at least 5 contiguous amino acid residues, at least 10 contiguous amino acid residues, at least 15 contiguous amino acid residues, at least 20 contiguous amino acid residues, at least 25 contiguous amino acid residues, at least 40 contiguous amino acid residues, at least 50 contiguous amino acid residues, at least 60 contiguous amino residues, at least 70 contiguous amino acid residues, at least 80 contiguous amino acid residues, at least 90 contiguous amino acid residues, at least contiguous 100 amino acid residues, at least 125 contiguous amino acid residues, at least 150 contiguous amino acid residues, at least 175 contiguous amino acid residues, at least 200 contiguous amino acid residues, or at least 250 contiguous amino acid residues of the amino acid sequence of a hPD-L1 polypeptide or an antibody that specifically binds to a hPD-L1 polypeptide. In a specific embodiment, a fragment of a hPD-L1 polypeptide or an antibody that specifically binds to a hPD-L1 antigen retains at least 1, at least 2, or at least 3 functions of the polypeptide or antibody.

The term "free" refers to a polypeptide, for example, PD-L1 or fragments and variants thereof, that is combined with a buffer, wherein the polypeptide is not associated with a cell surface or cell membrane. As such, the term "free" can refer to a polypeptide that is capable of surface expression (i.e., includes one or more transmembrane domains or membrane association domains), but that is not, in its present state, expressed on the surface of a cell or bound to a protein that is expressed on the surface of a cell. A free polypeptide can also refer to a free recombinant or native or unbound polypeptide. In the context of phage display, a free antigen can be selected in solution (referred to herein as a "soluble selection") or adsorbed to a surface, for example, adsorbed to the surface of a 96 well plate (referred to herein as "biopanning selection").

The term "fusion protein" as used herein refers to a polypeptide that comprises an amino acid sequence of an antibody and an amino acid sequence of a heterologous polypeptide or protein (i.e., a polypeptide or protein not normally a part of the antibody (e.g., a non-anti-hPD-L1 antigen antibody)). The term "fusion" when used in relation to hPD-L1 or to an anti-hPD-L1 antibody refers to the joining of a peptide or polypeptide, or fragment, variant and/or derivative thereof, with a heterologous peptide or polypeptide. Preferably, the fusion protein retains the biological activity of the hPD-L1 or anti-hPD-L1 antibody. In certain embodiments, the fusion protein comprises a hPD-L1 antibody VH domain, VL domain, VH CDR (one, two or three VH CDRs), and/or VL CDR (one, two or three VL CDRs), wherein the fusion protein specifically binds to a hPD-L1 epitope.

The term "heavy chain" when used in reference to an antibody refers to five distinct types, called alpha ($\alpha$), delta ($\delta$), epsilon ($\epsilon$), gamma ($\gamma$) and mu ($\mu$), based on the amino acid sequence of the heavy chain constant domain. These distinct types of heavy chains are well known and give rise to five classes of antibodies, IgA, IgD, IgE, IgG and IgM, respectively, including four subclasses of IgG, namely IgG1, IgG1, IgG3 and IgG4. Preferably the heavy chain is a human heavy chain. In one example, the heavy chain is a disabled IgG isotype, e.g. a disabled IgG4. In certain embodiments, the antibodies of the invention comprise a human gamma 4 constant region. In another embodiment, the heavy chain constant region does not bind Fc-γ receptors, and e.g. comprises a Leu235Glu mutation. In another embodiment, the heavy chain constant region comprises a Ser228Pro mutation to increase stability. In another embodiment, the heavy chain constant region is IgG4-PE.

The term "host" as used herein refers to an animal, preferably a mammal, and most preferably a human.

The term "host cell" as used herein refers to the particular subject cell transfected with a nucleic acid molecule and the progeny or potential progeny of such a cell. Progeny of such a cell may not be identical to the parent cell transfected with the nucleic acid molecule due to mutations or environmental influences that may occur in succeeding generations or integration of the nucleic acid molecule into the host cell genome.

The term "an IL-2 cytokine" as used herein refers to a cytokine-like molecule which has a similar activity to a wild-type IL-2. It may have activity at the high ($\alpha\beta\gamma$) affinity IL-2 receptor and/or the intermediate affinity ($\alpha\beta$) IL-2 receptor. The cytokine may be a variant IL-2 cytokine having one or more amino acid deletions, substitutions or additions.

The term "immunomodulatory agent" and variations thereof including, but not limited to, immunomodulatory agents, as used herein refer to an agent that modulates a host's immune system. In certain embodiments, an immunomodulatory agent is an immunosuppressant agent. In certain other embodiments, an immunomodulatory agent is an immunostimulatory agent. In accordance with the invention, an immunomodulatory agent used in the combination therapies of the invention does not include an anti-hPD-L1 antibody or antigen-binding fragment. Immunomodulatory agents include, but are not limited to, small molecules, peptides, polypeptides, proteins, fusion proteins, antibodies, inorganic molecules, mimetic agents, and organic molecules.

The term "in combination" in the context of the administration of other therapies refers to the use of more than one therapy. The use of the term "in combination" does not restrict the order in which therapies are administered to a subject with a disease. A first therapy can be administered before (e.g., 1 minute, 45 minutes, 30 minutes, 45 minutes, 1 hour, 2 hours, 4 hours, 6 hours, 12 hours, 24 hours, 48 hours, 72 hours, 96 hours, 1 week, 2 weeks, 3 weeks, 4 weeks, 5 weeks, 6 weeks, 8 weeks, or 12 weeks), concurrently, or after (e.g., 1 minute, 45 minutes, 30 minutes, 45 minutes, 1 hour, 2 hours, 4 hours, 6 hours, 12 hours, 24 hours, 48 hours, 72 hours, 96 hours, 1 week, 2 weeks, 3 weeks, 4 weeks, 5 weeks, 6 weeks, 8 weeks, or 12 weeks) the administration of a second therapy to a subject which had, has, or is susceptible to a hPD-L1-mediated disease. Any additional therapy can be administered in any order with the other additional therapies. In certain embodiments, the antibodies of the invention can be administered in combination with one or more therapies (e.g., therapies that are not the antibodies of the invention that are currently administered to prevent, treat, manage, and/or ameliorate a hPD-L1-mediated disease. Non-limiting examples of therapies that can be administered in combination with an antibody of the invention include analgesic agents, anaesthetic agents, antibiotics, or immunomodulatory agents or any other agent listed in the U.S. Pharmacopoeia and/or Physician's Desk Reference.

The term "immunocytokine", as used herein refers to an antibody format which is fused to a cytokine molecule. The antibody format may be any of those described herein, and the cytokine may be fused directly, or by means of a linker or chemical conjugation to either the N- or C-terminus of the heavy or the light chain of the antibody format.

As used herein, "injection device" refers to a device that is designed for carrying out injections, an injection including the steps of temporarily fluidically coupling the injection device to a person's tissue, typically the subcutaneous tissue. An injection further includes administering an amount of liquid drug into the tissue and decoupling or removing the injection device from the tissue. In some embodiments, an injection device can be an intravenous device or IV device, which is a type of injection device used when the target tissue is the blood within the circulatory system, e.g., the blood in a vein. A common, but non-limiting example of an injection device is a needle and syringe.

As used herein, "instructions" refers to a display of written, printed or graphic matter on the immediate container of an article, for example the written material displayed on a vial containing a pharmaceutically active agent, or details on the composition and use of a product of interest included in a kit containing a composition of interest. Instructions set forth the method of the treatment as contemplated to be administered or performed.

An "isolated" or "purified" antibody or protein is one that has been identified, separated and/or recovered from a component of its production environment (e.g., natural or recombinant) For example, the antibody or protein is substantially free of cellular material or other contaminating proteins from the cell or tissue source from which the antibody is derived, or substantially free of chemical precursors or other chemicals when chemically synthesized. The language "substantially free of cellular material" includes preparations of an antibody in which the antibody is separated from cellular components of the cells from which it is isolated or recombinantly produced. Thus, an antibody that is substantially free of cellular material includes preparations of antibody having less than about 30%, 20%, 10%, or 5% (by dry weight) of heterologous protein (also referred to herein as a "contaminating protein"). When the antibody is recombinantly produced, it is also preferably substantially free of culture medium, i.e., culture medium represents less than about 20%, 10%, or 5% of the volume of the protein preparation. When the antibody is produced by chemical synthesis, it is preferably substantially free of chemical precursors or other chemicals, i.e., it is separated from chemical precursors or other chemicals which are involved in the synthesis of the protein. Accordingly such preparations of the antibody have less than about 30%, 20%, 10%, 5% (by dry weight) of chemical precursors or compounds other than the antibody of interest. In a preferred embodiment, antibodies of the invention are isolated or purified.

The terms "Kabat numbering," and like terms are recognized in the art and refer to a system of numbering amino acid residues which are more variable (i.e. hypervariable) than other amino acid residues in the heavy chain variable regions of an antibody, or an antigen binding portion thereof (Kabat et al. (1971) Ann. NY Acad. Sci. 190:382-391 and, Kabat et al. (1991) Sequences of Proteins of Immunological Interest, Fifth Edition, U.S. Department of Health and Human Services, NIH Publication No. 91-3242). For the heavy chain variable region, the hypervariable region typically ranges from amino acid positions 31 to 35 for CDR1, amino acid positions 50 to 65 for CDR2, and amino acid positions 95 to 102 for CDR3.

"Label" or "labelled" as used herein refers to the addition of a detectable moiety to a polypeptide, for example, a radiolabel, fluorescent label, enzymatic label, chemiluminescent label or a biotinyl group or gold. Radioisotopes or radionuclides may include 3H, 14C, 15N, 35S, 90Y, 99Tc, 115In, 125I, 131I, fluorescent labels may include rhodamine, lanthanide phosphors or FITC and enzymatic labels may include horseradish peroxidase, β-galactosidase, luciferase, alkaline phosphatase. Additional labels include, by way of illustration and not limitation: enzymes, such as glucose-6-phosphate dehydrogenase ("G6PDH"), alpha-D-galactosidase, glucose oxydase, glucose amylase, carbonic anhydrase, acetylcholinesterase, lysozyme, malate dehydrogenase and peroxidase; dyes (e.g. cyanine dyes, e.g. Cy5TM, Cy5.5TM. or Cy7TM); additional fluorescent labels or fluorescers include, such as fluorescein and its derivatives, fluorochrome, GFP (GFP for "Green Fluorescent Protein"), other fluorescent proteins (e.g. mCherry, mTomato), dansyl, umbelliferone, phycoerythrin, phycocyanin, allophycocyanin, o-phthaldehyde, and fiuorescamine; fluorophores such as lanthanide cryptates and chelates e.g. Europium etc (Perkin Elmer and Cisbio Assays); chemoluminescent labels or chemiluminescers, such as isoluminol, luminol and the dioxetanes; sensitisers; coenzymes; enzyme substrates; particles, such as latex or carbon particles; metal sol; crystallite; liposomes; cells, etc., which may be further labelled with a dye, catalyst or other detectable group; molecules such as biotin, digoxygenin or 5-bromodeoxyuridine; toxin moieties, such as for example a toxin moiety selected from a group of Pseudomonas exotoxin (PE or a cytotoxic fragment or mutant thereof), Diptheria toxin or a cytotoxic fragment or mutant thereof, a botulinum toxin A, B, C, D, E or F, ricin or a cytotoxic fragment thereof e.g. ricin A, abrin or a cytotoxic fragment thereof, saporin or a cytotoxic fragment thereof, pokeweed antiviral toxin or a cytotoxic fragment thereof and bryodin 1 or a cytotoxic fragment thereof.

"Percent (%) amino acid sequence identity" and "homology" with respect to a peptide, polypeptide or antibody sequence are defined as the percentage of amino acid residues in a candidate sequence that are identical with the amino acid residues in the specific peptide or polypeptide sequence, after aligning the sequences and introducing gaps, if necessary, to achieve the maximum percent sequence identity, and not considering any conservative substitutions as part of the sequence identity. Alignment for purposes of determining percent amino acid sequence identity can be achieved in various ways that are within the skill in the art, for instance, using publicly available computer software such as BLAST, BLAST-2, ALIGN or MEG ALIGN™ (DNASTAR) software. In one embodiment, the % homology is about 70%. In one embodiment, the % homology is about 75%. In one embodiment, the % homology is about 80%. In one embodiment, the % homology is about 85%. In one embodiment, the % homology is about 90%. In one embodiment, the % homology is about 92%. In one embodiment, the % homology is about 95%. In one embodiment, the % homology is about 97%. In one embodiment, the % homology is about 98%. In one embodiment, the % homology is about 99%. In one embodiment, the % homology is about 100%.

The term "naturally occurring" or "native" when used in connection with biological materials such as nucleic acid molecules, polypeptides, host cells, and the like, refers to those which are found in nature and not manipulated by a human being.

As used herein, "packaging" refers to how the components are organized and/or restrained into a unit fit for distribution and/or use. Packaging can include, e.g., boxes, bags, syringes, ampoules, vials, tubes, clamshell packaging, barriers and/or containers to maintain sterility, labelling, etc.

The term "pharmaceutically acceptable" as used herein means being approved by a regulatory agency of the Federal or a state government, or listed in the U.S. Pharmacopeia, European Pharmacopeia or other generally recognized Pharmacopeia for use in animals, and more particularly in humans.

As used herein, the term "polynucleotide," "nucleotide," nucleic acid" "nucleic acid molecule" and other similar terms are used interchangeable and include DNA, RNA, mRNA and the like.

As used herein, the terms "prevent," "preventing," and "prevention" refer to the total or partial inhibition of the development, recurrence, onset or spread of a hPD-L1-mediated disease and/or symptom related thereto, resulting from the administration of a therapy or combination of therapies provided herein (e.g., a combination of prophylactic or therapeutic agents, such as an antibody of the invention).

The term "soluble" refers to a polypeptide, such as PD-L1 and variants or fragments thereof, that is lacking one or more transmembrane or cytoplasmic domains found in the native or membrane-associated form. In one embodiment, the "soluble" form of PD-L1 lacks both the transmembrane domain and the cytoplasmic domain.

The term "subject" or "patient" refers to any animal, including, but not limited to, mammals. As used herein, the term "mammal" refers to any vertebrate animal that suckle their young and either give birth to living young (eutharian or placental mammals) or are egg-laying (metatharian or nonplacental mammals). Examples of mammalian species include, but are not limited to, humans and other primates, including non-human primates such as chimpanzees and other apes and monkey species; farm animals such as cattle, sheep, pigs, goats and horses; domestic mammals such as dogs and cats; laboratory animals including rodents such as mice, rats (including cotton rats) and guinea pigs; birds, including domestic, wild and game birds such as chickens, turkeys and other gallinaceous birds, ducks, geese, and the like.

As used herein "substantially all" refers to refers to at least about 60%, at least about 70%, at least about 75%, at least about 80%, at least about 85%, at least about 90%, at least about 95%, at least about 98%, at least about 99%, or about 100%.

The term "substantially free of surfactant" as used herein refers to a formulation of an antibody that specifically binds to a hPD-L1 antigen, said formulation containing less than 0.0005%, less than 0.0003%, or less than 0.0001% of surfactants and/or less than 0.0005%, less than 0.0003%, or less than 0.0001% of surfactants.

The term "substantially free of salt" as used herein refers to a formulation of an antibody that specifically binds to a hPD-L1 antigen, said formulation containing less than 0.0005%, less than 0.0003%, or less than 0.0001% of inorganic salts.

The term "surfactant" as used herein refers to organic substances having amphipathic structures; namely, they are composed of groups of opposing solubility tendencies, typically an oil-soluble hydrocarbon chain and a water-soluble ionic group. Surfactants can be classified, depending on the charge of the surface-active moiety, into anionic, cationic, and non-ionic surfactants. Surfactants are often used as wetting, emulsifying, solubilizing, and dispersing agents for various pharmaceutical compositions and preparations of biological materials.

As used herein, the term "tag" refers to any type of moiety that is attached to, e.g., a polypeptide and/or a polynucleotide that encodes a hPD-L1 or hPD-L1 antibody or antigen binding fragment thereof. For example, a polynucleotide that encodes a hPD-L1, hPD-L1 antibody or antigen binding fragment thereof can contain one or more additional tag-encoding nucleotide sequences that encode a, e.g., a detectable moiety or a moiety that aids in affinity purification. When translated, the tag and the antibody can be in the form of a fusion protein. The term "detectable" or "detection" with reference to a tag refers to any tag that is capable of being visualized or wherein the presence of the tag is otherwise able to be determined and/or measured (e.g., by quantitation). A non-limiting example of a detectable tag is a fluorescent tag.

As used herein, the term "therapeutic agent" refers to any agent that can be used in the treatment, management or amelioration of a hPD-L1-mediated disease and/or a symptom related thereto. In certain embodiments, the term "therapeutic agent" refers to an antibody of the invention. In certain other embodiments, the term "therapeutic agent" refers to an agent other than an antibody of the invention. Preferably, a therapeutic agent is an agent which is known to be useful for, or has been or is currently being used for the treatment, management or amelioration of a hPD-L1-mediated disease or one or more symptoms related thereto. In specific embodiments, the therapeutic agent is a fully human anti-hPD-L1 antibody, such as a fully human anti-hPD-L1 monoclonal antibody.

As used herein, the term "therapy" refers to any protocol, method and/or agent that can be used in the prevention, management, treatment and/or amelioration of a hPD-L1-mediated disease (e.g. cancer). In certain embodiments, the terms "therapies" and "therapy" refer to a biological therapy, supportive therapy, and/or other therapies useful in the prevention, management, treatment and/or amelioration of a hPD-L1-mediated disease known to one of skill in the art such as medical personnel.

The terms "treat," "treatment" and "treating" refer to the reduction or amelioration of the progression, severity, and/or duration of a hPD-L1-mediated disease (e.g., cancer) resulting from the administration of one or more therapies (including, but not limited to, the administration of one or more prophylactic or therapeutic agents, such as an antibody of the invention). In specific embodiments, such terms refer to the reduction or inhibition of the binding of hPD-L1 to PD-1, the reduction or inhibition of the binding of hPD-L1 to CD80, and/or the inhibition or reduction of one or more symptoms associated with a hPD-L1-mediated disease, such as cancer. In specific embodiments, such terms refer to the reduction or inhibition of the binding of hPD-L1 to PD-1 and/or CD80, and/or the inhibition or reduction of one or more symptoms associated with a hPD-L1-mediated disease, such as cancer. In an example, the cell is a human cell. In specific embodiments, a prophylactic agent is a fully human anti-hPD-L1 antibody, such as a fully human anti-hPD-L1 monoclonal antibody.

The term "variable region" or "variable domain" refers to a portion of the PD-L1 and heavy chains, typically about the amino-terminal 120 to 130 amino acids in the heavy chain and about 100 to 110 amino acids in the light chain, which differ extensively in sequence among antibodies and are used in the binding and specificity of each particular antibody for its particular antigen. The variability in sequence is concentrated in those regions called complimentarily determining regions (CDRs) while the more highly conserved regions in the variable domain are called framework regions (FR). The CDRs of the PD-L1 and heavy chains are primarily responsible for the interaction of the antibody with antigen. Numbering of amino acid positions used herein is according to the EU Index, as in Kabat et al. (1991) Sequences of proteins of immunological interest. (U.S. Department of Health and Human Services, Washington, D.C.) 5th ed. ("Kabat et al."). In preferred embodiments, the variable region is a human variable region.

Definitions of common terms in cell biology and molecular biology can be found in "The Merck Manual of Diagnosis and Therapy", 19th Edition, published by Merck Research Laboratories, 2006 (ISBN 0-911910-19-0); Robert S. Porter et al. (eds.), The Encyclopedia of Molecular Biology, published by Blackwell Science Ltd., 1994 (ISBN 0-632-02182-9); Benjamin Lewin, Genes X, published by Jones & Bartlett Publishing, 2009 (ISBN-10: 0763766321); Kendrew et al. (Eds.), Molecular Biology and Biotechnology: a Comprehensive Desk Reference, published by VCH Publishers, Inc., 1995 (ISBN 1-56081-569-8) and Current Protocols in Protein Sciences 2009, Wiley Intersciences, Coligan et al., eds.

Unless otherwise stated, the present invention was performed using standard procedures, as described, for example in Sambrook et al., Molecular Cloning: A Laboratory Manual (4 ed.), Cold Spring Harbor Laboratory Press, Cold Spring Harbor, N.Y., USA (2012); Davis et al., Basic Methods in Molecular Biology, Elsevier Science Publishing, Inc., New York, USA (1995); or Methods in Enzymology: Guide to Molecular Cloning Techniques Vol. 152, S. L. Berger and A. R. Kimmel Eds., Academic Press Inc., San Diego, USA (1987); Current Protocols in Protein Science (CPPS) (John E. Coligan, et al., ed., John Wiley and Sons, Inc.), Current Protocols in Cell Biology (CPCB) (Juan S. Bonifacino et al. ed., John Wiley and Sons, Inc.), and Culture of Animal Cells: A Manual of Basic Technique by R. Ian Freshney, Publisher: Wiley-Liss; 5th edition (2005), Animal Cell Culture Methods (Methods in Cell Biology, Vol. 57, Jennie P. Mather and David Barnes editors, Academic Press, 1st edition, 1998) which are all incorporated by reference herein in their entireties.

Other terms are defined herein within the description of the various aspects of the invention.

Many tumour cells express surface molecules that are specific to cancer that can serve as diagnostic and/or therapeutic antibody targets. Examples of cell surface proteins expressed by tumour molecules that can be useful as biomarkers include, for example, members of the B7 family of proteins, major histocompatibility complex molecules (MHC), cytokine and growth factor receptors such as the receptor for eipdermal growth factor (EGFR). The B7 family is a group of proteins that are members of the immunoglobulin (Ig) superfamily of cell-surface proteins that bind to receptors on lymphocytes to regulate immune responses. The family includes transmembrane or glycosylphosphatidylinositol (GPI)-linked proteins characterized by extracellular Ig-like domains (IgV and IgC domains related to the variable and constant domains of immunoglobulins). All members have short cytoplasmic domains. There are seven known members of the B7 family: B7-1, B7-2, PD-L1 (B7-H1), PD-L2, B7-H2, B7-H3, and B7-H4.

The complete amino acid sequence for PD-L1 can be found in NCBI Reference Sequence: NP_054862.1 (SEQ ID No:1), which refers to many journal articles, including, for example, Dong, H., et al. (1999), "PD-L1, a third member of the B7 family, co-stimulates T-cell proliferation and interleukin-10 secretion," Nat. Med. 5 (12), 1365-1369, the disclosure of which is hereby incorporated by reference herein in its entirety. The amino acid sequence of PD-L1 includes a 30 amino acid long cytoplasmic domain that is unique to PD-L1, which shows little homology to other molecules, including other B7 family members.

In one embodiment, the antibody is a polyclonal antibody. Methods for generating polyclonal antibodies are known, and include, for example, inoculating a suitable mammal with an antigen to induce the immune system of the animal to produce immunoglobulins (IgGs) that specifically bind the injected antigen. Examples of suitable mammals include, for example, mouse, guinea pig, hamster, rat, rabbit sheep or goat. The polyclonal IgG is then typically purified from the mammal's serum. In one embodiment, the antibody is a polyclonal antibody that binds to a surface expressed protein. In another embodiment, the antibody is a polyclonal antibody that specifically binds to a member of the B7 family of proteins. In a more specific embodiment, the antibody is a polyclonal antibody that specifically binds PD-L1. In another embodiment, the antibody is a polyclonal antibody that specifically binds surface expressed PD-L1. In a more particular embodiment, the polyclonal antibody or antigen binding fragment thereof specifically binds human PD-L1. In another embodiment, the antibody is a polyclonal antibody that specifically binds soluble PD-L1. The term "soluble" also refers to a protein, such as PD-L1 that is lacking one or more transmembrane domain or cytoplasmic domains. In one embodiment, the "soluble" form of PD-L1 lacks both the transmembrane domain and the cytoplasmic domain. In one embodiment, the antibody is a polyclonal antibody that binds "free" PD-L1 (i.e., PD-L1 that is not associated with a cell membrane or surface, either directly or indirectly).

In another embodiment, the antibody can be a monoclonal antibody. Methods of making monoclonal antibodies are known and include, for example, fusing myeloma cells with the cells from an animal that was immunized with the desired antigen. In other embodiments, the monoclonal antibodies may be generated using recombinant DNA technology. In one embodiment, the antibody is a monoclonal antibody that specifically binds a surface expressed protein. In one embodiment, the antibody is a fully human monoclonal antibody. In another embodiment, the antibody is a monoclonal antibody that specifically binds to a member of the B7 family of proteins. In a more specific embodiment, the antibody is a monoclonal antibody that specifically binds PD-L1. In another embodiment, the antibody is a monoclonal antibody that specifically binds surface expressed PD-L1. In a more particular embodiment, the monoclonal antibody or antigen binding fragment thereof specifically binds human PD-L1. In another embodiment, the antibody is a monoclonal antibody that specifically binds soluble PD-L1. In one embodiment, the antibody is a monoclonal antibody that specifically binds soluble PD-L1 that is lacking one or more transmembrane domain or cytoplasmic domains. In one embodiment, the antibody is a monoclonal antibody that specifically binds soluble PD-L1 that is lacking both the transmembrane domain and the cytoplasmic domain. In one embodiment, the antibody is a monoclonal antibody that binds "free" PD-L1 (i.e., PD-L1 that is not associated with a cell membrane or surface, either directly or indirectly).

In an example the binding site(s) of the antibody or fragment are selected from a plurality (e.g., library) of binding sites. For example, the plurality of binding sites comprises or consists of a plurality of 4-chain antibodies or fragments thereof, e.g., dAbs, Fabs or scFvs. Suitable methods for producing pluralities of binding sites for screening include phage display (producing a phage display library of antibody binding sites), ribosome display (producing a ribosome display library of antibody binding sites), yeast display (producing a yeast display library of antibody binding sites), or immunisation of a non-human vertebrate (e.g., a rodent, e.g., a mouse or rat, e.g., a Velocimouse™, Kymouse™, Xenomouse™, Aliva Mouse™, HuMab Mouse™, Omnimouse™, Omnirat™ or MeMo Mouse™) with hPD-L1 or a hPD-L1 epitope and isolation of a repertoire of antibody-producing cells (e.g., a B-cell, plasma cell or plasmablast repertoire) and/or a repertoire of isolated antibodies, fragments or binding sites.

PD-L1 binding ability, specificity and affinity (Kd, Koff and/or Kon) can be determined by any routine method in the art, e.g., by surface plasmon resonance (SPR). The term "Kd" or "KD", as used herein, is intended to refer to the equilibrium dissociation constant of a particular antibody-antigen interaction. Such binding measurements can be made using a variety of binding assays known in the art, e.g., using surface plasmon resonance (SPR), such as by Biacore™ or using the ProteOn XPR36™ (Bio-Rad®), using KinExA® (Sapidyne Instruments, Inc), or using ForteBio Octet (Pall ForteBio Corp.).

In one embodiment, the surface plasmon resonance (SPR) is carried out at 25° C. In another embodiment, the SPR is carried out at 37° C.

In one embodiment, the SPR is carried out at physiological pH, such as about pH7 or at pH7.6 (e.g., using Hepes buffered saline at pH7.6 (also referred to as HBS-EP)).

In one embodiment, the SPR is carried out at a physiological salt level, e.g., 150 mM NaCl.

In one embodiment, the SPR is carried out at a detergent level of no greater than 0.05% by volume, e.g., in the presence of P20 (polysorbate 20; e.g., Tween-20™) at 0.05% and EDTA at 3 mM.

In one example, the SPR is carried out at 25° C. or 37° C. in a buffer at pH7.6, 150 mM NaCl, 0.05% detergent (e.g., P20) and 3 mM EDTA. The buffer can contain 10 mM Hepes. In one example, the SPR is carried out at 25° C. or 37° C. in HBS-EP. HBS-EP is available from Teknova Inc (California; catalogue number H8022).

In an example, the affinity of the antibody or fragment is determined using SPR by:
1. Coupling anti-mouse (or other relevant human, rat or non-human vertebrate antibody constant region species-matched) IgG (e.g., Biacore™ BR-1008-38) to a biosensor chip (e.g., GLM chip) such as by primary amine coupling;
2. Exposing the anti-mouse IgG (or other matched species antibody) to a test IgG antibody to capture test antibody on the chip;
3. Passing the test antigen over the chip's capture surface at 1024 nM, 256 nM, 64 nM, 16 nM, 4 nM with a 0 nM (i.e. buffer alone); and
4. And determining the affinity of binding of test antibody to test antigen using surface plasmon resonance, e.g., under an SPR condition discussed above (e.g., at 25° C. in physiological buffer). SPR can be carried out using any standard SPR apparatus, such as by Biacore™ or using the ProteOn XPR36 (Bio-Rad®).

Regeneration of the capture surface can be carried out with 10 mM glycine at pH1.7. This removes the captured antibody and allows the surface to be used for another interaction. The binding data can be fitted to 1:1 model inherent using standard techniques, e.g., using a model inherent to the ProteOn XPR36™ analysis software.

The present inventors have identified a number of antibodies having specificity for hPD-L1, which have a number of potential utilities and benefits over existing antibodies. For example, the antibodies described herein may have one or more of the following properties:
  a. Specificity for blocking only one of the ligands of PD-L1 (e.g. blocks CD80/PD-L1 interaction, but not PD-1/PD-L1 interaction)
  b. Immunogenicity/lack of side effects
  c. Solubility
  d. Stability
  e. Ease of formulation
  f. Frequency of dosing and/or route of administration
  g. Manufacturability (e.g. expression, ease of purification, isoforms)

1D05 has a heavy chain variable region ($V_H$) amino acid sequence of Seq ID No:33, comprising the CDRH1 amino acid sequence of Seq ID No:27 (IMGT) or Seq ID No:30 (Kabat), the CDRH2 amino acid sequence of Seq ID No:28 (IMGT) or Seq ID No:31 (Kabat), and the CDRH3 amino acid sequence of Seq ID No:29 (IMGT) or Seq ID No:32 (Kabat). The heavy chain nucleic acid sequence of the $V_H$ domain is Seq ID No:34. 1D05 has a light chain variable region ($V_L$) amino acid sequence of Seq ID No:43, comprising the CDRL1 amino acid sequence of Seq ID No:37 (IMGT) or Seq ID No:40 (Kabat), the CDRL2 amino acid sequence of Seq ID No:38 (IMGT) or Seq ID No:41 (Kabat), and the CDRL3 amino acid sequence of Seq ID No:39 (IMGT) or Seq ID No:42 (Kabat). The light chain nucleic acid sequence of the $V_L$ domain is Seq ID No:44. The $V_H$ domain may be combined with any of the heavy chain constant region sequences described herein, e.g. Seq ID No:193, Seq ID No:195, Seq ID No:197, Seq ID No:199, Seq ID No:201, Seq ID No:203, Seq ID No:205 or Seq ID No:340. The $V_L$ domain may be combined with any of the light chain constant region sequences described herein, e.g. Seq ID Nos:207, 209, 211, 213, 215, 217, 219, 221, 223, 225, 227, 229, 231, 233, 235 and 237. A full length heavy chain amino acid sequence is Seq ID No:35 (heavy chain nucleic acid sequence Seq ID No:36). A full length light chain amino acid sequence is Seq ID No:45 (light chain nucleic acid sequence Seq ID No:46).

84G09 has a heavy chain variable ($V_H$) region amino acid sequence of Seq ID No:13, comprising the CDRH1 amino acid sequence of Seq ID No:7 (IMGT) or Seq ID No:10 (Kabat), the CDRH2 amino acid sequence of Seq ID No:8 (IMGT) or Seq ID No:11 (Kabat), and the CDRH3 amino acid sequence of Seq ID No:9 (IMGT) or Seq ID No:12 (Kabat). The heavy chain nucleic acid sequence of the $V_H$ domain is Seq ID No:14. 84G09 has a light chain variable region ($V_L$) amino acid sequence of Seq ID No:23, comprising the CDRL1 amino acid sequence of Seq ID No:17 (IMGT) or Seq ID No:20 (Kabat), the CDRL2 amino acid sequence of Seq ID No:18 (IMGT) or Seq ID No:21 (Kabat), and the CDRL3 amino acid sequence of Seq ID No:19 (IMGT) or Seq ID No:22 (Kabat). The light chain nucleic acid sequence of the $V_L$ domain is Seq ID No:24. The $V_H$ domain may be combined with any of the heavy chain constant region sequences described herein, e.g. Seq ID No:193, Seq ID No:195, Seq ID No:197, Seq ID No:199, Seq ID No:201, Seq ID No:203, Seq ID No:205 or Seq ID No:340. The $V_L$ domain may be combined with any of the light chain constant region sequences described herein, e.g. Seq ID Nos:207, 209, 211, 213, 215, 217, 219, 221, 223, 225, 227, 229, 231, 233, 235 and 237. A full length heavy chain amino acid sequence is Seq ID No:15 (heavy chain nucleic acid sequence Seq ID No:16). A full length light chain amino acid sequence is Seq ID No:25 (light chain nucleic acid sequence Seq ID No:26).

1D05 HC mutant 1 has a heavy chain variable (VH) region amino acid sequence of Seq ID No:47, comprising the CDRH1 amino acid sequence of Seq ID No:27 (IMGT) or Seq ID No:30 (Kabat), the CDRH2 amino acid sequence of Seq ID No:28 (IMGT) or Seq ID No:31 (Kabat), and the CDRH3 amino acid sequence of Seq ID No:29 (IMGT) or Seq ID No:32 (Kabat). 1D05 HC mutant 1 has a light chain variable region (VL) amino acid sequence of Seq ID No:43, comprising the CDRL1 amino acid sequence of Seq ID No:37 (IMGT) or Seq ID No:40 (Kabat), the CDRL2 amino acid sequence of Seq ID No:38 (IMGT) or Seq ID No:41 (Kabat), and the CDRL3 amino acid sequence of Seq ID No:39 (IMGT) or Seq ID No:42 (Kabat). The light chain nucleic acid sequence of the VL domain is Seq ID No:44. The VH domain may be combined with any of the heavy chain constant region sequences described herein, e.g. Seq ID No:193, Seq ID No:195, Seq ID No:197, Seq ID No:199, Seq ID No:201, Seq ID No:203, Seq ID No:205 or Seq ID No:340. The VL domain may be combined with any of the light chain constant region sequences described herein, e.g. Seq ID Nos:207, 209, 211, 213, 215, 217, 219, 221, 223, 225, 227, 229, 231, 233, 235 and 237. A full length light chain amino acid sequence is Seq ID No:45 (light chain nucleic acid sequence Seq ID No:46).

1D05 HC mutant 2 has a heavy chain variable (VH) region amino acid sequence of Seq ID No:48, comprising the CDRH1 amino acid sequence of Seq ID No:27 (IMGT) or Seq ID No:30 (Kabat), the CDRH2 amino acid sequence of Seq ID No:28 (IMGT) or Seq ID No:31 (Kabat), and the CDRH3 amino acid sequence of Seq ID No:29 (IMGT) or Seq ID No:32 (Kabat). 1D05 HC mutant 2 has a light chain variable region (VL) amino acid sequence of Seq ID No:43, comprising the CDRL1 amino acid sequence of Seq ID No:37 (IMGT) or Seq ID No:40 (Kabat), the CDRL2 amino acid sequence of Seq ID No:38 (IMGT) or Seq ID No:41 (Kabat), and the CDRL3 amino acid sequence of Seq ID No:39 (IMGT) or Seq ID No:42 (Kabat). The light chain nucleic acid sequence of the VL domain is Seq ID No:44. The VH domain may be combined with any of the heavy chain constant region sequences described herein, e.g. Seq ID No:193, Seq ID No:195, Seq ID No:197, Seq ID No:199, Seq ID No:201, Seq ID No:203, Seq ID No:205 or Seq ID No:340. The VL domain may be combined with any of the light chain constant region sequences described herein, e.g. Seq ID Nos:207, 209, 211, 213, 215, 217, 219, 221, 223, 225, 227, 229, 231, 233, 235 and 237. A full length light chain amino acid sequence is Seq ID No:45 (light chain nucleic acid sequence Seq ID No:46).

1D05 HC mutant 3 has a heavy chain variable (VH) region amino acid sequence of Seq ID No:49, comprising the CDRH1 amino acid sequence of Seq ID No:27 (IMGT) or Seq ID No:30 (Kabat), the CDRH2 amino acid sequence of Seq ID No:28 (IMGT) or Seq ID No:31 (Kabat), and the CDRH3 amino acid sequence of Seq ID No:29 (IMGT) or Seq ID No:32 (Kabat). 1D05 HC mutant 3 has a light chain variable region (VL) amino acid sequence of Seq ID No:43, comprising the CDRL1 amino acid sequence of Seq ID No:37 (IMGT) or Seq ID No:40 (Kabat), the CDRL2 amino acid sequence of Seq ID No:38 (IMGT) or Seq ID No:41 (Kabat), and the CDRL3 amino acid sequence of Seq ID No:39 (IMGT) or Seq ID No:42 (Kabat). The light chain nucleic acid sequence of the VL domain is Seq ID No:44. The VH domain may be combined with any of the heavy chain constant region sequences described herein, e.g. Seq ID No:193, Seq ID No:195, Seq ID No:197, Seq ID No:199, Seq ID No:201, Seq ID No:203, Seq ID No:205 or Seq ID No:340. The VL domain may be combined with any of the light chain constant region sequences described herein, e.g. Seq ID Nos:207, 209, 211, 213, 215, 217, 219, 221, 223, 225, 227, 229, 231, 233, 235 and 237. A full length light chain amino acid sequence is Seq ID No:45 (light chain nucleic acid sequence Seq ID No:46).

1D05 HC mutant 4 has a heavy chain variable (VH) region amino acid sequence of Seq ID No:342, comprising the CDRH1 amino acid sequence of Seq ID No:27 (IMGT) or Seq ID No:30 (Kabat), the CDRH2 amino acid sequence of Seq ID No:28 (IMGT) or Seq ID No:31 (Kabat), and the CDRH3 amino acid sequence of Seq ID No:29 (IMGT) or Seq ID No:32 (Kabat). 1D05 HC mutant 4 has a light chain variable region (VL) amino acid sequence of Seq ID No:43, comprising the CDRL1 amino acid sequence of Seq ID No:37 (IMGT) or Seq ID No:40 (Kabat), the CDRL2 amino acid sequence of Seq ID No:38 (IMGT) or Seq ID No:41 (Kabat), and the CDRL3 amino acid sequence of Seq ID No:39 (IMGT) or Seq ID No:42 (Kabat). The light chain nucleic acid sequence of the VL domain is Seq ID No:44. The VH domain may be combined with any of the heavy chain constant region sequences described herein, e.g. Seq ID No:193, Seq ID No:195, Seq ID No:197, Seq ID No:199, Seq ID No:201, Seq ID No:203, Seq ID No:205 or Seq ID No:340. The VL domain may be combined with any of the light chain constant region sequences described herein, e.g. Seq ID Nos:207, 209, 211, 213, 215, 217, 219, 221, 223, 225, 227, 229, 231, 233, 235 and 237. A full length light chain amino acid sequence is Seq ID No:45 (light chain nucleic acid sequence Seq ID No:46).

1D05 LC mutant 1 has a heavy chain variable (VH) region amino acid sequence of Seq ID No:33, comprising the CDRH1 amino acid sequence of Seq ID No:27 (IMGT) or Seq ID No:30 (Kabat), the CDRH2 amino acid sequence of Seq ID No:28 (IMGT) or Seq ID No:31 (Kabat), and the CDRH3 amino acid sequence of Seq ID No:29 (IMGT) or Seq ID No:32 (Kabat). The heavy chain nucleic acid sequence of the VH domain is Seq ID No:34. 1D05 LC mutant 1 has a light chain variable region (VL) amino acid sequence of Seq ID No:50, comprising the CDRL1 amino acid sequence of Seq ID No:37 (IMGT) or Seq ID No:40 (Kabat), and CDRL3 amino acid sequence of Seq ID No:39 (IMGT) or Seq ID No:42 (Kabat). The CDRL2 sequence of 1D05 LC Mutant 1 is as defined by the Kabat or IMGT systems from the VL sequence of Seq ID No:50. The VH domain may be combined with any of the heavy chain constant region sequences described herein, e.g. Seq ID No:193, Seq ID No:195, Seq ID No:197, Seq ID No:199, Seq ID No:201, Seq ID No:203, Seq ID No:205 or Seq ID No:340. The VL domain may be combined with any of the light chain constant region sequences described herein, e.g. Seq ID Nos:207, 209, 211, 213, 215, 217, 219, 221, 223, 225, 227, 229, 231, 233, 235 and 237. A full length heavy chain amino acid sequence is Seq ID No:35 (heavy chain nucleic acid sequence Seq ID No:36).

1D05 LC mutant 2 has a heavy chain variable (VH) region amino acid sequence of Seq ID No:33, comprising the CDRH1 amino acid sequence of Seq ID No:27 (IMGT) or Seq ID No:30 (Kabat), the CDRH2 amino acid sequence of Seq ID No:28 (IMGT) or Seq ID No:31 (Kabat), and the CDRH3 amino acid sequence of Seq ID No:29 (IMGT) or Seq ID No:32 (Kabat). The heavy chain nucleic acid sequence of the VH domain is Seq ID No:34. 1D05 LC mutant 2 has a light chain variable region (VL) amino acid sequence of Seq ID No:51, comprising the CDRL1 amino acid sequence of Seq ID No:37 (IMGT) or Seq ID No:40 (Kabat), the CDRL2 amino acid sequence of Seq ID No:38 (IMGT) or Seq ID No:41 (Kabat), and the CDRL3 amino acid sequence of Seq ID No:39 (IMGT) or Seq ID No:42 (Kabat). The VH domain may be combined with any of the heavy chain constant region sequences described herein, e.g. Seq ID No:193, Seq ID No:195, Seq ID No:197, Seq ID No:199, Seq ID No:201, Seq ID No:203, Seq ID No:205 or Seq ID No:340. The VL domain may be combined with any of the light chain constant region sequences described herein, e.g. Seq ID Nos:207, 209, 211, 213, 215, 217, 219, 221, 223, 225, 227, 229, 231, 233, 235 and 237. A full length heavy chain amino acid sequence is Seq ID No:35 (heavy chain nucleic acid sequence Seq ID No:36).

1D05 LC mutant 3 has a heavy chain variable (VH) region amino acid sequence of Seq ID No:33, comprising the CDRH1 amino acid sequence of Seq ID No:27 (IMGT) or Seq ID No:30 (Kabat), the CDRH2 amino acid sequence of Seq ID No:28 (IMGT) or Seq ID No:31 (Kabat), and the CDRH3 amino acid sequence of Seq ID No:29 (IMGT) or Seq ID No:32 (Kabat). The heavy chain nucleic acid sequence of the VH domain is Seq ID No:34. 1D05 LC mutant 3 has a light chain variable region (VL) amino acid sequence of Seq ID No:298, comprising the CDRL1 amino acid sequence of Seq ID No:37 (IMGT) or Seq ID No:40 (Kabat), and the CDRL3 amino acid sequence of Seq ID No:39 (IMGT) or Seq ID No:42 (Kabat). The CDRL2 sequence of 1D05 LC Mutant 3 is as defined by the Kabat or IMGT systems from the VL sequence of Seq ID No:298. The light chain nucleic acid sequence of the VL domain is Seq ID No:44. The VH domain may be combined with any of the heavy chain constant region sequences described herein, e.g. Seq ID No:193, Seq ID No:195, Seq ID No:197, Seq ID No:199, Seq ID No:201, Seq ID No:203, Seq ID No:205 or Seq ID No:340. The VL domain may be combined with any of the light chain constant region sequences described herein, e.g. Seq ID Nos:207, 209, 211, 213, 215, 217, 219, 221, 223, 225, 227, 229, 231, 233, 235 and 237. A full length heavy chain amino acid sequence is Seq ID No:35 (heavy chain nucleic acid sequence Seq ID No:36). A full length light chain amino acid sequence is Seq ID No:45 (light chain nucleic acid sequence Seq ID No:46).

411B08 has a heavy chain variable (VH) region amino acid sequence of Seq ID No:58, comprising the CDRH1 amino acid sequence of Seq ID No:52 (IMGT) or Seq ID No:55 (Kabat), the CDRH2 amino acid sequence of Seq ID No:53 (IMGT) or Seq ID No:56 (Kabat), and the CDRH3 amino acid sequence of Seq ID No:54 (IMGT) or Seq ID No:57 (Kabat). The heavy chain nucleic acid sequence of the VH domain is Seq ID No:59. 411B08 has a light chain variable region (VL) amino acid sequence of Seq ID No:68, comprising the CDRL1 amino acid sequence of Seq ID No:62 (IMGT) or Seq ID No:65 (Kabat), the CDRL2 amino acid sequence of Seq ID No:63 (IMGT) or Seq ID No:66 (Kabat), and the CDRL3 amino acid sequence of Seq ID No:64 (IMGT) or Seq ID No:67 (Kabat). The light chain nucleic acid sequence of the VL domain is Seq ID No:69. The VH domain may be combined with any of the heavy chain constant region sequences described herein, e.g. Seq ID No:193, Seq ID No:195, Seq ID No:197, Seq ID No:199, Seq ID No:201, Seq ID No:203, Seq ID No:205 or Seq ID No:340. The VL domain may be combined with any of the light chain constant region sequences described herein, e.g. Seq ID Nos:207, 209, 211, 213, 215, 217, 219, 221, 223, 225, 227, 229, 231, 233, 235 and 237. A full length heavy chain amino acid sequence is Seq ID No:60 (heavy chain nucleic acid sequence Seq ID No:61). A full length light chain amino acid sequence is Seq ID No:70 (light chain nucleic acid sequence Seq ID No:71).

411C04 has a heavy chain variable (VH) region amino acid sequence of Seq ID No:78, comprising the CDRH1 amino acid sequence of Seq ID No:72 (IMGT) or Seq ID No:75 (Kabat), the CDRH2 amino acid sequence of Seq ID No:73 (IMGT) or Seq ID No:76 (Kabat), and the CDRH3 amino acid sequence of Seq ID No:74 (IMGT) or Seq ID No:77 (Kabat). The heavy chain nucleic acid sequence of the VH domain is Seq ID No:79. 411C04 has a light chain variable region (VL) amino acid sequence of Seq ID No:88, comprising the CDRL1 amino acid sequence of Seq ID No:82 (IMGT) or Seq ID No:85 (Kabat), the CDRL2 amino acid sequence of Seq ID No:83 (IMGT) or Seq ID No:86 (Kabat), and the CDRL3 amino acid sequence of Seq ID No:84 (IMGT) or Seq ID No:87 (Kabat). The light chain nucleic acid sequence of the VL domain is Seq ID No:89. The VH domain may be combined with any of the heavy chain constant region sequences described herein, e.g. Seq ID No:193, Seq ID No:195, Seq ID No:197, Seq ID No:199, Seq ID No:201, Seq ID No:203, Seq ID No:205 or Seq ID No:340. The VL domain may be combined with any of the light chain constant region sequences described herein, e.g. Seq ID Nos:207, 209, 211, 213, 215, 217, 219, 221, 223, 225, 227, 229, 231, 233, 235 and 237. A full length heavy chain amino acid sequence is Seq ID No:80 (heavy chain nucleic acid sequence Seq ID No:81). A full length light chain amino acid sequence is Seq ID No:90 (light chain nucleic acid sequence Seq ID No:91).

411D07 has a heavy chain variable (VH) region amino acid sequence of Seq ID No:98, comprising the CDRH1 amino acid sequence of Seq ID No:92 (IMGT) or Seq ID No:95 (Kabat), the CDRH2 amino acid sequence of Seq ID No:93 (IMGT) or Seq ID No:96 (Kabat), and the CDRH3 amino acid sequence of Seq ID No:94 (IMGT) or Seq ID No:97 (Kabat). The heavy chain nucleic acid sequence of the VH domain is Seq ID No:99. 411D07 has a light chain variable region (VL) amino acid sequence of Seq ID No:108, comprising the CDRL1 amino acid sequence of Seq ID No:102 (IMGT) or Seq ID No:105 (Kabat), the CDRL2 amino acid sequence of Seq ID No:103 (IMGT) or Seq ID No:106 (Kabat), and the CDRL3 amino acid sequence of Seq ID No:104 (IMGT) or Seq ID No:107 (Kabat). The light chain nucleic acid sequence of the VL domain is Seq ID No:109. The VH domain may be combined with any of the heavy chain constant region sequences described herein, e.g. Seq ID No:193, Seq ID No:195, Seq ID No:197, Seq ID No:199, Seq ID No:201, Seq ID No:203, Seq ID No:205 or Seq ID No:340. The VL domain may be combined with any of the light chain constant region sequences described herein, e.g. Seq ID Nos:207, 209, 211, 213, 215, 217, 219, 221, 223, 225, 227, 229, 231, 233, 235 and 237. A full length heavy chain amino acid sequence is Seq ID No:100 (heavy chain nucleic acid sequence Seq ID No:101). A full length light chain amino acid sequence is Seq ID No: 110 (light chain nucleic acid sequence Seq ID No:111).

385F01 has a heavy chain variable (VH) region amino acid sequence of Seq ID No:118, comprising the CDRH1 amino acid sequence of Seq ID No:112 (IMGT) or Seq ID No:115 (Kabat), the CDRH2 amino acid sequence of Seq ID No:113 (IMGT) or Seq ID No:116 (Kabat), and the CDRH3 amino acid sequence of Seq ID No:114 (IMGT) or Seq ID No:117 (Kabat). The heavy chain nucleic acid sequence of the VH domain is Seq ID No:119. 385F01 has a light chain variable region (VL) amino acid sequence of Seq ID No:128, comprising the CDRL1 amino acid sequence of Seq ID No:122 (IMGT) or Seq ID No:125 (Kabat), the CDRL2 amino acid sequence of Seq ID No:123 (IMGT) or Seq ID No:126 (Kabat), and the CDRL3 amino acid sequence of Seq ID No:124 (IMGT) or Seq ID No:127 (Kabat). The light chain nucleic acid sequence of the VL domain is Seq ID No:129. The VH domain may be combined with any of the heavy chain constant region sequences described herein, e.g. Seq ID No:193, Seq ID No:195, Seq ID No:197, Seq ID No:199, Seq ID No:201, Seq ID No:203, Seq ID No:205 or Seq ID No:340. The VL domain may be combined with any of the light chain constant region sequences described herein, e.g. Seq ID Nos:207, 209, 211, 213, 215, 217, 219, 221, 223, 225, 227, 229, 231, 233, 235 and 237. A full length heavy chain amino acid sequence is Seq ID No:120 (heavy chain nucleic acid sequence Seq ID No:121). A full length light chain amino acid sequence is Seq ID No:130 (light chain nucleic acid sequence Seq ID No:131).

386H03 has a heavy chain variable (VH) region amino acid sequence of Seq ID No:158, comprising the CDRH1 amino acid sequence of Seq ID No:152 (IMGT) or Seq ID No:155 (Kabat), the CDRH2 amino acid sequence of Seq ID No:153 (IMGT) or Seq ID No:156 (Kabat), and the CDRH3 amino acid sequence of Seq ID No:154 (IMGT) or Seq ID No:157 (Kabat). The heavy chain nucleic acid sequence of the VH domain is Seq ID No:159. 386H03 has a light chain variable region (VL) amino acid sequence of Seq ID No:168, comprising the CDRL1 amino acid sequence of Seq ID No:162 (IMGT) or Seq ID No:165 (Kabat), the CDRL2 amino acid sequence of Seq ID No:163 (IMGT) or Seq ID No:166 (Kabat), and the CDRL3 amino acid sequence of Seq ID No:164 (IMGT) or Seq ID No:167 (Kabat). The light chain nucleic acid sequence of the VL domain is Seq ID No:169. The VH domain may be combined with any of the heavy chain constant region sequences described herein, e.g. Seq ID No:193, Seq ID No:195, Seq ID No:197, Seq ID No:199, Seq ID No:201, Seq ID No:203, Seq ID No:205 or Seq ID No:340. The VL domain may be combined with any of the light chain constant region sequences described herein, e.g. Seq ID Nos:207, 209, 211, 213, 215, 217, 219, 221, 223, 225, 227, 229, 231, 233, 235 and 237. A full length heavy chain amino acid sequence is Seq ID No:160 (heavy chain nucleic acid sequence Seq ID No:161). A full length light chain amino acid sequence is Seq ID No:170 (light chain nucleic acid sequence Seq ID No:171).

389A03 has a heavy chain variable (VH) region amino acid sequence of Seq ID No:178, comprising the CDRH1 amino acid sequence of Seq ID No:172 (IMGT) or Seq ID No:175 (Kabat), the CDRH2 amino acid sequence of Seq ID No:173 (IMGT) or Seq ID No:176 (Kabat), and the CDRH3 amino acid sequence of Seq ID No:174 (IMGT) or Seq ID No:177 (Kabat). The heavy chain nucleic acid sequence of the VH domain is Seq ID No:179. 389A03 has a light chain variable region (VL) amino acid sequence of Seq ID No:188, comprising the CDRL1 amino acid sequence of Seq ID No:182 (IMGT) or Seq ID No:185 (Kabat), the CDRL2 amino acid sequence of Seq ID No:183 (IMGT) or Seq ID No:186 (Kabat), and the CDRL3 amino acid sequence of Seq ID No:184 (IMGT) or Seq ID No:187 (Kabat). The light chain nucleic acid sequence of the VL domain is Seq ID No:189. The VH domain may be combined with any of the heavy chain constant region sequences described herein, e.g.

Seq ID No:193, Seq ID No:195, Seq ID No:197, Seq ID No:199, Seq ID No:201, Seq ID No:203, Seq ID No:205 or Seq ID No:340. The VL domain may be combined with any of the light chain constant region sequences described herein, e.g. Seq ID Nos:207, 209, 211, 213, 215, 217, 219, 221, 223, 225, 227, 229, 231, 233, 235 and 237. A full length heavy chain amino acid sequence is Seq ID No:180 (heavy chain nucleic acid sequence Seq ID No:181). A full length light chain amino acid sequence is Seq ID No:190 (light chain nucleic acid sequence Seq ID No:191).

413D08 has a heavy chain variable (VH) region amino acid sequence of Seq ID No:138, comprising the CDRH1 amino acid sequence of Seq ID No:132 (IMGT) or Seq ID No:135 (Kabat), the CDRH2 amino acid sequence of Seq ID No:133 (IMGT) or Seq ID No:136 (Kabat), and the CDRH3 amino acid sequence of Seq ID No:134 (IMGT) or Seq ID No:137 (Kabat). The heavy chain nucleic acid sequence of the VH domain is Seq ID No:139. 413D08 has a light chain variable region (VL) amino acid sequence of Seq ID No:148, comprising the CDRL1 amino acid sequence of Seq ID No:142 (IMGT) or Seq ID No:145 (Kabat), the CDRL2 amino acid sequence of Seq ID No:143 (IMGT) or Seq ID No:146 (Kabat), and the CDRL3 amino acid sequence of Seq ID No:144 (IMGT) or Seq ID No:147 (Kabat). The light chain nucleic acid sequence of the VL domain is Seq ID No:149. The VH domain may be combined with any of the heavy chain constant region sequences described herein, e.g. Seq ID No:193, Seq ID No:195, Seq ID No:197, Seq ID No:199, Seq ID No:201, Seq ID No:203, Seq ID No:205 or Seq ID No:340. The VL domain may be combined with any of the light chain constant region sequences described herein, e.g. Seq ID Nos:207, 209, 211, 213, 215, 217, 219, 221, 223, 225, 227, 229, 231, 233, 235 and 237. A full length heavy chain amino acid sequence is Seq ID No: 140 (heavy chain nucleic acid sequence Seq ID No:141). A full length light chain amino acid sequence is Seq ID No:150 (light chain nucleic acid sequence Seq ID No:151).

413G05 has a heavy chain variable (VH) region amino acid sequence of Seq ID No:244, comprising the CDRH1 amino acid sequence of Seq ID No:238 (IMGT) or Seq ID No:241 (Kabat), the CDRH2 amino acid sequence of Seq ID No:239 (IMGT) or Seq ID No:242 (Kabat), and the CDRH3 amino acid sequence of Seq ID No:240 (IMGT) or Seq ID No:243 (Kabat). The heavy chain nucleic acid sequence of the VH domain is Seq ID No:245. 413G05 has a light chain variable region (VL) amino acid sequence of Seq ID No:254, comprising the CDRL1 amino acid sequence of Seq ID No:248 (IMGT) or Seq ID No:251 (Kabat), the CDRL2 amino acid sequence of Seq ID No:249 (IMGT) or Seq ID No:252 (Kabat), and the CDRL3 amino acid sequence of Seq ID No:250 (IMGT) or Seq ID No:253 (Kabat). The light chain nucleic acid sequence of the VL domain is Seq ID No:255. The VH domain may be combined with any of the heavy chain constant region sequences described herein, e.g. Seq ID No:193, Seq ID No:195, Seq ID No:197, Seq ID No:199, Seq ID No:201, Seq ID No:203, Seq ID No:205 or Seq ID No:340. The VL domain may be combined with any of the light chain constant region sequences described herein, e.g. Seq ID Nos:207, 209, 211, 213, 215, 217, 219, 221, 223, 225, 227, 229, 231, 233, 235 and 237. A full length heavy chain amino acid sequence is Seq ID No:246 (heavy chain nucleic acid sequence Seq ID No:247). A full length light chain amino acid sequence is Seq ID No:256 (light chain nucleic acid sequence Seq ID No:257).

413F09 has a heavy chain variable (VH) region amino acid sequence of Seq ID No:264, comprising the CDRH1 amino acid sequence of Seq ID No:258 (IMGT) or Seq ID No:261 (Kabat), the CDRH2 amino acid sequence of Seq ID No:259 (IMGT) or Seq ID No:262 (Kabat), and the CDRH3 amino acid sequence of Seq ID No:260 (IMGT) or Seq ID No:263 (Kabat). The heavy chain nucleic acid sequence of the VH domain is Seq ID No:265. 413F09 has a light chain variable region (VL) amino acid sequence of Seq ID No:274, comprising the CDRL1 amino acid sequence of Seq ID No:268 (IMGT) or Seq ID No:271 (Kabat), the CDRL2 amino acid sequence of Seq ID No:269 (IMGT) or Seq ID No:272 (Kabat), and the CDRL3 amino acid sequence of Seq ID No:270 (IMGT) or Seq ID No:273 (Kabat). The light chain nucleic acid sequence of the VL domain is Seq ID No:275. The VH domain may be combined with any of the heavy chain constant region sequences described herein, e.g. Seq ID No:193, Seq ID No:195, Seq ID No:197, Seq ID No:199, Seq ID No:201, Seq ID No:203, Seq ID No:205 or Seq ID No:340. The VL domain may be combined with any of the light chain constant region sequences described herein, e.g. Seq ID Nos:207, 209, 211, 213, 215, 217, 219, 221, 223, 225, 227, 229, 231, 233, 235 and 237. A full length heavy chain amino acid sequence is Seq ID No:266 (heavy chain nucleic acid sequence Seq ID No:267). A full length light chain amino acid sequence is Seq ID No:276 (light chain nucleic acid sequence Seq ID No:277).

414B06 has a heavy chain variable (VH) region amino acid sequence of Seq ID No:284, comprising the CDRH1 amino acid sequence of Seq ID No:278 (IMGT) or Seq ID No:281 (Kabat), the CDRH2 amino acid sequence of Seq ID No:279 (IMGT) or Seq ID No:282 (Kabat), and the CDRH3 amino acid sequence of Seq ID No:280 (IMGT) or Seq ID No:283 (Kabat). The heavy chain nucleic acid sequence of the VH domain is Seq ID No:285. 414B06 has a light chain variable region (VL) amino acid sequence of Seq ID No:294, comprising the CDRL1 amino acid sequence of Seq ID No:288 (IMGT) or Seq ID No:291(Kabat), the CDRL2 amino acid sequence of Seq ID No:289 (IMGT) or Seq ID No:292 (Kabat), and the CDRL3 amino acid sequence of Seq ID No:290 (IMGT) or Seq ID No:293 (Kabat). The light chain nucleic acid sequence of the VL domain is Seq ID No:295. The VH domain may be combined with any of the heavy chain constant region sequences described herein, e.g. Seq ID No:193, Seq ID No:195, Seq ID No:197, Seq ID No:199, Seq ID No:201, Seq ID No:203, Seq ID No:205 or Seq ID No:340. The VL domain may be combined with any of the light chain constant region sequences described herein, e.g. Seq ID Nos:207, 209, 211, 213, 215, 217, 219, 221, 223, 225, 227, 229, 231, 233, 235 and 237. A full length heavy chain amino acid sequence is Seq ID No:286 (heavy chain nucleic acid sequence Seq ID No:287). A full length light chain amino acid sequence is Seq ID No:296 (light chain nucleic acid sequence Seq ID No:297).

The antibodies of the invention are described with respect to the following concepts, aspects and embodiments. Unless otherwise stated, all concepts, embodiments and aspects are to be read as being able to be combined with any other concept, aspect or embodiment, unless such combination would not make technical sense or is explicitly stated otherwise.

Concept 1. An antibody or a fragment thereof, which specifically binds to hPD-L1 as defined by Seq ID No:1, and competes for binding to said hPD-L1 with the antibody 1D05, wherein the antibody or fragment comprises a $V_H$ domain which comprises a CDRH3 comprising the motif $X_1GSGX_2YGX_3X_4FD$, wherein $X_1$, $X_2$ and $X_3$ are independently any amino acid, and $X_4$ is either present or absent, and if present, may be any amino acid.

In these concepts, antibodies or fragments may include or may not include bispecific antibodies. In one embodiment, in these concepts, antibodies or fragments includes bispecific antibodies. In one embodiment, a bispecific antibody does not include a FIT-Ig format. In one embodiment, a bispecific antibody does not include a mAb2 format. In one embodiment, a bispecific antibody does not include either a FIT-Ig format or a mAb2 format. In one embodiment, the antibody or fragment in these concepts includes a bispecific antibody, but does not include a bispecific antibody having a FIT-Ig format. In one embodiment, the antibody or fragment in these concepts includes a bispecific antibody, but does not include a bispecific antibody having a mAb2 format. In one embodiment, the antibody or fragment in these concepts includes a bispecific antibody, but does not include a bispecific antibody having a FIT-Ig format or a mAb2 format. In another embodiment, in these concepts, antibodies or fragments include dual binding antibodies.

Preferably, an antibody or a fragment thereof that specifically binds to a hPD-L1 antigen does not cross-react with other antigens (but may optionally cross-react with PD-L1 of a different species, e.g., rhesus, cynomolgus, or murine). An antibody or a fragment thereof that specifically binds to a hPD-L1 antigen can be identified, for example, by immunoassays, BIAcore™, or other techniques known to those of skill in the art. An antibody or a fragment thereof binds specifically to a hPD-L1 antigen when it binds to a hPD-L1 antigen with higher affinity than to any cross-reactive antigen as determined using experimental techniques, such as radioimmunoassays (RIA) and enzyme-linked immunosorbent assays (ELISAs). Typically, a specific or selective reaction will be at least twice background signal or noise and more typically more than 10 times background. See, e.g., Paul, ed., 1989, Fundamental Immunology Second Edition, Raven Press, New York at pages 332-336 for a discussion regarding antibody specificity.

In one embodiment, the antibody or fragment is a human antibody. In one embodiment, the antibody or fragment is a human antibody or fragment. In one embodiment, the antibody or fragment is a fully human antibody or fragment. In one embodiment, the antibody or fragment is a fully human monoclonal antibody or fragment.

There is also provided concept 1a: An antibody or a fragment thereof, that specifically binds to hPD-L1 as defined by Seq ID No:1, and competes for binding to said hPD-L1 with the antibody 411B08, wherein the antibody or fragment comprises a VH domain which comprises a CDRH3 comprising the motif ARX1RX2X3SDX4X5D, wherein X1, X2, X3, X4 and X5 are independently any amino acid.

There is also provided concept 1b: An antibody or a fragment thereof, that specifically binds to hPD-L1 as defined by Seq ID No:1, and competes for binding to said hPD-L1 with the antibody 411B08, wherein the antibody or fragment comprises a VH domain which comprises a CDRH3 comprising the motif X1RDGSGSY, wherein X1 is any amino acid.

Concept 2. The antibody or fragment according to concept 1, wherein X1 is a hydroxyl-containing amino acid, optionally T.

In one embodiment, the hydroxyl-containing amino acid is Serine. In one embodiment, the hydroxyl-containing amino acid is Cysteine. In one embodiment, the hydroxyl-containing amino acid is Threonine. In one embodiment, the hydroxyl-containing amino acid is Methionine. In one embodiment, the hydroxyl-containing amino acid is Serine or Cysteine. In one embodiment, the hydroxyl-containing amino acid is Serine or Threonine. In one embodiment, the hydroxyl-containing amino acid is Serine or Methionine. In one embodiment, the hydroxyl-containing amino acid is Cysteine or Threonine. In one embodiment, the hydroxyl-containing amino acid is Cysteine or Methionine. In one embodiment, the hydroxyl-containing amino acid is Threonine or Methionine.

In one embodiment, the hydroxyl-containing amino acid is selected from serine, cysteine, threonine and methionine.

Concept 2a. The antibody or fragment according to concept 1a, wherein X1 is an aliphatic amino acid or an amide amino acid.

In one embodiment, X1 is selected from Asparagine (N) and valine (V). In one embodiment, X1 is valine. In one embodiment, X1 is asparagine.

Concept 2b. The antibody or fragment according to concept 1b, wherein X1 is an aliphatic amino acid.

In one embodiment, X1 is selected from alanine (A) or valine (V). In one embodiment, X1 is valine. In one embodiment, X1 is alanine.

Concept 3. The antibody or fragment according to concept 1 or concept 2, wherein X2 is a basic amino acid, optionally K.

In one embodiment, the hydroxyl-containing amino acid is Histidine. In one embodiment, the hydroxyl-containing amino acid is Lysine. In one embodiment, the hydroxyl-containing amino acid is Arginine. In one embodiment, the hydroxyl-containing amino acid is Histidine or Lysine. In one embodiment, the hydroxyl-containing amino acid is Histidine or Arginine. In one embodiment, the hydroxyl-containing amino acid is Lysine or Arginine.

In one embodiment, the hydroxyl-containing amino acid is selected from Histidine, Lysine and Arginine.

Concept 3a. The antibody or fragment according to concept 1a or concept 2a, wherein X2 is an aliphatic amino acid or an amide amino acid.

In one embodiment, X2 is selected from leucine (L), isoleucine (I), Valine (V), Asparagine (N) and glutamine (Q). In one embodiment, X2 is selected from leucine (L), isoleucine (I) and Valine (V). In one embodiment, X2 is selected from Asparagine (N) and glutamine (Q) In one embodiment, X2 is selected from leucine (L) and glutamine (Q). In one embodiment, X2 is leucine (L). In one embodiment, X2 is glutamine (Q).

Concept 4. The antibody or fragment according to any one of concepts 1 to 3, wherein X2 is a hydroxyl-containing amino acid, optionally S or T.

In one embodiment, the hydroxyl-containing amino acid is Serine. In one embodiment, the hydroxyl-containing amino acid is Cysteine. In one embodiment, the hydroxyl-containing amino acid is Threonine. In one embodiment, the hydroxyl-containing amino acid is Methionine. In one embodiment, the hydroxyl-containing amino acid is Serine or Cysteine. In one embodiment, the hydroxyl-containing amino acid is Serine or Threonine. In one embodiment, the hydroxyl-containing amino acid is Serine or Methionine. In one embodiment, the hydroxyl-containing amino acid is Cysteine or Threonine. In one embodiment, the hydroxyl-containing amino acid is Cysteine or Methionine. In one embodiment, the hydroxyl-containing amino acid is Threonine or Methionine.

In one embodiment, the hydroxyl-containing amino acid is selected from serine, cysteine, threonine and methionine.

Concept 4a. The antibody or fragment according to any one of concepts 1a, 2a or 3a, wherein X3 is an aromatic amino acid.

In one embodiment, $X_3$ is selected from Phenylalanine (F), Tyrosine (Y) and Tryptophan (W). In one embodiment, $X_3$ is selected from Tyrosine (Y) and Tryptophan (W). In one embodiment, $X_3$ is Tyrosine (Y). In one embodiment, $X_3$ is Tryptophan (W).

Concept 5. The antibody or fragment according to any one of concepts 1 to 4, wherein $X_3$ is an aromatic amino acid, optionally W.

In one embodiment, the hydroxyl-containing amino acid is Phenylalanine. In one embodiment, the hydroxyl-containing amino acid is Tyrosine. In one embodiment, the hydroxyl-containing amino acid is Tryptophan. In one embodiment, the hydroxyl-containing amino acid is Phenylalanine or Tyrosine. In one embodiment, the hydroxyl-containing amino acid is Phenylalanine or Tryptophan. In one embodiment, the hydroxyl-containing amino acid is Tyrosine or Tryptophan.

In one embodiment, the hydroxyl-containing amino acid is selected from Phenylalanine, Tyrosine and Tryptophan.

Concept 5a. The antibody or fragment according to any one of concepts 1a, 2a, 3a or 4a wherein X4 is an aromatic amino acid.

In one embodiment, X4 is selected from Phenylalanine (F), Tyrosine (Y) and Tryptophan (W). In one embodiment, X4 is selected from Tyrosine (Y) and Phenylalanine (F). In one embodiment, X4 is Tyrosine (Y). In one embodiment, X4 is Phenylalanine (F).

Concept 6. The antibody or fragment according to any one of concepts 1 to 5, wherein X4 is absent.

Concept 6a. The antibody or fragment according to any one of concepts 1a, 2a, 3a, 4a or 5a wherein X5 is an aliphatic amino acid or an hydroxyl-containing amino acid.

In one embodiment, X5 is selected from leucine (L), isoleucine (I), Valine (V), Serine (S), Cysteine (C) and Threonine (T). In one embodiment, X5 is selected from leucine (L), isoleucine (I) and Valine (V). In one embodiment, X5 is selected from Serine (S), Cysteine (C) and Threonine (T). In one embodiment, X5 is selected from leucine (L) and Serine (S). In one embodiment, X5 is Serine (S). In one embodiment, X5 is leucine (L).

Concept 7. The antibody or fragment according to any one of concepts 1 to 5, wherein X4 is present.

Concept 8. The antibody or fragment according to concept 7, wherein X4 is an aliphatic amino acid, optionally G.

In one embodiment, the hydroxyl-containing amino acid is selected from Glycine, Alanine, Valine, Leucine and Isoleucine.

In one embodiment, the hydroxyl-containing amino acid is selected from Glycine and Alanine. In one embodiment, the hydroxyl-containing amino acid is selected from Glycine and Valine. In one embodiment, the hydroxyl-containing amino acid is selected from Glycine and Leucine. In one embodiment, the hydroxyl-containing amino acid is selected from Glycine and Isoleucine. In one embodiment, the hydroxyl-containing amino acid is selected from Alanine and Valine. In one embodiment, the hydroxyl-containing amino acid is selected from Alanine and Leucine. In one embodiment, the hydroxyl-containing amino acid is selected from Alanine and Isoleucine. In one embodiment, the hydroxyl-containing amino acid is selected from Valine and Leucine. In one embodiment, the hydroxyl-containing amino acid is selected from Valine and Isoleucine. In one embodiment, the hydroxyl-containing amino acid is selected from, Leucine and Isoleucine.

In one embodiment, the hydroxyl-containing amino acid selected from three of each of Glycine, Alanine, Valine, Leucine and Isoleucine. In one embodiment, the hydroxyl-containing amino acid selected from four of each of Glycine, Alanine, Valine, Leucine and Isoleucine.

Concept 9. An antibody or a fragment thereof, optionally according to any one of concepts 1 to 8, which specifically binds to hPD-L1, and competes for binding to said hPD-L1 with the antibody 1D05, wherein the antibody or fragment comprises a VH domain which comprises the CDRH3 sequence of SEQ ID NO:29 or 32, or the CDRH3 sequence of SEQ ID NO:29 or 32 comprising 6 or fewer amino acid substitutions.

Concept 9a: An antibody or a fragment thereof, optionally according to any one of concepts 1 to 8, which specifically binds to hPD-L1, and competes for binding to said hPD-L1 with the antibody 84G09, wherein the antibody or fragment comprises a VH domain which comprises the CDRH3 sequence of SEQ ID NO:9 or 12, or the CDRH3 sequence of SEQ ID NO:9 or 12 comprising 6 or fewer amino acid substitutions.

Concept 9b: An antibody or a fragment thereof, optionally according to any one of concepts 1 to 8, which specifically binds to hPD-L1, and competes for binding to said hPD-L1 with the antibody 411B08, wherein the antibody or fragment comprises a VH domain which comprises the CDRH3 sequence of SEQ ID NO:54 or 57, or the CDRH3 sequence of SEQ ID NO:54 or 57 comprising 6 or fewer amino acid substitutions.

Concept 9c: An antibody or a fragment thereof, optionally according to any one of concepts 1 to 8, which specifically binds to hPD-L1, and competes for binding to said hPD-L1 with the antibody 411C04, wherein the antibody or fragment comprises a VH domain which comprises the CDRH3 sequence of SEQ ID No:74 or 77, or the CDRH3 sequence of SEQ ID NO:74 or 77 comprising 6 or fewer amino acid substitutions.

Concept 9d: An antibody or a fragment thereof, optionally according to any one of concepts 1 to 8, which specifically binds to hPD-L1, and competes for binding to said hPD-L1 with the antibody 411D07, wherein the antibody or fragment comprises a VH domain which comprises the CDRH3 sequence of SEQ ID NO:94 or 97, or the CDRH3 sequence of SEQ ID NO:94 or 97 comprising 3 or fewer amino acid substitutions.

Concept 9e: An antibody or a fragment thereof, optionally according to any one of concepts 1 to 8, which specifically binds to hPD-L1, and competes for binding to said hPD-L1 with the antibody 385F01, wherein the antibody or fragment comprises a VH domain which comprises the CDRH3 sequence of SEQ ID NO:114 or 117, or the CDRH3 sequence of SEQ ID NO:114 or 117 comprising 6 or fewer amino acid substitutions.

Concept 9f: An antibody or a fragment thereof, optionally according to any one of concepts 1 to 8, which specifically binds to hPD-L1, and competes for binding to said hPD-L1 with the antibody 386H03, wherein the antibody or fragment comprises a VH domain which comprises the CDRH3 sequence of SEQ ID NO:144 or 147, or the CDRH3 sequence of SEQ ID NO:144 or 147 comprising 3 or fewer amino acid substitutions.

Concept 9g: An antibody or a fragment thereof, optionally according to any one of concepts 1 to 8, which specifically binds to hPD-L1, and competes for binding to said hPD-L1 with the antibody 389A03, wherein the antibody or fragment comprises a VH domain which comprises the CDRH3 sequence of SEQ ID NO:174 or 177, or the CDRH3 sequence of SEQ ID NO:174 or 177 comprising 6 or fewer amino acid substitutions.

Concept 9h: An antibody or a fragment thereof, optionally according to any one of concepts 1 to 8, which specifically binds to hPD-L1, and competes for binding to said hPD-L1 with the antibody 413D08, wherein the antibody or fragment comprises a VH domain which comprises the CDRH3 sequence of SEQ ID NO:134 or 137, or the CDRH3 sequence of SEQ ID NO:134 or 137 comprising 5 or fewer amino acid substitutions.

Concept 9i: An antibody or a fragment thereof, optionally according to any one of concepts 1 to 8, which specifically binds to hPD-L1, and competes for binding to said hPD-L1 with the antibody 413G05, wherein the antibody or fragment comprises a VH domain which comprises the CDRH3 sequence of SEQ ID NO:240 or 243, or the CDRH3 sequence of SEQ ID NO:240 or 243 comprising 6 or fewer amino acid substitutions.

Concept 9j: An antibody or a fragment thereof, optionally according to any one of concepts 1 to 8, which specifically binds to hPD-L1, and competes for binding to said hPD-L1 with the antibody 413F09, wherein the antibody or fragment comprises a VH domain which comprises the CDRH3 sequence of SEQ ID NO:260 or 263, or the CDRH3 sequence of SEQ ID NO:260 or 263 comprising 6 or fewer amino acid substitutions.

Concept 9k: An antibody or a fragment thereof, optionally according to any one of concepts 1 to 8, which specifically binds to hPD-L1, and competes for binding to said hPD-L1 with the antibody 414B06, wherein the antibody or fragment comprises a VH domain which comprises the CDRH3 sequence of SEQ ID NO:280 or 283, or the CDRH3 sequence of SEQ ID NO:280 or 283 comprising 6 or fewer amino acid substitutions.

In all of concepts 9, 9a to k, 17, 17a to k, 18, 18a to k, 19, 19a to k, 22, 22a to k, 23, 23a to k, 24 and 24a to k, in one embodiment, the CDR comprises one amino acid substitution, which may be a conservative amino acid substitution. In all of concepts 9, 9a to k, 17, 17a to k, 18, 18a to k, 19, 19a to k, 22, 22a to k, 23, 23a to k, 24 and 24a to k, in one embodiment, the CDR comprises two amino acid substitutions, which may be conservative amino acid substitutions. In all of concepts 9, 9a to k, 17, 17a to k, 18, 18a to k, 19, 19a to k, 22, 22a, 22b, 22d, 22f, 22g, 24 and 24a to k, in one embodiment, the CDR comprises three amino acid substitutions, which may be conservative amino acid substitutions. In all of concepts 9, 9a to c, 9e, 9g to k, 17, 17a to c, 17e, 17g to k, 19, 19a, 22, 22d, 22f, 22g, 24 and 24a to k, in one embodiment, the CDR comprises four amino acid substitutions, which may be conservative amino acid substitutions. In all of concepts 9, 9a to c, 9e, 9g to k, 17, 17a to c, 17e, 17g to k, 22d, 22f and 22g, in one embodiment, the CDR comprises five amino acid substitutions, which may be conservative amino acid substitutions. In all of concepts 9, 9a to c, 9e, 9g, 9i to k, 17, 17a to c, 17e, 17g and 17i to k, in one embodiment, the CDR comprises six amino acid substitutions, which may be conservative amino acid substitutions.

Amino acid substitutions include alterations in which an amino acid is replaced with a different naturally-occurring amino acid residue. Such substitutions may be classified as "conservative", in which case an amino acid residue contained in a polypeptide is replaced with another naturally occurring amino acid of similar character either in relation to polarity, side chain functionality or size. Such conservative substitutions are well known in the art. Substitutions encompassed by the present invention may also be "non-conservative", in which an amino acid residue which is present in a peptide is substituted with an amino acid having different properties, such as naturally-occurring amino acid from a different group (e.g. substituting a charged or hydrophobic amino; acid with alanine), or alternatively, in which a naturally-occurring amino acid is substituted with a non-conventional amino acid.

In one embodiment, the conservative amino acid substitutions are as described herein. For example, the substitution may be of Y with F, T with S or K, P with A, E with D or Q, N with D or G, R with K, G with N or A, T with S or K, D with N or E, I with L or V, F with Y, S with T or A, R with K, G with N or A, K with R, A with S, K or P. In another embodiment, the conservative amino acid substitutions may be wherein Y is substituted with F, T with A or S, I with L or V, W with Y, M with L, N with D, G with A, T with A or S, D with N, I with L or V, F with Y or L, S with A or T and A with S, G, T or V.

Concept 10. An antibody or fragment which specifically binds to hPD-L1 and comprises a VH domain comprising a CDRH3 of from 12 to 20 amino acids and which is derived from the recombination of a human VH gene segment, a human D gene segment and a human JH gene segment, wherein the human JH gene segment is IGHJ5 (e.g. IGHJ5*02).

In one embodiment, the CDRH3 is from 14 to 17 amino acids and the human JH gene segment is IGHJ5 (e.g. IGHJ5*02).

There is also provided as concept 10a an antibody or fragment which specifically binds to hPD-L1 and comprises a VH domain comprising a CDRH3 of from 8 to 16 amino acids and which is derived from the recombination of a human VH gene segment, a human D gene segment and a human JH gene segment, wherein the human JH gene segment is selected from IGHJ4 (e.g. IGHJ4*02), IGHJ5 (e.g. IGHJ5*02) and IGHJ6 (e.g. IGHJ6*02).

In another embodiment, the human JH gene segment is IGHJ6 (e.g. IGHJ6*02). In another embodiment, the CDRH3 is of from 10 to 17 amino acids and the human JH gene segment is IGHJ6 (e.g. IGHJ6*02).

In another embodiment, the human JH gene segment is IGHJ4 (e.g. IGHJ4*02). In another embodiment, the CDRH3 is from 7 to 17 amino acids and the human JH gene segment is IGHJ4 (e.g. IGHJ4*02).

Concept 11. The antibody or fragment according to concept 10 or 10a, wherein the human VH gene segment is IGHV3 (e.g. IGHV3-9, such as IGHV3-9*01).

There is also provided as concept 11a an antibody or fragment according to concept 10 or 10a, wherein the human VH gene segment is selected from IGHV3 (e.g. IGHV3-9, such as IGHV3-9*01 or e.g. IGHV3-7, such as IGHV3-7*01 or e.g. IGHV3-33, such as IGHV3-33*01 or e.g. IGHV3-11, such as IGHV3-11*01 or e.g. IGHV3-23, such as IGHV3-23*04), or IGHV4 (e.g. IGHV4-4, such as IGHV4-4*02 or e.g. IGHV4-39, such as IGHV4-39*01).

In one embodiment, the human VH gene segment is IGHV3 (e.g. IGHV3-7, such as IGHV3-7*01). In one embodiment, the human VH gene segment is IGHV3 (e.g. IGHV3-33, such as IGHV3-33*01). In one embodiment, the human VH gene segment is IGHV3 (e.g. IGHV3-11, such as IGHV3-11*01). In one embodiment, the human VH gene segment is IGHV3 (e.g. IGHV3-23, such as IGHV3-23*04).

In one embodiment, the human VH gene segment is IGHV4 (e.g. e.g. IGHV4-4, such as IGHV4-4*02). In one embodiment, the human VH gene segment is IGHV4 (e.g. IGHV4-39, such as IGHV4-39*01).

There is also provided as concept 11b an antibody or fragment according to concept 10, 10a, 11 or 11a, wherein the human D gene segment is selected from IGHD1 (e.g.

IGHD1-20, such as IGHD1-20*01), IGHD3 (e.g. IGHD3-10, such as IGHD3-10*01), IGHD4 (e.g. IGHD4-11, such as IGHD4-11*01), IGHD5 (e.g. IGHD5-7, such as IGHD5-18*01), and IGHD6 (e.g. IGHD6-13, such as IGHD6-13*01).

In one embodiment, the human D gene segment is IGHD1 (e.g. IGHD1-20, such as IGHD1-20*01). In one embodiment, the human D gene segment is IGHD3 (e.g. IGHD3-10, such as IGHD3-10*01). In one embodiment, the human D gene segment is IGHD4 (e.g. IGHD4-11, such as IGHD4-11*01). In one embodiment, the human D gene segment is IGHD5 (e.g. IGHD5-18, such as IGHD5-19*01). In one embodiment, the human D gene segment is IGHD6 (e.g. IGHD6-13, such as IGHD6-13*01).

Concept 12. The antibody or fragment according to concept 10, 10a, 11, 11a or 11b, wherein the antibody or fragment comprises a VL domain which is derived from the recombination of a human Vκ gene segment, and a human Jκ gene segment, wherein the human Vκ gene segment is IGκV1D (e.g. IGκV1D-39, such as IGκV1D-39*01).

There is also provided as concept 12a an antibody or fragment according to any of concepts 10, 10a, 11, 11a or 11b, wherein the human Vκ gene segment is selected from IGκV1 (e.g. IGκV1-17, such as IGκV1-17*01 or e.g. IGκV1-9, such as IGκV1-9*d01 or e.g. IGκV1D-12, such as IGκV1D-12*02 or e.g. IGκV1D-39, such as IGκV1D-39*01), and IGκV4 (e.g. IGκV4-1, such as IGκV4-1*01).

In one embodiment, the human Vκ gene segment is IGκV1 (e.g. IGκV1-17, such as IGκV1-17*01). In one embodiment, the human Vκ gene segment is IGκV1 (e.g. IGκV1-9, such as IGκV1-9*d01). In one embodiment, the human Vκ gene segment is IGκV1 (e.g. IGκV1D-12, such as IGκV1D-12*02). In one embodiment, the human Vκ gene segment is IGκV1 (e.g. IGκV1D-39, such as IGκV1D-39*01).

In one embodiment, the human Vκ gene segment is IGκV1 IGκV4 (e.g. IGκV4-1, such as IGκV4-1*01)

There is also provided as concept 12b an antibody or fragment according to concept 10, 10a, 11 or 11a, wherein the human JK gene segment is selected from IGκJ1 (e.g. IGκJ1*01), IGκJ2 (e.g. IGκJ2*04), IGκJ3 (e.g. IGκJ3*01), IGκJ4 (e.g. IGκJ4*01) or IGκJ5 (e.g. IGκJ5*01).

In one embodiment, the human Jκ gene segment is IGκJ1 (e.g. IGκJ1*01). In one embodiment, the human Jκ gene segment is IGκ2 (e.g. IGκJ2*04). In one embodiment, the human JK gene segment is IGκJ3 (e.g. IGκJ3*01). In one embodiment, the human JK gene segment is IGκJ4 (e.g. IGκJ4*01). In one embodiment, the human Jκ gene segment is IGκJ5 (e.g. IGκJ5*01).

Concept 13. An antibody or fragment thereof which specifically binds to an epitope that is identical to an epitope to which the antibody 1D05 specifically binds.

Concept 13a. An antibody or fragment thereof which specifically binds to an epitope that is identical to an epitope to which the antibody 84G09 specifically binds.

Concept 13b. An antibody or fragment thereof which specifically binds to an epitope that is identical to an epitope to which the antibody 411B08 specifically binds.

Concept 13c. An antibody or fragment thereof which specifically binds to an epitope that is identical to an epitope to which the antibody 411C04 specifically binds.

Concept 13d. An antibody or fragment thereof which specifically binds to an epitope that is identical to an epitope to which the antibody 411D07 specifically binds.

Concept 13e. An antibody or fragment thereof which specifically binds to an epitope that is identical to an epitope to which the antibody 385F01 specifically binds.

Concept 13f. An antibody or fragment thereof which specifically binds to an epitope that is identical to an epitope to which the antibody 386H03 specifically binds.

Concept 13g. An antibody or fragment thereof which specifically binds to an epitope that is identical to an epitope to which the antibody 389A03 specifically binds.

Concept 13h. An antibody or fragment thereof which specifically binds to an epitope that is identical to an epitope to which the antibody 413D08 specifically binds.

Concept 13i. An antibody or fragment thereof which specifically binds to an epitope that is identical to an epitope to which the antibody 413G05 specifically binds.

Concept 13j. An antibody or fragment thereof which specifically binds to an epitope that is identical to an epitope to which the antibody 413F09 specifically binds.

Concept 13k. An antibody or fragment thereof which specifically binds to an epitope that is identical to an epitope to which the antibody 414B06 specifically binds.

The antibodies described in these concepts have the sequences as described hereinabove.

In one embodiment, there is provided an antibody which specifically bind to an epitope which is substantially similar to an epitope to which any of the antibodies in concept 13, 13 a to 13k bind.

Contact amino acid residues involved in the interaction of antibody and antigen may be determined by various known methods to those skilled in the art.

In one embodiment, sequential replacement of the amino acids of the antigen sequence (using standard molecular biology techniques to mutate the DNA of the coding sequence of the antigen), in this case hPD-L1 with Alanine (a.k.a Alanine scan), or another unrelated amino acid, may provide residues whose mutation would reduce or ablate the ability of the antibody to recognise the antigen in question. Binding may be assessed using standard techniques, such as, but not limited to, SPR, HTRF, ELISA (which are described elsewhere herein). Other substitutions could be made to enhance the disruption of binding such as changing the charge on the side chain of antigen sequence amino acids (e.g. Lysine change to glutamic acid), switching polar and non-polar residues (e.g. Serine change to leucine). The alanine scan or other amino substitution method may be carried out either with recombinant soluble antigen, or where the target is a cell membrane target, directly on cells using transient or stable expression of the mutated versions.

In one embodiment, protein crystallography may be used to determine contact residues between antibody and antigen (i.e. to determine the epitope to which the antibody binds), crystallography allows the direct visualisation of contact residues involved in the antibody-antigen interaction. As well as standard X-ray crystallography, cryo-electro microscopy has been used to determine contact residues between antibodies and HIV capsid protein (see Lee, Jeong Hyun, et al. "Antibodies to a conformational epitope on gp41 neutralize HIV-1 by destabilizing the Env spike.", Nature communications, 6, (2015)).

In one embodiment, if the antibody recognises a linear epitope, short peptides based on the antigen sequence can be produced and binding of the antibody to these peptides can be assessed using standard techniques, such as, but not limited to, SPR, HTRF, ELISA (which are described elsewhere herein). Further investigation of the epitope could be provided by performing an Alanine scan on any peptides that show binding Alternative to linear peptides, conformational scans could be carried out using Pepscan technology (http://www.pepscan.com/) using their chemical linkage of peptides onto scaffolds, which has been used to determine discontinuous epitopes on CD20 targeting antibodies (Niederfellner, Gerhard, et al. "Epitope characterization and crystal structure of GA101 provide insights into the molecular basis for type I/II distinction of CD20 antibodies.", Blood, 118.2, (2011), 358-367.).

In one embodiment, limited proteolytic digestion and mass spectrophotometry can be used to identify binding epitopes. The antibody-antigen complex is digested by a protease, such as, but not limited to, trypsin. The digested complex peptides are compared to antibody-alone and antigen-alone digestion mass spectrophotometry to determine if a particular epitope is protected by the complexation. Further work involving amino acid substitution, competition binding, may then be employed to narrow down to individual amino acid residues involved in the interaction (see, for example, Suckau, Detlev, et al. "Molecular epitope identification by limited proteolysis of an immobilized antigen-antibody complex and mass spectrometric peptide mapping.", Proceedings of the National Academy of Sciences, 87.24, (1990), 9848-9852).

Thus, in one embodiment, the contact residues of the epitope are identified with an unrelated amino acid scan (e.g. alanine scan). In another embodiment, an unrelated amino acid scan (e.g. alanine scan) is carried out using a technique selected from SPR, HTRF, ELISA, X-ray crystallography, cryo-electro microscopy and a combination of limited proteolytic digestion and mass spectrometry. In one embodiment, the unrelated amino acid scan (e.g. alanine scan) is carried out using HTRF. In one embodiment, the unrelated amino acid scan (e.g. alanine scan) is carried out using ELISA.

When the alanine scan is carried out with either ELISA or HTRF, an amino acid residue is identified as contributing to the epitope if the reduction in signal is at least 25%. In one embodiment, the reduction in signal is at least 30%. In one embodiment, the reduction in signal is at least 35%. In one embodiment, the reduction in signal is at least 40%. In one embodiment, the reduction in signal is at least 45%. In one embodiment, the reduction in signal is at least 50%. In one embodiment, the reduction in signal is at least 55%. In one embodiment, the reduction in signal is at least 60%. In one embodiment, the reduction in signal is at least 70%. In one embodiment, the reduction in signal is at least 75%. In one embodiment, the reduction in signal is at least 80%. In one embodiment, the reduction in signal is at least 85%. In one embodiment, the reduction in signal is at least 90%.

When the alanine scan is carried out with SPR, an amino acid residue is identified as contributing to the epitope if there is at least a 10-fold reduction in affinity. In one embodiment, the reduction in affinity is at least 15 fold. In one embodiment, the reduction in affinity is at least 20 fold. In one embodiment, the reduction in affinity is at least 30 fold. In one embodiment, the reduction in affinity is at least 40 fold. In one embodiment, the reduction in affinity is at least 50 fold. In one embodiment, the reduction in affinity is at least 100 fold.

In one embodiment, the contact residues of the epitope are identified by X-ray crystallography. In one embodiment, the contact residues of the epitope are identified by cryo-electro microscopy. In one embodiment, the contact residues of the epitope are identified by a combination of limited proteolytic digestion and mass spectrometry.

Concept 14. The antibody or fragment according to concept 13, wherein the epitope is identified by unrelated amino acid scanning, or by X-ray crystallography.

Concept 15. The antibody or fragment according to concept 14, wherein the contact residues of the epitope are defined by a reduction in affinity of at least 10-fold in an unrelated amino acid scan, e.g. an alanine scan as determined by SPR.

In one embodiment, the reduction in affinity is at least 15 fold. In one embodiment, the reduction in affinity is at least 20 fold. In one embodiment, the reduction in affinity is at least 30 fold. In one embodiment, the reduction in affinity is at least 40 fold. In one embodiment, the reduction in affinity is at least 50 fold. In one embodiment, the reduction in affinity is at least 100 fold.

SPR may be carried out as described hereinabove.

Concept 16. An antibody or fragment thereof which competes for binding to hPD-L1 with the antibody 1D05.

Competition may be determined by surface plasmon resonance (SPR), such techniques being readily apparent to the skilled person. SPR may be carried out using Biacore™, Proteon™ or another standard SPR technique. Such competition may be due, for example, to the antibodies or fragments binding to identical or overlapping epitopes of hPD-L1. In one embodiment, competition is determined by ELISA, such techniques being readily apparent to the skilled person. In one embodiment, competition is determined by homogenous time resolved fluorescence (HTRF), such techniques being readily apparent to the skilled person. In one embodiment, competition is determined by fluorescence activated cell sorting (FACS), such techniques being readily apparent to the skilled person. In one embodiment, competition is determined by ForteBio Octet® Bio-Layer Interferometry (BLI) such techniques being readily apparent to the skilled person.

In one embodiment, the antibody or fragment competes (e.g., in a dose-dependent manner) with hPD-1 (or a fusion protein thereof) for binding to cell surface-expressed hPD-L1. In one embodiment, the antibody or fragment competes (e.g., in a dose-dependent manner) with hPD-1 (or a fusion protein thereof) for binding to soluble hPDL-1.

In one embodiment, the antibody or fragment partially or completely inhibits binding of PD-1 and/or CD80 to cell surface-expressed PD-L1, such as hPD-L1. In another embodiment, the antibody or fragment partially or completely inhibits binding of hPD-1 and/or CD80 to soluble hPD-L1. In some embodiments, the antibody or fragment partially or completely increases the secretion of IFNγ, CD25 and IL-2 from a cell having cell surface-expressed PD-1. In one embodiment, the antibody or fragment partially or completely inhibits binding of CD80 to soluble hPD-L1, but does not show any detectable inhibition of the binding of PD-1 to cell surface-expressed PD-L1. In one embodiment, the antibody or fragment partially or completely inhibits binding of CD80 to soluble hPD-L1, but does not show any detectable inhibition of the binding of PD-1 to soluble PD-L1.

Concept 16a. An antibody or fragment thereof which competes for binding to hPD-L1 with the antibody 84G09.

Concept 16b. An antibody or fragment thereof which competes for binding to hPD-L1 with the antibody 411B08.

Concept 16c. An antibody or fragment thereof which competes for binding to hPD-L1 with the antibody 411C04.

Concept 16d. An antibody or fragment thereof which competes for binding to hPD-L1 with the antibody 411D07.

Concept 16e. An antibody or fragment thereof which competes for binding to hPD-L1 with the antibody 385F01.

Concept 16f. An antibody or fragment thereof which competes for binding to hPD-L1 with the antibody 386H03.

Concept 16g. An antibody or fragment thereof which competes for binding to hPD-L1 with the antibody 389A03.

Concept 16h. An antibody or fragment thereof which competes for binding to hPD-L1 with the antibody 413D08.

Concept 16i. An antibody or fragment thereof which competes for binding to hPD-L1 with the antibody 413G05.

Concept 16j. An antibody or fragment thereof which competes for binding to hPD-L1 with the antibody 413F09.

Concept 16k. An antibody or fragment thereof which competes for binding to hPD-L1 with the antibody 414B06.

The antibodies have the sequences as described hereinabove.

Concept 17. The antibody or fragment according to any one of concepts 10 to 16, wherein the VH domain comprises the CDRH3 sequence of SEQ ID NO:29 or 32, or the CDRH3 sequence of SEQ ID NO:29 or 32 comprising 6 or fewer amino acid substitutions.

Concept 17a: An antibody or a fragment thereof according to any one of concepts 10 to 16 (but when dependent on concept 13, it is dependent on concept 13a, and when dependent on concept 16, it is dependent on concept 16a), wherein the VH domain comprises the CDRH3 sequence of SEQ ID NO:9 or 12, or the CDRH3 sequence of SEQ ID NO:9 or 12 comprising 6 or fewer amino acid substitutions.

Concept 17b: An antibody or a fragment thereof according to any one of concepts 10 to 16 (but when dependent on concept 13, it is dependent on concept 13b, and when dependent on concept 16, it is dependent on concept 16b), wherein the VH domain comprises the CDRH3 sequence of SEQ ID NO:54 or 57, or the CDRH3 sequence of SEQ ID NO:54 or 57 comprising 6 or fewer amino acid substitutions.

Concept 17c: An antibody or a fragment thereof according to any one of concepts 10 to 16 (but when dependent on concept 13, it is dependent on concept 13c, and when dependent on concept 16, it is dependent on concept 16c), wherein the a VH domain comprises the CDRH3 sequence of SEQ ID NO:74 or 77, or the CDRH3 sequence of SEQ ID NO:74 or 77 comprising 6 or fewer amino acid substitutions.

Concept 17d: An antibody or a fragment thereof according to any one of concepts 10 to 16 (but when dependent on concept 13, it is dependent on concept 13d, and when dependent on concept 16, it is dependent on concept 16d), wherein the VH domain comprises the CDRH3 sequence of SEQ ID NO:94 or 97, or the CDRH3 sequence of SEQ ID NO:94 or 97 comprising 3 or fewer amino acid substitutions.

Concept 17e: An antibody or a fragment thereof according to any one of concepts 10 to 16 (but when dependent on concept 13, it is dependent on concept 13e, and when dependent on concept 16, it is dependent on concept 16e), wherein the VH domain comprises the CDRH3 sequence of SEQ ID NO:114 or 117, or the CDRH3 sequence of SEQ ID NO:114 or 117 comprising 6 or fewer amino acid substitutions.

Concept 17f: An antibody or a fragment thereof according to any one of concepts 10 to 16 (but when dependent on concept 13, it is dependent on concept 13f, and when dependent on concept 16, it is dependent on concept 16f), wherein the VH domain comprises the CDRH3 sequence of SEQ ID NO:144 or 147, or the CDRH3 sequence of SEQ ID NO:144 or 147 comprising 3 or fewer amino acid substitutions.

Concept 17g: An antibody or a fragment thereof according to any one of concepts 10 to 16 (but when dependent on concept 13, it is dependent on concept 13g, and when dependent on concept 16, it is dependent on concept 16g), wherein the VH domain comprises the CDRH3 sequence of SEQ ID NO:174 or 177, or the CDRH3 sequence of SEQ ID NO:174 or 177 comprising 6 or fewer amino acid substitutions.

Concept 17h: An antibody or a fragment thereof according to any one of concepts 10 to 16 (but when dependent on concept 13, it is dependent on concept 13h, and when dependent on concept 16, it is dependent on concept 16h), wherein the VH domain comprises the CDRH3 sequence of SEQ ID NO134 or 137, or the CDRH3 sequence of SEQ ID NO:134 or 137 comprising 5 or fewer amino acid substitutions.

Concept 17i: An antibody or a fragment thereof according to any one of concepts 10 to 16 (but when dependent on concept 13, it is dependent on concept 13i, and when dependent on concept 16, it is dependent on concept 16i), wherein the VH domain comprises the CDRH3 sequence of SEQ ID NO:240 or 243, or the CDRH3 sequence of SEQ ID NO:240 or 243 comprising 6 or fewer amino acid substitutions.

Concept 17j: An antibody or a fragment thereof according to any one of concepts 10 to 16 (but when dependent on concept 13, it is dependent on concept 13j, and when dependent on concept 16, it is dependent on concept 16j), wherein the a VH domain comprises the CDRH3 sequence of SEQ ID NO:260 or 263, or the CDRH3 sequence of SEQ ID NO:260 or 263 comprising 6 or fewer amino acid substitutions.

Concept 17k: An antibody or a fragment thereof according to any one of concepts 10 to 16 (but when dependent on concept 13, it is dependent on concept 13k, and when dependent on concept 16, it is dependent on concept 16k), wherein the VH domain comprises the CDRH3 sequence of SEQ ID NO:280 or 283, or the CDRH3 sequence of SEQ ID NO:280 or 283 comprising 6 or fewer amino acid substitutions.

Concept 18. The antibody or fragment according to any preceding concept, wherein the VH domain comprises the CDRH1 sequence of SEQ ID NO:27 or 30 or the CDRH1 sequence of SEQ ID NO:27 or 30 comprising 3, 2 or 1 amino acid substitution(s).

Concept 18a: An antibody or a fragment thereof according to any preceding concept (but when dependent on concept 9, it is dependent on concept 9a, when dependent on concept 13, it is dependent on concept 13a, when dependent on concept 16, it is dependent on concept 16a, and when dependent on concept 17, it is dependent on concept 17a), wherein the VH domain comprises the CDRH1 sequence of SEQ ID NO: 7 or 10, or the CDRH1 sequence of SEQ ID NO: 7 or 10 comprising 3, 2 or 1 amino acid substitution(s).

Concept 18b: An antibody or a fragment thereof according to any preceding concept (but when dependent on concept 9, it is dependent on concept 9b, when dependent on concept 13, it is dependent on concept 13b, when dependent on concept 16, it is dependent on concept 16b, and when dependent on concept 17, it is dependent on concept 17b), wherein the VH domain comprises the CDRH1 sequence of SEQ ID NO: 52 or 55, or the CDRH1 sequence of SEQ ID NO: 52 or 55 comprising 3, 2 or 1 amino acid substitution(s).

Concept 18c: An antibody or a fragment thereof according to any preceding concept (but when dependent on concept 9, it is dependent on concept 9c, when dependent on concept 13, it is dependent on concept 13c, when dependent on concept 16, it is dependent on concept 16c, and when dependent on concept 17, it is dependent on concept 17c), wherein the VH domain comprises the CDRH1 sequence of SEQ ID NO: 72 or 75, or the CDRH1 sequence of SEQ ID NO: 72 or 75 comprising 3, 2 or 1 amino acid substitution(s).

Concept 18d: An antibody or a fragment thereof according to any preceding concept (but when dependent on concept 9, it is dependent on concept 9d, when dependent on concept 13, it is dependent on concept 13d, when dependent on concept 16, it is dependent on concept 16d, and when dependent on concept 17, it is dependent on concept 17d), wherein the VH domain comprises the CDRH1 sequence of SEQ ID NO: 92 or 95, or the CDRH1 sequence of SEQ ID NO: 92 or 95 comprising 3, 2 or 1 amino acid substitution(s).

Concept 18e: An antibody or a fragment thereof according to any preceding concept (but when dependent on concept 9, it is dependent on concept 9e, when dependent on concept 13, it is dependent on concept 13e, when dependent on concept 16, it is dependent on concept 16e, and when dependent on concept 17, it is dependent on concept 17e), wherein the VH domain comprises the CDRH1 sequence of SEQ ID NO: 112 or 115, or the CDRH1 sequence of SEQ ID NO:112 or 115 comprising 3, 2 or 1 amino acid substitution(s).

Concept 18f: An antibody or a fragment thereof according to any preceding concept (but when dependent on concept 9, it is dependent on concept 9f, when dependent on concept 13, it is dependent on concept 13f, when dependent on concept 16, it is dependent on concept 16f, and when dependent on concept 17, it is dependent on concept 17f), wherein the VH domain comprises the CDRH1 sequence of SEQ ID NO: 142 or 145, or the CDRH1 sequence of SEQ ID NO: 142 or 145 comprising 3, 2 or 1 amino acid substitution(s).

Concept 18g: An antibody or a fragment thereof according to any preceding concept (but when dependent on concept 9, it is dependent on concept 9g, when dependent on concept 13, it is dependent on concept 13g, when dependent on concept 16, it is dependent on concept 16g, and when dependent on concept 17, it is dependent on concept 17g), wherein the VH domain comprises the CDRH1 sequence of SEQ ID NO: 172 or 175, or the CDRH1 sequence of SEQ ID NO: 172 or 175 comprising 3, 2 or 1 amino acid substitution(s).

Concept 18h: An antibody or a fragment thereof according to any preceding concept (but when dependent on concept 9, it is dependent on concept 9h, when dependent on concept 13, it is dependent on concept 13h, when dependent on concept 16, it is dependent on concept 16h, and when dependent on concept 17, it is dependent on concept 17h), wherein the VH domain comprises the CDRH1 sequence of SEQ ID NO:132 or 135, or the CDRH1 sequence of SEQ ID NO:132 or 135 comprising 3, 2 or 1 amino acid substitution(s).

Concept 18i: An antibody or a fragment thereof according to any preceding concept (but when dependent on concept 9, it is dependent on concept 9i, when dependent on concept 13, it is dependent on concept 13i, when dependent on concept 16, it is dependent on concept 16i, and when dependent on concept 17, it is dependent on concept 17i), wherein the VH domain comprises the CDRH1 sequence of SEQ ID NO: 238 or 241, or the CDRH1 sequence of SEQ ID NO: 238 or 241 comprising 3, 2 or 1 amino acid substitution(s).

Concept 18j: An antibody or a fragment thereof according to any preceding concept (but when dependent on concept 9, it is dependent on concept 9j, when dependent on concept 13, it is dependent on concept 13j, when dependent on concept 16, it is dependent on concept 16j, and when dependent on concept 17, it is dependent on concept 17j), wherein the VH domain comprises the CDRH1 sequence of SEQ ID NO: 258 or 261, or the CDRH1 sequence of SEQ ID NO: 258 or 261 comprising 3, 2 or 1 amino acid substitution(s).

Concept 18k: An antibody or a fragment thereof according to any preceding concept (but when dependent on concept 9, it is dependent on concept 9k, when dependent on concept 13, it is dependent on concept 13k, when dependent on concept 16, it is dependent on concept 16k, and when dependent on concept 17, it is dependent on concept 17k), wherein the VH domain comprises the CDRH1 sequence of SEQ ID NO: 278 or 281, or the CDRH1 sequence of SEQ ID NO: 278 or 281 comprising 3, 2 or 1 amino acid substitution(s).

Concept 19. The antibody or fragment according to any preceding concept, wherein the VH domain comprises the CDRH2 sequence of SEQ ID NO:28 or 31, or the CDRH2 sequence of SEQ ID NO:28 or 31 comprising 4 or fewer amino acid substitutions.

Concept 19a: An antibody or a fragment thereof according to any preceding concept (but when dependent on concept 9, it is dependent on concept 9a, when dependent on concept 13, it is dependent on concept 13a, when dependent on concept 16, it is dependent on concept 16a, when dependent on concept 17, it is dependent on concept 17a, and when dependent on concept 18, it is dependent on concept 18a), wherein the VH domain comprises the CDRH2 sequence of SEQ ID NO: 8 or 11, or the CDRH2 sequence of SEQ ID NO:8 or 11 comprising 4 or fewer amino acid substitutions.

Concept 19b: An antibody or a fragment thereof according to any preceding concept (but when dependent on concept 9, it is dependent on concept 9b, when dependent on concept 13, it is dependent on concept 13b, when dependent on concept 16, it is dependent on concept 16b, when dependent on concept 17, it is dependent on concept 17b, and when dependent on concept 18, it is dependent on concept 18b), wherein the VH domain comprises the CDRH2 sequence of SEQ ID NO:53 or 56, or the CDRH2 sequence of SEQ ID NO:53 or 56 comprising 3, 2 or 1 amino acid substitution(s).

Concept 19c: An antibody or a fragment thereof according to any preceding concept (but when dependent on concept 9, it is dependent on concept 9c, when dependent on concept 13, it is dependent on concept 13c, when dependent on concept 16, it is dependent on concept 16c, when dependent on concept 17, it is dependent on concept 17c, and when dependent on concept 18, it is dependent on concept 18c), wherein the VH domain comprises the CDRH2 sequence of SEQ ID NO:73 or 76, or the CDRH2 sequence of SEQ ID NO:73 or 76 comprising 3, 2 or 1 amino acid substitution(s).

Concept 19d: An antibody or a fragment thereof according to any preceding concept (but when dependent on concept 9, it is dependent on concept 9d, when dependent on concept 13, it is dependent on concept 13d, when dependent on concept 16, it is dependent on concept 16d, when dependent on concept 17, it is dependent on concept 17d, and when dependent on concept 18, it is dependent on concept 18d), wherein the VH domain comprises the CDRH2 sequence of SEQ ID NO:93 or 96, or the CDRH2 sequence of SEQ ID NO:93 or 96 comprising 3, 2 or 1 amino acid substitution(s).

Concept 19e: An antibody or a fragment thereof according to any preceding concept (but when dependent on concept 9, it is dependent on concept 9e, when dependent on concept 13, it is dependent on concept 13e, when dependent on concept 16, it is dependent on concept 16e, when dependent on concept 17, it is dependent on concept 17e, and when dependent on concept 18, it is dependent on concept 18e), wherein the VH domain comprises the CDRH2 sequence of SEQ ID NO:113 or 116, or the CDRH2 sequence of SEQ ID NO:113 or 116 comprising 3, 2 or 1 amino acid substitution(s).

Concept 19f: An antibody or a fragment thereof according to any preceding concept (but when dependent on concept 9, it is dependent on concept 9f, when dependent on concept 13, it is dependent on concept 13f, when dependent on concept 16, it is dependent on concept 16f, when dependent on concept 17, it is dependent on concept 17f, and when dependent on concept 18, it is dependent on concept 18f), wherein the VH domain comprises the CDRH2 sequence of SEQ ID NO:143 or 146, or the CDRH2 sequence of SEQ ID NO:143 or 146 comprising 3, 2 or 1 amino acid substitution(s).

Concept 19g: An antibody or a fragment thereof according to any preceding concept (but when dependent on concept 9, it is dependent on concept 9g, when dependent on concept 13, it is dependent on concept 13g, when dependent on concept 16, it is dependent on concept 16g, when dependent on concept 17, it is dependent on concept 17g, and when dependent on concept 18, it is dependent on concept 18g), wherein the VH domain comprises the CDRH2 sequence of SEQ ID NO:173 or 176, or the CDRH2 sequence of SEQ ID NO:173 or 176 comprising 3, 2 or 1 amino acid substitution(s).

Concept 19h: An antibody or a fragment thereof according to any preceding concept (but when dependent on concept 9, it is dependent on concept 9h, when dependent on concept 13, it is dependent on concept 13h, when dependent on concept 16, it is dependent on concept 16h, when dependent on concept 17, it is dependent on concept 17h, and when dependent on concept 18, it is dependent on concept 18h), wherein the VH domain comprises the CDRH2 sequence of SEQ ID NO:133 or 136, or the CDRH2 sequence of SEQ ID NO:133 or 136 comprising 3, 2 or 1 amino acid substitution(s).

Concept 19i: An antibody or a fragment thereof according to any preceding concept (but when dependent on concept 9, it is dependent on concept 9i, when dependent on concept 13, it is dependent on concept 13i, when dependent on concept 16, it is dependent on concept 16i, when dependent on concept 17, it is dependent on concept 17i, and when dependent on concept 18, it is dependent on concept 18i), wherein the VH domain comprises the CDRH2 sequence of SEQ ID NO:239 or 242, or the CDRH2 sequence of SEQ ID NO:239 or 242 comprising 3, 2 or 1 amino acid substitution(s).

Concept 19j: An antibody or a fragment thereof according to any preceding concept (but when dependent on concept 9, it is dependent on concept 9j, when dependent on concept 13, it is dependent on concept 13j, when dependent on concept 16, it is dependent on concept 16j, when dependent on concept 17, it is dependent on concept 17j, and when dependent on concept 18, it is dependent on concept 18j), wherein the VH domain comprises the CDRH2 sequence of SEQ ID NO:259 or 262, or the CDRH2 sequence of SEQ ID NO:259 or 262 comprising 3, 2 or 1 amino acid substitution(s).

Concept 19k: An antibody or a fragment thereof according to any preceding concept (but when dependent on concept 9, it is dependent on concept 9k, when dependent on concept 13, it is dependent on concept 13k, when dependent on concept 16, it is dependent on concept 16k, when dependent on concept 17, it is dependent on concept 17k, and when dependent on concept 18, it is dependent on concept 18k), wherein the VH domain comprises the CDRH2 sequence of SEQ ID NO:279 or 282, or the CDRH2 sequence of SEQ ID NO:279 or 282 comprising 3, 2 or 1 amino acid substitution(s).

Concept 20. The antibody or fragment according to any preceding concept, wherein the VH domain comprises an amino acid sequence of SEQ ID NO:33, or a heavy chain variable domain amino acid sequence that is at least 80% (e.g. at least 85%, or at least 90%) identical to SEQ ID NO:33.

Concept 20a: An antibody or a fragment thereof according to any preceding concept (but when dependent on concept 9, it is dependent on concept 9a, when dependent on concept 13, it is dependent on concept 13a, when dependent on concept 16, it is dependent on concept 16a, when dependent on concept 17, it is dependent on concept 17a, when dependent on concept 18, it is dependent on concept 18a, and when dependent on concept 19, it is dependent on concept 19a), wherein the VH domain comprises an amino acid sequence of SEQ ID NO:13, or a heavy chain variable domain amino acid sequence that is at least 80% (e.g. at least 85%, or at least 90%) identical to SEQ ID NO:13.

Concept 20b: An antibody or a fragment thereof according to any preceding concept (but when dependent on concept 9, it is dependent on concept 9b, when dependent on concept 13, it is dependent on concept 13b, when dependent on concept 16, it is dependent on concept 16b, when dependent on concept 17, it is dependent on concept 17b, when dependent on concept 18, it is dependent on concept 18b, and when dependent on concept 19, it is dependent on concept 19b), wherein the VH domain comprises an amino acid sequence of SEQ ID NO:58, or a heavy chain variable domain amino acid sequence that is at least 80% (e.g. at least 85%, or at least 90%) identical to SEQ ID NO:58.

Concept 20c: An antibody or a fragment thereof according to any preceding concept (but when dependent on concept 9, it is dependent on concept 9c, when dependent on concept 13, it is dependent on concept 13c, when dependent on concept 16, it is dependent on concept 16c, when dependent on concept 17, it is dependent on concept 17c, when dependent on concept 18, it is dependent on concept 18c, and when dependent on concept 19, it is dependent on concept 19c), wherein the VH domain comprises an amino acid sequence of SEQ ID NO:78, or a heavy chain variable domain amino acid sequence that is at least 80% (e.g. at least 85%, or at least 90%) identical to SEQ ID NO:78.

Concept 20d: An antibody or a fragment thereof according to any preceding concept (but when dependent on concept 9, it is dependent on concept 9d, when dependent on concept 13, it is dependent on concept 13d, when dependent on concept 16, it is dependent on concept 16d, when dependent on concept 17, it is dependent on concept 17d, when dependent on concept 18, it is dependent on concept 18d, and when dependent on concept 19, it is dependent on concept 19d), wherein the VH domain comprises an amino acid sequence of SEQ ID NO:98, or a heavy chain variable domain amino acid sequence that is at least 80% (e.g. at least 85%, or at least 90%) identical to SEQ ID NO:98.

Concept 20e: An antibody or a fragment thereof according to any preceding concept (but when dependent on concept 9, it is dependent on concept 9e, when dependent on concept 13, it is dependent on concept 13e, when dependent on concept 16, it is dependent on concept 16e, when dependent on concept 17, it is dependent on concept 17e, when dependent on concept 18, it is dependent on concept 18e, and when dependent on concept 19, it is dependent on concept 19e), wherein the VH domain comprises an amino acid sequence of SEQ ID NO:118, or a heavy chain variable domain amino acid sequence that is at least 80% (e.g. at least 85%, or at least 90%) identical to SEQ ID NO:118.

Concept 20f: An antibody or a fragment thereof according to any preceding concept (but when dependent on concept 9, it is dependent on concept 9f, when dependent on concept 13, it is dependent on concept 13f, when dependent on concept 16, it is dependent on concept 16f, when dependent on concept 17, it is dependent on concept 17f, when dependent on concept 18, it is dependent on concept 18f, and when dependent on concept 19, it is dependent on concept 19f), wherein the VH domain comprises an amino acid sequence of SEQ ID NO:158, or a heavy chain variable domain amino acid sequence that is at least 80% (e.g. at least 85%, or at least 90%) identical to SEQ ID NO:158.

Concept 20g: An antibody or a fragment thereof according to any preceding concept (but when dependent on concept 9, it is dependent on concept 9g, when dependent on concept 13, it is dependent on concept 13g, when dependent on concept 16, it is dependent on concept 16g, when dependent on concept 17, it is dependent on concept 17g, when dependent on concept 18, it is dependent on concept 18g, and when dependent on concept 19, it is dependent on concept 19g), wherein the VH domain comprises an amino acid sequence of SEQ ID NO:178, or a heavy chain variable domain amino acid sequence that is at least 80% (e.g. at least 85%, or at least 90%) identical to SEQ ID NO:178.

Concept 20h: An antibody or a fragment thereof according to any preceding concept (but when dependent on concept 9, it is dependent on concept 9h, when dependent on concept 13, it is dependent on concept 13h, when dependent on concept 16, it is dependent on concept 16h, when dependent on concept 17, it is dependent on concept 17h, when dependent on concept 18, it is dependent on concept 18h, and when dependent on concept 19, it is dependent on concept 19h), wherein the VH domain comprises an amino acid sequence of SEQ ID NO:138, or a heavy chain variable domain amino acid sequence that is at least 80% (e.g. at least 85%, or at least 90%) identical to SEQ ID NO:138.

Concept 20i: An antibody or a fragment thereof according to any preceding concept (but when dependent on concept 9, it is dependent on concept 9i, when dependent on concept 13, it is dependent on concept 13i, when dependent on concept 16, it is dependent on concept 16i, when dependent on concept 17, it is dependent on concept 17i, when dependent on concept 18, it is dependent on concept 18i, and when dependent on concept 19, it is dependent on concept 19i), wherein the VH domain comprises an amino acid sequence of SEQ ID NO:244, or a heavy chain variable domain amino acid sequence that is at least 80% (e.g. at least 85%, or at least 90%) identical to SEQ ID NO:244.

Concept 20j: An antibody or a fragment thereof according to any preceding concept (but when dependent on concept 9, it is dependent on concept 9j, when dependent on concept 13, it is dependent on concept 13j, when dependent on concept 16, it is dependent on concept 16j, when dependent on concept 17, it is dependent on concept 17j, when dependent on concept 18, it is dependent on concept 18j, and when dependent on concept 19, it is dependent on concept 19j), wherein the VH domain comprises an amino acid sequence of SEQ ID NO:264, or a heavy chain variable domain amino acid sequence that is at least 80% (e.g. at least 85%, or at least 90%) identical to SEQ ID NO:264.

Concept 20k: An antibody or a fragment thereof according to any preceding concept (but when dependent on concept 9, it is dependent on concept 9k, when dependent on concept 13, it is dependent on concept 13k, when dependent on concept 16, it is dependent on concept 16k, when dependent on concept 17, it is dependent on concept 17k, when dependent on concept 18, it is dependent on concept 18k, and when dependent on concept 19, it is dependent on concept 19k), wherein the VH domain comprises an amino acid sequence of SEQ ID NO:284, or a heavy chain variable domain amino acid sequence that is at least 80% (e.g. at least 85%, or at least 90%) identical to SEQ ID NO:284.

In one embodiment, the amino acid sequence is at least 70% identical to the specified Seq ID No. In one embodiment, the amino acid sequence is at least 75% identical to the specified Seq ID No. In one embodiment, the amino acid sequence is at least 95% identical to the specified Seq ID No. In one embodiment, the amino acid sequence is at least 96% identical to the specified Seq ID No. In one embodiment, the amino acid sequence is at least 97% identical to the specified Seq ID No. In one embodiment, the amino acid sequence is at least 98% identical to the specified Seq ID No. In one embodiment, the amino acid sequence is at least 99% identical to the specified Seq ID No. In one embodiment, the amino acid sequence is at least 99.5% identical to the specified Seq ID No.

Concept 21. The antibody or fragment according to any preceding concept comprising first and second copies of said VH domain.

Concept 22. The antibody or fragment according to any preceding concept, comprising a VL domain which comprises the CDRL1 sequence of SEQ ID NO:37 or 40, or the CRDL1 sequence of SEQ ID NO:37 or 40 comprising 3 or fewer amino acid substitutions.

Concept 22a: An antibody or a fragment thereof according to any preceding concept (but when dependent on concept 9, it is dependent on concept 9a, when dependent on concept 13, it is dependent on concept 13a, when dependent on concept 16, it is dependent on concept 16a, when dependent on concept 17, it is dependent on concept 17a, when dependent on concept 18, it is dependent on concept 18a, when dependent on concept 19, it is dependent on concept 19a, and when dependent on concept 20, it is dependent on concept 20a), comprising a VL domain, which comprises the CDRL1 sequence of SEQ ID NO:17 or 20, or the CDRL1 sequence of SEQ ID NO:17 or 20 comprising 3 or fewer amino acid substitutions.

Concept 22b: An antibody or a fragment thereof according to any preceding concept (but when dependent on concept 9, it is dependent on concept 9b, when dependent on concept 13, it is dependent on concept 13b, when dependent on concept 16, it is dependent on concept 16b, when dependent on concept 17, it is dependent on concept 17b, when dependent on concept 18, it is dependent on concept 18b, when dependent on concept 19, it is dependent on concept 19b, and when dependent on concept 20, it is dependent on concept 20b), comprising a VL domain which comprises the CDRL1 sequence of SEQ ID NO:62 or 65, or the CDRL1 sequence of SEQ ID NO:62 or 65 comprising 3 or fewer amino acid substitutions.

Concept 22c: An antibody or a fragment thereof according to any preceding concept (but when dependent on concept 9, it is dependent on concept 9c, when dependent on concept 13, it is dependent on concept 13c, when dependent on concept 16, it is dependent on concept 16c, when dependent on concept 17, it is dependent on concept 17c, when dependent on concept 18, it is dependent on concept 18c, when dependent on concept 19, it is dependent on concept 19c, and when dependent on concept 20, it is dependent on concept 20c), comprising a VL domain which comprises the CDRL1 sequence of SEQ ID NO:82 or 85, or the CDRL1 sequence of SEQ ID NO:82 or 85 comprising 2 or 1 amino acid substitution(s).

Concept 22d: An antibody or a fragment thereof according to any preceding concept (but when dependent on concept 9, it is dependent on concept 9d, when dependent on concept 13, it is dependent on concept 13d, when dependent on concept 16, it is dependent on concept 16d, when dependent on concept 17, it is dependent on concept 17d, when dependent on concept 18, it is dependent on concept 18d, when dependent on concept 19, it is dependent on concept 19d, and when dependent on concept 20, it is dependent on concept 20d), comprising a VL domain which comprises the CDRL1 sequence of SEQ ID NO:102 or 105, or the CDRL1 sequence of SEQ ID NO:102 or 105 comprising 5 or fewer amino acid substitutions.

Concept 22e: An antibody or a fragment thereof according to any preceding concept (but when dependent on concept 9, it is dependent on concept 9e, when dependent on concept 13, it is dependent on concept 13e, when dependent on concept 16, it is dependent on concept 16e, when dependent on concept 17, it is dependent on concept 17e, when dependent on concept 18, it is dependent on concept 18e, when dependent on concept 19, it is dependent on concept 19e, and when dependent on concept 20, it is dependent on concept 20e), comprising a VL domain which comprises the CDRL1 sequence of SEQ ID NO:122 or 125, or the CDRL1 sequence of SEQ ID NO:122 or 125 comprising 2 or 1 amino acid substitution(s).

Concept 22f: An antibody or a fragment thereof according to any preceding concept (but when dependent on concept 9, it is dependent on concept 9f, when dependent on concept 13, it is dependent on concept 13f, when dependent on concept 16, it is dependent on concept 16f, when dependent on concept 17, it is dependent on concept 17f, when dependent on concept 18, it is dependent on concept 18f, when dependent on concept 19, it is dependent on concept 19f, and when dependent on concept 20, it is dependent on concept 20f), comprising a VL domain which comprises the CDRL1 sequence of SEQ ID NO:162 or 165, or the CDRL1 sequence of SEQ ID NO:162 or 165 comprising 5 or fewer amino acid substitutions.

Concept 22g: An antibody or a fragment thereof according to any preceding concept (but when dependent on concept 9, it is dependent on concept 9g, when dependent on concept 13, it is dependent on concept 13g, when dependent on concept 16, it is dependent on concept 16g, when dependent on concept 17, it is dependent on concept 17g, when dependent on concept 18, it is dependent on concept 18g, when dependent on concept 19, it is dependent on concept 19g, and when dependent on concept 20, it is dependent on concept 20g), comprising a VL domain which comprises the CDRL1 sequence of SEQ ID NO:182 or 185, or the CDRL1 sequence of SEQ ID NO:182 or 185 comprising 5 or fewer amino acid substitutions.

Concept 22h: An antibody or a fragment thereof according to any preceding concept (but when dependent on concept 9, it is dependent on concept 9h, when dependent on concept 13, it is dependent on concept 13h, when dependent on concept 16, it is dependent on concept 16h, when dependent on concept 17, it is dependent on concept 17h, when dependent on concept 18, it is dependent on concept 18h, when dependent on concept 19, it is dependent on concept 19h, and when dependent on concept 20, it is dependent on concept 20h), comprising a VL domain which comprises the CDRL1 sequence of SEQ ID NO:142 or 145, or the CDRL1 sequence of SEQ ID NO:142 or 145 comprising 2 or 1 amino acid substitution(s).

Concept 22i: An antibody or a fragment thereof according to any preceding concept (but when dependent on concept 9, it is dependent on concept 9i, when dependent on concept 13, it is dependent on concept 13i, when dependent on concept 16, it is dependent on concept 16i, when dependent on concept 17, it is dependent on concept 17i, when dependent on concept 18, it is dependent on concept 18i, when dependent on concept 19, it is dependent on concept 19i, and when dependent on concept 20, it is dependent on concept 20i), comprising a VL domain which comprises the CDRL1 sequence of SEQ ID NO:248 or 251, or the CDRL1 sequence of SEQ ID NO:248 or 251 comprising 2 or 1 amino acid substitution(s).

Concept 22j: An antibody or a fragment thereof according to any preceding concept (but when dependent on concept 9, it is dependent on concept 9j, when dependent on concept 13, it is dependent on concept 13j, when dependent on concept 16, it is dependent on concept 16j, when dependent on concept 17, it is dependent on concept 17j, when dependent on concept 18, it is dependent on concept 18j, when dependent on concept 19, it is dependent on concept 19j, and when dependent on concept 20, it is dependent on concept 20j), comprising a VL domain which comprises the CDRL1 sequence of SEQ ID NO:268 or 271, or the CDRL1 sequence of SEQ ID NO:268 or 271 comprising 2 or 1 amino acid substitution(s).

Concept 22k: An antibody or a fragment thereof according to any preceding concept (but when dependent on concept 9, it is dependent on concept 9k, when dependent on concept 13, it is dependent on concept 13k, when dependent on concept 16, it is dependent on concept 16k, when dependent on concept 17, it is dependent on concept 17k, when dependent on concept 18, it is dependent on concept 18k, when dependent on concept 19, it is dependent on concept 19k, and when dependent on concept 20, it is dependent on concept 20k), comprising a VL domain which comprises the CDRL1 sequence of SEQ ID NO:288 or 291, or the CDRL1 sequence of SEQ ID NO:288 or 291 comprising 2 or 1 amino acid substitution(s).

Concept 23. The antibody or fragment according to any preceding concept, comprising a or said VL domain, which VL domain comprises the CDRL2 sequence of SEQ ID NO:38 or 41, or the CRDL2 sequence of SEQ ID NO:38 or 41 comprising 2 or 1 amino acid substitution(s), for example a CDRL2 sequence of Seq ID No:50.

Concept 23a: An antibody or a fragment thereof according to any preceding concept (but when dependent on concept 9, it is dependent on concept 9a, when dependent on concept 13, it is dependent on concept 13a, when dependent on concept 16, it is dependent on concept 16a, when dependent on concept 17, it is dependent on concept 17a, when dependent on concept 18, it is dependent on concept 18a, when dependent on concept 19, it is dependent on concept 19a, when dependent on concept 20, it is dependent on concept 20a, and when dependent on concept 22, it is dependent on concept 22a), comprising a or said VL domain, which VL domain comprises the CDRL2 sequence of SEQ ID NO:18 or 21, or the CDRL2 sequence of SEQ ID NO:18 or 21 comprising 2 or 1 amino acid substitution(s).

Concept 23b: An antibody or a fragment thereof according to any preceding concept (but when dependent on concept 9, it is dependent on concept 9b, when dependent on concept 13, it is dependent on concept 13b, when dependent on concept 16, it is dependent on concept 16b, when dependent on concept 17, it is dependent on concept 17b, when dependent on concept 18, it is dependent on concept 18b, when dependent on concept 19, it is dependent on concept 19b, when dependent on concept 20, it is dependent on concept 20b, and when dependent on concept 22, it is dependent on concept 22b), comprising a or said VL domain, which VL domain comprises the CDRL2 sequence of SEQ ID NO:63 or 66, or the CDRL2 sequence of SEQ ID NO:63 or 66 comprising one amino acid substitution.

Concept 23c: An antibody or a fragment thereof according to any preceding concept (but when dependent on concept 9, it is dependent on concept 9c, when dependent on concept 13, it is dependent on concept 13c, when dependent on concept 16, it is dependent on concept 16c, when dependent on concept 17, it is dependent on concept 17c, when dependent on concept 18, it is dependent on concept 18c, when dependent on concept 19, it is dependent on concept 19c, when dependent on concept 20, it is dependent on concept 20c, and when dependent on concept 22, it is dependent on concept 22c), comprising a or said VL domain, which VL domain comprises the CDRL2 sequence of SEQ ID NO:83 or 86, or the CDRL2 sequence of SEQ ID NO:83 or 86 comprising one amino acid substitution.

Concept 23d: An antibody or a fragment thereof according to any preceding concept (but when dependent on concept 9, it is dependent on concept 9d, when dependent on concept 13, it is dependent on concept 13d, when dependent on concept 16, it is dependent on concept 16d, when dependent on concept 17, it is dependent on concept 17d, when dependent on concept 18, it is dependent on concept 18d, when dependent on concept 19, it is dependent on concept 19d, when dependent on concept 20, it is dependent on concept 20d, and when dependent on concept 22, it is dependent on concept 22d), comprising a or said VL domain, which VL domain comprises the CDRL2 sequence of SEQ ID NO:103 or 106, or the CDRL2 sequence of SEQ ID NO:103 or 106 comprising one amino acid substitution.

Concept 23e: An antibody or a fragment thereof according to any preceding concept (but when dependent on concept 9, it is dependent on concept 9e, when dependent on concept 13, it is dependent on concept 13e, when dependent on concept 16, it is dependent on concept 16e, when dependent on concept 17, it is dependent on concept 17e, when dependent on concept 18, it is dependent on concept 18e, when dependent on concept 19, it is dependent on concept 19e, when dependent on concept 20, it is dependent on concept 20e, and when dependent on concept 22, it is dependent on concept 22e), comprising a or said VL domain, which VL domain comprises the CDRL2 sequence of SEQ ID NO:123 or 126, or the CDRL2 sequence of SEQ ID NO:123 or 126 comprising one amino acid substitution.

Concept 23f: An antibody or a fragment thereof according to any preceding concept (but when dependent on concept 9, it is dependent on concept 9f, when dependent on concept 13, it is dependent on concept 13f, when dependent on concept 16, it is dependent on concept 16f, when dependent on concept 17, it is dependent on concept 17f, when dependent on concept 18, it is dependent on concept 18f, when dependent on concept 19, it is dependent on concept 19f, when dependent on concept 20, it is dependent on concept 20f, and when dependent on concept 22, it is dependent on concept 220, comprising a or said VL domain, which VL domain comprises the CDRL2 sequence of SEQ ID NO:153 or 156, or the CDRL2 sequence of SEQ ID NO:153 or 156 comprising one amino acid substitution.

Concept 23g: An antibody or a fragment thereof according to any preceding concept (but when dependent on concept 9, it is dependent on concept 9g, when dependent on concept 13, it is dependent on concept 13g, when dependent on concept 16, it is dependent on concept 16g, when dependent on concept 17, it is dependent on concept 17g, when dependent on concept 18, it is dependent on concept 18g, when dependent on concept 19, it is dependent on concept 19g, when dependent on concept 20, it is dependent on concept 20g, and when dependent on concept 22, it is dependent on concept 22g), comprising a or said VL domain, which VL domain comprises the CDRL2 sequence of SEQ ID NO:183 or 186, or the CDRL2 sequence of SEQ ID NO:183 or 186 comprising one amino acid substitution.

Concept 23h: An antibody or a fragment thereof according to any preceding concept (but when dependent on concept 9, it is dependent on concept 9h, when dependent on concept 13, it is dependent on concept 13h, when dependent on concept 16, it is dependent on concept 16h, when dependent on concept 17, it is dependent on concept 17h, when dependent on concept 18, it is dependent on concept 18h, when dependent on concept 19, it is dependent on concept 19h, when dependent on concept 20, it is dependent on concept 20h, and when dependent on concept 22, it is dependent on concept 22h), comprising a or said VL domain, which VL domain comprises the CDRL2 sequence of SEQ ID NO:143 or 146, or the CDRL2 sequence of SEQ ID NO:143 or 146 comprising one amino acid substitution.

Concept 23i: An antibody or a fragment thereof according to any preceding concept (but when dependent on concept 9, it is dependent on concept 9i, when dependent on concept 13, it is dependent on concept 13i, when dependent on concept 16, it is dependent on concept 16i, when dependent on concept 17, it is dependent on concept 17i, when dependent on concept 18, it is dependent on concept 18i, when dependent on concept 19, it is dependent on concept 19i, when dependent on concept 20, it is dependent on concept 20i, and when dependent on concept 22, it is dependent on concept 22i), comprising a or said VL domain, which VL domain comprises the CDRL2 sequence of SEQ ID NO:249 or 252, or the CDRL2 sequence of SEQ ID NO:249 or 252 comprising one amino acid substitution.

Concept 23j: An antibody or a fragment thereof according to any preceding concept (but when dependent on concept 9, it is dependent on concept 9j, when dependent on concept 13, it is dependent on concept 13j, when dependent on concept 16, it is dependent on concept 16j, when dependent on concept 17, it is dependent on concept 17j, when dependent on concept 18, it is dependent on concept 18j, when dependent on concept 19, it is dependent on concept 19j, when dependent on concept 20, it is dependent on concept 20j, and when dependent on concept 22, it is dependent on concept 22j), comprising a or said VL domain, which VL domain comprises the CDRL2 sequence of SEQ ID NO:269 or 272, or the CDRL2 sequence of SEQ ID NO:269 or 272 comprising one amino acid substitution.

Concept 23k: An antibody or a fragment thereof according to any preceding concept (but when dependent on concept 9, it is dependent on concept 9k, when dependent on concept 13, it is dependent on concept 13k, when dependent on concept 16, it is dependent on concept 16k, when dependent on concept 17, it is dependent on concept 17k, when dependent on concept 18, it is dependent on concept 18k, when dependent on concept 19, it is dependent on concept 19k, when dependent on concept 20, it is dependent on concept 20k, and when dependent on concept 22, it is dependent on concept 22k), comprising a or said VL domain, which VL domain comprises the CDRL2 sequence of SEQ ID NO:289 or 292, or the CDRL2 sequence of SEQ ID NO:289 or 292 comprising one amino acid substitution.

Concept 24. The antibody or fragment according to any preceding concept, comprising a or said VL domain, which VL domain comprises the CDRL3 sequence of SEQ ID NO:39 or 42, or the CRDL3 sequence of SEQ ID NO:39 or 42 comprising 4 or fewer amino acid substitutions.

Concept 24a: An antibody or a fragment thereof according to any preceding concept (but when dependent on concept 9, it is dependent on concept 9a, when dependent on concept 13, it is dependent on concept 13a, when dependent on concept 16, it is dependent on concept 16a, when dependent on concept 17, it is dependent on concept 17a, when dependent on concept 18, it is dependent on concept 18a, when dependent on concept 19, it is dependent on concept 19a, when dependent on concept 20, it is dependent on concept 20a, when dependent on concept 22, it is dependent on concept 22a, and when dependent on concept 23, it is dependent on concept 23a), comprising a or said VL domain, which VL domain comprises the CDRL3 sequence of SEQ ID NO:19 or 22, or the CDRL3 sequence of SEQ ID NO: 19 or 22 comprising 4 or fewer amino acid substitutions.

Concept 24b: An antibody or a fragment thereof according to any preceding concept (but when dependent on concept 9, it is dependent on concept 9b, when dependent on concept 13, it is dependent on concept 13b, when dependent on concept 16, it is dependent on concept 16b, when dependent on concept 17, it is dependent on concept 17b, when dependent on concept 18, it is dependent on concept 18b, when dependent on concept 19, it is dependent on concept 19b, when dependent on concept 20, it is dependent on concept 20b, when dependent on concept 22, it is dependent on concept 22b, and when dependent on concept 23, it is dependent on concept 23b), comprising a or said VL domain, which VL domain comprises the CDRL3 sequence of SEQ ID NO:64 or 67, or the CDRL3 sequence of SEQ ID NO:64 or 67 comprising 4 or fewer amino acid substitutions.

Concept 24c: An antibody or a fragment thereof according to any preceding concept (but when dependent on concept 9, it is dependent on concept 9c, when dependent on concept 13, it is dependent on concept 13c, when dependent on concept 16, it is dependent on concept 16c, when dependent on concept 17, it is dependent on concept 17c, when dependent on concept 18, it is dependent on concept 18c, when dependent on concept 19, it is dependent on concept 19c, when dependent on concept 20, it is dependent on concept 20c, when dependent on concept 22, it is dependent on concept 22c, and when dependent on concept 23, it is dependent on concept 23c), comprising a or said VL domain, which VL domain comprises the CDRL3 sequence of SEQ ID NO:84 or 87, or the CDRL3 sequence of SEQ ID NO:84 or 87 comprising 4 or fewer amino acid substitutions.

Concept 24d: An antibody or a fragment thereof according to any preceding concept (but when dependent on concept 9, it is dependent on concept 9d, when dependent on concept 13, it is dependent on concept 13d, when dependent on concept 16, it is dependent on concept 16d, when dependent on concept 17, it is dependent on concept 17d, when dependent on concept 18, it is dependent on concept 18d, when dependent on concept 19, it is dependent on concept 19d, when dependent on concept 20, it is dependent on concept 20d, when dependent on concept 22, it is dependent on concept 22d, and when dependent on concept 23, it is dependent on concept 23d), comprising a or said VL domain, which VL domain comprises the CDRL3 sequence of SEQ ID NO:104 or 107, or the CDRL3 sequence of SEQ ID NO:104 or 107 comprising 4 or fewer amino acid substitutions.

Concept 24e: An antibody or a fragment thereof according to any preceding concept (but when dependent on concept 9, it is dependent on concept 9e, when dependent on concept 13, it is dependent on concept 13e, when dependent on concept 16, it is dependent on concept 16e, when dependent on concept 17, it is dependent on concept 17e, when dependent on concept 18, it is dependent on concept 18e, when dependent on concept 19, it is dependent on concept 19e, when dependent on concept 20, it is dependent on concept 20e, when dependent on concept 22, it is dependent on concept 22e, and when dependent on concept 23, it is dependent on concept 23e), comprising a or said VL domain, which VL domain comprises the CDRL3 sequence of SEQ ID NO:124 or 127, or the CDRL3 sequence of SEQ ID NO:124 or 127 comprising 4 or fewer amino acid substitutions.

Concept 24f: An antibody or a fragment thereof according to any preceding concept (but when dependent on concept 9, it is dependent on concept 9f, when dependent on concept 13, it is dependent on concept 13f, when dependent on concept 16, it is dependent on concept 16f, when dependent on concept 17, it is dependent on concept 17f, when dependent on concept 18, it is dependent on concept 18f, when dependent on concept 19, it is dependent on concept 19f, when dependent on concept 20, it is dependent on concept 20f, when dependent on concept 22, it is dependent on concept 22f, and when dependent on concept 23, it is dependent on concept 230, comprising a or said VL domain, which VL domain comprises the CDRL3 sequence of SEQ ID NO:164 or 167, or the CDRL3 sequence of SEQ ID NO:164 or 167 comprising 4 or fewer amino acid substitutions.

Concept 24g: An antibody or a fragment thereof according to any preceding concept (but when dependent on concept 9, it is dependent on concept 9g, when dependent on concept 13, it is dependent on concept 13g, when dependent on concept 16, it is dependent on concept 16g, when dependent on concept 17, it is dependent on concept 17g, when dependent on concept 18, it is dependent on concept 18g, when dependent on concept 19, it is dependent on concept 19g, when dependent on concept 20, it is dependent on concept 20g, when dependent on concept 22, it is dependent on concept 22g, and when dependent on concept 23, it is dependent on concept 23g), comprising a or said VL domain, which VL domain comprises the CDRL3 sequence of SEQ ID NO:184 or 187, or the CDRL3 sequence of SEQ ID NO:184 or 187 comprising 4 or fewer amino acid substitutions.

Concept 24h: An antibody or a fragment thereof according to any preceding concept (but when dependent on concept 9, it is dependent on concept 9h, when dependent on concept 13, it is dependent on concept 13h, when dependent on concept 16, it is dependent on concept 16h, when dependent on concept 17, it is dependent on concept 17h, when dependent on concept 18, it is dependent on concept 18h, when dependent on concept 19, it is dependent on concept 19h, when dependent on concept 20, it is dependent on concept 20h, when dependent on concept 22, it is dependent on concept 22h, and when dependent on concept 23, it is dependent on concept 23h), comprising a or said VL domain, which VL domain comprises the CDRL3 sequence of SEQ ID NO:144 or 147, or the CDRL3 sequence of SEQ ID NO:144 or 147 comprising 4 or fewer amino acid substitutions.

Concept 24i: An antibody or a fragment thereof according to any preceding concept (but when dependent on concept 9, it is dependent on concept 9i, when dependent on concept 13, it is dependent on concept 13i, when dependent on concept 16, it is dependent on concept 16i, when dependent on concept 17, it is dependent on concept 17i, when dependent on concept 18, it is dependent on concept 18i, when dependent on concept 19, it is dependent on concept 19i, when dependent on concept 20, it is dependent on concept 20i, when dependent on concept 22, it is dependent on concept 22i, and when dependent on concept 23, it is dependent on concept 23i), comprising a or said VL domain, which VL domain comprises the CDRL3 sequence of SEQ ID NO:250 or 253, or the CDRL3 sequence of SEQ ID NO:250 or 253 comprising 4 or fewer amino acid substitutions.

Concept 24j: An antibody or a fragment thereof according to any preceding concept (but when dependent on concept 9, it is dependent on concept 9j, when dependent on concept 13, it is dependent on concept 13j, when dependent on concept 16, it is dependent on concept 16j, when dependent on concept 17, it is dependent on concept 17j, when dependent on concept 18, it is dependent on concept 18j, when dependent on concept 19, it is dependent on concept 19j, when dependent on concept 20, it is dependent on concept 20j, when dependent on concept 22, it is dependent on concept 22j, and when dependent on concept 23, it is dependent on concept 23j), comprising a or said VL domain, which VL domain comprises the CDRL3 sequence of SEQ ID NO:270 or 273, or the CDRL3 sequence of SEQ ID NO:270 or 273 comprising 4 or fewer amino acid substitutions.

Concept 24k: An antibody or a fragment thereof according to any preceding concept (but when dependent on concept 9, it is dependent on concept 9k, when dependent on concept 13, it is dependent on concept 13k, when dependent on concept 16, it is dependent on concept 16k, when dependent on concept 17, it is dependent on concept 17k, when dependent on concept 18, it is dependent on concept 18k, when dependent on concept 19, it is dependent on concept 19k, when dependent on concept 20, it is dependent on concept 20k, when dependent on concept 22, it is dependent on concept 22k, and when dependent on concept 23, it is dependent on concept 23k), comprising a or said VL domain, which VL domain comprises the CDRL3 sequence of SEQ ID NO:290 or 293, or the CDRL3 sequence of SEQ ID NO:290 or 293 comprising 4 or fewer amino acid substitutions.

Concept 25. The antibody or fragment according to any preceding concept, comprising a or said VL domain, which VL domain comprises an amino acid sequence of SEQ ID NO:43, or a light chain variable domain amino acid sequence that is at least 80% (e.g. at least 85%, or at least 90%) identical to SEQ ID NO:43 (for example the VL domain sequence in the light chain sequence of Seq ID No:50, 51 or 298).

Concept 25a: An antibody or a fragment thereof according to any preceding concept (but when dependent on concept 9, it is dependent on concept 9a, when dependent on concept 13, it is dependent on concept 13a, when dependent on concept 16, it is dependent on concept 16a, when dependent on concept 17, it is dependent on concept 17a, when dependent on concept 18, it is dependent on concept 18a, when dependent on concept 19, it is dependent on concept 19a, when dependent on concept 20, it is dependent on concept 20a, when dependent on concept 22, it is dependent on concept 22a, when dependent on concept 23, it is dependent on concept 23a, and when dependent on concept 24, it is dependent on concept 24a), wherein the VL domain comprises an amino acid sequence of SEQ ID NO:23, or a light chain variable domain amino acid sequence that is at least 80% (e.g. at least 85%, or at least 90%) identical to SEQ ID NO:23.

Concept 25b: An antibody or a fragment thereof according to any preceding concept (but when dependent on concept 9, it is dependent on concept 9b, when dependent on concept 13, it is dependent on concept 13b, when dependent on concept 16, it is dependent on concept 16b, when dependent on concept 17, it is dependent on concept 17b, when dependent on concept 18, it is dependent on concept 18b, when dependent on concept 19, it is dependent on concept 19b, when dependent on concept 20, it is dependent on concept 20b, when dependent on concept 22, it is dependent on concept 22a, when dependent on concept 23, it is dependent on concept 23b, and when dependent on concept 24, it is dependent on concept 24b), wherein the VL domain comprises an amino acid sequence of SEQ ID NO:68, or a light chain variable domain amino acid sequence that is at least 80% (e.g. at least 85%, or at least 90%) identical to SEQ ID NO:68.

Concept 25c: An antibody or a fragment thereof according to any preceding concept (but when dependent on concept 9, it is dependent on concept 9c, when dependent on concept 13, it is dependent on concept 13c, when dependent on concept 16, it is dependent on concept 16c, when dependent on concept 17, it is dependent on concept 17c, when dependent on concept 18, it is dependent on concept 18c, when dependent on concept 19, it is dependent on concept 19c, when dependent on concept 20, it is dependent on concept 20c, when dependent on concept 22, it is dependent on concept 22c, when dependent on concept 23, it is dependent on concept 23c, and when dependent on concept 24, it is dependent on concept 24c), wherein the VL domain comprises an amino acid sequence of SEQ ID NO:88, or a light chain variable domain amino acid sequence that is at least 80% (e.g. at least 85%, or at least 90%) identical to SEQ ID NO:88.

Concept 25d: An antibody or a fragment thereof according to any preceding concept (but when dependent on concept 9, it is dependent on concept 9d, when dependent on concept 13, it is dependent on concept 13d, when dependent on concept 16, it is dependent on concept 16d, when dependent on concept 17, it is dependent on concept 17d, when dependent on concept 18, it is dependent on concept 18d, when dependent on concept 19, it is dependent on concept 19d, when dependent on concept 20, it is dependent on concept 20d, when dependent on concept 22, it is dependent on concept 22d, when dependent on concept 23, it is dependent on concept 23d, and when dependent on concept 24, it is dependent on concept 24d), wherein the VL domain comprises an amino acid sequence of SEQ ID NO:108, or a light chain variable domain amino acid sequence that is at least 80% (e.g. at least 85%, or at least 90%) identical to SEQ ID NO:108.

Concept 25e: An antibody or a fragment thereof according to any preceding concept (but when dependent on concept 9, it is dependent on concept 9e, when dependent on concept 13, it is dependent on concept 13e, when dependent on concept 16, it is dependent on concept 16e, when dependent on concept 17, it is dependent on concept 17e, when dependent on concept 18, it is dependent on concept 18e, when dependent on concept 19, it is dependent on concept 19e, when dependent on concept 20, it is dependent on concept 20e, when dependent on concept 22, it is dependent on concept 22e, when dependent on concept 23, it is dependent on concept 23e, and when dependent on concept 24, it is dependent on concept 24e), wherein the VL domain comprises an amino acid sequence of SEQ ID NO:128, or a light chain variable domain amino acid sequence that is at least 80% (e.g. at least 85%, or at least 90%) identical to SEQ ID NO:128.

Concept 25f: An antibody or a fragment thereof according to any preceding concept (but when dependent on concept 9, it is dependent on concept 9f, when dependent on concept 13, it is dependent on concept 13f, when dependent on concept 16, it is dependent on concept 16f, when dependent on concept 17, it is dependent on concept 17f, when dependent on concept 18, it is dependent on concept 18f, when dependent on concept 19, it is dependent on concept 19f, when dependent on concept 20, it is dependent on concept 20f, when dependent on concept 22, it is dependent on concept 22f, when dependent on concept 23, it is dependent on concept 23f, and when dependent on concept 24, it is dependent on concept 24O, wherein the VL domain comprises an amino acid sequence of SEQ ID NO:168, or a light chain variable domain amino acid sequence that is at least 80% (e.g. at least 85%, or at least 90%) identical to SEQ ID NO:168.

Concept 25g: An antibody or a fragment thereof according to any preceding concept (but when dependent on concept 9, it is dependent on concept 9g, when dependent on concept 13, it is dependent on concept 13g, when dependent on concept 16, it is dependent on concept 16g, when dependent on concept 17, it is dependent on concept 17g, when dependent on concept 18, it is dependent on concept 18g, when dependent on concept 19, it is dependent on concept 19g, when dependent on concept 20, it is dependent on concept 20g, when dependent on concept 22, it is dependent on concept 22g, when dependent on concept 23, it is dependent on concept 23g, and when dependent on concept 24, it is dependent on concept 24g), wherein the VL domain comprises an amino acid sequence of SEQ ID NO:188, or a light chain variable domain amino acid sequence that is at least 80% (e.g. at least 85%, or at least 90%) identical to SEQ ID NO:188.

Concept 25h: An antibody or a fragment thereof according to any preceding concept (but when dependent on concept 9, it is dependent on concept 9h, when dependent on concept 13, it is dependent on concept 13h, when dependent on concept 16, it is dependent on concept 16h, when dependent on concept 17, it is dependent on concept 17h, when dependent on concept 18, it is dependent on concept 18h, when dependent on concept 19, it is dependent on concept 19h, when dependent on concept 20, it is dependent on concept 20h, when dependent on concept 22, it is dependent on concept 22h, when dependent on concept 23, it is dependent on concept 23h, and when dependent on concept 24, it is dependent on concept 24h), wherein the VL domain comprises an amino acid sequence of SEQ ID NO:148, or a light chain variable domain amino acid sequence that is at least 80% (e.g. at least 85%, or at least 90%) identical to SEQ ID NO:148.

Concept 25i: An antibody or a fragment thereof according to any preceding concept (but when dependent on concept 9, it is dependent on concept 9i, when dependent on concept 13, it is dependent on concept 13i, when dependent on concept 16, it is dependent on concept 16i, when dependent on concept 17, it is dependent on concept 17i, when dependent on concept 18, it is dependent on concept 18i, when dependent on concept 19, it is dependent on concept 19i, when dependent on concept 20, it is dependent on concept 20i, when dependent on concept 22, it is dependent on concept 22i, when dependent on concept 23, it is dependent on concept 23i, and when dependent on concept 24, it is dependent on concept 24i), wherein the VL domain comprises an amino acid sequence of SEQ ID NO:254, or a light chain variable domain amino acid sequence that is at least 80% (e.g. at least 85%, or at least 90%) identical to SEQ ID NO:254.

Concept 25j: An antibody or a fragment thereof according to any preceding concept (but when dependent on concept 9, it is dependent on concept 9j, when dependent on concept 13, it is dependent on concept 13j, when dependent on concept 16, it is dependent on concept 16j, when dependent on concept 17, it is dependent on concept 17j, when dependent on concept 18, it is dependent on concept 18j, when dependent on concept 19, it is dependent on concept 19j, when dependent on concept 20, it is dependent on concept 20j, when dependent on concept 22, it is dependent on concept 22j, when dependent on concept 23, it is dependent on concept 23j, and when dependent on concept 24, it is dependent on concept 24j), wherein the VL domain comprises an amino acid sequence of SEQ ID NO:274, or a light chain variable domain amino acid sequence that is at least 80% (e.g. at least 85%, or at least 90%) identical to SEQ ID NO:274.

Concept 25k: An antibody or a fragment thereof according to any preceding concept (but when dependent on concept 9, it is dependent on concept 9k, when dependent on concept 13, it is dependent on concept 13k, when dependent on concept 16, it is dependent on concept 16k, when dependent on concept 17, it is dependent on concept 17k, when dependent on concept 18, it is dependent on concept 18k, when dependent on concept 19, it is dependent on concept 19k, when dependent on concept 20, it is dependent on concept 20k, when dependent on concept 22, it is dependent on concept 22k, when dependent on concept 23, it is dependent on concept 23k, and when dependent on concept 24, it is dependent on concept 24k), wherein the VL domain comprises an amino acid sequence of SEQ ID NO:294, or a light chain variable domain amino acid sequence that is at least 80% (e.g. at least 85%, or at least 90%) identical to SEQ ID NO:294.

In one embodiment, the amino acid sequence is at least 70% identical to the specified Seq ID No. In one embodiment, the amino acid sequence is at least 75% identical to the specified Seq ID No. In one embodiment, the amino acid sequence is at least 95% identical to the specified Seq ID No. In one embodiment, the amino acid sequence is at least 96% identical to the specified Seq ID No. In one embodiment, the amino acid sequence is at least 97% identical to the specified Seq ID No. In one embodiment, the amino acid sequence is at least 98% identical to the specified Seq ID No. In one embodiment, the amino acid sequence is at least 99% identical to the specified Seq ID No. In one embodiment, the amino acid sequence is at least 99.5% identical to the specified Seq ID No.

Concept 26. The antibody or fragment according to any one of concepts 12 to 21, comprising first and second copies of a or said VL domain.

Concept 27. The antibody or fragment according to any preceding concept which specifically binds to cynomolgus PD-L1 as defined by Seq ID No:2.

In one embodiment, the antibody or fragment binds to cynomolgus PDL-1 with an affinity of less than 1 nM (e.g. from 1 nM to 0.01 pM or from 1 nM to 0.1 pM, or from 1 nM to 1 pM). In one embodiment, the antibody or fragment binds to cynomolgus PDL-1 with an affinity of less than 10 nM (e.g. from 10 nM to 0.01 pM or from 10 nM to 0.1 pM, or from 10 nM to 1 pM). In one embodiment, the antibody or fragment binds to cynomolgus PDL-1 with an affinity of less than 0.1 nM (e.g. from 0.1 nM to 0.01 pM or from 0.1 nM to 0.1 pM, or from 0.1 nM to 1 pM). In one embodiment, the antibody or fragment binds to cynomolgus PDL-1 with an affinity of less than 0.01 nM (e.g. from 0.011 nM to 0.01 pM or from 0.01 nM to 0.1 pM).

In one embodiment, the antibody or fragment binds to cynomolgus PD-L1 with an affinity of within 2-fold of the affinity to hPD-L1. In one embodiment, the antibody or fragment binds to cynomolgus PD-L1 with an affinity of within 4-fold of the affinity to hPD-L1. In one embodiment, the antibody or fragment binds to cynomolgus PD-L1 with an affinity of within 5-fold of the affinity to hPD-L1. In one embodiment, the antibody or fragment binds to cynomolgus PD-L1 with an affinity of within 6-fold of the affinity to hPD-L1. In one embodiment, the antibody or fragment binds to cynomolgus PD-L1 with an affinity of within 8-fold of the affinity to hPD-L1. In one embodiment, the antibody or fragment binds to cynomolgus PD-L1 with an affinity of within 10-fold of the affinity to hPD-L1.

In one embodiment, the antibody or fragment does not detectably bind to cynomolgus PD-L1. In one embodiment, the antibody or fragment does not detectably bind to murine PD-L1.

In one embodiment, the antibody or fragment binds to murine PDL-1 with an affinity of less than 1 nM (e.g. from 1 nM to 0.01 pM or from 1 nM to 0.1 pM, or from 1 nM to 1 pM). In one embodiment, the antibody or fragment binds to murine PDL-1 with an affinity of less than 10 nM (e.g. from 10 nM to 0.01 pM or from 10 nM to 0.1 pM, or from 10 nM to 1 pM). In one embodiment, the antibody or fragment binds to murine PDL-1 with an affinity of less than 0.1 nM (e.g. from 0.1 nM to 0.01 pM or from 0.1 nM to 0.1 pM, or from 0.1 nM to 1 pM). In one embodiment, the antibody or fragment binds to murine PDL-1 with an affinity of less than 0.01 nM (e.g. from 0.011 nM to 0.01 pM or from 0.01 nM to 0.1 pM).

Concept 28. The antibody or fragment according to any preceding concept, wherein the antibody or fragment comprises a kappa light chain.

Kappa light chain constant region amino acid and nucleotide sequences can be found in Seq ID Nos:206 to 215.

In one embodiment, the light chain may be a lambda light chain Lambda light chain constant region amino acid and nucleotide sequences can be found in Seq ID Nos:216 to 237.

Concept 29. The antibody or fragment according to any one of concepts 9 to 28, wherein the amino acid substitutions are conservative amino acid substitutions, optionally wherein the conservative substitutions are from one of six groups (each group containing amino acids that are conservative substitutions for one another) selected from:
1) Alanine (A), Serine (S), Threonine (T);
2) Aspartic acid (D), Glutamic acid (E);
3) Asparagine (N), Glutamine (Q);
4) Arginine (R), Lysine (K);
5) Isoleucine (I), Leucine (L), Methionine (M), Valine (V); and
6) Phenylalanine (F), Tyrosine (Y), Tryptophan (W).

Conservative substitutions may be as described above in concept 9.

Concept 30. The antibody or fragment according to any preceding concept, wherein the antibody or fragment comprises a constant region, such as a human constant region, for example an effector-null human constant region, e.g. an IgG4 constant region or an IgG1 constant region, optionally wherein the constant region is IgG4-PE (Seq ID No:199), or a disabled IgG1 as defined in Seq ID No:205.

In other embodiments, the antibody or fragment is any of the isotypes or constant regions as defined hereinabove. In one embodiment, the constant region is wild-type human IgG1 (Seq ID No:340). For example, the constant region is an effector-enabled IgG1 constant region, optionally having ADCC and/or CDC activity. In one embodiment, the constant region is engineered for enhanced ADCC and/or CDC and/or ADCP.

The IgG4 constant region may be any of the IgG4 constant region amino acid sequences, or encoded by any of the nucleic acid sequences of Seq ID Nos:192 to 203.

The antibody-dependent cell phagocytosis (ADCP) mechanism is discussed in Gill et al., "Antibody-Dependent Phagocytosis of Tumor Cells by Macrophages: A Potent Effector Mechanism of Monoclonal Antibody Therapy of Cancer", Cancer Res., 75(23), Dec. 1, 2015.

The potency of Fc-mediated effects may be enhanced by engineering the Fc domain by various established techniques. Such methods increase the affinity for certain Fc-receptors, thus creating potential diverse profiles of activation enhancement. This can achieved by modification of one or several amino acid residues (e.g. as described in Lazar et al., 2006, Proc. Natl. Acad. Sci. U.S.A., Mar. 14; 103(11): 4005-10) or by altering the natural glycosylation profile of the Fc domain by, for example, generating under fucosylated or de-fucosylated variants (as described in Natsume et al., 2009, Drug Des. Devel. Ther., 3:7-16 or by Zhou Q., Biotechnol. Bioeng., 2008, Feb. 15, 99(3):652-65)). For example, to increase ADCC, residues in the hinge region can be altered to increase binding to Fc-gamma Rill (see, for example, Shields et al., 2001, J. Biol. Chem., Mar. 2; 276(9):6591-604).

Equally, the enhancement of CDC may be achieved by amino acid changes that increase affinity for Clq, the first component of the classic complement activation cascade (see Idusogie et al., J. Immunol., 2001, 166:2571-2575). Another approach is to create a chimeric Fc domain created from human IgG1 and human IgG3 segments that exploit the higher affinity if IgG3 for Clq (Natsume et al., 2008, Cancer Res., 68: 3863-3872).

Concept 31. The antibody or fragment according to concept 30, wherein the constant region is a murine constant region.

In other embodiments, the constant region may be of any non-human mammalian origin, e.g. rat, mouse, hamster, guinea pig, dog, cat, horse, chicken, llama, dromedary, etc. In one embodiment, the constant region is a rat constant region. In another embodiment, the constant region is a llama constant region.

Concept 32. The antibody or fragment according to concept 30 or concept 31, wherein the constant region has CDC and/or ADCC activity.

Concept 33. The antibody according to any preceding concept wherein the:
a) $V_H$ domain comprises an amino acid sequence of SEQ ID No:33 and the $V_L$ domain comprises an amino acid sequence of SEQ ID No:43;
b) $V_H$ domain comprises an amino acid sequence that is at least 85% identical to SEQ ID No:33, and the $V_L$ domain comprises an amino acid sequence that is at least 85% identical to SEQ ID No:43;
c) $V_H$ domain comprises an amino acid sequence of the $V_H$ domain of SEQ ID No:47 and the $V_L$ domain comprises an amino acid sequence of SEQ ID No:43;
d) $V_H$ domain comprises an amino acid sequence of the $V_H$ domain of SEQ ID No:48 and the $V_L$ domain comprises an amino acid sequence of SEQ ID No:43;

e) V$_H$ domain comprises an amino acid sequence of the V$_H$ domain of SEQ ID No:49 and the V$_L$ domain comprises an amino acid sequence of SEQ ID No:43;

f) V$_H$ domain comprises an amino acid sequence of the V$_H$ domain of SEQ ID No:342 and the V$_L$ domain comprises an amino acid sequence of SEQ ID No:43;

g) VH domain comprises an amino acid sequence of SEQ ID No:33 and the V$_L$ domain comprises an amino acid sequence of the V$_L$ domain of SEQ ID No:50;

h) V$_H$ domain comprises an amino acid sequence of the V$_H$ domain of SEQ ID No:47 and the V$_L$ domain comprises an amino acid sequence of the V$_L$ domain of SEQ ID No:50;

i) V$_H$ domain comprises an amino acid sequence of the V$_H$ domain of SEQ ID No:48 and the V$_L$ domain comprises an amino acid sequence of the V$_L$ domain of SEQ ID No:50;

j) VH domain comprises an amino acid sequence of the V$_H$ domain of SEQ ID No:49 and the V$_L$ domain comprises an amino acid sequence of the V$_L$ domain of SEQ ID No:50;

k) V$_H$ domain comprises an amino acid sequence of the V$_H$ domain of SEQ ID No:342 and the V$_L$ domain comprises an amino acid sequence of the V$_L$ domain of SEQ ID No:50;

l) V$_H$ domain comprises an amino acid sequence of SEQ ID No:33 and the V$_L$ domain comprises an amino acid sequence of the V$_L$ domain of SEQ ID No:51;

m) V$_H$ domain comprises an amino acid sequence of the V$_H$ domain of SEQ ID No:47 and the V$_L$ domain comprises an amino acid sequence of the V$_L$ domain of SEQ ID No:51;

n) V$_H$ domain comprises an amino acid sequence of the V$_H$ domain of SEQ ID No:48 and the V$_L$ domain comprises an amino acid sequence of the V$_L$ domain of SEQ ID No:51;

o) V$_H$ domain comprise an amino acid sequence of the V$_H$ domain of SEQ ID No:49 and the V$_L$ domain comprises an amino acid sequence of the V$_L$ domain of SEQ ID No:51;

p) VH domain comprise an amino acid sequence of the V$_H$ domain of SEQ ID No:342 and the V$_L$ domain comprises an amino acid sequence of the V$_L$ domain of SEQ ID No:51;

q) VH domain comprises an amino acid sequence of SEQ ID No:33 and the V$_L$ domain comprises an amino acid sequence of the V$_L$ domain of SEQ ID No:298;

r) V$_H$ domain comprises an amino acid sequence of the V$_H$ domain of SEQ ID No:47 and the V$_L$ domain comprises an amino acid sequence of the V$_L$ domain of SEQ ID No:298;

s) V$_H$ domain comprises an amino acid sequence of the V$_H$ domain of SEQ ID No:48 and the V$_L$ domain comprises an amino acid sequence of the V$_L$ domain of SEQ ID No:298;

t) V$_H$ domain comprise an amino acid sequence of the V$_H$ domain of SEQ ID No:49 and the V$_L$ domain comprises an amino acid sequence of the V$_L$ domain of SEQ ID No:298;

u) V$_H$ domain comprise an amino acid sequence of the V$_H$ domain of SEQ ID No:342 and the V$_L$ domain comprises an amino acid sequence of the V$_L$ domain of SEQ ID No:298;

v) V$_H$ domain comprises an amino acid sequence of SEQ ID No:58 and the V$_L$ domain comprises an amino acid sequence of SEQ ID No:68;

w) VH domain comprises an amino acid sequence that is at least 85% identical to SEQ ID No:58, and the V$_L$ domain comprise an amino acid sequence that is at least 85% identical to SEQ ID No:68;

X) V$_H$ domain comprises an amino acid sequence of SEQ ID No:78 and the V$_L$ domain comprises an amino acid sequence of SEQ ID No:88;

y) VH domain comprises an amino acid sequence that is at least 85% identical to SEQ ID No:78, and the V$_L$ domain comprises an amino acid sequence that is at least 85% identical to SEQ ID No:88;

z) VH domain comprises an amino acid sequence of SEQ ID No:98 and the V$_L$ domain comprises an amino acid sequence of SEQ ID No:108;

aa) V$_H$ domain comprises an amino acid sequence that is at least 85% identical to SEQ ID No:98, and the V$_L$ domain comprises an amino acid sequence that is at least 85% identical to SEQ ID No:108;

bb) V$_H$ domain comprises an amino acid sequence of SEQ ID No:118 and the V$_L$ domain comprises an amino acid sequence of SEQ ID No:128;

cc) V$_H$ domain comprises an amino acid sequence that is at least 85% identical to SEQ ID No:118, and the V$_L$ domain comprises an amino acid sequence that is at least 85% identical to SEQ ID No:128;

dd) V$_H$ domain comprises an amino acid sequence of SEQ ID No:158 and the V$_L$ domain comprises an amino acid sequence of SEQ ID No:168;

ee) V$_H$ domain comprises an amino acid sequence that is at least 85% identical to SEQ ID No:158, and the V$_L$ domain comprises an amino acid sequence that is at least 85% identical to SEQ ID No:168;

ff) V$_H$ domain comprises an amino acid sequence of SEQ ID No:178 and the V$_L$ domain comprises an amino acid sequence of SEQ ID No:188;

gg) VH domain comprises an amino acid sequence that is at least 85% identical to SEQ ID No:178, and the V$_L$ domain comprises an amino acid sequence that is at least 85% identical to SEQ ID No:188;

hh) V$_H$ domain comprises an amino acid sequence of SEQ ID No:138 and the V$_L$ domain comprises an amino acid sequence of SEQ ID No:148;

ii) V$_H$ domain comprises an amino acid sequence that is at least 85% identical to SEQ ID No:138 and the V$_L$ domain comprises an amino acid sequence that is at least 85% identical to SEQ ID No:148;

jj) VH domain comprises an amino acid sequence of SEQ ID No:244 and the V$_L$ domain comprises an amino acid sequence of SEQ ID No:254;

kk) V$_H$ domain comprises an amino acid sequence that is at least 85% identical to SEQ ID No:244, and the V$_L$ domain comprises an amino acid sequence that is at least 85% identical to SEQ ID No:254;

ll) V$_H$ domain comprises an amino acid sequence of SEQ ID No:264 and the V$_L$ domain comprises an amino acid sequence of SEQ ID No:274;

mm) V$_H$ domain comprises an amino acid sequence that is at least 85% identical to SEQ ID No:264, and the V$_L$ domain comprises an amino acid sequence that is at least 85% identical to SEQ ID No:274;

nn) V$_H$ domain comprises an amino acid sequence of SEQ ID No:284 and the V$_L$ domain comprises an amino acid sequence of SEQ ID No:294; and oo) V$_H$ domain comprises an amino acid sequence that is at least 85% identical to SEQ ID No:284, and the V$_L$ domain comprises an amino acid sequence that is at least 85% identical to SEQ ID No:294.

In one embodiment, the amino acid sequence is at least 70% identical to the specified Seq ID No. In one embodiment, the amino acid sequence is at least 75% identical to the specified Seq ID No. In one embodiment, the amino acid sequence is at least 95% identical to the specified Seq ID No. In one embodiment, the amino acid sequence is at least 96% identical to the specified Seq ID No. In one embodiment, the amino acid sequence is at least 97% identical to the specified Seq ID No. In one embodiment, the amino acid sequence is at least 98% identical to the specified Seq ID No. In one embodiment, the amino acid sequence is at least 99% identical to the specified Seq ID No. In one embodiment, the amino acid sequence is at least 99.5% identical to the specified Seq ID No Concept 34. The antibody according to any preceding concept wherein the antibody comprises a heavy chain and a light chain, and a) the heavy chain amino acid sequence comprises an amino acid sequence of SEQ ID No:35 and the light chain amino acid sequence comprises an amino acid sequence of SEQ ID No:45;

b) the heavy chain amino acid sequence comprises an amino acid sequence that is at least 85% identical to SEQ ID No:35 and the light chain amino acid sequence comprises an amino acid sequence that is at least 85% identical to SEQ ID No:45;

c) the heavy chain amino acid sequence comprises an amino acid sequence of SEQ ID No:47 and the light chain amino acid sequence comprises an amino acid sequence of SEQ ID No:45;

d) the heavy chain amino acid sequence comprises an amino acid sequence of SEQ ID No:48 and the light chain amino acid sequence comprises an amino acid sequence of SEQ ID No:45;

e) the heavy chain amino acid sequence comprises an amino acid sequence of SEQ ID No:49 and the light chain amino acid sequence comprises an amino acid sequence of SEQ ID No:45;

f) the heavy chain amino acid sequence comprises an amino acid sequence of SEQ ID No:342 and the light chain amino acid sequence comprises an amino acid sequence of SEQ ID No:45;

g) the heavy chain amino acid sequence comprises an amino acid sequence of SEQ ID No:35 and the light chain amino acid sequence comprises an amino acid sequence of SEQ ID No:50;

h) the heavy chain amino acid sequence comprises an amino acid sequence of SEQ ID No:47 and the light chain amino acid sequence comprises an amino acid sequence of SEQ ID No:50;

i) the heavy chain amino acid sequence comprises an amino acid sequence of SEQ ID No:48 and the light chain amino acid sequence comprises an amino acid sequence of SEQ ID No:50;

j) the heavy chain amino acid sequence comprises an amino acid sequence of SEQ ID No:49 and the light chain amino acid sequence comprises an amino acid sequence of SEQ ID No:50;

k) the heavy chain amino acid sequence comprises an amino acid sequence of SEQ ID No:342 and the light chain amino acid sequence comprises an amino acid sequence of SEQ ID No:50;

l) the heavy chain amino acid sequence comprises an amino acid sequence of SEQ ID No:35 and the light chain amino acid sequence comprises an amino acid sequence of SEQ ID No:51;

m) the heavy chain amino acid sequence comprises an amino acid sequence of SEQ ID No:47 and the light chain amino acid sequence comprises an amino acid sequence of SEQ ID No:51;

n) the heavy chain amino acid sequence comprises an amino acid sequence of SEQ ID No:48 and the light chain amino acid sequence comprises an amino acid sequence of SEQ ID No:51;

o) the heavy chain amino acid sequence comprises an amino acid sequence of SEQ ID No:49 and the light chain amino acid sequence comprises an amino acid sequence of SEQ ID No:51;

p) the heavy chain amino acid sequence comprises an amino acid sequence of SEQ ID No:342 and the light chain amino acid sequence comprises an amino acid sequence of SEQ ID No:51;

q) the heavy chain amino acid sequence comprises an amino acid sequence of SEQ ID No:35 and the light chain amino acid sequence comprises an amino acid sequence of SEQ ID No:298;

r) the heavy chain amino acid sequence comprises an amino acid sequence of SEQ ID No:47 and the light chain amino acid sequence comprises an amino acid sequence of SEQ ID No:298;

s) the heavy chain amino acid sequence comprises an amino acid sequence of SEQ ID No:48 and the light chain amino acid sequence comprises an amino acid sequence of SEQ ID No:298;

t) the heavy chain amino acid sequence comprises an amino acid sequence of SEQ ID No:49 and the light chain amino acid sequence comprises an amino acid sequence of SEQ ID No:298;

u) the heavy chain amino acid sequence comprises an amino acid sequence of SEQ ID No:342 and the light chain amino acid sequence comprises an amino acid sequence of SEQ ID No:298;

v) the heavy chain amino acid sequence comprises an amino acid sequence of SEQ ID No:60 and the light chain amino acid sequence comprises an amino acid sequence of SEQ ID No:70;

w) the heavy chain amino acid sequence comprises an amino acid sequence that is at least 85% identical to SEQ ID No:60, and the light chain amino acid sequence comprises an amino acid sequence that is at least 85% identical to SEQ ID No:70;

x) the heavy chain amino acid sequence comprises an amino acid sequence of SEQ ID No:80 and the light chain amino acid sequence comprises an amino acid sequence of SEQ ID No:90;

y) the heavy chain amino acid sequence comprises an amino acid sequence that is at least 85% identical to SEQ ID No:80, and the light chain amino acid sequence comprises an amino acid sequence that is at least 85% identical to SEQ ID No:90;

z) the heavy chain amino acid sequence comprises an amino acid sequence of SEQ ID No:100 and the light chain amino acid sequence comprises an amino acid sequence of SEQ ID No:110;

aa) the heavy chain amino acid sequence comprises an amino acid sequence that is at least 85% identical to SEQ ID No:100, and the light chain amino acid sequence comprises an amino acid sequence that is at least 85% identical to SEQ ID No:110;

bb) the heavy chain amino acid sequence comprises an amino acid sequence of SEQ ID No:120 and the light chain amino acid sequence comprises an amino acid sequence of SEQ ID No:130;

cc) the heavy chain amino acid sequence comprises an amino acid sequence that is at least 85% identical to SEQ ID No:120, and the light chain amino acid sequence comprises an amino acid sequence that is at least 85% identical to SEQ ID No:130;

dd) the heavy chain amino acid sequence comprises an amino acid sequence of SEQ ID No:160 and the light chain amino acid sequence comprises an amino acid sequence of SEQ ID No:170;

ee) the heavy chain amino acid sequence comprises an amino acid sequence that is at least 85% identical to SEQ ID No:160, and the light chain amino acid sequence comprises an amino acid sequence that is at least 85% identical to SEQ ID No:170;

ff) the heavy chain amino acid sequence comprises an amino acid sequence of SEQ ID No:180 and the light chain amino acid sequence comprises an amino acid sequence of SEQ ID No:190;

gg) the heavy chain amino acid sequence comprises an amino acid sequence that is at least 85% identical to SEQ ID No:180, and the light chain amino acid sequence comprises an amino acid sequence that is at least 85% identical to SEQ ID No:190 hh) the heavy chain amino acid sequence comprises an amino acid sequence of SEQ ID No:140 and the light chain amino acid sequence comprises an amino acid sequence of SEQ ID No:150;

ii) the heavy chain amino acid sequence comprises an amino acid sequence that is at least 85% identical to SEQ ID No:140, and the light chain amino acid sequence comprises an amino acid sequence that is at least 85% identical to SEQ ID No:150;

jj) the heavy chain amino acid sequence comprises an amino acid sequence of SEQ ID No:246 and the light chain amino acid sequence comprises an amino acid sequence of SEQ ID No:256;

kk) the heavy chain amino acid sequence comprises an amino acid sequence that is at least 85% identical to SEQ ID No:246, and the light chain amino acid sequence comprises an amino acid sequence that is at least 85% identical to SEQ ID No:256;

ll) the heavy chain amino acid sequence comprises an amino acid sequence of SEQ ID No:266 and the light chain amino acid sequence comprises an amino acid sequence of SEQ ID No:276;

mm) the heavy chain amino acid sequence comprises an amino acid sequence that is at least 85% identical to SEQ ID No:266, and the light chain amino acid sequence comprises an amino acid sequence that is at least 85% identical to SEQ ID No:276;

nn) the heavy chain amino acid sequence comprises an amino acid sequence of SEQ ID No:286 and the light chain amino acid sequence comprises an amino acid sequence of SEQ ID No:296; and oo) the heavy chain amino acid sequence comprises an amino acid sequence that is at least 85% identical to SEQ ID No:286, and the light chain amino acid sequence comprises an amino acid sequence that is at least 85% identical to SEQ ID No:296.

In one embodiment, the amino acid sequence is at least 70% identical to the specified Seq ID No. In one embodiment, the amino acid sequence is at least 75% identical to the specified Seq ID No. In one embodiment, the amino acid sequence is at least 95% identical to the specified Seq ID No. In one embodiment, the amino acid sequence is at least 96% identical to the specified Seq ID No. In one embodiment, the amino acid sequence is at least 97% identical to the specified Seq ID No. In one embodiment, the amino acid sequence is at least 98% identical to the specified Seq ID No. In one embodiment, the amino acid sequence is at least 99% identical to the specified Seq ID No. In one embodiment, the amino acid sequence is at least 99.5% identical to the specified Seq ID No.

Concept 35. The antibody or fragment according to any preceding concept which competes for binding to hPD-L1 with the antibody 1D05, optionally wherein the competition for binding to hPDL-1 is conducted using SPR.

SPR may be carried out as described hereinabove, or as described in concept 16.

Concept 36. The antibody or fragment according to any preceding concept wherein the antibody or fragment is capable of inhibiting PD-L1-mediated suppression of T-cells, optionally wherein the suppression of T-cells is measured by an increase in one or more of IFNγ, IL-2, CD25 or proliferation of T-cells in an assay that provides co-stimulation by either direct CD3/CD28 stimulation, super-antigen stimulation or provides co-stimulation by co-incubation with cells capable of inducing a T-cell response.

The measurements may be carried out with any suitable technique. For example, the measurements may be taken with ELISA, HTRF, BRDU incorporation (proliferation), electrochemiluminescence (ECL) or flow cytometry (e.g. FACS). These techniques are well-known to those skilled in the art and are described elsewhere herein. In one embodiment, the assay is flow cytometry. In one embodiment, the assay is ELISA. In one embodiment, the assay is HTRF.

In one embodiment, the suppression of T-cells is measured by an increase in IFNγ. In one embodiment, the suppression of T-cells is measured by an increase in IL-2. In one embodiment, the suppression of T-cells is measured by an increase in CD25. In one embodiment, the suppression of T-cells is measured by an increase in IFNγ and IL-2. In one embodiment, the suppression of T-cells is measured by an increase in IFNγ and CD25. In one embodiment, the suppression of T-cells is measured by an increase in CD25 and IL-2. In one embodiment, the suppression of T-cells is measured by an increase in IFNγ, IL-2 and CD25.

In one embodiment, the co-stimulation is provided by direct CD3/CD28 stimulation.

In one embodiment, the co-stimulation is provided by a superantigen, such as staphylococcal enterotoxin B (SEB).

In one embodiment, the assay provides co-stimulation by co-incubation with cells capable of inducing a T-cell response. Such cells may be antigen-presenting cells (APCs), for example monocytes, B-cells or dendritic cells. In one embodiment, the assay provides co-stimulation by co-incubation with APCs. In one embodiment, the assay provides co-stimulation by co-incubation with monocytes. In one embodiment, the assay provides co-stimulation by co-incubation with B-cells. In one embodiment, the assay provides co-stimulation by co-incubation with dendritic cells.

Concept 37. A bispecific antibody or fusion protein comprising an antibody or fragment thereof as defined in any preceding concept.

Concept 37a. A dual binding antibody or fusion protein comprising an antibody or fragment thereof as defined in any preceding concept.

A dual binding antibody has the meaning as set out above.

Concept 38. The bispecific antibody according to concept 37, wherein the bispecific format is selected from DVD-Ig, mAb2, FIT-Ig, mAb-dAb, dock and lock, SEEDbody, scDiabody-Fc, diabody-Fc, tandem scFv-Fc, Fab-scFv-Fc, Fab-scFv, intrabody, BiTE, diabody, DART, TandAb, scDiabody, scDiabody-CH3, Diabody-CH3, minibody, knobs-in-holes, knobs-in-holes with common light chain, knobs-in-holes with common light chain and charge pairs, charge pairs, charge pairs with common light chain, in particular mAb2, knob-in-holes, knob-in-holes with common light chain, knobs-in-holes with common light chain and charge pairs and FIT-Ig, e.g. mAb2 and FIT-Ig.

In one embodiment, the bispecific format is selected from DVD-Ig, mAb2, FIT-Ig, mAb-dAb, dock and lock, Fab-arm exchange, SEEDbody, Triomab, LUZ-Y, Fcab, κλ-body, orthogonal Fab, scDiabody-Fc, diabody-Fc, tandem scFv-Fc, Fab-scFv-Fc, Fab-scFv, intrabody, BiTE, diabody, DART, TandAb, scDiabody, scDiabody-CH3, Diabody-CH3, Triple body, Miniantibody, minibody, TriBi minibody, scFv-CH3 KIH, scFv-CH-CL-scFv, F(ab')2-scFv, scFv-KIH, Fab-scFv-Fc, tetravalent HCab, ImmTAC, knobs-in-holes, knobs-in-holes with common light chain, knobs-in-holes with common light chain and charge pairs, charge pairs, charge pairs with common light chain, DT-IgG, DutaMab, IgG(H)-scFv, scFv-(H)IgG, IgG(L)-scFv, scFv-(L)IgG, IgG(L,H)-Fv, IgG(H)-V, V(H)-IgG, IgG(L)-V, V(L)-IgG, KIH IgG-scFab, 2scFv-IgG, IgG-2scFv, scFv4-Ig and zybody.

In one embodiment, the bispecific format is selected from DVD-Ig, FIT-Ig, mAb-dAb, dock and lock, Fab-arm exchange, SEEDbody, Triomab, LUZ-Y, Fcab, κλ-body, orthogonal Fab, scDiabody-Fc, diabody-Fc, tandem scFv-Fc, Fab-scFv-Fc, Fab-scFv, intrabody, BiTE, diabody, DART, TandAb, scDiabody, scDiabody-CH3, Diabody-CH3, Triple body, Miniantibody, minibody, TriBi minibody, scFv-CH3 KIH, scFv-CH-CL-scFv, F(ab')2-scFv, scFv-KIH, Fab-scFv-Fc, tetravalent HCab, ImmTAC, knobs-in-holes, knobs-in-holes with common light chain, knobs-in-holes with common light chain and charge pairs, charge pairs, charge pairs with common light chain, DT-IgG, DutaMab, IgG(H)-scFv, scFv-(H)IgG, IgG(L)-scFv, scFv-(L)IgG, IgG(L,H)-Fv, IgG(H)-V, V(H)-IgG, IgG(L)-V, V(L)-IgG, KIH IgG-scFab, 2scFv-IgG, IgG-2scFv, scFv4-Ig and zybody, for example DVD-Ig, FIT-Ig, mAb-dAb, dock and lock, SEEDbody, scDiabody-Fc, diabody-Fc, tandem scFv-Fc, Fab-scFv-Fc, Fab-scFv, intrabody, BiTE, diabody, DART, TandAb, scDiabody, scDiabody-CH3, Diabody-CH3, minibody, knobs-in-holes, knobs-in-holes with common light chain, knobs-in-holes with common light chain and charge pairs, charge pairs, charge pairs with common light chain, in particular knob-in-holes, knob-in-holes with common light chain, knobs-in-holes with common light chain and charge pairs and FIT-Ig, e.g. FIT-Ig.

In one embodiment, the bispecific format is selected from DVD-Ig, mAb2, mAb-dAb, dock and lock, Fab-arm exchange, SEEDbody, Triomab, LUZ-Y, Fcab, κλ-body, orthogonal Fab, scDiabody-Fc, diabody-Fc, tandem scFv-Fc, Fab-scFv-Fc, Fab-scFv, intrabody, BiTE, diabody, DART, TandAb, scDiabody, scDiabody-CH3, Diabody-CH3, Triple body, Miniantibody, minibody, TriBi minibody, scFv-CH3 KIH, scFv-CH-CL-scFv, F(ab')2-scFv, scFv-KIH, Fab-scFv-Fc, tetravalent HCab, ImmTAC, knobs-in-holes, knobs-in-holes with common light chain, knobs-in-holes with common light chain and charge pairs, charge pairs, charge pairs with common light chain, DT-IgG, DutaMab, IgG(H)-scFv, scFv-(H)IgG, IgG(L)-scFv, scFv-(L)IgG, IgG(L,H)-Fv, IgG(H)-V, V(H)-IgG, IgG(L)-V, V(L)-IgG, KIH IgG-scFab, 2scFv-IgG, IgG-2scFv, scFv4-Ig and zybody, for example DVD-Ig, mAb2, mAb-dAb, dock and lock, SEEDbody, scDiabody-Fc, diabody-Fc, tandem scFv-Fc, Fab-scFv-Fc, Fab-scFv, intrabody, BiTE, diabody, DART, TandAb, scDiabody, scDiabody-CH3, Diabody-CH3, minibody, knobs-in-holes, knobs-in-holes with common light chain, knobs-in-holes with common light chain and charge pairs, charge pairs, charge pairs with common light chain, in particular mAb2, knob-in-holes, knob-in-holes with common light chain, knobs-in-holes with common light chain and charge pairs, and knob-in-holes with common light chain, e.g. mAb2.

In one embodiment, the bispecific format is selected from DVD-Ig, mAb-dAb, dock and lock, Fab-arm exchange, SEEDbody, Triomab, LUZ-Y, Fcab, κλ-body, orthogonal Fab, scDiabody-Fc, diabody-Fc, tandem scFv-Fc, Fab-scFv-Fc, Fab-scFv, intrabody, BiTE, diabody, DART, TandAb, scDiabody, scDiabody-CH3, Diabody-CH3, Triple body, Miniantibody, minibody, TriBi minibody, scFv-CH3 KIH, scFv-CH-CL-scFv, F(ab')2-scFv, scFv-KIH, Fab-scFv-Fc, tetravalent HCab, ImmTAC, knobs-in-holes, knobs-in-holes with common light chain, knobs-in-holes with common light chain and charge pairs, charge pairs, charge pairs with common light chain, DT-IgG, DutaMab, IgG(H)-scFv, scFv-(H)IgG, IgG(L)-scFv, scFv-(L)IgG, IgG(L,H)-Fv, IgG(H)-V, V(H)-IgG, IgG(L)-V, V(L)-IgG, KIH IgG-scFab, 2scFv-IgG, IgG-2scFv, scFv4-Ig and zybody, for example DVD-Ig, mAb-dAb, dock and lock, SEEDbody, scDiabody-Fc, diabody-Fc, tandem scFv-Fc, Fab-scFv-Fc, Fab-scFv, intrabody, BiTE, diabody, DART, TandAb, scDiabody, scDiabody-CH3, Diabody-CH3, minibody, knobs-in-holes, knobs-in-holes with common light chain, knobs-in-holes with common light chain and charge pairs, charge pairs, charge pairs with common light chain, in particular knob-in-holes, knobs-in-holes with common light chain and charge pairs, and knob-in-holes with common light chain.

Concept 39. The bispecific antibody according to concept 37 or concept 38, wherein the bispecific antibody specifically binds to hPD-L1 and another target antigen selected from immune checkpoint inhibitors (such as PD-1, CTLA-4, TIGIT, TIM-3, LAG-3 and VISTA, e.g. TIGIT, TIM-3 and LAG-3), immune modulators (such as BTLA, hHVEM, CSF1R, CCR4, CD39, CD40, CD73, CD96, CXCR2, CXCR4, CD200, GARP, SIRPα, CXCL9, CXCL10 and CD155, e.g. GARP, SIRPα, CXCR4, BTLA, hVEM and CSF1R), immune activators (such as CD137, GITR, OX40, CD40, CXCR3 (e.g. agonistic anti-CXCR3 antibodies), CD3, ICOS (e.g. agonistic anti-ICOS antibodies), for example. ICOS, CD137, GITR and OX40).

In one embodiment, the another target antigen is an immune checkpoint inhibitor, such as PD-1, CTLA-4, TIGIT, TIM-3, LAG-3 and VISTA, e.g. TIGIT, CTLA-4, TIM-3 and LAG-3. In one embodiment, the another target antigen is an immune modulator, such as BTLA, hHVEM, CSF1R, CCR4, CD39, CD40, CD73, CD96, CXCR2, CXCR4, CD200, GARP, SIRPα, CXCL9, CXCL10 and CD155, e.g. GARP, SIRPα, CXCR4, BTLA, hVEM and CSF1R. In one embodiment, the another target antigen is an immune activator, such as CD137, GITR, OX40, CD40, CXCR3 (e.g. agonistic anti-CXCR3 antibodies), CD3 and ICOS (e.g. agonistic anti-ICOS antibodies), for example ICOS, CD137, GITR and OX40). In one embodiment, the another target antigen is CTLA-4. In one embodiment, the another target antigen is TIGIT. In one embodiment, the another target antigen is TIM-3. In one embodiment, the another target antigen is LAG-3. In one embodiment, the another target antigen is GITR. In one embodiment, the another target antigen is VISTA. In one embodiment, the another target antigen is CD137. In one embodiment, the another target antigen is SIRPa. In one embodiment, the another target antigen is CXCL10. In one embodiment, the another target antigen is CD155. In one embodiment, the another target antigen is CD40.

Concept 40. The bispecific antibody according to concept 39, wherein the another target antigen is TIGIT or LAG3.

In any of concepts 37 to 40, if the antibody or fragment thereof has the heavy and light variable region sequences of 84G09, then the bispecific antibody shall be interpreted as not including a mAb2 format wherein the Fcab has binding affinity to LAG3.

In one embodiment, the bispecific antibody has a FIT-Ig format which comprises a full antibody (e.g. an antibody comprising a light chain comprising a VL and CL and a heavy chain comprising VH, CH1, CH2 and CH3) which binds hPD-L1 (optionally wherein the antibody has a structure as defined in any one of concepts 1 to 40) and a Fab which binds TIGIT. In one embodiment, the bispecific antibody has a FIT-Ig format which comprises a full antibody (e.g. an antibody comprising a light chain comprising a VL and CL and a heavy chain comprising VH, CH1, CH2 and CH3) which binds TIGIT and a Fab which binds hPD-L1 (optionally wherein the antibody has a structure as defined in any one of concepts 1 to 40).

In one embodiment, the bispecific antibody has a FIT-Ig format which comprises a full antibody (e.g. an antibody comprising a light chain comprising a VL and CL and a heavy chain comprising VH, CH1, CH2 and CH3) which binds hPD-L1 (optionally wherein the antibody has a structure as defined in any one of concepts 1 to 40) and a Fab which binds GITR. In one embodiment, the bispecific antibody has a FIT-Ig format which comprises a full antibody (e.g. an antibody comprising a light chain comprising a VL and CL and a heavy chain comprising VH, CH1, CH2 and CH3) which binds GITR and a Fab which binds hPD-L1 (optionally wherein the antibody has a structure as defined in any one of concepts 1 to 40).

In one embodiment, the bispecific antibody has a FIT-Ig format which comprises a full antibody (e.g. an antibody comprising a light chain comprising a VL and CL and a heavy chain comprising VH, CH1, CH2 and CH3) which binds hPD-L1 (optionally wherein the antibody has a structure as defined in any one of concepts 1 to 40) and a Fab which binds ICOS (e.g. binds with agonistic activity). In one embodiment, the bispecific antibody has a FIT-Ig format which comprises a full antibody (e.g. an antibody comprising a light chain comprising a VL and CL and a heavy chain comprising VH, CH1, CH2 and CH3) which binds ICOS (e.g. binds with agonistic activity) and a Fab which binds hPD-L1 (optionally wherein the antibody has a structure as defined in any one of concepts 1 to 40).

In one embodiment, the bispecific antibody has a FIT-Ig format which comprises a full antibody (e.g. an antibody comprising a light chain comprising a VL and CL and a heavy chain comprising VH, CH1, CH2 and CH3) which binds hPD-L1 (optionally wherein the antibody has a structure as defined in any one of concepts 1 to 40) and a Fab which binds TIM-3. In one embodiment, the bispecific antibody has a FIT-Ig format which comprises a full antibody (e.g. an antibody comprising a light chain comprising a VL and CL and a heavy chain comprising VH, CH1, CH2 and CH3) which binds TIM-3 and a Fab which binds hPD-L1 (optionally wherein the antibody has a structure as defined in any one of concepts 1 to 40).

In one embodiment, the bispecific antibody has a FIT-Ig format which comprises a full antibody (e.g. an antibody comprising a light chain comprising a VL and CL and a heavy chain comprising VH, CH1, CH2 and CH3) which binds hPD-L1 (optionally wherein the antibody has a structure as defined in any one of concepts 1 to 40) and a Fab which binds CD137. In one embodiment, the bispecific antibody has a FIT-Ig format which comprises a full antibody (e.g. an antibody comprising a light chain comprising a VL and CL and a heavy chain comprising VH, CH1, CH2 and CH3) which binds CD137 and a Fab which binds hPD-L1 (optionally wherein the antibody has a structure as defined in any one of concepts 1 to 40).

In one embodiment, the bispecific antibody has a FIT-Ig format which comprises a full antibody (e.g. an antibody comprising a light chain comprising a VL and CL and a heavy chain comprising VH, CH1, CH2 and CH3) which binds hPD-L1 (optionally wherein the antibody has a structure as defined in any one of concepts 1 to 40) and a Fab which binds CD3. In one embodiment, the bispecific antibody has a FIT-Ig format which comprises a full antibody (e.g. an antibody comprising a light chain comprising a VL and CL and a heavy chain comprising VH, CH1, CH2 and CH3) which binds CD3 and a Fab which binds hPD-L1 (optionally wherein the antibody has a structure as defined in any one of concepts 1 to 40).

Any of the targets listed above may be applied to the FIT-Ig structure.

Concept 41. An antibody or fragment as defined in any preceding concept for use in treating or preventing a hPD-L1-mediated disease or condition, e.g. selected from neoplastic or non-neoplastic disease, chronic viral infections, and malignant tumours, such as melanoma, Merkel cell carcinoma, non-small cell lung cancer (squamous and non-squamous), renal cell cancer, bladder cancer, head and neck squamous cell carcinoma, mesothelioma, virally induced cancers (such as cervical cancer and nasopharyngeal cancer), soft tissue sarcomas, haematological malignancies such as Hodgkin's and non-Hodgkin's disease and diffuse large B-cell lymphoma (for example melanoma, Merkel cell carcinoma, non-small cell lung cancer (squamous and non-squamous), renal cell cancer, bladder cancer, head and neck squamous cell carcinoma and mesothelioma or for example virally induced cancers (such as cervical cancer and nasopharyngeal cancer) and soft tissue sarcomas).

Concept 42. Use of an antibody or fragment as defined in any one of concepts 1 to 40 in the manufacture of a medicament for administration to a human for treating or preventing a hPD-L1 mediated disease or condition in the human, e.g. selected from neoplastic or non-neoplastic disease, chronic viral infections, and malignant tumours, such as melanoma, Merkel cell carcinoma, non-small cell lung cancer (squamous and non-squamous), renal cell cancer, bladder cancer, head and neck squamous cell carcinoma, mesothelioma, virally induced cancers (such as cervical cancer and nasopharyngeal cancer), soft tissue sarcomas, haematological malignancies such as Hodgkin's and non-Hodgkin's disease and diffuse large B-cell lymphoma (for example melanoma, Merkel cell carcinoma, non-small cell lung cancer (squamous and non-squamous), renal cell cancer, bladder cancer, head and neck squamous cell carcinoma and mesothelioma or for example virally induced cancers (such as cervical cancer and nasopharyngeal cancer) and soft tissue sarcomas).

Concept 43. A method of treating or preventing a hPD-L1 mediated disease or condition, e.g. selected from neoplastic or non-neoplastic disease, chronic viral infections, and malignant tumours, such as melanoma, Merkel cell carcinoma, non-small cell lung cancer (squamous and non-squamous), renal cell cancer, bladder cancer, head and neck squamous cell carcinoma, mesothelioma, virally induced cancers (such as cervical cancer and nasopharyngeal cancer), soft tissue sarcomas, haematological malignancies such as Hodgkin's and non-Hodgkin's disease and diffuse large B-cell lymphoma (for example melanoma, Merkel cell carcinoma, non-small cell lung cancer (squamous and non-squamous), renal cell cancer, bladder cancer, head and neck squamous cell carcinoma and mesothelioma or for example virally induced cancers (such as cervical cancer and nasopharyngeal cancer) and soft tissue sarcomas) in a human, comprising administering to said human a therapeutically effective amount of an antibody or fragment as defined in any one of concepts 1 to 40, wherein the hPD-L1 mediated disease or condition is thereby treated or prevented.

In any of concepts 41 to 43, the hPD-L1 mediated disease may be any of those as described herein. In one embodiment, in any of concepts 41 to 43, the hPD-L1 mediated disease is a virally induced cancer, such as cervical cancer and nasopharyngeal cancer, for example cervical cancers caused by HPV infection. In one embodiment, in any of concepts 41 to 43, the hPD-L1 mediated disease is a chronic viral infection. In one embodiment, in any of concepts 41 to 43, the hPD-L1 mediated disease is a neoplastic disease. In one embodiment, in any of concepts 41 to 43, the hPD-L1 mediated disease is a non-neoplastic disease. In one embodiment, in any of concepts 41 to 43, the hPD-L1 mediated disease is a malignant tumour. In one embodiment, in any of concepts 41 to 43, the hPD-L1 mediated disease is a cancer which is known to be responsive to PD-L1 therapy, such as melanoma, Merkel cell carcinoma, non-small cell lung cancer (squamous and non-squamous), renal cell cancer, bladder cancer, head and neck squamous cell carcinoma, mesothelioma. In one embodiment, in any of concepts 41 to 43, the hPD-L1 mediated disease is a cancer which is a soft tissue sarcoma.

Concept 44. The antibody or fragment according to concept 41, the use according to concept 42 or the method according to concept 43, wherein the hPD-L1-mediated disease or condition is cancer.

Concept 45. The antibody or fragment, the use or the method according to concept 44, wherein the cancer is selected from melanoma, Merkel cell carcinoma, non-small cell lung cancer (squamous and non-squamous), renal cell cancer, bladder cancer, head and neck squamous cell carcinoma and mesothelioma or is selected from virally induced cancers (such as cervical cancer and nasopharyngeal cancer) and soft tissue sarcomas.

Concept 46. The antibody or fragment, use or the method according to any one of concepts 41 to 45, further comprising administering to the human a further therapy, for example a further therapeutic agent, optionally wherein the further therapeutic agent is independently selected from the group consisting of:
  a. other immune checkpoint inhibitors (such as anti-TIM-3 antibodies, anti-CTLA-4 antibodies, anti-TIGIT antibodies and anti-LAG-3 antibodies);
  b. immune stimulators (such as anti-OX40 antibodies, anti-GITR antibodies, anti-CD137 antibodies, anti-ICOS antibodies and anti-CD40 antibodies);
  c. chemokine receptor antagonists (such as CXCR4, CCR4 and CXCR2);
  d. targeted kinase inhibitors (such as CSF-1R or VEGFR inhibitors);
  e. angiogenesis inhibitors (such as anti-VEGF-A or Delta-like Ligand-4);
  f. immune stimulating peptides or chemokines (such as CXCL9 or CXCL10);
  g. cytokines (such as IL-15 and IL-21);
  h. bispecific T-cell engagers (BiTEs) having at least one specificity against CD3 (e.g. CD3/CD19 BiTE);
  i. other bi-specific molecules (for example IL-15-containing molecules targeted towards tumour associated antigens, for example Epidermal growth factor receptors such as EGFR, Her-2, New York Esophageal Cancer-1 (NY-ESO-1), GD2, EpCAM or Melanoma Associated Antigen-3 (MAGE-A3));
  j. oncolytic viruses (such as HSV virus (optionally which secretes GMCSF), Newcastle disease virus and Vaccinia virus);
  k. vaccination with tumour associated antigens (such as New York Esophageal Cancer-1 [NY-ESO-1], Melanoma Associated Antigen-3 [MAGE-3]);
  l. cell-based therapies (such as chimeric Antigen Receptor-T cells (CAR-T) for example expressing anti-CD19, anti-EpCam or anti-mesothelin); and
  m. adoptive transfer of tumour specific T-cells or LAK cells, or optionally wherein the further therapy is chemotherapy, radiotherapy and surgical removal of tumours.

Chemotherapeutic agents may any as described hereinabove, in particular agents that induce immunogenic cell death, for example platinum therapies, such as oxaliplatin. In one embodiment, the chemotherapy is a standard of care cytotoxic chemotherapy for the cancer being treated.

In this aspect, the bispecific molecules include "bispecific antibodies" and antibody fusion proteins, including those formats and molecules described in concepts 37 to 40.

The further therapeutic agents of this concept may be delivered by any method, which methods are well-known to those skilled in the art. For example, the further therapeutic agents may be delivered orally, systemically or locally (to the tumour environment). In one embodiment, the further therapeutic agent is delivered orally. In one embodiment, the further therapeutic agent is delivered systemically (e.g. intravenously). In one embodiment, the further therapeutic agent is delivered locally to the tumour environment.

Compositions and routes of administration are described in more detail hereinbelow.

Concept 47. The antibody or fragment, use or the method according to concept 46, wherein the further therapeutic agent is administered sequentially or simultaneously with the anti-hPD-L1 antibody or fragment.

Concept 48. A pharmaceutical composition comprising an antibody of fragment as defined in any one of concepts 1 to 40 and a pharmaceutically acceptable excipient, diluent or carrier and optionally further comprising a further therapeutic agent independently selected from the group consisting of:
  a) other immune checkpoint inhibitors (such as anti-TIM-3 antibodies, anti-CTLA-4 antibodies, anti-TIGIT antibodies and anti-LAG-3 antibodies);
  b) immune stimulators (such as anti-OX40 antibodies, anti-GITR antibodies, anti-CD137 antibodies, anti-ICOS antibodies and anti-CD40 antibodies);
  c) chemokine receptor antagonists (such as CXCR4, CCR4 and CXCR2);
  d) targeted kinase inhibitors (such as CSF-1R or VEGFR inhibitors);
  e) angiogenesis inhibitors (such as anti-VEGF-A or Delta-like Ligand-4);
  f) immune stimulating peptides or chemokines (such as CXCL9 or CXCL10);
  g) cytokines (such as IL-15 and IL-21);
  h) bispecific T-cell engagers (BiTEs) having at least one specificity against CD3 (e.g. CD3/CD19 BiTE);
  i) other bi-specific molecules (for example IL-15-containing molecules targeted towards tumour associated antigens, for example Epidermal growth factor receptors such as EGFR, Her-2, New York Esophageal Cancer-1 (NY-ESO-1), GD2, EpCAM or Melanoma Associated Antigen-3 (MAGE-A3));

j) oncolytic viruses (such as HSV virus (optionally which secretes GMCSF), Newcastle disease virus and Vaccinia virus);

k) vaccination with tumour associated antigens (such as New York Esophageal Cancer-1 [NY-ESO-1], Melanoma Associated Antigen-3 [MAGE-3]);

l) cell-based therapies (such as chimeric Antigen Receptor-T cells (CAR-T) for example expressing anti-CD19, anti-EpCam or anti-mesothelin); and m) adoptive transfer of tumour specific T-cells or LAK cells.

Pharmaceutical formulations are well-known to those skilled in the art. In one embodiment, the antibody or fragment is administered intravenously. In one embodiment, the antibody or fragment is administered subcutaneously.

In an example, an antibody or fragment as disclosed herein is contained in a medical container, e.g., a vial, syringe, IV container or an injection device (such as an intraocular or intravitreal injection device). In an example, the antibody or fragment is in vitro, for example, in a sterile container.

In one embodiment, the composition is formulated in accordance with routine procedures as a pharmaceutical composition adapted for intravenous administration to human beings. Typically, compositions for intravenous administration are solutions in sterile isotonic aqueous buffer. Where necessary, the composition may also include a solubilizing agent and a local anesthetic such as lignocamne to ease pain at the site of the injection. Such compositions, however, may be administered by a route other than intravenous.

Generally, the ingredients of compositions are supplied either separately or mixed together in unit dosage form, for example, as a dry lyophilized powder or water free concentrate in a hermetically sealed container such as an ampoule or sachette indicating the quantity of active agent. Where the composition is to be administered by infusion, it can be dispensed with an infusion bottle containing sterile pharmaceutical grade water or saline. Where the composition is administered by injection, an ampoule of sterile water for injection or saline can be provided so that the ingredients may be mixed prior to administration.

In this aspect, the bispecific molecules include "bispecific antibodies" and antibody fusion proteins, including those formats and molecules described in concepts 37 to 40.

The further therapeutic agents of this concept may be delivered by any method, which methods are well-known to those skilled in the art. For example, the further therapeutic agents may be delivered orally, systemically or locally (to the tumour environment). In one embodiment, the further therapeutic agent is delivered orally. In one embodiment, the further therapeutic agent is delivered systemically (e.g. intravenously). In one embodiment, the further therapeutic agent is delivered locally to the tumour environment.

Concept 49. A pharmaceutical composition according to concept 48, or a kit comprising a pharmaceutical composition as defined in concept 48, wherein the composition is for treating and/or preventing a hPD-L1-mediated condition or disease, e.g. selected from neoplastic or non-neoplastic disease, chronic viral infections, and malignant tumours, such as melanoma, Merkel cell carcinoma, non-small cell lung cancer (squamous and non-squamous), renal cell cancer, bladder cancer, head and neck squamous cell carcinoma, mesothelioma, virally induced cancers (such as cervical cancer and nasopharyngeal cancer), soft tissue sarcomas, haematological malignancies such as Hodgkin's and non-Hodgkin's disease, diffuse large B-cell lymphoma.

Concept 50. A pharmaceutical composition according to concept 48 or concept 49 in combination with, or kit according to concept 49 comprising, a label or instructions for use to treat and/or prevent said disease or condition in a human; optionally wherein the label or instructions comprise a marketing authorisation number (e.g., an FDA or EMA authorisation number); optionally wherein the kit comprises an IV or injection device that comprises the antibody or fragment.

Concept 51. A method of modulating PD-1/PD-L1 interaction in a patient, comprising administering an effective amount of an antibody or fragment as defined in any one of concepts 1 to 40 to said patient.

In another embodiment, there is provided a method of modulating CD80/PD-L1 interaction in a patient, comprising administering an effective amount of an antibody or fragment as defined in any one of concepts 1 to 40 to said patient. In another embodiment, the antibody or fragment modulates CD80/PD-L1 interaction, but does not modulate PD-1/PD-L1 interaction. In another embodiment, the antibody or fragment blocks CD80/PD-L1 interaction, but does not block PD-1/PD-L1 interaction. In another embodiment, the antibody or fragment inhibits CD80/PD-L1 interaction, but does not inhibit PD-1/PD-L1 interaction.

Concept 52. A method of inhibiting PD-L1 activity in a patient, comprising administering an effective amount of an antibody or fragment as defined in any one of concepts 1 to 40 to said patient.

In one embodiment, the antibody or fragment blocks or inhibits PD-1 binding to PD-L1. In one embodiment, the antibody or fragment blocks or inhibits CD80 binding to PD-L1.

Concept 53. A method of treating a proliferative disease in an animal (e.g. a human), comprising administering an effective amount of an antibody or fragment as defined in any one of concepts 1 to 40 to said patient.

Proliferative diseases may be any as described elsewhere herein.

Concept 54. A method of detecting PD-L1 expression in a sample, comprising contacting the sample with an antibody or fragment as defined in any one of concepts 1 to 40.

Concept 55. A method comprising contacting a biological sample with an antibody or fragment as defined in any one of concepts 1 to 40 to form a complex with PD-L1 present in the sample and measuring the presence, absence or level of the complex in the biological sample.

Concept 56. The method according to concept 55, wherein the presence, absence and/or level of PD-L1 expression is detected prior to treatment and a high level of surface expressed PD-L1 is indicative of successful treatment.

Concept 57. The method according to concept 55, wherein the presence, absence and/or level of PD-L1 expression is detected during treatment as an early response biomarker.

Concept 58. The method according to concept 55 or concept 57, wherein the presence, absence and/or level of PD-L1 expression is detected during or after treatment to help determine one or more of: whether treatment has been successful, whether treatment should continue, and/or whether treatment should be modified.

Concept 59. The method according to any one of concepts 55 to 58, wherein therapy comprises treatment with an anti-PD-L1 antibody, optionally as defined in any one of concepts 1 to 40.

Concept 60. A method for monitoring therapy efficacy, the method comprising detecting expression of surface expressed PD-L1 in a patient prior to therapy, and during or after therapy, wherein an antibody or fragment as defined in any one of concepts 1 to 40 is used to detect expression of surface expressed PD-L1.

Concept 61. The method according to concept 60, wherein surface expressed PD-L1 expression is detected in vivo.

Concept 62. The method according to concept 60, wherein surface expressed PD-L1 expression is detected in a tissue sample in vitro.

Concept 63. A method for identifying binding partners for PD-L1, the method comprising immunoprecipitating an intact protein complex comprising PD-L1 using an antibody or fragment as defined in any one of concepts 1 to 40.

Concept 64. A method of diagnosing a disease in a human subject associated with altered PD-L1 expression comprising the steps of contacting a biological sample from the human subject with an antibody as defined in concepts 1 to 40 to form a complex between the antibody and PD-L1 present in the sample; and detecting the amount of the complex.

Concept 65. A nucleic acid that encodes the CDRH3 of an antibody or fragment as defined in any one of concepts 1 to 40.

Concept 65a. There is also provided a nucleic acid that encodes the CDRH2 of an antibody or fragment as defined in any one of concepts 1 to 40.

Concept 65b. There is also provided a nucleic acid that encodes the CDRH1 of an antibody or fragment as defined in any one of concepts 1 to 40.

Concept 65c. There is also provided a nucleic acid that encodes the CDRL1 of an antibody or fragment as defined in any one of concepts 1 to 40.

Concept 65d. There is also provided a nucleic acid that encodes the CDRL2 of an antibody or fragment as defined in any one of concepts 1 to 40.

Concept 65e. There is also provided a nucleic acid that encodes the CDRL3 of an antibody or fragment as defined in any one of concepts 1 to 40.

In one embodiment, the nucleic acid is an isolated and purified nucleic acid.

Concept 66. A nucleic acid that encodes a VH domain and/or a VL domain of an antibody or fragment as defined in any one of concepts 1 to 40.

The $V_H$ and $V_L$ domain nucleic acid sequences of the invention are provided in the sequence listing. In one embodiment, the nucleic acid sequence is at least 70% identical to the specified Seq ID No. In one embodiment, the nucleic acid sequence is at least 75% identical to the specified Seq ID No. In one embodiment, the nucleic acid sequence is at least 95% identical to the specified Seq ID No. In one embodiment, the nucleic acid sequence is at least 96% identical to the specified Seq ID No. In one embodiment, the nucleic acid sequence is at least 97% identical to the specified Seq ID No. In one embodiment, the nucleic acid sequence is at least 98% identical to the specified Seq ID No. In one embodiment, the nucleic acid sequence is at least 99% identical to the specified Seq ID No. In one embodiment, the nucleic acid sequence is at least 99.5% identical to the specified Seq ID No.

Concept 67. The nucleic acid according to concept 66 comprising a nucleotide sequence that is at least 80% identical to the sequence of SEQ ID NO:36 and/or SEQ ID NO:46.

Concept 67a. A nucleic acid according to concept 66 comprising a nucleotide sequence that is at least 80% identical to the sequence of SEQ ID NO:16 and/or SEQ ID NO:26.

Concept 67b. A nucleic acid according to concept 66 comprising a nucleotide sequence that is at least 80% identical to the sequence of SEQ ID NO:61 and/or SEQ ID NO:71.

Concept 67c. A nucleic acid according to concept 66 comprising a nucleotide sequence that is at least 80% identical to the sequence of SEQ ID NO:81 and/or SEQ ID NO:91.

Concept 67d. A nucleic acid according to concept 66 comprising a nucleotide sequence that is at least 80% identical to the sequence of SEQ ID NO:101 and/or SEQ ID NO:111.

Concept 67e. A nucleic acid according to concept 66 comprising a nucleotide sequence that is at least 80% identical to the sequence of SEQ ID NO:121 and/or SEQ ID NO:131.

Concept 67f. A nucleic acid according to concept 66 comprising a nucleotide sequence that is at least 80% identical to the sequence of SEQ ID NO:161 and/or SEQ ID NO:171.

Concept 67g. A nucleic acid according to concept 66 comprising a nucleotide sequence that is at least 80% identical to the sequence of SEQ ID NO:181 and/or SEQ ID NO:191.

Concept 67h. A nucleic acid according to concept 66 comprising a nucleotide sequence that is at least 80% identical to the sequence of SEQ ID NO:141 and/or SEQ ID NO:151.

Concept 67i. A nucleic acid according to concept 66 comprising a nucleotide sequence that is at least 80% identical to the sequence of SEQ ID NO:247 and/or SEQ ID NO:257.

Concept 67j. A nucleic acid according to concept 66 comprising a nucleotide sequence that is at least 80% identical to the sequence of SEQ ID NO:267 and/or SEQ ID NO:277.

Concept 67k. A nucleic acid according to concept 66 comprising a nucleotide sequence that is at least 80% identical to the sequence of SEQ ID NO:287 and/or SEQ ID NO:297.

In one embodiment, the nucleic acid sequence is at least 70% identical to the specified Seq ID No. In one embodiment, the nucleic acid sequence is at least 75% identical to the specified Seq ID No. In one embodiment, the nucleic acid sequence is at least 95% identical to the specified Seq ID No. In one embodiment, the nucleic acid sequence is at least 96% identical to the specified Seq ID No. In one embodiment, the nucleic acid sequence is at least 97% identical to the specified Seq ID No. In one embodiment, the nucleic acid sequence is at least 98% identical to the specified Seq ID No. In one embodiment, the nucleic acid sequence is at least 99% identical to the specified Seq ID No. In one embodiment, the nucleic acid sequence is at least 99.5% identical to the specified Seq ID No.

Concept 68. A nucleic acid that encodes a heavy chain or a light chain of an antibody as defined in any one of concepts 1 to 40.

Concept 69. A vector comprising the nucleic acid of any one of concepts 65 to 68; optionally wherein the vector is a CHO or HEK293 vector.

Concept 70. A host comprising the nucleic acid of any one of concepts 65 to 68 or the vector of concept 69.

The inventors have described immunocytokines which comprise an antibody which binds to an immune checkpoint inhibitor, such as PD-L1 fused to either the N-terminus or C-terminus of the heavy chain or the light chain (for example, the C-terminus of the heavy or light chain, and in particular the light chain). The immunocytokines comprise a cytokine molecule, which may be IL-2 or a variant thereof (including variant having a 1 to 10 amino acid deletion at the N-terminus). The antibodies as described hereinabove may be used in any immunocytokine described herein.

Without being bound by theory, immunocytokines of the invention may provide one or more of the following advantageous properties:
  synergistic activity (by virtue of therapeutic activity of antibody Fab portion in combination with the cytokine)
  improved tumour targeting
  ability to retain effector functions such as CDC, ADCC and/or ADCP
  reduced off-target effects
  reduced toxicity (e.g. compared to free cytokine or cytokine when fused to the heavy chain of an immunocytokine)
  reduced immunogenicity
  lower dose/frequency of dosing
  Specificity for blocking only one of the ligands of PD-L1 (e.g. blocks CD80/PD-L1 interaction, but not PD-1/PD-L1 interaction)
  Solubility
  Stability
  Ease of formulation
  Frequency of dosing and/or route of administration
  Manufacturability (e.g. expression, ease of purification, isoforms)

1D05 ICK comprises a heavy chain amino acid sequence of Seq ID No:299, and a light chain amino acid sequence of Seq ID No:300. The light chain comprises a V$_L$ domain comprising the CDRs and V$_L$ sequence of antibody 1D05 described hereinabove, fused at the heavy chain to full length, wild-type, human IL-2 cytokine. It does not contain a linker peptide. The heavy chain comprises a V$_H$ domain comprising the CDRs and V$_H$ sequence of antibody 1D05 described hereinabove, fused to a disabled IgG constant region (Seq ID No:205).

1D05 D5-9 ICK comprises a heavy chain comprising a VH region amino acid sequence of Seq ID No:33 (comprising the CDRs of 1D05 as described hereinabove) fused to a disabled IgG1 constant region with an amino acid sequence of Seq ID No:205. The light chain comprises a VL amino acid sequence of Seq ID No:43 (comprising the CDRs of 1D05 as described hereinabove) directly fused at the C-terminus to IL-2 D5-9 (Seq ID No:303), which is directly fused to amino acids 21 to 133 of hIL-2 (Seq ID No:324).

1D05 D1-9 ICK comprises a heavy chain comprising a VH region amino acid sequence of Seq ID No:33 (comprising the CDRs of 1D05 as described hereinabove) fused to a disabled IgG1 constant region with an amino acid sequence of Seq ID No:205. The light chain comprises a VL amino acid sequence of Seq ID No:43 (comprising the CDRs of 1D05 as described hereinabove) directly fused at the C-terminus to IL-2 D1-9 (Seq ID No:304), which is directly fused to amino acids 21 to 133 of hIL-2 (Seq ID No:324).

1D05 D5-7 ICK comprises a heavy chain comprising a VH region amino acid sequence of Seq ID No:33 (comprising the CDRs of 1D05 as described hereinabove) fused to a disabled IgG1 constant region with an amino acid sequence of Seq ID No:205. The light chain comprises a VL amino acid sequence of Seq ID No:43 (comprising the CDRs of 1D05 as described hereinabove) directly fused at the C-terminus to IL-2 D5-7 (Seq ID No:305), which is directly fused to amino acids 21 to 133 of hIL-2 (Seq ID No:324).

1D05 D1 ICK comprises a heavy chain comprising a VH region amino acid sequence of Seq ID No:33 (comprising the CDRs of 1D05 as described hereinabove) fused to a disabled IgG1 constant region with an amino acid sequence of Seq ID No:205. The light chain comprises a VL amino acid sequence of Seq ID No:43 (comprising the CDRs of 1D05 as described hereinabove) directly fused at the C-terminus to IL-2 D1 (Seq ID No:306), which is directly fused to amino acids 21 to 133 of hIL-2 (Seq ID No:324).

1D05 D1-2 ICK comprises a heavy chain comprising a VH region amino acid sequence of Seq ID No:33 (comprising the CDRs of 1D05 as described hereinabove) fused to a disabled IgG1 constant region with an amino acid sequence of Seq ID No:205. The light chain comprises a VL amino acid sequence of Seq ID No:43 (comprising the CDRs of 1D05 as described hereinabove) directly fused at the C-terminus to IL-2 D1-2 (Seq ID No:307), which is directly fused to amino acids 21 to 133 of hIL-2 (Seq ID No:324).

1D05 D1-3 ICK comprises a heavy chain comprising a VH region amino acid sequence of Seq ID No:33 (comprising the CDRs of 1D05 as described hereinabove) fused to a disabled IgG1 constant region with an amino acid sequence of Seq ID No:205. The light chain comprises a VL amino acid sequence of Seq ID No:43 (comprising the CDRs of 1D05 as described hereinabove) directly fused at the C-terminus to IL-2 D1-3 (Seq ID No:308), which is directly fused to amino acids 21 to 133 of hIL-2 (Seq ID No:324).

1D05 D1-4 ICK comprises a heavy chain comprising a VH region amino acid sequence of Seq ID No:33 (comprising the CDRs of 1D05 as described hereinabove) fused to a disabled IgG1 constant region with an amino acid sequence of Seq ID No:205. The light chain comprises a VL amino acid sequence of Seq ID No:43 (comprising the CDRs of 1D05 as described hereinabove) directly fused at the C-terminus to IL-2 D1-4 (Seq ID No:309), which is directly fused to amino acids 21 to 133 of hIL-2 (Seq ID No:324).

1D05 D1-5 ICK comprises a heavy chain comprising a VH region amino acid sequence of Seq ID No:33 (comprising the CDRs of 1D05 as described hereinabove) fused to a disabled IgG1 constant region with an amino acid sequence of Seq ID No:205. The light chain comprises a VL amino acid sequence of Seq ID No:43 (comprising the CDRs of 1D05 as described hereinabove) directly fused at the C-terminus to IL-2 D1-5 (Seq ID No:310), which is directly fused to amino acids 21 to 133 of hIL-2 (Seq ID No:324).

1D05 D1-6 ICK comprises a heavy chain comprising a VH region amino acid sequence of Seq ID No:33 (comprising the CDRs of 1D05 as described hereinabove) fused to a disabled IgG1 constant region with an amino acid sequence of Seq ID No:205. The light chain comprises a VL amino acid sequence of Seq ID No:43 (comprising the CDRs of 1D05 as described hereinabove) directly fused at the C-terminus to IL-2 D1-6 (Seq ID No:311), which is directly fused to amino acids 21 to 133 of hIL-2 (Seq ID No:324).

1D05 D1-7 ICK comprises a heavy chain comprising a VH region amino acid sequence of Seq ID No:33 (comprising the CDRs of 1D05 as described hereinabove) fused to a disabled IgG1 constant region with an amino acid sequence of Seq ID No:205. The light chain comprises a VL amino acid sequence of Seq ID No:43 (comprising the CDRs of 1D05 as described hereinabove) directly fused at the C-terminus to IL-2 D1-7 (Seq ID No:312), which is directly fused to amino acids 21 to 133 of hIL-2 (Seq ID No:324).

1D05 D1-8 ICK comprises a heavy chain comprising a VH region amino acid sequence of Seq ID No:33 (comprising the CDRs of 1D05 as described hereinabove) fused to a disabled IgG1 constant region with an amino acid sequence of Seq ID No:205. The light chain comprises a VL amino acid sequence of Seq ID No:43 (comprising the CDRs of 1D05 as described hereinabove) directly fused at the C-terminus to IL-2 D1-8 (Seq ID No:313), which is directly fused to amino acids 21 to 133 of hIL-2 (Seq ID No:324).

1D05 D9 ICK comprises a heavy chain comprising a VH region amino acid sequence of Seq ID No:33 (comprising the CDRs of 1D05 as described hereinabove) fused to a disabled IgG1 constant region with an amino acid sequence of Seq ID No:205. The light chain comprises a VL amino acid sequence of Seq ID No:43 (comprising the CDRs of 1D05 as described hereinabove) directly fused at the C-terminus to IL-2 D9 (Seq ID No:314), which is directly fused to amino acids 21 to 133 of hIL-2 (Seq ID No:324).

1D05 D9-8 ICK comprises a heavy chain comprising a VH region amino acid sequence of Seq ID No:33 (comprising the CDRs of 1D05 as described hereinabove) fused to a disabled IgG1 constant region with an amino acid sequence of Seq ID No:205. The light chain comprises a VL amino acid sequence of Seq ID No:43 (comprising the CDRs of 1D05 as described hereinabove) directly fused at the C-terminus to IL-2 D9-8 (Seq ID No:315), which is directly fused to amino acids 21 to 133 of hIL-2 (Seq ID No:324).

1D05 D9-7 ICK comprises a heavy chain comprising a VH region amino acid sequence of Seq ID No:33 (comprising the CDRs of 1D05 as described hereinabove) fused to a disabled IgG1 constant region with an amino acid sequence of Seq ID No:205. The light chain comprises a VL amino acid sequence of Seq ID No:43 (comprising the CDRs of 1D05 as described hereinabove) directly fused at the C-terminus to IL-2 D9-7 (Seq ID No:316), which is directly fused to amino acids 21 to 133 of hIL-2 (Seq ID No:324).

1D05 D9-6 ICK comprises a heavy chain comprising a VH region amino acid sequence of Seq ID No:33 (comprising the CDRs of 1D05 as described hereinabove) fused to a disabled IgG1 constant region with an amino acid sequence of Seq ID No:205. The light chain comprises a VL amino acid sequence of Seq ID No:43 (comprising the CDRs of 1D05 as described hereinabove) directly fused at the C-terminus to IL-2 D9-6 (Seq ID No:317), which is directly fused to amino acids 21 to 133 of hIL-2 (Seq ID No:324).

1D05 D9-4 ICK comprises a heavy chain comprising a VH region amino acid sequence of Seq ID No:33 (comprising the CDRs of 1D05 as described hereinabove) fused to a disabled IgG1 constant region with an amino acid sequence of Seq ID No:205. The light chain comprises a VL amino acid sequence of Seq ID No:43 (comprising the CDRs of 1D05 as described hereinabove) directly fused at the C-terminus to IL-2 D9-4 (Seq ID No:318), which is directly fused to amino acids 21 to 133 of hIL-2 (Seq ID No:324).

1D05 D9-3 ICK comprises a heavy chain comprising a VH region amino acid sequence of Seq ID No:33 (comprising the CDRs of 1D05 as described hereinabove) fused to a disabled IgG1 constant region with an amino acid sequence of Seq ID No:205. The light chain comprises a VL amino acid sequence of Seq ID No:43 (comprising the CDRs of 1D05 as described hereinabove) directly fused at the C-terminus to IL-2 D9-3 (Seq ID No:319), which is directly fused to amino acids 21 to 133 of hIL-2 (Seq ID No:324).

1D05 D9-2 ICK comprises a heavy chain comprising a VH region amino acid sequence of Seq ID No:33 (comprising the CDRs of 1D05 as described hereinabove) fused to a disabled IgG1 constant region with an amino acid sequence of Seq ID No:205. The light chain comprises a VL amino acid sequence of Seq ID No:43 (comprising the CDRs of 1D05 as described hereinabove) directly fused at the C-terminus to IL-2 D9-2 (Seq ID No:320), which is directly fused to amino acids 21 to 133 of hIL-2 (Seq ID No:324).

1D05 D2-6 ICK comprises a heavy chain comprising a VH region amino acid sequence of Seq ID No:33 (comprising the CDRs of 1D05 as described hereinabove) fused to a disabled IgG1 constant region with an amino acid sequence of Seq ID No:205. The light chain comprises a VL amino acid sequence of Seq ID No:43 (comprising the CDRs of 1D05 as described hereinabove) directly fused at the C-terminus to IL-2 D2-6 (Seq ID No:321), which is directly fused to amino acids 21 to 133 of hIL-2 (Seq ID No:324).

1D05 D3-7 ICK comprises a heavy chain comprising a VH region amino acid sequence of Seq ID No:33 (comprising the CDRs of 1D05 as described hereinabove) fused to a disabled IgG1 constant region with an amino acid sequence of Seq ID No:205. The light chain comprises a VL amino acid sequence of Seq ID No:43 (comprising the CDRs of 1D05 as described hereinabove) directly fused at the C-terminus to IL-2 D3-7 (Seq ID No:322), which is directly fused to amino acids 21 to 133 of hIL-2 (Seq ID No:324).

IL-2 D4-8 ICK comprises a heavy chain comprising a VH region amino acid sequence of Seq ID No:33 (comprising the CDRs of 1D05 as described hereinabove) fused to a disabled IgG1 constant region with an amino acid sequence of Seq ID No:205. The light chain comprises a VL amino acid sequence of Seq ID No:43 (comprising the CDRs of 1D05 as described hereinabove) directly fused at the C-terminus to IL-2 D4-8 (Seq ID No:323), which is directly fused to amino acids 21 to 133 of hIL-2 (Seq ID No:324).

In any of the ICK constructs above, the VH region of the 1D05 antibody may be exchanged for the VH region of mutated 1D05—Heavy Chain mutant 1 (Seq ID No:47), mutated 1D05—Heavy Chain mutant 2 (Seq ID No:48), mutated 1D05—Heavy Chain mutant 3 (Seq ID No:49) or mutated 1D05—Heavy Chain mutant 4 (Seq ID No:342).

In any of the ICK constructs above, the VL region of the 1D05 antibody may be exchanged for the VL region of mutated 1D05-Light Chain mutant 1 (Seq ID No:50), mutated 1D05

Light Chain mutant 2 (Seq ID No:51) or mutated 1D05-Light Chain mutant 3 (Seq ID No:298).

In any of the ICK constructs above, both the VH and VL region of the 1D05 antibody may be exchanged for both the VH and VL regions of any of the other antibodies described herein, i.e. 84G09, 411B08, 411C04, 411D07, 385F01, 413D08, 386H03, 389A03, 413G05, 413F09 and 414B06.

Immunocytokines may be described in the following sentences or aspects. Unless otherwise apparent, the features of any of the concepts described hereinabove apply mutatis mutandis to any of the aspects hereinbelow.

Aspect 1. An immunocytokine comprising an immunoglobulin heavy chain and an immunoglobulin light chain, wherein the heavy chain comprises in N- to C-terminal direction:

a) A $V_H$ domain comprising CDRH1, CDRH2 and CDRH3; and
b) A heavy chain constant region;
and wherein the light chain comprises in N- to C-terminal direction:
c) A $V_L$ domain comprising CDRL1, CDRL2 and CDRL3;
d) A light chain constant region, ($C_L$);
e) Optionally, a linker, (L); and
f) An IL-2 cytokine;
wherein the $V_H$ domain and $V_L$ domain are comprised by an antigen-binding site that specifically binds to hPD-L1 as defined by Seq ID No:1, and competes for binding to said hPD-L1 with the antibody 1D05; and
wherein the immunocytokine comprises a $V_H$ domain which comprises a CDRH3 comprising the motif $X_1GSGX_2YGX_3X_4FD$, wherein $X_1$, $X_2$ and $X_3$ are independently any amino acid, and $X_4$ is either present or absent, and if present, may be any amino acid.

In the aspects described herein, CDR sequences may be determined according to any method known to those skilled in the art, such as using the Kabat method, the IMGT method or the Chothia method, each of which are described in more detail herein. In one embodiment, the CDR regions are human CDR regions.

In addition to the CDR regions, the VH and/or VL domains may further comprise framework regions, such as FW1, FW2 and FW3. The VH and/or VL domains may be of any origin described herein, and may be for example, fully human, humanised, murine or camelid. In one embodiment, the VH and/or VL domains are human VH and/or VL domains. CDRs may be of a non-human origin (e.g. mouse origin) and be grafted onto human framework regions. In another embodiment, the CDRs are synthetic.

In another embodiment, VH regions may be selected from the group consisting of an antibody variable domain (e.g., a VL or a VH, an antibody single variable domain (domain antibody or dAb), a camelid VHH antibody single variable domain, a shark immunoglobulin single variable domain (NARV), a Nanobody™ or a camelised VH single variable domain); a T-cell receptor binding domain; an immunoglobulin superfamily domain; an agnathan variable lymphocyte receptor; a fibronectin domain (e.g., an Adnectin™); an antibody constant domain (e.g., a CH3 domain, e.g., a CH2 and/or CH3 of an Fcab™) wherein the constant domain is not a functional CH1 domain; an scFv; an (scFv)2; an sc-diabody; an scFab; a centyrin and an epitope binding domain derived from a scaffold selected from CTLA-4 (Evibody™); a lipocalin domain; Protein A such as Z-domain of Protein A (e.g., an Affibody™ or SpA); an A-domain (e.g., an Avimer™ or Maxibody™); a heat shock protein (such as and epitope binding domain derived from GroEI and GroES); a transferrin domain (e.g., a trans-body); ankyrin repeat protein (e.g., a DARPin™); peptide aptamer; C-type lectin domain (e.g., Tetranectin™); human γ-crystallin or human ubiquitin (an affilin); a PDZ domain; scorpion toxin; and a kunitz type domain of a human protease inhibitor.

The constant region comprises at least two heavy chain constant region domains selected from CH1, CH2, CH3 and CH4. In one embodiment, the constant region comprises (or consists of) a CH1 domain and a CH2 domain. In one embodiment, the constant region comprises (or consists of) a CH1 domain, a hinge region and a CH2 domain. In one embodiment, the constant region comprises (or consists of) a CH1 domain and a CH3 domain, and optionally a hinge region. In one embodiment, the constant region comprises (or consists of) a CH1 domain and a CH4 domain, and optionally a hinge region. In one embodiment, the constant region comprises (or consists of) a CH1 domain, a CH2 domain and a CH3 domain, and optionally a hinge region. In one embodiment, the constant region comprises (or consists of) a CH1 domain, a CH2 domain and a CH4 domain, and optionally a hinge region. In one embodiment, the constant region comprises (or consists of) a CH1 domain, a CH3 domain and a CH4 domain, and optionally a hinge region. In one embodiment, the constant region comprises (or consists of) a full constant region.

The constant region may be of any isotype described herein, e.g. IgA, IgD, IgE, IgG, and IgM. In one embodiment, the constant region is of any origin described herein, and may be for example, human, murine or camelid. In one embodiment, the constant region is a (full) human constant region. In one embodiment, the constant region is a human IgG constant region. In one embodiment, the constant region is a (full) human IgG1 constant region. In one embodiment, the constant region is an effector null (full) human IgG1 constant region. In one embodiment, the constant region has CDC and/or ADCC and/or ADCP activity. In one embodiment, the constant region is engineered to enhance the CDC and/or ADCC and/or ADCP activity. The constant region may be any of the constant regions described in concepts 30 to 32 hereinabove.

The light chain constant region may be a kappa or lambda light chain constant region. The light chain constant region may be as described in concept 28 hereinabove.

An IL-2 cytokine is a cytokine molecule which confers IL-2 activity on one or both of the intermediate affinity IL-2 Receptor (αβ) and the high affinity IL-2 receptor (αβγ). An IL-2 cytokine includes variant IL-2 cytokines. An IL-2 cytokine may be of human origin or of non-human origin, for example of a non-human mammal, including, but not limit to, primates (e.g. monkeys such a rhesus macaque or cynomolgus), rodents (such as mice, rats and guinea pigs) farm animals, (such as cattle, sheep, pigs, goats, horses, chickens, turkeys, ducks and geese), and domestic mammals (such as dogs and cats). In one embodiment, an IL-2 cytokine is a human IL-2 cytokine.

As used herein, a "variant IL-2 cytokine" is a cytokine having up to 10 amino acids deleted from the N terminal sequence, in combination with up to 5 amino acid substitutions, deletions or additions elsewhere in the IL-2 cytokine. In one embodiment, the variant IL-2 cytokine comprises (or consists of) up to 10 (e.g. 1, 2, 3, 4, 5, 6, 7, 8, 9 or 10) amino acid deletions from the N-terminal sequence (e.g. within the first 20, or first 15, or first 10 amino acids of the wild-type IL-2 sequence in question), in combination with up to 5 (e.g. 1, 2, 3, 4 or 5) amino acid substitutions elsewhere in the IL-2 cytokine. In one embodiment, the variant IL-2 cytokine comprises (or consists of) up to 10 (e.g. 1, 2, 3, 4, 5, 6, 7, 8, 9 or 10) amino acid deletions from the N-terminal sequence (e.g. within the first 15 amino acids of the wild-type IL-2 sequence in question), in combination with up to 5 (e.g. 1, 2, 3, 4 or 5) amino acid substitutions elsewhere in the IL-2 cytokine. In one embodiment, the variant IL-2 cytokine comprises (or consists of) up to 10 (e.g. 1, 2, 3, 4, 5, 6, 7, 8, 9 or 10) amino acid deletions from the N-terminal sequence (e.g. within the first 10 amino acids of the wild-type IL-2 sequence in question), in combination with up to 5 (e.g. 1, 2, 3, 4 or 5) amino acid substitutions elsewhere in the IL-2 cytokine. In one embodiment, the variant IL-2 cytokine comprises (or consists of) up to 10 (e.g. 1, 2, 3, 4, 5, 6, 7, 8, 9 or 10) amino acid deletions from the N-terminal sequence (e.g. within the first 10 amino acids of the wild-type IL-2 sequence in question), in combination with up to 4 (e.g. 1, 2, 3 or 4) amino acid substitutions elsewhere in the IL-2 cytokine. In one embodiment, the variant IL-2 cytokine comprises (or consists of) up to 10 (e.g. 1, 2, 3, 4, 5, 6, 7, 8, 9 or 10) amino acid deletions from the N-terminal sequence (e.g. within the first 10 amino acids of the wild-type IL-2 sequence in question), in combination with up to 3 (e.g. 1, 2 or 3) amino acid substitutions elsewhere in the IL-2 cytokine. In one embodiment, the variant IL-2 cytokine comprises (or consists of) up to 10 (e.g. 1, 2, 3, 4, 5, 6, 7, 8, 9 or 10) amino acid deletions from the N-terminal sequence (e.g. within the first 10 amino acids of the wild-type IL-2 sequence in question), in combination with up to 2 (e.g. 1 or 2) amino acid substitutions elsewhere in the IL-2 cytokine. In one embodiment, the variant IL-2 cytokine comprises (or consists of) up to 10 (e.g. 1, 2, 3, 4, 5, 6, 7, 8, 9 or 10) amino acid deletions from the N-terminal sequence (e.g. within the first 10 amino acids of the wild-type IL-2 sequence in question), in combination with 1 amino acid substitution elsewhere in the IL-2 cytokine.

In one embodiment, the variant IL-2 cytokine comprises (or consists of) up to 9 (e.g. 1, 2, 3, 4, 5, 6, 7, 8 or 9) amino acid deletions from the N-terminal sequence (e.g. within the first 20, or first 15, or first 10 amino acids of the wild-type IL-2 sequence in question), in combination with up to 4 (e.g. 1, 2, 3 or 4) amino acid substitutions elsewhere in the IL-2 cytokine. In one embodiment, the variant IL-2 cytokine comprises (or consists of) up to 9 (e.g. 1, 2, 3, 4, 5, 6, 7, 8 or 9) amino acid deletions from the N-terminal sequence (e.g. within the first 20, or first 15, or first 10 amino acids of the wild-type IL-2 sequence in question), in combination with up to 4 (e.g. 1, 2, 3 or 4) amino acid substitutions elsewhere in the IL-2 cytokine. In one embodiment, the variant IL-2 cytokine comprises (or consists of) up to 9 (e.g. 1, 2, 3, 4, 5, 6, 7, 8 or 9) amino acid deletions from the N-terminal sequence (e.g. within the first 20, or first 15, or first 10 amino acids of the wild-type IL-2 sequence in question), in combination with up to 4 (e.g. 1, 2, 3 or 4) amino acid substitutions elsewhere in the IL-2 cytokine.

In one embodiment, the variant IL-2 cytokine comprises (or consists of) up to 8 (e.g. 1, 2, 3, 4, 5, 6, 7 or 8) amino acid deletions from the N-terminal sequence (e.g. within the first 20, or first 15, or first 10 amino acids of the wild-type IL-2 sequence in question), in combination with up to 4 (e.g. 1, 2, 3 or 4) amino acid substitutions elsewhere in the IL-2 cytokine. In one embodiment, the variant IL-2 cytokine comprises (or consists of) up to 8 (e.g. 1, 2, 3, 4, 5, 6, 7 or 8) amino acid deletions from the N-terminal sequence (e.g. within the first 20, or first 15, or first 10 amino acids of the wild-type IL-2 sequence in question), in combination with up to 4 (e.g. 1, 2, 3 or 4) amino acid substitutions elsewhere in the IL-2 cytokine. In one embodiment, the variant IL-2 cytokine comprises (or consists of) up to 8 (e.g. 1, 2, 3, 4, 5, 6, 7 or 8) amino acid deletions from the N-terminal sequence (e.g. within the first 20, or first 15, or first 10 amino acids of the wild-type IL-2 sequence in question), in combination with up to 4 (e.g. 1, 2, 3 or 4) amino acid substitutions elsewhere in the IL-2 cytokine.

In one embodiment, the variant IL-2 cytokine comprises (or consists of) up to 7 (e.g. 1, 2, 3, 4, 5, 6 or 7) amino acid deletions from the N-terminal sequence (e.g. within the first 20, or first 15, or first 10 amino acids of the wild-type IL-2 sequence in question), in combination with up to 4 (e.g. 1, 2, 3 or 4) amino acid substitutions elsewhere in the IL-2 cytokine. In one embodiment, the variant IL-2 cytokine comprises (or consists of) up to 7 (e.g. 1, 2, 3, 4, 5, 6 or 7) amino acid deletions from the N-terminal sequence (e.g. within the first 20, or first 15, or first 10 amino acids of the wild-type IL-2 sequence in question), in combination with up to 4 (e.g. 1, 2, 3 or 4) amino acid substitutions elsewhere in the IL-2 cytokine. In one embodiment, the variant IL-2 cytokine comprises (or consists of) up to 7 (e.g. 1, 2, 3, 4, 5, 6 or 7) amino acid deletions from the N-terminal sequence (e.g. within the first 20, or first 15, or first 10 amino acids of the wild-type IL-2 sequence in question), in combination with up to 4 (e.g. 1, 2, 3 or 4) amino acid substitutions elsewhere in the IL-2 cytokine.

In one embodiment, the variant IL-2 cytokine comprises (or consists of) up to 6 (e.g. 1, 2, 3, 4, 5 or 6) amino acid deletions from the N-terminal sequence (e.g. within the first 20, or first 15, or first 10 amino acids of the wild-type IL-2 sequence in question), in combination with up to 4 (e.g. 1, 2, 3 or 4) amino acid substitutions elsewhere in the IL-2 cytokine. In one embodiment, the variant IL-2 cytokine comprises (or consists of) up to 6 (e.g. 1, 2, 3, 4, 5 or 6) amino acid deletions from the N-terminal sequence (e.g. within the first 20, or first 15, or first 10 amino acids of the wild-type IL-2 sequence in question), in combination with up to 4 (e.g. 1, 2, 3 or 4) amino acid substitutions elsewhere in the IL-2 cytokine. In one embodiment, the variant IL-2 cytokine comprises (or consists of) up to 6 (e.g. 1, 2, 3, 4, 5 or 6) amino acid deletions from the N-terminal sequence (e.g. within the first 20, or first 15, or first 10 amino acids of the wild-type IL-2 sequence in question), in combination with up to 4 (e.g. 1, 2, 3 or 4) amino acid substitutions elsewhere in the IL-2 cytokine.

In one embodiment, the variant IL-2 cytokine comprises (or consists of) up to 5 (e.g. 1, 2, 3, 4 or 5) amino acid deletions from the N-terminal sequence (e.g. within the first 20, or first 15, or first 10 amino acids of the wild-type IL-2 sequence in question), in combination with up to 4 (e.g. 1, 2, 3 or 4) amino acid substitutions elsewhere in the IL-2 cytokine. In one embodiment, the variant IL-2 cytokine comprises (or consists of) up to 5 (e.g. 1, 2, 3, 4 or 5) amino acid deletions from the N-terminal sequence (e.g. within the first 20, or first 15, or first 10 amino acids of the wild-type IL-2 sequence in question), in combination with up to 4 (e.g. 1, 2, 3 or 4) amino acid substitutions elsewhere in the IL-2 cytokine. In one embodiment, the variant IL-2 cytokine comprises (or consists of) up to 5 (e.g. 1, 2, 3, 4 or 5) amino acid deletions from the N-terminal sequence (e.g. within the first 20, or first 15, or first 10 amino acids of the wild-type IL-2 sequence in question), in combination with up to 4 (e.g. 1, 2, 3 or 4) amino acid substitutions elsewhere in the IL-2 cytokine.

In one embodiment, the variant IL-2 cytokine comprises (or consists of) up to 4 (e.g. 1, 2, 3 or 4) amino acid deletions from the N-terminal sequence (e.g. within the first 20, or first 15, or first 10 amino acids of the wild-type IL-2 sequence in question), in combination with up to 4 (e.g. 1, 2, 3 or 4) amino acid substitutions elsewhere in the IL-2 cytokine. In one embodiment, the variant IL-2 cytokine comprises (or consists of) up to 4 (e.g. 1, 2, 3 or 4) amino acid deletions from the N-terminal sequence (e.g. within the first 20, or first 15, or first 10 amino acids of the wild-type IL-2 sequence in question), in combination with up to 4 (e.g. 1, 2, 3 or 4) amino acid substitutions elsewhere in the IL-2 cytokine. In one embodiment, the variant IL-2 cytokine comprises (or consists of) up to 4 (e.g. 1, 2, 3 or 4) amino acid deletions from the N-terminal sequence (e.g. within the first 20, or first 15, or first 10 amino acids of the wild-type IL-2 sequence in question), in combination with up to 4 (e.g. 1, 2, 3 or 4) amino acid substitutions elsewhere in the IL-2 cytokine.

In one embodiment, the variant IL-2 cytokine comprises (or consists of) up to 3 (e.g. 1, 2 or 3) amino acid deletions from the N-terminal sequence (e.g. within the first 20, or first 15, or first 10 amino acids of the wild-type IL-2 sequence in question), in combination with up to 4 (e.g. 1, 2, 3 or 4) amino acid substitutions elsewhere in the IL-2 cytokine. In one embodiment, the variant IL-2 cytokine comprises (or consists of) up to 3 (e.g. 1, 2 or 3) amino acid deletions from the N-terminal sequence (e.g. within the first 20, or first 15, or first 10 amino acids of the wild-type IL-2 sequence in question), in combination with up to 4 (e.g. 1, 2, 3 or 4) amino acid substitutions elsewhere in the IL-2 cytokine. In one embodiment, the variant IL-2 cytokine comprises (or consists of) up to 3 (e.g. 1, 2 or 3) amino acid deletions from the N-terminal sequence (e.g. within the first 20, or first 15, or first 10 amino acids of the wild-type IL-2 sequence in question), in combination with up to 4 (e.g. 1, 2, 3 or 4) amino acid substitutions elsewhere in the IL-2 cytokine.

In one embodiment, the variant IL-2 cytokine comprises (or consists of) 1 or 2 amino acid deletions from the N-terminal sequence (e.g. within the first 20, or first 15, or first 10 amino acids of the wild-type IL-2 sequence in question), in combination with up to 4 (e.g. 1, 2, 3 or 4) amino acid substitutions elsewhere in the IL-2 cytokine. In one embodiment, the variant IL-2 cytokine comprises (or consists of) 1 or 2 amino acid deletions from the N-terminal sequence (e.g. within the first 20, or first 15, or first 10 amino acids of the wild-type IL-2 sequence in question), in combination with up to 4 (e.g. 1, 2, 3 or 4) amino acid substitutions elsewhere in the IL-2 cytokine. In one embodiment, the variant IL-2 cytokine comprises (or consists of) 1 or 2 amino acid deletions from the N-terminal sequence (e.g. within the first 20, or first 15, or first 10 amino acids of the wild-type IL-2 sequence in question), in combination with up to 4 (e.g. 1, 2, 3 or 4) amino acid substitutions elsewhere in the IL-2 cytokine.

Substitutions elsewhere in the IL-2 cytokine are defined further in aspect 44 hereinbelow.

Particular IL-2 cytokines and variant IL-2 cytokines are further defined in aspects 40 to 45 hereinbelow.

The amino acid sequence of the α-chain of human IL-2 is provided in Seq ID No:327. The amino acid sequence of the β-chain of human IL-2 is provided in Seq ID No:328. The amino acid sequence of the γ-chain of human IL-2 is provided in Seq ID No:239.

Aspect 1a. An immunocytokine comprising an immunoglobulin heavy chain and an immunoglobulin light chain, wherein the heavy chain comprises in N- to C-terminal direction:
a) A $V_H$ domain comprising CDRH1, CDRH2 and CDRH3; and
b) A heavy chain constant region;
and wherein the light chain comprises in N- to C-terminal direction:
c) A $V_L$ domain comprising CDRL1, CDRL2 and CDRL3;
d) A light chain constant region, ($C_L$);
e) Optionally, a linker, (L); and
f) An IL-2 cytokine;
wherein the $V_H$ domain and $V_L$ domain are comprised by an antigen-binding site that specifically binds to an antigen selected from: an immune checkpoint inhibitor (such as PD-1, CTLA-4, TIGIT, TIM-3, LAG-3 and VISTA, e.g. TIGIT, TIM-3 and LAG-3), an immune modulator (such as BTLA, hHVEM, CSF1R, CCR4, CD39, CD40, CD73, CD96, CXCR2, CXCR4, CD200, GARP, SIRPα, CXCL9, CXCL10 and CD155, e.g. GARP, SIRPα, CXCR4, BTLA, hVEM and CSF1R), and an immune activator (such as CD137, GITR, OX40, CD40, CXCR3 (e.g. agonistic activity against CXCR3), CD3 and ICOS (e.g. agonistic activity against ICOS), for example, ICOS, CD137, GITR and OX40).

Any of the embodiments of aspect 1 apply mutatis mutandis to aspect 1a. Any of the features or embodiments of aspects 2 to 54 apply mutatis mutandis to aspect 1a. Any of the features of the antibodies or other embodiments or features of concepts 1 to 70 apply mutatis mutandis to aspect 1a.

In one embodiment, the antigen-binding site specifically binds PD-L1, e.g. hPD-L1. In one embodiment, the PD-L1 antigen-binding site comprises the CDRH1, CDRH2, CDR3, CDRL1, CDRL2 and CDRL3 from any one of the anti-PD-L1 antibodies selected from atezolizumab (Roche), avelumab (Merck), BMS-936559 (BMS), durvalumab (Medimmune) and any of the PD-L1 antibodies disclosed in WO2016/061142, WO2016/022630, WO2016/007235, WO2015/173267, WO2015/181342, WO2015/109124, WO2015/112805, WO2015/061668, WO2014/159562, WO2014/165082, WO2014/100079, WO2014/055897, WO2013/181634, WO2013/173223, WO2013/079174, WO2012/145493, WO2011/066389, WO2010/077634, WO2010/036959 or WO2007/005874.

In one embodiment, the antigen-binding site specifically binds ICOS, e.g. hICOS. In one embodiment, the antigen-binding site specifically binds ICOS, e.g. hICOS and is an agonist to ICOS, e.g. hICOS. In one embodiment, the antigen-binding site specifically binds ICOS, e.g. hICOS and is an antagonist to ICOS, e.g. hICOS.

In any of the following embodiments, a particular antigen-binding site specifically binds to a human target. In one embodiment, the antigen-binding site specifically binds an immune checkpoint inhibitor. In one embodiment, the antigen-binding site specifically binds an immune checkpoint inhibitor selected from PD-1, CTLA-4, TIGIT, TIM-3, LAG-3 and VISTA. In one embodiment, the antigen-binding site specifically binds an immune checkpoint inhibitor selected from TIGIT, CTLA-4, TIM-3 and LAG-3. In one embodiment, the antigen-binding site specifically binds TIGIT. In one embodiment, the antigen-binding site specifically binds TIM-3. In one embodiment, the antigen-binding site specifically binds LAG-3. In one embodiment, the antigen-binding site specifically binds CTLA-4.

In one embodiment, the antigen-binding site specifically binds an immune modulator. In one embodiment, the antigen-binding site specifically binds an immune modulator selected from BTLA, hHVEM, CSF1R, CCR4, CD39, CD40, CD73, CD96, CXCR2, CXCR4, CD200, GARP, SIRPα, CXCL9, CXCL10 and CD155. In one embodiment, the antigen-binding site specifically binds an immune modulator selected from GARP, SIRPα, CXCR4, BTLA, hVEM and CSF1R. In one embodiment, the antigen-binding site specifically binds GARP. In one embodiment, the antigen-binding site specifically binds SIRPα. In one embodiment, the antigen-binding site specifically binds CXCR4. In one embodiment, the antigen-binding site specifically binds BTLA. In one embodiment, the antigen-binding site specifically binds hVEM. In one embodiment, the antigen-binding site specifically binds CSF1R.

In one embodiment, the antigen-binding site specifically binds an immune activator. In one embodiment, the antigen-binding site specifically binds an immune activator selected from CD137, GITR, OX40, CD40, CXCR3 (e.g. agonistic activity against CXCR3), CD3 and ICOS (e.g. agonistic activity against ICOS). In one embodiment, the antigen-binding site specifically binds an immune activator selected from ICOS, CD137, GITR and OX40. In one embodiment, the antigen-binding site specifically binds CD137, e.g. hCD137. In one embodiment, the antigen-binding site specifically binds GITR, e.g. hGITR. In one embodiment, the antigen-binding site specifically binds OX40, e.g. hOX40.

Aspect 1b. An immunocytokine comprising an immunoglobulin heavy chain and an immunoglobulin light chain, wherein the heavy chain comprises in N- to C-terminal direction:
  a) A $V_H$ domain comprising CDRH1, CDRH2 and CDRH3; and
  b) A heavy chain constant region;
  c) Optionally, a linker, (L); and
  d) An IL-2 cytokine;
  and wherein the light chain comprises in N- to C-terminal direction:
  e) A $V_L$ domain comprising CDRL1, CDRL2 and CDRL3; and
  f) A light chain constant region, (CO;
  wherein the $V_H$ domain and $V_L$ domain are comprised by an antigen-binding site that specifically binds to an antigen selected from: an immune checkpoint inhibitor (such as PD-1, CTLA-4, TIGIT, TIM-3, LAG-3 and VISTA, e.g. TIGIT, TIM-3 and LAG-3), an immune modulator (such as BTLA, hHVEM, CSF1R, CCR4, CD39, CD40, CD73, CD96, CXCR2, CXCR4, CD200, GARP, SIRPα, CXCL9, CXCL10 and CD155, e.g. GARP, SIRPα, CXCR4, BTLA, hVEM and CSF1R), and an immune activator (such as CD137, GITR, OX40, CD40, CXCR3 (e.g. agonistic anti-CXCR3 antibodies), CD3 and ICOS (e.g. agonistic anti-ICOS antibodies), for example ICOS, CD137, GITR and OX40).

Any of the embodiments of aspect 1 and/or aspect 1a apply mutatis mutandis to aspect 1b. Any of the features or embodiments of aspects 2 to 54 apply mutatis mutandis to aspect 1b. Any of the features of the antibodies or other embodiments or features of concepts 1 to 70 apply mutatis mutandis to aspect 1b.

In one embodiment, the antigen binding site specifically binds any of the antigens as set out in aspect 1a.

In one embodiment, the antigen-binding site specifically bind to hPD-L1 as defined by Seq ID No:1, and competes for binding to said hPD-L1 with the antibody 1D05; and wherein the immunocytokine comprises a VH domain which comprises a CDRH3 comprising the motif X1GSGX2YGX3X4FD, wherein X1, X2 and X3 are independently any amino acid, and X4 is either present or absent, and if present, may be any amino acid.

In either of aspect 1 or 1a, the wording of part f) may be substituted to read: "f) a cytokine, e.g. selected from IL-7, IL-15, IL-21, IL-12, GM-CSF, TNFα, TGFβ, CXCL9, CXCL10 and interferon-α". In 1b, the wording of part d) may be substituted for "d) a cytokine, e.g. selected from IL-7, IL-15, IL-21, IL-12, GM-CSF, TNFα, TGFβ, CXCL9, CXCL10 and interferon-α". Thus, the immunocytokines as disclosed herein may contain cytokines other than a cytokine having IL-2 cytokine activity. In one embodiment, the cytokine is IL-7 (Seq ID No:330). In one embodiment, the cytokine is IL-15 (Seq ID No:331). In one embodiment, the cytokine is IL-21 (Seq ID No:332). In one embodiment, the cytokine is IL-12, comprising the α-chain (Seq ID No:336) and the β-chain (Seq ID No:337). In one embodiment, the cytokine is GM-CSF (Seq ID No:333). In one embodiment, the cytokine is TNFα (Seq ID No:335). In one embodiment, the cytokine is TGFβ. In one embodiment, the cytokine is CXCL9 (Seq ID No:338). In one embodiment, the cytokine is CXCL10 (Seq ID No:339). In one embodiment, the cytokine is interferon-α (Seq ID No:334).

In another embodiment, the cytokine is an immune-stimulating cytokine. In another embodiment, the cytokine is a T-cell stimulating cytokine.

Aspect 2. An immunocytokine according to aspect 1, wherein X1 is a hydroxyl-containing amino acid, optionally T.

Aspect 3. An immunocytokine according to aspect 1 or aspect 2, wherein X2 is a basic amino acid, optionally K.

Aspect 4. An immunocytokine according to any one of aspects 1 to 3, wherein X2 is a hydroxyl-containing amino acid, optionally S or T.

Aspect 5. The immunocytokine according to any one of claims 1 to 4, wherein X3 is an aromatic amino acid, optionally W.

Aspect 6. An immunocytokine according to any one of aspects 1 to 5, wherein X4 is absent.

Aspect 7. An immunocytokine according to any one of aspects 1 to 5, wherein X4 is present.

Aspect 8. An immunocytokine according to aspect 7, wherein X4 is an aliphatic amino acid, optionally G.

The features of aspects 2 to 7 may be as defined in any of concepts 2 to 7 hereinabove Aspect 9. An immunocytokine comprising an immunoglobulin heavy chain and an immunoglobulin light chain, wherein the heavy chain comprises in N- to C-terminal direction:
  a) A $V_H$ domain comprising CDRH1, CDRH2 and CDRH3; and
  b) A heavy chain constant region;
  and wherein the light chain comprises in N- to C-terminal direction:
  c) A $V_L$ domain comprising CDRL1, CDRL2 and CDRL3;
  d) A light chain constant region, ($C_L$);
  e) Optionally, a linker, (L); and
  f) An IL-2 cytokine;
  wherein the $V_H$ domain and $V_L$ domain are comprised by an antigen-binding site that specifically binds to hPD-L1, and competes for binding to said hPD-L1 with the antibody 1D05, wherein the antibody or fragment comprises a $V_H$ domain which comprises the CDRH3 sequence of SEQ ID NO:29 or 32, or the CDRH3 sequence of SEQ ID NO:29 or 32 comprising 6 or fewer amino acid substitutions, optionally, wherein the immunocytokine is according to any one of aspects 2 to 8.

In this aspect, any of the features of CDRH3 described in concepts 9, and 9a to k, and any of the embodiments of concept 9 apply mutatis mutandis Aspect 10. An immunocytokine comprising an immunoglobulin heavy chain and an immunoglobulin light chain, wherein the heavy chain comprises in N- to C-terminal direction:
  a) A $V_H$ domain comprising CDRH1, CDRH2 and CDRH3; and
  b) A heavy chain constant region;
  and wherein the light chain comprises in N- to C-terminal direction:
  c) A $V_L$ domain comprising CDRL1, CDRL2 and CDRL3;
  d) A light chain constant region, ($C_L$);
  e) Optionally, a linker, (L); and
  f) An IL-2 cytokine;

wherein the $V_H$ domain and $V_L$ domain are comprised by an antigen-binding site that specifically binds to hPD-L1; and wherein the $V_H$ domain comprises a CDRH3 of from 12 to 20 amino acids and which is derived from the recombination of a human $V_H$ gene segment, a human D gene segment and a human $J_H$ gene segment, wherein the human $J_H$ gene segment is IGHJ5 (e.g. IGHJ5*02).

In this aspect, any of the features of CDRH3 described in concepts 10 and 10a apply mutatis mutandis Aspect 11. An immunocytokine according to aspect 10, wherein the human $V_H$ gene segment is IGHV3 (e.g. IGHV3-9, such as IGHV3-9*01).

In this aspect, any of the features of the gene segments described in concept 11, 11a or 11b apply mutatis mutandis.

Aspect 12. An immunocytokine according to aspect 10 or aspect 11, wherein the antibody or fragment comprises a VL domain which is derived from the recombination of a human Vκ gene segment, and a human Jκ gene segment, wherein the human VL gene segment is IGκV1D (e.g. IGκV1D-39, such as IGκV1D-39*01).

In this aspect, any of the features of the gene segments described in concept 12, 12a or 12b apply mutatis mutandis.

Aspect 13. An immunocytokine comprising an immunoglobulin heavy chain and an immunoglobulin light chain, wherein the heavy chain comprises in N- to C-terminal direction:

a) A $V_H$ domain comprising CDRH1, CDRH2 and CDRH3; and
b) A heavy chain constant region;
and wherein the light chain comprises in N- to C-terminal direction:
c) A $V_L$ domain comprising CDRL1, CDRL2 and CDRL3;
d) A light chain constant region, ($C_L$);
e) Optionally, a linker, (L); and
f) An IL-2 cytokine;
wherein the $V_H$ domain and $V_L$ domain are comprised by an antigen-binding site that specifically binds to an epitope that is identical to an epitope to which the antibody 1D05 specifically binds.

In this aspect, any of the features of the epitopes, assays and other embodiments described in any of concepts 13 and 13a to 13k apply mutatis mutandis Aspect 14. An immunocytokine according to aspect 13, wherein the epitope is identified by an unrelated amino acid scan, or by X-ray crystallography.

Aspect 15. An immunocytokine according to aspect 14, wherein the contact residues of the epitope are defined by a reduction in affinity of at least 10-fold in an unrelated amino acid scan, e.g. an alanine scan as determined by SPR.

In this aspect, any of the features of concept 15 apply mutatis mutandis.

Aspect 16. An immunocytokine comprising an immunoglobulin heavy chain and an immunoglobulin light chain, wherein the heavy chain comprises in N- to C-terminal direction:

a) A $V_H$ domain comprising CDRH1, CDRH2 and CDRH3; and
b) A heavy chain constant region;
and wherein the light chain comprises in N- to C-terminal direction:
c) A $V_L$ domain comprising CDRL1, CDRL2 and CDRL3;
d) A light chain constant region, ($C_L$);
e) Optionally, a linker, (L); and
f) An IL-2 cytokine;
wherein the $V_H$ domain and $V_L$ domain are comprised by an antigen-binding site which competes for binding to hPD-L1 with the antibody 1D05.

In this aspect, any of the features of the antibodies of concepts 16a to 16k or any of the competitive assays and other embodiments described in concept 16, or the features of concept 35 apply mutatis mutandis.

Aspect 17. An immunocytokine according to any one of aspects 10 to 16, wherein the VH domain comprises the CDRH3 sequence of SEQ ID NO:29 or 32, or the CDRH3 sequence of SEQ ID NO:29 or 32 comprising 6 or fewer amino acid substitutions.

In this aspect, any of the features of the antibodies of concepts 17a to 17k apply mutatis mutandis.

Aspect 18. An immunocytokine according to any preceding aspect, wherein the VH domain comprises the CDRH1 sequence of SEQ ID NO:27 or 30 or the CDRH1 sequence of SEQ ID NO:27 or 30 comprising 3, 2 or 1 amino acid substitution(s).

In this aspect, any of the features of the antibodies of concepts 18a to 18k apply mutatis mutandis.

Aspect 19. An immunocytokine according to any preceding aspect, wherein the VH domain comprises the CDRH2 sequence of SEQ ID NO:28 or 31, or the CDRH2 sequence of SEQ ID NO:28 or 31 comprising 4 or fewer amino acid substitutions.

In this aspect, any of the features of the antibodies of concepts 19a to 19k apply mutatis mutandis.

Aspect 20. An immunocytokine according to any preceding aspect, wherein the VH domain comprises an amino acid sequence of SEQ ID NO:33, or a heavy chain variable domain amino acid sequence that is at least 80% (e.g. at least 85%, or at least 90%) identical to SEQ ID NO:33 (for example the VH domain sequence in any of the heavy chain sequences of Seq ID Nos:47 to 49).

In this aspect, any of the features of the antibodies of concepts 20a to 20k or any of the embodiments of concept 20 apply mutatis mutandis.

Aspect 21. An immunocytokine according to any preceding aspect comprising first and second copies of said heavy chain.

Aspect 22. An immunocytokine according to any preceding aspect, comprising a VL domain which comprises the CDRL1 sequence of SEQ ID NO:37 or 40, or the CRDL1 sequence of SEQ ID NO:37 or 40 comprising 3 or fewer amino acid substitutions.

In this aspect, any of the features of the antibodies of concepts 22a to 22k apply mutatis mutandis.

Aspect 23. An immunocytokine according to any preceding aspect, comprising a VL domain which comprises the CDRL2 sequence of SEQ ID NO:38 or 41, or the CRDL2 sequence of SEQ ID NO:38 or 41 comprising 2 or 1 amino acid substitution(s), for example a CDRL2 sequence of Seq ID No:50.

In this aspect, any of the features of the antibodies of concepts 23a to 23k apply mutatis mutandis.

Aspect 24. An immunocytokine according to any preceding aspect, comprising a VL domain which comprises the CDRL3 sequence of SEQ ID NO:39 or 42, or the CRDL3 sequence of SEQ ID NO:39 or 42 comprising 4 or fewer amino acid substitutions.

In this aspect, any of the features of the antibodies of concepts 24a to 24k apply mutatis mutandis.

Aspect 25. An immunocytokine according to any preceding aspect, comprising a VL domain which comprises an amino acid sequence of SEQ ID NO:43, or a light chain variable domain amino acid sequence that is at least 80%

(e.g. at least 85%, or at least 90%) identical to SEQ ID NO:43 (for example the VL domain sequence in the light chain sequence of Seq ID No:50 or 51).

In this aspect, any of the features of the antibodies of concepts 25a to 25k or any of the embodiments of concept 25 apply mutatis mutandis.

Aspect 26. An immunocytokine according to any preceding aspect comprising first and second copies of said light chain.

Aspect 27. An immunocytokine according to any preceding aspect which specifically binds to cynomolgus PD-L1 as defined by Seq ID No:2.

In this aspect, any of embodiments of concept 27 apply mutatis mutandis.

Aspect 28. An immunocytokine according to any preceding aspect, wherein the antibody or fragment comprises a kappa light chain.

In this aspect, any of the embodiments of concept 28 apply mutatis mutandis.

Aspect 29. An immunocytokine according to any one of aspects 9 to 28, wherein the amino acid substitutions are conservative amino acid substitutions, optionally wherein the conservative substitutions are from one of six groups (each group containing amino acids that are conservative substitutions for one another) selected from:
1) Alanine (A), Serine (S), Threonine (T);
2) Aspartic acid (D), Glutamic acid (E);
3) Asparagine (N), Glutamine (Q);
4) Arginine (R), Lysine (K);
5) Isoleucine (I), Leucine (L), Methionine (M), Valine (V); and
6) Phenylalanine (F), Tyrosine (Y), Tryptophan (W).

In this aspect, any of the embodiments of concept 9 apply mutatis mutandis.

Aspect 30. An immunocytokine according to any preceding aspect, wherein the antibody or fragment comprises a constant region, e.g. an IgG1 constant region, optionally wherein the constant region is a disabled IgG1 as defined in Seq ID No:205.

In this aspect, any of the features or the embodiments of concept 30, 31 or 32 apply mutatis mutandis.

Aspect 31. An immunocytokine according to any preceding aspect wherein the:
A) $V_H$ domain comprises an amino acid sequence of SEQ ID No:33 and the $V_L$ domain comprises an amino acid sequence of SEQ ID No:43;
B) $V_H$ domain comprises an amino acid sequence that is at least 85% identical to SEQ ID No:33, and the $V_L$ domain comprises an amino acid sequence that is at least 85% identical to SEQ ID No:43;
C) $V_H$ domain comprises an amino acid sequence of the $V_H$ domain of SEQ ID No:47 and the $V_L$ domain comprises an amino acid sequence of SEQ ID No:43;
D) $V_H$ domain comprises an amino acid sequence of the $V_H$ domain of SEQ ID No:48 and the $V_L$ domain comprises an amino acid sequence of SEQ ID No:43;
E) $V_H$ domain comprises an amino acid sequence of the $V_H$ domain of SEQ ID No:49 and the $V_L$ domain comprises an amino acid sequence of SEQ ID No:43;
F) $V_H$ domain comprises an amino acid sequence of SEQ ID No:33 and the $V_L$ domain comprises an amino acid sequence of the $V_L$ domain of SEQ ID No:50;
G) $V_H$ domain comprises an amino acid sequence of the $V_H$ domain of SEQ ID No:47 and the $V_L$ domain comprises an amino acid sequence of the $V_L$ domain of SEQ ID No:50;
H) $V_H$ domain comprises an amino acid sequence of the $V_H$ domain of SEQ ID No:48 and the $V_L$ domain comprises an amino acid sequence of the $V_L$ domain of SEQ ID No:50;
I) $V_H$ domain comprises an amino acid sequence of the $V_H$ domain of SEQ ID No:49 and the $V_L$ domain comprises an amino acid sequence of the $V_L$ domain of SEQ ID No:50;
J) $V_H$ domain comprises an amino acid sequence of SEQ ID No:33 and the $V_L$ domain comprises an amino acid sequence of the $V_L$ domain of SEQ ID No:51;
K) $V_H$ domain comprises an amino acid sequence of the $V_H$ domain of SEQ ID No:47 and the $V_L$ domain comprises an amino acid sequence of the $V_L$ domain of SEQ ID No:51;
L) $V_H$ domain comprises an amino acid sequence of the $V_H$ domain of SEQ ID No:48 and the $V_L$ domain comprises an amino acid sequence of the $V_L$ domain of SEQ ID No:51;
M) $V_H$ domain comprise an amino acid sequence of the $V_H$ domain of SEQ ID No:49 and the $V_L$ domain comprises an amino acid sequence of the $V_L$ domain of SEQ ID No:51;
N) $V_H$ domain comprises an amino acid sequence of SEQ ID No:33 and the $V_L$ domain comprises an amino acid sequence of the $V_L$ domain of SEQ ID No:298;
O) $V_H$ domain comprises an amino acid sequence of the $V_H$ domain of SEQ ID No:47 and the $V_L$ domain comprises an amino acid sequence of the $V_L$ domain of SEQ ID No:298;
P) $V_H$ domain comprises an amino acid sequence of the $V_H$ domain of SEQ ID No:48 and the $V_L$ domain comprises an amino acid sequence of the $V_L$ domain of SEQ ID No:298;
Q) VH domain comprise an amino acid sequence of the $V_H$ domain of SEQ ID No:49 and the $V_L$ domain comprises an amino acid sequence of the $V_L$ domain of SEQ ID No:298;
R) $V_H$ domain comprises an amino acid sequence of SEQ ID No:58 and the $V_L$ domain comprises an amino acid sequence of SEQ ID No:68;
S) $V_H$ domain comprises an amino acid sequence that is at least 85% identical to SEQ ID No:58, and the $V_L$ domain comprise an amino acid sequence that is at least 85% identical to SEQ ID No:68;
T) $V_H$ domain comprises an amino acid sequence of SEQ ID No:78 and the $V_L$ domain comprises an amino acid sequence of SEQ ID No:88;
U) $V_H$ domain comprises an amino acid sequence that is at least 85% identical to SEQ ID No:78, and the $V_L$ domain comprises an amino acid sequence that is at least 85% identical to SEQ ID No:88;
V) $V_H$ domain comprises an amino acid sequence of SEQ ID No:98 and the $V_L$ domain comprises an amino acid sequence of SEQ ID No:108;
W) $V_H$ domain comprises an amino acid sequence that is at least 85% identical to SEQ ID No:98, and the $V_L$ domain comprises an amino acid sequence that is at least 85% identical to SEQ ID No:108;
X) $V_H$ domain comprises an amino acid sequence of SEQ ID No:118 and the $V_L$ domain comprises an amino acid sequence of SEQ ID No:128;
Y) $V_H$ domain comprises an amino acid sequence that is at least 85% identical to SEQ ID No:118, and the $V_L$ domain comprises an amino acid sequence that is at least 85% identical to SEQ ID No:128;

Z) V_H domain comprises an amino acid sequence of SEQ ID No:158 and the V_L domain comprises an amino acid sequence of SEQ ID No:168;

AA) V_H domain comprises an amino acid sequence that is at least 85% identical to SEQ ID No:158, and the V_L domain comprises an amino acid sequence that is at least 85% identical to SEQ ID No:168;

BB) V_H domain comprises an amino acid sequence of SEQ ID No:178 and the V_L domain comprises an amino acid sequence of SEQ ID No:188;

CC) V_H domain comprises an amino acid sequence that is at least 85% identical to SEQ ID No:178, and the V_L domain comprises an amino acid sequence that is at least 85% identical to SEQ ID No:188;

DD) V_H domain comprises an amino acid sequence of SEQ ID No:138 and the V_L domain comprises an amino acid sequence of SEQ ID No:148;

EE) V_H domain comprises an amino acid sequence that is at least 85% identical to SEQ ID No:13, and the V_L domain comprises an amino acid sequence that is at least 85% identical to SEQ ID No:148;

FF) V_H domain comprises an amino acid sequence of SEQ ID No:244 and the V_L domain comprises an amino acid sequence of SEQ ID No:254;

GG) V_H domain comprises an amino acid sequence that is at least 85% identical to SEQ ID No:244, and the V_L domain comprises an amino acid sequence that is at least 85% identical to SEQ ID No:254;

HH) V_H domain comprises an amino acid sequence of SEQ ID No:264 and the V_L domain comprises an amino acid sequence of SEQ ID No:274;

II) V_H domain comprises an amino acid sequence that is at least 85% identical to SEQ ID No:264, and the V_L domain comprises an amino acid sequence that is at least 85% identical to SEQ ID No:274;

JJ) V_H domain comprises an amino acid sequence of SEQ ID No:284 and the V_L domain comprises an amino acid sequence of SEQ ID No:294;

KK) V_H domain comprises an amino acid sequence that is at least 85% identical to SEQ ID No:284, and the V_L domain comprises an amino acid sequence that is at least 85% identical to SEQ ID No:294;

LL) V_H domain comprises an amino acid sequence of SEQ ID No:13 and the V_L domain comprises an amino acid sequence of SEQ ID No:23; and MM) V_H domain comprises an amino acid sequence that is at least 85% identical to SEQ ID No:13, and the V_L domain comprises an amino acid sequence that is at least 85% identical to SEQ ID No:23.

In one embodiment, the amino acid sequence is at least 70% identical to the specified Seq ID No. In one embodiment, the amino acid sequence is at least 75% identical to the specified Seq ID No. In one embodiment, the amino acid sequence is at least 95% identical to the specified Seq ID No. In one embodiment, the amino acid sequence is at least 96% identical to the specified Seq ID No. In one embodiment, the amino acid sequence is at least 97% identical to the specified Seq ID No. In one embodiment, the amino acid sequence is at least 98% identical to the specified Seq ID No. In one embodiment, the amino acid sequence is at least 99% identical to the specified Seq ID No. In one embodiment, the amino acid sequence is at least 99.5% identical to the specified Seq ID No Aspect 32. An immunocytokine according to any preceding aspect wherein the:

A) V_H and the constant region comprise an amino acid sequence of SEQ ID No:299 and V_L and C_L comprise an amino acid sequence of SEQ ID No:45;

B) V_H and the constant region comprise an amino acid sequence that is at least 85% identical to SEQ ID No:299, and the V_L and C_L comprise an amino acid sequence that is at least 85% identical to SEQ ID No:45;

C) V_H and the constant region comprise an amino acid sequence of SEQ ID No:47 and V_L and C_L comprise an amino acid sequence of SEQ ID No:45;

D) V_H and the constant region comprise an amino acid sequence of SEQ ID No:48 and V_L and C_L comprise an amino acid sequence of SEQ ID No:45;

E) V_H and the constant region comprise an amino acid sequence of SEQ ID No:49 and V_L and C_L comprise an amino acid sequence of SEQ ID No:45;

F) V_H and the constant region comprise an amino acid sequence of SEQ ID No:238 and V_L and C_L comprise an amino acid sequence of SEQ ID No:50;

G) V_H and the constant region comprise an amino acid sequence of SEQ ID No:47 and V_L and C_L comprise an amino acid sequence of SEQ ID No:50;

H) V_H and the constant region comprise an amino acid sequence of SEQ ID No:48 and V_L and C_L comprise an amino acid sequence of SEQ ID No:50;

I) V_H and the constant region comprise an amino acid sequence of SEQ ID No:49 and V_L and C_L comprise an amino acid sequence of SEQ ID No:50;

J) V_H and the constant region comprise an amino acid sequence of SEQ ID No:299 and V_L and C_L comprise an amino acid sequence of SEQ ID No:51;

K) V_H and the constant region comprise an amino acid sequence of SEQ ID No:47 and V_L and C_L comprise an amino acid sequence of SEQ ID No:51;

L) V_H and the constant region comprise an amino acid sequence of SEQ ID No:48 and V_L and C_L comprise an amino acid sequence of SEQ ID No:51;

M) V_H and the constant region comprise an amino acid sequence of SEQ ID No:49 and V_L and C_L comprise an amino acid sequence of SEQ ID No:51;

N) V_H and the constant region comprise an amino acid sequence of SEQ ID No:299 and V_L and C_L comprise an amino acid sequence of SEQ ID No:298;

O) V_H and the constant region comprise an amino acid sequence of SEQ ID No:47 and V_L and C_L comprise an amino acid sequence of SEQ ID No:298;

P) V_H and the constant region comprise an amino acid sequence of SEQ ID No:48 and V_L and C_L comprise an amino acid sequence of SEQ ID No:298;

Q) VH and the constant region comprise an amino acid sequence of SEQ ID No:49 and V_L and C_L comprise an amino acid sequence of SEQ ID No:298;

R) V_H and the constant region comprise an amino acid sequence of SEQ ID No:60 and V_L and C_L comprise an amino acid sequence of SEQ ID No:70;

S) V_H and the constant region comprise an amino acid sequence that is at least 85% identical to SEQ ID No:60, and the V_L and C_L comprise an amino acid sequence that is at least 85% identical to SEQ ID No:70;

T) V_H and the constant region comprise an amino acid sequence of SEQ ID No:80 and V_L and C_L comprise an amino acid sequence of SEQ ID No:90;

U) V_H and the constant region comprise an amino acid sequence that is at least 85% identical to SEQ ID No:80, and the $V_L$ and $C_L$ comprise an amino acid sequence that is at least 85% identical to SEQ ID No:90;

V) $V_H$ and the constant region comprise an amino acid sequence of SEQ ID No:100 and $V_L$ and $C_L$ comprise an amino acid sequence of SEQ ID No:110;

W) $V_H$ and the constant region comprise an amino acid sequence that is at least 85% identical to SEQ ID No:100, and the $V_L$ and $C_L$ comprise an amino acid sequence that is at least 85% identical to SEQ ID No:110;

X) $V_H$ and the constant region comprise an amino acid sequence of SEQ ID No:120 and $V_L$ and $C_L$ comprise an amino acid sequence of SEQ ID No:130;

Y) $V_H$ and the constant region comprise an amino acid sequence that is at least 85% identical to SEQ ID No:120, and the $V_L$ and $C_L$ comprise an amino acid sequence that is at least 85% identical to SEQ ID No:130;

Z) $V_H$ and the constant region comprise an amino acid sequence of SEQ ID No:160 and $V_L$ and $C_L$ comprise an amino acid sequence of SEQ ID No:170;

AA) $V_H$ and the constant region comprise an amino acid sequence that is at least 85% identical to SEQ ID No:160, and the $V_L$ and $C_L$ comprise an amino acid sequence that is at least 85% identical to SEQ ID No:170;

BB) $V_H$ and the constant region comprise an amino acid sequence of SEQ ID No:180 and $V_L$ and $C_L$ comprise an amino acid sequence of SEQ ID No:190;

CC) $V_H$ and the constant region comprise an amino acid sequence that is at least 85% identical to SEQ ID No:180, and the $V_L$ and $C_L$ comprise an amino acid sequence that is at least 85% identical to SEQ ID No:190;

DD) $V_H$ and the constant region comprise an amino acid sequence of SEQ ID No:140 and $V_L$ and $C_L$ comprise an amino acid sequence of SEQ ID No:150;

EE) $V_H$ and the constant region comprise an amino acid sequence that is at least 85% identical to SEQ ID No:140, and the $V_L$ and $C_L$ comprise an amino acid sequence that is at least 85% identical to SEQ ID No:150;

FF) $V_H$ and the constant region comprise an amino acid sequence of SEQ ID No:246 and $V_L$ and $C_L$ comprise an amino acid sequence of SEQ ID No:256;

GG) $V_H$ and the constant region comprise an amino acid sequence that is at least 85% identical to SEQ ID No:246, and the $V_L$ and $C_L$ comprise an amino acid sequence that is at least 85% identical to SEQ ID No:256;

HH) $V_H$ and the constant region comprise an amino acid sequence of SEQ ID No:266 and $V_L$ and $C_L$ comprise an amino acid sequence of SEQ ID No:276;

II) $V_H$ and the constant region comprise an amino acid sequence that is at least 85% identical to SEQ ID No:266, and the $V_L$ and $C_L$ comprise an amino acid sequence that is at least 85% identical to SEQ ID No:276;

JJ) $V_H$ and the constant region comprise an amino acid sequence of SEQ ID No:286 and $V_L$ and $C_L$ comprise an amino acid sequence of SEQ ID No:296; and KK) $V_H$ and the constant region comprise an amino acid sequence that is at least 85% identical to SEQ ID No:286, and the $V_L$ and $C_L$ comprise an amino acid sequence that is at least 85% identical to SEQ ID No:296;

LL) $V_H$ and the constant region comprise an amino acid sequence of SEQ ID No:15 and $V_L$ and $C_L$ comprise an amino acid sequence of SEQ ID No:25; and MM) $V_H$ and the constant region comprise an amino acid sequence that is at least 85% identical to SEQ ID No:15, and the $V_L$ and $C_L$ comprise an amino acid sequence that is at least 85% identical to SEQ ID No:25.

In one embodiment, the amino acid sequence is at least 70% identical to the specified Seq ID No. In one embodiment, the amino acid sequence is at least 75% identical to the specified Seq ID No. In one embodiment, the amino acid sequence is at least 95% identical to the specified Seq ID No. In one embodiment, the amino acid sequence is at least 96% identical to the specified Seq ID No. In one embodiment, the amino acid sequence is at least 97% identical to the specified Seq ID No. In one embodiment, the amino acid sequence is at least 98% identical to the specified Seq ID No. In one embodiment, the amino acid sequence is at least 99% identical to the specified Seq ID No. In one embodiment, the amino acid sequence is at least 99.5% identical to the specified Seq ID No.

Aspect 33. An immunocytokine according to any preceding aspect wherein the antigen-binding site specifically binds PD-L1, whilst the IL-2 cytokine binds the high affinity (αβγ) IL-2 receptor (IL-2R).

In one embodiment, the antigen binding site binds PD-L1 simultaneously to the IL-2 cytokine binding the αβγ IL-2R. In one embodiment, the antigen binding site binds PD-L1 sequentially to the IL-2 cytokine binding the αβγ IL-2R. In one embodiment, the IL-2 cytokine additionally binds the intermediate (βγ) IL-2R.

Aspect 34. An immunocytokine according to any preceding aspect wherein the immunocytokine is capable of inhibiting PD-L1-mediated suppression of T-cells.

In one embodiment, the immunocytokine inhibits PD-L1-mediated suppression of T-cells. In one embodiment, the immunocytokine inhibits PD-L1-mediated suppression of T-cells in an in vitro assay. In another embodiment, the antigen binding site has any of the features or embodiments of concept 51 or 52.

In another embodiment, the antigen binding site blocks or inhibits PD-1 binding to PD-L1. In one embodiment, the antigen binding site blocks or inhibits CD80 binding to PD-L1.

Aspect 35. An immunocytokine according to any preceding aspect wherein the immunocytokine is capable of increasing IL-2R-mediated T-cell activation.

In one embodiment, the immunocytokine increases IL-2R-mediated T-cell activation. In one embodiment, the immunocytokine increases IL-2R-mediated T-cell activation in an in vitro assay.

Aspect 36. An immunocytokine according to aspect 34 or aspect 35, wherein the suppression of T-cells or the increase in IL-2R-mediated T-cell activation is measured by an increase in one or more of IFNγ, IL-2, CD25 or proliferation of T-cells in an assay that provides co-stimulation by either direct CD3/CD28 stimulation, superantigen stimulation or provides co-stimulation by co-incubation with cells capable of inducing a T-cell response.

The measurements may be carried out with any suitable technique. For example, the measurements may be taken with ELISA, HTRF, BRDU incorporation (proliferation), electrochemiluminescence (ECL) or flow cytometry (e.g.

FACS). These techniques are well-known to those skilled in the art and are described elsewhere herein. In one embodiment, the assay is flow cytometry. In one embodiment, the assay is ELISA. In one embodiment, the assay is HTRF.

In this aspect, when aspect 36 is dependent on aspect 34, any of the features or embodiments of concept 36 apply mutatis mutandis.

When Aspect 36 is dependent on Aspect 35, in one embodiment, the increase in IL-2R-mediated T-cell activation is measured by an increase in one or both of IFNγ and CD25.

When Aspect 36 is dependent on Aspect 35, in one embodiment, the co-stimulation is provided by direct CD3/CD28 stimulation.

When Aspect 36 is dependent on Aspect 35, in one embodiment, the co-stimulation is provided by a superantigen, such as staphylococcal enterotoxin B (SEB).

When Aspect 36 is dependent on Aspect 35, in one embodiment, the assay provides co-stimulation by co-incubation with cells capable of inducing a T-cell response. Such cells may be antigen-presenting cells (APCs), for example monocytes, B-cells or dendritic cells. In one embodiment, the assay provides co-stimulation by co-incubation with APCs. In one embodiment, the assay provides co-stimulation by co-incubation with monocytes. In one embodiment, the assay provides co-stimulation by co-incubation with B-cells. In one embodiment, the assay provides co-stimulation by co-incubation with dendritic cells.

Aspect 37. An immunocytokine according to any preceding aspect which does not comprise a linker (L), or an immunocytokine according to any preceding claim wherein the CL of d) is directly fused to the cytokine off).

In one embodiment, the CL of the light chain or the heavy chain is directly fused to the cytokine.

In one embodiment of aspect 1b, the CL of b) is directly fused to the cytokine of d).

Aspect 38. An immunocytokine according to any one of aspects 1 to 37, wherein the linker is a peptide linker of 1 to 20 amino acids in length.

In one embodiment, the linker is peptide linker of 1 to 15 amino acids in length. In one embodiment, the linker is peptide linker of 1 to 10 amino acids in length. In one embodiment, the linker is peptide linker of 1 to 5 amino acids in length.

In one embodiment, the linker may be a chemical linker. In the case of recombinant fusion proteins, the linkers are encoded by nucleic acid sequences located in frame, in between the coding regions for the different immunocytokine portions. In the case of synthetic proteins, the linker peptides are introduced during synthesis.

Linkers are well-known to those skilled in the art. For example, see described in Denardo et al., 1998, Clin. Cancer Res., 4(10):2483-90; Peterson et al., 1999, Bioconjug. Chem. 10(4):553-7; and Zimmerman et al., 1999, Nucl. Med. Biol., 26(8):943-50.

Aspect 39. An immunocytokine according to aspect 38, wherein the linker peptide is selected from poly-G or (G4S)X, wherein X is 1, 2, 3 or 4.

In other embodiments, the linker may be selected from STG, GSTG, RS, TVAAPS, GGGGS, GSTVAAPS, TVAAPSGS or GSTVAAPSGS. In another embodiment, the linker is Gln-Arg-Val-Asp (derived from N-terminus of canine kappa constant region). In another embodiment, the linker is GGNGT or YGNGT.

Aspect 40. An immunocytokine according to any preceding aspect wherein the IL-2 cytokine is human IL-2 (hIL-2) or a variant thereof IL-2 variants are as described in aspect 1.

There is also provided a variant cytokine, which may be any of the non-IL-2 cytokines described herein (including the non-IL-2 cytokines described in aspect 1, e.g. selected from IL-7, IL-15, IL-21, IL-12, GM-CSF, TNFα, CXCL9, CXCL10 and interferon-α). The definition of a variant IL-2 cytokine applies mutatis mutandis to the other cytokines (including immune stimulating cytokines and T-cell stimulating cytokines) described herein.

Aspect 41. An immunocytokine according to aspect 40, wherein the hIL-2 comprises or consists of the amino acid sequence of Seq ID No:301.

Aspect 42. An immunocytokine according to aspect 40, wherein the hIL-2 comprises a variant of IL-2 which comprises a modification at the N-terminus, optionally a deletion of from 1 to 10 amino acids.

As used in this aspect, a modification at the N-terminus of any of the cytokines described herein (including the non-IL-2 cytokines described in aspect 1, e.g. selected from IL-7, IL-15, IL-21, IL-12, GM-CSF, TNFα, CXCL9, CXCL10 and interferon-α) refers to one or more (such as 1 to 10, e.g. 1 to 5) amino acid substitutions, deletions or additions.

In one embodiment, the modification is one or more (such as 1 to 10, e.g. 1 to 5) amino acid substitutions at the N-terminus of the cytokine. Substitutions may be conservative substitutions, for example, as defined in concept 9, concept 29 or aspect 29. In one embodiment, the modification is a deletion. In another embodiment, the modification is an N-terminal deletion, for example, any of the deletions described in concept 9. In one embodiment, the modification (such as a deletion of 1 to 10 amino acids) is within the final 50 amino acids of the N-terminus of the cytokine, e.g. the IL-2 cytokine. In one embodiment, the modification (such as a deletion of 1 to 10 amino acids) within the final 30 amino acids of the N-terminus of the cytokine, e.g. the IL-2 cytokine. In one embodiment, the modification (such as a deletion of 1 to 10 amino acids) within the final 25 amino acids of the N-terminus of the cytokine, e.g. the IL-2 cytokine. In one embodiment, the modification (such as a deletion of 1 to 10 amino acids) within the final 20 amino acids of the N-terminus of the cytokine, e.g. the IL-2 cytokine. In one embodiment, the modification (such as a deletion of 1 to 10 amino acids) within the final 15 amino acids of the N-terminus of the cytokine, e.g. the IL-2 cytokine. In one embodiment, the modification (such as a deletion of 1 to 10 amino acids) within the final 10 amino acids of the N-terminus of the cytokine, e.g. the IL-2 cytokine.

In one embodiment, the modification is a deletion of 1 to 9 amino acids from within the final 10 amino acids of the N-terminus of the cytokine, such as a deletion of the final 1 to 9 amino acids of the N-terminus of the cytokine. In one embodiment, the modification is a deletion of 1 to 8 amino acids from within the final 10 amino acids of the N-terminus of the cytokine, such as a deletion of the final 1 to 8 amino acids of the N-terminus of the cytokine. In one embodiment, the modification is a deletion of 1 to 7 amino acids from within the final 10 amino acids of the N-terminus of the cytokine, such as a deletion of the final 1 to 7 amino acids of the N-terminus of the cytokine. In one embodiment, the modification is a deletion of 1 to 6 amino acids from within the final 10 amino acids of the N-terminus of the cytokine, such as a deletion of the final 1 to 6 amino acids of the N-terminus of the cytokine. In one embodiment, the modification is a deletion of 1 to 5 amino acids from within the final 10 amino acids of the N-terminus of the cytokine, such as a deletion of the final 1 to 5 amino acids of the N-terminus of the cytokine. In one embodiment, the modification is a deletion of 1 to 4 amino acids from within the final 10 amino acids of the N-terminus of the cytokine, such as a deletion of the final 1 to 4 amino acids of the N-terminus of the cytokine. In one embodiment, the modification is a deletion of 1 to 3 amino acids from within the final 10 amino acids of the N-terminus of the cytokine, such as a deletion of the final 1 to 3 amino acids of the N-terminus of the cytokine. In one embodiment, the modification is a deletion of 1 or 2 amino acids from within the final 10 amino acids of the N-terminus of the cytokine, such as a deletion of the final 1 or 2 amino acids of the N-terminus of the cytokine. In one embodiment, the modification is a deletion of 1 amino acid from within the final 10 amino acids of the N-terminus of the cytokine, such as a deletion of the final amino acid of the N-terminus of the cytokine. In a particular embodiment, the cytokine is an IL-2 cytokine, such as a human IL-2 cytokine.

In one embodiment, the deletion is of the 9th amino acid from the N-terminus of the cytokine, e.g. the IL-2 cytokine, for example the human IL-2 cytokine. In one embodiment, the deletion is of the 8th and 9th amino acid from the N-terminus of the cytokine, e.g. the IL-2 cytokine, for example the human IL-2 cytokine. In one embodiment, the deletion is of the 7th, 8th and 9th amino acid from the N-terminus of the cytokine, e.g. the IL-2 cytokine, for example the human IL-2 cytokine. In one embodiment, the deletion is of the 6th to 9th amino acid from the N-terminus of the cytokine, e.g. the IL-2 cytokine, for example the human IL-2 cytokine. In one embodiment, the deletion is of the 4th to 9th amino acid from the N-terminus of the cytokine, e.g. the IL-2 cytokine, for example the human IL-2 cytokine. In one embodiment, the deletion is of the 3rd to 9th amino acid from the N-terminus of the cytokine, e.g. the IL-2 cytokine, for example the human IL-2 cytokine. In one embodiment, the deletion is of the 2nd to 9th amino acid from the N-terminus of the cytokine, e.g. the IL-2 cytokine, for example the human IL-2 cytokine. In one embodiment, the deletion is of the 2nd to 6th amino acid from the N-terminus of the cytokine, e.g. the IL-2 cytokine, for example the human IL-2 cytokine. In one embodiment, the deletion is of the 3rd to 7th amino acid from the N-terminus of the cytokine, e.g. the IL-2 cytokine, for example the human IL-2 cytokine. In one embodiment, the deletion is of the 4th to 8th amino acid from the N-terminus of the cytokine, e.g. the IL-2 cytokine, for example the human IL-2 cytokine.

Aspect 42a. A variant hIL-2 comprising an N-terminal modification of any of the aspects or features of aspect 42. In one embodiment of aspect 42a, the variant hIL-2 is a purified variant hIL-2. In another embodiment of aspect 42a, the variant hIL-2 is an isolated and purified variant hIL-2.

Aspect 43. An immunocytokine according to aspect 40 or aspect 42, wherein the hIL-2 comprises a variant IL-2 comprising an N-terminal sequence selected from Seq ID No:303 to 323.

Aspect 43a. A variant hIL-2 comprising an N-terminal sequence selected from Seq ID No:303 to 323.

In one embodiment of aspect 43a, the variant hIL-2 is a purified variant hIL-2. In another embodiment of aspect 43a, the variant hIL-2 is an isolated and purified variant hIL-2.

Aspect 44. An immunocytokine according to any one of aspects 40, 42 or 43 wherein the hIL-2 variant comprises one or more (such as 1 to 5, e.g. one or two) mutations independently selected from the following:

1) D20 (such as D20T);
2) R38 (such as R38W, R38A or R38Q);
3) F42 (such as F42A or F42K);
4) Y45 (such as Y45A);
5) E62 (such as E62A);
6) N88 (such as N88R);
7) C125 (such as C125S);
8) Q126 (such as Q126W); or
9) R38 and F42 (such as R38W and F42K or R38A and F42A);

wherein the residue numbering is defined with reference to the human wild-type IL-2 sequence, Seq ID No:301.

Aspect 44a. A variant hIL-2 according to any one of aspects 42a or 43a wherein the hIL-2 variant comprises one or more (such as 1 to 5, e.g. one or two) mutations independently selected from the following:

1) D20 (such as D20T);
2) R38 (such as R38W, R38A or R38Q);
3) F42 (such as F42A or F42K);
4) Y45 (such as Y45A);
5) E62 (such as E62A);
6) N88 (such as N88R);
7) C125 (such as C125S);
8) Q126 (such as Q126W); or
9) R38 and F42 (such as R38W and F42K or R38A and F42A);

wherein the residue numbering is defined with reference to the human wild-type IL-2 sequence, Seq ID No:301.

In one embodiment, the variant hIL-2 comprises (or consists) of an R38 (such as R38W, R38A or R38Q, e.g. R38A) mutation. In one embodiment, the variant hIL-2 comprises (or consists) of an F42 (such as F42A or F42K, e.g. F42A) mutation. In one embodiment, the variant hIL-2 comprises (or consists) of a Y45 (such as Y45A) mutation. In one embodiment, the variant hIL-2 comprises (or consists) of an E62 (such as E62A) mutation.

In one embodiment, the variant hIL-2 comprises (or consists) of an R38 (such as R38W, R38A or R38Q, e.g. R38A) mutation and an F42 (such as F42A or F42K, e.g. F42A) mutation. In one embodiment, the variant hIL-2 comprises (or consists) of an R38 (such as R38W, R38A or R38Q, e.g. R38A) and a Y45 (such as Y45A) mutation. In one embodiment, the variant hIL-2 comprises (or consists) of an R38 (such as R38W, R38A or R38Q, e.g. R38A) mutation and an E62 (such as E62A). In one embodiment, the variant hIL-2 comprises (or consists) of a Y45 (such as Y45A) mutation and an E62 (such as E62A). In one embodiment, the variant hIL-2 comprises (or consists) of an F42 (such as F42A or F42K, e.g. F42A) mutation and an E62 (such as E62A) mutation. In one embodiment, the variant hIL-2 comprises (or consists) of an F42 (such as F42A or F42K, e.g. F42A) mutation and a Y45 (such as Y45A) mutation.

In one embodiment, the variant hIL-2 comprises (or consists) of an R38 (such as R38W, R38A or R38Q, e.g. R38A) mutation, an F42 (such as F42A or F42K, e.g. F42A) mutation and a Y45 (such as Y45A) mutation. In one embodiment, the variant hIL-2 comprises (or consists) of an R38 (such as R38W, R38A or R38Q, e.g. R38A) mutation, an F42 (such as F42A or F42K, e.g. F42A) mutation and an E62 (such as E62A) mutation. In one embodiment, the variant hIL-2 comprises (or consists) of an R38 (such as R38W, R38A or R38Q, e.g. R38A) mutation, a Y45 (such as Y45A) mutation and an E62 (such as E62A) mutation.

In one embodiment, the variant hIL-2 comprises (or consists) of an R38 (such as R38W, R38A or R38Q, e.g. R38A) mutation, an F42 (such as F42A or F42K, e.g. F42A)

mutation, a Y45 (such as Y45A) mutation and an E62 (such as E62A) mutation. In one embodiment, the variant hIL-2 comprises (or consists) of an R38A, F42A, Y45A and an E62A mutation.

Other hIL-2 mutations are known to those skilled in the art. In one embodiment, the hIL-2 mutations are those described in WO2012/062228 (see claims 2 to 7, incorporated herein by reference). In one embodiment, the hIL-2 mutations are those described in WO1999/60128 (see claims 6, 7, 8, 10, 11 and 12 incorporated herein by reference). In one embodiment, the hIL-2 mutations are those described in WO1993/20849 (see claims 4 and 5 incorporated herein by reference). In one embodiment, the hIL-2 mutations are those described in WO2003/015697 (see claims 7 and 10 incorporated herein by reference). In one embodiment, the hIL-2 mutations are those described in WO2005/007121 (see claims 9 to 14 incorporated herein by reference). In one embodiment, the hIL-2 mutations are those described in WO2005/086798 (see claims 5 to 10 incorporated herein by reference). In one embodiment, the hIL-2 mutations are those described in WO2005/086751 (see claims 5 to 9 incorporated herein by reference). In one embodiment, the hIL-2 mutations are those described in WO2009/061853 (see claim 5 incorporated herein by reference). In one embodiment, the hIL-2 mutations are those described in WO2012/088446 (see claims 3 to 8 and 11 to 13 incorporated herein by reference). In one embodiment, the hIL-2 mutations are those described in WO2012/107417 (see claims 2, 4, 6 and 9, incorporated herein by reference). In one embodiment, the hIL-2 mutations are those described in WO2012/119093 (see claims 1 to 7, incorporated herein by reference). In one embodiment, the hIL-2 mutations are those described in WO2015/164815 (see claims 3 to 19, incorporated herein by reference).

In these aspects, where the residue numbering is defined with reference to the human wild-type IL-2 sequence, if, for example, there is a single amino acid deletion from the N-terminus of the cytokine, and the claim described an N88 amino acid mutation, then, for the variant IL-2 having the single amino acid deletion, the N will in fact be at position 87. If the cytokine has 3 amino acids deleted from the N terminus, and the mutation is an F42A mutation, then the position to be mutated, will in fact be F39 in the variant sequence.

Aspect 45. An immunocytokine according to aspect 40, wherein the hIL-2 comprises a variant IL-2 consists of an N-terminal sequence selected from Seq ID No:242 to 262 fused to the amino acids sequence of Seq ID No:324.

In one embodiment, the immunocytokine is 1D05 D1-9 ICK. In one embodiment, the immunocytokine is 1D05 D1-9. In one embodiment, the immunocytokine is 1D05 D9-2 ICK. In one embodiment, the immunocytokine is 1D05 D9-7 ICK.

Aspect 45a. A variant hIL-2 comprising an N-terminal sequence selected from Seq ID No:303 to 323 fused to the amino acids sequence of Seq ID No:324.

In one embodiment of aspect 44a, the variant hIL-2 is a purified variant hIL-2. In another embodiment of aspect 44a, the variant hIL-2 is an isolated and purified variant hIL-2.

Aspect 46. An immunocytokine according to any preceding aspect, wherein the IL-2 cytokine binds to the high affinity ($\alpha\beta\gamma$) IL-2 receptor with a potency less than free IL-2, for example with an EC50 of greater than 20 pM, greater than 50 pM or greater than 100 pM, e.g. when measured in a cell-based proliferative assay.

Free IL-2 has a potency of approximately 10 pM against the $\alpha\beta\gamma$ (high affinity) receptor in a cell-based proliferative assay. As used herein, EC50 refers to the effective concentration to give 50% of maximal activation of the IL2R. The higher the EC50, the less potent the substance is, thus a substance having an EC50 of 1 pM is more potent than a substance with an EC50 of 1 nM. The sequences of the $\alpha$-chain, $\beta$-chain and $\gamma$-chain are provided in Seq ID Nos: 327, 328 and 329 respectively.

In one embodiment, the IL-2 cytokine has an EC50 in the range of 5 pM to 20 pM. In one embodiment, the EC50 is in the range of 5 pM to 1 nM. In one embodiment, the EC50 is in the range of 5 pM to 750 pM, 5 pM to 500 pM, 5 pM to 250 pM or 5 pm to 100 pM, e.g. 5 pM to 50 pM.

In one embodiment, the EC50 is in the range of 10 pM to 1 nM. In one embodiment, the EC50 is in the range of 10 pM to 750 pM, 10 pM to 500 pM, 10 pM to 250 pM or 10 pm to 100 pM, e.g. 10 pM to 50 pM, or 10 pM to 30 pM.

In one embodiment, the EC50 is in the range of 20 pM to 1 nM. In one embodiment, the EC50 is in the range of 20 pM to 750 pM, 20 pM to 500 pM, 20 pM to 250 pM or 20 pm to 100 pM, e.g. 20 pM to 50 pM.

In another embodiment, the IL-2 cytokine has an EC50 in the range of 50 pM to 1 nM. In one embodiment, the EC50 is in the range of 50 pM to 750 pM, 50 pM to 500 pM, 50 pM to 250 pM or 50 pm to 100 pM, e.g. 50 pM to 75 pM. In another embodiment, the IL-2 cytokine has an EC50 in the range of 100 pM to 1 nM. In one embodiment, the EC50 is in the range of 100 pM to 800 pM, 100 pM to 700 pM, 100 pM to 600 pM or 100 pm to 500 pM, e.g. 100 pM to 400 pM. In another embodiment, the IL-2 cytokine has an EC50 in the range of 100 pm to 300 pM. In another embodiment, the IL-2 cytokine has an EC50 in the range of 100 pm to 200 pM.

In another embodiment, the EC50 is greater than 5 pM. In another embodiment, the EC50 is greater than 10 pM. In another embodiment, the EC50 is greater than 20 pM. In another embodiment, the EC50 is greater than 30 pM, greater than 40 pM, greater than 50 pM, greater than 60 pM or greater than 70 pM. In another embodiment, the EC50 is greater than 100 pM, greater than 125 pM, greater than 150 pM, greater than 175 pM or greater than 200 pM. In another embodiment, the EC50 is greater than 250 pM, greater than 300 pM, greater than 350 pM, greater than 400 pM. In another embodiment, the EC50 is greater than 500 pM, greater than 600 pM, greater than 700 pM or greater than 800 pM.

In one embodiment, the EC50 is less than 5nM. In one embodiment, the EC50 is less than 1 nM. In one embodiment, the EC50 is less than 800 pM. In one embodiment, the EC50 is less than 700 pM, the EC50 is less than 600 pM. In one embodiment, the EC50 is less than 500 pM. In one embodiment, the EC50 is less than 400 pM. In one embodiment, the EC50 is less than 300 pM. In one embodiment, the EC50 is less than 200 pM. In one embodiment, the EC50 is less than 100 pM. In one embodiment, the EC50 is less than 50 pM.

The potency of the immunocytokine against the $\alpha\beta\gamma$ IL-2R may be measured in a cell-based proliferative assay, which are well-known to those skilled in the art and are detailed more in the Examples hereinbelow (see Example 13 and FIG. 12A-12F).

Aspect 47. An immunocytokine according to any preceding aspect, wherein the IL-2 binds to the intermediate affinity ($\beta\gamma$) IL-2 receptor with a potency less than free IL-2, for example with an EC50 of greater than 1 nM, greater than 5 nM or greater than 10 nM, e.g. when measured in a cell-based proliferative assay.

Free IL-2 has a potency of approximately 100 pM against the βγ (intermediate affinity) receptor in a cell-based proliferative assay. As used herein, EC50 refers to the effective concentration to give 50% of maximal activation of the IL-2R. The higher the EC50, the less potent the substance is, thus a substance having an EC50 of 1 pM is more potent than a substance with an EC50 of 1 nM. The sequences of the α-chain, β-chain and γ-chain are provided in Seq ID Nos: 327, 328 and 329 respectively.

In one embodiment, the EC50 is in the range of 1 to 100 nM. In one embodiment, the EC50 is in the range of 10 nM to 100 nM. In one embodiment, the EC50 is in the range of 20 nM to 100 nM. In another embodiment, the IL-2 cytokine has an EC50 in the range of 30 nM to 100 nM, 40 nM to 100 nM, 50 nM to 100 nM. In one embodiment, the EC50 is in the range of 50 nM to 100 nM, 60 nM to 100 nM, 70 nM to 100 nM.

In one embodiment, the EC50 is in the range of 1 to 50 nM. In one embodiment, the EC50 is in the range of 10 nM to 50 nM. In one embodiment, the EC50 is in the range of 20 nM to 50 nM. In another embodiment, the IL-2 cytokine has an EC50 in the range of 30 nM to 50 nM or 40 nM to 50 nM.

In one embodiment, the EC50 is in the range of 1 to 10 nM. In one embodiment, the EC50 is in the range of 1 to 20 nM. In one embodiment, the EC50 is in the range of 1 to 30 nM. In one embodiment, the EC50 is in the range of 1 nM to 9 nM. In one embodiment, the EC50 is in the range of 1 nM to 8 nM. In another embodiment, the IL-2 cytokine has an EC50 in the range of 1 nM to 7 nM, 1 nM to 6 nM or 1 nM to 5 nM.

In another embodiment, the EC50 is greater than 0.5 nM, greater than 0.6 nM, greater than 0.7 nM, greater than 0.8 nM or greater than 0.9 nM. In another embodiment, the EC50 is greater than 1 nM, greater than 1.25 nM, greater than 1.5 nM, greater than 1.75 nM or greater than 2 nM. In another embodiment, the EC50 is greater than 2.5 nM, greater than 3 nM, greater than 3.5 nM, greater than 4 nM. In another embodiment, the EC50 is greater than 5 nM, greater than 6 nM, greater than 7 nM or greater than 8 nM. In a particular embodiment, the EC50 is greater than 1 nM.

In one embodiment, the EC50 is less than 10 nM. In one embodiment, the EC50 is less than 20 nM. In one embodiment, the EC50 is less than 30 nM. In one embodiment, the EC50 is less than 40 nM. In one embodiment, the EC50 is less than 50 nM.

In one embodiment, the EC50 is less than 100 nM. In one embodiment, the EC50 is less than 200 nM. In one embodiment, the EC50 is less than 300 nM.

In another embodiment, the EC50 is less than 75 nM or less than 50 nM.

In one embodiment, the IL-2 shows no detectable potency against the βγ IL-2R in a cell-based proliferative assay.

The potency of the immunocytokine against the βγ IL-2R may be measured in a cell-based proliferative assay, which are well-known to those skilled in the art and are detailed more in the Examples hereinbelow (see Example 13 and FIG. 12A-12F).

Aspect 48. An immunocytokine according to any preceding aspect, wherein the IL-2 preferentially binds to the high affinity (αβγ) IL-2 receptor over the intermediate affinity (βγ) IL-2 receptor.

Aspect 49. An immunocytokine according to aspect 48, wherein the ratio of IL-2 potency against the high affinity (αβγ) IL-2 receptor:intermediate affinity (βγ) IL-2 receptor is at least 2:1.

In one embodiment, the ratio is at least 3:1. In one embodiment, the ratio is at least 4:1. In one embodiment, the ratio is at least 5:1. In one embodiment, the ratio is at least 7.5:1. In one embodiment, the ratio is at least 10:1. In one embodiment, the ratio is at least 12.5:1. In one embodiment, the ratio is at least 15:1. In one embodiment, the ratio is at least 17.5:1. In one embodiment, the ratio is at least 20:1.

In another embodiment, the ratio is at least 50:1. In another embodiment, the ratio is at least 75:1. In another embodiment, the ratio is at least 100:1. In another embodiment, the ratio is at least 250:1. In another embodiment, the ratio is at least 500:1. In another embodiment, the ratio is at least 750:1. In another embodiment, the ratio is at least 1000:1.

In another embodiment, the ratio is at least 1250:1. In another embodiment, the ratio is at least 1500:1. In another embodiment, the ratio is at least 1750:1. In another embodiment, the ratio is at least 2000:1.

Aspect 50. An immunocytokine according to any preceding aspect, wherein the antigen binding site binds to hPD-L1 with an affinity of less than 500 pM (e.g. less than 300 pM or less than 200 pM), optionally wherein the immunocytokine provides a ratio of the potency of the IL-2 cytokine against the high affinity (αβγ) receptor: affinity of the anti-PD-L1 antigen binding site against hPD-L1 of at least 2:1.

In one embodiment, the antigen binding site binds to hPD-L1 with an affinity of less than 200 pM. In one embodiment, the antigen binding site binds to hPD-L1 with an affinity of less than 100 pM, or less than 50 pM.

In one embodiment, the antigen binding site binds to hPD-L1 with an affinity of between 50 pM and 500 pM, or between 75 pM and 500 pM, or between 100 pM and 500 pM or between 200 pM and 500 pM.

In one embodiment, the antigen binding site binds to hPD-L1 with an affinity of between 50 pM and 400 pM, or between 50 pM and 300 pM, or between 50 pM and 200 pM or between 50 pM and 100 pM.

In one embodiment, the antigen binding site binds to hPD-L1 with an affinity of between 100 pM and 500 pM, or between 100 pM and 400 pM, or between 100 pM and 300 pM.

In one embodiment, the ratio of the potency of the IL-2 cytokine against the high affinity (αβγ) receptor: affinity of the anti-PD-L1 antigen binding site against hPD-L1 is at least 3:1. In one embodiment, the ratio of the potency of the IL-2 cytokine against the high affinity (αβγ) receptor: affinity of the anti-PD-L1 antigen binding site against hPD-L1 is at least 4:1. In one embodiment, the ratio of the potency of the IL-2 cytokine against the high affinity (αβγ) receptor: affinity of the anti-PD-L1 antigen binding site against hPD-L1 is at least 5:1. In one embodiment, the ratio of the potency of the IL-2 cytokine against the high affinity (αβγ) receptor: affinity of the anti-PD-L1 antigen binding site against hPD-L1 is at least 7:1. In one embodiment, the ratio of the potency of the IL-2 cytokine against the high affinity (αβγ) receptor: affinity of the anti-PD-L1 antigen binding site against hPD-L1 is at least 10:1

Aspect 50a. An immunocytokine according to any preceding aspect, wherein the antigen binding site binds to mPD-L1 (Seq ID No:325) with an affinity of less than 500 nM (e.g. less than 100 nM, less than 10 nM or less than 1 nm).

In one embodiment, the antigen binding site binds to hPD-L1 with an affinity of between 1 nM and 500 nM, or between 1 nM and 250 nM, or between 1 nM and 100 nM, or between 1 nM and 50 nM.

In one embodiment, the antigen binding site binds to hPD-L1 with an affinity of between 10 nM and 500 nM, or between 10 nM and 250 nM, or between 10 nM and 100 nM, or between 1 nM and 50 nM, in particular between 10 nM and 100 nM.

In one embodiment, the antigen binding site binds to hPD-L1 with an affinity of between 100 nM and 500 nM, or between 100 nM and 400 nM, or between 100 nM and 300 nM, or between 100 nM and 200 nM.

The affinity of the antigen-binding site to hPD-L1 or mPD-L1 may be measured by any technique well-known to those skilled in the art. In one embodiment, the affinity is measured using SPR, the details of which are provided hereinabove.

Aspect 51. An immunocytokine as defined in any preceding aspect for use in treating or preventing a hPD-L1-mediated disease or condition, e.g. selected from neoplastic or non-neoplastic disease, chronic viral infections, and malignant tumours, such as melanoma, breast cancer, ovarian cancer, Merkel cell carcinoma, non-small cell lung cancer (squamous and non-squamous), renal cell cancer, bladder cancer, colorectal cancer (without MSI or microsatellite instability), head and neck squamous cell carcinoma, mesothelioma, virally induced cancers (such as cervical cancer and nasopharyngeal cancer), soft tissue sarcomas, haematological malignancies such as Hodgkin's and non-Hodgkin's disease, diffuse large B-cell lymphoma (for example melanoma, breast cancer, ovarian cancer, Merkel cell carcinoma, non-small cell lung cancer (squamous and non-squamous), renal cell cancer, bladder cancer, colorectal cancer (without MSI or microsatellite instability), head and neck squamous cell carcinoma and mesothelioma or for example virally induced cancers (such as cervical cancer and nasopharyngeal cancer) and soft tissue sarcomas).

Aspect 52. Use of an immunocytokine as defined in any one of aspects 1 to 50 in the manufacture of a medicament for administration to a human for treating or preventing a hPD-L1 mediated disease or condition in the human, e.g. wherein the hPD-L1 mediated disease or condition is selected from neoplastic or non-neoplastic disease, chronic viral infections, and malignant tumours, such as melanoma, breast cancer, ovarian cancer, Merkel cell carcinoma, non-small cell lung cancer (squamous and non-squamous), renal cell cancer, bladder cancer, colorectal cancer (without MSI or microsatellite instability), head and neck squamous cell carcinoma, mesothelioma, virally induced cancers (such as cervical cancer and nasopharyngeal cancer), soft tissue sarcomas, haematological malignancies such as Hodgkin's and non-Hodgkin's disease, diffuse large B-cell lymphoma (for example melanoma, breast cancer, ovarian cancer, Merkel cell carcinoma, non-small cell lung cancer (squamous and non-squamous), renal cell cancer, bladder cancer, colorectal cancer (without MSI or microsatellite instability), head and neck squamous cell carcinoma and mesothelioma or for example virally induced cancers (such as cervical cancer and nasopharyngeal cancer) and soft tissue sarcomas).

Aspect 53. A method of treating or preventing a hPD-L1 mediated disease or condition, e.g. selected from neoplastic or non-neoplastic disease, chronic viral infections, and malignant tumours, such as melanoma, breast cancer, ovarian cancer, Merkel cell carcinoma, non-small cell lung cancer (squamous and non-squamous), renal cell cancer, bladder cancer, colorectal cancer (without MSI or microsatellite instability), head and neck squamous cell carcinoma, mesothelioma, virally induced cancers (such as cervical cancer and nasopharyngeal cancer), soft tissue sarcomas, haematological malignancies such as Hodgkin's and non-Hodgkin's disease, diffuse large B-cell lymphoma (for example melanoma, breast cancer, ovarian cancer, Merkel cell carcinoma, non-small cell lung cancer (squamous and non-squamous), renal cell cancer, bladder cancer, colorectal cancer (without MSI or microsatellite instability), head and neck squamous cell carcinoma and mesothelioma or for example virally induced cancers (such as cervical cancer and nasopharyngeal cancer) and soft tissue sarcomas) in a human, comprising administering to said human a therapeutically effective amount of an immunocytokine as defined in any one of aspects 1 to 50, wherein the hPD-L1 mediated disease or condition is thereby treated or prevented.

In any of aspects 51 to 13, the hPD-L1 mediated disease may be any of those as described herein. In one embodiment, in any of aspects 51 to 53, the hPD-L1 mediated disease is a virally induced cancer, such as cervical cancer and nasopharyngeal cancer, for example cervical cancers caused by HPV infection. In one embodiment, in any of aspects 51 to 53, the hPD-L1 mediated disease is a chronic viral infection. In one embodiment, in any of aspects 51 to 53, the hPD-L1 mediated disease is a neoplastic disease. In one embodiment, in any of aspects 51 to 53, the hPD-L1 mediated disease is a non-neoplastic disease. In one embodiment, in any of aspects 51 to 53, the hPD-L1 mediated disease is a malignant tumour. In one embodiment, in any of aspects 51 to 53, the hPD-L1 mediated disease is a cancer which is known to be responsive to PD-L1 therapy, such as melanoma, Merkel cell carcinoma, non-small cell lung cancer (squamous and non-squamous), renal cell cancer, bladder cancer, head and neck squamous cell carcinoma, mesothelioma. In one embodiment, in any of aspects 51 to 53, the hPD-L1 mediated disease is a cancer which is a soft tissue sarcoma.

Aspect 54. The immunocytokine according to aspect 51, the use according to aspect 52 or the method according to aspect 53, wherein the hPD-L1-mediated disease or condition is cancer.

Aspect 55. The immunocytokine, the use or the method according to aspect 54, wherein the cancer is selected from melanoma, Merkel cell cancer, non-small cell lung cancer, bladder cancer, Non-Hodgkin's lymphomas, colorectal cancer with microsatellite instability (MSI) or a cancer selected from breast cancer, ovarian cancer, colorectal cancer (without MSI or microsatellite instability), in particular melanoma and renal cell cancer.

In one embodiment, the cancer is a cancer which is known to be responsive to both IL-2 therapy and PD-L1 therapy, such as melanoma and renal cell cancer.

In one embodiment, the cancer is colorectal cancer with microsatellite instability (MSI). In one embodiment, the cancer is breast cancer. In one embodiment, the cancer is ovarian cancer.

Aspect 56. The immunocytokine, use or the method according to any one of aspects 51 to 55, further comprising administering to the human a further therapy, for example a further therapeutic agent, optionally wherein the further therapeutic agent is independently selected from the group consisting of:
  A) other immune checkpoint inhibitors (such as anti-TIM-3 antibodies, anti-CTLA-4 antibodies, anti-TIGIT antibodies and anti-LAG-3 antibodies);
  B) immune stimulators (such as anti-OX40 antibodies, anti-GITR antibodies, anti-CD137 antibodies, anti-ICOS antibodies and anti-CD40 antibodies);
  C) chemokine receptor antagonists (such as CXCR4, CCR4 and CXCR2);

D) targeted kinase inhibitors (such as CSF-1R or VEGFR inhibitors);
E) angiogenesis inhibitors (such as anti-VEGF-A or Delta-like Ligand-4);
F) immune stimulating peptides or chemokines (such as CXCL9 or CXCL10);
G) cytokines (such as IL-15 and IL-21);
H) bispecific T-cell engagers (BiTEs) having at least one specificity against CD3 (e.g. CD3/CD19 BiTE);
I) other bi-specific molecules (for example IL-15-containing molecules targeted towards tumour associated antigens, for example Epidermal growth factor receptors such as EGFR, Her-2, New York Esophageal Cancer-1 (NY-ESO-1), GD2, EpCAM or Melanoma Associated Antigen-3 (MAGE-A3));
J) oncolytic viruses (such as HSV virus (optionally which secretes GMCSF), Newcastle disease virus and Vaccinia virus);
K) vaccination with tumour associated antigens (such as New York Esophageal Cancer-1 [NY-ESO-1], Melanoma Associated Antigen-3 [MAGE-3]);
L) cell-based therapies (such as chimeric Antigen Receptor-T cells (CAR-T) for example expressing anti-CD19, anti-EpCam or anti-mesothelin); and
M) adoptive transfer of tumour specific T-cells or LAK cells, or optionally wherein the further therapy is chemotherapy, radiotherapy and surgical removal of tumours.

In this aspect, any of the features and embodiments of concept 46 apply mutatis mutandis.

In this aspect, the bispecific molecules include "bispecific antibodies" and antibody fusion proteins, including those formats and molecules described in concepts 37 to 40.

Aspect 57. A pharmaceutical composition comprising an immunocytokine as defined in any one of aspects 1 to 50 and a pharmaceutically acceptable excipient, diluent or carrier and optionally further comprising a further therapeutic agent independently selected from the group consisting of:
A) other immune checkpoint inhibitors (such as anti-TIM-3 antibodies, anti-CTLA-4 antibodies, anti-TIGIT antibodies and anti-LAG-3 antibodies);
B) immune stimulators (such as anti-OX40 antibodies, anti-GITR antibodies, anti-CD137 antibodies, anti-ICOS antibodies and anti-CD40 antibodies);
C) chemokine receptor antagonists (such as CXCR4, CCR4 and CXCR2);
D) targeted kinase inhibitors (such as CSF-1R or VEGFR inhibitors);
E) angiogenesis inhibitors (such as anti-VEGF-A or Delta-like Ligand-4);
F) immune stimulating peptides or chemokines (such as CXCL9 or CXCL10);
G) cytokines (such as IL-15 and IL-21);
H) bispecific T-cell engagers (BiTEs) having at least one specificity against CD3 (e.g. CD3/CD19 BiTE);
I) other bi-specific molecules (for example IL-15-containing molecules targeted towards tumour associated antigens, for example Epidermal growth factor receptors such as EGFR, Her-2, New York Esophageal Cancer-1 (NY-ESO-1), GD2, EpCAM or Melanoma Associated Antigen-3 (MAGE-A3));
J) oncolytic viruses (such as HSV virus (optionally which secretes GMCSF), Newcastle disease virus and Vaccinia virus);
K) vaccination with tumour associated antigens (such as New York Esophageal Cancer-1 [NY-ESO-1], Melanoma Associated Antigen-3 [MAGE-3]);
L) cell-based therapies (such as chimeric Antigen Receptor-T cells (CAR-T) for example expressing anti-CD19, anti-EpCam or anti-mesothelin); and
M) adoptive transfer of tumour specific T-cells or LAK cells.

In one embodiment, the further therapeutic agent is administered sequentially or simultaneously with the immunocytokine.

In this aspect, any of the features and embodiments of concept 48 apply mutatis mutandis.

In this aspect, the bispecific molecules include "bispecific antibodies" and antibody fusion proteins.

Aspect 58. A pharmaceutical composition according to aspect 57, or a kit comprising a pharmaceutical composition as defined in aspect 57, wherein the composition is for treating and/or preventing a hPD-L1 mediated disease or condition, e.g. selected from neoplastic or non-neoplastic disease, chronic viral infections, and malignant tumours, such as melanoma, breast cancer, ovarian cancer, Merkel cell carcinoma, non-small cell lung cancer (squamous and non-squamous), renal cell cancer, bladder cancer, colorectal cancer (without MSI or microsatellite instability), head and neck squamous cell carcinoma, mesothelioma, virally induced cancers (such as cervical cancer and nasopharyngeal cancer), soft tissue sarcomas, haematological malignancies such as Hodgkin's and non-Hodgkin's disease, diffuse large B-cell lymphoma (for example melanoma, breast cancer, ovarian cancer, Merkel cell carcinoma, non-small cell lung cancer (squamous and non-squamous), renal cell cancer, bladder cancer, colorectal cancer (without MSI or microsatellite instability), head and neck squamous cell carcinoma and mesothelioma or for example virally induced cancers (such as cervical cancer and nasopharyngeal cancer) and soft tissue sarcomas).

Aspect 59. A pharmaceutical composition according to aspect 57 or aspect 58 in combination with, or kit according to aspect 58 comprising a label or instructions for use to treat and/or prevent said disease or condition in a human; optionally wherein the label or instructions comprise a marketing authorisation number (e.g., an FDA or EMA authorisation number); optionally wherein the kit comprises an IV or injection device that comprises the immunocytokine.

Aspect 60. A method of treating a proliferative disease in an animal (e.g. a human), comprising administering an effective amount of an immunocytokine as defined in any one of aspects 1 to 50 to said patient.

Proliferative diseases may be any as described elsewhere herein.

Aspect 61. A nucleic acid that encodes a heavy chain and/or a light chain of an immunocytokine as defined in any one of aspects 1 to 50.

In one embodiment, the nucleic acid encodes a light chain of an immunocytokine as defined in any one of aspects 1 to 50.

Aspect 62. A vector comprising the nucleic acid as defined in aspect 61; optionally wherein the vector is a CHO or HEK293 vector.

Aspect 63. A host comprising the nucleic acid as defined in aspect 61 or the vector as defined in aspect 62.

Unless otherwise apparent from the context, the uses for antibodies or fragments applies mutatis mutandis to the immunocytokines of the invention.

In one embodiment, the PD-L1 specific antibodies described herein and antigen binding fragments thereof can be used for therapeutic modulation of the PD-1/PD-L1 pathway. In one embodiment, the PD-L1 specific antibody or fragment thereof is as described in any concept, aspect or embodiment herein.

In one embodiment, the antibody or antibody binding fragment specifically binds to PD-L1 and thereby inhibits PD-L1 activity. In another embodiment, the antibody or antibody binding fragment specifically binds to PD-L1 and thereby inhibits binding of PD-L1 to PD-1. In another embodiment, the antibody or antibody binding fragment specifically binds to PD-L1 and thereby inhibits binding of PD-L1 to B7-1. In yet another embodiment, the antibody or antigen binding fragment thereof blocks PD-L1 induced T-cell suppression and thereby enhance anti-tumour immunity.

In yet another embodiment, the antibody or antigen binding fragment thereof is capable of stimulating one or more of the following activities: T-cell proliferation, IFN-γ, CD25 and/or IL-2 secretion in mixed lymphocyte reactions.

In one embodiment, the antibody or antigen binding fragment thereof specifically binds PD-L1 and inhibits PD-L1 induced cell proliferation, for example, tumour cell proliferation and/or inhibits tumour cell survival. In another embodiment, the antibody or antigen binding fragment thereof specifically binds PD-L1 and thereby inhibits PD-L1 mediated suppression of T-cells, including, but not limited to, tumour reactive T-cells, thereby enhancing anti-tumour cytolytic T-cell activity. In other embodiments, the antibodies or binding fragments thereof as described herein inhibit tumour cell adhesion, motility, invasion and cellular metastasis, and reduce tumour growth. In other embodiments, the antibodies or binding fragments thereof can bind to cells expressing PD-L1, including tumour and non-tumour cells, and recruit, by means of interaction with the Fc portion of the antibody, cellular effector functions against the target cells by mechanisms including but not limited to antibody dependent cellular cytotoxicity (ADCC) and antibody dependent cellular phagocytosis (ADCP).

Still further embodiments include methods of treating a proliferative or invasion-related disease in a mammal by administering to the animal a therapeutically effective dose of an antibody or antigen binding fragment thereof. In another embodiment, the antibodies or antigen binding fragments thereof can be used in a method for treating a mammal suffering from a disease selected from: neoplastic or non-neoplastic disease, chronic viral infection, and a malignant tumour, wherein the method includes administering to the mammal a therapeutically effective dose of an antibody or antigen binding fragment thereof.

Still further embodiments include methods of treating a disease of immunological dysfunction in a mammal by administering to the animal a therapeutically effective dose of an antibody or antigen binding fragment thereof as described herein. Exemplary immunological dysfunction in humans includes diseases of neurological deficit, such as Alzheimer's disease.

Exemplary cancers in humans include a Merkel cell carcinoma, breast cancer, prostate cancer, basal cell carcinoma, biliary tract cancer, bladder cancer, bone cancer, brain and CNS cancer (e.g. gliomblastoma), cervical cancer, choriocarcinoma, colon and rectum cancer, connective tissue cancer, cancer of the digestive system; endometrial cancer, esophageal cancer; eye cancer; cancer of the head and neck; nasopharyngeal cancer; gastric cancer; intra-epithelial neoplasm; kidney cancer; larynx cancer; leukemia; liver cancer; lung cancer (e.g. small cell and non-small cell); lymphoma including Hodgkin's and Non-Hodgkin's lymphoma including but not limited to DLBCL; Chronic lymphocytic leu-kaemia, melanoma; uveal melanoma, myeloma, neuroblastoma, oral cavity cancer (e.g., lip, tongue, mouth, and pharynx); ovarian cancer; pancreatic cancer, retinoblastoma; rhabdomyosarcoma; rectal cancer, renal cancer (renal cell carcinoma (RCC)), cancer of the respiratory system; sarcoma, skin cancer; stomach cancer, testicular cancer, thyroid cancer; uterine cancer, cancer of the urinary system, as well as other carcinomas and sarcomas. Further examples of virally induced cancers including; Nasopharyngeal carcinoma, certain Types of NHL (for example but not limited to EBV+CNS lymphomas, DLBCL and BL, Hodgkins lymphoma (thought to be EBV driven) HPV-related cervical and head an neck squamous cell carcinomas); HBV hepatocellular carcinoma.

Exemplary chronic infections in humans include HIV, hepatitis B virus (HBV), and hepatitis C virus (HCV).

Proliferative or invasion-related diseases that can be treated with the antibodies or antigen binding fragments described herein include neoplastic diseases, and the metastasis associated with such neoplastic disease, such as, melanoma, uveal melanoma, skin cancer, small cell lung cancer, non-small cell lung cancer, salivary gland, glioma, hepatocellular (liver) carcinoma, gallbladder cancer, thyroid tumour, bone cancer, gastric (stomach) cancer, prostate cancer, breast cancer (including triple negative breast cancer), ovarian cancer, cervical cancer, uterine cancer, vulval cancer, endometrial cancer, testicular cancer, bladder cancer, lung cancer, glioblastoma, thyroid cancer, endometrial cancer, kidney cancer, colon cancer, colorectal cancer, pancreatic cancer, esophageal carcinoma, brain/CNS cancers, neuronal cancers, head and neck cancers (including but not limited to squamous cell carcinoma of the head and neck (SCCHN)), mesothelioma, sarcomas, biliary (cholangiocarcinoma), small bowel adenocarcinoma, pediatric malignancies, epidermoid carcinoma, sarcomas, cancer of the pleural/peritoneal membranes and leukaemia, including acute myeloid leukaemia, acute lymphoblastic leukaemia, and multiple myeloma. Treatable chronic viral infections include HIV, hepatitis B virus (HBV), and hepatitis C virus (HCV) in humans, simian immunodeficiency virus (SIV) in monkeys, and lymphocytic choriomeningitis virus (LCMV) in mice.

The antibody or antigen binding fragment thereof can be administered alone, or in combination with other antibodies or chemo therapeutic drugs, radiation therapy or therapeutic vaccines. In one embodiment, the antibody or antigen binding fragment thereof is administered as an antibody-drug conjugate in which the antibody or antigen binding fragment thereof is linked to a drug moiety such as a cytotoxic or cytostatic agent. The use of antibody-drug conjugates for the local delivery of cytotoxic or cytostatic agents in the treatment of cancer allows targeted delivery of the drug moiety to tumours, and intracellular accumulation therein, where systemic administration of unconjugated drug may result in unacceptable levels of toxicity. Drugs in antibody drug conjugates can include, but are not limited to, daunomycin, doxorubicin, methotrexate, and vindesine. Toxins can also be used in antibody-toxin conjugates, including, for example, bacterial toxins such as diphtheria toxin, plant toxins such as ricin, small molecule toxins such as geldanamycin. The toxins may effect their cytotoxic and cytostatic effects by mechanisms including tubulin binding, DNA binding, or topoisomerase.

In another embodiment, the antibodies or antigen binding fragments can be used to detect the presence, absence and/or level of surface expressed PD-L1 expression in a sample. PD-L1 surface expression can be detected in vivo and/or in vitro and is useful in helping diagnose diseases or conditions that involve expression and/or overexpression of PD-L1.

In another embodiment, the PD-L1 specific antibodies or antigen binding fragments thereof can be used for the assessment of expression and localization of PD-L1 in a biological sample from a patient. In one embodiment, the biological sample is a tissue sample and PD-L1 expression is detected using known methods such as FLOW cytometry, IHC in fresh tissue, IHC in FFPE tissue and/or IHC in frozen tissue. In other embodiments, the biological sample is blood, plasma or serum.

In one embodiment, the antibody or antibody fragment described herein is labeled with a detectable moiety, for example, a radiolabel, fluorescent label, enzymatic label chemiluminescent labeled or a biotinyl group. Radioisotopes or radionuclides may include 3H, 14C, 15N, 35S, 90Y, 99Tc, 115In, 125I, 131I, fluorescent labels may include rhodamine, lanthanide phosphors or FITC and enzymatic labels may include horseradish peroxidase, β-galactosidase, luciferase, alkaline phosphatase. Additional labels include, by way of illustration and not limitation: enzymes, such as glucose-6-phosphate dehydrogenase ("G6PDH"), alpha-D-galactosidase, glucose oxydase, glucose amylase, carbonic anhydrase, acetylcholinesterase, lysozyme, malate dehydrogenase and peroxidase; dyes; additional fluorescent labels or fluorescers include, such as fluorescein and its derivatives, fluorochrome, GFP (GFP for "Green Fluorescent Protein"), dansyl, umbelliferone, phycoerythrin, phycocyanin, allophycocyanin, o-phthaldehyde, and fiuorescamine; fluorophores such as lanthanide cryptates and chelates e.g. Europium etc (Perkin Elmer and Cisbio Assays); chemoluminescent labels or chemiluminescers, such as isoluminol, luminol and the dioxetanes; sensitisers; coenzymes; enzyme substrates; particles, such as latex or carbon particles; metal sol; crystallite; liposomes; cells, etc., which may be further labelled with a dye, catalyst or other detectable group; molecules such as biotin, digoxygenin or 5-bromodeoxyuridine; toxin moieties, such as for example a toxin moiety selected from a group of *Pseudomonas* exotoxin (PE or a cytotoxic fragment or mutant thereof), Diptheria toxin or a cytotoxic fragment or mutant thereof, a botulinum toxin A, B, C, D, E or F, ricin or a cytotoxic fragment thereof e.g. ricin A, abrin or a cytotoxic fragment thereof, saporin or a cytotoxic fragment thereof, pokeweed antiviral toxin or a cytotoxic fragment thereof and bryodin 1 or a cytotoxic fragment thereof.

In one embodiment, the antibody or antigen binding fragment thereof can be administered to a patient, wherein the antibody or antigen binding fragment is conjugated to a label. The presence of the label in the patient can be measured or observed, wherein a relatively high amount of the label may indicate a high risk of disease and a relatively low amount of the label may indicate a relatively low risk of the disease. In one embodiment, the label is a contrast agent, isotopic tag, or fluorescent marker, such as green fluorescent protein.

In one embodiment, the antibody or antigen binding fragment is used to monitor therapy that involves the use of other therapeutic agents, including, for example, chemotherapeutic agents or other antibodies that specifically bind PD-L1. In one embodiment, the antibody does not compete with the therapeutic PD-L1 antibodies.

In one embodiment, detection of PD-L1 expression can be used to guide patient selection. In one embodiment, the antibodies or antigen binding fragments thereof can be used to assist in patient selection for therapeutic antibody treatment with an anti-PD-L1 antibody, including, but not limited to anti-PD-L1 antibodies disclosed in WO2011/066389, entitled "Targeted Binding Agents Against B7-H1." In another embodiment, the antibodies or antigen binding fragments thereof can be used to assist in patient selection for treatment with immunotherapies such as anti-PD-L1, anti-CTLA4, anti-OX40, anti-PD-1, vaccines etc. In some cases, higher levels of PD-L1 may be indicative of successful therapy, whereas lower levels may indicate a reduced likelihood of success. Preferential expression of splice variants and/or protein processing may produce unique protein mixture profiles which may impact a patient's response to treatment or may change following treatment. These profiles may help to identify patients and define patient subsets who should receive treatment, continue to receive treatment or who should receive an alternative treatment. In another embodiment, the antibodies or antigen binding fragments thereof can be used for detection of PD-L1 isoforms. Patient samples can include, for example, blood, plasma, serum, sputum, saliva, urine, CSF, tears, exhaled exogenous particle samples, cell supernatant, cell or tissue lysate or tissue samples.

In one embodiment, the antibodies or antigen binding fragments thereof can be used to identify the presence, absence and/or level of PD-L1 expression at baseline, i.e., before treatment.

In another embodiment, the PD-L1 specific antibodies or antigen binding fragments thereof can be used as an exclusion marker to suggest treatment with therapies that do not target PD-L1. In another embodiment, the PD-L1 specific antibodies or antigen binding fragments thereof can be used as a prognostic marker for life expectancy. In particular, PD-L1 expression on tumours is linked to poor prognosis and life expectancy can be estimated based on historical data within tumour types.

Methods for detection of proteins are known, and include, for example, IHC, FLOW cytometery, Western blotting and Mass Spectroscopy, Immunoprecipitation, aptamers, immuno-PCR., and protein array.

The antibodies can be used to guide therapy. For example, the antibodies or antigen binding fragments thereof can be used to identify the presence, absence and/or level of PD-L1 expression during or after treatment. In one embodiment, the antibodies or antigen binding fragments thereof can be used as early response biomarkers to assist in patient management, drug approval and reimbursement. In another embodiment, the antibodies or antigen binding fragments thereof can be used to identify the presence, absence and/or level of PD-L1 expression to help guide therapy. For example, PD-L1 expression can help determine whether the treatment is effective, and hence, whether or not treatment should be continued, or whether the dose should be adjusted (increased or decreased) and whether a combination regimen should be changed. For example, in one embodiment, the PD-L1 specific antibodies or antigen binding fragments thereof can be used for determining receptor occupancy of PD-L1 on cells in a patient treated with anti-PD-L1 therapy for dose setting (PK/PD). In particular, receptor occupancy can be used as a measure of target engagement or target coverage. Estimates of the amount or duration of target engagement needed to elicit a biological or clinical response could be used to determine if a patient has been dosed sufficiently or not. In particular, the antibodies can be used to assist in evaluating the relationship between, dose, exposure, receptor occupancy, pharmacodynamic response and clinical benefit.

In another embodiment, the PD-L1 specific antibodies or antigen binding fragments thereof can be used for patient monitoring, to help evaluate whether a course of treatment is effective and whether or not treatment should be continued. For example, in one embodiment, the antibodies or antigen binding fragments thereof can be used detect expression before a patient receives therapeutic treatment that targets PD-L1. In another embodiment, the antibodies or antigen binding fragments thereof can be used to detect expression during therapy or after a patient has received therapeutic anti-PD-L1 treatment. In another embodiment, the antibodies or antigen binding fragments thereof can be used as an early response marker to assist in the determination as to whether or not a course of therapy is effective and should be continued or discontinued. In one embodiment, the expression of PD-L1 is detected after washout, wherein the term "washout" refers to a period of time after which the administered drug has been eliminated from the body. In particular, expression of PD-L1 may be detected after washout if the patient is treated with anti-PD-L1 therapy that competes with the detection antibody. However, if the patient is treated with an antibody that does not compete with an anti-PD-L1 antibody, such as anti-CTLA-4 or anti-PD-1, detection can be performed without waiting for washout. In another embodiment, the detection antibody can bind to PD-L1 but not compete with a therapeutic antibody that binds to PD-L1. In this situation, washout may not be necessary. The washout period can vary depending upon many factors, but is generally a period of at least about 1, 2, 3, 4, 5, or 6 weeks and up to about 1, 2, 3, 4, 5 or 6 months from the most recent chemotherapy or immunotherapy treatment. The antibodies or antigen binding fragments thereof can be used to determine expression of PD-L1 on biopsy samples or on circulating tumour cells (CTC).

In one embodiment, labelled antibodies or antigen binding fragments thereof can be used to identify a peripheral correlate to enable non-invasive assessment of tumour status pre, during and post treatment.

Methods for detection of proteins are known, and include, for example, IHC, flow cytometery, Western blotting and Mass Spectroscopy, immunoprecipitation, aptamers, immuno-PCR., and protein array.

In another embodiment, antibodies or antigen binding fragments thereof can be used as a capture reagent or detection reagent for examination of the protein binding partners of PD-L1 protein species in the context of a protein "pull-down." A protein "pull down" refers to immunoprecipitation of intact protein complexes, such as antigen along with any proteins or ligands that are bound to it—also known as co-immunoprecipitation (Co-IP). Co-IP works by selecting an antibody that targets a known protein that is believed to be a member of a larger complex of proteins. By targeting the known member with an antibody it may become possible to pull the entire protein complex out of solution and thereby identify unknown members of the complex. Complete understanding of the regulation of immune recognition through and PD-1 axis vs. CTLA-4 etc. is not fully understood. As such, antibodies and antigen binding fragments could improve knowledge of the interplay among accessory proteins and factors, which may determine a patient's propensity to respond to specific therapies or immunotherapy in general.

Unless otherwise apparent from the context, the compositions for antibodies or fragments applies mutatis mutandis to the immunocytokines of the invention.

In one embodiment, there is provided a pharmaceutical composition comprising an effective amount of an antibody or antigen binding fragment and a pharmaceutically acceptable carrier. An effective amount of antibody to be employed therapeutically will depend, for example, upon the therapeutic objectives, the route of administration, and the condition of the patient. In one embodiment, the composition includes other excipients or stabilizers.

Pharmaceutically acceptable carriers are known and include carriers, excipients, or stabilizers that are nontoxic to the cell or mammal being exposed thereto at the dosages and concentrations employed. Often the physiologically acceptable carrier is an aqueous pH buffered solution. Examples of physiologically acceptable carriers include buffers such as phosphate, citrate, and other organic acids; antioxidants including ascorbic acid; low molecular weight (less than about 10 residues) polypeptide; proteins, such as serum albumin, gelatin, or immunoglobulins; hydrophilic polymers such as polyvinylpyrrolidone; amino acids such as glycine, glutamine, asparagine, arginine or lysine; monosaccharides, disaccharides, and other carbohydrates including glucose, mannose, or dextrins; chelating agents such as Ethylenediaminetetraacetic acid (EDTA); sugar alcohols such as mannitol or sorbitol; salt-forming counterions such as sodium; and/or nonionic surfactants such as TWEEN™, polyethylene glycol (PEG), and PLURONICS™.

The antibodies or antigen binding fragments can be administered intravenously or through the nose, lung, for example, as a liquid or powder aerosol (lyophilized). The composition can also be administered parenterally or subcutaneously. When administered systemically, the composition should be sterile, pyrogen-free and in a physiologically acceptable solution having due regard for pH, isotonicity and stability. These conditions are known to those skilled in the art.

Methods of administering a prophylactic or therapeutic agent (e.g., an antibody as disclosed herein), or pharmaceutical composition include, but are not limited to, parenteral administration (e.g., intradermal, intramuscular, intraperitoneal, intravenous and subcutaneous), epidural, and mucosal (e.g., intranasal and oral routes). In a specific embodiment, a prophylactic or therapeutic agent (e.g., an antibody as disclosed herein), or a pharmaceutical composition is administered intranasally, intramuscularly, intravenously, or subcutaneously. The prophylactic or therapeutic agents, or compositions may be administered by any convenient route, for example by infusion or bolus injection, by absorption through epithelial or mucocutaneous linings (e.g., oral mucosa, intranasal mucosa, rectal and intestinal mucosa, etc.) and may be administered together with other biologically active agents. Administration can be systemic or local. Each dose may or may not be administered by an identical route of administration. In one embodiment, an anti-PD-L1 antibody or fragment as disclosed herein may be administered via multiple routes of administration simultaneously or subsequently to other doses of the same or a different anti-PD-L1 antibody or fragment as disclosed herein.

Various delivery systems are known and can be used to administer a prophylactic or therapeutic agent (e.g., an antibody or fragment as disclosed herein), including, but not limited to, encapsulation in liposomes, microparticles, microcapsules, recombinant cells capable of expressing the antibody, receptor-mediated endocytosis (see, e.g., Wu and Wu, J. Biol. Chem. 262:4429-4432 (1987)), construction of a nucleic acid as part of a retroviral or other vector, etc. In addition, pulmonary administration can also be employed, e.g., by use of an inhaler or nebulizer, and formulation with an aerosolizing agent. See, e.g., U.S. Pat. Nos. 6,019,968, 5,985,320, 5,985,309, 5,934,272, 5,874,064, 5,855,913, 5,290,540, and 4,880,078; and PCT Publication Nos. WO92/

19244, WO97/32572, WO97/44013, WO98/31346, and WO99/66903, each of which is incorporated herein by reference their entirety.

In a specific embodiment, it may be desirable to administer a prophylactic or therapeutic agent, or a pharmaceutical composition as described herein locally to the area in need of treatment. This may be achieved by, for example, local infusion, by topical administration (e.g., by intranasal spray), by injection, or by means of an implant, said implant being of a porous, non-porous, or gelatinous material, including membranes, such as sialastic membranes, or fibres. When administering an anti-PD-L1 antibody or fragment, care must be taken to use materials to which the antibody does not absorb.

Unless otherwise apparent from the context, the kits and articles of manufacture for antibodies or fragments applies mutatis mutandis to the immunocytokines of the invention.

In one embodiment, the invention provides a kit for detecting PD-L1 in a biological sample. The kit can be used to screen for PD-L1 related diseases. In one embodiment, the kit includes an antibody or antigen binding fragment and a means for determining whether the antibody or antigen binding fragment is bound to PD-L1 in a sample. In one embodiment, the antibody or antigen binding fragment is labelled. In another embodiment, the antibody or antigen binding fragment is an unlabelled primary antibody and the kit includes means for detecting the primary antibody. In one embodiment, the means for detecting includes a labelled secondary antibody that is an anti-immmunoglobulin antibody. The antibody may be labelled with any suitable marker, including, for example, a fluorochrome, an enzyme, a radionuclide and a radiopaque material. Suitable antibodies and antigen binding fragments are described in detail above.

In one embodiment, a kit for detecting PD-L1 is provided, wherein the kit includes an antibody or antigen binding fragment described herein. In one embodiment, the kit may also include instructions and one or more reagents for detecting PD-L1. In one embodiment, the kit includes an antigen or antigen binding fragment described herein, along with instructions for preparing a formalin-fixed paraffin-embedded (FFPE) tissue sample for IHC and/or one or more reagents for IHC. In one embodiment, the kit includes an antigen or antigen binding fragment described herein as a primary antibody and a secondary antibody that specifically binds thereto. In one embodiment, the kit includes a labeled antigen or antigen binding fragment described herein, wherein the label includes a fluorescent label such as fluoroscein or rhodamine or an enzymatic reporter such as horseradish peroxidase (HRP) or alkaline phosphatase (AP). In one embodiment, the kit includes a blocking reagent that includes at least about 1% and up to about 5%, or between about 2% and 3%, or about 2% cold water fish skin gelatin protein (CWF) in a buffer, such as phosphate buffered saline (PBS). In one embodiment, the kit includes buffer for antigen retrieval, such as a citrate buffer, for example sodium citrate, at a concentration of at least about 1, 2, 5, or 10 mM and up to about 10, 15 or 20 mM and at a pH between about 5.5 and 9, or a pH of about 6.

In another embodiment, a kit for treating diseases involving the expression of PD-L1 is provided, wherein the kit includes an antibody or antigen binding fragment described herein and instructions to administer the antibody or antigen binding fragment to a subject in need of treatment. There is also provided a pharmaceutical or diagnostic pack or kit comprising one or more containers filled with one or more of the ingredients of the pharmaceutical compositions as disclosed herein, such as one or more anti-PD-L1 antibodies or fragments provided herein. Optionally associated with such container(s) can be a notice in the form prescribed by a governmental agency regulating the manufacture, use or sale of pharmaceuticals or biological products, which notice reflects approval by the agency of manufacture, use or sale for human administration, e.g., an authorisation number.

In another embodiment, an article of manufacture that includes a container in which a composition containing an antibody or antigen binding fragment described herein and a package insert or label indicating that the composition can be used to treat diseases characterized by the expression or overexpression of PD-L1 is provided. In one embodiment, there is provided a kit for treating and/or preventing a PD-L1-mediated condition or disease, the kit comprising an antibody or fragment as disclosed herein in any embodiment or combination of embodiments (and optionally a further therapeutic agent as described elsewhere herein) optionally in combination with a label or instructions for use to treat and/or prevent said disease or condition in a human; optionally wherein the label or instructions comprise a marketing authorisation number (e.g., an FDA or EMA authorisation number); optionally wherein the kit comprises an IV or injection device that comprises the antibody or fragment. In another embodiment, the kit comprises an antibody or antigen binding fragment thereof contained within a container or an IV bag. In another embodiment, the container or IV bag is a sterile container or a sterile IV bag. In another embodiment, the antibody or antigen binding fragment therefore is formulated into a pharmaceutical composition contained within a (sterile) container or contained within a (sterile) IV bag. In a further embodiment, the kit further comprises instructions for use.

EXAMPLES

Example 1

Antigen Preparation, Immunization Procedures, and Hybridoma Generation

The following example provides a detailed description of the generation and identification of a panel of anti-human PD-L1 monoclonal antibodies using the KyMouse™ system (see, e.g., WO2011/004192, WO2011/158009 and WO2013/061098). To this end, genetically engineered mice containing a large number of human immunoglobulin genes were immunized with soluble recombinant human PD-L1 or surface expressed human PD-L1 displayed on mouse embryonic fibroblast (MEF) cells. Various immunization regimens, including conventional intraperitoneal injections as well as a rapid immunisation at multiple sites (RIMMS) regimen were set up, boosting animals over several weeks (see detailed methods below). At the end of each regime, secondary lymphoid tissue such as the spleen, and in some cases, the lymph nodes were removed. Tissues were prepared into a single cell suspension and fused with SP2/0 cells to generate a stable hybridoma cell line.

Materials and Methods a) Generation of stably transfected MEF and CHO-S cells expressing human PD-L1:

Full length human PD-L1 sequence (SEQ ID No: 1 also known as B7-H1) was codon optimized for mammalian expression and cloned into an expression vector under the CMV promoter flanked by 3' and 5' piggyBac specific terminal repeat sequences, facilitating stable integration into the cell genome (see: "A hyperactive piggyBac transposase for mammalian applications"; Yusa K., et al., Proc. Natl. Acad. Sci. USA., 108(4): 1531-6, 2011 Jan. 25). Furthermore, the expression vector contained a puromycin selection cassette to facilitate stable cell line generation. The human PD-L1 expression plasmid was co-transfected with a plasmid encoding piggyBac transposase into an in-house derived mouse embryonic fibroblast (MEF) cell line (embryos used to generate this line were obtained from a 129S5 crossed to C57/BL6 female mouse) and CHO-S cells using the FreeStyle Max transfection reagent (Invitrogen) according to manufacturer instructions. 24 hours after transfection, the media was supplemented with puromycin and grown for at least two weeks to select a stable cell line with media being exchanged every 3 to 4 days. The expression of hPD-L1 was assessed by flow cytometry using an anti-human PD-L1-PE conjugated antibody (eBioscience). Complete MEF media was made up of Dulbecco's Modified Eagle's Medium (Gibco) supplemented with 10% v/v fetal bovine serum (Gibco). Complete CHO-S media was made up of CD-CHO media (Gibco) supplemented with 8 mM Glutamax (Gibco). Transfected CHO cells were used for screening purposes (see Example 2).

b) Preparation of MEF Cells for Mouse Immunizations:

Cell culture medium was removed and cells washed once with 1×PBS. Cells were treated for 5 minutes with trypsin to loosen cells from tissue culture surface. Cells were collected and trypsin neutralized by the addition of complete MEF media. Cells were then centrifuged at 300 g for 10 minutes and washed with 25 mL of 1×PBS. Cells were counted and resuspended at the appropriate concentration in 1×PBS.

c) Immunisations with PD-L1

Genetically engineered Kymouse™ HK strain, containing human immunoglobulin genes producing human kappa (HK) light chain antibodies (Lee et al, Nature Biotechnology, 32, 6-363, 2014) were immunized by various immunisation regimens for the generation of human anti-PD-L1 antibodies.

Mice were immunised either with soluble recombinant hPD-L1 (R&D Systems, 156-B7, Fc chimera) using a modified sub-cutaneous immunisation procedure (RIMMS; modified after Kilpatrick et al., ("Rapid development of affinity matured monoclonal antibodies using RIMMS"; Hybridoma. 1997 August; 16(4):381-9.) 1997, hereafter referred to as KM031), or by using soluble recombinant hPD-L1 in a prime-rest-boost regime by sub-cutaneous administration (hereafter referred to as KM032) or by combination of soluble recombinant hPD-L1 and stably transfected MEF cells expressing hPD-L1 administered intraperitoneally (hereafter referred to as KM033). Sigma Adjuvant System was used for all immunisations and rest intervals were usually between 2 and 3 weeks. Serum from serial or terminal blood samples were analysed for the presence of specific antibodies by ELISA and flow cytometry and the titre data was used (where possible) to select mice to be used for hybridoma fusions. A further regimen, KM042 immunising with MEF-PD-L1 cells alone, or protein alone in a prime-rest-boost setting, was also performed, but out of six antibodies confirmed to bind to hPD-L1, no neutralising antibodies were identified.

d) Cloning and Expression of Recombinant Proteins

DNA sequences encoding PD-L1 were purchased as synthetic DNA strings and cloned into appropriate mammalian expression vectors for transient expression in Expi293 and CHO cells. The sequence listing shows the sequences of the antigens, where available, and affinity tags for purification/labelling (shown in bold and underlined), see Seq ID Nos: 3 to 6.

e) Determining Serum Titre by Reverse PD-L1 ELISA Protocol

Titres in mouse serum samples were determined using a reverse PD-L1 ELISA protocol. Anti-mouse IgG capture antibody (Southern Biotech) (4 µg/mL diluted in PBS, 50 µL/well) was adsorbed to 96 well low auto-fluorescent, high protein binding plates (Costar) overnight at 4° C. Excess IgG was removed by washing three times with PBS-Tween (0.1% v/v) and the wells were blocked with 1% w/v bovine serum albumin (BSA, Sigma) in PBS for 1 hour at room temperature, after which plates were washed three times with PBS-Tween (0.1% v/v). A titration of mouse serum was prepared, diluting samples in reagent diluent (0.1% w/v BSA/PBS). 50 µL/well of this titration was then added to ELISA plates. To determine the change in activity level due to immunization, serum from each animal prior to immunization was diluted to $1/100$ in reagent diluent and 50 µL/well added to the ELISA plate. Following incubation, plates were washed as before to remove unbound proteins. Biotinylated hPD-L1-his (in-house generated protein, Seq ID No: 3, labelled in-house using Sulfo-NHS-LC-Biotin (Thermo)), used at 100 ng/mL in reagent diluent; 50 µL/well) was then added to the plates and incubated at room temperature for 1 hour. Unbound biotinylated hPD-L1 was removed by washing with PBS-Tween (0.1% v/v), while the remaining biotinylated hPD-L1 was detected by addition of streptavidin-HRP (Sigma) diluted $1/10000$ in reagent diluent. Following incubation for 1 hour at room temperature, plates were washed as described before and 50 µL TMB (Sigma) was added to the plate. The reaction was stopped by adding 50 µL 1M sulphuric acid (Fluka Analytical). The OD at 450 nm was measured on an Envision plate reader (PerkinElmer). Titres were not performed for KM032 as only one mouse was immunised. For KM031, titres were performed on terminal bleeds only.

f) Determination of Serum Titres by Flow Cytometry Using CHO-S Expressed hPD-L1:

CHO-S cells expressing hPD-L1, suspended in FACS buffer (PBS+1% w/v BSA+0.1% w/v sodium azide) were distributed to a 96-well, V-bottom plate (Greiner) at a density of $10^5$ cells per well. A titration of mouse serum was prepared, diluting samples in FACS buffer. 50 µL/well of this titration was then added to the cell plate. To determine the change in activity level due to immunization, serum from each animal prior to immunization was diluted to $1/100$ in FACS buffer and 25 µL/well added to the cells. Cells were incubated at 4° C. for 1 hour. Cells were washed twice with 150 µL PBS, centrifuging after each wash step and aspirating supernatant (centrifuged at 300×g for 3 minutes). To detect antibody binding, PE goat-anti-mouse IgG (Jackson ImmunoResearch) was diluted $1/500$ in FACS buffer and 50 µL was added to the cells. Cells were incubated 1 hour at 4° C. in the dark, then washed twice with 150 µL PBS as above. To fix cells, 100 µL 2% v/v paraformaldehyde was added and cells incubated for 30 minutes at 4° C. Cells were then pelleted by centrifugation at 300×g and the plates resuspended in 50 µL of FACS buffer. PE signal intensity (geometric mean) was measured by flow cytometry using a BD FACS Array instrument. Titres were performed by this method for KM033 only.

g) Murine Tissue Isolation and Preparation:

Following final boost, mice were culled and spleens were excised from immunized mice, washed in 1×PBS and kept on ice until further processing. Tissues were prepared in buffer containing 1×PBS (Invitrogen) and 3% heat-inactivated FBS (Invitrogen). Splenocytes were dispersed by mashing the tissue through a 45 µm strainer (BD Falcon) and rinsing with 30 mL 3% FBS/PBS buffer before centrifugation at 700 g for 10 minutes at 4° C. To remove red blood cells, the pelleted splenocytes were resuspended in 4 mL Red Blood Cell Lysis Buffer (Sigma). After 4 minutes of incubation, the lysis reaction was stopped by addition of 3% FBS/1×PBS buffer. Cell clumps were filtered out with a 45 µm strainer. The remaining splenocytes were pelleted for further procedures. For KM031 and KM032, axillary, inguinal and mesenteric lymph nodes were also removed and placed in sterile 1×PBS on ice until further processing. The lymph nodes were processed separately from splenocytes. Lymph node cells were prepared as above, but did not undergo red blood cell lysis. The remaining lymph node cells were pelleted for further procedures.

h) Hybridoma Fusion:

Spleen and lymph node cells were pooled from KM031 and also from KM032 and subjected to a negative selection method using the MACS® Separation system. Briefly, where lymph nodes were used those cells were pooled with the splenocytes from the corresponding mice after red blood cell lysis and total cell number determined. Cells were resuspended in 100 µL 3% FBS/PBS buffer per $10^7$ cells, before adding 10 µL of Pan B Cell Biotin-Antibody Cocktail (Cat#130-095-813) per $10^7$ total cells and 10 µL of anti-IgD-Biotin antibody (Cat#130-096-979) and incubated for 10 minutes at 4° C. 2 mL FBS/PBS buffer was added and the cells were spun down at 700 g for 10 minutes. The supernatant was aspirated completely and 100 uL fresh buffer was added, then 30 uL Anti-Biotin MicroBeads (Cat#130-047-302) was added per $10^7$ cells along with 7 µL Anti-Mouse IgM MicroBeads (Miltenyi Biotec). The cells were incubated for 15 minutes in the refrigerator. The cells/MicroBeads mixture was then applied to a pre-wetted LD column (Miltenyi Biotec) placed in a magnetic MACS Separator and washed with 3% FBS/PBS buffer. The unlabelled cells that flowed through the column were collected in 3% FBS/PBS buffer.

KM033 cells were subjected to a positive selection method using the MACS® Separation system. After red blood cell lysis, splenocytes were resuspended in 80 µL 3% FBS/PBS buffer per $10^7$ cells, before adding anti-mouse IgG1 (Cat#130-047-101) plus anti-mouse IgG2a+b MicroBeads (Cat#130-047-201) and incubated for 15 minutes at 4° C. The cell/MicroBead mixture was then applied to a pre-wetted LS column (Miltenyi Biotec) placed in a magnetic MACS Separator and washed with 3% FBS/PBS buffer. IgG positive cells were collected in the labelled, column-bound fraction in 3% FBS/PBS buffer.

Enriched B-cells were treated with CpG (Hokkaido System Science) overnight (final concentration 25 µM) and the following day washed once in BSA fusion buffer (0.3 M D-Sorbitol, 0.11 mM calcium acetate hydrate, 0.5 mM magnesium acetate tetrahydrate and 0.1% BSA (v/w), adjusted to pH 7.2). Washed cells were resuspended in 200 µL BSA fusion buffer and cell count determined. SP2/0 cells were treated in the same way, but washed twice instead of once with BSA fusion buffer. B-cells fused at a ratio of 3:1 with SP2/0 myeloma cells by electrofusion using a BTX ECM 2001 Electro Cell Manipulator (Harvard Apparatus). Each fusion was left overnight in recovery medium (Dulbecco's Modified Eagle's Medium (high glucose, no phenol red) supplemented with OPI (Sigma), 1× L-Glutamax (Gibco), 20% FBS (Gibco, batch-tested for hybridoma) and 0.05 mM 2-mercaptoethanol), then resuspended in 1 part recovery medium and 9 parts semi-solid medium (ClonaCell-HY Hybridoma Selection Medium D, Stemcell Technologies) and seeded onto 10 cm petri dishes. Visible colonies were picked 12 days later into 96-well plates and cultured for another 2 to 3 days prior to screening.

Example 2

Hybridoma Supernatant Screening

After generation of hybridoma clones, the hybridoma supernatant was assessed in a sequential primary and secondary screen and appropriate hybridoma clones selected based on criteria of antibody binding to human PD-L1 and receptor neutralization activity. In the screening cascades described, 9317 hybridoma clones were tested and 120 identified as primary hits. Thereafter, 36 hybridoma clones were confirmed by using secondary screening criteria (see details in Materials and Methods and Table 1). Among the clones identified by secondary screen, four clones were selected by the inventors to be part of the antibody shortlist, dependent upon desired selection criteria (see details in Example 3).

Materials and Methods a) Primary Screen—Binding to Cell-Expressed Human PD-L1:

Supernatants collected from hybridoma cells were screened for the ability of secreted antibodies to bind to hPD-L1 expressed on the surface of CHO-S cells. To determine CHO-S hPD-L1 binding, cells were plated in black-walled, clear-bottom tissue culture treated 384-well plates (Costar) at $1\times10^4$/well in F12 media (Gibco) supplemented with 10% FBS (Gibco) and cultured overnight. Culture media was removed from 384-well assay plates. At least 5 µL of hybridoma supernatant or 5 □L MIH1 at 2 µg/mL in hybridoma maintaining media (HMM) or isotype IgG1 control antibody (referred to in some instances as Cm7, Sigma M9269, at a final concentration of 1 µg/mL) diluted in HMM were added to each well. HMM was made up of Advanced DMEM (Gibco) supplemented with 1× Glutamax (Gibco), 20% v/v FBS (Gibco), 0.05 mM β-Mercaptoethanol, 1× HT supplement (Gibco), and 1× penicillin/streptomycin (Gibco). 45 µL FACS buffer containing 500 ng/mL IRDye 800CW anti-Mouse Ab (LICOR) and 0.2 µM DRAQ5 (Biostatus) was added to each well. Plates were incubated for 1 hour at 4° C. Supernatant was aspirated and 25 µL 4% v/v paraformaldehyde added and plates were incubated for 15 minutes at room temperature. Plates were washed twice with 100 µL PBS and then the wash buffer was completely removed. Fluorescence intensity was read by scanning plates using an Odyssey Infrared Imaging System (LI-COR®). Anti-mouse binding (800 nm channel) was normalised to cell number (700 nm channel) according to the LI-COR® recommended algorithm. Percent effect was calculated as detailed below (Equation 1). Total binding was defined using reference antibody at a final assay concentration of µg/mL. Non-specific binding was defined using mouse IgG1 isotype control (Sigma) at a final assay concentration of 0.2 µg/mL. Criteria for hit selection were based on assay signal and visual inspection of scanned plates.

Equation 1: Calculation of Percentage Effect from Primary Screen (LI-COR) and HTRF Using 800% Resp values (LI-COR) or 665/620 nm ratio (see equation 2) (HTRF)

$$\text{Percent effect} = \frac{(\text{sample well} - \text{non-specific binding}) \times 100}{(\text{total binding} - \text{non-specific binding})}$$

Non-specific binding=values from wells containing isotype control mouse IgG1

Total Binding=values from wells containing reference antibody b) Primary Screen: Binding to Recombinant Human PD-L1:

In parallel to screening for binding to CHO-S expressed PD-L1, supernatants collected from hybridoma wells were screened for the ability of secreted antibodies to bind to hPD-L1 expressed as a recombinant protein (produced in-house). Binding of secreted antibodies to recombinant PD-L1 were identified by HTRF® (Homogeneous Time-Resolved Fluorescence, Cisbio) assay format using biotinylated hPD-L1. 10 µL hybridoma supernatant was transferred to a white 384 well, low-volume, non-binding surface polystyrene plate (Greiner). 5 µL 230 nM biotinylated hPD-L1 his diluted in HTRF assay buffer (PBS (Sigma)+ 0.53 M KF (Sigma)+0.1% w/v BSA (Sigma)) was pre-incubated with 10 µL hybridoma supernatant or 10 µL reference antibody diluted to 3.3 nM working concentration for 1 hour at room temperature. For negative control wells, 10 µL HMM was added. Streptavidin D2 (Cisbio), and goat anti-mouse IgG (Southern Biotech) labelled with Europium cryptate (Cisbio) were both diluted 1/100 in HTRF assay buffer, and 5 µL of this mixture added to all wells. The plate was left to incubate in the dark for 2 hours prior to reading time resolved fluorescence at 620 nm and 665 nm emission wavelengths using an EnVision plate reader (Perkin Elmer). More details of the HTRF® assay technology can be found in Mathis (1995) Clinical Chemistry 41(9), 1391-1397.

Data were analysed by calculating 665/620 ratio and percent effect for each sample according to equation 2 and equation 1 respectively.

Equation 2: Calculation of 665/620 Ratio $$665/620 \text{ ratio} = (\text{sample } 665/620 \text{ nm value}) \times 10000$$

In general, criteria for hit selection were based on greater than or equal to 10 percent effect. In some instances, hit selection was based on greater than or equal to 20 percent effect.

Progression to secondary screen was based on a combination of data from recombinant PD-L1 binding hits and binding to human PD-L1 expressed on CHO cells.

c) Secondary Screen: Binding to Cell Expressed Recombinant Human PD-L1 or Natively Expressed hPD-L1 and Binding Affinity To determine whether wells selected using the primary screen selection criteria had the required characteristics set by the inventors, a number of assays were performed. Hybridoma clones selected as hits from primary screening were cultured for 3 days and the supernatants collected from hybridoma cells were tested to assess whether the secreted antibodies that bind to in some cases CHO-S expressed hPD-L1, or in some cases ES2 cells. In addition, the ability to neutralise recombinant hPD-1 Fc, binding to CHO-S hPD-L1 or ES2 cells was also assessed. Binding of antibodies to human PD-L1 by SPR was also tested.

d) Binding to Cell Expressed hPD-L1 and Neutralisation and hPD-L1 Binding to PD-1

Binding of hybridoma supernatants was tested for ability to bind to either CHO-S cells expressing hPD-L1 or ES2 cells. CHO-S cells expressing hPD-L1 (generated in-house), or ES2 cells (ATCC CRL-1978) natively expressing hPD-L1 were diluted in FACS buffer and were distributed to a 96 well V-bottom plate (Greiner) at a density of 0.5 to $1 \times 10^5$ cells per well. Cells were washed with 150 µL PBS and centrifuged at 300 g for 3 minutes. Supernatant was aspirated and 150 µL PBS added. This wash step was repeated.

25 µL hybridoma supernatant was added to the washed cells and incubated for 10-15 minutes. Reference antibody was diluted 2 µg/mL and 25 µL added to cells. 25 µL human PD1-Fc (in-house, Seq ID No: 4, or Sino Biologicals) was diluted to 500 ng/mL in FACS buffer was then added to wells. Cells were incubated at 4° C. for 30 minutes. Cells were washed twice with 150 µL FACS buffer, centrifuging at 300 g for 3 minutes after each wash step and aspirating supernatant.

To detect antibody and receptor binding, 50 µL goat anti-human IgG-PE (Jackson ImmunoResearch) and APC anti-mouse IgG (Jackson ImmunoResearch) diluted 1/500 in FACS buffer was added to the cells. Cells were incubated for 30 minutes at 4° C. in the dark. Cells were washed twice as above and resuspended in FACS buffer for analysis. PE and APC signal intensity (geometric mean) was measured by flow cytometry using a BD FACS Array instrument. Data was plotted as geometric mean values without further calculation.

e) Determination of Affinity by Surface Plasmon Resonance

Label-free surface plasmon resonance (SPR) analysis was carried out on the ProteOn XPR36 (BioRad) array SPR machine. An anti-mouse IgG capture surface was created on a GLC biosensor chip using amine coupling of an anti-mouse IgG from GE Healthcare. Test antibodies were captured on this surface and human PD-L1 (in-house) was used as the analyte at 256 nM, 64 nM, 16 nM, 4 nM and 1 nM. The assay was carried out at 25° C. using HBS-EP (Teknova H8022). Buffer alone was used to reference the binding sensorgrams. The data was analysed using the 1:1 model inherent to the ProteOn XPR36 analysis software. In some instances, hybridoma supernatants were used as the source of antibody; in other instances, antibody was purified from hybridoma supernatant prior to analysis (see below).

f) Purification of Antibodies from Hybridoma Supernatant

Protein G resin in a gravity-flow column was first washed with water, then 50 mM sodium hydroxide or IgG Elute (Pierce) and was then equilibrated with tissue culture grade PBS. Clarified hybridoma supernatant containing 10% v/v 10× tissue culture grade PBS was applied several times to the equilibrated protein G column. Resin was washed with tissue culture grade PBS to remove unbound material. Antibody was then eluted with IgG Elute (Pierce) and the eluted fraction was then neutralized with 100 mM final TRIS, at pH 8.0. The eluted fraction was then concentrated down to <1.5 mL by centrifugation in a 10 kDa cut-off centrifugal filter unit. Tissue culture grade PBS was then added and the sample was concentrated down again to <1.5 mL. Protein concentration was quantified at $OD_{280}$ using the molar extinction coefficient inherent to the Nanodrop for IgG. Finally, sample was analysed on a SDS-PAGE to assess purity.

TABLE 1

Summary of hybridoma clone screening

| Experiment ID | Number of hybridoma screened | Number of Primary hits cherry picked | Number of secondary hits confirmed | Number of Lead Candidate mAbs |
|---|---|---|---|---|
| KM031 | 1872 | 41 | 4 | 0 |
| KM032 | 115 | 14 | 6 | 1 |
| KM033 | 7330 | 66 | 26 | 1 |

Example 3

Antibody Shortlist Selection Criteria

Binding to hPD-L1 natively expressed on ES2 cells, or neutralisation of recombinant human PD-1 binding to ES2 cells were used as criteria for secondary screen hit selection. Hits to progress to purification and further characterisation were determined by a combination of high affinity for human PD-L1 and neutralisation capacity.

After the selection and characterization of shortlisted antibodies, their fully-human variable domains were recovered using RT-PCR using a mixture of forward and reverse primers. Antibodies were reformatted into a human IgG1 backbone and expressed using a transient expression system in CHO-S cells.

Materials and Methods a) RNA Isolation from Hybridoma Cells:

Total RNA was extracted from hybridoma cells using TRIzol™ Reagent (Invitrogen). The quantity and quality of the isolated RNA was analysed spectrophotometrically.

b) Antibody Variable Domain Recovery by RT-PCR:

Selected clones were used to prepare total RNA, which was used in an RT-PCR reaction to recover the heavy and light chain V-regions. Murine IgG-specific reverse primers and human Ig-leader sequence-specific forward primer sets were used for the heavy chains. Murine kappa constant region specific reverse primers and human kappa-leader sequence specific forward primer sets were used for the kappa light chains. The RT-PCR products were separated by agarose gel electrophoresis with the DNA of the predicted size being gel purified and sequenced in the forward and reverse directions. Alternatively, the RT-PCR products were subcloned into a cloning vector and DNA of individual colonies submitted for sequencing.

Example 4

Selection of Final Lead Panel

Recombinantly expressed antibodies were analysed by SPR to confirm binding to cynomolgus monkey PD-L1, as well as human PD-L1. Antibodies were also tested in a dendritic cell-T-cell mixed lymphocyte reaction (MLR) for ability to enhance IFNγ production (FIG. 1). Antibodies with consistent immune-stimulatory effects in the MLR, and binding to both human and cynomolgus PD-L1 were selected as the final lead panel—these were designated as clone 84G09 and clone 1D05. Data in FIG. 1 is from a single experiment. A further five experiments were conducted and showed similar results (84G09 showed activity in 3 out of 5 experiments, 1D05 showed activity in 3 out of 4 experiments, 1A01 showed activity is 1 out of 3 experiments and 8B09 showed activity in 0 out of 3 experiments). One further experiment failed (including positive control).

Materials and Methods a) Surface Plasmon Resonance for Analysis of Antibodies with Human Constant Region Label-free surface plasmon resonance (SPR) analysis was carried out on the ProteOn XPR36 (BioRad) array SPR machine. An anti-human IgG capture surface was created on a GLC biosensor chip using a combination of anti-human Fc antibodies (Jackson Labs 09-005-008,109-006-008 and 309-006-008) by amine coupling. Test antibodies were captured on this surface and human PD-L1-his and cynomolgus monkey PD-L1-FLAG (in-house, Seq ID No: 5) was used as the analyte at 128 nM, 32 nM, 8 nM, 2 nM, 0.5 nM and 0 nM. The data was analysed using the 1:1 model inherent to the ProteOn XPR36 analysis software.

b) Dendritic Cell—T Cell MLR (Mixed Lymphocyte Reaction)

Dendritic cells were generated from monocytic precursors. Monocytic precursors were isolated from peripheral blood mononuclear cells (PBMCs) isolated using Ficoll-Paque plus (GE Healthcare) density gradient centrifugation from leukoreduction system chambers (NHSBT). Monocytes were isolated from PBMCs using negative selection magnetic separation beads (Miltenyi Biotec). Monocytes were plated in 96-well, flat-bottom TC plates at $5 \times 10^4$/well and $1 \times 10^4$/well and cultured with cytokines GM-CSF and IL-4 (both Peprotech) at 100 ng/mL for 7 days in culture media (Advanced RPMI (Gibco) supplemented with 10% v/v FBS and 2 nM glutamine (culture medium).

After 7 days, T-cells were isolated from allogeneic PBMC using negative selection magnetic separation beads (Miltenyi). After isolation the isolation buffer was removed by centrifugation and aspiration. The cells were resuspended at $1 \times 10^6$ cells/mL in culture medium, and 100 µL of T-cells were added to all wells with the exception of the DC-only wells. An additional 100 of culture medium was added to the DC-only and T-cell-only wells. Serial three-fold dilutions of antibodies were prepared in culture medium (top concentration 60 nM final). 10 µL of each dilution was added to cells.

The cells were incubated for five days at 37° C. After this period IFN-γ was measured by Duoset ELISA (R&D Systems) according to manufacturer's instructions.

Example 5

In Depth Characterisation of Lead Antibodies

Lead antibodies 84G09 and 1D05 were subjected to in-depth characterisation, including SPR at 37° C., full titrations of antibodies in neutralisation assays, and confirmation of binding to PD-L1 but not PD-L2. Antibodies were also expressed with a human IgG4(PE) constant region (Seq ID No: 199) for analysis by mixed lymphocyte reaction. Lead antibodies retain sub-nanomolar affinity at 37° C., and show potent neutralisation of PD-L1 binding to both PD-1 and CD80. Antibodies do not cross-react with PD-L2, bind natively expressed PD-L1 on dendritic cells, and are potent stimulators of IFNγ production in an MLR.

a) Human PD-L1/PD-1 Neutralisation Assay (ELISA)

Figure 2:
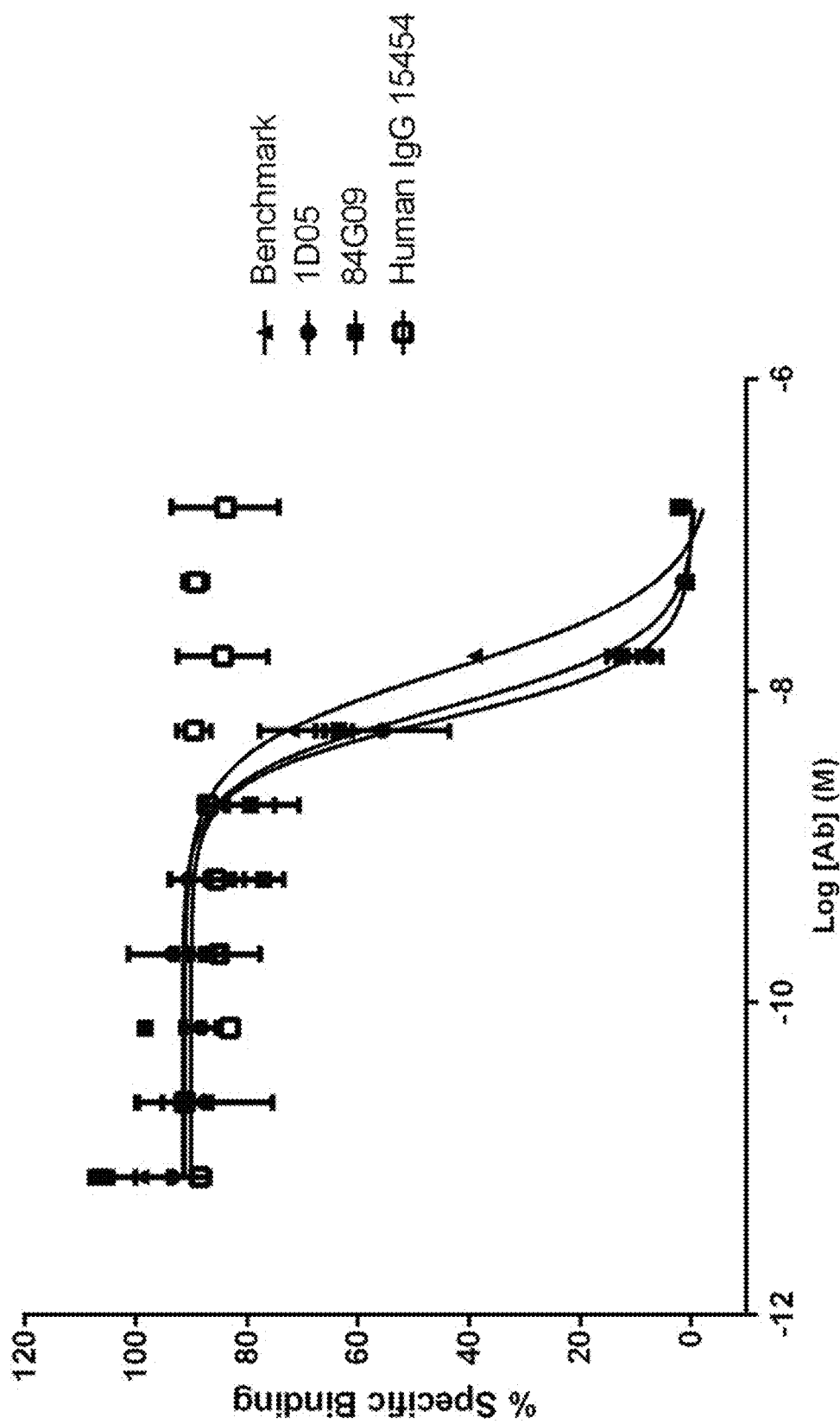
FIG. 2: PD-L1 direct neutralisation ELISA with PD-1 receptor. Neutralisation profiles of 1D05 and 84G09 compared to a benchmark anti-PD-L1 antibody and isotype control. Data representative of three independent experiments.

PD-1 Fc (in house, Seq ID No:6) diluted to 1 µg/mL was adsorbed to 96-well, low auto-fluorescent, high protein binding plates (Costar) overnight at 4° C. Excess protein was removed by washing with PBS-Tween (0.1% v/v) and the wells were blocked with 1% w/v bovine serum albumin (BSA, Sigma) in PBS for 1 hour at room temperature, after which plates were washed as described previously. 30 µL titration (⅓ dilution) of antibody was added to a 96-well non-binding plate diluted in ELISA assay buffer (PBS+0.1% BSA). 30 µL biotinylated PD-L1 his (in-house, Seq ID No:3) at 50 nM working concentration (25 nM final assay concentration [FAC]) was added to the plate excluding control wells where 30 µL ELISA assay buffer was added. The plate was incubated for 30 minutes before transferring 50 µL to the coated plates. The coated plates were incubated for 1 hour at room temperature. Excess protein was removed by washing with PBS-Tween (0.1% v/v). PD-L1 binding was detected using streptavidin labelled Europium (Perkin Elmer) diluted ¹⁄₁₀₀₀ in DELFIA assay buffer (Perkin Elmer). Plates were washed with TBS (Tris buffered saline)-Tween (0.1% v/v) and 50 μL/well of DELFIA Enhancement solution (Perkin Elmer) was added to the plate. Time-resolved fluorescence was measured at 615 nm on an Envision plate reader (PerkinElmer). $IC_{50}$ values were determined using GraphPad Prism software by curve fitting using a four-parameter logistic equation (Equation 5). Results are shown in FIG. 2 and summarised in Table 2.

Equation 5: Percentage of Receptor Binding (ELISA) Based on fluorescence at 615 nm $$\% \text{ of specific binding} = \frac{\text{sample value} - \text{non-specific binding}}{\text{total binding} - \text{non-specific binding}} \times 100$$

Total binding=biotinylated PD-L1 (no antibody)
Non-specific binding=no biotinylated PD-L1

Equation 6: Four Parameter Logistic Calculation $$Y = \text{Bottom} + (\text{Top} - \text{Bottom})/(1 + 10^{((\log IC50 - X)^*\text{Hill-Slope})})$$

X=logarithm of concentration.
Y=specific binding (equation 6)
Top and Bottom=Plateaus in same units as Y (specific binding)
Log $IC_{50}$ in same units as X. Y starts at Bottom and goes to Top with a sigmoid shape. Specific binding decreases as X increases.

c) CHO Human PD-L1/PD-1 or CD80 Neutralisation Assay (Flow Cytometry)

Figure 3:
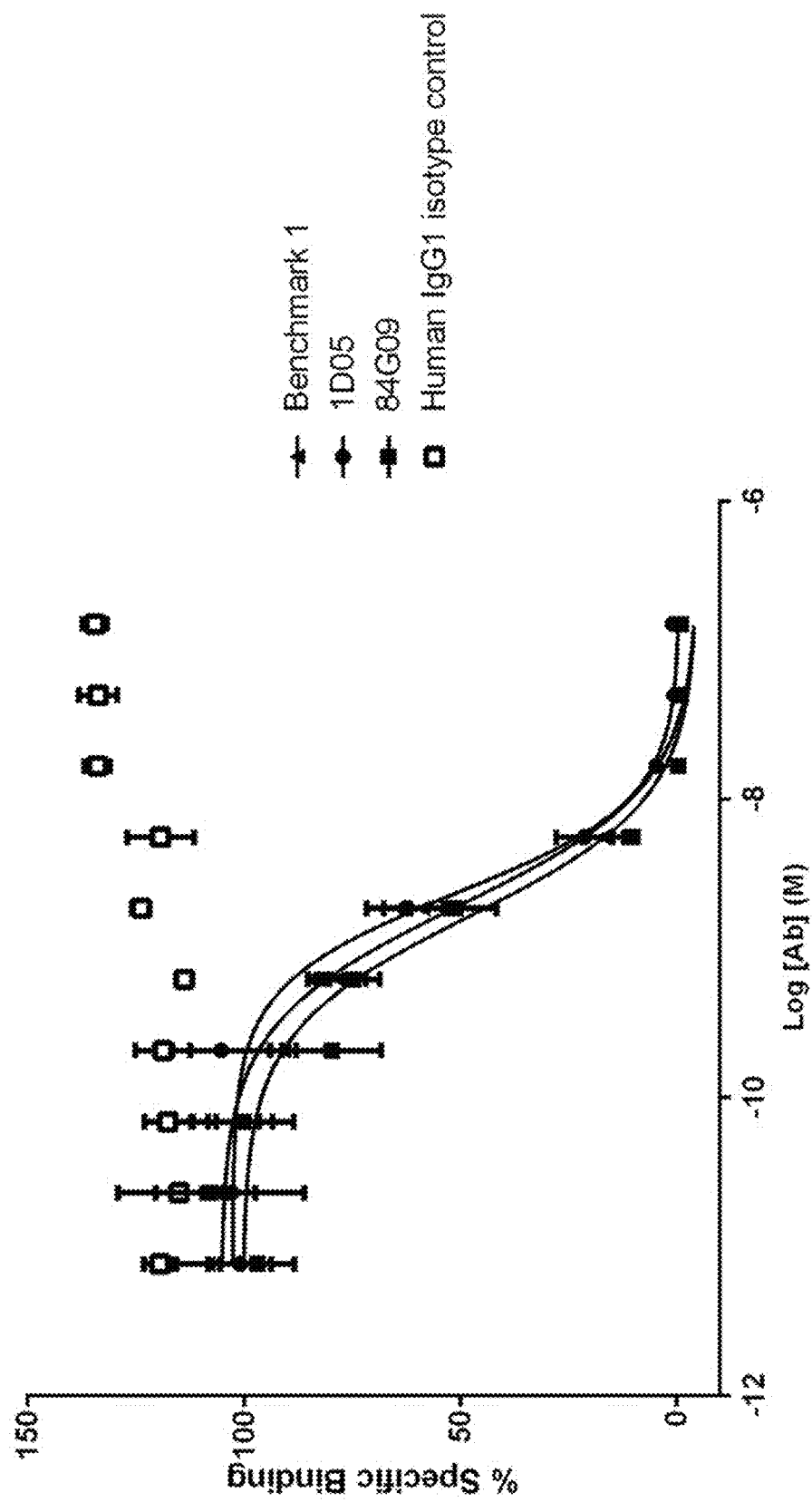
FIG. 3: Human PD-L1 CHO-S FACS neutralisation with PD-1 receptor. Neutralisation profiles of 1D05 and 84G09 compared to a benchmark anti-PD-L1 antibody and isotype control. Data representative of three independent experiments.
Figure 4:
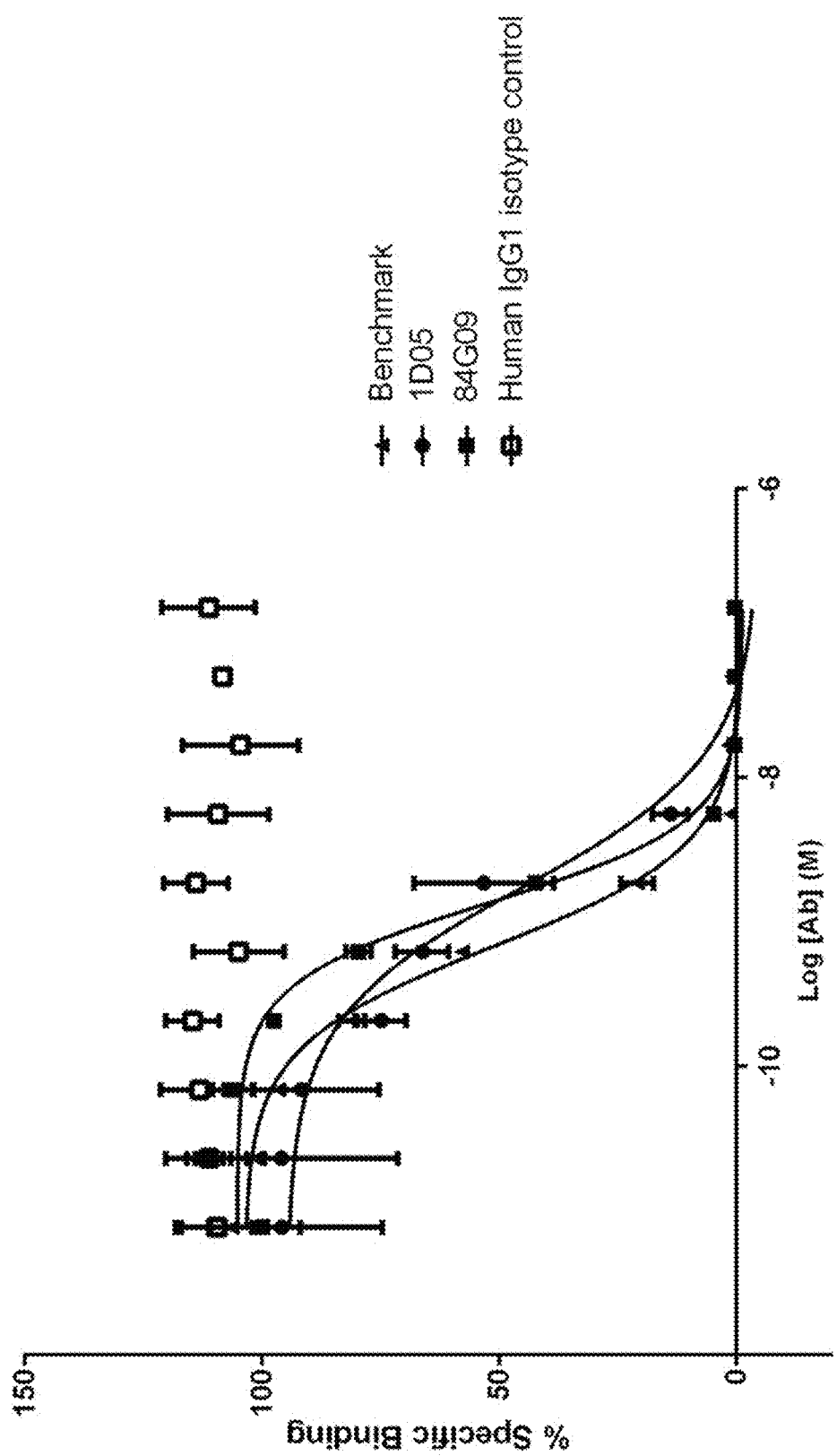
FIG. 4: Human PD-L1 CHO FACS neutralisation with CD80 receptor. Neutralisation profiles of the 1D05 and 84G09 compared to the benchmark anti-PD-L1 antibody and isotype control. Data representative of three independent experiments.

CHO-S cells untransfected (referred to as WT) or transfected with hPD-L1 were diluted in FACS buffer and were distributed to a 96-well V-bottom plate (Greiner) at a density of $1 \times 10^5$ cells per well. Biotinylated human PD-1-Fc (in-house expressed, Seq ID No:6) or CD80-Fc (R&D Systems) were prepared as a titrations from 1 μM final assay concentration (FAC), ½ dilution series in FACS buffer. Antibody titrations were prepared from 300 nM working concentration, 150 nM FAC, as a ⅓ dilution series in FACS buffer. Biotinylated PD-1 or CD80 were diluted in FACS buffer to 60 nM working concentration, 30 nM FAC. Plates were centrifuged at 300×g for 3 minutes to supernatant aspirated. 25 μL ligand and 25 μL antibody solution (or 50 μL of ligand titration) were added to cells and incubated at 4° C. for 1 hour. Cells were washed with 150 μL of PBS and centrifuged at 300 g for 3 minutes. Supernatant was aspirated and 150 μL PBS added. This wash step was repeated. Presence of bound CD80 or PD-1 was detected by addition of 50 μL of streptavidin-AlexaFluor 647 (Jackson ImmunoResearch) diluted 1/500 in FACS buffer. Cells were incubated 30 minutes at 4° C. in the dark. Cells were washed as previously described. To fix cells, 100 μL 2% v/v paraformaldehyde was added and cells incubated for 30 minutes at 4° C., cells were pelleted by centrifugation at 300×g and the plates resuspended in 50 μL FACS buffer. AlexaFluor 647 signal intensity (geometric mean) was measured by flow cytometry using a BD FACS Array instrument. Results are shown in FIGS. 3 and 4 and summarised in Table 2.

Equation 4: Percentage of Receptor Binding (Flow Cytometry) Based on geometric mean fluorescence $$\% \text{ of specific binding} = \frac{\text{sample value} - \text{non-specific binding}}{\text{total binding} - \text{non-specific binding}} \times 100$$

Total binding=biotinylated PD-1 or CD80 only (no antibody)
Non-specific binding=no ligand streptavidin AlexaFluor 647 only

TABLE 2

Summary of lead antibody binding and neutralisation of PD-L1 binding to PD-1 or CD80

| | | | Receptor Neutralisation (mean of n = 3) | | |
|---|---|---|---|---|---|
| Clone ID | Human PD-L1 (nM at 37° C.) | Cyno PD-L1 (nM at 37° C.) | PD-L1/PD-1 neutralisation (FACS) $IC_{50}$ (nM) | PD-L1/CD80 neutralisation (FACS) $IC_{50}$ (nM) | PD-L1/PD-1 neutralisation (ELISA) $IC_{50}$ (nM) |
| 1D05 | 0.42 | 0.43 | 2.21 | 1.18 | 5.21 |
| 84G09 | 0.43 | 0.52 | 1.82 | 1.60 | 7.90 |
| Benchmark | 0.25 | 4.79 | 1.85 | 1.42 | 14.1 | d) PD-L1/PD-L2 Binding

Figure 5A:
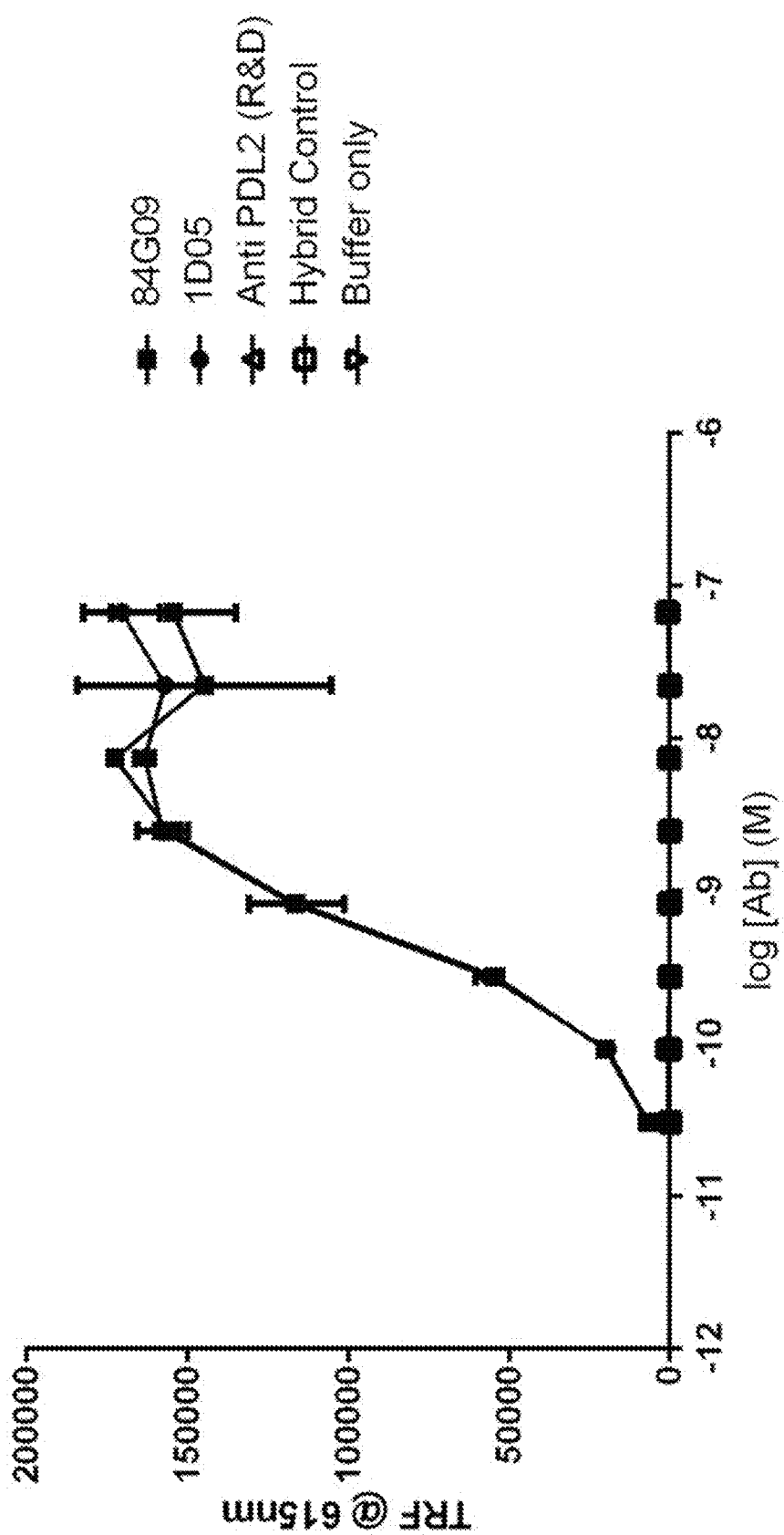
FIGS. 5A-5B: Binding of lead antibodies to PD-L1 but not PD-L2. Lead antibodies bind to plate bound PD-L1 (FIG. 5A) but not PD-L2 (FIG. 5B). An anti-PD-L2 antibody was used as a control. Data are expressed as time resolved fluorescence units at 615 nm. Data representative of two independent experiments.
Figure 5B:
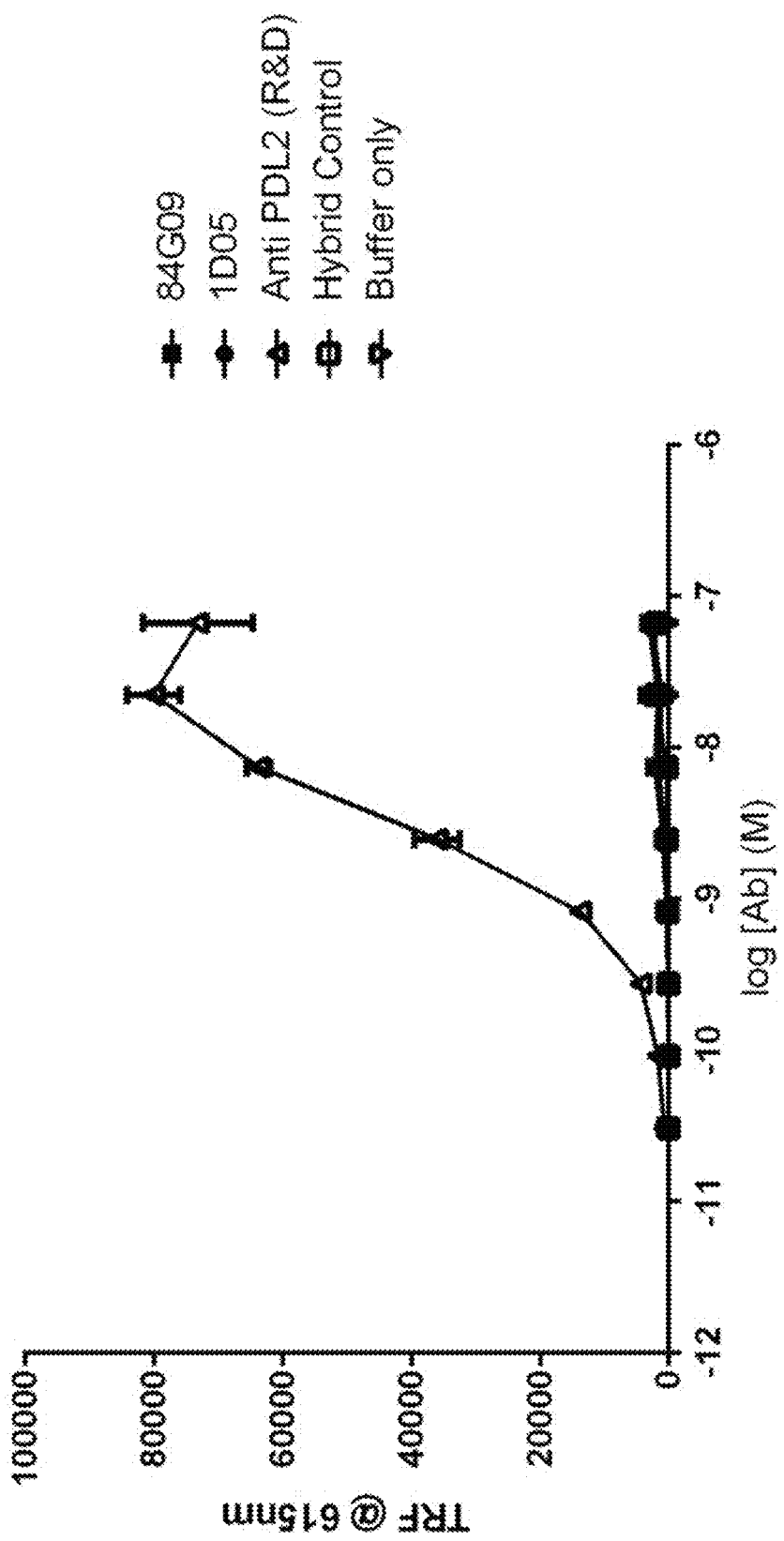

PD-L1-Fc (R&D Systems) and PD-L2-Fc (R&D Systems) were diluted to 2 μg/mL and separately adsorbed to 96-well, high protein binding plates (Greiner) overnight at 4° C. Excess protein was removed by washing with PBS-Tween (0.1% v/v) and the wells were blocked with 250 uL/well Pierce Protein Free Blocking Buffer (Thermo, 37572) for 1 hour, after which plates were washed as described previously. Biotinylated anti-PD-L1 antibodies (in-house) or anti-PD-L2 control antibody (R&D systems) were diluted in blocking buffer and three-fold serial dilutions performed from 10 μg/mL. 100 μL each antibody dilution was added to the plates in duplicate and incubated for 1 hour at room temperature. Antibody binding was detected using streptavidin labelled Europium (Perkin Elmer) diluted 1/1000 in DELFIA assay buffer (Perkin Elmer). Plates were washed with TBS (Tris buffered saline)-Tween (0.1% v/v) and 50 μL/well of DELFIA Enhancement solution (Perkin Elmer) was added to the plate. Time-resolved fluorescence was measured at 615 nm on an Envision plate reader (PerkinElmer). Results are shown in FIG. 5.

e) SPR Analysis

Label-free surface plasmon resonance (SPR) analysis was performed as per Example 4, except the assay was performed at 37° C. Additionally, due to artefacts of running the assay at 37° C., the best referencing of the binding sensorgrams was found to be using a sensorgrams from a negative control antibody using the same concentrations of human PD-L1. Results are shown in Table 2.

f) Mixed Lymphocyte Reaction

Figure 6:
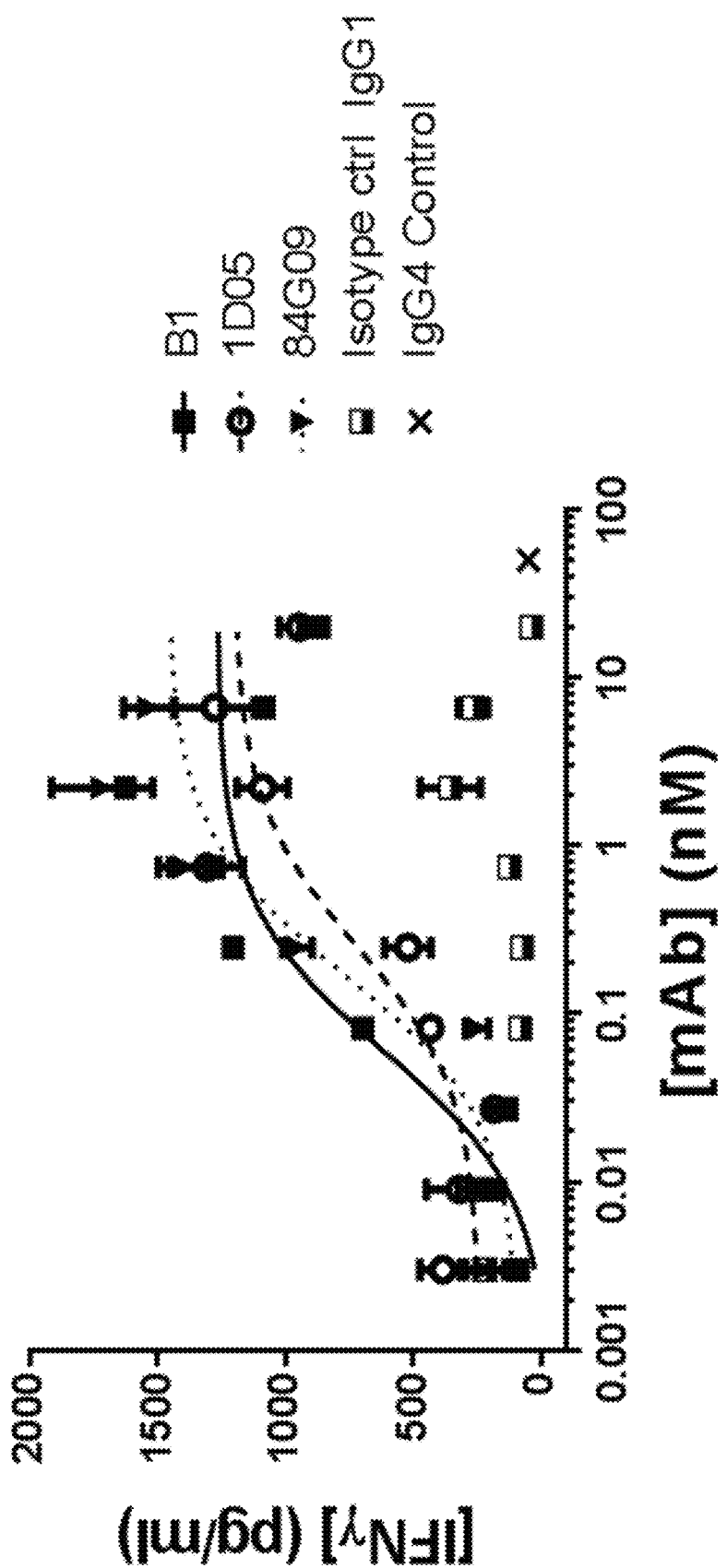
FIG. 6: Lead antibodies induce IFNγ production in a Dendritic Cell-T-cell mixed lymphocyte reaction. Immature dendritic cells were co-cultured with allogeneic CD4+T-cells in the presence of antibodies for 5 days. IFNγ was measured in supernatants by ELISA. Data are representative of three independent experiments. B1 refers to a benchmark antibody.
Figure 7A:
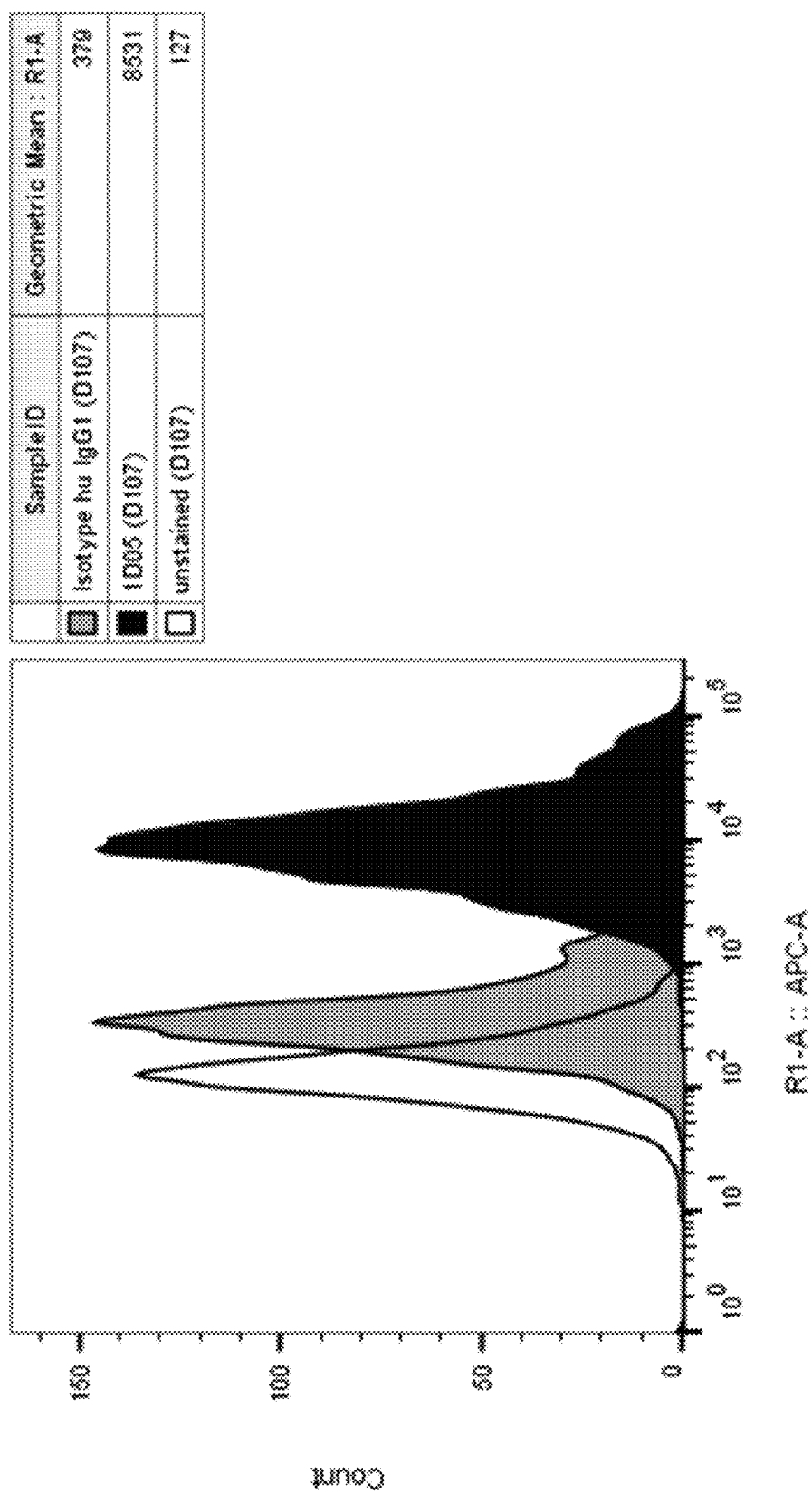
FIGS. 7A-7B: Lead antibodies bind to natively expressed PD-L1 on dendritic cells. Dendritic cells were generated from monocyte precursors with GM-CSF and IL-4 and stained with lead antibodies (FIG. 7A) 1D05 and (FIG. 7B) 84G09, and isotype control directly labelled with AlexaFluor647. Data shown is from one blood donor, representative of four donors.
Figure 7B:
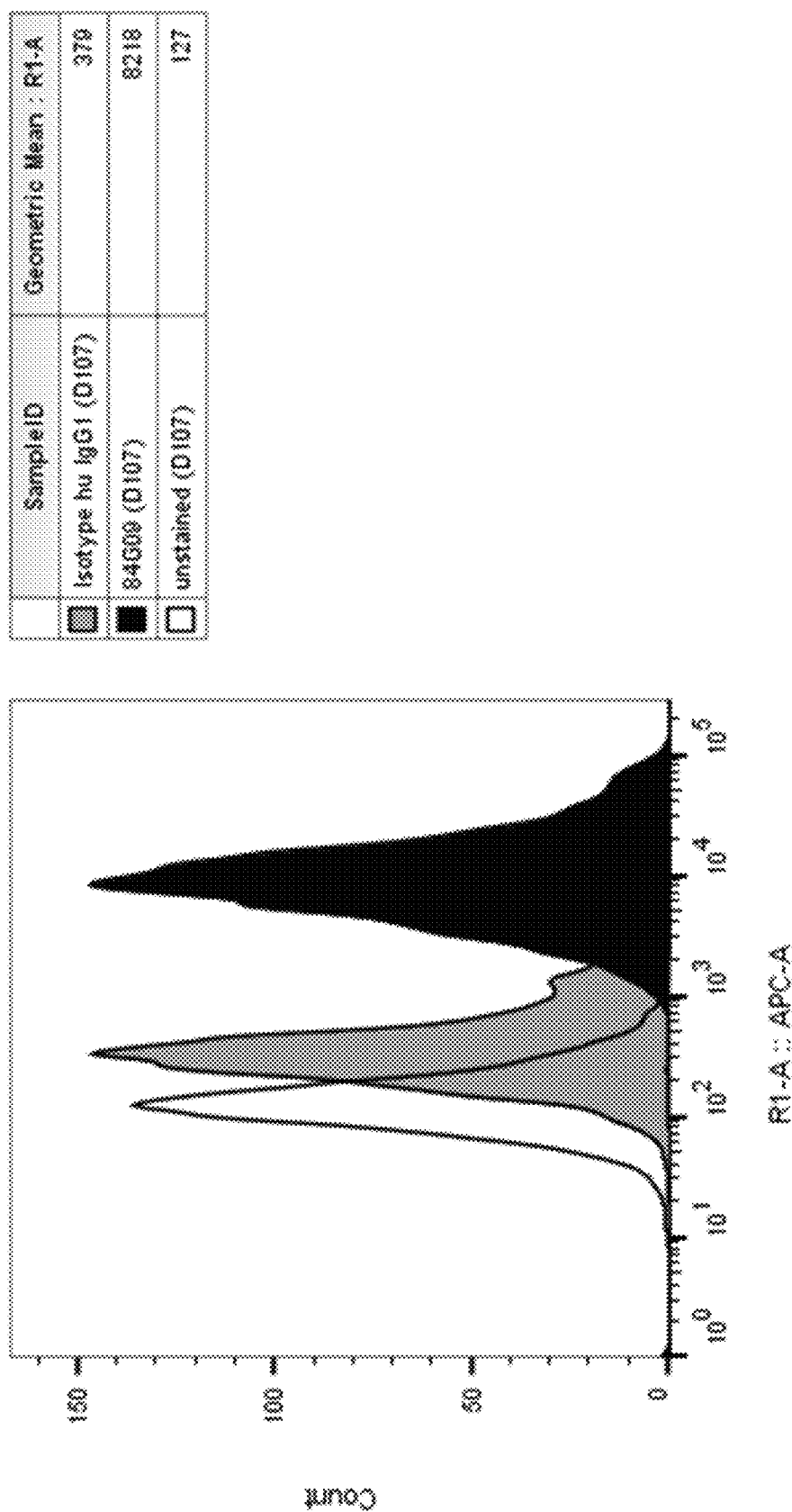

Expanded CD4$^+$ T-cells were thawed and rested in AIM V© medium (Gibco) at 37° C., 5% $CO_2$ overnight prior to the assay day. Serial dilutions of anti-human PD-L1 mAbs were prepared in the AIM medium at 4× final concentration. 50 μL of diluted mAbs was added to 96-well, U-bottom plates. $1 \times 10^4$ immature dendritic cells (iDC) in 50 μL AIM medium and $1 \times 10^5$ expanded CD4$^+$ T-cells (expanded using Dynabeads Human T-Activator CD3/CD28 by Life Technologies (Invitrogen/Applied Biosystems; Cat No: 11131D), according to manufacturer's instructions) in 100 μL AIM medium were added to the antibody dilutions in each well. Control wells include: CD4$^+$ T-cells alone, iDC alone, CD4$^+$ T-cell and iDC with or without IgG isotype control antibodies in 200 μL AIM medium. Reaction plates were incubated for 5 days in a humidified incubator (37° C. in 5% $CO_2$). At the end of the assay, the plate was spun down (528 xg for 3 minutes) and 100 μL of supernatant was collected from the wells by gentle pipetting. Supernatants were analysed using human IFNγ Quantikine ELISA kit (R&D Systems) according to manufacturer's instructions. Results are shown in FIG. 6.

g) Sequencing and Characterisation of Gene Segment Usage of 1D05 and 84G09

Antibodies were sequenced by Source Bioscience, and V-genes were compared to germline sequences.

TABLE 3

V region usage of lead antibodies

| Antibody clone ID | V gene | D gene | J gene | CDR3 length (aa) | CDR3 mutations from germline (aa) | V gene | J gene | CDR3 length (aa) | CDR3 mutations from germline (aa) |
|---|---|---|---|---|---|---|---|---|---|
| 1D05 | IGHV3-9*01 | IGHD3-10*01 | IGHJ5*02 | 16 | 6 | IGKV1D-39*01 | IGKJ5*1 | 9 | 1 |
| 84G09 | IGHV3-9*01 | IGHD3-10*01 | IGHJ5*02 | 15 | 4 | IGKV1D-39*01 | IGKJ5*1 | 9 | 4 |

Example 6

Antigen Preparation, Immunization Procedures, and Antigen-Specific B Cell Sorting and V-Region Recovery Additional anti-human PD-L1 monoclonal antibodies were generated using the KyMouse™ system previously described. Genetically engineered HK mice were immunized with soluble recombinant human and mouse PD-L1 or surface expressed human and mouse PD-L1 displayed on mouse embryonic fibroblast (MEF) cells. Serum titres were performed by reverse ELISA and mice with the highest titres were selected for processing. At the end of each regime, spleen and lymph nodes were removed. Tissues were prepared into a single cell suspension and stained for sorting antigen-specific B-cells by FACS.

Materials and Methods a) Immunisation of Mice

Mice were immunised with soluble recombinant human PD-L1 or a combination of human and mouse PD-L1 protein (in-house) as per the schedule described in Example 1 for KM032 (hereafter described as KM121). Mice were also immunised with human PD-L1 protein, and MEF cells expressing human or mouse PD-L1, as per the schedule described in Example 1 for KM033 (hereafter described as KM122). MEF cells expressing mouse PD-L1 were generated as per Example 1, but substituting mouse PD-L1 sequences for the human PD-L1 sequences, and substituting anti-mouse PD-L1 detection antibody (eBioscience) for the anti-human PD-L1 detection antibody.

b) Determining Serum Titre by Reverse PD-L1 ELISA Protocol

Titres in mouse serum samples were determined using a reverse PD-L1 ELISA protocol as per Example 1, with the following changes. In-house generated hPD-L1-his was labelled in-house using Lightning Link kit (Innova Biosciences), and used at 1 µg/mL in reagent diluent; 50 µL/well). Bound hPD-L1 was detected by addition of streptavidin-Europium (Perkin Elmer) diluted ⅟1000 in DELFIA assay buffer (Perkin Elmer). Following incubation for 1 hour at room temperature in the dark, plates were washed using TBS (Tris buffered saline)-Tween (0.1% v/v) and 50 µL/well of DELFIA Enhancement solution (Perkin Elmer) was added to the plate. Time-resolved fluorescence was measured at 615 nm on an Envision plate reader (PerkinElmer). Fluorescence data was plotted as Europium counts.

c) Sorting of Antigen-Specific B Cells and Retrieval of V-Regions

The methods used were substantially as described in Example 1 of PCT application WO2015/040401. In brief, splenocytes and lymph node cells isolated from KM121 and KM122 immunisation regimes were stained with an antibody cocktail containing markers for the selection of cells of interest (CD19), whereas unwanted cells were excluded from the final sorted population (IgM, IgD, 7AAD). CD19+ B-cells were further labelled with human PD-L1 (Seq ID No:1) and mouse PD-L1 (Seq ID No: 325, labelled with AlexaFluor647 and AlexaFluor488, respectively, in-house using Lightning Link kits) to detect B-cells producing specific antibodies—cells binding human PD-L1, or both human and mouse PD-L1 were selected. These cells were single cell sorted by FACS into lysis buffer. V-region sequences were recovered using RT-PCR and two further rounds of PCR, then bridged to mouse IgG1 constant region and expressed in HEK293 cells. Supernatants from HEK293 cells were screened for the presence of PD-L1 binding antibodies. This method is hereafter referred to as BCT.

Example 7

Supernatant Screening

BCT supernatants were screened by HTRF, and selected primary hits further screened for binding to cell-expressed recombinant hPD-L1 and neutralisation of PD-1 binding, and for affinity of binding to human, cynomolgus and mouse PD-L1 recombinant protein by SPR, as described in this Example. KM121 antibodies with an affinity of 1 nM or better for human and in some cases also cynomolgus PD-L1 were taken forward for further characterisation. For KM122, antibodies with the capacity to neutralise PD-1 binding to cell-expressed PD-L1 were taken forward, along with high affinity (<1 nM) binding to both human and cynomolgus PD-L1. Antibodies did not bind to mouse PD-L1.

a) Primary Screen—Binding to Recombinant Human PD-L1 (BCT Supernatants)

Supernatants collected from BCT expression were screened for the ability of secreted antibodies to bind to hPD-L1 expressed as a recombinant protein (produced in-house). Binding of secreted antibodies to recombinant human and mouse PD-L1 were identified by HTRF® (Homogeneous Time-Resolved Fluorescence, Cisbio) assay format using FluoProbes®647H (Innova Biosciences) labelled PD-L1 (referred to herein as 647 hPD-L1 or 647 mPD-L1 for human PD-L1 and mouse PD-L1 labelled with FluoProbes®647H respectively). 5 µL BCT supernatant was transferred to a white 384-well, low-volume, non-binding surface polystyrene plate (Greiner). 5 µL of 25 nM 647 hPD-L1 or 647 mPD-L1 diluted in HTRF assay buffer was added to all wells. Reference antibody was diluted in BCT media (Gibco #A14351-01) to 40 nM and 5 µL added to plate. For negative control wells, 5 µL of mouse IgG1 (Sigma M9269 in some instances referred to as CM7) diluted to 40 nM in BCT media was added. Binding of secreted antibodies to PD-L1 was detected by addition of 10 µL of goat anti-mouse IgG (Southern Biotech) directly labelled with Europium cryptate (Cisbio) diluted 1/2000 in HTRF assay buffer. The plate was left to incubate in the dark for 2 hours prior to reading time resolved fluorescence at 620 nm and 665 nm emission wavelengths using an EnVision plate reader (Perkin Elmer).

Data were analysed by calculating 665/620 ratio and percent effect for each sample according to equation 2 and equation 1 respectively.

For KM121, primary hits were selected based on greater than or equal to 30 percent effect whereas for KM122 primary hits were selected based on greater than or equal to 40 percent effect.

Progression to secondary screen was based on data from recombinant PD-L1 binding.

b) Secondary Screen—Binding to Cell Expressed hPD-L1 and Neutralisation of hPD-L1 Binding to PD-1 (BCT Supernatants)

Binding of BCT supernatants were tested for ability to bind to CHO-S cells expressing hPD-L1. CHO-S cells expressing hPD-L1 (generated in-house), were diluted in FACS buffer (PBS 1% BSA 0.1% sodium azide) and were distributed to a 96-well, V-bottom plate (Greiner) at a density of 0.5-1×105 cells per well. Cells were washed with 150 µL PBS and centrifuged at 300 g for 3 minutes. Supernatant was aspirated and 150 µL PBS added. This wash step was repeated.

25 µL BCT neat supernatant, reference antibody or control antibody diluted to 300 nM in BCT media was added to the washed cells. 25 µL of 30 nM biotinylated human PD-1 (in-house) was added and cells were incubated at 4° C. for 60 minutes. 150 µL FACS buffer was added and cells washed as described above. To detect biotinylated PD-1 and anti-PD-L1 antibody binding, Streptavidin-647 (Jackson ImmunoResearch) and anti-Mouse PE (Jackson ImmunoResearch) were each diluted 1/500 in FACS buffer and 50 µL of this mixture added to cells. Cells were incubated 4° C. for 60 minutes. Cells were washed twice with 150 µL FACS buffer, centrifuging at 300 g for 3 minutes after each wash step and aspirating supernatant. Cells were fixed by addition of 50 µL 4% paraformaldehyde overnight. Cells were washed once as above and resuspended in FACS buffer for analysis. PE and APC signal intensity (geometric mean) was measured by flow cytometry using a BD FACS Array instrument. Data was plotted as geometric mean values without further calculation.

For KM121, secondary hits were selected based on high affinity (<1 nM) binding to human PD-L1. For KM122, secondary hits were selected based on comparable high affinity (<1 nM) binding human and cynomolgus PD-L1 and ability to neutralise PD-1 binding to cell-expressed PD-L1. Results are summarised in Table 4.

TABLE 4

Summary of BCT clone screening

| Experiment ID | Number of BCT supernatants screened | Number of Primary hits cherry picked | Number of secondary hits confirmed |
|---|---|---|---|
| KM121 | 984 | 162 | 7* |
| KM122 | 1312 | 263 | 4 |

*three of these secondary hits were not included in the primary screen and were screened by SPR and neutralisation only c) Analysis of Binding by Surface Plasmon Resonance SPR analysis was carried out on the ProteOn XPR36 Array system. Anti-mouse IgG (GE Healthcare BR-1008-38) was immobilised on a GLM chip by primary amine coupling. Antibodies were directly captured from BCT supernatants. Human, mouse and cynomolgus PD-L1 were used as analytes and passed over the captured antibodies at a single concentration. The binding sensorgrams are double referenced with a 0 nM (ie buffer alone) injection, and the data is analysed using the 1:1 model inherent to the ProteOn analysis software. The assay is carried out at 25° C. and used HBS-EP as running buffer.

Example 8

Characterisation of Selected Antibodies

Figure 8:
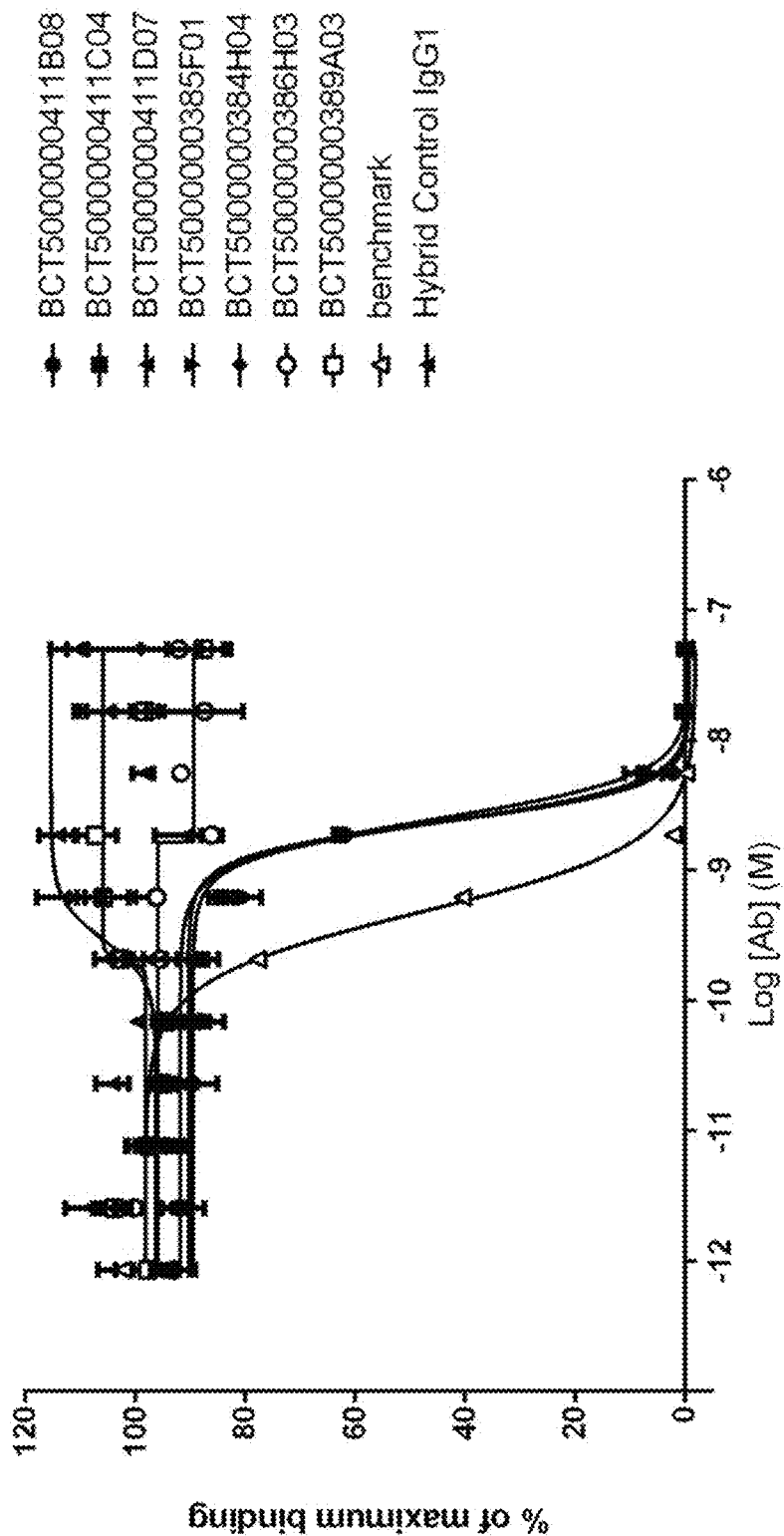
FIG. 8: PD-L1 direct neutralisation ELISA with PD-1 receptor. Neutralisation profiles of KM121 hits compared to a benchmark anti-PD-L1 antibody and isotype control. Data representative of two independent experiments.
Figure 9:
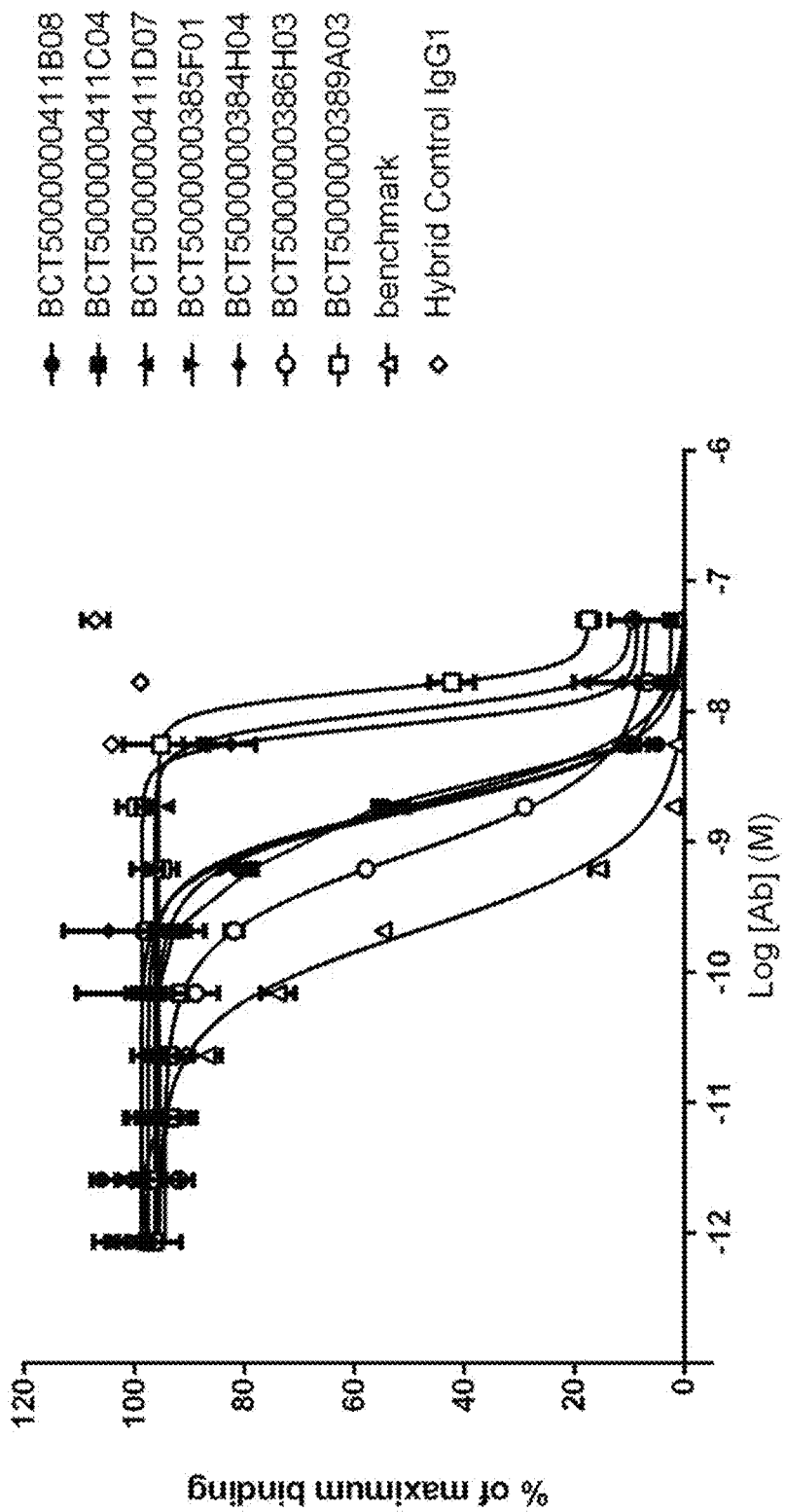
FIG. 9: PD-L1 direct neutralisation ELISA with CD80 receptor. Neutralisation profiles of KM121 hits compared to a benchmark anti-PD-L1 antibody and isotype control. Data representative of two independent experiments.
Figure 10A:
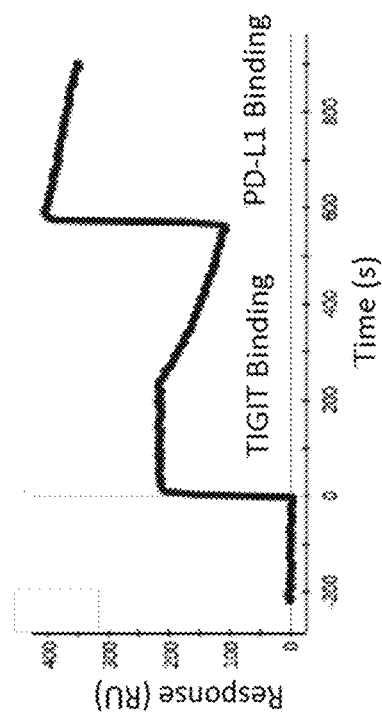
FIGS. 10A-10D: Bispecific binding as measured by SPR, with PD-L1 as first antigen, and TIGIT as second antigen.
Figure 10B:
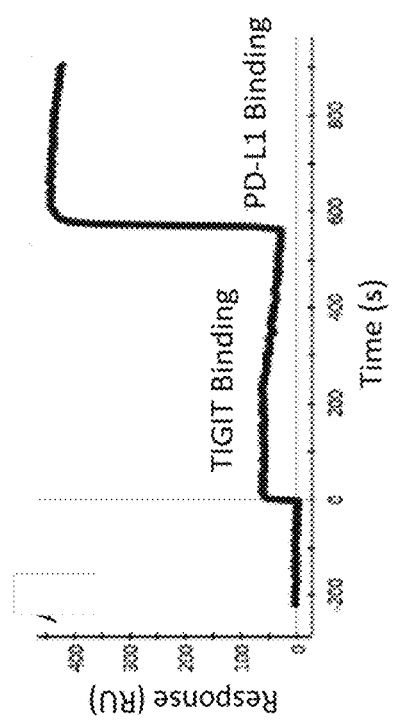
Figure 10C:
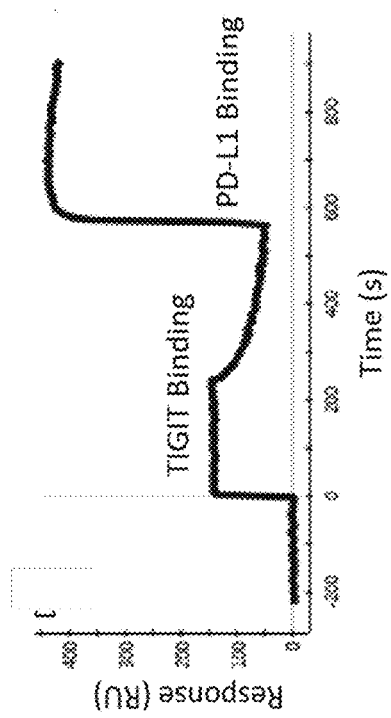
Figure 10D:
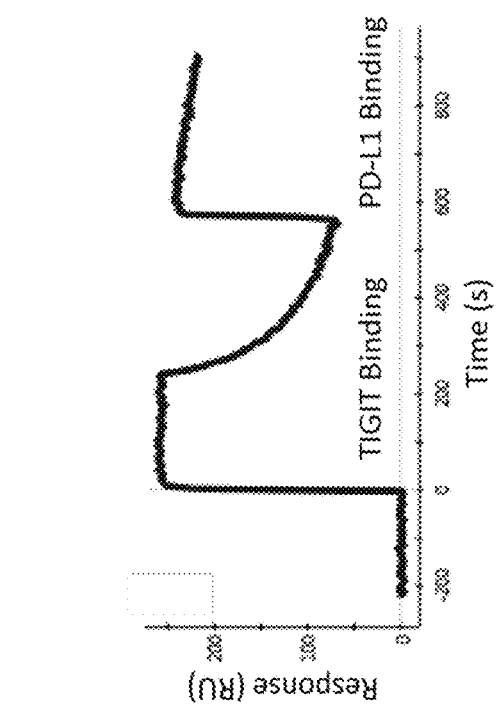
Figure 11A:
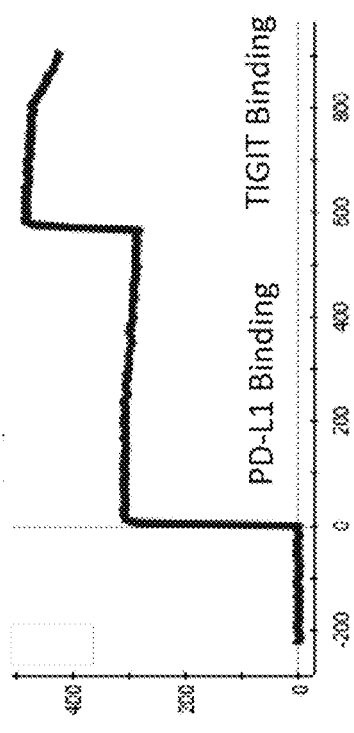
FIGS. 11A-11D: Bispecific binding as measured by SPR, with TIGIT as first antigen, and PD-L1 as second antigen.
Figure 11C:
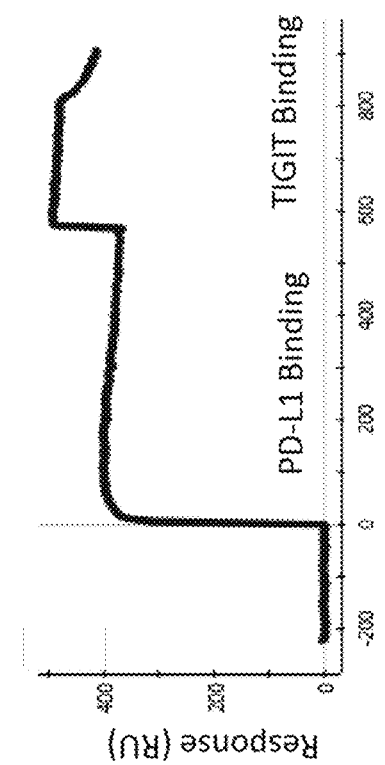
Figure 11B:
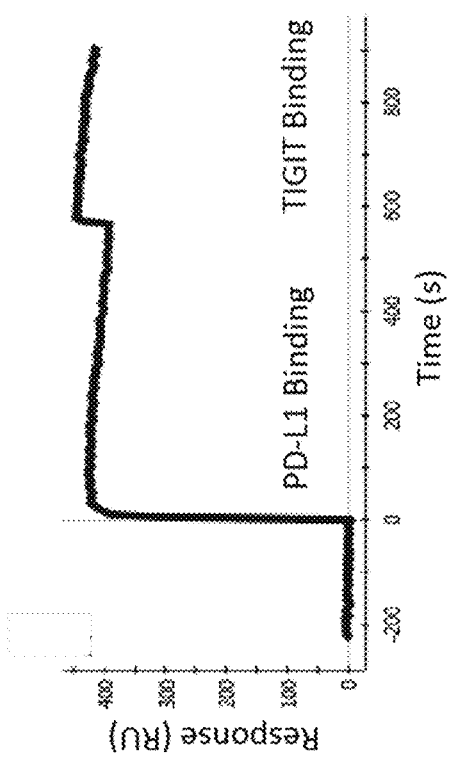
Figure 11D:
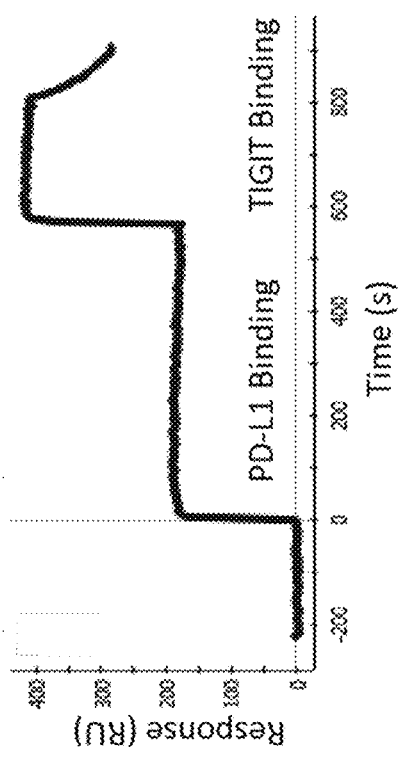

Selected hits were re-expressed with a human IgG1 constant region and sent for sequencing at Source Bioscience. V region usage is listed in Table 5. Hits were then analysed in an ELISA to determine their ability to neutralise PD-L1/PD-1 interactions, and PD-L1/CD80 interactions. All seven KM121 hits were able to neutralise PD-L1/CD80 interactions; however, four antibodies did not neutralise PD-L1/PD-1. Antibodies shown to neutralise both PD-1 and CD80 interactions with PD-L1 will be further screened for their ability to increase IFNγ in an autologous APC-T co-culture assay. KM122 hits are yet to be tested in the neutralisation assay. Results are shown in FIGS. 8 and 9.

Materials and Methods a) PD-L1/PD-1 and PD-L1/CD80 Neutralisation ELISA

CD80 (R&D Systems) or PD-1 (in-house) diluted to 2.5 µg/mL were adsorbed to 96-well, low auto-fluorescent, high protein binding plates (Costar) overnight at 4° C. Excess protein was removed by washing with PBS-Tween (0.1% v/v) and the wells were blocked with 1% w/v bovine serum albumin (BSA, Sigma) in PBS for 1 hour at room temperature, after which plates were washed with PBS-Tween as above. 60 µL of a titration (three-fold serial dilution) of antibody was added to a 96-well, non-binding plate diluted in ELISA assay buffer (PBS+0.1% BSA). 60 µL of biotin labelled PD-L1 at 16 nM working concentration (8 nM FAC) was added to the plate excluding control wells where 60 µL ELISA assay buffer was added. The plate was incubated for 30 minutes before transferring 50 µL to the coated plates. The coated plates were incubated for 1 hour at room temperature. Excess protein was removed by washing with PBS-Tween (0.1% v/v). PD-L1 binding was detected using streptavidin labelled europium (Perkin Elmer) diluted 1/1000 in DELFIA assay buffer (Perkin Elmer). The plates were washed with TBS (Tris buffered saline)-Tween (0.1% v/v) and 50 µL/well of DELFIA Enhancement solution (Perkin Elmer) was added to the plate. Time-resolved fluorescence was measured at 615 nm on an Envision plate reader (PerkinElmer). Percentage specific binding was calculated as defined in equation 5. $IC_{50}$ values were determined using GraphPad Prism software by curve fitting using a four-parameter logistic equation (Equation 6).

TABLE 5

V Gene usage for antibody leads

| Regime | Antibody clone ID | V gene | D gene | J gene | CDR3 length (aa) | CDR3 mutations from germline (aa) | V gene | J gene | CDR3 length (aa) | CDR3 from germline (aa) |
|---|---|---|---|---|---|---|---|---|---|---|
| KM121 | 411B08 | IGHV3-7*01 | IGHD4-11*01 | IGHJ4*02 | 12 | 7 | IGKV1D-12*02 | IGKJ3*01 | 9 | 3 |
| KM121 | 411C04 | IGHV3-7*01 | IGHD4-11*01 | IGHJ4*02 | 12 | 6 | IGKV1D-12*02 | IGKJ3*01 | 9 | 1 |
| KM121 | 411D07 | IGHV4-4*02 | IGHD3-10*01 | IGHJ4*02 | 8 | 1 | IGKV4-1*01 | IGKJ2*04 | 8 | 2 |
| KM121 | 386H03 | IGHV4-4*02 | IGHD3-10*01 | IGHJ4*02 | 8 | 2 | IGKV4-1*01 | IGKJ2*04 | 8 | 1 |
| KM121 | 389A03 | IGHV4-39*01 | IGHD6-13*01 | IGHJ1*01 | 13 | 6 | IGKV4-1*01 | IGKJ1*01 | 9 | 1 |
| KM121 | 385F01 | IGHV3-7*01 | IGHD4-11*01 | IGHJ4*02 | 12 | 7 | IGKV1D-12*02 | IGKJ3*01 | 9 | 1 |
| KM122 | 413D08 | IGHV3-33*01 | IGHD5-18*01 | IGHJ6*02 | 11 | 3 | IGKV1-17*01 | IGKJ1*01 | 9 | 1 |
| KM122 | 413G05 | IGHV3-11*01 | IGHD1-20*01 | IGHJ6*02 | 16 | 5 | IGKV1D-12*02 | IGKJ4*01 | 9 | 1 |
| KM122 | 413F09 | IGHV3-23*04 | IGHD5-18*01 | IGHJ4*02 | 16 | 8 | IGKV1-9*d01 | IGKJ5*01 | 9 | 3 |
| KM122 | 414B06 | IGHV3-7*01 | IGHD5-24*01 | IGHJ4*02 | 12 | 6 | IGKV1D-12*02 | IGKJ3*01 | 9 | 0 |

Example 9

Testing of Lead Anti-PD-L1 Antibodies in an Autologous Co-Culture Assay

The effects of anti-PD-L1 antibodies on IFNγ production are analysed in a co-culture of purified peripheral blood monocytes and CD45RO$^+$ memory T-cells from the same donor. In brief, monocytes are isolated by negative selection using magnetic separation beads (Miltenyi Biotec). CD45RO$^+$ T-cells are isolated by a first round of negative selection for CD3$^+$ T cells, and one round of positive selection for CD45RO$^+$ cells (Miltenyi Biotec). Cell subsets are co-cultured at a 1:1 ratio in RPMI 10% hiFBS in the presence of anti-CD3 (UCHT1, eBioscience) to provide TCR stimulation, and antibodies under investigation. Supernatants are taken after 4 days for analysis of IFNγ by MSD (Meso Scale Discovery).

Example 10

Bispecific FIT-Ig Molecules Targeting PD-L1 and TIGIT

Bispecific FIT-Ig constructs were constructed substantially as described in Example 1 of International Application WO2015/103072 (in the name of EpiMab Biotherapeutics).

The bispecific constructs, having a FIT-Ig structure, as described in FIG. 1 of WO2015/103072 were expressed in CHO cells with a vector ratio of: Construct 1 DNA: 50%, Construct 2: DNA 25%: Construct 3 DNA 25% of total DNA in the transient transfection. The bispecific molecules were purified by standard Protein A and size exclusion chromatography. In this regard, Construct 1 is the polypeptide chain made up of $VL_A$-CL-$VH_B$-CH1-CH2-CH3 in FIG. 1 of WO2015/103072. Construct 2 is the polypeptide chain made up of $VH_A$-CH1 in FIG. 1 of WO2015/103072, and Construct 3 is the polypeptide chain made up of $VL_B$-CL in FIG. 1 of WO2015/103072.

SPR analysis was used to determine affinities of the various arms of the bispecific and the parental monospecific antibodies were used to determine if the affinities had been altered in the bispecific molecule. Sequential binding of antigens were used to test whether the bispecific constructs were capable of binding on both arms of the bispecific.

TABLE 6

Bispecific antibody constructs and control monospecific antibodies

| Full name | Alias | Native variable domain[1] | Additional Domain[2] |
|---|---|---|---|
| 1D05/in-house anti-TIGIT | Bispecific 1 | 1D05 (anti-PD-L1)* | Kymab TIGIT |
| In-house anti-TIGIT/1D05 | Bispecific 2 | Kymab TIGIT | 1D05 (anti-PD-L1)* |
| Tool anti-TIGIT/Tool anti-PD-L1 | Bispecific 3 | Tool anti-TIGIT | Tool anti-PD-L1 |
| Tool anti-PD-L1/Tool anti-TIGIT | Bispecific 4 | Tool anti-PD-L1 | Tool anti-TIGIT |
| 1D05 | Antibody 1 | In-house anti-PD-L1* | na |
| Kymab TIGIT | Antibody 2 | In-house anti- TIGIT | na |

TABLE 6-continued

Bispecific antibody constructs and control monospecific antibodies

| Full name | Alias | Native variable domain[1] | Additional Domain[2] |
|---|---|---|---|
| Tool PD-L1 | Antibody 3 | Tool anti-PD-L1 | na |
| Tool TIGIT | Antibody 4 | Tool anti-TIGIT | na |

*1D05 has the $V_H$ sequence of Seq ID No: 33 and the $V_L$ sequence of Seq ID No: 43, and a heavy chain constant region of Seq ID No: 205
[1]"Native Variable domain" corresponds to the antigen-binding site formed by $VH_B$ and $VL_B$ in FIG. 1 of WO2015/103072
[2]"Additional domain" corresponds to the antigen binding site formed by $VH_A$ and $VL_A$ in FIG. 1 of WO2015/103072 a) Kinetic Analysis

An anti-human IgG capture surface was created by a mix of 3 anti-human Fc antibodies (Jackson Labs 109-005-008, 109-006-008 and 309-006-008) immobilised on a GLC chip by primary amine coupling. Control monospecific antibodies or Bispecific antibody constructs were captured on this surface and human PD-L1 or TIGIT was used as analyte at 512 nM, 128 nM, 32 nM, 8 nM and 2 nM with 0 nM (i.e. buffer alone) used to double reference the binding sensorgrams. The assay was run at 25° C., using HBS-EP as running buffer. The sensorgrams were fitted to the 1:1 model inherent to the ProteOn analysis software.

TABLE 7

TIGIT Binding

| Full name | Alias | Ka | Kd | KD (nM) |
|---|---|---|---|---|
| 1D05/in-house anti-TIGIT | Bispecific 1 | 2.38E+06 | 2.65E−03 | 1.11 |
| In-house anti-TIGIT/1D05 | Bispecific 2 | 1.12E+06 | 2.02E−03 | 1.8 |
| Tool anti-TIGIT/Tool anti-PD-L1 | Bispecific 3 | 2.10E+06 | 3.69E−03 | 1.75 |
| Tool anti-PD-L1/Tool anti-TIGIT | Bispecific 4 | 3.22E+06 | 2.98E−03 | 0.93 |
| 1D05 | Antibody 1 | nbs | nbs | nbs |
| Kymab TIGIT | Antibody 2 | 1.58E+06 | 2.27E−03 | 1.44 |
| Tool PD-L1 | Antibody 3 | nbs | nbs | nbs |
| Tool TIGIT | Antibody 4 | 3.16E+06 | 5.42E−03 | 1.72 |

TABLE 8

PD-L1 Binding

| Full name | Alias | Ka | Kd | KD (nM) |
|---|---|---|---|---|
| 1D05/in-house anti-TIGIT | Bispecific 1 | 6.03E+05 | 1.61E−04 | 0.27 |
| In-house anti-TIGIT/1D05 | Bispecific 2 | 1.04E+06 | 2.14E−04 | 0.21 |
| Tool anti-TIGIT/Tool anti-PD-L1 | Bispecific 3 | 1.25E+06 | 1.22E−04 | 0.1 |
| Tool anti-PD-L1/Tool anti-TIGIT | Bispecific 4 | 7.36E+05 | 1.57E−04 | 0.21 |
| 1D05 | Antibody 1 | 9.71E+05 | 3.36E−04 | 0.35 |
| Kymab TIGIT | Antibody 2 | nbs | nbs | nbs |
| Tool PD-L1 | Antibody 3 | 1.05E+06 | 2.08E−04 | 0.2 |
| Tool TIGIT | Antibody 4 | nbs | nbs | nbs | b) Bispecific Binding

Using the same anti-human IgG capture surface created for kinetic analysis, the Bispecific antibody constructs were captured on this surface and recombinant PD-L1 or TIGIT was used as analyte at 512 nM, 128 nM, 32 nM, 8 nM and 2 nM with 0 nM (i.e. buffer alone) used to double reference the binding sensorgrams. The assay was carried out by injecting PD-L1 followed by TIGIT with no regeneration between analyte injections, and also with TIGIT followed by PD-L1. The sensorgrams for the double referenced 512 nM are shown in FIGS. 10 and 11.

Example 11

Generation and Expression of Anti-PD-L1-IL-2 Immunocytokine Constructs

Immunocytokines were generated by fusing wild type IL-2 (SEQ ID No:301), or IL-2 containing deletions in the first nine amino acids (see SEQ ID Nos: 303 to 323), to the light chain of anti-PD-L1 antibody 1D05 (see Seq ID No:45). These were paired with an IgG1 effector-disabled variant of 1D05 heavy chain (Seq ID No:205). Wild type IL-2 fused to the heavy chain of 1D05 was generated for use as a control (SEQ ID No:302) and paired with the unmodified light chain of 1D05 (Seq ID No:45). Twenty-two immunocytokines were successfully expressed and characterised further. One light chain construct, 1D05 D1 did not express successfully.

Materials and Methods

The DNA sequences encoding the anti-PD-L1 (antibody 1D05) immunocytokine (C-terminal IL-2 fusion to light chain) were purchased as synthetic DNA strings and cloned into the pTT5 expression vector using the Golden Gate cloning strategy. The heavy chain sequence of 1D05, includes a constant region which is a disabled IgG1 variant with changes from wild-type shown in bold (Seq ID No:299). The light chain of antibody 1D05 has full length wild type IL-2 sequence (underlined) fused to the C-terminus of the Kappa constant region (Seq ID No:300). Overlap PCR using appropriate oligonucleotide primers were used to generate variants of N-terminal of IL-2 (see Seq ID No:300 where IL-2 the sequence is underlined and the region to be varied is shown in bold). Variant sequences were cloned into the pTT5 expression vector using the Golden Gate method. The wild type and variant constructs were transfected to Expi293™ cells for expression.

Example 12

Generation of IL-2R Transfectant Cells for Screening

In order to differentiate between immunocytokine activity on the high affinity (αβγ) and intermediate affinity (βγ) IL-2 receptors, IL-2R transfectants were generated. TF-1 cells, expressing endogenous common γ chain, were transfected with β, or α and β receptor subunits, to impart responsiveness to IL-2. The proliferative response to immunocytokines was then analysed using these cells (see Example 13).

Materials and Methods

Two recombinant cell lines were generated to distinguish between signalling through high affinity (αβγ) and intermediate affinity (βγ) IL-2R. The erythroleukemia cell line TF-1 (European Collection of Authenticated Cell Cultures) shows complete growth dependency on granulocyte-macrophage colony-stimulating factor (GM-CSF) or interleukin-3 (IL-3). The first cell line generated was transfected with full length human IL-2Rβ (CD122) only. The second cell line was generated by transfecting the full length human IL-2Rα (CD25) into the first cell line.

The transfected sequences were codon optimized for mammalian expression and cloned into an expression vector under the CMV promoter flanked by 3' and 5' piggyBac specific terminal repeat sequences facilitating stable integration into the cell genome (see: "A hyperactive piggyBac transposase for mammalian applications"; Yusa K., et al., Proc. Natl. Acad. Sci. USA., 108(4): 1531-6, 2011 Jan. 25). Furthermore, the expression vector for each subunit contained a different selection cassette to facilitate stable cell line generation. The β subunit was selected using puromycin (Sigma) and the α subunit using geneticin (Gibco). The a subunit was transfected into cells already expressing the β subunit.

The expression plasmids were co-transfected with a plasmid encoding piggyBac transposase into the TF1 cell line by electroporation using the Lonza 4-D nucleofector transfection X kit system according to manufacturer instructions. 24 hours after transfection, complete media was supplemented with the appropriate selection and cells grown for at least 3 weeks to select a stable line, with media being exchanged every 3 to 4 days. The expression of the recombinant human subunits was assessed by flow cytometry using anti-human CD122 (IL-2Rα) APC conjugated antibody (eBioscience) and anti-human CD25 (IL-2Rα) PE conjugated antibody (eBioscience). Endogenous common γ chain expression was confirmed with anti-human CD132 (common γ chain) PE conjugated antibody (eBioscience). As expression was low, CD122$^+$ cells were sorted by fluorescence activated cell sorting (FACS) and further cultured under selection. There was uniform expression of a chain after transfection, and therefore these cells were not sorted.

Complete TF1 media was made up of RPMI medium 1640 (Gibco) plus GM-CSF (2 ng/mL) and supplemented with 10% v/v heat inactivated fetal bovine serum (hiFBS, Gibco). Once responsiveness to IL-2 was confirmed, transfected cell lines were maintained in RPMI 1640, 10% hiFBS and 5 ng/mL recombinant human IL-2 with (αβ) or without (β) geneticin.

Example 13

Assessing Ability of Immunocytokine Constructs to Signal Through IL-2R

Figure 12A:
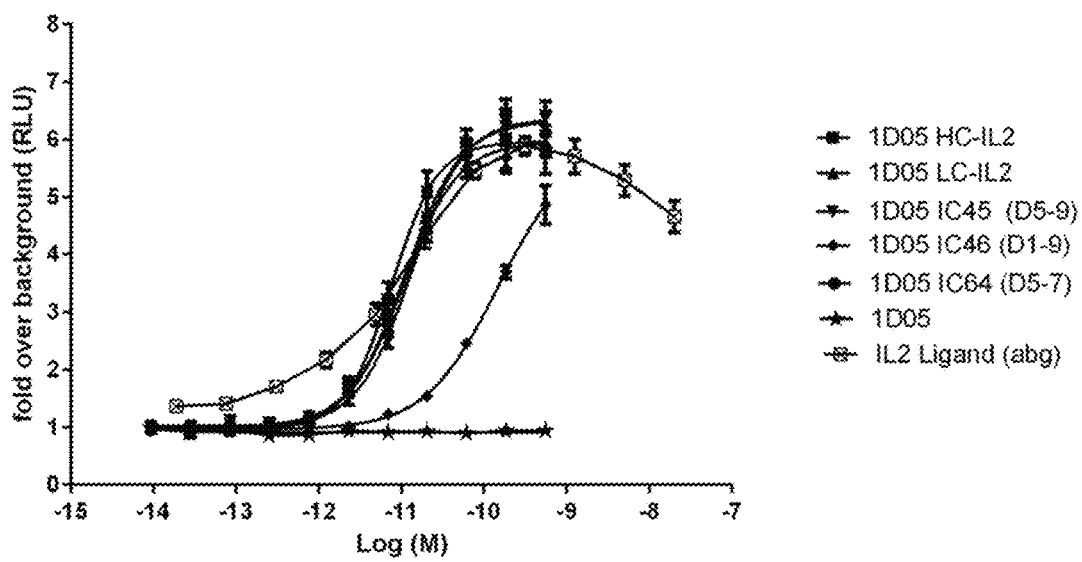
FIG. 12A-12C: Ability of immunocytokine constructs to induce proliferation in IL-2Rαβγ expressing TF-1 cells, compared with equimolar concentrations of free IL-2. Data shown are from a single experiment, representative of three experiments.
Figure 12B:
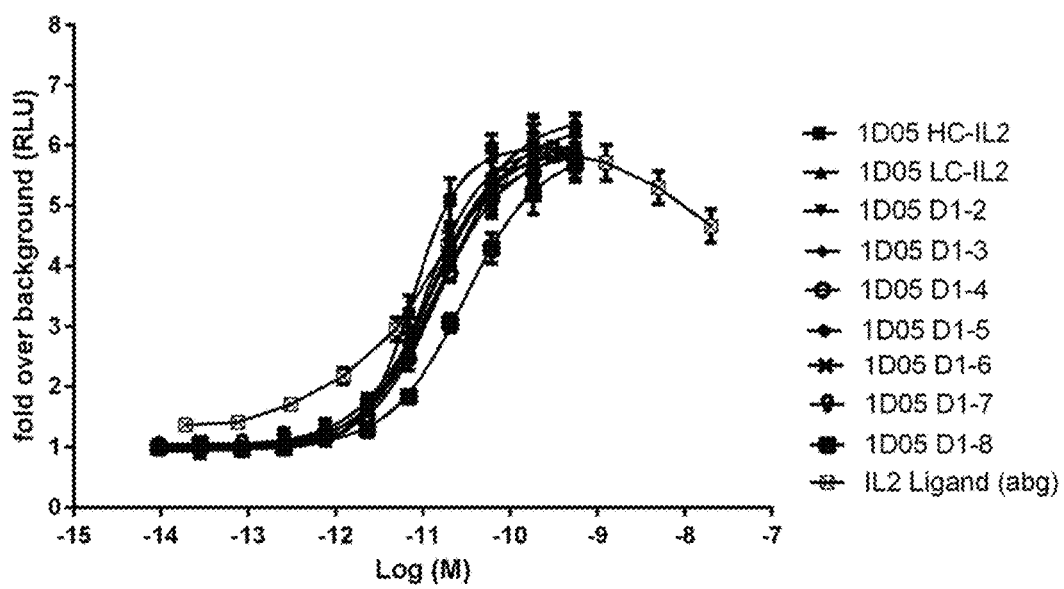
Figure 12C:
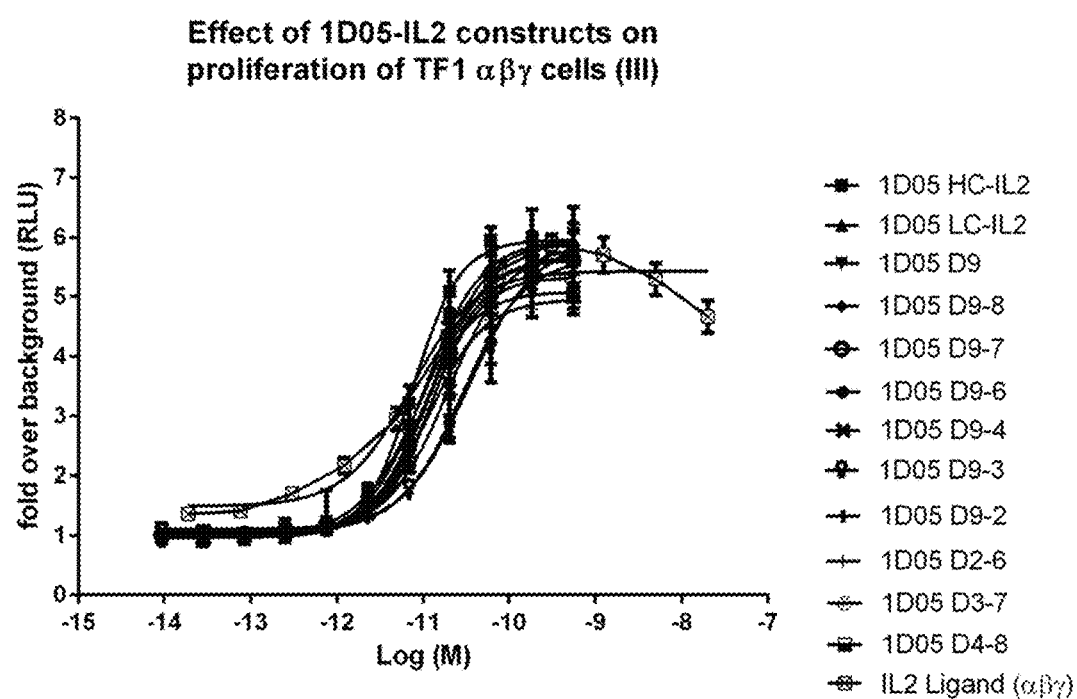
Figure 12D:
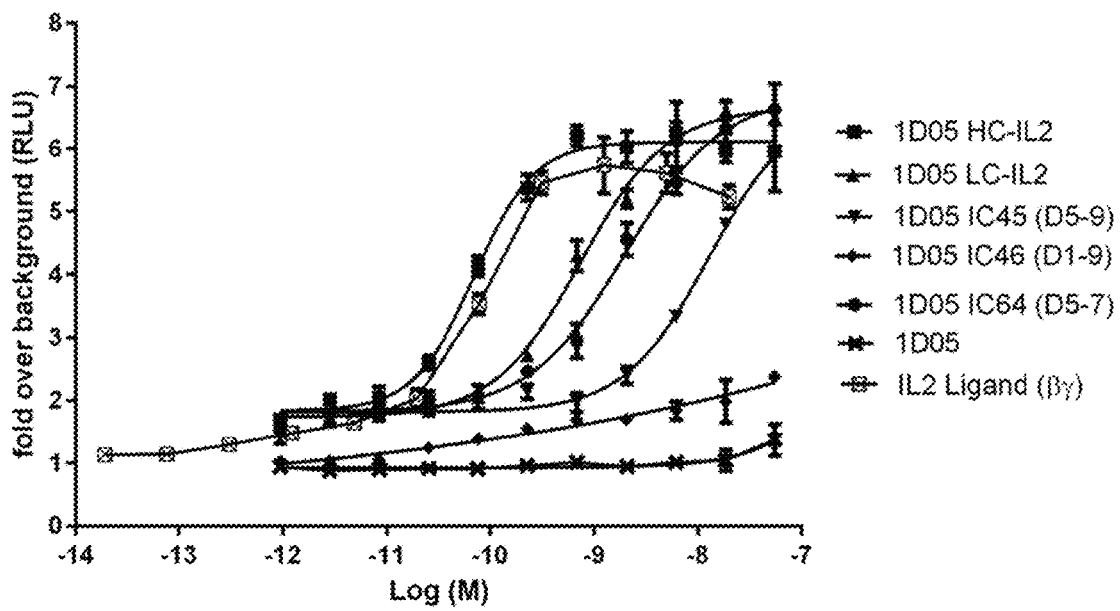
FIG. 12D-12F: Ability of immunocytokine constructs to induce proliferation in IL-2Rβγ expressing TF-1 cells, compared with equimolar concentrations of free IL-2. Data shown are from a single experiment, representative of four experiments.
Figure 12E:
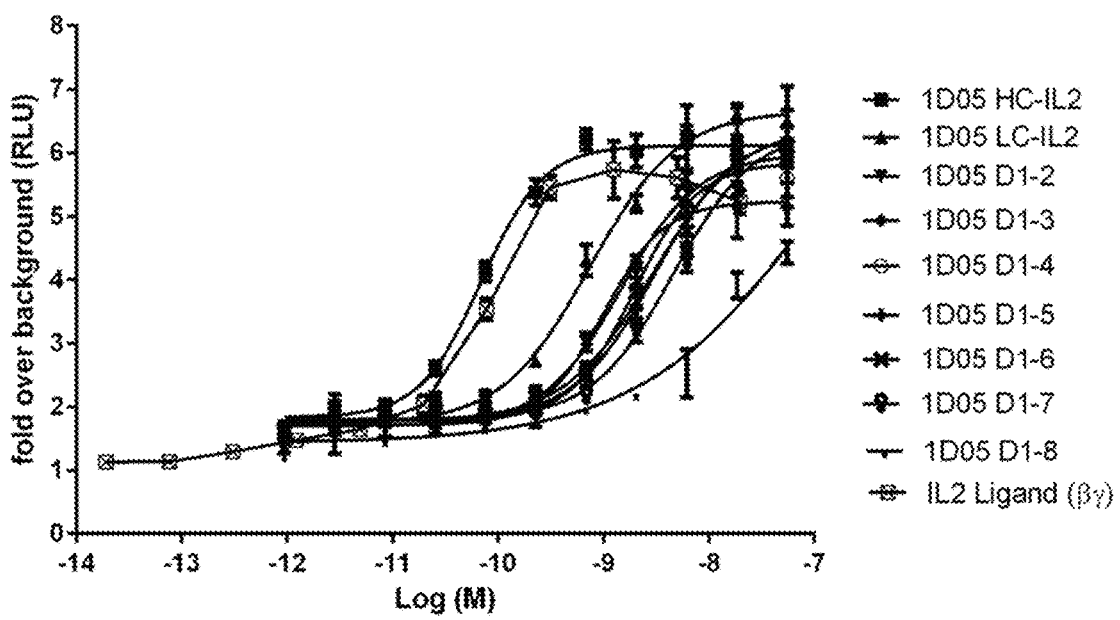
Figure 12F:
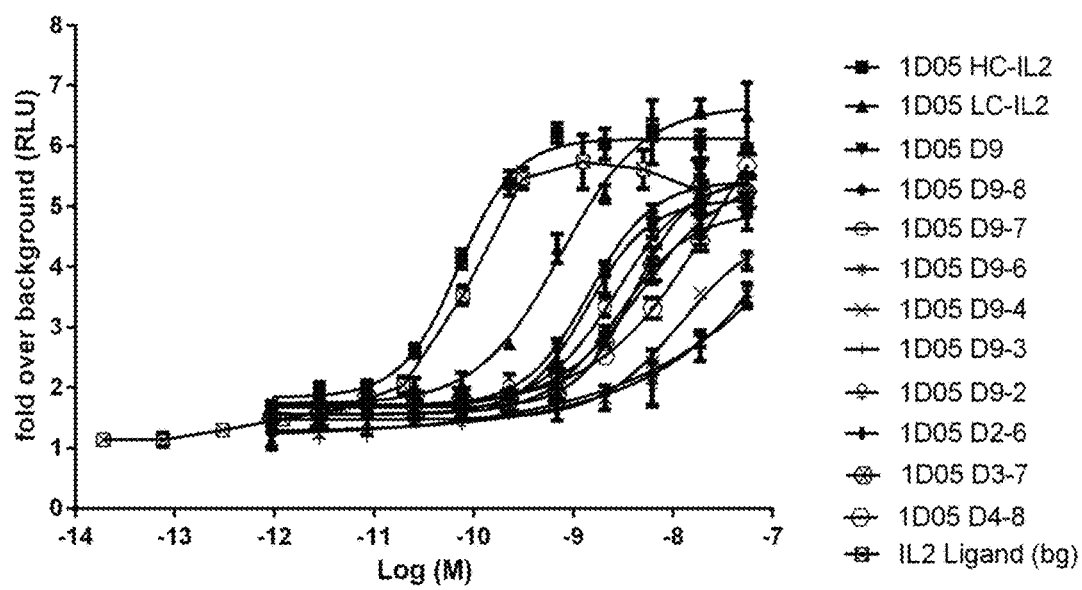

Immunocytokines were assessed for their ability to induce proliferation of TF1 cell lines transfected with the βsubunit, or with both the α and β subunits of IL-2R. Cells were starved of cytokines overnight, then stimulated with titrations of each immunocytokine. CellTiter-Glo® was used to determine the number of viable cells in culture after 3 days, based on quantitation of the ATP present. There was a broad range of activities of the immunocytokines on IL-2Rα, with the largest IL-2 deletions having the greatest reduction on proliferation, compared with equimolar amounts of free IL-2. The effect on αβγ activity is not as pronounced, but again the greatest reduction in proliferation is seen with the largest IL-2 deletions. Deletions in the first few N-terminal amino acids of IL-2 allow for fine tuning of cytokine activity. A representative experiment is shown in FIGS. 12(a) and (b).

Materials and Methods

IL-2R transfected TF1 cells were routinely cultured in RPMI+10% fetal bovine serum (culture medium) with the addition of IL-2 (Peprotech) at 5 ng/mL for the β transfected cell line and IL-2 at 5 ng/mL and Geneticin (Gibco) at 350 μg/mL for the αβ transfected cell line. Prior to testing of immunocytokine constructs, the cells were harvested by centrifugation and aspirated to remove the supernatant. The cells were washed in PBS to remove cytokines and antibiotics. Cells were resuspended in fresh culture medium at $10^5$ cells/mL, without supplements and returned to the incubator overnight.

The cells were harvested by centrifugation and aspirated to remove the supernatant. Cells were resuspended in complete medium and 30 μL of cell solution was added to the plate (white walled tissue culture treated 384 well plate) wells to achieve an initial cell concentration of 1250 cells/well.

The IL-2 ligand was prepared as serial four-fold dilutions from 300 ng/mL final assay concentration (FAC) (600 ng/mL working) in culture media. The immunocytokine constructs were titrated from 0.1 μg/mL (three-fold dilutions) for testing on the αβγ cell line and 10 μg/mL (three-fold dilutions) for the βγ cell line. 30 μL of titrations were added to the cell plate. To control wells, 30 μL of culture media without IL-2 was added. To reduce evaporation effect the outermost rows/columns of the plate were filled with 80 μL of culture media. The plates were then incubated for 3 days at 37° C., 5% CO2. Following the culture period proliferation of TF-1 cells was assessed by addition of 30 μL of Cell Titre Glo (Promega) to all wells. The plate was incubated at room temperature for 10 minutes then read using ultrasensitive luminescence filter.

Equation 1: Calculation of Fold Over Background from TF-1 Proliferation Assay $$\text{fold over background} = \frac{\text{sample } RLU}{\text{mean over background } RLU}$$

RLU=relative luminescence units

Data expressed as fold over background. Background was defined as wells containing cells but no cytokine Example 14

Binding of Immunocytokines to PD-L1

Surface plasmon resonance was used to confirm the ability of the immunocytokine constructs to bind PD-L1. The presence of the IL-2 on the light chain does not have any detrimental effect on binding (Table 9). Four constructs with a range of IL-2 activities were shortlisted for further characterisation—these were 1D05 ID1-9 ICK, 1D05 D1-8 ICK, 1D05 D9-2 ICK and 1D05 D9-7 ICK

TABLE 9

Affinity of 1D05 binding to PD-L1 is unaffected by the fusion of IL-2 to the antibody, as measured by surface plasmon resonance. Data shown is from a single experiment

| Sample Name | KD (nM) |
|---|---|
| 1D05 | 0.171 |
| 1D05 HC-IL2 | 0.240 |
| 1D05 LC-IL2 | 0.207 |
| 1D05IC45 (D5-9) | 0.203 |
| 1D05 IC46 (D1-9) | 0.195 |
| 1D05 IC64 (D5-7) | 0.214 |
| 1D05 D1-2 | 0.187 |
| 1D05 D1-3 | 0.199 |
| 1D05 D1-4 | 0.186 |
| 1D05 D1-5 | 0.203 |
| 1D05 D1-6 | 0.211 |
| 1D05 D1-7 | 0.178 |
| 1D05 D1-8 | 0.190 |
| 1D05 D9 | 0.205 |
| 1D05 D9-8 | 0.225 |
| 1D05 D9-7 | 0.200 |
| 1D05 D9-6 | 0.211 |
| 1D05 D9-4 | 0.175 |
| 1D05 D9-3 | 0.171 |
| 1D05 D9-2 | 0.189 |
| 1D05 D2-6 | 0.201 |
| 1D05 D3-7 | 0.203 |
| 1D05 D4-8 | 0.208 |
| benchmark | 0.099 |

Materials and Methods

Analysis of Immunocytokines by Surface Plasmon Resonance

Label-free surface plasmon resonance (SPR) analysis was carried out on the ProteOn XPR36 (BioRad) array SPR machine. An anti-human IgG capture surface was created on a GLC biosensor chip using amine coupling of an anti-human IgG from GE Healthcare. Test antibodies were captured on this surface and human PD-L1 (in-house) was used as the analyte at 64 nM, 16 nM, 4 nM, 1 nM and 0.25 nM. The assay was carried out at 25° C. using HBS-EP (Teknova H8022). Buffer alone was used to reference the binding sensorgrams. The data was analysed using the 1:1 model inherent to the ProteOn XPR36 analysis software.

Example 15

Assessing Capacity of Immunocytokines to Neutralise the Interaction of PD-L1 and PD-1/CD80

Figure 13A:
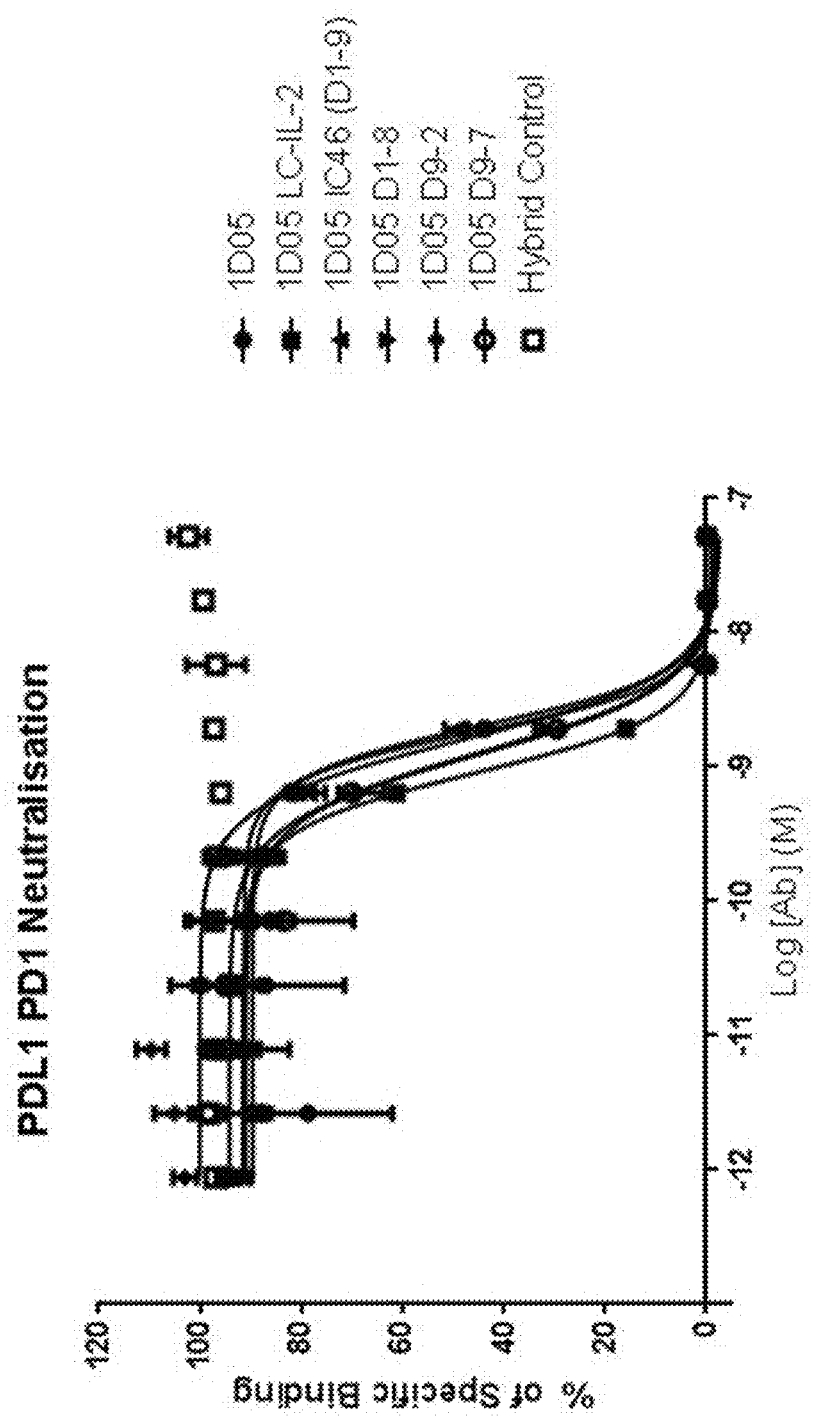
FIG. 13A: Capacity of 1D05 antibody to neutralise the interaction between PD-1 and PD-L1 is unaffected by the fusion of IL-2 to the antibody, as measured in a neutralisation ELISA. Data shown are from a single experiment, representative of three experiments.
Figure 13B:
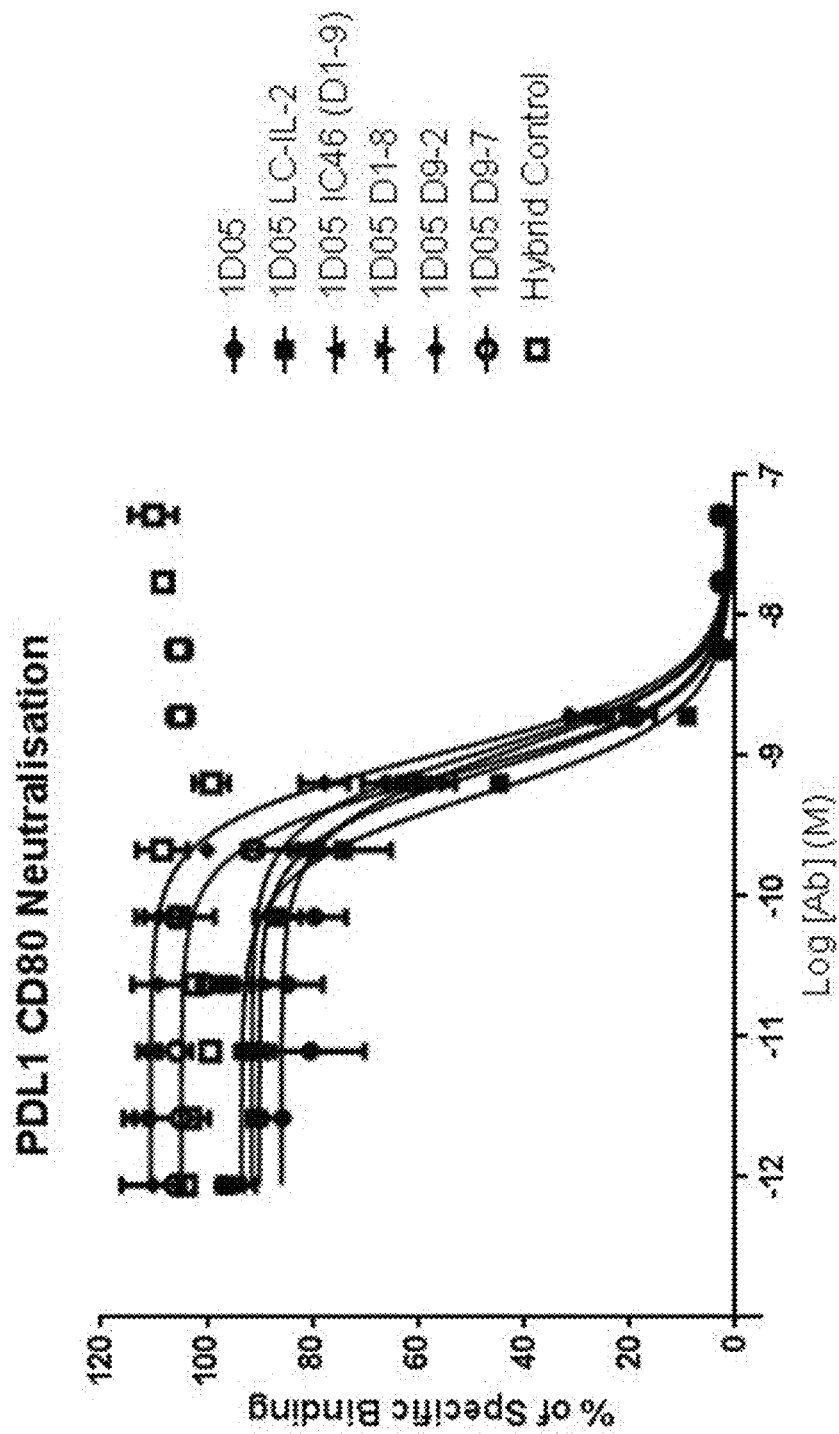
FIG. 13B: Capacity of 1D05 antibody to neutralise the interaction between CD80 and PD-L1 is unaffected by the fusion of IL-2 to the antibody, as measured in a neutralisation ELISA. Data shown are from a single experiment, representative of three experiments.

To ensure that fusion of the IL-2 molecule to the antibody did not disrupt its neutralisation capacity, shortlisted immunocytokines were tested in a neutralisation ELISA. The shortlisted immunocytokines tested did not differ from wild type antibody in their ability to neutralise interactions between PD-L1 and PD-1, and PD-L1 and CD80. Results are shown in FIG. 13 and Table 10. Values in the table are the means of three independent experiments.

TABLE 10

Summary of neutralisation ELISA data, expressed as mean of three independent experiments

| Clone | PD1-PD-L1 Neutralisation IC$_{50}$ (nM) | CD80-PD-L1 Neutralisation IC$_{50}$ (nM) |
|---|---|---|
| 1D05 | 1.41 | 0.882 |
| 1D05 LC-IL-2 | 0.833 | 0.505 |
| 1D05 IC46 (D1-9) | 1.75 | 1.07 |
| 1D05 D1-8 | 1.16 | 0.745 |
| 1D05 D9-2 | 1.55 | 0.947 |
| 1D05 D9-7 | 1.15 | 0.70 |
| Hybrid Control | N/A | N/A |

Materials and Methods a) PD-L1/PD-1 or PD-L1/CD80 Neutralisation ELISA

CD80 (R&D Systems) or PD-1 (in house) diluted to 2.5 µg/mL were adsorbed to 96-well, low auto-fluorescent, high protein binding plates (Costar) overnight at 4° C. Excess protein was removed by washing with PBS-Tween (0.1% v/v) and the wells were blocked with 1% w/v bovine serum albumin (BSA, Sigma) in PBS for 1 hour at room temperature, after which plates were washed as described previously. 60 µL of a titration (three-fold dilutions from 100 nM) of antibody was added to a 96-well, non-binding plate diluted in ELISA assay buffer (PBS+0.1% BSA). 60 µL of biotinylated PD-L1 (in house, labelled with Lightning Link Biotinylation kit) at 16 nM working concentration (8 nM FAC) was added to the plate excluding control wells where 60 µL ELISA assay buffer was added. The plate was incubated for 30 min before transferring 50 µL to the coated plates.

The coated plates were incubated for 1 hour at room temperature. Excess protein was removed by washing with PBS-Tween (0.1% v/v). PD-L1 binding was detected using streptavidin labelled Europium (Perkin Elmer) diluted 1/1000 in DELFIA assay buffer (Perkin Elmer). The plates were washed with TBS (Tris buffered saline)-Tween (0.1% v/v) and 50 µL/well of DELFIA Enhancement solution (Perkin Elmer) was added to the plate. The time-resolved fluorescence was measured at 615 nm on an Envision plate reader (PerkinElmer). Percentage specific binding was calculated as defined in equation 2.

Equation 2: Percentage of Receptor Binding (ELISA) Based on fluorescence at 615 nm $$\% \text{ of specific binding} = \frac{\text{sample value} - \text{non-specific binding}}{\text{total binding} - \text{non-specific binding}} \times 100$$

Total binding=biotinylated PD-L1 (no antibody)
Non-specific binding=no biotinylated PD-L1
IC$_{50}$ values were determined using GraphPad Prism software by curve fitting using a four-parameter logistic equation (Equation 1) from the percentage specific binding (Equation 1).

Example 16

De-Immunisation of Anti-PD-L1 Antibody

To reduce the possibility of adverse immunological reactions based around the anti-PD-L1-immunocytokine, a series of 1D05 antibody mutants (Seq ID Nos:47 to 51) was created with anticipated lower potential of immunogenicity, as determined by T-cell epitope analysis software (tbc). The mutations can be single or in combination. Mutants were assessed for their ability to bind PD-L1 with the same affinity as the wild-type molecule by SPR as described in Example 14, with the addition of human PD-L1 analyte at 256 nM. Mutations under investigation are included as Seq ID Nos:47 to 51, indicated by underlined and bold text. The $V_H$ framework mutations (Seq ID Nos:47 and 48) do not have any detrimental effects on binding. The V to A mutation in CDR2 (Seq ID No:50) was detrimental to binding, and so an alternative mutation will be analysed (V to Y, Seq ID No:298). Results are shown in Table 11

TABLE 11

| Heavy Chain | Light Chain | KD (nM) |
| --- | --- | --- |
| 1D05 - IgG1 disabled (LAGA) Seq ID No: 299 | 1D05 kappa (Seq ID No: 45) | 0.29 |
| 1D05 V to A change in $V_H$ (Seq ID No: 47), IgG1 disabled (LAGA, Seq ID No: 205) | 1D05 kappa (Seq ID No: 45) | 0.33 |
| 1D05 F to S change in VH (Seq ID No: 48), IgG1 disabled (LAGA, Seq ID No: 205) | 1D05 kappa (Seq ID No: 45) | 0.23 |
| 1D05 V to A & F to S change in $V_H$ (Seq ID No: 342), IgG1 disabled (LAGA, Seq ID No: 205) | 1D05 kappa (Seq ID No: 45) | 0.23 |
| 1D05 - IgG1 disabled (LAGA) Seq ID No: 299 | 1D05 kappa, V to A change (Seq ID No: 50) | 2.66 |
| 1D05 V to A change in $V_H$ (Seq ID No: 47), IgG1 disabled (LAGA, Seq ID No: 205) | 1D05 kappa, V to A change (Seq ID No: 50) | 2.8 |
| 1D05 F to S change in $V_H$ (Seq ID No: 48), IgG1 disabled (LAGA, Seq ID No: 205) | 1D05 kappa, V to A change (Seq ID No: 50) | 1.94 |
| 1D05 V to A & F to S change in $V_H$ (Seq ID No: 342), IgG1 disabled (LAGA, Seq ID No: 205) | 1D05 kappa, V to A change (Seq ID No: 50) | 1.94 |

INCORPORATION BY REFERENCE

All references cited herein, including patents, patent applications, papers, text books and the like, and the references cited therein, to the extent that they are not already, are hereby incorporated herein by reference in their entirety.

EQUIVALENTS

The foregoing written specification is considered to be sufficient to enable one skilled in the art to practice the invention. The foregoing description and Examples detail certain preferred embodiments of the invention. It will be appreciated, however, that the invention may be practiced in many ways and the invention should be construed in accordance with the appended claims and any equivalents thereof It will be understood that particular configurations, aspects, examples, clauses and embodiments described herein are shown by way of illustration and not as limitations of the invention. Any part of this disclosure may be read in combination with any other part of the disclosure, unless otherwise apparent from the context.

SEQUENCE LISTING

| SEQ ID NO: | Name | Description | Sequence |
|---|---|---|---|
| 1 | Human PD-L1 | NCBI number: NP 054862.1 (ECD highlighted in BOLD, cytoplasmic domain underlined) | MRIFAVFIFMTYWHLLNAFTVTVPKDLYVVEYGSNMTIECKFPVEKQ LDLAALIVYWEMEDKNIIQFVHGEEDLKVQHSSYRQRARLLKDQL SLGNAALRITDVKLQDAGVYRCMISYGGADYKRITVKVNAPYNKIN QRILVVDPVTSEHELTCQAEGYPKAEVIWTSSDHQVLSGKTTTTNS KREEKLFNVTSTLRINTTTNEIFYCTFRRLDPEENHTAELVIPELPLA HPPNERTHLVILGAILLCLGVALTFIFRLRKGRMMDVKKCGIQDTNSK KQSDTHLEET |
| 2 | Cyno PD-L1 | NCBI number: XP 014973154.1 (ECD highlighted in BOLD) | MGWSCIILFLVATATGVHSMPTVTVPKDLYVVEYGSNMTIECKFPVE KQLDLTSLIVVWEMEDKNIIQFVHGEEDLKVQHSNVRQRAQLLKD QLSLGNAALRITDVKLQDAGVYRCMISYGGADYKRITVKVNAPYN KINQRILVVDPVTSEHELTCQAEGYPKAEVIWTSSDHQVLSGKTTT TNSKREEKLLNVTSTLRINTTANEIFYCIFRRLDPEENHTAELVIPEL PLALPPNERT |
| 3 | Human PD-L1 Hits | Human PD-L1 ECD with C-terminal His tag | MRIFAVFIFMTYWHLLNAFTVTVPKDLYVVEYGSNMTIECKFPVEKQL DLAALIVYWEMEDKNIIQFVHGEEDLKVQHSSYRQRARLLKDQLSGN AALQITDVKLQDAGVYRCMISYGGADYKRITVKVNAPYNKINQRILVV DPVTSEHELTCQAEGYPKAEVIWTSSDHQVLSGKTTTTNSKREEKLFNV TSTLRINTTTNEIFYCTFRRLDPEENHTAELVIPELPLAHPPNERTHHHH HH |
| 4 | Human PD-L1 Fc | Human PD-L1 ECD with C-term Fc fusion (in bold) | MRIFAVFIFMTYWHLLNAFTVTVPKDLYVVEYGSNMTIECKFPVEKQL DLAALIVYWEMEDKNIIQFVHGEEDLKVQHSSYRQRARLLKDQLSGN AALQITDVKLQDAGVYRCMISYGGADYKRITVKVNAPYNKINQRILVV DPVTSEHELTCQAEGYPKAEVIWTSSDHQVLSGKTTTTNSKREEKLFNV TSTLRINTTTNEIFYCTFRRLDPEENHTAELVIPELPLAHPPNERTIEGRE PKSCDKTHTCPPCPAPELLGGPSVFLFPPKPKDTLMISRTPEVTCVV VDVSHEDPEVKFNWYVDGVEVHNAKTKPREEQYNSTYRVVSVLTV LHQDWLNGKEYKCKVSNKALPAPIEKTISKAKGQPREPQVYTLPPS RDELTKNQVSLTCLVKGFYPSDIAVEWESNGQPENNYKTTPPVLDS DGSFFLYSKLTVDKSRWQQGNVFSCSVMHEALHNHYTQKSLSLSP GK |
| 5 | Cyno PD-L1 FLAG | Cynomolgus PD-L1 ECD with N-term FLAG tag | MGWSCIILFLVATATGVHSMPTVTVPKDLYVVEYGSNMTIECKFPVEK QLDLTSLIVVWEMEDKNIIQFVHGEEDLKVQHSNVRQAQLLKDQLSL GNAALRITDVKLQDAGVYRCMISYGGADYKRITVKVNAPYNKINQRIL VVDPVTSEHELTCQAEGYPKAEVIWTSSDHQVLSGKTTTTNSKREEKL LNVTSTLRINTTANEIFYCIFRRLDPEENHTAELVIPELPLALPPNERTDY KDDDDK |
| 6 | Human PD-1 Fc | Human PD-1 full length sequnce derived from cDNA as human Fc fusion | MGWSCIILFLVATATGVHSLDSPDRPWNPPTFSPALLVVTEGDNATFTC SFSNTSESFVLNWYRMSPSNQTDKLAAFPEDRSQPGQDCRFRVTQLPN GRDFHMSVVRARRNDSGTYLCGAISLAPKAQIKESLRAELRVTERRAE VPTAHPSPSPRPAGQKLENLYRIGIEGRMDEPKSCDKTHTCPPCPAP ELLGGPSVFLFPPKPKDTLMISRTPEVTCVVVDVSHEDPEVKFNWY VDGVEVHNAKTKPREEQYNSTYRVVSVLTVLHQDWLNGKEYKCK VSNKALPAPIEKTISKAKGQPREPCIVYTLPPSRDELTKNCIVSLTCLV |

-continued

SEQUENCE LISTING

| SEQ ID NO:Name | Description | Sequence |
|---|---|---|
| 7 | 84G09 - CDRH1 (IMGT) | Amino acid sequence of CDRH1 of 84G09 using IMGT | GFTFDDYA |
| 8 | 84G09 - CDRH2 (IMGT) | Amino acid sequence of CDRH2 of 84G09 using IMGT | ISWKSNII |
| 9 | 84G09 - CDRH3 (IMGT) | Amino acid sequence of CDRH3 of 84G09 using IMGT | ARDITGSGSYGWFDP |
| 10 | 84G09 - CDRH1 (Kabat) | Amino acid sequence of CDRH1 of 84G09 using Kabat | DYAMH |
| 11 | 84G09 - CDRH2 (Kabat) | Amino acid sequence of CDRH2 of 84G09 using Kabat | GISWKSNIIGYADSVKG |
| 12 | 84G09 - CDRH3 (Kabat) | Amino acid sequence of CDRH3 of 84G09 using Kabat | DITGSGSYGWFDP |
| 13 | 84G09 - Heavy chain variable region | Amino acid sequence of V$_H$ of 84G09 | EVQLVESGGGLVQPGRSLRLSCAASGFTFDDYAMHWVRQTPGKGLEW VSGISWkSnilGYADSVKGRFTISRDNAKNSLYLQMNSLRAEDTALYYC ARDITGSGSYGWFDPWGQGTLVTVSS |
| 14 | 84G09 - Heavy chain variable region | Nucleic acid sequence of V$_H$ of 84G09 | CAAGAAAAAGCTTGCGCCACCATGGAGTTTGGGCTGAGCTGGATTT TCCTTTTGGCTATTTTAAAAGGTGTCCAGTGAAGTACAATTGGTG GAGTCCGGGGAGGCTTGGTACAGCCTGGCAGGTCCCTGAGACTCT CCTGTGCAGCCTCTGGATTCACCTTTGATGATTATGCCATGCACTGG GTCCGACAAACTCCAGGGAAGGGCCTGGAGTGGGTCTCAGGTATAA GTTGGAAGAGTAATATCATAGGCTATGCGGACTCTGTGAAGGGCCG ATTCACCATCTCCAGAGACAACGCCAAGAACTCCCTGTATCTGCAA ATGAACAGTCTGAGAGCTGAGGACACGCCCTTGTATTATTGTGCAA GAGATATAACGGGTTCGGGAGTTATGGCTGGTTCGACCCCTGGGG CCAGGGAACCCTGGTCACCGTCTCCTCAGCCAAACGACACCCCCA TCTGTCTATCCACTGGCCCCTGAAATCTGCTAAAACTCAGCCTCCG |
| 15 | 84G09 - full heavy chain sequence | Amino acid sequence of 84G09 heavy chain (mutations from germline are shown in small letters) | EVQLVESGGGLVQPGRSLRLSCAASGFTFDDYAMHWVRQTPGKGLEW VSGISWKSNIIGYADSVKGRFTISRDNAKNSLYLQMNSLRAEDTALYYC ARDITGSGSYGWFDPWGQGTLVTVSSASTKGPSVFPLAPCSRSTSESTA ALGCLVKDYFPEPVTVSWNSGALTSGVHTFPAVLQSSGLYSLSSVVTVP SSSLGTKTYTCNVDHKPSNTKVDKRVESKYGPPCPPCPAPEFEGGPSVF LFPPKPKDTLMISRTPEVTCVVVDVSQEDPEVQFNWYVDGVEVHNAKT KPREEQFNSTYRVVSVLTVLHQDWLNGKEYKCKVSNKGLPSSIEKTISK AKGQPREPQVVTLPPSQEEMTKNQVSLTCLVKGFYPSDIAVEWESNGQ PENNYKTTPPVLDSDGSFFLYSRLTVDKSRWQEGNVFSCSVMHEALHN HYTQKSLSLSLGK |

SEQUENCE LISTING

| SEQ ID NO: | Name | Description | Sequence |
|---|---|---|---|
| 16 | 84G09 – full heavy chain sequence | Nucleic acid sequence of 84G09 heavy chain | GAAGTGCAGCTGGTGGAATCTGGCGGCGGACTGGTGCAGCCTGGCA GATCCCTGAGACTGTCTTGTGCCGCCTCCGGCTTCCACCTTCGACGAC TACGCTATGCACTGGGTGCGACAGACCCCTGGCAAGGGCCTGGAAT GGGTGTCCGGCATTCCTGGAAGTCAACATCATCGGCTACGCCGA CTCCGTGAAGGGCCGGTTCACCATCTCCGGGACAACGCCAAGAAC TCCCTGTACCTGCAGATGAACAGCCTGAGAGCTGAGGACACCGCCC TGTACTACTGCGCCAGAGACATCACCGGCTCCGGCTCCTACGATG GTTCGATCCTTGGGCACGGCCACCCTGTGTTCCTTGGCCGTCCTGCCA GCACCAAGGGCCCCTCTGTTCCCTCTGGGCTGCCTGTGAAGGACTACTT CCCCGAGCCTGTGACCGTGTCCTGGAACTCTGGCGCTGACCAGCG GAGTGCACACCTTCCCTGCTGTGCTGCAGTCTCCAGTCTCCTGGCACCCAGAC CTGTCCTCCGTCGTGACCGTGCCTTCCAGCTCTTGGGCCTGACCAAGTGAC CTACATCTGCAACGTGAACCACAAGCCCTCCAACACCAAGGTGAC AAGAAGTGGAACCCAAGTCCTGCGACAAGACCCACACCTGTCCCC CTTGTCTCCGCCCCGAACTGCTGGGCGGACCTTCCGTGTTCCTGTTCC CCCAAAGCCCAAGGACACCCTGATGATCTCCCGGACCCCTGAAGTGAC GACCTGCGTGGTGGTGGATGTGTCCACGAGGACCCTGAAGTGAAG TTCAATTGGTACGTGGACGGCGTGGAAGTGCACAATGCCAAGACCA AGCCTAGAGAGGAACAGTACTACTCCACCTACCGGGTGGTGTCCGT GCTGACCGTGCTGCACCAGGATTGGCTGAACGGCAAAGAGTACAAG TGCAAGGTGTCCAACAAGGCCCTGCCCGCCCCCATCGAAAAGACCA TCTCCAAGGCCAAGGGCCAGCCCCGGGAACCCCAGGTGTACACACT GCCCCCCTAGCAGGGACGAGCTGACCAAGAACCAGGTGTCCCTGACC TGTCTCGTGAAAGGCTTCTACCCCTCCGATATCGCCGTGAATGGGA GTGGAACGGCAGCCTGAGAACAATACAAGACCACCCCCCCTGTG CTGGACTCCGACGGCTCATTCTTCCTGTACAGCAAGCTGACAGTGGA CAAGTCCGGTGGCAGCAGGGCAACGTGTTCTCCTGCTCCGTGATGC ACGAGGCCCTGCACAACCACTACACCCCAGAAGTCCCTGTCCCTGAG CCCCGGCAAG |
| 17 | 84G09 – CDRH1 (IMGT) | Amino acid sequence of CDRH1 of 84G09 using IMGT | QSISSY |
| 18 | 84G09 – CDRH2 (IMGT) | Amino acid sequence of CDRH2 of 84G09 using IMGT | VAS |
| 19 | 84G09 – CDRH3 (IMGT) | Amino acid sequence of CDRH3 of 84G09 using IMGT | QQSYSNPIT |
| 20 | 84G09 – CDRH1 (Kabat) | Amino acid sequence of CDRH1 of 84G09 using Kabat | RASQSISSYLN |
| 21 | 84G09 – CDRH2 (Kabat) | Amino acid sequence of CDRH2 of 84G09 using Kabat | VASSLQS |
| 22 | 84G09 – CDRH3 (Kabat) | Amino acid sequence of CDRH3 of 84G09 using Kabat | QQSYSNPIT |

| SEQ ID NO | Name | Description | Sequence |
|---|---|---|---|
| 23 | 84G09 – Light chain variable region | Amino acid sequence of V$_L$ of 84G09 | DIQMTQSPSSLSASVGDRVTITCRASQSISSYLNWYQQKPGKAPKPLIYV ASSLQSGVPSSFSGSGSGTDFTLTISSLQPEDFATYYCQQSYSNPITFGQG TRLEIK |
| 24 | 84G09 – Light chain variable region | Nucleic acid sequence of V$_L$ of 84G09 | GACATCCAGATGACCCAGTCTCCATCCTCCCTGTCTGCATCTGTAGG AGACAGAGTCACCATCACTTGCCGGGCAAGTCAGAGCATTAGCAGC TATTTAAATTGGTATCAGCAGAAACCAGGGAAAGCCCCTAAGCCC TGATCTATGTTGCATCCAGTTTGCAAAGTGGGTCCCATCAAGTTC AGTGGCAGTGGATCTGGGACAGATTTCACTCTCACCATCAGCAGTCT GCAACCTGAAGATTTTGCAACTTACTACTGTCAACAGAGTTACAGTA ATCCGATCACCTTCGGCCAAGGGACACGACTGGAGATCAAA |
| 25 | 84G09 – full light chain sequence | Amino acid sequence of 84G09 light chain (mutations from germline are shown in small letters) | DIQMTQSPSSLSASVGDRVTITCRASQSISSYLNWYQQKPGKAPKPLIYV ASSLQSGVPSSFSGSGSGTDFTLTISSLQPEDFATYYCQQSYSNPITFGQG TRLEIKRTVAAPSVFIFPPSDEQLKSGTASVVCLLNNFYPREAKVQWKV DNALQSGNSQESVTEQDSKDSTYSLSSTLTLSKADYEKHKVYACEVTH QGLSSPVTKSFNRGEC |
| 26 | 84G09 – full light chain sequence | Nucleic acid sequence of 84G09 light chain | GACATCCAGATGACCCAGTCTCCATCCTCCCTGTCTGCATCTGTAGG AGACAGAGTCACCATCACTTGCCGGGCAAGTCAGAGCATTAGCAGC TATTTAAATTGGTATCAGCAGAAACCAGGGAAAGCCCCTAAGCCC TGATCTATGTTGCATCCAGTTTGCAAAGTGGGTCCCATCAAGTTC AGTGGCAGTGGATCTGGGACAGATTTCACTCTCACCATCAGCAGTCT GCAACCTGAAGATTTTGCAACTTACTACTGTCAACAGAGTTACAGTA ATCCGATCACCTTCGGCCAAGGGACACGACTGGAGATCAAACGTAC GGTGGCCGCTCCGTCTTCATCTTCCCGCCATCTGATGAGCAGTTGAAATAACAGGTCACTTTGCAACTTCTGTGTGCCTGCTGAATCAACCAACCTTCTAC CCCCGCGAGGCCAAGGTACAGTGGAAGGTGGATAACGCCCTCCAAGT CCGGAACTCCCAGGAATCCGTGACCGAGCAGGACTCCAAGGACACAG CACCTACTACAGCCTCAGCACCCTGACGCTGAGCAAAGCCGACTACG AGAAGCACAAGGTGTACGCCTGCGAAGTGACCCACCAGGGCCTGTC TAGCCCCGTGACCAAGTCTTTCAACCGGGGCGAGTGT |
| 27 | 1D05 – CDRH1 (IMGT) | Amino acid sequence of CDRH1 of 1D05 using IMGT | GFTFDDYA |
| 28 | 1D05 – CDRH2 (IMGT) | Amino acid sequence of CDRH2 of 1D05 using IMGT | ISWIRTGI |
| 29 | 1D05 – CDRH3 (IMGT) | Amino acid sequence of CDRH3 of 1D05 using IMGT | AKDMKGSGTYGGWFDT |
| 30 | 1D05 – CDRH1 (Kabat) | Amino acid sequence of CDRH1 of 1D05 using Kabat | DYAMH |
| 31 | 1D05 – CDRH2 (Kabat) | Amino acid sequence of CDRH2 of 1D05 using Kabat | GISWIRTGIYADSVKG |

| SEQ ID NO: | Name | Description | Sequence |
|---|---|---|---|
| 32 | 1D05 – CDRH3 (Kabat) | Amino acid sequence of CDRH3 of 1D05 using Kabat | DMKGSGTYGGWFDT |
| 33 | 1D05 – Heavy chain variable region | Amino acid sequence of V$_H$ of 1D05 (mutations from germline are shown in small letters) | EVQLVESGGGLVQPGRSLRLSCAASGFTFDDYAMHWVRQVPGKGLEW VSGISWirtGIGYADSVKGRFTIFRDNAKNSLYLQMNSLRAEDTALYYCA KDMKGSGTYGGMFDTWGQGTLVTVSS |
| 34 | 1D05 – Heavy chain variable region | Nucleic acid sequence of V$_H$ of 1D05 | AAGCTTGCCGCCACCATGGAGTTTGGGCTGAGCTGGATTTTCCTTTT GGCTATTTTAAAAGTGTCCAGTGTGAAGTGCAGCTGGTGGAGTCT GGGGGAGGCTTGGTGCAGCCTGGCAGGTCCCTGAGACTCTCCTGTG CAGCCTCTGGATTCACCTTTGATGATTATGCCATGCACTGGGTCCGG CAAGTTCCAGGAAGGCCTGGAACTGGTCTCAGGCATTAGTTGGA TTCGTACTGGCATAGGCTATGCGGACTCTGTGAAGGGCCGATTCACC ATTTCAGAGACAACGCCAAGAATTCCTGTATCTGCAAATGAACA GTCTGAGAGCTGAGGACTATGCGGGTGGTTCGACACCTGGGGCCAG GAAGGGTTCGGGGACTTATGGAGGCTGGTTCGACACCTGGGGCCAG GGAACCCTGGTCACCGTCTCCTCAGCCAAAACAACAGCCCCATCGG TCTATCCACTGGCCCCTGC |
| 35 | 1D05 – full heavy chain sequence | Amino acid sequence of 1D05 heavy chain | EVQLVESGGGLVQPGRSLRLSCAASGFTFDDYAMHWVRQVPGKGLEW VSGISWIRTGIGYADSVKGRFTIFRDNAKNSLYLQMNSLRAEDTALYYC AKDMKGSGTYGGWFDTWGQGTLVTVSSASTKGPSVFPLAPCSRSTSES TAALGCLVKDYFPEPVTVSWNSGALTSGVHTFPAVLQSSGLYSLSSVV TVPSSSLGTKTYTCNVDHKPSNTKVDKRVESKYGPPCPPCPAPEFEGGP SVFLFPPKPKDTLMISRTPEVTCVVVDVSQEDPEVQFNWYVDGVEVHN AKTKPREEQFNSTYRVVSVLTVLHQDWLNGKEYKCKVSNKGLPSSIEK TISKAKGQPREPQVYTLPPSQEEMTKNQVSLTCLVKGFYPSDIAVEMES NGQPENNYKTTPPVLDSDGSFFLYSRLTVDKSRWQEGNVFSCSVMHEA LHNHYTQKSLSLSLGK |
| 36 | 1D05 – full heavy chain sequence | Nucleic acid sequence of 1D05 heavy chain | GAAGTGCAGCTGGTGGAATCTGGCGGCGGACTGGTGCAGCCTGGCA GATCCCTGAGACTGTCTTGTGCCGCCTCCGGCTTCACCTTCGACGAC TACGCTATGCACTGGGTCCGACAGGTGCCAGGCAAGGGCTGAAT GGGTGTCCGGCATCTCTTGGATCCGAACGGCATCGGCTACGCCGA CTCTGTGAAGGGCCGGTTCACCATCTTCCGGGACAACGCCAAGAAC TCCCTGTACCTGCAGATGAACAGCCTGCGGGCCGAGGACACCGCCC TGTACTACTGCGCCAAGGACATGAAGGGCTCGGCACTACGGCGG ATGGTTCGATACTTGGGGCCCTGTTCCTGTCCCCCCTCCAGCAAG CCAGCACCAAGGGCCCCTGTGTTCCTGGGCCTGCCTCTGGAAGGACT ACTTCCCCGAGCCTGTGACCGTGTCCTGGAACTCTGGCGCTCTGACC AGCGGAGTGCACACCTTCCCTGTGCCTGCCAGTCCTCCGGCCTGTA CTCCCTGTCCTCCGTGGCCGGCCTCTGGTCCAGCCTCTCTGGGCACCCAGGT AGACCTACATCTGCAACGTGACCACCAAGCCCTCCAACACCAAGGT GGACAAGAAGTGGACACCACCAAGTGCCACAAGACCACCTGT CCCCCTTGTCCTCCCCCAAGCCCAAGGACACCCTCATGATCTCCGGACCCCC GTTCCCCCAAAGCCCAAGGACACCCTCATGATCTCCCGGACCCCC GAAGTGACCTGCGTGGTGGTGGATGTGCCAGGACCCTGAGG TGAAGTTCAATTGGTACGTGGACGGCGTGGAAGTGCACAACGCCAA |

-continued

SEQUENCE LISTING

| SEQ ID NO:Name | Description | Sequence |
|---|---|---|
| | | GACCAAGCCTAGAGAGGAAACAGTACAACTCCACTACCGGTGGTG<br>TCCGTGCTGACCGTGCTGACCAGGATTGGCTGACAAGAGT<br>ACAAGTGCAAGGTGTCCAACAAGCCCTGCCTGCCCCATCGAAAA<br>GACCATCTCCAAGGCCAAGGGCCAGCCCCGGGAACCCAGTGTAC<br>ACACTGCCCCCTAGAGGACGAGCTGACCAAGAACCAGTGTCCC<br>TGACCTGTCTGTGAAAGGCTTCTACCCCTCCGATATCGCCGTGGA<br>TGGGAGTGCAACGCCAGCCTGAGAACAACTACAAGACCACCCCCC<br>CTGTGCTGGACTCCGACGGCTCATTCTTCCTGTACAGCAAGCTGACA<br>GTGGACAAGTCCCGGTGGCAGCAGGGCAACGTGTTCTCCTGCTCCG<br>TGATGCACGAGGCCCTGCACAACCACTACACCCAGAAGTCCCTGT<br>CCTGAGCCCCGGCAAG |
| 37 | 1D05 - CDRH1<br>(IMGT) | Amino acid sequence of CDRL1<br>of 1D05 using IMGT | QSISSY |
| 38 | 1D05 - CDRH2<br>(IMGT) | Amino acid sequence of CDRL2<br>of 1D05 using IMGT | VAS |
| 39 | 1D05 - CDRH3<br>(IMGT) | Amino acid sequence of CDRL3<br>of 1D05 using IMGT | QQSYSTPIT |
| 40 | 1D05 - CDRH1<br>(Kabat) | Amino acid sequence of CDRL1<br>of 1D05 using Kabat | RASQSISSYLN |
| 41 | 1D05 - CDRH2<br>(Kabat) | Amino acid sequence of CDRL2<br>of 1D05 using Kabat | VASSLQS |
| 42 | 1D05 - CDRH3<br>(Kabat) | Amino acid sequence of CDRL3<br>of 1D05 using Kabat | QQSYSTPIT |
| 43 | 1D05 - Light chain variable region | Amino acid sequence of V_L of 1D05 (mutations from germline are shown in small letters) | DIQMTQSPSSLSASVGDRVTITCRASQSISSYLNWYQQKPGKAPKLLIYv<br>ASSLQSGVPSRFSGSGSGTDFTLTISSLQPEDFATYYCQQSYSTPITFGQG<br>TRLEIK |
| 44 | 1D05 - Light chain variable region | Nucleic acid sequence of V_L of 1D05 | AAAGCTTGCCGCCACCATGAGCTCCCTGCTCAGCTTCTGGGGCTCC<br>TGCTACTCTGGCCTCCGAGGTGCAGATGACTCCAGATGACCCA<br>GTCTCCATCCTCCCTGTCTGCATCTGTAGGAGACAGAGTCACCATCA<br>CTTGCCGGGCAAGTCAGAGCATTAGCAGCTATTTAAATTGGTATCAG<br>CAGAAACCAGGGAAGGCCCCTAAACTCCTGATCTATGTTGCATCCA<br>GTTTGCAAAGTGGGGTCCCATCAAGGTTCAGTGGCAGTGGATCTGG<br>GACAGATTTCACTCTCACTATCAGCAGTCTGCAACCTGAAGATTTTG<br>CAACTTACTACTGTCAACAGAGTTACAGTACCCCGATCACCTTCGGC<br>CAAGGGACACGTCTGGAGATCAAACGTACGATGCTGCACCAACT |
| 45 | 1D05 - full light chain sequence | Amino acid sequence of 1D05 light chain | DIQMTQSPSSLSASVGDRVTITCRASQSISSYLNWYQQKPGKAPKLLIYV<br>ASSLQSGVPSRFSGSGSGTDFTLTISSLQPEDFATYYCQQSYSTPITFGQG<br>TRLEIKRTVAAPSVFIFPPSDEQLKSGTASVVCLLNNFYPREAKVQMKV<br>DNALQSGNSQESVTEQDSKDSTYSLSSTLTLSKADYEKHKVYACEVTH<br>QGLSSPVTKSFNRGEC |

-continued

SEQUENCE LISTING

| SEQ ID NO: | Name | Description | Sequence |
|---|---|---|---|
| 46 | 1D05 — full light chain sequence | Nucleic acid sequence of 1D05 light chain | GACATCCAGATGACCCAGTCCCCCTCCAGCCTGTCTGCTTCCGTGGG<br>CGACAGAGTGACCATCACCTGTCGGGCCTCCCAGTCCATCTCCTCCT<br>ACCTGAACTGGTATCAGCAGAAGCCCGGCAAGGCCCCCAAGCTGCT<br>GATCTACGTGGCCAGCTCTCTGCAGTCCGGCGTGCCCTCTAGATTCT<br>CCGGCTCTGGCTCTGGCACCGACTTTACCCTGACCATCAGCTCCCTG<br>CAGCCCGAGGACTTCGCCACCTACTACTGCCAGCAGTCCTACTCCAC<br>CCCTATCACCTTCGGCCAGGGCACCCGGCTGGAAATCAAACGTACG<br>GTGGCCGCTCCCTCCGTGTTCATCTTCCCACCTTCCGACGAGCAGCT<br>GAAGTCCGGCACCGCTTCTGTCGTGTGCCTGCTGAACAACTTCTACC<br>CCCGCGAGGCCAAGGTGCAGTGGAAGGTGGACAACGCCCTGCAGTC<br>CGGCAACTCCCAGGAATCCGTGACCGAGCAGGACTCCAAGGACAGC<br>ACCTACTCCCTGTCCTCCACCCTGACCCTGTCCAAGGCCGACTACGA<br>GAAGCACAAGGTGTACGCCTGCGAAGTGACCCACCAGGGCCTGTCT<br>AGCCCCGTGACCAAGTCTTTCAACCGGGGCGAGTGT |
| 47 | Mutated 1D05 — HC mutant 1 | Amino acid sequence of 1D05 heavy chain with V to A back-mutation in framework region to germline highlighted with IgG1 disabled (LAGA) constant region | EVQLVESGGGLVQPGRSLRLSCAASGFTFDDYAMHWVRQAPGKGLEW<br>VSGISWIRTGIGYADSVKGRFTIFRDNAKNSLYLQMNSLRAEDTALYYC<br>AKDMKGSGTYGGWFDTWGQGTLVTVSSASTKGPSVFPLAPCSRSTSES<br>TAALGCLVKDYFPEPVTVSWNSGALTSGVHTFPAVLQSSGLYSLSSVV<br>TVPSSSLGTKTYTCNVDHKPSNTKVDKRVESKYGPPCPPCPAPELAGAP<br>SVFLFPPKPKDTLMISRTPEVTCVVVDVSQEDPEVQFNWYVDGVEVHN<br>AKTKPREEQFNSTYRVVSVLTVLHQDWLNGKEYKCKVSNKGLPSSIEK<br>TISKAKGQPREPQVYTLPPSQEEMTKNQVSLTCLVKGFYPSDIAVEWES<br>NGQPENNYKTTPPVLDSDGSFFLYSRLTVDKSRWQEGNVFSCSVMHEA<br>LHNHYTQKSLSLSLGK |
| 48 | Mutated 1D05 — HC mutant 2 | Amino acid sequence of 1D05 heavy chain with F to S back-mutation in framework region to germline highlighted with IgG1 disabled (LAGA) constant region | EVQLVESGGGLVQPGRSLRLSCAASGFTFDDYAMHWVRQVPGKGLEW<br>VSGISWIRTGIGYADSVKGRFTISRDNAKNSLYLQMNSLRAEDTALYYC<br>AKDMKGSGTYGGWFDTWGQGTLVTVSSASTKGPSVFPLAPCSRSTSES<br>TAALGCLVKDYFPEPVTVSWNSGALTSGVHTFPAVLQSSGLYSLSSVV<br>TVPSSSLGTKTYTCNVDHKPSNTKVDKRVESKYGPPCPPCPAPELAGAP<br>SVFLFPPKPKDTLMISRTPEVTCVVVDVSQEDPEVQFNWYVDGVEVHN<br>AKTKPREEQFNSTYRVVSVLTVLHQDWLNGKEYKCKVSNKGLPSSIEK<br>TISKAKGQPREPQVYTLPPSQEEMTKNQVSLTCLVKGFYPSDIAVEWES<br>NGQPENNYKTTPPVLDSDGSFFLYSRLTVDKSRWQEGNVFSCSVMHEA<br>LHNHYTQKSLSLSLGK |
| 49 | Mutated 1D05 — HC mutant 3 | Amino acid sequence of 1D05 heavy chain with ELLG to -PVA back-mutation in constant region to germline highlighted | EVQLVESGGGLVQPGRSLRLSCAASGFTFDDYAMHWVRQVPGKGLEW<br>VSGISWIRTGIGYADSVKGRFTIFRDNAKNSLYLQMNSLRAEDTALYYC<br>AKDMKGSGTYGGWFDTWGQGTLVTVSSASTKGPSVFPLAPCSRSTSES<br>TAALGCLVKDYFPEPVTVSWNSGALTSGVHTFPAVLQSSGLYSLSSVV<br>TVPSSSLGTKTYTCNVDHKPSNTKVDKRVESKYGPPCPPCPAP-<br>PVAGPSVFLFPPKPKDTLMISRTPEVTCVVVDVSQEDPEVQFNWYVDG<br>VEVHNAKTKPREEQFNSTYRVVSVLTVLHQDWLNGKEYKCKVSNKGL<br>PSSIEKTISKAKGQPREPQVYTLPPSQEEMTKNQVSLTCLVKGFYPSDIA<br>VEWESNGQPENNYKTTPPVLDSDGSFFLYSRLTVDKSRWQEGNVFSCS<br>VMHEALHNHYTQKSLSLSLGK |

SEQUENCE LISTING -continued

| SEQ ID NO: | Name | Description | Sequence |
|---|---|---|---|
| 50 | Mutated 1D05 — LC mutant 1 | Amino acid sequence of 1D05 kappa light chain with V to A back-mutation in CDRL2 to germline highlighted | DIQMTQSPSSLSASVGDRVTITCRASQSISSYLNWYQQKPGKAPKLLIYA ASSLQSGVPSRFSGSGSGTDFTLTISSLQPEDFATYYCQQSYSTPITFGQG TRLEIKRTVAAPSVFIFPPSDEQLKSGTASVVCLLNNFYPREAKVQWKV DNALQSGNSQESVTEQDSKDSTYSLSSTLTLSKADYEKHKVYACEVTH QGLSSPVTKSFNRGEC |
| 51 | Mutated 1D05 — LC mutant 2 | Amino acid sequence of 1D05 kappa light chain with L to F back-mutation in framework to germline highlighted | DIQMTQSPSSLSASVGDRVTITCRASQSISSYLNWYQQKPGKAPKLFIYV ASSLQSGVPSRFSGSGSGTDFTLTISLQPEDFATYYCQQSYSTPITFGQG TRLEIKRTVAAPSVFIFPPSDEQLKSGTASVVCLLNNFYPREAKVQMKV DNALQSGNSQESVTEQDSKDSTYSLSSTLTLSKADYEKHKVYACEVTH QGLSSPVTKSFNRGEC |
| 52 | 411B08 — CDRH1 (IMGT) | Amino acid sequence of CDRH1 of 411B08 using IMGT | GFTFSSYW |
| 53 | 411B08 — CDRH2 (IMGT) | Amino acid sequence of CDRH2 of 411B08 using IMGT | IKEDGSEK |
| 54 | 411B08 — CDRH3 (IMGT) | Amino acid sequence of CDRH3 of 411B08 using IMGT | ARNRLYSDFLDN |
| 55 | 411B08 — CDRH1 (Kabat) | Amino acid sequence of CDRH1 of 411B08 using Kabat | SYWMS |
| 56 | 411B08 — CDRH2 (Kabat) | Amino acid sequence of CDRH2 of 411B08 using Kabat | NIKEDGSEKYYVDSVKG |
| 57 | 411B08 — CDRH3 (Kabat) | Amino acid sequence of CDRH3 of 411B08 using Kabat | NRLYSDFLDN |
| 58 | 411B08 — Heavy chain variable region | Amino acid sequence of $V_H$ of 411B08 | EVQLVESGGGLVQPGGSLRLSCAASGFTFSSYWMSWVRQAPGKGLEW VANIKEDGSEKYYVDSVKGRFTISRDNAKNSLYLQMNSLRAEDTSVYY |
| 59 | 411B08 — Heavy chain variable region | Nucleic acid sequence of $V_H$ of 411B08 | CARNRLYSDFLDNWGQGTLVTVSS GAGGTGCAGCTGGTGGAGTCTGGGGGAGGCTTGGTCCAGCCTGGG GTCCCTGAGACTCTCCTGTGCAGCCTCTGGATTCACGTTTAGTAGC TATTGGATGAGTTGGGTCCGCCAGGCTCCAGGGAAGGGTCGGAGT GGGTGGCCAACATCAAAGAAGATGGAAGTGAGAAATACTATGTCGA CTCTGTGAAGGGCCGATTCACCATCTCCAGAGACAACGCCAAGAAC TCACTGTATCTGCAAATGAACAGCCTGAGAGCCGAGGACACGCTG TGTATTACTGTGCGAGAAATCGACTCTACAGTGACTTCCTTGACAAC TGGGGCCAGGGAACCCTGGTCACCGTCTCCTCAG |
| 60 | | Amino acid sequence of 411B08 heavy chain | EVQLVESGGGLVQPGGSLRLSCAASGFTFSSYWMSWVRQAPGKGLEW VANIKEDGSEKYYVDSVKGRFTISRDNAKNSLYLQMNSLRAEDTSVYY CARNRLYSDFLDNWGQGTLVTVSSASTKGPSVFPLAPSSKSTSGGTAA LGCLVKDYFPEPVTVSWNSGALTSGVHTFPAVLQSSGLYSLSSVVTVPS SSLGTQTYICNVNHKPSNTKVDKKVEPKSCDKTHTCPPCPAPELLGGPS VFLFPPKPKDTLMISRTPEVTCVVVDVSHEDPEVKFNWYVDGVEVHNA |

SEQUENCE LISTING

| SEQ ID NO: | Name | Description | Sequence |
|---|---|---|---|
| 61 | | Nucleic acid sequence of 411B08 heavy chain | KTKPREEQYNSTYRVVSVLTVLHQDWLNGKEYKCKVSNKALPAPIEKT ISKAKGQPREPQVYTLPPSRDELTKNQVSLTCLVKGFYPSDIAVEWESN GQPENNYKTTPPVLDSDGSFFLYSKLTVDKSRWQQGNVFSCSVMHEAL HNHYTQKSLSLSPGK<br><br>GAGGTGCAGCTGGTGGAGTCTGGGGGAGGCTTGGTCCAGCCTGGGG GGTCCCTGAGACTCTCCTGTGCAGCCTCTGGATTCACGTTTAGTAGC TATTGGATGAGTTGGGTCCGCCAGGCTCCAGGGAAGGGGCTGGAGT GGGTGGCCAACATCAAAGAAGATGAAAGTGAGAAATACTATGTCGA CTCTGTGAAGGGCCGATTCACCATCTCCAGAGACAACGCCAAGAAC TCACTGTATCTGCAAATGAACAGCCTGAGAGCCGAGGACACGTCTG TGTATTACTGTGCGAGAAATCAGTCGACTTCCTTGACAAC TGGGGCCAGGGAACCCTGGTCACCGTCTCCTCAGCCAGCACCAAGG GCCCCTCTGTGTTCCCCTGGCCCCTGTGCAGCAAGTCCACCTCTGGC GGAACAGCCGCTCTGGGCTGCCTCTGAACTCTGAAGGACTACTTCCCCGAGC CTGTGACCGTGTCCTGGAACTCTGGCGCTCTGACCAGCGGAGTGCAC ACCTTCCCTGCTGTGCTCCAGTCTCCTCCGGCCTGTACTCCCTGTCCTCC GTCGTGACCGTGCCCTTCCAGCTCTCGGCACCCAGACCAAGGTGACAAGGTG CAACGTGAACACACAAGCCCTCCAACACCAAGGTGGACAAGAAGTG GAACCCAAGTCTGCGACAAGACCCACATCTGTCCCCCTTGTCTCTGC CCCTGAACTGCTGGGCGGACCTTCCGTGTTCCTGTTCCCCAAAGC CAAGGACACACCCTGATGATCTCCACGAGGACCCTGAAGTGAAGTTCAATTGG TACGTGGACGGCGTGAAGTGCACAAGCCAAGACCTAGAG AGGAACAGTACAACTCCACCTACCGGGTGGTGTCCGTGCTGACCGT GCTGCACCAGGATTGCTGAACGGCAAGAGTACAAGTGCAAGGTG TCCAACAAGGCCCTGCCTGCCCCCATCGAAAAGACCATCTCCAAGG CCAAGGGCCAGCCCCGGGAACCCAGGTGTACACACTGCCCCCTAG CAGGGACGAGCTGACCAAGAACCAGGTGTCCTGACCTGTCTGTG AAAGGCTTCTACCCCTCCGATATCGCCGTGGAATGGGAGTCCAACG GCCAGCCTGAGAACAACTACAAGACCACCCCCCCTGCTGGACTC CGACGGCTCATTCTTCCTGTACAGCAAGCTGACAGTGGACAAGTCCC GGTGGCAGCAGGGCAACGTGTTCTCCTGCTCCGTGATGCACGAGC CCTGCACAACCACTACACCCAGAAGTCCCTGTCCCTGAGCCCCGGC AAG |
| 62 | 411B08 – CDRL1 (IMGT) | Amino acid sequence of CDRL1 of 411B08 using IMGT | QGVSSSW |
| 63 | 411B08 – CDRL2 (IMGT) | Amino acid sequence of CDRL2 of 411B08 using IMGT | GAS |
| 64 | 411B08 – CDRL3 (IMGT) | Amino acid sequence of CDRL3 of 411B08 using IMGT | QQANSIPFT |
| 65 | 411B08 – CDRL1 (Kabat) | Amino acid sequence of CDRL1 of 411B08 using Kabat | RASQGVSSWLA |

| SEQ ID NO: | Name | Description | Sequence |
|---|---|---|---|
| 66 | 411B08 – CDRL2 (Kabat) | Amino acid sequence of CDRL2 of 411B08 using Kabat | GASSLQS |
| 67 | 411B08 – CDRL3 (Kabat) | Amino acid sequence of CDRL3 of 411B08 using Kabat | QQANSIPFT |
| 68 | 411B08 – Light chain variable region | Amino acid sequence of V_L of 411B08 | DIQMTQSPSSVSASVGDRVTITCRASQGVSSWLAWYQQKSGKAPKLLI YGASSLQSGVPSRFSGSGSGTEFILTISSLQPEDFATYYCQQANSIPFTFG PGTKVDIK |
| 69 | 411B08 – Light chain variable region | Nucleic acid sequence of V_L of 411B08 | GACATCCAGATGACCCAGTCTCCATCTTCCGTGTCTGCATCTGTCGG AGACAGAGTCACCATCACTTGTCGGGCGAGTCAGGGTGTTAGCAGC TGGTTAGCCTGGTATCAGCAGAAATCAGGGAAAGCCCCTAAGCTCC TGATCTATGGTGCATCCAGTTTGCAAAGTGGGGTCCCATCAAGATTC AGCGGCAGTGGATCTGGGACAGAGATTCATTCTCACCATCAGCAGCC TGCAGCCTGAAGATTTTGCGGCCTTACTATTGTCAACAGGCTAACAGT ATCCCATTCACTTTCGGCCCTGGGACCAAAGTGGATATCAAAC |
| 70 | 411B08 – full light chain sequence | Amino acid sequence of 411B08 light chain | DIQMTQSPSSVSASVGDRVTITCRASQGVSSWLAWYQQKSGKAPKLLI YGASSLQSGVPSRFSGSGSGTEFILTISSLQPEDFATYYCQQANSIPFTFG PGTKVDIKRTVAAPSVFIFPPSDEQLKSGTASVVCLLNNFYPREAKVQW KVDNALQSGNSQESVTEQDSKDSTYSLSSTLTLSKADYEKHKVYACEV THQGLSSPVTKSFNRGEC |
| 71 | 411B08 – full light chain sequence | Nucleic acid sequence of 411B08 light chain | GACATCCAGATGACCCAGTCTCCATCTTCCGTGTCTGCATCTGTCGG AGACAGAGTCACCATCACTTGTCGGGCGAGTCAGGGTGTTAGCAGC TGGTTAGCCTGGTATCAGCAGAAATCAGGGAAAGCCCCTAAGCTCC TGATCTATGGTGCATCCAGTTTGCAAAGTGGGGTCCCATCAAGATTC AGCGGCAGTGGATCTGGGACAGAGTTCATTCTCACCATCAGCAGCC TGCAGCCTGAAGATTTTGCAACTTACTATTGTCAACAGGCTAACAGT ATCCCATTCACTTTCGGCCCTGGGACCAAAGTGGATATCAAACGTAC GGTGGCCGCTCCCTCCGTCTTCATCTTCCCACCTTCCGACGAGCAGC TGAAGTCCGGCACCGCTTCTGTGTGCCTGCTGAACAACTTCTAC CCCCGCGAGGCCAAGGTGCAGTGGAAGGTGACAACGCCCTGCAGT CCGGCAACTCCCAGGAATCCGTCACCGAGCAGGACTCCAAGGACAG CACCTACTCCCTGTCCTCCACCCTGACCCTGTCCAAGGCCGACTACG AGAAGCACAAGGTGTACGCCTGCGAAGTGACCCACCAGGGCCTGTC TAGCCCCGTGACCAAGTCTTTCAACCGGGGCGAGTGT |
| 72 | 411C04 – CDRH1 (IMGT) | Amino acid sequence of CDRH1 of 411C04 using IMGT | GFTFSSYW |
| 73 | 411C04 – CDRH2 (IMGT) | Amino acid sequence of CDRH2 of 411C04 using IMGT | IKEDGSEK |
| 74 | 411C04 – CDRH3 (IMGT) | Amino acid sequence of CDRH3 of 411C04 using IMGT | ARVRLYSDFLDY |

-continued

SEQUENCE LISTING

| SEQ ID NO: | Name | Description | Sequence |
|---|---|---|---|
| 75 | 411C04 – CDRH1 (Kabat) | Amino acid sequence of CDRH1 of 411C04 using Kabat | SYWMS |
| 76 | 411C04 – CDRH2 (Kabat) | Amino acid sequence of CDRH2 of 411C04 using Kabat | NIKEDGSEKYYVDSLKG |
| 77 | 411C04 – CDRH3 (Kabat) | Amino acid sequence of CDRH3 of 411C04 using Kabat | VRLYSDFLDY |
| 78 | 411C04 – Heavy chain variable region | Amino acid sequence of V$_H$ of 411C04 | EVQLVDSGGGLVQPGGSLRLSCAASGFTFSSYWMSWVRQAPGKGLEW VANIKEDGSEKYYVDSLKGRFTISRDNAKNSLYLQMNSLRAEDTSVYY CARVRLYSDFLDYWGQGTLVTVSS |
| 79 | 411C04 – Heavy chain variable region | Nucleic acid sequence of V$_H$ of 411C04 | GAGGTGCAGCTGGTGGACTCTGGGGGAGGCTTGGTCCAGCCTGGGG GGTCCCTGAGACTCTCCTGTGCAGCCTCTGGATTCACGTTTAGTAGC TATTGGATGAGTTGGGTCCGCCAGGCTCCAGGAAAGGGGCTGGAGT GGGTGGCCAACATAAAAGAAGATGGAAGTGAGAAATACTATGTAG ACTCTTTGAAGGGCCGATTCACCATCTCCAGAGACAACGCAAGAA CTCACTGTATCTGCAAATGAACAGCCTGAGAGCCGAGGACACGTCT GTGTATTACTGTGCGAGAGTTCGACTCTACAGTGACTTCCTTGACTA CTGGGGCCAGGGAACCCTGGTCACCGTCTCCTCAG |
| 80 | 411C04 – full heavy chain sequence | Amino acid sequence of 411C04 heavy chain | EVQLVDSGGGLVQPGGSLRLSCAASGFTFSSYWMSWVRQAPGKGLEW VANIKEDGSEKYYVDSLKGRFTISRDNAKNSLYLQMNSLRAEDTSVYY CARVRLYSDFLDYWGQGTLVTVSSASTKGPSVFPLAPSSKSTSGGTAA LGCLVKDYFPEPVTVSWNSGALTSGVHTFPAVLQSSGLYSLSSVVTVPS SSLGTQTYICNVNHKPSNTKVDKKVEPKSCDKTHTCPPCPAPELLGGPS VFLFPPKPKDTLMISRTPEVTCVVVDVSHEDPEVKFNWYVDGVEVHNA KTKPREQYNSTYRVVSVLTVLHQDWLNGKEYKCKVSNKALPAPIEKT ISKAKGQPREPQVYTLPPSRDELTKNQVSLTCLVKGFYPSDIAVEWESN GQPENNYKTTPPVLDSDGSFFLYSKLTVDKSRWQQGNVFSCSVMHEAL HNHYTQKSLSLSPGK |
| 81 | 411C04 – full heavy chain sequence | Nucleic acid sequence of 411C04 heavy chain | GAGGTGCAGCTGGTGGACTCTGGGGGAGGCTTGGTCCAGCCTGGGG GGTCCCTGAGACTCTCCTGTGCAGCCTCTGGATTCACGTTTAGTAGC TATTGGATGAGTTGGGTCCGCCAGGCTCCAGGAAAGGGGCTGGAGT GGGTGGCCAACATAAAAGAAGATGGAAGTGAGAAATACTATGTAG ACTCTTTGAAGGGCCGATTCACCATCTCCAGAGACAACGCAAGAA CTCACTGTATCTGCAAATGAACAGCCTGAGAGCCGAGGACACGTCT GTGTATTACTGTGCGAGAGTTCGACTCTACAGTGACTTCCTTGACTA CTGGGGCCAGGGAACCCTGGTCACCGTCTCCTCAGCCTCCACCAAG GGCCCCTCCGTCTTCCCCCTGGCGCCCTGCTCCAAGAGCACCTCTGG CGGAACAGCCGCTCTGGGCTGCCTGGTCAAGGACTACTTCCCCGAG CCTGTGACCGTGTCCTGGAACTCTGGCGCCCTGACCAGCGGAGTGCA CACCTTCCCTGCTGTGCTGCAGTCCTCCGGCCTGTACTCCCTGTCCTC CGTCGTGACCGTGCCTTCCAGCTCTCTGGGCACCCAGACCTACATCT GCAACGTGAACCACAAGCCCTCCAACACCAAGGTGACAAGAAGGT GAACCCAAGTCCTGCGACAAGACCCACACCTGTCCCCCTTGTCCTG CCCCTGAACTGCTGGGCGGACCTTCCGTGTTCCTGTTCCCCCCAAAG |

-continued

SEQUENCE LISTING

| SEQ ID NO:Name | Description | Sequence |
|---|---|---|
| | | CCCAAGGACACCCTGATGATCTCCCGGACCCCCGAAGTGACCTGCG |
| | | TGGTGGTGGATGTGTCCCACGAGGACCCTGAAGTGAAGTTCAATTG |
| | | GTACGTGGACGGCGTGGAAGTGCACAACGCCAAGACCAAGCCTAGA |
| | | GAGGAACAGTACAACTCCACTTACCGGGTGGTGTCCGTGCTGACCG |
| | | TGCTGCACCAGGATTGGCTGAACGGCAAAGAGTACAAGTGCAAGGT |
| | | GTCCAACAAGGCCCTGCCTGCCCCCATCGAAAAGACCATCTCCAAG |
| | | GCCAAGGGCCAGCCCCGGGAACCCCAGGTGTACACACTGCCCCCTA |
| | | GCAGGGACGAGCTGACCAAGAACCAGGTGTCCCTGACCTGTCTGGT |
| | | GAAAGGCTTCTACCCCTCCGATATCGCCGTGGAATGGGAGTCCAAC |
| | | GGCCAGCCTGAGAACAACTACAAGACCACCCCCCCTGTGCTGGACT |
| | | CCGACGGCTCATTCTTCCTGTACAGCAAGCTGACAGTGGACAAGTCC |
| | | CGGTGGCAGCAGGGCAACGTGTTCTCCTGCTCCGTGATGCACGAGG |
| | | CCCTGCACAACCACTACACCCAGAAGTCCCTGTCCCTGAGCCCCGG |
| | | CAAG |
| 82 | Amino acid sequence of CDRL1 of 411C04 using IMGT | QGVSSW |
| 83 | Amino acid sequence of CDRL2 of 411C04 using IMGT | GAS |
| 84 | Amino acid sequence of CDRL3 of 411C04 using IMGT | QQANSIPFT |
| 85 | Amino acid sequence of CDRL1 of 411C04 using Kabat | RASQGVSSWLA |
| 86 | Amino acid sequence of CDRL2 of 411C04 using Kabat | GASSLQS |
| 87 | Amino acid sequence of CDRL3 of 411C04 using Kabat | QQANSIPFT |
| 88 | Amino acid sequence of V$_L$ of 411C04 | DIQMTQSPSSVSASVGDRVTITCRASQGVSSWLAWYQQKSGKAPKLLI YGASSLQSGVPSRFSGSGSGTEFILSISSLQPEDFATYYCQQANSIPFTFG PGTKVDIK |
| 89 | Nucleic acid sequence of V$_L$ of 411C04 | GACATCCAGATGACCCAGTCTCCATCTTCCGTGTCTGCATCTGTCGG AGACAGAGTCACCATCACTTGTCGGGCGAGTCAGGGTGTTAGCAGT TGGTTAGCCTGGTATCAGCAGAAATCAGGGAAAGCCCCTAAGCTCC TGATCTATGGTGCCTCCAGTTTGCAAAGTGGGGTCCCATCAAGATTC AGCGGCAGTGGATCTGGGACAGAGTTCATTCTCAGCATCAGCAGCC TGCAGCCTGAAGATTTTGCAACTTACTATTGTCAACAGGCTAACAGT ATCCCATTCACTTTCGGCCCTGGGACCAAAGTGGATATCAAAC |
| 90 | Amino acid sequence of 411C04 full light chain sequence | DIQMTQSPSSVSASVGDRVTITCRASQGVSSWLAWYQQKSGKAPKLLI YGASSLQSGVPSRFSGSGSGTEFILSISSLQPEDFATYYCQQANSIPFTFG PGTKVDIKRTVAAPSVFIFPPSDEQLKSGTASVVCLLNNFYPREAKVQW |

SEQUENCE LISTING

| SEQ ID NO: | Name | Description | Sequence |
|---|---|---|---|
| 91 | 411C04 – full light chain sequence | Nucleic acid sequence of 411C04 light chain | KVDNALQSGNSQESVTEQDSKDSTYSLSSTLTLSKADYEKHKVYACEV<br>THQGLSSPVTKSFNRGEC<br>GACATCCAGATGACCCAGTCTCCATCTTCCGTGTCTGCATCTGTCGG<br>AGACAGAGTCACCATCACTTGTCGGGCGAGTCAGGGTGTTAGCAGT<br>TGGTTAGCCTGGTATCAGCAGAAATCAGGGAAAGCCCCTAAGCTCC<br>TGATCTATGGTGCCTCCAGTTTGCAAAGTGGGGTCCCATCAAGATTC<br>AGCGGCAGTGGATCTGGGACAGAGTTCATTCTCAGCATCAGCAGCC<br>TGCAGCCTGAAGATTTTGCAACTTACTATTGTCAACAGGCTAACAGT<br>ATCCATTCACTTTCGGCCCTGGGACCAAAGTGGATATCAAACGTAC<br>GGTGGCCGCTCCCTCCGTGTTCATCTTCCCGCCATCTGATGAGCAGC<br>TGAAGTCCGGCACCGCTTCTGTCGTGTGCCTGCTGAACAACTTCTAC<br>CCCCGCGAGGCCAAGGTGCAGTGGAAGGTGGACAACGCCCTGCAGT<br>CCGGCAACTCCCAGGAATCCGTGACCGAGCAGGACTCCAAGGACAG<br>CACCTACTCCCTGTCCTCCACCCTGACCCTGTCCAAGGCCGACTACG<br>AGAAGCACAAGGTGTACGCCTGCGAAGTGACCACCACGGCCTGTC<br>TAGCCCCGTGACCAAGTCTTTCAACCGGGGCGAGTGT |
| 92 | 411D07 – CDRH1 (IMGT) | Amino acid sequence of CDRH1 of 411D07 using IMGT | GGSIISSDW |
| 93 | 411D07 – CDRH2 (IMGT) | Amino acid sequence of CDRH2 of 411D07 using IMGT | IFHSGRT |
| 94 | 411D07 – CDRH3 (IMGT) | Amino acid sequence of CDRH3 of 411D07 using IMGT | ARDGSGSY |
| 95 | 411D07 – CDRH1 (Kabat) | Amino acid sequence of CDRH1 of 411D07 using Kabat | SSDWWN |
| 96 | 411D07 – CDRH2 (Kabat) | Amino acid sequence of CDRH2 of 411D07 using Kabat | EIFHSGRTNYNPSLKS |
| 97 | 411D07 – CDRH3 (Kabat) | Amino acid sequence of CDRH3 of 411D07 using Kabat | DGSGSY |
| 98 | 411D07 – Heavy chain variable region | Amino acid sequence of V_H of 411D07 | QVQLQESGPGLVKPSGTLSLTCIVSGGSIISSDWWNWVRQPPKGLEWI<br>GEIFHSGRTNYNPSLKSRVTISIDKSKNQFSLRLSSVTAADTAVYYCARD<br>GSGSYWGQGTLVTVSS |
| 99 | 411D07 – Heavy chain variable region | Nucleic acid sequence of V_H of 411D07 | CAGGTGCAGCTGCAGGAGTCGGGCCCAGGACTGGTGAAGCCTTCGG<br>GGACCCTGTCCCTCACCTGCATTGTCTCTGGTGGCTCCATCATCAGT<br>AGTGACTGGTGGAATTGGGTCCGCCAGCCCCCAGGGAAGGGGCTGG<br>AGTGGATTGGAGAAATCTTTCATAGTGGGAGGACCAACTACAACCC<br>GTCCCTCAAGAGTCGAGTCACCATATCAATAGACAAGTCCAAGAAT<br>CAGTTCTCCCTGAGCTGAGCTCTGTGACCGCCGCGGACACGGCCGT<br>GTATTACTGTGCGAGAGATGTTCGGGAGATGTTACTGGGGCCAGGGA<br>ACCCTGGTCACCGTCTCCTCAG |

| SEQ ID NO: | Name | Description | Sequence |
|---|---|---|---|
| 100 | 411D07 – full heavy chain sequence | Amino acid sequence of 411D07 heavy chain | QVQLQESGPGLVKPSCTLSLTCIVSGGSIISSDWNWVRQPPGKGLEWI GEIFHSGRTNYNPSLKSRVTISIDKSKNQFSLRLSSVTAADTAVYYCARD GSGSTWGQGTLVTVSSASTKGPSVFPLAPSSKSTSGTAALGCLVKDY FPEPVTVSWNSGALTSGVHTFPAVLQSSGLYSLSSVVTVPSSSLGTQTYI CNVNHKPSNTKVDKKVEPKSCDKHTCPPCPAPELLGGPSVFLFPPKPK DTLMISRTPEVTCVVVDVSHEDPEVKFNWYVDGVEVHNAKTKPREEQ YNSTYRVVSVLTVLHQDWLNGKEYKCKVSNKALPAPIEKTISKAKGQP REPQVYTLPPSRDELTKNQVSLTCLVKGFYPSDIAVEWESNGQPENNY KTTPPVLDSDGSFFLYSKLTVDKSRWQQGNVFSCSVMHEALHNHYTQ KSLSLSPGK |
| 101 | 411D07 – full heavy chain sequence | Nucleic acid sequence of 411D07 heavy chain | CAGGTGCAGCTGCAGGAGTCGGGCCCAGGACTGGTGAAGCCTTCGG GGACCCTGTCCTCCTCACCTGCATTGTCTCTGGTGGCTCCATCATCAGT AGTGACTGGTGGAATTGGGTCCGCCAGCCCCCAGGGAAGGGGCTGG AGTGGATTGGAGAAATCTTTCATAGTGGGAGGACCAACTACAACC GTCCCTCAAGAGTCGAGTCACCATATCAATAGACAAGTCCAAGAAT CAGTTCTCCCTGAGGCTGAGCTCTGTGACCGCCGCGGACACGGCCGT GTATTACTGTGCGAGAGATGGTTCGGGAGCTACTTGGGGCCAGGGA ACCCTGGTCACCGTCTCCTCAGCCAGCACCAAGGGCCCCTCTGTGTT CCCTCTGGCCCCCTTCCAGCAAGTCCACCTCTGGCGAACAGCCGCTC TGGGCTGCCCTGTCCTGAAGGACTACTTCCCCGAGCCTGTGACCGTGTCC TGGAACTCTGGCGCTCTGACCAGCGGAGTGCACACCTTCCCTGCTGT GCTGCAGTCTCTGGCCTGTACTCCTCCTGTCCTCGTCGTGACCGTGC CTTCCAGCTCTCTGGGCACCCAGACCTACATCTGCAACGTGAACCAC AAGCCCTCCAACACCAAGGTGGACAAGAAGGTGGAACCCAAGTCCT GCGACAAGACCCACACCTGTCCCCCTTGTCCTGCCCCTGAACTGCTG GGGGACCCTTCCGTGTTCCTGTTCCCCCCAAAGCCCAAGGACACCCT GATGATCTCCCGGACCCCTGAAGTGAAGTTCAATTGGTACGTGGACGGCG TCCCACGAGGACCTCCGTGAAGTGAAGCCAAGACCAAGACCAAGACAGTA ACTCCACTCACCGGGTGGTGTCCGTGCTGACCGTGCTGCACCAGGAT TGGCTGAACGGCAAAGAGTACAAGTGCAAGGTGTCCAACAAGGCCC TGCCTGCCCCATCGAAAAGACCATCTCCAAGGCCAAGGGCCAGCC CCGGGAACCCCAGGTGTACACACTGCCCCCTAGCAGGGACGAGCTG ACCAAGAACCAGGTGTCCGTGACCTGTCTGGTGAAGGCTTCTACCC CTCCGATATCGCCGTGGAATGGGAGTCCAACGGCCAGCCTGAGAAC AACTACAAGACCACCCCCCCTGTCCTGGACTCCGACGGCTCATTCTT CCTGTACAGCAAGCTGACAGTGGACAAGTCCCGGTGGCAGGGC AACGTGTTCTCCTGCTCCGTGATGCACGAGGCCCTGCACAACCACTA CACCCAGAAGTCCCTGTCCCTGAGCCCCGGCAAG |
| 102 | 411D07 – CDRL1 (IMGT) | Amino acid sequence of CDRL1 of 411D07 using IMGT | QSVLYSSNNKNY |
| 103 | 411D07 – CDRL2 (IMGT) | Amino acid sequence of CDRL2 of 411D07 using IMGT | WAS |
| 104 | 411D07 – CDRL3 (IMGT) | Amino acid sequence of CDRL3 of 411D07 using IMGT | QQYYSNRS |

| SEQ ID NO: | Name | Description | Sequence |
|---|---|---|---|
| 105 | 411D07 – CDRL1 (Kabat) | Amino acid sequence of CDRL1 of 411D07 using Kabat | KSSQSVLYSSNNKNYLA |
| 106 | 411D07 – CDRL2 (Kabat) | Amino acid sequence of CDRL2 of 411D07 using Kabat | WASTRES |
| 107 | 411D07 – CDRL3 (Kabat) | Amino acid sequence of CDRL3 of 411D07 using Kabat | QQYYSNRS |
| 108 | 411D07 – Light chain variable region | Amino acid sequence of $V_L$ of 411D07 | DIVMTQSPDSLAVSLGERATINCKSSQSVLYSSNNKNYLAWYQQKSGQ PPKLLIYWASTRESGVPDRFSGSGSGTDFTLTISSLQTEDVAVYYCQQY YSNRSFPGQGTKLEIK |
| 109 | 411D07 – Light chain variable region | Nucleic acid sequence of $V_L$ of 411D07 | GACATCGTGATGATGACCCAGTCTCCAGACTCCCTGGCTGTGTCTCTGGG CGAGAGGGCCACCATCAACTGCAAGTCCAGTCAGAGTGTTTTATAC AGCTCCAACAATAAGAATTACTTAGCTTGGTACCAGCAGAAATCAG GACAGCCTCCTAAGTTGCTCATTTACTGGGCATCTACCCGGGAATCC GGGGTCCCTGACCGATTCAGTGGCAGCGGGTCTGGGACAGATTTCA CTCTCACCATCAGCCTGCAGACTGAAGATGTGGCAGTTTATTAC TGTCAGCAATATTATAGTAATCGCAGTTTTGGCCAGGGACCAAGCT GGAGATCAAAC |
| 110 | 411D07 – full light chain sequence | Amino acid sequence of 411D07 light chain | DIVMTQSPDSLAVSLGERATINCKSSQSVLYSSNNKNYLAWYQQKSGQ PPKLLIYWASTRESGVPDRFSGSGSGTDFTLTISSLQTEDVAVYYCQQY YSNRSFPGQGTKLEIKRTVAAPSVFIFPPSDEQLKSGTASVVCLLNNFYPR EAKVQWKVDNALQSGNSQESVTEQDSKDSTYSLSSTLTLSKADYEKH KVYACEVTHQGLSSPVTKSFNRGEC |
| 111 | 411D07 – full light chain sequence | Nucleic acid sequence of 411D07 light chain | GACATCGTGATGATGACCCAGTCTCCAGACTCCCTGGCTGTGTCTCTGGG CGAGAGGGCCACCATCAACTGCAAGTCCAGTCAGAGTGTTTTATAC AGCTCCAACAATAAGAATTACTTAGCTTGGTACCAGCAGAAATCAG GACAGCCTCCTAAGTTGCTCATTTACTGGGCATCTACCCGGGAATCC GGGGTCCCTGACCGATTCAGTGGCAGCGGGTCTGGGACAGATTTCA CTCTCACCATCAGCCTGCAGACTGAAGATGTGGCAGTTTATTAC TGTCAGCAATATTATAGTAATCGCAGTTTTGGCCAGGGACCAAGCT GGAGATCAAACGTACGGTGGCTGCACCATCTGTCTTCATCTTCCCAC CTTCCGACGAGCAGTTGAAGTCCGGAACCGCTTCTGTCGTGTGCCTG CTGAACAACTTCTACCCCCGCGAGCCAAGGTCAGTGAAGGTGG ACAACGCCCTGCAGTCCGGCAACTCCCAGGAATCCGTACCGAGCA GGACTCCAAGGACAGCACCTACTCCCTGTCCTCCACCCTGACCCTGT CCAAGGCCGACTACGAGAAGCACAAGGTGTACGCCTGCGAAGTGAC CCACCAGGGCCTGTCTAGCCCCGTGACCAAGTCTTTCAACCGGGGC GAGTGT |
| 112 | 385F01 – CDRH1 (IMGT) | Amino acid sequence of CDRH1 of 385F01 using IMGT | GFTFSSYW |

-continued

| SEQ ID NO: | Name | Description | SEQUENCE LISTING Sequence |
|---|---|---|---|
| 113 | 385F01 – CDRH2 (IMGT) | Amino acid sequence of CDRH2 of 385F01 using IMGT | IKEDGSEK |
| 114 | 385F01 – CDRH3 (IMGT) | Amino acid sequence of CDRH3 of 385F01 using IMGT | ARNRLYSDFLDN |
| 115 | 385F01 – CDRH1 (Kabat) | Amino acid sequence of CDRH1 of 385F01 using Kabat | SYWMS |
| 116 | 385F01 – CDRH2 (Kabat) | Amino acid sequence of CDRH2 of 385F01 using Kabat | NIKEDGSEKYYVDSVKG |
| 117 | 385F01 – CDRH3 (Kabat) | Amino acid sequence of CDRH3 of 385F01 using Kabat | NRLYSDFLDN |
| 118 | 385F01 – Heavy chain variable region | Amino acid sequence of $V_H$ of 385F01 | EVQLVESGGGLVQPGGSLRLSCAASGFTFSSYWMSWVRQAPGKGLEW VANIKEDGSEKYYVDSVKGRFTISRDNAKNSLYLQMNSLRAEDTSVYY CARNRLYSDFLDNWGQGTLVTVSS |
| 119 | 385F01 – Heavy chain variable region | Nucleic acid sequence of $V_H$ of 385F01 | GAGGTGCAGCTGGTGGAGTCTGGGGGAGGCTTGGTCCAGCCTGGGG GGTCCCTGAGACTCTCCTGTGCAGCCTCTGGATTCACGTTTAGTAGC TATTGGATGAGTTGGGTCCGCCAGGCTCCAGGGAAGGGGCTGGAGT GGGTGGCCAACATCAAAGAAGATGGAAGTGAGAAATACTATGTCGA CTCTGTGAAGGGCCGATTCACCATCTCCAGAGACAACGCCAAGAAC TCACTGTATCTGCAAATGAACAGCCTGAGAGCTGAGGACACGTCTG TGTATTACTGTGCGAGAAATCGACTCTACAGTGACTTCCTTGACAAC TGGGGCCAGGGAACCCTGGTCACCGTCTCCTCAG |
| 120 | 385F01 – full heavy chain sequence | Amino acid sequence of 385F01 heavy chain | EVQLVESGGGLVQPGGSLRLSCAASGFTFSSYWMSWVRQAPGKGLEW VANIKEDGSEKYYVDSVKGRFTISRDNAKNSLYLQMNSLRAEDTSVYY CARNRLYSDFLDNWGQGTLVTVSSASTKGPSVFPLAPSSKSTSGGTAA LGCLVKDYFPEPVTVSWNSGALTSGVHTFPAVLQSSGLYSLSSVVTVPS SSLGTQTYICNVNHKPSNTKVDKKVEPKSCDKTHTCPPCPAPELLGGPS VFLFPPKPKDTLMISRTPEVTCVVVDVSHEDPEVKFNWYVDGVEVHNA KTKPREEQYNSTYRVVSVLTVLHQDWLNGKEYKCKVSNKALPAPIEKT ISKAKGQPREPQVYTLPPSRDELTKNQVSLTCLVKGFYPSDIAVEWESN GQPENNYKTTPPVLDSDGSFFLYSKLTVDKSRWQQGNVFSCSVMHEAL HNHYTQKSLSLSPGK |
| 121 | 385F01 – full heavy chain sequence | Nucleic acid sequence of 385F01 heavy chain | GAGGTGCAGCTGGTGGAGTCTGGGGGAGGCTTGGTCCAGCCTGGGG GGTCCCTGAGACTCTCCTGTGCAGCCTCTGGATTCACGTTTAGTAGC TATTGGATGAGTTGGGTCCGCCAGGCTCCAGGGAAGGGGCTGGAGT GGGTGGCCAACATCAAAGAAGATGGAAGTGAGAAATACTATGTCGA CTCTGTGAAGGGCCGATTCACCATCTCCAGAGACAACGCCAAGAAC TCACTGTATCTGCAAATGAACAGCCTGAGAGCTGAGGACACGTCTG TGTATTACTGTGCGAGAAATCGACTCTACAGTGACTTCCTTGACAAC TGGGGCCAGGGAACCCTGGTCACCGTCTCCTCAGCCTCCACCAAGG GCCCCTCTGTGTTCCCTCTGGCCCCTTGCTCCAAGTCCACCTCTGGC |

-continued

SEQUENCE LISTING

| SEQ ID NO:Name | Description | Sequence |
|---|---|---|
| | | GGAACAGCCCTCTGGGCTGCCTCGTGAAGGACTACTTCCCCGAGC |
| | | CTGTGACCGTGTCCTGGAACTCTGGCGCTCTGACCAGCGGAGTGCAC |
| | | ACCTTCCCTGCTGTGCTGCAGTCCTCCGGCCTGTACTCCCTGTCCTCC |
| | | GTCGTGACCGTGCCTTCCAGCTCTCTGGGCACCCAGACCTACATCTG |
| | | CAACGTGAACCACAAGCCCTCCAACACCAAGGTGGACAAGAAGGTG |
| | | GAACCCAAGTCCTGCGACAAGACCCACACCTGTCCCCCTGTCCTGC |
| | | CCCTGAACTGCTGGGCGGACCTTCCGTGTTCCTGTTCCCCCCAAAGC |
| | | CCAAGGACACCCTGATGATCTCCAGGACCCCTGAAGTGACCTGCGT |
| | | GGTGTGGATGTGTCCCACGAAGTGCACAATGCCAAGACCAAGCCTAGAG |
| | | TACGTGACGGCGTGGAAGTGCACAATGCCAAGACCAAGCCTAGAG |
| | | AGGAACAGTACAACTCCACCTACCGGGTGGTGTCCGTGCTGACCGT |
| | | GCTGCACCAGGA7TGGCTGAACGGCAAGAGTACAAGTGCAAGGTG |
| | | TCCAACAAGGCCCTGCCTGCCCCATCGAAAAGACCATCTCCAAGG |
| | | CCAAGGGCCAGCCCCGGGAACCCCAGGTGTACACACTGCCCCCTAG |
| | | CAGGGACGAGCTGACCAAGAACCAGGTGTCCCTGACCTGTCTCGTG |
| | | AAAGGCTTCTACCCCTCCGATATCGCCGTGAATGGGAGTCCAACG |
| | | GCCAGCCTGAGAACAACTACAAGACCACCCCCCCTGTCCTGGACTC |
| | | CGACGGCTCATTCTTCCTGTACAGCAAGCTGACAGTGGACAAGTCC |
| | | CGTGGCAGCAGGGCAACGTGTTCTCCTGCTCCGTGATGCACGAGGC |
| | | CCTGCACAACCACTACACCCAGAAGTCCCTGTCCCTGAGCCCCGGC |
| | | AAG |
| 122 | 38F01 – CDRL1 (IMGT) | Amino acid sequence of CDRL1 of 385F01 using IMGT | QGVSSW |
| 123 | 385F01 – CDRL2 (IMGT) | Amino acid sequence of CDRL2 of 385F01 using IMGT | GAS |
| 124 | 385F01 – CDRL3 (IMGT) | Amino acid sequence of CDRL3 of 385F01 using IMGT | QQANSIPFT |
| 125 | 385F01 – CDRL1 (Kabat) | Amino acid sequence of CDRL1 of 385F01 using Kabat | RASQGVSSWLA |
| 126 | 385F01 – CDRL2 (Kabat) | Amino acid sequence of CDRL2 of 385F01 using Kabat | GASSLQS |
| 127 | 385F01 – CDRL3 (Kabat) | Amino acid sequence of CDRL3 of 385F01 using Kabat | QQANSIPFT |
| 128 | 385F01 – Light chain variable region | Amino acid sequence of V$_L$ of 385F01 | DIQMTQSPSSVSASVGDRVTITCRASQGVSSWLAWYQQKSGKAPKLLI YGASSLQSGVPSRFSGSGSGTEFILTISSLQPEDFATYYCQQANSIPFTFG PGTKVDIK |
| 129 | 385F01 – Light chain variable region | Nucleic acid sequence of V$_L$ of 385F01 | GACATCCAGATGACCCAGTCTCCATCTTCCGTGTCTGCATCTGTCGG AGACAGAGTCACCATCACTTGTCGGGCGAGTCAGGGTGTTAGCAGC TGGTTAGCCTGGTATCAGCAGAAATCAGGAAAGCCCCTAAGCTCC TGATCTATGGTGCATCCAGTTTGCAAAGTGGGGTCCCATCAAGATTC AGCGGCAGTGGATCTGGGACAGAGTTCATTCTCACCATCAGCAGCC |

-continued

SEQUENCE LISTING

| SEQ ID NO: | Name | Description | Sequence |
|---|---|---|---|
| 130 | 385F01 – full light chain sequence | Amino acid sequence of 385F01 light chain | TGCAGCCTGAAGATTTTGCAACTTACTATTGTCAACAGGCTAACAGT ATCCATTCACTTTCGGCCCTGGGACCAAAGTGGATATCAAAC DIQMTQSPSSVSASVGDRVTITCRASQGVSSWLAWYQQKSGKAPKLLI YGASSLQSGVPSRFSGSGSGTEFILTISSLQPEDFATYYCQQANSIPFTFG PGTKVDIKRTVAAPSVFIFPPSDEQLKSGTASVVCLLNNFYPREAKVQW KVDNALQSGNSQESVTEQDSKDSTYSLSSTLTLSKADYEKHKVYACEV THQGLSSPVTKSFNRGEC |
| 131 | 385F01 – full light chain sequence | Nucleic acid sequence of 385F01 light chain | GACATCCAGATGACCCAGTCTCCATCTTCCGTGTCTGCATCTGTCGG AGACAGAGTCACCATCACTTGTCGGGCAGTCAGGGTGTTAGCAGC TGGTTAGCCTGGTATCAGCAGAAATCAGGGAAAGCCCCTAAGCTCC TGATCTATGGTGCATCCAGTTTGCAAAGTGGGGTCCCATCAAGATTC AGCGGCAGTGGATCTGGGACAGAGTTCATTCTCACCATCAGCAGCC TGCAGCCTGAAGATTTTGCAACTTACTATTGTCAACAGGCTAACAGT ATCCCATTCACTTTCGGCCCTGGGACCAAAGTGGATATCAAAGTAC GGTGGCCGCTCCCTCCGTGTTCATCTTCCCACCTTCCGAACAGAGC TGAAGTCCGGCACCGCTTCTGTGTGCCTGCTGAACAACTTCTAC CCCCGCGAGGCCAAGGTGCAGTGGAAGGTGGACAACGCCCTGCAGT CCGGCAACTCCCAGGAATCCGTGACCGAGCAGGACTCCAAGGACAG CACCTACTCCCTGTCCTCCACCCTGACCCTGAGCAAGGCCGACTACG AGAAGCACAAGGTGTACGCCTGCGAAGTGACCCACCAGGGCCTGTC TAGCCCCGTGACCAAGTCTTTCAACCGGGGCGAGTGT |
| 132 | 413D08 – CDRH1 (IMGT) | Amino acid sequence of CDRH1 of 413D08 using IMGT | GFTFRIYG |
| 133 | 413D08 – CDRH2 (IMGT) | Amino acid sequence of CDRH2 of 413D08 using IMGT | IWYDGSNK |
| 134 | 413D08 – CDRH3 (IMGT) | Amino acid sequence of CDRH3 of 413D08 using IMGT | ARDMDYFGMDV |
| 135 | 413D08 – CDRH1 (Kabat) | Amino acid sequence of CDRH1 of 413D08 using Kabat | IYGMH |
| 136 | 413D08 – CDRH2 (Kabat) | Amino acid sequence of CDRH2 of 413D08 using Kabat | VIWYDGSNKYYADSVKG |
| 137 | 413D08 – CDRH3 (Kabat) | Amino acid sequence of CDRH3 of 413D08 using Kabat | DMDYFGMDV |
| 138 | 413D08 – Heavy chain variable region | Amino acid sequence of V_H of 413D08 | QVQLVESGGGVVQPGRSLRLSCAASGFTFRIYGMHWVRQAPGKGLEW VAVIWYDGSNKYYADSVKGRFTISRDNSDNTLYLQMNSLRAEDTAVY YCARDMDYFGMDVWGQGTTVTVSS |
| 139 | 413D08 – Heavy chain variable region | Nucleic acid sequence of V_H of 413D08 | CAGGTGCAGCTGGTGGAGTCTGGGGGAGGCGTGGTCCAGCCTGGGA GGTCCCTGAGACTCTCCTGTGCAGCCTCTGGATTCACCTTCCGTATT TATGGCATGCACTGGGTCCGCCAGGCTCCAGGCAAGGGGCTGGAGT |

| SEQ ID NO:Name | Description | Sequence |
|---|---|---|
| | | GGGTGGCAGTTATATGTATGATGGAAGTAATAAATACTATGCTGA CTCCGTGAAGGGCCGATTCACCATCTCCAGAGACAATTCCGACAAC ACGCTGTATCTGCAAATGAACAGCCTGAGAGCCGAGGACACGGCTG TGTATTACTGTGCGAGAGATATGGACTACTTCGGTATGGACGTCTGG GGCCAAGGGACCACGGTCACCGTCTCCTCAG |
| 140 | 413D08 – full heavy chain sequence | Amino acid sequence of 413D08 heavy chain | QVQLVESGGGVVQPGRSLRLSCAASGFTFRIYGMHWVRQAPGKGLEM VAVIWYDGSNKYYADSVKGRFTISRDNSDNTLYLQMNSLRAEDTAVY YCARDMDYFGMDVWGQGTTVTVSSASTKGPSVFPLAPSSKSTSGGTA ALGCLVKDYFPEPVTVSWNSGALTSGVHTFPAVLQSSGLYSLSSVVTVP SSSLGTQTYICNVNHKPSNTKVDKKVEPKSCDKTHTCPPCPAPELLGGP SVFLFPPKPKDTLMISRTPEVTCVVVDVSHEDPEVKFNWYVDGVEHN AKTKPREEQYNSTYRVVSVLTVLHQDWLNGKEYKCKVSNKALPAPIE KTISKAKGQPREPQVYTLPPSRDELTKNQVSLTCLVKGFYPSDIAVEWE SNGQPENNYKTTPPVLDSDGSFFLYSKLTVDKSRWQQGNVFSCSVMHE ALHNHYTQKSLSLSPGK |
| 141 | 413D08 – full heavy chain sequence | Nucleic acid sequence of 413D08 heavy chain | CAGGTGCAGCTGGTGGAGTCTGGGGGAGGCGTGGTCCAGCCTGGA GTCCCTGAGACTCTCCTGTGCAGCCTCTGGATTCACCTTCCGTATT TATGGCATGCACTGGGTCCGCCAGGCTCCAGGCAAGGGGCTGGAGT GGGTGGCAGTTATATGTATGATGGAAGTAATAAATACTATGCTGA CTCCGTGAAGGGCCGATTCACCATCTCCAGAGACAATTCCGACAAC ACGCTGTATCTGCAAATGAACAGCCTGAGAGCCGAGGACACGGCTG TGTATTACTGTGCGAGAGATATGGACTACTTCGGTATGGACGTCTGG GGCCAAGGGACCACGGTCACCGTCTCCTCAGCAAGTACCAAGGGCC CCTCTGTGTTCCCTGGCCTGCCTCCAGCAAGTCACCTCTGGCCGA ACAGCCGCTCTGGGCTGCCTGGTGAAGGACTACTTCCCCGAGCCTGT GACCGTGTCCTGGAACTCTGGCGCTCTGACCAGCGGAGTGCACACC TTCCCTGCTGTGCTGCAGTCCTCCGGCCTGTACTCCCTGTCTCCGTC GTGACCGTGCCTTCCAGCTCTCTGGGCACCCAGACCTACATCTGCAA CGTGAACCACAAGCCCTCCAACACCAAGGTGGACAAGAAGGTGGA ACCCAAGTCCTGCGACAAGACCCACACCTGTCCCCCTTGTCCTGCCC CTGAACTGCTGGGCGGACCTTCCGTGTTCCTGTTCCCCCCAAAGCCC AAGGACACCCTGATGATCTCCCGGACCCCCGAAGTGACCTGCGTGG TGGTGGATGTGTCCCACGAGGACCCTGAAGTGAAGTTCAATTGGTA CGTGGACGGCGTGGAAGTGCACAACGCCAAGACCAAGCCTAGAGA GGAACAGTACAACTCCACCTACCGGGTGGTGTCCGTGCTGACCGTG CTGCACCAGGATTGGCTGAACGGCAAAGAGTACAAGTGCAAGGTGT CCAACAAGGCCCTGCCTGCCCCCATCGAAAAGACCATCTCCAAGGC CAAGGGCCAGCCCCGAGAACCCCAGGTGTACACACTGCCCCCTAGC AGGGACGAGCTGACCAAGAACCAGGTGTCCCTGACCTGTCTCGTGA AAGGCTTCTACCCCTCCGATATCGCCGTGGAATGGGAGTCCAACGG CCAGCCTGAGAACAACTACAAGACACCCCCCTGTGCTGGACAAGTCC GACGGCTCATTCTTCCTGTACAGCAAGCTGACAGTGGACAAGTCCC GGTGGCAGCAGGGCAACGTGTTCTCCTGCTCCGTGATGCACGAGGC CCTGCACAACCACTACACCCAGAAGTCCCTGTCCCTGAGCCCCGGC AAG |

| SEQ ID NO: | Name | Description | Sequence |
|---|---|---|---|
| 142 | 413D08 – CDRL1 (IMGT) | Amino acid sequence of CDRL1 of 413D08 using IMGT | QGIRND |
| 143 | 413D08 – CDRL2 (IMGT) | Amino acid sequence of CDRL2 of 413D08 using IMGT | AAS |
| 144 | 413D08 – CDRL3 (IMGT) | Amino acid sequence of CDRL3 of 413D08 using IMGT | LQHNSYPRT |
| 145 | 413D08 – CDRL1 (Kabat) | Amino acid sequence of CDRL1 of 413D08 using Kabat | RASQGIRNDLG |
| 146 | 413D08 – CDRL2 (Kabat) | Amino acid sequence of CDRL2 of 413D08 using Kabat | AASSLQS |
| 147 | 413D08 – CDRL3 (Kabat) | Amino acid sequence of CDRL3 of 413D08 using Kabat | LQHNSYPRT |
| 148 | 413D08 – Light chain variable region | Amino acid sequence of V$_L$ of 413D08 | DLQMTQSPSSLSASVGDRVTITCRASQGIRNDLGWYQQKPGKAPKRLI YAASSLQSGVPSRFSGSGSGTEFTLTISSLQPEDFATYYCLQHNSYPRTF GQGTKVEIK |
| 149 | 413D08 – Light chain variable region | Nucleic acid sequence of V$_L$ of 413D08 | GACCTCCAGATGACCCAGTCTCCATCTCCCTGTCTGCATCTGTAGG AGACAGAGTCACCATCACTTGCCGGGCAAGTCAGGGCATTAGAAAT GATTTAGGCTGGTATCAGCAGAAACCAGGGAAAGCCCCTAAGCGCC TGATCTATGCTGCATCCAGTTTGCAAAGTGGGGTCCCATCAAGGTTC AGCGGCAGTGGATCTGGGACAGAATTCACTCTCACAATCAGCAGCC TGCAGCCTGAAGATTTTGCAACTTATTACTGTCTACAGCATAATAGT TACCCTCGGACGTTCGGCCAAGGGACCAAGGTGGAAATCAAAC |
| 150 | 413D08 – full light chain sequence | Amino acid sequence of 413D08 light chain | DLQMTQSPSSLSASVGDRVTITCRASQGIRNDLGWYQQKPGKAPKRLI YAASSLQSGVPSRFSGSGSGTEFTLTISSLQPEDFATYYCLQHNSYPRTF GQGTKVEIKRTVAAPSVFIFPPSDEQLKSGTASVVCLLNNFYPREAKVQ WKVDNALQSGNSQESVTEQDSKDSTYSLSSTLTLSKADYEKHKVYACE VTHQGLSSPVTKSFNRGEC |
| 151 | 413D08 – full light chain sequence | Nucleic acid sequence of 413D08 light chain | GACCTCCAGATGACCCAGTCTCCATCTCCCTGTCTGCATCTGTAGG AGACAGAGTCACCATCACTTGCCGGGCAAGTCAGGGCATTAGAAAT GATTTAGGCTGGTATCAGCAGAAACCAGGGAAAGCCCCTAAGCGCC TGATCTATGCTGCATCCAGTTTGCAAAGTGGGGTCCCATCAAGGTTC AGCGGCAGTGGATCTGGGACAGAATTCACTCTCACAATCAGCAGCC TGCAGCCTGAAGATTTTGCAACTTATTACTGTCTACAGCATAATAGT TACCCTCGGACGTTCGGCCAAGGGACCAAGGTGGAAATCAAACGTA CGGTGGCTGCTCCCTCCGTGTTCATCTTCCCGCCATCTGACGAGCAG CTGAAGTCCGGCACCGCTTCTGTCGTGTGCCTGCTGAACAACTTCTA CCCCCGCGAGGCCAAGGTGCAGTGGAAGGTGGACAACGCCCTGCAG TCCGGCAACTCCCAGGAATCCGTGACCGAGCAGGACTCCAAGGACA GCACCTACTCCCTGTCCTCCACCCTGACCCTGTCCAAGGCCGACTAC |

-continued

SEQUENCE LISTING

| SEQ ID NO: | Name | Description | Sequence |
|---|---|---|---|
| | | | GAGAAGCACCAAGGTGTACGCCTGCGAAGTGACCCACCAGGGCCTGT |
| | | | CTAGCCCCGTGACCAAGTCTTTCAACCGGGGCGAGTGT |
| 152 | 386H03 – CDRH1 (IMGT) | Amino acid sequence of CDRH1 of 386H03 using IMGT | GGSISSSDW |
| 153 | 386H03 – CDRH2 (IMGT) | Amino acid sequence of CDRH2 of 386H03 using IMGT | IFHSGNT |
| 154 | 386H03 – CDRH3 (IMGT) | Amino acid sequence of CDRH3 of 386H03 using IMGT | VRDGSGSY |
| 155 | 386H03 – CDRH1 (Kabat) | Amino acid sequence of CDRH1 of 386H03 using Kabat | SSDWS |
| 156 | 386H03 – CDRH2 (Kabat) | Amino acid sequence of CDRH2 of 386H03 using Kabat | EIFHSGNTNYNPSLKS |
| 157 | 386H03 – CDRH3 (Kabat) | Amino acid sequence of CDRH3 of 386H03 using Kabat | DGSGSY |
| 158 | 386H03 – Heavy chain variable region | Amino acid sequence of $V_H$ of 386H03 | QVQLQESGPGLVKPSGTLSLTCAVSGGSISSSDWSWVRQPPGKGLEW IGEIFHSGNTNYNPSLKSRVTISVDKSKNQISLRLNSVTAADTAVYYCVR DGSGSYWGQGTLVTVSS |
| 159 | 386H03 – Heavy chain variable region | Nucleic acid sequence of $V_H$ of 386H03 | CAGGTGCAGCTGCAGGAGTCGGGCCCAGGACTGGTGAAGCCTTCGG GGACCCTGTCCCTCACCTGCGCTGTCTCTGGTGGCTCCATCAGCAGT AGTGACTGGTGGAGTTGGGTCCGCCAGCCCCCAGGGAAGGGGCTGG AGTGGATTGGGGAAATCTTTCATAGTGGGAACACCAACTACAACCC GTCCCTCAAGAGTCGAGTCACCATATCTGTGACCGCGGACACGGCCG CAGATCTCCCTGAGGCTGAACTCTGTGACCGCTGACACGGCCGTGT ATTACTGTGTGAGAGATGGTTCGGGAGTTACTGGGGCCAGGG AACCCTGGTCACCGTCTCCTCAG |
| 160 | 386H03 – full heavy chain sequence | Amino acid sequence of 386H03 heavy chain | QVQLQESGPGLVKPSGTLSLTCAVSGGSISSSDWSWVRQPPGKGLEW IGEIFHSGNTNYNPSLKSRVTISVDKSKNQISLRLNSVTAADTAVYYCVR DGSGSYWGQGTLVTVSSASTKGPSVFPLAPSSKSTSGGTAALGCLVKD YFPEPVTVSWNSGALTSGVHTFPAVLQSSGLYSLSSVVTVPSSSLGTQT YICNVNHKPSNTKVDKKVEPKSCDKTHTCPPCPAPELLGGPSVFLFPPK PKDTLMISRTPEVTCVVVDVSHEDPEVKFNWYVDGVEVHNAKTKPRE EQYNSTYRVVSVLTVLHQDWLNGKEYKCKVSNKALPAPIEKTISKAKG QPREPQVYTLPPSRDELTKNQVSLTCLVKGFYPSDIAVEWESNGQPENN YKTTPPVLDSDGSFFLYSKLTVDKSRWQQGNVFSCSVMHEALHNHYT QKSLSLSPGK |
| 161 | 386H03 – full heavy chain sequence | Nucleic acid sequence of 386H03 heavy chain | CAGGTGCAGCTGCAGGAGTCGGGCCCAGGACTGGTGAAGCCTTCGG GGACCCTGTCCCTCACCTGCGCTGTCTCTGGTGGCTCCATCAGCAGT AGTGACTGGTGGAGTTGGGTCCGCCAGCCCCCAGGAAGGGGCTGG AGTGGATTGGGGAAATCTTTCATAGTGGGAACACCAACTACAACCC |

| SEQ ID NO: | Name | Description | Sequence |
|---|---|---|---|
| | | | GTCCCTCAAGAGTCGAGTCACCATATCAGTAGACAAGTCCAAGAAC |
| | | | CAGATCTCCCTGAGGCTGAACTCTGTGACCGCCGCGGACACGGCCG |
| | | | TGTATTACTGTGTGAGAGATGGTTCGGGAGTTACTGGGGCCAGGG |
| | | | AACCCTGGTCACCGTCTCCTCAGCAAGTCCACCTCTGGCGCACCAAGCCCTCTGTGT |
| | | | TCCCTCTGCCCCTTCGTGAAGGACTACTTCCCCGAGCCTGTGACCGTGTC |
| | | | CTGGAACTCTGGCGCTCGACCAGCGAGTGCACACCTTCCCTGCTG |
| | | | TGCTGCAGTCCTCCGGCCTGTACTCCCTGTCCTCCGTCGTGACCGTG |
| | | | CCTTCCAGCTCTCTGGGCACCCAGACCTACATCTGCAACGTGAACCA |
| | | | CAAGCCCTCCAACACCAAGGTGGACAAGAAGGTGGAACCCAAGTCC |
| | | | TGCGACAAGACCCACACCTGTCCCCCTTGTCCTGCCCCTGAACTGCT |
| | | | GGGCGGACCTTCCGTGTTCCTGTTCCCCCCAAAGCCCAAGGACACCC |
| | | | TGATGATCTCCCGGACCCCTGAAGTGAAGTTCAATTGGTACGTGGACGGC |
| | | | GTCGAAGTGCACAACGCCAAGACCAAGCCTAGAGAGGAACAGTAC |
| | | | AACTCCACCTACCGGGTGGTGTCCGTGCTGACCGTGCTGCACCAGG |
| | | | ATTGGCTGAACGGCAAAGAGTACAAGTGCAAGGTGTCCAACAAGGC |
| | | | CCTGCCTGCCCCCATCGAAAAGACCATCTCCAAGGCCAAGGGCCAG |
| | | | CCCCGGGAACCCCAGGTGTACACACTGCCCCCTAGCAGGACGAGC |
| | | | TGACCAAGAACCAGGTGTCCCTGACCTGTCTGGTGAAAGGCTTCTAC |
| | | | CCCTCCGATATCGCCGTGGAATGGGAGTCCAACGGCCAGCCTGAGA |
| | | | ACAACTACAAGACCACCCCCCTGTGTCTGGACAAGTCCGACGGCTCATTC |
| | | | TTCCTGTACAGCAAGCTGACAGTGGACAAGTCCCGGTGGCAGCAGG |
| | | | GCAACGTGTTCTCCTGCTCCGTGATGCACGAGGCCCTGCACAACCAC |
| | | | TACACCCAGAAGTCCCTGTCCCTGAGCCCCGGCAAG |
| 162 | 386H03 – CDRL1 (IMGT) | Amino acid sequence of CDRL1 of 386H03 using IMGT | QSVLYSSNNKNY |
| 163 | 386H03 – CDRL2 (IMGT) | Amino acid sequence of CDRL2 of 386H03 using IMGT | WAS |
| 164 | 386H03 – CDRL3 (IMGT) | Amino acid sequence of CDRL3 of 386H03 using IMGT | QQYYSTRS |
| 165 | 386H03 – CDRL1 (Kabat) | Amino acid sequence of CDRL1 of 386H03 using Kabat | KSSQSVLYSSNNKNYLA |
| 166 | 386H03 – CDRL2 (Kabat) | Amino acid sequence of CDRL2 of 386H03 using Kabat | WASTRES |
| 167 | 386H03 – CDRL3 (Kabat) | Amino acid sequence of CDRL3 of 386H03 using Kabat | QQYYSTRS |
| 168 | 386H03 – Light chain variable region | Amino acid sequence of V_L of 386H03 | DIVMTQSPDSLAVSLGERATINCKSSQSVLYSSNNKNYLAWYQQKPGQ PPKLLIYWASTRESGVPDRFSGSGSGTDFTLTISSLQAEDVAVYYCQQY YSTRSFGQGTKLEIK |

-continued

SEQUENCE LISTING

| SEQ ID NO: | Name | Description | Sequence |
|---|---|---|---|
| 169 | 386H03 – Light chain variable region | Nucleic acid sequence of V$_L$ of 386H03 | GACATCGTGATGACCCAGTCTCCAGACTCCCTGGCTGTGTCTCTGGG CGAGAGGGCCACCATCAACTGCAAGTCCAGCCAGAGTGTTTTATAC AGCTCCAACAATAAGAACTACTTAGCTTGGTACCAGCAGAAACCAG GACAGCCTCCTAAACTGCTCATTTACTGGGCATCTACCCGGGAATCC GGGGTCCCTGACCGATTCAGTGGCAGCGGGTCTGGGACAGATTTCA CTCTCACCATCAGCAGCCTGCAGGCTGAAGATGTGGCAGTTTATTAC TGTCAGCAATATTATAGTACTCCAGTTTTCGGCCAGGGGACCAAGCT GGAGATCAAAC |
| 170 | 386H03 – full light chain sequence | Amino acid sequence of 386H03 light chain | DIVMTQSPDSLAVSLGERATINCKSSQSVLYSSNNKNYLAWYQQKPGQ PPKLLIYWASTRESGVPDRFSGSGSGTDFTLTISSLQAEDVAVYYCQQY YSTRSFGQGTKLEIKRTVAAPSVFIFPPSDEQLKSGTASVVCLLNNFYPR EAKVQWKVDNALQSGNSQESVTEQDSKDSTYSLSSTLTLSKADYEKH KVYACEVTHQGLSSPVTKSFNRGEC |
| 171 | 386H03 – full light chain sequence | Nucleic acid sequence of 386H03 light chain | GACATCGTGATGACCCAGTCTCCAGACTCCCTGGCTGTGTCTCTGGG CGAGAGGGCCACCATCAACTGCAAGTCCAGCCAGAGTGTTTTATAC AGCTCCAACAATAAGAACTACTTAGCTTGGTACCAGCAGAAACCAG GACAGCCTCCTAAACTGCTCATTTACTGGGCATCTACCCGGGAATCC GGGGTCCCTGACCGATTCAGTGGCAGCGGGTCTGGGACAGATTTCA CTCTCACCATCAGCAGCCTGCAGGCTGAAGATGTGGCAGTTTATTAC TGTCAGCAATATTATAGTACTCGGTTTTGGCCAGGGGACCAAGCT GGAGATCAAACGTACGGTGGCTGCACCATCTGTCTTCATCTTCCCAC CTTCCGACGAGCAGCTGAAGTCGGGAGCCCAAGTGCAGTGGAAGGTG GACAACGCCCTGCAATCTGGGAACTCCCAGGAATCCGTAACCGAGCA GGACTCCAAGGACAGCACCTACTCCCTGTCCTCCACCCTGACCCTGT CCAAGGCTGACTACGAGAAGCACAAAGTGTACGCCTGCGAAGTGAC CCACCAGGGCCTGTCTAGCCCCGTGACCAAGTCTTTCAACCGGGGC GAGTGT |
| 172 | 389A03 – CDRH1 (IMGT) | Amino acid sequence of CDRH1 of 389A03 using IMGT | GGSISSSSYY |
| 173 | 389A03 – CDRH2 (IMGT) | Amino acid sequence of CDRH2 of 389A03 using IMGT | IYSTGYT |
| 174 | 389A03 – CDRH3 (IMGT) | Amino acid sequence of CDRH3 of 389A03 using IMGT | AISTAAGPEYFHR |
| 175 | 389A03 – CDRH1 (Kabat) | Amino acid sequence of CDRH1 of 389A03 using Kabat | SSSYYCG |
| 176 | 389A03 – CDRH2 (Kabat) | Amino acid sequence of CDRH2 of 389A03 using Kabat | SIYSTGYTYNPSLKS |
| 177 | 389A03 – CDRH3 (Kabat) | Amino acid sequence of CDRH3 of 389A03 using Kabat | STAAGPEYFHR |

SEQUENCE LISTING

| SEQ ID NO: | Name | Description | Sequence |
|---|---|---|---|
| 178 | 389A03 - Heavy chain variable region | Amino acid sequence of V$_H$ of 389A03 | QLQESGPGLVKPSETLSLTCTVSGGSISSSSYYCGWIRQPPGKGLDWIGS IYSTGVTYYNPSLKSRVTISIDTSKNQFSCLILTSVTAADTAVYYCAISTA AGPEYFHRWGQGTLVTVSS |
| 179 | 389A03 - Heavy chain variable region | Nucleic acid sequence of V$_H$ of 389A03 | CAGCTGCAGGAGTCGGGCCCAGGCCTGGTGAAGCCTTCGGAGACCC TGTCCCTCACCTGCACTGTCTCTGGTGGCTCCATCAGCAGTAGTAGT TATTACTGCGGCTGGATCCGCCAGCCCCCTGGAAGGGGCTGGACT GGATTGGGAGTATCTATTCTACTGGGTACACCTACAACCCGTCC CTCAAGAGTCGAGTCACCATTTCCATAGACACGTCCAAGAACCAGT TCTCATGCCTGATACTGACCTCGTGACCGCCGAGACACGGCTGTG TATTACTGCGCGATAAGTACAGCAGCCTGGCCCTGAATACTTCCATCG CTGGGGCCAGGGCACCCTGGTCACCGTCTCCTCAG |
| 180 | 389A03 - full heavy chain sequence | Amino acid sequence of 389A03 heavy chain | QLQESGPGLVKPSETLSLTCTVSGGSISSSSYYCGWIRQPPGKGLDWIGS IYSTGVTYYNPSLKSRVTISIDTSKNQFSCLILTSVTAADTAVYYCAISTA AGPEYFHRWGQGTLVTVSSASTKGPSVFPLAPSSKSTSGGTAALGCLV KDYFPEPVTVSWNSGALTSGVHTFPAVLQSSGLYSLSSVVTVPSSSLGT QTYICNVNHKPSNTKVDKKVEPKSCDKTHTCPPCPAPELLGGPSVFLFP PKPKDTLMISRTPEVTCVVVDVSHEDPEVKFNWYDGVEVHNAKTKP REEQYNSTYRVVSVLTVLHQDWLNGKEYKCKVSNKALPAPIEKTISKA KGQPREPQVVTLPPSRDELTKNQVSLTCLVKGFYPSDIAVEWESNGQPE NNYKTTPPVLDSDGSFFLYSKLTVDKSRWQQGNVFSCSVMHEALHNH YTQKSLSLSPGK |
| 181 | 389A03 - full heavy chain sequence | Nucleic acid sequence of 389A03 heavy chain | CAGCTGCAGGAGTCGGGCCCAGGCCTGGTGAAGCCTTCGGAGACCC TGTCCCTCACCTGCACTGTCTCTGGTGGCTCCATCAGCAGTAGTAGT TATTACTGCGGCTGGATCCGCCAGCCCCCTGGGAAGGGGCTGGACT GGATTGGGAGTATCTATTCTACTGGGTACACCTACAACCCGTCC CTCAAGAGTCGAGTCACCATTTCCATAGACACGTCCAAGAACCAGT TCTCATGCCTGATACTGACCTCGTGACCGCCGAGACACGGCTGTG TATTACTGCGCGATAAGTACAGCAGCCTGGCCCTGAATACTTCCATCG CTGGGGCCAGGGCACCCTGGTCACCGTCTCCTCAGCCAGCACCAAG GGCCCCTCTGTTCCCCTTCCGGCCTGCCTCCAGGACTACTTCCCTGG CCTGTCGACCGTGTCCTGGAACTCTGGCGCTTCGACCAGCGAGTGCA CACCTTCCCTGCTGTCCTGCAGTCCTCCGGCTACTCCCTGTCCTC CGTCGTGACCGTGCCTTCCAGCTCTTCGGGCACCCAGACCTACATCT GCAACGTGAACCACAAGCCCTCCAACACCAAGGTGACAAGAAGGT GAACCCCAAGTCCTGCGACAAGACCCACACCTGTCCCCCTTGTCCTG CCCCTGAACTGCTGGGCGGACCTTCCGTGTTCCTGTTCCCCCCAAAG CCCAAGGACACCCTGATGATCTCCCGGACCCCTGAAGTGACCTGCG TGGTGGTGGATGTGTCCCACGAGGACCCTGAAGTGAAGTTCAATTG GTACGTGGACGGCGTGGAAGTGCACAACGCCAAGACCAAGCCTAGA GAGGAACAGTACAACTCCACCTACCGGGTGGTGTCCGTGCTGACCG TGCTGCACCAGGATTGGCTGAACGGCAAAGGCAAAGTACAAGTGCAAGGT GTCCAACAAGGCCCTGCCTGCCCCCATCGAACGCCGAAAAGACCATCTCCAAG GCCAAGGGCCAGCCCCGAGAACCCCAGGTGTACACTGCCCCCTA GCAGGACGAGCTGACCAAGAACCAGGTGTCCCTGACCTGTCTGT |

| SEQ ID NO: | Name | Description | SEQUENCE LISTING Sequence |
|---|---|---|---|
| | | | GAAAGGCTTCTACCCTCGATATGCCGTGGAATGGAGTCCAAC GGCCAGCCTGAGAACAACTACAAGACCACCCCCCTGTGCTGGACT CCGACGGCTCATTCTTCCTGTACAGCAGCTGACGTGACAAGTCC CGGTGGCAGCAGGGCAACGTGTTCTCCTGCTCCGTGATGCACGAG CCCTGCACACCACTACACCCAGAAGTCCCTGTCCCTGAGCCCCGG CAAG |
| 182 | 389A03 – CDRL1 (IMGT) | Amino acid sequence of CDRL1 of 389A03 using IMGT | QSVLYSSNSKNF |
| 183 | 389A03 – CDRL2 (IMGT) | Amino acid sequence of CDRL2 of 389A03 using IMGT | WAS |
| 184 | 389A03 – CDRL3 (IMGT) | Amino acid sequence of CDRL3 of 389A03 using IMGT | QQYYSTPRT |
| 185 | 389A03 – CDRL1 (Kabat) | Amino acid sequence of CDRL1 of 389A03 using Kabat | KSSQSVLYSSNSKNFLA |
| 186 | 389A03 – CDRL2 (Kabat) | Amino acid sequence of CDRL2 of 389A03 using Kabat | WASTRGS |
| 187 | 389A03 – CDRL3 (Kabat) | Amino acid sequence of CDRL3 of 389A03 using Kabat | QQYYSTPRT |
| 188 | 389A03 – Light chain variable region | Amino acid sequence of $V_L$ of 389A03 | DIVMTQSPDSLAVSLGERATINCKSSQSVLYSSNSKNFLAWYQQKPGQP PKLFIYWASTRGSGVPDRISGSGSGTDFNLTISSLQAEDVAVYYCQQYY STPRTFGQGTKVEIK |
| 189 | 389A03 – Light chain variable region | Nucleic acid sequence of $V_L$ of 389A03 | GACATCGTGATGACCCAGTCTCCAGACTCCCTGGCTGTGTCTCTGGG CGAGAGGGCCACCATCAACTGCAAGTCCAGCCAGAGTGTTTATAC AGCTCCAACAGTAAGAACTTCTTAGCTTGGTACCAGCAGAAACCGG GACAGCCTCCTAAGCTGTTCATTTACTGGGCATCTACCCGGGATCA GGGGTCCCTGACCGAATCAGTGGCAGCGGGTCTGAAGATGTGCAGTTTCA ATCTCACCATCAGCAGCCTGCAGGCTGAAGATGTGGCAGTTTATTAC TGTCAACAATATTATAGTACTCCTCGGACGTTCGGCCAAGGGACCA AGGTGGAGATCAAAC |
| 190 | 389A03 – full light chain sequence | Amino acid sequence of 389A03 light chain | DIVMTQSPDSLAVSLGERATINCKSSQSVLYSSNSKNFLAWYQQKPGQP PKLFIYWASTRGSGVPDRISGSGSGTDFNLTISSLQAEDVAVYYCQQYY STPRTFGQGTKVEIKRTVAAPSVFIFPPSDEQLKSGTASVVCLLNNFYPR EAKVQWKVDNALQSGNSQESVTEQDSKDSTYSLSSTLTLSKADYEKH KVYACEVTHQGLSSPVTKSFNRGEC |
| 191 | 389A03 – full light chain sequence | Nucleic acid sequence of 389A03 light chain | GACATCGTGATGACCCAGTCTCCAGACTCCCTGGCTGTGTCTCTGGG CGAGAGGGCCACCATCAACTGCAAGTCCAGCCAGAGTGTTTATAC AGCTCCAACAGTAAGAACTTCTTAGCTTGGTACCAGCAGAAACCGG GACAGCCTCCTAAGCTGTTCATTTACTGGGCATCTACCCGGGATCC GGGGTCCCTGACCGAATCAGTGGCAGCGGGTCTGGGACAGATTTCA |

| SEQ ID NO: | Name | Description | Sequence |
|---|---|---|---|
| | | | ATCTCACCATCAGCAGCCTGCAGGCTGAAGATGTGCAGTTTATTAC |
| | | | TGTCAACAATATTATAGTACTTCCTCGGACGTTCGGCCAAGGGACCA |
| | | | AGGTGGAGATCAAACTACGTGCGCTCACCTCCTCCGTTCATCTTC |
| | | | CCACCTTCCGACGAGCAGCTGAAGTCCGGCACCGCTTCTGTGTG |
| | | | CCTGCTGAACAACTTCTACCCCGGAGGCCAAGTGCAGTGGAAG |
| | | | GTGGACAACGCCCTGCAGTCCGGCAACTCCAGGAATCCGTGACCG |
| | | | AGCAGGACTCCAAGGACGACTACGAGAAGCACAAGTGTACGCCTGACC |
| | | | CTGTCCAAGGCCGACTACGAGAAGCACAAGGTGTACGCCTGACC |
| | | | TGACCCACCAGGGCCTGTCTAGCCCCGTGACCAAGTCTTTCAACCGG |
| | | | GGCGAGTGT |
| 192 | Human IgG4 heavy chain constant region #1 | IGHG*01 Heavy Chain Constant Region Nucleotide Sequence | gcttccaccaaggccatcgtctcccccctggcgcctgtccaggagcacctccgagagcacagcgccct gggctgcctggtcaaggactacttccccgaaccggtgacggtgtcgtggaactcaggcgccctgaccagcggc gtgcacacctttccggctgtcctacacctgcaacgtagatcacaagcccagcaacaccaaggtgacaagagagttg agtccaaatatggtccccatgagtccacctgagtcctgggggacctcagtcttcctgttccc cccaaaaccaaggacactctcatgatctccggacccctgaggtcacgtcgtggtggtggacgtgagccag gaagacccgaggtcaagtccaggcacgtgtggtggtcagcgtcctcaacgtgtcctcaccgctgaaccgga aggagtacaagtgcaaggtctccaacaaagcctccatctccaaagccaaagg gcagcccgagagccacaggtgtacaccctgccccatcgcgacgaccccccatcgcgacgtgagtgggagaaggga gacctgcctgtcaagaccaagggccctcccgtgctggactccagcgtcctcttcctctacagcaggctaaccgtggacaa gagcaggtgcaggtggagggaatgttcttctatgtcatgaagcatgaggctctgcacaaccactacacacaga agagcctccctgtctctgggtaa |
| 193 | | IGHG*01 Heavy Chain Constant Region Amino Acid Sequence | ASTKGPSVFPLAPCSRSTSESTAALGCLVKDYFPEPVTVSWNSGALTSG VHTFPAVLQSSGLYSLSSVVTVPSSSLGTKTYTCNVDHKPSNTKVDKRV ESKYGPPCPSCPAPEFLGGPSVFLFPPKPKDTLMISRTPEVTCVVVDVSQ EDPEVQFNWYVDGVEVHNAKTKPREEQFNSTYRVVSVLTVLHQDWL NGKEYKCKVSNKGLPSSIEKTISKAKGQPREPQVYTLPPSQEEMTKNQV SLTCLVKGFYPSDIAVEWESNGQPENNYKTTPPVLDSDGSFFLYSRLTV DKSRWQEGNVFSCSVMHEALHNHYTQKSLSLSLGK |
| 194 | Human IgG4 heavy chain constant region #2 | IGHG*02 Heavy Chain Constant Region Nucleotide Sequence | gcttccaccaaggccatcgtctcccccctggcgcctgtccaggagcacctccgagagcacagcgccct gggctgcctggtcaaggactacttccccgaaccggtgacggtgtcgtggaactcaggcgccctgaccagcggc gtgcacacctttccggctgtcctacacctgcaacgtagatcacaagcccagcaacaccaaggtgacaagagagttg agtccaaatatggtccccatgagtccacctgagtcctgggggacctcagtcttcctgttccc cccaaaaccaaggacactctcatgatctccggacccctgaggtcacgtcgtggtggtggacgtgagccag gaagacccgaggtcaagtccaggcacgtgtggtggtcagcgtcatgccaagacaaagccgcgg aggagtacaagtgcaaggtctccaacaaagcctccatctccaaaaccatctccaaagccaaagg gacctgcctgagccacaggtgtacaccctgccccatcgaggagatgaccaagaaccaggtcagct gacctgcctgtcaagggcttctaccccgagcgatcccgtggactccagcgtcctcttcctctacagcaggctaaccgtggacaa gagcaggtgcaggtggagggaatgttcttctatgtcatgaagcatgaggctctgcacaaccactacacacaga agagcctccctgtctctgggtaa |

| SEQ ID NO: | Name | Description | Sequence |
|---|---|---|---|
| 195 | | Heavy Chain Constant Region Amino Acid Sequence | ASTKGPSVFPLAPCSRSTSESTAALGCLVKDYFPEPVTVSWNSGALTSG VHTFPAVLQSSGLYSLSSVVTVPSSSLGTKTYTCNVDHKPSNTKVDKRV ESKYGPPCPSCPAPEFLGGPSVFLFPPKPKDTLMISRTPEVTCVVVDVSQ EDPEVQFNWYVDGVEVHNAKTKPREEQFNSTYRVVSVLTVVHQDWL NGKEYKCKVSNKGLPSSIEKTISKAKGQPREPQVYTLPPSQEEMTKNQV SLTCLVKGFYPSDIAVEWESNGQPENNYKTTPPVLDSDGSFFLYSRLTV DKSRWQEGNVFSCSVMHEALHNHYTQKSLSLSLGK |
| 196 | Human IgG4 heavy chain constant region #3 IGHG*03 | Heavy Chain Constant Region Nucleotide Sequence | gcttccaccaaggccatccgtcttcccctggcgccctgctccaggagcacctccgagagcacagccgcct gggctgcctgtcaaggactacttcccgaaccggtgacggtgtcgtggaactcaggcgccctgaccagcggc gtgcacaccttcccggctgtcctacagtctcctcaggactctactccctcagcagctgtgaccgtgccctcagc agcttggcacagaagccttacacccctgaaggtctgatcacaagctggacaagagtg agtccaaatatggtcccccatgcccaccatgtcccaggacctgtccagtcctgtccagtcttcctgttccc ccaaaacccaaggacactctcatgatctcccggaccctgaggtcacgtgcgtggtggtggacgtgagccag gaagacccgggtcaagttccagttcaactggtacgtggatggcgtggaggtgcataatgccaagacaaagccgcgg gaggagcagttcaacagcacgtaccgtgtggtcagcgtcctcaccgtcctgcaccaggactggctgaacggca aggagtacaagtgcaaggtctccaacaaaggcctcccgtcctccatcgagaaaaccatctccaaagccaagg gcagcccgagacaggtgtacaccctgcccccatccgcgacctgatccggtgagtgggagcaatgggcagccgg gaccctgtccaaaggcttctacccagcgacctgcctcgtgaaaggcttctacccagcgacatcgccgtggagtgggagagcaatgggcagccggaga caactacaagaccacgcctcccgtgctggactccgacggctccttcttcctctacagcaggctaaccgtggacaa gagcaggtggcaggaggggaatgtcttctcatgtcgtgatgcatgaggctctgcacaaccactacacacaga agagcctctccctgtctctgggtaaa |
| 197 | | Heavy Chain Constant Region Amino Acid Sequence | ASTKGPSVFPLAPCSRSTSESTAALGCLVKDYFPEPVTVSWNSGALTSG VHTFPAVLQSSGLYSLSSVVTVPSSSLGTKTYTCNVDHKPSNTKVDKRV ESKYGPPCPSCPAPEFLGGPSVFLFPPKPKDTLMISRTPEVTCVVVDVSQ EDPEVQFNWYVDGVEVHNAKTKPREEQFNSTYRVVSVLTVVHQDWL NGKEYKCKVSNKGLPSSIEKTISKAKGQPREPQVYTLPPSQEEMTKNQV SLTCLVKGFYPSDIAVEWESNGQPENNYKTTPPVLDSDGSFFLYSRLTV DKSRWQEGNVFSCSVMHEALHNHYTQKSLSLSLGK |
| 198 | IgG4 heavy chain constant region | Heavy Chain Constant Region Nucleotide Sequence – Synthetic Version A | gcttccaccaaggccctccatccgtcttccccctggcgccctgctccaggagcacctccgagagcacgccgcc tgggctgcctgtcaaggactacttcccgaaccagtgacggtgtcgtggaactcaggcgccctgaccagcgg cgtgcacaccttcccggctgtcctacagtctcctcaggactctactccctcagcagctgtgaccgtgcctccag cagcttgggacacgaagaccatcacctgcaacgtagatcacaagcccagcaacaccaaggtgacaagagagtt agtccaaatatgtcccaccatgcccaccatgcccagtcccggcctgaatttgaggggggaccatcagtcttcctgttcc ccccaaaacccaaggacacctcatgatctccccggacccctgagtcacgtgcgtggtggtggacgtgagcca ggaagacccggagttcaactggtacgtggatggcgtggaggtgcataatgccaagacaaagccgcg gaggagcagttcaacagcacgtaccgtgtggtcagcgtcctcaccgtcctgcaccaggactggctgaacggc aaggagtacaagtgcaaggtctccaacaaaggcctcccgtcctccatcgagaaaaccatctccaaagccaag gcagcccgagaaccaggtgtacaccctgcccccatccaggaggagatgaccaagaaccaggtcagc ctgacctgcctggtcaaaggcttctacccagcgacatcgccgtggagtgggagagcaatggcagccggaga acaatacaagaccacgcctcccgtgctgactccgacggctccttcttcctctacagcaggctaaccgtggaca aagacggtggcaggagggaatgtcttctcatgtccgtgatgcatgaggctctgcacaaccactacacacag aagagcctctccctgtctctgggtaaa |

-continued

SEQUENCE LISTING

| SEQ ID NO:Name | Description | Sequence |
|---|---|---|
| 199 IgG4 heavy chain constant region — IgG4-PE | Heavy Chain Constant Region Amino Acid Sequence — Encoded by Synthetic Version A, B & C | ASTKGPSVFPLAPCSRSTSESTAALGCLVKDYFPPEPVTVSWNSGALTSG VHTFPAVLQSSGLYSLSSVVTVPSSSLGTKTYTCNVDHKPSNTKVDKRV ESKYGPPCPAPEFEGGPSVFLFPPKPKDTLMISRTPEVTCVVVDVSQ EDPEVQFNWYVDGVEVHNAKTKPREEQFNSTYRVVSVLTVLHQDWL NGKEYKCKVSNKGLPSSIEKTISKAKGQPREPQVYTLPPSQEEMTKNQV SLTCLVKGFYPSDIAVEWESNGQPENNYKTTPPVLDSDGSFFLYSRLTV DKSRWQEGNVFSCSVMHEALHNHYTQKSLSLSLGK |
| 200 IgG4 heavy chain constant region | Heavy Chain Constant Region Nucleotide Sequence — Synthetic Version B | gcctccaccaaggggcctagcgtgttccctctcgccccctgtgttccaggtccacaagcgagtccaccgtgcct cggctgtctggtgaaagactacttccccgagcccgtgaccgtctcctggaatagcggagcctgacctccggcgt gcacacattccccgctgaccagcagcgactgtatagcctgagcagcgtggtgaccgtgccagctccca gctcggcaccaaaacctacacctgcaacgtggaccacaagccctccaacaccaaggtggacaagcgggtgg agagcaagtacggccccccctgcccttcctgccctgagttcgaggggggaccctccgttcctgttcc cccaaaccaaggacaccctgatgatctccggacaccgagtgacctgtgtggtcgtggacgtcagcag gaggacccgaggtgcagttcaattgtatgtgacggtgagcgtgcacaaccaaagcttccaag gaggacaagtgcaagtgtccaactacaaggtgtgagcgtgctccagtcccctgaagacatcagcagctaagg ccagtggagggagccagtgtataccccatcctagcaggaagatgaccaagacacaagtgctcctg acctgctggtgaaggattctaccctcctgacagccgcaataccgtggagtgaagcaatgccagccccgagaaca actacaaaacaaccctccccgtcgtctcccgtctgatgcacgaggccctgcacaattactactaccaccagaag gcagtggcagagggcaacgtgttctcctgttccgtgatgcacgaggccctgcacaattactactaccaccagaag agcctctccctgtccctgggcaag |
| 201 IgG4 heavy chain constant region | Heavy Chain Constant Region Nucleotide Sequence — Synthetic Version C | gccagcaccaaggggccttccgtgttccccctggcctgcagcaggagcacctcgaatccacagtgcct gggctgtctggtgaaggactacttccccgagcccgtgaccgtgagctggaacagcggcctgacatccggcg tccacacctttccctgccgtccagtcctccgtggacagcagcgtgaccgtgccctccagcagcctgggcacccag acctacacctgcaacgtgaaccacaagcccagcaacaccaaggtggacaagagagttgaga gcaagtacggcccctcctgccctccgattcgaaggggccccagcgtctgttccctcc taagccaaggacaccctcatgatcagcggacaccgagtgacctgcgttggtgtgatgtgagccagag gacctgaggtccagtcaactggatggtgcagcgtggtgagcgtgcacaacgccaagacccggaag agcagtcaactccactacaaggtggtcagcgtgctcaccgtcctgcatcaggactggctgaacggcaagga gtacaagtgcaaggtgcaataagggacctccaagcagaccatctccaaggctaaagcca gccccggaacctcagtgtacaccctcctcgacagcgacgatccttttctgtactccaggctgaccgtggataagtccag atagaccaccctccggtcctgcagtcgtccggatgaccgtcccaataccactactaccccagaagtccc gtggcaggagcaagtgtcagctgctcgacgtggagaaccgcagagcccagcaacacaagtcccgacagtagcag ctgagcctcctgctccctgggaaag |
| 202 IgG4 heavy chain constant region | Heavy Chain Constant Region Nucleotide Sequence — Synthetic Version D | gcctccaccaagggaccatccgtcttcccccctggcgccccctgctccaggagcaccggccccgacctccag cgtcaacctcccggctgtctcccagtcctcaggactcctcagacctactcctcagcagccgtgctgctcagagtt cagcttgggcacgaagaccatcaccaggcaccatcacctaagagcccgtatgtcccccaaacatggccc cccaaaacccaaggacaccctcatgatctcccgagccctgaggtcagcgtggtggtggacgtgagccca ggaagacccgaggtccagttcaactggtacgtggatggcgtggagtgcataatgccaagacaaagccgcg ggggagcagttcaacagcacgtaccgtgtggtcagcgtcctcaccgtcctcgagacccaagaaatgactggctgaatggcaaggag tacaagtgcaaggtcttcaacaaagccctcccagccccatcgatgagaaaccatctccaaagccaag gcaggcccgagagccacaggtgtacaccctgccccccatcccgggagggaagatgaccaagaaccaggtcagc |

-continued

SEQUENCE LISTING

| SEQ ID NO: | Name | Description | Sequence |
|---|---|---|---|
| 203 | | Heavy Chain Constant Region Amino Acid Sequence - encoded by Synthetic Version D | ctgacctgcctggtcaaaggcttctacccagcgacatcgccgtggagtgggagagcaatgggcagccggaga acaactacaagaccacgcctcccgtgctggactccgacggctccttcttcctctacagcaggctaaccgtggaca agagcaggtggcaggagggggaatgtcttctcatgctccgtgatgcatgaggctctgcacaaccactacacacag aagagcctctccctgtctctgggtaaa<br><br>ASTKGPSVFPLAPCSRSTSESTAALGCLVKDYFPEPVTVSWNSGALTSG VHTFPAVLQSSGLYSLSSVVTVPSSSLGTKTYTCNVDHKPSNTKVDKRV ESKYGPPCPPCPAPPVAGGPSVFLFPPKPKDTLMISRTPEVTCVVVDVSQ EDPEVQFNWYVDGVEVHNAKTKPREEQFNSTYRVVSVLTVLHQDWL NGKEYKCKVSNKGLPSSIEKTISKAKGQPREPQVYTLPPSQEEMTKNQV SLTCLVKGFYPSDIAVEWESNGQPENNYKTTPPVLDSDGSFFLYSRLTV DKSRWQEGNVFSCSVMHEALHNHYTQKSLSLSLGK |
| 204 | Disabled Human IgG1 heavy chain constant region | Heavy Chain Constant Region Nucleotide Sequence | gcctcaccaagggcccatcggtcttcccccctggcaccctcctccaagagcacctctgggggcacagcggcc ctgggctgcctggtcaaggactacttccccgaaccggtgacggtgtcgtggaactcaggcgccctgaccagcgg cgtgcacaccttcccggctgtcctacagtcctcaggactctactccctcagcagcgtggtgaccgtgccctccag cagcttgggcacccagacctacatctgcaacgtgaatcacaagcccagcaacaccaaggtggacaagaaagtg gagcccaaatcttgtgacaaaactcacacatgcccaccgtgcccagcacctgaactcctggggggaccgtcagt cttcctcttcccccccaaaaccaaggacaccctcatgatctcccggacccctgaggtcacatgcgtggtggtgga cgtgagccacgaagaccctgaggtcaagttcaactggtacgtggacggcgtggaggtgcataatgccaagacaa agccgcgggaggagcagtacaacagcacgtaccgtgtggtcagcgtcctcaccgtcctgcaccaggactgg ctgaatggcaaggagtacaagtgcaaggtctccaacaaagccctcccagcccccatcgagaaaaccatctccaa agccaaagggcagccccgagaaccacaggtgtacaccctgccccatcccgggatgagctgaccaagaacca ggtcagcctgacctgcctggtcaaaggcttctatcccagcgacatcgccgtggagtgggagagcaatgggcag ccggagaacaactacaagaccacgcctcccgtgctggactccgacggctccttcttcctctacagcaagctcacc gtggacaagagcaggtggcagcaggggaacgtcttctcatgctccgtgatgcatgaggctctgcacaaccacta cacgcagaagagcctctccctgtctccgggtaaa |
| 205 | | Heavy Chain Constant Region Amino Acid Sequence | ASTKGPSVFPLAPSSKSTSGGTAALGCLVKDYFPEPVTVSWNSGALTSG VHTFPAVLQSSGLYSLSSVVTVPSSSLGTQTYICNVNHKPSNTKVDKKV EPKSCDKTHTCPPCPAPELAGAPSVFLFPPKPKDTLMISRTPEVTCVVVD VSHEDPEVKFNWYVDGVEVHNAKTKPREEQYNSTYRVVSVLTVLHQD WLNGKEYKCKVSNKALPAPIEKTISKAKGQPREPQVYTLPPSRDELTKN QVSLTCLVKGFYPSDIAVEWESNGQPENNYKTTPPVLDSDGSFFLYSKL TVDKSRWQQGNVFSCSVMHEALHNHYTQKSLSLSPGK |
| 206 | Human Cκ constant region | Cκ Light Chain Constant Region Nucleotide Sequence | cgtacggtggccgctcccctccgtgttcatcttcccaccttccgatgagcagcagttgaaagtgaaggtggacaacgcgctctgtcg tgtgcctgctgaacaacttctaccccgcgaggccaaagtgcagtggaaggtggacaacgccctccaatcgggt caactcccaggaatccgtgaccgagcaggacagcaaggacagcacctacctcctccagttcctccccgacctgt ccaagtccgactacgagaagcacaaagtgtacgcctgcgaagtgacccaccccaggcgctgtccagcccgtga ccaagtcttcaacaggggcgagtgt |
| 207 | | Cκ Light Chain Constant Region Amino Acid Sequence | RTVAAPSVFIFPPSDEQLKSGTASVVCLLNNFYPREAKVQWKVDNALQ SGNSQESVTEQDSKDSTYSLSSTLTLSKADYEKHKVYACEVTHQGLSSP VTKSFNRGEC |

| | IGKC*01 | | |

SEQUENCE LISTING

| SEQ ID NO: | Name | Description | Sequence |
|---|---|---|---|
| 208 | Human Cκ constant region IGKC*02 | Cκ Light Chain Constant Region Nucleotide Sequence | cgaactgtggctgcaccatctgtcttcatcttcccgccatctgatgagcagtt-gaaatctggaactgcctctgttgtgtgcctgctgaataacttctcagagcaggagagcaaagtacagtggaaggtgataacgccctccaatcggtaactcccagagagactacgagaaacacaaagtctacgcctgcgaagtcaccatcagcagcctgagcaaagcagactacgagaaacacaaagtctacgcctgcgaagtcacccatcagggcctgagctcgcccgtcacaaagagcttcaacaggggagagtgt |
| 209 | | Cκ Light Chain Constant Region Amino Acid Sequence | RTVAAPSVFIFPPSDEQLKSGTASVVCLLNNFYPREAKVQWKVDNALQSGNSQESVTEQDSKDSTYSLSSTLTLSKADYEKHKVYAGEVTHQGLSSP |
| 210 | Human Cκ constant region IGKC*03 | Cκ Light Chain Constant Region Nucleotide Sequence | cgaactgtggctgcaccatctgtcttcatctcccgccatctgatgagcagtt-gaaatctggaactgcctctgttgtgtgcctgctgaataacttctcagagcaggagagcaaagtacagtggaaggtgataacgccctccaatcggtaactcccagagagtgtcagcaggacagcaggacagcagcacctacagcctcagcagcaccctgacgctgagcaaagcagactacgagaaacacaaagtctacgcctgcgaagtcaccatcagggcctcgagctcgcccgtcacaaagagcttcaacaggggagagtgt |
| 211 | | Cκ Light Chain Constant Region Amino Acid Sequence | RTVAAPSVFIFPPSDEQLKSGTASVVCLLNNFYPREAKVQRKVDNALQGNSQESVTEQDSKDSTYSLSSTLTLSKADYEKHKVYACEVTHQGLSSPVTKSFNRGEC |
| 212 | Human Cκ constant region IGKC*04 | Cκ Light Chain Constant Region Nucleotide Sequence | cgaactgtggctgcaccatctgtcttcatttcccgccatctgatgagcagtt-gaaatctggaactgcctctgttgtgtgcctgctgaataacttctcagagcaggagagcaaagtacagtggaaggtgataacgccctccaatcggtaactcccagagagactacgagaaacacaaagtctacgcctgcgaagtcaccatcagggcctcgagctcgcccgtcacaaagagcttcaacaggggagagtgt |
| 213 | | Cκ Light Chain Constant Region Amino Acid Sequence | RTVAAPSVFIFPPSDEQLKSGTASVVCLLNNFYPREAKVQWKVDNALQSGNSQESVTEQDSKDSTYSLSSTLTLSKADYEKHKLYACEVTHQGLSSPVTKSFNRGEC |
| 214 | Human Cκ constant region IGKC*05 | Cκ Light Chain Constant Region Nucleotide Sequence | cgaactgtggctgcaccatctgtcttcatttcccgccatctgatgagcagtt-gaaatctggaactgcctctgttgtgtgcctgctgaataacttctcagagcaggagagcaaagtacagtggaaggtgataacgccctccaatcggtaactcccagagagactacgagaaacacaaagtctacgcctgcgaagtcaccatcagggcctcgagctcgcccgtcacaaagagcagactacgagaaacacaaagtctacgcctgcgaagtcaccatcagggcctcgagctcgcccgtcacaaagagcttcaacaggggagagtgc |
| 215 | | Cκ Light Chain Constant Region Amino Acid Sequence | RTVAAPSVFIFPPSDEQLKSGTASVVCLLNNFYPREAKVQWKVDNALQSGNSQESVTEQDSKDSTYSLSNTLTLSKADYEKHKVYACEVTHQGLSSPVTKSFNRGEC |
| 216 | Human Cλ constant region IGCλ1*01 | Cλ Light Chain Constant Region Nucleotide Sequence | cccaaggccaaccccactgttccgccctcctgaggagctccaagccacactagtgtgcctgatcgactctcacccggagctgtgacagtgcttgaagcagtggcagatggcagccccgtcaaggcgggagtggagaccgaccaaaccccaacagagagccagcagcactgagcgctgagcccgagcactgcagtcgaagtgccaagagagctaccctacggcagctgccaggtcaaggcgacgccgagcagtggaagacagaccctacggcaggcatgtagtgccaggtcgccaggtcacggtgaccgtgccccagcaacctcgacgtgggccctacagaatgttca |

SEQUENCE LISTING

| SEQ ID NO:Name | Description | Sequence |
|---|---|---|
| 217 Human Cλ constant region | Cλ Light Chain Constant Region Amino Acid Sequence | PKANPTVTLFPPSSEELQANKATLVCLISDFYPGAVTVAWKADGSPVK AGVETTKPSKQSNNKYAASSYLSLTPEQWKSHRSYSCQVTHEGSTVEK TVAPTECS |
| 218 IGCλ1*02 | Cλ Light Chain Constant Region Nucleotide Sequence | ggtcagcccaaggccaaccccactgtcactctgttcccgccctcctctgaggagctcca actagtgtctgatcagtgactcttacccggagctgtgacagtggctgaaggcagatggcagcccgtcaa gcgggagtggagaccaacaaccctccaaacagagcaacaacagtcccacagaagctacagctgccagtgacctggcc tgacgcccgagcagtggaagtcccacagaagctacagctgccagtgcacgtcaccgtgaaggagcaccgtggaga agacagtggccctacagaatgttca |
| 219 | Cλ Light Chain Constant Region Amino Acid Sequence | GQPKANPTVTLFPPSSEELQANKATLVCLISDFYPGAVTTVAWKADGSP VKAGVETTKPSKQSNNKYAASSYLSLTPEQWKSHRSYSCQVTHEGSTV EKTVAPTECS |
| 220 IGCλ2*01 | Cλ Light Chain Constant Region Nucleotide Sequence – Version A | ggtcagcccaaggccaaccccactgtcactctgttcccgccctcctctgaggagctcca actagtgtctgatcagtgactcctacccggagctgtgaagcagtggcagcccctgagcc gcgggagtggagaccaacaaccctccaaacagagcaactacagctgccagtcccaggagcagtggcagcagcagctgagcc tgacgcccgagcagtggaagtcccacagaagctacagctgccaggtcaccgtgaaggagcaccgtggaga agacagtggccctacagaatgttca |
| 221 | Cλ Light Chain Constant Region Nucleotide Sequence – Version B | ggccagcctaaggccgctccttctgtgacccgtcccttgaccctgaccggccgactgacccaccctcctgaggaactgcaggctaacaagccac cctcgtgctgacagcgactttacccgtgcgggctggaaggctgatagtctcctgtgaa ggccggctgaaaccaccccttccaagcgtcctacagctgccaggtgaccaaccgccgaagtgaccaccgaggctgccaccctgtcctga ccctgagcagtggaagtcccacgtgtcctactcctgtcaggtgaccaccgaggctccaccgtgaaagac cgtggctcctaccggtgctcc |
| 222 | Cλ Light Chain Constant Region Nucleotide Sequence – Version C | ggccagcctaaagtgccccgagcgtcaccctgttccctccctcagcggaggagctccaggcggcaggcaacaaggcca cccctgtgctgctgactctcgactctgtctatccggcctgtgaccgctgtgaaagcgctgggaaagccgactccagccccctgtcaa agcggggtggagaccaacaccctccaagcagtccaacaaagtaccgccgtccagctactctcctcctga ccctgagcagtggaagtcccacgtgtcctactcctgtcaggtgaccaccgaggctccaccgtgaaagac cgtgccccaccgagtgctcc |
| 223 | Cλ Light Chain Constant Region Amino Acid Sequence – Encoded by Version A, B & C | GQPKANPTVTLFPPSSEELQANKATLVCLISDFYPGAVTVAWKADGSP VKAGVETTKPSKQSNNKYAASSYLSLTPEQWKSHRSYSCQVTHEGSTV EKTVAPTECS |
| 224 IGCλ2*02 | Cλ Light Chain Constant Region Nucleotide Sequence | ggtcagcccaaggctgccccctgtcctcctgttcccgccctcctctgaggagctcaaggccaacaaggccac actgtgtgctccataagtgacttctacccggacgtgcacagtggccctgaaggcagatagcagcccgtca acgcggagtggagaccaacaaccctccaaacaagctacaacaagtacgcggcagcagcagctatctgagcc tgacgcctgagcagtggaagtcccacagaagctacacgccgtgcaggtcaccgtgaaggagcaccgtggaga agacagtggccctacagaatgttca |
| 225 | Cλ Light Chain Constant Region Amino Acid Sequence | GQPKAAPSVTLFPPSSEELQANKATLVCLISDFYPGAVTVAWKADSSPV KAGVETTPSKQSNNKYAASSYLSLTPEQWKSHRSYSCQVTHEGSTVE KTVAPTECS |

| SEQ ID NO:Name | | Description | Sequence |
|---|---|---|---|
| 226 | Human Cλ constant region IGCλ*01 | Cλ Light Chain Constant Region Nucleotide Sequence | cccaaggctgccccctcggtcactctgttcccaccctcctctgaggagcttcaagccaacaaggccacactggtg tgtcttcataagtgacttctacccggagacgtgacagttgcctgaaggcagatagcagcccctcaaggcggg ggtggagaccaccacctccaaacaaagcaacaaagctacagctgccggtcacgtcacgccatgagctgagc tgagcagtgaagtcccaacagctacagctgccggtcacgtgaaggagcaccgtggagaacagt tgccctacggaatgttca |
| 227 | | Cλ Light Chain Constant Region Amino Acid Sequence | PKAAPSVTLFPPSSEELQANKATLVCLISDFYPGAVTVAWKADSSPVKA GVETTTPSKQSNNKYAASSYLSLTPEQWKSHKSYSCQVTHEGSTVEKT VAPTECS |
| 228 | Human Cλ constant region IGCλ*02 | Cλ Light Chain Constant Region Nucleotide Sequence | ggtcagcccaaggctgccccctcggtcactcttgttcccaccctcctgaggagctcctccaagccaacaaggccccgtcaa actggtgtgtctcataagtgacttctacccgggacagtgacagtgcctgaaggcagatagcagcccctgagcc gcgggggtgaaccaccaccctccaaacaaagcaacaaagctacagctgccggtcagcagtctactgagc tgacgcctgagcagtggaagtcccacaaagctacagctgccggtcacgtgaaggagcaccgtggaga agacagtggccctacggaatgttca |
| 229 | | Cλ Light Chain Constant Region Amino Acid Sequence | GQPKAAPSVTLFPPSSEELQANKATLVCLISDFYPGPVTVAWKADSSPV KAGVETTTPSKQSNNKYAASSYLSLTPEQWKSHKSYSCQVTHEGSTVE KTVAPTECS |
| 230 | Human Cλ constant region IGCλ*03 | Cλ Light Chain Constant Region Nucleotide Sequence | ggtcagcccaaggctgccccctcggtcactctgttcccaccctcctctgaggagcttcaagccaacaaggccac actggtgtgtctcataagtgacttctacccggagactggctgaaggccgcagatagcagcccctgtca aggcgggagttggagaccaccaccctccaaacaacaaagctacagctgccagtctactgagc ctgacgcctgagcctgagcagtggaagtcccaaacaagctacagctgccagtcacgtcacgcatgaaggagcaccgtggag aagacagtggccctacagaatgttca |
| 231 | | Cλ Light Chain Constant Region Amino Acid Sequence | GQPKAAPSVTLFPPSSEELQANKATLVCLISDFYPGAVTVAWKADSSPV KAGVETTTPSKQSNNKYAASSYLSLTPEQWKSHKSYSCQVTHEGSTVE KTVAPTECS |
| 232 | Human Cλ constant region IGCλ*04 | Cλ Light Chain Constant Region Nucleotide Sequence | ggtcagcccaaggctgccccctcggtcactctgttccgccctcctgaggagcttcaagccaacaaggccac actggtgtgtctcataagtgacttctacccgggagccgtgacagtggcctgaaggcagatagcagcccctgagc aggcgggagttggagaccaccaccctccaaacaagcaacaagctacagctgccagtcagcagctacctgagc ctgacgcctgagcctgagcagtggaagtcccaaagctacagctgccagtcacgtcacgcatgaaggagcaccgtggag aagacagtggccctacagaatgttca |
| 233 | | Cλ Light Chain Constant Region Amino Acid Sequence | GQPKAAPSVTLFPPSSEELQANKATLVCLISDFYPGAVTVAWKADSSPV KAGVETTTPSKQSNNKYAASSYLSLTPEQWKSHRSYSCQVTHEGSTVE KTVAPTECS |
| 234 | Human Cλ constant region IGCλ6*01 | Cλ Light Chain Constant Region Nucleotide Sequence | ggtcagcccaaggctgcccatcggtcactcttgttccgccctcctgaggagctcctccaagccaacaaggccacgtca actggtgtgctgatcagtgacttctacccgggagctgaaagtggcctgaaggcagatggcagcccctgtca acacggggtggagaccaccaccctccaaacaagcaacaaagctacagctgccagtcagcagctacctgagc ctgacgcctgagcagtggaagtcccacagaagctacagctgccagtcacgtcacgcatgaaggagcaccgtggag aagacagtggccctgcagaatgttca |

| SEQ ID NO:Name | Description | Sequence |
|---|---|---|
| 235 | Cλ Light Chain Constant Region Amino Acid Sequence | GQPKAAPSVTLFPPSSEELQANKATLVCLISDFYPGAVKVAWKADGSP VNTGVETTTPSKQSNNKYAASSYLSLTPEQWKSHRSYSCQVTHEGSTV EKTVAPAECS |
| 236 | Human Cλ IGCλ7*02 constant region Cλ Light Chain Constant Region Nucleotide Sequence | ggtcagcccaaggctgccccatcggtcactctgttcccaccctcctctgaggagcttcaagccaacaaggccac actggtgtctctgtaagtgacttctaccgggagccgtgacagtgcctggctggaaggcagatggcagcccgtca agtgggagtggagaccaccaaaccctccaaacagagcaacaacaagtacgcggccagcagctacctgagcc tgacgcccgagcagtggaagtcccacagaagctacagctgccaggtcacgcatgaagggagcaccgtggag aagacagtggcccctgcagaatgctct |
| 237 | Cλ Light Chain Constant Region Amino Acid Sequence | GQPKAAPSVTLFPPSSEELQANKATLVCLVSDFYPGAVTVAWKADGSP VKVGVETTKPSKQSNNKYAASSYLSLTPEQWKSHRSYSCRVTHEGSTV EKTVAPAECS |
| 238 | 413G05 – CDRH1 (IMGT) Amino acid sequence of CDRH1 of 413G05 using IMGT | GFTFSDYY |
| 239 | 413G05 – CDRH2 (IMGT) Amino acid sequence of CDRH2 of 413G05 using IMGT | ISTSGSTI |
| 240 | 413G05 – CDRH3 (IMGT) Amino acid sequence of CDRH3 of 413G05 using IMGT | ARGITGTNFYHYGLGV |
| 241 | 413G05 – CDRH1 (Kabat) Amino acid sequence of CDRH1 of 413G05 using Kabat | DYYMS |
| 242 | 413G05 – CDRH2 (Kabat) Amino acid sequence of CDRH2 of 413G05 using Kabat | YISTSGSTIYYADSVKG |
| 243 | 413G05 – CDRH3 (Kabat) Amino acid sequence of CDRH3 of 413G05 using Kabat | GITGTNFYHYGLGV |
| 244 | 413G05 – Heavy chain variable region Amino acid sequence of V_H of 413G05 | QVQLVESGGGLVKPGGSLRLSCAASGFTFSDYYMSWIRQVPGKGLEW VSYISTSGSTIYYADSVKGRFTISRDNAKNSLYLQMNSLRAEDAAVYHC ARGITGTNFYHYGLGVWGQGTTVTVSS |
| 245 | 413G05 – Heavy chain variable region Nucleic acid sequence of V_H of 413G05 | CAGGTCCAGCTTGGTGGAGTCTGGGGGAGGCTTGGTCAAGCCTGGAG GGTCCCTGAGACTCTCCTGTGCAGCCTCTGGATTCACCTTCAGTGAC TACTACATGAGCTGGATCCGCCAGGTTCCAGGGAAGGGGCTGGAGT GGGTTTCATACATTAGTACTAGTGGTAGTACCATATACTACGCAGAC TCTGTGAAGGGCCGATTCACCATCTCCAGGGACAACGCCAAGAACT CACTGTATCTACAAATGAACAGCCTGAGAGCCGAGGACGCGGCCGT GTATCACTGTGCGAGAGGTATAACTGGAACTAACTTCTACCACTACG GTTTGGGCGTCTGGGGCCAAGGGACCACGGTCACCGTCTCCTCAG |
| 246 | 413G05 – full heavy chain sequence Amino acid sequence of 413G05 heavy chain | QVQLVESGGGLVKPGGSLRLSCAASGFTFSDYYMSWIRQVPGKGLEW VSYISTSGSTIYYADSVKGRFTISRDNAKNSLYLQMNSLRAEDAAVYHC ARGITGTNFYHYGLGVWGQGTTVTVSSASTKGPSVFPLAPSSKSTSGGT |

SEQUENCE LISTING

| SEQ ID NO: | Name | Description | Sequence |
|---|---|---|---|
| | | | AALGCLVKDYFPEPVTVSWNSGALTSGVHTFPAVLQSSGLYSLSSVVT VPSSSLGTQTYICNVNHKPSNTKVDKKVEPKSCDKTHTCPPCPAPELLG GPSVFLFPPKPKDTLMISRTPEVTCVVVDVSHEDPEVKFNWYVDGVEV HNAKTKPREEQYNSTYRVVSVLTVLHQDWLNGKEYKCKVSNKALPAP IEKTISKAKGQPREPQVYTLPPSRDELTKNQVSLTCLVKGFYPSDIAVEW ESNGQPENNYKTTPPVLDSDGSFFLYSKLTVDKSRWQQGNVFSCSVMH EALHNHYTQKSLSLSPGK |
| 247 | 413G05 – full heavy chain sequence | Nucleic acid sequence of 413G05 heavy chain | CAGGTCAGCTGGTGGAGTCTGGGGGAGGCTTGGTCAAGCCTGGAG GGTCCCTGAGACTCTCCTGTGCAGCCTCTGGATTCACCTTCAGTGAC TACTACATGAGCTGGATCCGCCAGGTTCCAGGGAAGGGGCTGGAGT GGGTTTCATACATTAGTACTAGTGGTAGTACCATATACTACGCAGAC TCTGTGAAGGGCCGATTCACCATCTCCAGGGACAACGCCAAGAACT CACTGTATCTACAAATGAACAGCCTGAGAGCCGAGGACACGGCCGT GTATCACTGTGCGAGAGGTATAACTGGAACTAACTTCTACCACTACG GTTTGGGCGTCTGGGGCCAAGGGACCACGGTCACCGTCTCCTCAGC CAGCACCAAGGGCCCCTCTGTTCCCTCTGGCCTCCTGCCCTCCAAGT CCACCTCTGGCGGAACAGCCGCTCTGGGCTGCCTGGTGAAGGACTA CTTCCCCGAGCCTGTGACCGTGTCCTGGAACTCTGGCGCTCTGACCA GCGGAGTGCACACCTTCCCTGCTGTGCTGCAGTCCTCCGGCCTGTAC TCCCTGTCCTCCGTGGTGACCGTGCCTTCCAGCTCCTCTGGGCACCCA GACTACATCTGCAACGTGAACCAAGTCCTGCGACAAGAACCACCTGTC CCCCTTGTCTGCCCCTGAACTCCTGGGCCGGACCTTCCGTGTTCCTG TTCCCCCCAAAGCCCAAGGACACCCTGATGATCTCCCGAGACCCCG AAGTGACCTGCGTGGTGGTGGATGTGTCCCACGAGGAGTGCACAACGCCAAG ACCAAGCCTAGAGAGGAACAGTACAACTCCACCTACCGGGTGGTGT CCGTGCTGACCGTGCTGCACCAGGATTGGCTGAACGGCAAAGAGTA CAAGTGCAAGTGTCCAACAAGGCCCTGCCTGCCCCCATCGAAAAG ACCATCTCCAAGGCCAAGGGCCAGCCCCGGGAACCCAGGTGTACA CACTGCCCCCTAGCAGGGACGAGCTGACCAAGAACCAAGGTGTCCCT GACCTGTCTCGTGAAAGGCTTCTACCCCTCCGATATGCCGTGGAAT GGGAGTCCAACGGCCAGCCTGAGAACAACTACAAGACCACCCCCC TGTGCTGGACTCCGACGGCTCATTCTTCCTGTACAGCAAGCTGACAG TGGACAAGTCCCGGTGGCAGCAGGGCAACGTGTTCTCCTGCTCCGT GATGCACGAGGCCCTGCACAACCACTACACCCAGAAGTCCCTGTCC CTGAGCCCCGGCAAG |
| 248 | 413G05 – CDRL1 (IMGT) | Amino acid sequence of CDRL1 of 413G05 using IMGT | QGINSW |
| 249 | 413G05 – CDRL2 (IMGT) | Amino acid sequence of CDRL2 of 413G05 using IMGT | AAS |
| 250 | 413G05 – CDRL3 (IMGT) | Amino acid sequence of CDRL3 of 413G05 using IMGT | QQVNSFPLT |

| SEQ ID NO: | Name | Description | Sequence |
|---|---|---|---|
| 251 | 413G05 – CDRL1 (Kabat) | Amino acid sequence of CDRL1 of 413G05 using Kabat | RASQGINSWLA |
| 252 | 413G05 – CDRL2 (Kabat) | Amino acid sequence of CDRL2 of 413G05 using Kabat | AASTLQS |
| 253 | 413G05 – CDRL3 (Kabat) | Amino acid sequence of CDRL3 of 413G05 using Kabat | QQVNSFPLT |
| 254 | 413G05 – Light chain variable region | Amino acid sequence of $V_L$ of 413G05 | DIQMTQSPSSVSASVGDRVTITCRASQGINSWLAWYQQKPGKAPKLLIY AASTLQSGVPSRFSGSGSGADFTLTISSLQPEDFATYYCQQVNSFPLTFG GGTKVEIK |
| 255 | 413G05 – Light chain variable region | Nucleic acid sequence of $V_L$ of 413G05 | GACATCCAGATGACCCAGTCTCCATCTTCCGTGTCTGCATCTGTAGG AGACAGAGTCACCATCACTTGTCGGGCGAGTCAGGGTATTAACAGC TGGTTAGCCTGGTATCAGCAGAAACCAGGGAAAGCCCCTAAGCTCC TGATCTATGCTGCATCCACTTTGCAAAGTGGGGTCCCATCAAGGTTC AGCGGCAGTGGGTCTGGGACAGATTTCACTCTCACCATCAGCAGCC TGCAGCCTGAAGATTTTGCAACTTACTATTGTCAACAGGTTAACAGT TTCCCGCTCACTTTCGGCGGAGGGACCAAGGTGGAGATCAAAC |
| 256 | 413G05 – full light chain sequence | Amino acid sequence of 413G05 light chain | DIQMTQSPSSVSASVGDRVTITCRASQGINSWLAWYQQKPGKAPKLLIY AASTLQSGVPSRFSGSGSGADFTLTISSLQPEDFATYYCQQVNSFPLTFG GGTKVEIKRTVAAPSVFIFPPSDEQLKSGTASVVCLLNNFYPREAKVQW KVDNALQSGNSQESVTEQDSKDSTYSLSSTLTLSKADYEKHKVYACEV THQGLSSPVTKSFNRGEC |
| 257 | 413G05 – full light chain sequence | Nucleic acid sequence of 413G05 light chain | GACATCCAGATGACCCAGTCTCCATCTTCCGTGTCTGCATCTGTAGG AGACAGAGTCACCATCACTTGTCGGGCGAGTCAGGGTATTAACAGC TGGTTAGCCTGGTATCAGCAGAAACCAGGGAAAGCCCCTAAGCTCC TGATCTATGCTGCATCCACTTTGCAAAGTGGGGTCCCATCAAGGTTC AGCGGCAGTGGGTCTGGGACAGATTTCACTCTCACCATCAGCAGCC TGCAGCCTGAAGATTTTGCAACTTACTATTGTCAACAGGTTAACAGT TTCCCGCTCACTTTCGGCGGAGGGACCAAGGTGGAGATCAAACGTA CGGTGGCCGCTCCCTCCGTTCATCTTCCCACCTTCCGACGAGCAG CTGAAGTCCGGAACCGCCTCTGTCGTGTGCCTGCTGAACAACTTCTA CCCCCGCGAGGCCAAGGTGCAGTGGAAGGTGGACAACGCCCTGCAG AGCGGCAACTCCCAGGAATCCGTGACCGAGCAGGACTCCAAGGACA GCACCTACTCCCTGTCCTCCACCCTGACCCTGTCCAAGGCCGACTAC GAGAAGCACAAGGTGTACGCCTGCGAAGTGACCCACCAGGGCCTGT CTAGCCCCGTGACCAAGTCTTTCAACCGGGGCGAGTGT |
| 258 | 413F09 – CDRH1 (IMGT) | Amino acid sequence of CDRH1 of 413F09 using IMGT | GFTFSYYA |
| 259 | 413F09 – CDRH2 (IMGT) | Amino acid sequence of CDRH2 of 413F09 using IMGT | ISGGGNT |

| SEQ ID NO: | Name | Description | Sequence |
|---|---|---|---|
| 260 | 413F09 – CDRH3 (IMGT) | Amino acid sequence of CDRH3 of 413F09 using IMGT | AKDRMKQLVRAYYFDY |
| 261 | 413F09 – CDRH1 (Kabat) | Amino acid sequence of CDRH1 of 413F09 using Kabat | YYAMS |
| 262 | 413F09 – CDRH2 (Kabat) | Amino acid sequence of CDRH2 of 413F09 using Kabat | TISGGGNTHYADSVKG |
| 263 | 413F09 – CDRH3 (Kabat) | Amino acid sequence of CDRH3 of 413F09 using Kabat | DRMKQLVRAYYFDY |
| 264 | 413F09 – Heavy chain variable region | Amino acid sequence of V<sub>H</sub> of 413F09 | EVPLVESGGGLVQPGGSLRLSCAASGFTFSYYAMSWVRQAPGKGLDW VSTISGGGNTHYADSVKGRFTISRDNSKNTLYLHMNSLRAEDTAVYY CAKDRMKQLVRAYYFDYWGQGTLVTVSS |
| 265 | 413F09 – Heavy chain variable region | Nucleic acid sequence of V<sub>H</sub> of 413F09 | GAGGTGCCGCTGGTGAGTCTGGGGGAGGCTTGGTACAGCCTGGGG GGTCCCTGAGACTCTCCTGTGCAGCCTCTGGATTCACGTTTAGCTAC TATGCCATGAGCTGGGTCCGTCAGGCTCCAGGGAAGGGGCTGGACT GGGTCTCAACTATTAGTGGTGGTGGTAACACACTACGCAGA CTCCGTGAAGGGCCGATTCACTATATCCAGAGACAATTCCAAGAAC ACGCTGTATCTGCACATGAACAGCCTGAGAGCCGAAGACACGGCCG TCTATTACTGTGCGAAGGATCGGATGAAACAGCTCGTCCGGGCCTA CTACTTTGACTACTGGGGCCAGGGAACCCTGGTCACCGTCTCCTCAG |
| 266 | 413F09 – full heavy chain sequence | Amino acid sequence of 413F09 heavy chain | EVPLVESGGGLVQPGGSLRLSCAASGFTFSYYAMSWVRQAPGKGLDW VSTISGGGNTHYADSVKGRFTISRDNSKNTLYLHMNSLRAEDTAVYY CAKDRMKQLVRAYYFDYWGQGTLVTVSSASTKGPSVFPLAPSSKSTSG GTAALGCLVKDYFPEPVTVSWNSGALTSGVHTFPAVLQSSGLYSLSSV VTVPSSSLGTQTYICNVNHKPSNTKVDKKVEPKSCDKTHTCPPCPAPEL LGGPSVFLFPPKPKDTLMISRTPEVTCVVVDVSHEDPEVKFNWYVDGV EVHNAKTKPREEQYNSTYRVVSVLTVLHQDWLNGKEYKCKVSNKALP APIEKTISKAKGQPREPQVYTLPPSRDELTKNQVSLTCLVKGFYPSDIAV EWESNGQPENNYKTTPPVLDSDGSFFLYSKLTVDKSRWQQGNVFSCSV MHEALHNHYTQKSLSLSPGK |
| 267 | 413F09 – full heavy chain sequence | Nucleic acid sequence of 413F09 heavy chain | GAGGTGCCGCTGGTGAGTCTGGGGGAGGCTTGGTACAGCCTGGGG GGTCCCTGAGACTCTCCTGTGCAGCCTCTGGATTCACGTTTAGCTAC TATGCCATGAGCTGGGTCCGTCAGGCTCCAGGGAAGGGGCTGGACT GGGTCTCAACTATTAGTGGTGGTGGTAACACACTACGCAGA CTCCGTGAAGGGCCGATTCACTATATCCAGAGACAATTCCAAGAAC ACGCTGTATCTGCACATGAACAGCCTGAGAGCCGAAGACACGGCCG TCTATTACTGTGCGAAGGATCGGATGAAACAGCTCGTCCGGGCCTA CTACTTTGACTACTGGGGCCAGGGAACCCTGGTCACCGTCTCCTCAG CCAGCACCAAGGGCCCCTCTGTTCCCCTGGCCCCCTTCCAGCAAG TCCACCTCTGGCGCGGAACAGCGGCTCTGGGCTGCCTCGTGAAGGACT ACTTCCCCGAGCCTGTGACCGTGTCCTGGAACTCTGGCGCTCTGACC AGCGGAGTGCACACCTTCCCTGCTGTGCTGCAGTCCTCCGGCCTGTA CTCCCTGTCCCCGTCGTGACCGTGCCTTCCAGCTCTTCCAGCTCTGGGCACCC |

-continued

SEQUENCE LISTING

| SEQ ID NO:Name | Description | Sequence |
|---|---|---|
| | | AGACCTACATCTGCAACGTGAACCACACAAGCCCTCCAACACCAAGGT<br>GGACAAGAAGGTGGAACCCAGTCCTGCGACAAGACCCACACCTGT<br>CCCCCTTGTCCTGCCCCTGAACTGCTGGGCGGACCCTTCCGTGTTCCT<br>GTTCCCCCCAAAGCCCAAGGACACCCTGATGATCTCCGGACCCC<br>GAAGTGACCTGCGTGGTGGTGGATGTCCACGAGGACCCTGAAG<br>TGAAGTTCAATTGGTACGTGGACGGCGTGGAAGTGCACAACGCCAA<br>GACCAAGCCTAGAGAGGAACAGTACAACTCCACCTACCGGGTGGTG<br>TCCGTGCTGACCGTGCTGCACCAGGATTGGCTGAACGGCAAAGAGT<br>ACAAGTGCAAGGTGTCCAACAAGGCCCTGCCTGCCCCCATCGAAAA<br>GACCATCTCCAAGGCCAAGGGCCAGCCCCGGGAACCCAGGTGTAC<br>ACACTGCCCCCTAGCCAGGACGAGCTGACCAAGAACCAGGTGTCCC<br>TGACCTGTCTGTGAAAGGCTTCTACCCCTCGATATCGCCGTGGAA<br>TGGGAGTCCAACGGCCAGCCTGAGAACAACTACAAGACCACCCCC<br>CTGTGCTGGACTCCGACGGCTCATTCTTCCTGTACAGCAAGCTGACA<br>GTGGACAAGTCCCGGTGGCAGCAGGGCAACGTGTTCTCCTGCTCCG<br>TGATGCACGAGGCCCTGCACAACCACTACACCCAGAAGTCCCTGTC<br>CCTGAGCCCCGGCAAG |
| 268 | 413F09 — CDRL1<br>(IMGT) | Amino acid sequence of CDRL1<br>of 413F09 using IMGT | QDISTY |
| 269 | 413F09 — CDRL2<br>(IMGT) | Amino acid sequence of CDRL2<br>of 413F09 using IMGT | GTS |
| 270 | 413F09 — CDRL3<br>(IMGT) | Amino acid sequence of CDRL3<br>of 413F09 using IMGT | QQLHTDPIT |
| 271 | 413F09 — CDRL1<br>(Kabat) | Amino acid sequence of CDRL1<br>of 413F09 using Kabat | WASQDISTYLG |
| 272 | 413F09 — CDRL2<br>(Kabat) | Amino acid sequence of CDRL2<br>of 413F09 using Kabat | GTSSLQS |
| 273 | 413F09 — CDRL3<br>(Kabat) | Amino acid sequence of CDRL3<br>of 413F09 using Kabat | QQLHTDPIT |
| 274 | 413F09 — Light chain variable region | Amino acid sequence of $V_L$ of 413F09 | DIQLTQSPSFLSASVGDRVTITCWASQDISTYLGWYQQKPGKAPKLLIY<br>GTSSLQSGVPSRFSGSGSGTEFTLTISSLQPEDFATYYCQQLHTDPITFGQ<br>GTRLEIK |
| 275 | 413F09 — Light chain variable region | Nucleic acid sequence of $V_L$ of 413F09 | GACATCCAGTTGACCCAGTCTCCATCCTTCCTGTCTGCATCTGTAGG<br>AGACAGAGTCACCATCACTTGCTGGGCCAGTCAGGACATTAGCACT<br>TATTTAGGCTGGTATCAGCAAAAACCAGGGAAAGCCCCTAAGCTCC<br>TGATCTATGGTACATCCAGTTTGCAAAGTGGGGTCCATCAAGGTTC<br>AGCGGCAGTGGATCTGGGACAGAATTCACTCTCACAATCAGCAGCC<br>TGCAGCCTGAAGATTTTGCAACTTATTACTGTCAACAGCTTCATACT<br>GACCCGATCACCTTCGGCCAAGGGACCACGACTGGAGATCAAAC |

SEQUENCE LISTING

| SEQ ID NO: | Name | Description | Sequence |
|---|---|---|---|
| 276 | 413F09 – full light chain sequence | Amino acid sequence of 413F09 light chain | DIQLTQSPSFLSASVGDRVTITCWASQDISTYLGWYQQKPGKAPKLLIY GTSSLQSGVPSRFSGSGSGTEFTLTISSLQPEDFATYYCQQLHTDPITFGQ GTRLEIKRTVAAPSVFIFPPSDEQLKSGTASVVCLLNNFYPREAKVQWK VDNALQSGNSQESVTEQDSKDSTYSLSSTLTLSKADYEKHKVYACEVT HQGLSSPVTKSFNRGEC |
| 277 | 413F09 – full light chain sequence | Nucleic acid sequence of 413F09 light chain | GACATCCAGTTGACCCAGTCTCCATCCTTCCTGTCTGCATCTGTAGG AGACAGAGTCACCATCACTTGCTGGGCCAGTCAGGACATTAGCACT TATTTAGGCTGGTATCAGCAAAAACCAGGGAAAGCCCCTAAGCTC TGATCTATGGTACATCCAGTTTGCAAAGTGGGGTCCCATCAAGGTTC AGCGGCAGTGGATCTGGGACAGAATTCACTCTCACAATCAGCAGCC TGCAGCCTGAAGATTTTGCAACTTATTACTGTCAACAGCTTCATACT GACCCGATCACCTTCGGCCAAGGGACACGACTGGAGATCAAACGTA CGGTGGCCGCTCCCGTCTTCATCTTCCCACCTTCCGACGAGCAG CTGAAGTCCGGACACCGCTTCTGTGTGCTGCTGAACAACTTCTA CCCCCGCGAGGCCAAGGTGCAGTGGAAGGTGGACAACGCCCTGCAG TCCGGCAACTCCCAGGAATCCGTGACCGAGCAGGACTCCAAGGACA GAAGCACAAGGTGTACGCCTGCGAAGTGACCCACCAGGGCCTGT CTAGCCCCGTGACCAAGTCTTTCAACCGGGGCGAGTGT |
| 278 | 414B06 – CDRH1 (IMGT) | Amino acid sequence of CDRH1 of 414B06 using IMGT | GFTFSSYW |
| 279 | 414B06 – CDRH2 (IMGT) | Amino acid sequence of CDRH2 of 414B06 using IMGT | IKQDGSEK |
| 280 | 414B06 – CDRH3 (IMGT) | Amino acid sequence of CDRH3 of 414B06 using IMGT | ARVRQWSDYSDY |
| 281 | 414B06 – CDRH1 (Kabat) | Amino acid sequence of CDRH1 of 414B06 using Kabat | SYWMN |
| 282 | 414B06 – CDRH2 (Kabat) | Amino acid sequence of CDRH2 of 414B06 using Kabat | NIKQDGSEKYYVDSVKG |
| 283 | 414B06 – CDRH3 (Kabat) | Amino acid sequence of CDRH3 of 414B06 using Kabat | VRQWSDYSDY |
| 284 | 414B06 – Heavy chain variable region | Amino acid sequence of VH of 414B06 | EVHLVESGGLVQPGGSLRLSCAASGFTFSSYWMNWVRQAPGKGLEW VANIKQDGSEKYYVDSVKGRFTVSRDNAKNSLYLQMNSLRAEDTAVY YCARVRQWSDYSDYWGQGTPVTVSS |
| 285 | 414B06 – Heavy chain variable region | Nucleic acid sequence of VH of 414B06 | GAGGTGCACCTGGTGGAGTCTGGGGGAGGCTTGGTCCAGCCTGGGG GGTCCCTGAGACTCTCCTGTGCAGCCTCTGGATTCACCTTTAGTAGC TATTGGATGAACTGGGTCCGCCAGGCTCCAGGGAAGGGGCTGGAGT GGGTGGCCAACATAAAGCAAGATGGAAGTGAGAAATACTATGTGG ACTCTGTGAAGGGCCGCCTTCACCGTCTCCAGAGACAACGCCAAGAA |

| SEQ ID NO:Name | Description | Sequence |
|---|---|---|
| | | CTCACTGTATCTGCAAATGAACAGCCTGAGAGCCCGAGGACACGGCT GTGTATTACTGTGCGAGAGTTCGACAATGGTCCGACTACTCTGACTA CTGGGGCCAGGGAACCCCGGTCACCGTCTCCTCAG |
| 286 | 414B06 – full heavy chain sequence | Amino acid sequence of 414B06 heavy chain | EVHLVESGGGLVQPGGSLRLSCAASGFTFSSYWMNWVRQAPGKGLEW VANIKQDGSEKYYVDSVKGRFTVSRDNAKNSLYLQMNSLRAEDTAVY YCARVRQWSDYDYWQGTPVTVSSASTKGPSVFPLAPSSKSTSGGTA ALGCLVKDYFPEPVTVSWNSGALTSGVHTFPAVLQSSGLYSLSSVVTVP SSSLGTQTYICNVNHKPSNTKVDKKVEPKSCDKTHTCPPCPAPELLGGP SVFLFPPKPKDTLMISRTPEVTCVVVDVSHEDPEVKFNWYVDGVEVHN AKTKPREEQYNSTYRVVSVLTVLHQDWLNGKEYKCKVSNKALPAPIE KTISKAKGQPREPQVYTLPPSRDELTKNQVSLTCLVKGFYPSDIAVEWE SNGQPENNYKTTPPVLDSDGSFFLYSKLTVDKSRWQQGNVFSCSVMHE ALHNHYTQKSLSLSPGK |
| 287 | 414B06 – full heavy chain sequence | Nucleic acid sequence of 414B06 heavy chain | GAGGTGCACCTGGTGGAGTCTGGGGGAGGCTTGGTCCAGCCTGGGG GGTCCCTGAGACTCTCCTGTGCAGCCTCTGGATTCACCTTTAGTAGC TATTGGATGAACTGGGTCCGCCAGCTCCAGGGAAGGGGCTGGAGT GGGTGGCCAACATAAAGCAAGATGGAAGTGAGAAATACTATGTGG ACTCTGTGAAGGGCCGCTTCACCGTCTCCAGAGACAACGCCAAGAA CTCACTGTATCTGCAAATGAACAGCCTGAGAGCCGAGGACACGGCT GTGTATTACTGTGCGAGAGTTCGACAATGGTCCGACTACTCTGACTA CTGGGGCCAGGGAACCCCGGTCACCGTCTCCTCAGCCAGCACCAAG GGCCCCTCTGTGTTCCCCCTGGCCCCCTGCAGCAAGACTACTTCCGG CGGAACAGCCGCTCTGGGCTGCCTGGTCAAGGACTACTTCCCCGAG CCTGTGACCGTGTCCTGCTGGAACTCTGGCGCTCTGACCAGCGGAGTGCA CACCTTTCCCGCTGCCTTCCAGCTCTCCAGCCTCTGGGCTGTACTCCCTGTCCTC CGTCGTGACCGTGCCTTCCAGCTCTCAAGTCCTCAAACCAAGGTGGACAAGAAGT GAACCCAAGTCCTGCGACAAGACCCACACTGCTGTTCCTGTTCCCCCCAAAG CCCCTGAACTCTGGGCGGACCTTCCGGACATCTCCGGACCTGAAGTGACCTGCG TGGTGGATGTGTCCACAGAGGACCCTGAGGTGAAGTTCAATTG GTACGTGGACGGCGTGGAAGTGCACAACGCCAAGACCAAGCCTAGA GAGGAACAGTACAACTCCACCTACCGGGTGGTGTCCGTGCTGACCG TGCTGCACCAGGATTGGCTGAACGGCAAAGAGTACAAGTGCAAGT GTCCAACAAGGCCCTGCCTGCCCCATCGAAAAGACCATCTCCAAG GCCAAGGGCCAGCCCCGGGAACCCCAGGTGTACACACTGCCCCCTA GCAGGACGAGCTTCACCCTCGATATCGCCGTGGAATGGGAGTCCAAC GAAAGGCTTCACCCCTGATATCGCCGTGGAATGGGAGTCCAAC GGCCAGCCTGAGAACAACTACAAGACCACCCCTGTCCTGGACT CCGACGGCTCATTCTTCCTGTACAGCAAGCTGACCGTGGACAAGTCC CGGTGGCAGCAGGGAACGTGTTCTCCTGCTCCGTGATGCACGAGG CCCTGCACAACCACTACACCCAGAAGTCCCTGTCCCTGAGCCCGGG CAAG |
| 288 | 414B06 – CDRL1 (IMGT) | Amino acid sequence of CDRL1 of 414B06 using IMGT | QGISSW |

-continued

SEQUENCE LISTING

| SEQ ID NO:Name | Description | Sequence |
|---|---|---|
| 289 | 414B06 – CDRL2 (IMGT) | Amino acid sequence of CDRL2 of 414B06 using IMGT | AAS |
| 290 | 414B06 – CDRL3 (IMGT) | Amino acid sequence of CDRL3 of 414B06 using IMGT | QQANSFPFT |
| 291 | 414B06 – CDRL1 (Kabat) | Amino acid sequence of CDRL1 of 414B06 using Kabat | RASQGISSWLA |
| 292 | 414B06 – CDRL2 (Kabat) | Amino acid sequence of CDRL2 of 414B06 using Kabat | AASSLQS |
| 293 | 414B06 – CDRL3 (Kabat) | Amino acid sequence of CDRL3 of 414B06 using Kabat | QQANSFPFT |
| 294 | 414B06 – Light chain variable region | Amino acid sequence of V_L of 414B06 | DIQMTQSPSSVSASVGDRVTITCRASQGISSWLAWYQQKPGKAPKLLIY AASSLQSGVPSRFSGSGSGTDFTLTISSLQPEDFATYYCQQANSFPFTFG PGTKVDIK |
| 295 | 414B06 – Light chain variable region | Nucleic acid sequence of V_L of 414B06 | GACATCCAGATGACCCAGTCTCCATCTTCCGTGTCTGCATCTGTAGG AGACAGAGTCACCATCACTTGTCGGGCGAGTCAGGGTATTAGCAGC TGGTTAGCCTGGTATCAGCAGAAACCAGGGAAAGCCCCTAAGCTCC TGATCTATGCTGCATCCAGTTTGCAAAGTGGGGTCCCATCAAGGTTC AGCGGCAGTGGATCTGGGACAGATTTCACTCTCACCATCAGCAGCC TGCAGCCTGAAGATTTTGCAACTTACTATTGTCAACAGGCTAACAGT TTCCCATTCACTTTCGGCCCTGGGACCAAAGTGGATATCAAAC |
| 296 | 414B06 – full light chain sequence | Amino acid sequence of 414B06 light chain | DIQMTQSPSSVSASVGDRVTITCRASQGISSWLAWYQQKPGKAPKLLIY AASSLQSGVPSRFSGSGSGTDFTLTISSLQPEDFATYYCQQANSFPFTFG PGTKVDIKRTVAAPSVFIFPPSDEQLKSGTASVVCLLNNFYPREAKVQW KVDNALQSGNSQESVTEQDSKDSTYSLSSTLTLSKADYEKHKVYACEV THQGLSSPVTKSFNRGEC |
| 297 | 414B06 – full light chain sequence | Nucleic acid sequence of 414B06 light chain | GACATCCAGATGACCCAGTCTCCATCTTCCGTGTCTGCATCTGTAGG AGACAGAGTCACCATCACTTGTCGGGCGAGTCAGGGTATTAGCAGC TGGTTAGCCTGGTATCAGCAGAAACCAGGGAAAGCCCCTAAGCTCC TGATCTATGCTGCATCCAGTTTGCAAAGTGGGGTCCCATCAAGGTTC AGCGGCAGTGGATCTGGGACAGATTTCACTCTCACCATCAGCAGCC TGCAGCCTGAAGATTTTGCAACTTACTATTGTCAACAGGCTAACAGT TTCCCATTCACTTTCGGCCCTGGGACCAAAGTGGATATCAAACGTAC GGTGGCGGCTCCCTCCGTGTTCATCTTCCCACCTTCCGACGAGCAGC TGAAGTCCGGCACCGCTTCTGTGTGCCTGCTGAACAACTTCTAC CCCCGCGAGCCCAAGGTGCAGTGGAAGGTGACAACGCCCTGCAGT CCGGCAACTCCCTGGAATCCGTGACCGAGCAGGACTCCAAGGACTA CACCTACTCCCTGTCTCCACCCTGTCTCAAGGCCGACTACG AGAAGCACAAGTGTACGCCTGCGAAGTGACCCACCAGGGCCTGTC TAGCCCCGTGACCAAGTCTTTCAACCGGGGCGAGTGT |

-continued

SEQUENCE LISTING

| SEQ ID NO:Name | Description | Sequence |
|---|---|---|
| 298 Mutated 1D05 – LC mutant 3 | Amino acid sequence of 1D05 kappa light chain with V to Y mutation in CDRL2 highlighted | DIQMTQSPSSLSASVGDRVTITCRASQSISSYLNWYQQKPGKAPKLLIYY ASSLQSGVPSRFSGSGSGTDFTLTISSLQPEDFATYYCQQSYSTPITFGQG TRLEIKRTVAAPSVFIFPPSDEQLKSGTASVVCLLNNFYPREAKVQMKV DNALQSGNSQESVTEQDSKDSTYSLSSTLTLSKADYEKHKVYACEVTH QGLSSPVTKSFNRGEC |
| 299 1D05 – heavy chain disabled IgG1 Fc | Amino acid sequence of 1D05 disabled variant of IgG1 | EVQLVESGGGLVQPGRSLRLSCAASGFTFDDYAMHWVRQVPGKGLEW VSGISWIRTGIGYADSVKGRFTIFRDNAKNSLYLQMNSLRAEDTALYYC AKDMKGSGTYGGWFDTWGQGTLVTVSSASTKGPSVFPLAPSSKSTSG GTAALGCLVKDYFPEPVTVSWNSGALTSGVHTFPAVLQSSGLYSLSSV VTVPSSSLGTQTYICNVNHKPSNTKVDKKVEPKSCDKTHTCPPCPAPEL AGAPSVFLFPPKPKDTLMISRTPEVTCVVVDVSHEDPEVKFNWYDGV EVHNAKTKPREEQYNSTYRVVSVLTVLHQDWLNGKEYKCKVSNKALP APIEKTISKAKGQPREPQVYTLPPSRDELTKNQVSLTCLVKGFYPSDIAV EWESNGQPENNYKTTPPVLDSDGSFFLYSKLTVDKSRWQQGNVFSCSV MHEALHNHYTQKSLSLSPGK |
| 300 1D05 – light chain IL-2 fusion | 1D05 Light chain sequence fused to wild-type human IL-2 sequence (IL-2 amino acid sequence is underlined and region to be varied is shown in bold) | DIQMTQSPSSLSASVGDRVTITCRASQSISSYLNWYQQKPGKAPKLLIYV ASSLQSGVPSRFSGSGSGTDFTLTISSLQPEDFATYYCQQSYSTPITFGQG TRLEIKRTVAAPSVFIFPPSDEQLKSGTASVVCLLNNFYPREAKVQMKV DNALQSGNSQESVTEQDSKDSTYSLSSTLTLSKADYEKHKVYACEVTH QGLSSPVTKSFNRGECAPTSSSTKKTQLQLEHLLLDLQMILNGINNYK NPKLTRMLTFKFYMPKKATELKHLQCLEEELKPLEEVLNLAQSKNFHL RPRDLISNINVIVLELKGSETTFMCEYADETATIVEFLNRWITFCQSIISTL T |
| 301 Human IL-2 | Uniprot number: P60568 Full length amino acid sequence of human IL-2 (minus signal sequence) | APTSSSTKKTQLQLEHLLLDLQMILNGINNYKNPKLTRMLTFKFYMP KKATELKHLQCLEEELKPLEEVLNLAQSKNFHLRPRDLISNINVIVLELK GSETTFMCEYADETATIVEFLNRWITFCQSIISTLT |
| 302 Control 1D05 immunocytokine HC C-terminal fusion | Heavy chain 1D05 IgG1 variant fused at the N-terminus to wild-type human IL2 sequence (control) | EVQLVESGGGLVQPGRSLRLSCAASGFTFDDYAMHWVRQVPGKGLEW VSGISWIRTGIGYADSVKGRFTIFRDNAKNSLYLQMNSLRAEDTALYYC AKDMKGSGTYGGWFDTWGQGTLVTVSSASTKGPSVFPLAPSSKSTSG GTAALGCLVKDYFPEPVTVSWNSGALTSGVHTFPAVLQSSGLYSLSSV VTVPSSSLGTQTYICNVNHKPSNTKVDKKVEPKSCDKTHTCPPCPAPEL AGAPSVFLFPPKPKDTLMISRTPEVTCVVVDVSHEDPEVKFNWYDGV EVHNAKTKPREEQYNSTYRVVSVLTVLHQDWLNGKEYKCKVSNKALP APIEKTISKAKGQPREPQVYTLPPSRDELTKNQVSLTCLVKGFYPSDIAV EWESNGQPENNYKTTPPVLDSDGSFFLYSKLTVDKSRWQQGNVFSCSV MHEALHNHYTQKSLSLSPGKAPTSSSTKKTQLQLEHLLLDLQMILNGIN NYKNPKLTRMLTFKFYMPKKATELKHLQCLEEELKPLEEVLNLAQSKN FHLRPRDLISNINVIVLELKGSETTFMCEYADETATIVEFLNRWITFCQSII STLT |
| 303 IL-2 D5-9 | IL-2 IC45 (Del 5-9) N terminal IL-2 sequence | APTSKKTQLQLEHLLLD |

-continued

SEQUENCE LISTING

| SEQ ID NO: | Name | Description | Sequence |
|---|---|---|---|
| 304 | IL-2 D1-9 | IL-2 IC46 (Del 1-9) N terminal IL-2 sequence | TQLQLEHLLLD |
| 305 | IL-2 D5-7 | IL-2 IC64 (Del 5-7) N terminal IL-2 sequence | APTSKKTQLQLEHLLLD |
| 306 | IL-2 D1 | IL-2 D1 N terminal IL-2 sequence | PTSSSTKKTQLQLEHLLLD |
| 307 | IL-2 D1-2 | IL-2 D1-2 N terminal IL-2 sequence | TSSSTKKTQLQLEHLLLD |
| 308 | IL-2 D1-3 | IL-2 D1-3 N terminal IL-2 sequence | SSSTKKTQLQLEHLLLD |
| 309 | IL-2 D1-4 | IL-2 D1-4 N terminal IL-2 sequence | SSTKKTQLQLEHLLLD |
| 310 | IL-2 D1-5 | IL-2 D1-5 N terminal IL-2 sequence | STKKTQLQLEHLLLD |
| 311 | IL-2 D1-6 | IL-2 D1-6 N terminal IL-2 sequence | TKKTQLQLEHLLLD |
| 312 | IL-2 D1-7 | IL-2 D1-7 N terminal IL-2 sequence | KKKTQLQLEHLLLD |
| 313 | IL-2 D1-8 | IL-2 D1-8 N terminal IL-2 sequence | KTQLQLEHLLLD |
| 314 | IL-2 D9 | IL-2 D9 N terminal IL-2 sequence | APTSSSTKTQLQLEHLLLD |
| 315 | IL-2 D9-8 | IL-2 D9-8 N terminal IL-2 sequence | APTSSSTTQLQLEHLLLD |
| 316 | IL-2 D9-7 | IL-2 D9-7 N terminal IL-2 sequence | APTSSSTQLQLEHLLLD |
| 317 | IL-2 D9-6 | IL-2 D9-6 N terminal IL-2 sequence | APTSSTQLQLEHLLLD |
| 318 | IL-2 D9-4 | IL-2 D9-4 N terminal IL-2 sequence | APTTQLQLEHLLLD |
| 319 | IL-2 D9-3 | IL-2 D9-3 N terminal IL-2 sequence | APTQLQLEHLLLD |
| 320 | IL-2 D9-2 | IL-2 D9-2 N terminal IL-2 sequence | ATQLQLEHLLLD |

-continued

SEQUENCE LISTING

| SEQ ID NO:Name | Description | Sequence |
|---|---|---|
| 321 IL-2 D2-6 | IL-2 D2-6 N terminal IL-2 sequence | ATKKTQLQLEHLLLD |
| 322 IL-2 D3-7 | IL-2 D3-7 N terminal IL-2 sequence | APKKTQLQLEHLLLD |
| 323 IL-2 D4-8 | IL-2 D4-8 N terminal IL-2 sequence | APTKTQLEHLLLD |
| 324 C-terminal amino acid sequence of hIL-2 | Amino acids 21 to 133 of hIL-2 | LQMILNGINNYKNPKLTRMLTFKFYMPKKATELKHLQCLEEELKPLEE VLNLAQSKNFHLRPRDLISNINVIVLELKGSETTFMCEYADETATIVEFL NRWITFCQSIISTLT |
| 325 Mouse PD-L1 | Uniprot number: Q9EP73 (ECD highlighted in BOLD, and cytoplasmic domain <u>underlined</u>) | MRIFAGIIFTACCHLLRAFTITAPKDLYVVEYGSNVTMECRFPVEREL DLLALVVYWEKEDEQVIQFVAGEEDLKPQHSNFRGRASLPKDQLL KGNAALQITDVKLQDAGVYCCIISYGGADYKRITLKVNAPYRKINQ RISVDPATSEHELICQAEGYPEAEVIWTNSDHQPVSGKRSVTTSRTE GMLLNVTSSLRVNATANDVFYCTFWRSQPGQNHTAELIIPELPATH PPQNRTHWVLLGSILLFLIVSTVLLFLRKQVRMLDVEKCGVEDTSSK <u>NRNDTQFEET</u> |
| 326 Mouse PD-L1 ECD His | Mouse PD-L1 extracellular domain with his tag | FTITAPKDLYVVEYGSNVTMECRFPVERELDLLALVVYWEKEDEQVIQ FVAGEEDLKPQHSNFRGRASLPKDQLLKGNAALQITDVKLQDAGVYC CIISYGGADYKRITLKVNAPYRKINQRISVDPATSEHELICQAEGYPEAE VIWTNSDHQPVSGKRSVTTSRTEGMLLNVTSSLRVNATANDVFYCTFW RSQPGQNHTAELIIPELPATHPPQNR<u>THHHHHH</u> |
| 327 Human IL-2Rα chain | Human IL-2 receptor alpha chain | ELCDDDPPEIPHATFKAMAYKEGTMLNCECKRGFRRIKSGSLYMLCTG NSSHSSWDNQCQCTSSATRNTTKQVTPQPEEQKERKTTEMQSPMQPVD QASLPGHCREPPPWENEATERIYHFVVGQMVYYQCVQGYRALHRGPA ESVCKMTHGKTRWTQPQLICTGEMETSQFPGEEKPQASPEGRPESETSC LVTTDFQIQTEMAATMETSIFTTEYQVAVAGCVFLLISVLLLSGLTWQ RRQRKSRRTI |
| 328 Human IL-2Rβ chain | Human IL-2 receptor beta chain | AVNGTSQFTCFYNSRANISCVWSQDGALQDTSCQVHAWPDRRRWNQT CELLPVSQASWACNLILGAPDSQKLTTVDIVTLRVLCREGVRWRVMAI QDFKPFENLRLMAPISLQVVHVETHRCNISWEISQASHYFRHLEPEAR TLSPGHTWEEAPLLTLKQKQEWICLETLTPDTQYEFQVRVKPLQGEFTT WSPWSQPLAPRTKPAALGKDTIPWLGHLLVGLSGAFGFIILVYLLINCR NTGPWLKKVLKCNTPDPSKFFSQLSSEHGGDVQKWLSSPFPSSSFSPGG LAPEISPLEVLERDKVTQLLLQQDKVPEPASLSSNHSLTSCFTNQGYFFF HLPDALEIEACQVYFTYDPYSEEDPDEGVAGAPTGSSPQPLQPLSGEDD AYCTFPSRDDLLFSPSLLGGPSPSTAPGGSGAGEERMPPSLQERVPRD WDPQPLGPPTPGVPDLVDFQPPPELVLREAGEEVPDAGPREGVSFPWSR PPGQGEFRALNARLPLNTDAYLSLQELQGQDPTHLV |
| 329 Human IL-2Rγ chain | Human IL-2 receptor common gamma chain | LNTTILTPNGNEDTTADFFLTTMPTDSLSVSTLPLPEVQCFVFNVEYMN CTWNSSSEPQPTNLTLHYWYKNSDNDKVQKCSHYLFSEEITSGCQLQK KEIHLYQTFVVQLQDPREPRRQATQMLKLQNLVIPWAPENLTHLKLSES |

-continued

SEQUENCE LISTING

| SEQ ID NO:Name | Description | Sequence |
|---|---|---|
| 330 IL-7 | Human IL-7 amino acid sequence | QLELWNNRPLNHCLEHLVQRTDWDHSWTEQSVDYRHKFSLPSVDG QKRYTFRVRSRFNPLCGSAQHWSEWSHPIHWGSNTSKENPFLFALEAV VISVGSMGLIISLLCVYFWLERTMPRIPTLKNLEDLVTEYHGNFSAWSG VSKGLAESLQPDYSERLCLVSEIPPKGGALGEGPGASPCNQHSPYWAPP CYTLKPET |
| 331 IL-15 | Human IL-15 amino acid sequence | DCDIEGKDGKQYESVLMVSIDQLLDSMKEIGSNCLNNEFNFFKRHICDA NKEGMPLFRAARKLRQFLKMNSTGDFDLHLLKVSEGTTILNCTGQVK GRKPAALGEAQPTKSLEENKSLKEQKKLNDLCFLKRLLQEIKTCWNKIL MGTKEH |
| 332 IL-21 | Human IL-21 amino acid sequence | GIHVFILGCFSAGLPKTEANWVNVISDLKKIEDLIQSMHIDATLYTESDV HPSCKVTAMKCFLLELQVISLESGDASIHDTVENLIILANNSLSSNGNVT ESGCKECEELEEKNIKEFLQSFVHIVQMFINTS |
| 333 GM-CSF | Human GM-CSF amino acid sequence | QGQDRHMIRMRQLIDIVDQLKNYVNDLVPEFLPAPEDVETNCEWSAFS CFQKAQLKSANTGNNERIINVSIKKLKRKPPSTNAGRRQKHRLTCPSCD SYEKKPPKEFLERFKSLLQKMIHQHLSSRTHGSEDS |
| 334 IFNα | Human IFN-α amino acid sequence | APARSPSPSTQPWEHVNAIQEARRLLNLSRDTAAEMNETVEVISEMPDL QEPTCLQTRLELYKQGLRGSLTKLKGPLTMMASHYKQHCPPTPETSCA TQIITFESFKENLKDFLLVIPFDCWEPVQE |
| 335 TNFα | Extracellular portion of human TNF-α amino acid sequence | CDLPQNHGLLSRNTLVLLHQMRRISPFLCLKDRRDFRFPQEMVKGSQL QKAHVMSVLHEMLQQIFSLFHTERSSAAWNMTLDQLHTELHQQLQH LETCLLQVVGEGESAGAISSPALTLRRYFQGIRVVLKEKKYSDCAWEV VRMEIMKSLFLSTNMQERLRSKDRLGS |
| 336 IL-12α | Alpha chain of human IL-12 amino acid sequence | GPQREFPRDLSLISPLAQAVRSSSRTPSDKPVAHVVANPQAEGQLQWL NRRANALLANGVELRDNQLVVPSEGLYLIYSQVLFKGQGCPSTHVLLT HTISRIAVSYQTKVNLLSAIKSPCQRETPEGAEAKPMYEPIYLGGVFQLE KGDRLSAEINRPDYLDFAESGQVYFGIIAL |
| 337 IL-12β | Beta chain of human IL-12 amino acid sequence | RNLPVATPDPGMFPCLI-IHSQNLLRAVSNMLQKARQTLEFYPCTSEEID HEDITKDKTSTVEACLPLELTKNESCLNSRETSFITNGSCLASRKTSFMM ALCLSSIYEDLKMYQVEFKTMNAKLLMDPKRQIFLDQNMLAVIDELM QALNFNSETVPQKSSLEEPDFYKTKLKLCILLHAFRIRAVTIDRVMSYLN AS |
|  |  | IWELKKDVYVVELDWYPDAPGEMVLTCDTPEEDGITWTLDQSSEVL GSGKTLTIQVKEFGDAGQYTCHKGGEVLSHSLLLLHKKEDGIWSTDILK DQKEPKNKTFLRCEAKNYSGRFTCWWLTTISTDLITFSVKSSRGSSDPQG VTCGAATLSAERVRGDNKEYEYSVECQEDSACPAAEEESLPIEVMVDAV HKLKYENYTSSFFIRDIIKPDPPKNLQLKPLKNSRQVEVSWEYPDTWSTP HSYFSLTFCVQVQGKSKREKKDRVFTDKTSATVICRKNASIVRAQDR YYSSSWSEWASVPCS |

-continued

| SEQ ID NO: | Name | Description | SEQUENCE LISTING Sequence |
|---|---|---|---|
| 338 | CXCL9 | Human CXCL-9 amino acid sequence | TPVVRKGRCSCISTNQGTIHLQSLKDLKQFAPSPSCEKIEIIATLKNGVQT CLNPDSADVKELIKKWEKQVSQKKKQKNGKKHQKKKVLKVRKSQRS RQKKTT |
| 339 | CXCL10 | Human CXCL-10 amino acid sequence | VPLSRTVRCTCISISNQPVNPRSLEKLEIIPASQFCPRVEIIATMKKKGEKR CLNPESKAIKNLLKAVSKERSKRSP |
| 340 | Human WT IgG1 constant region | WT human IgG1 amino acid sequence | ASTKGPSVFPLAPSSKSTSGGTAALGCLVKDYFPEPVTVSWNSGALTSG VHTFPAVLQSSGLYSLSSVVTVPSSSLGTQTYICNVNHKPSNTKVDKKV EPKSCDKTHTCPPCPAPELLGGPSVFLFPPKPKDTLMISRTPEVTCVVVD VSHEDPEVKFNWYVDGVEVHNAKTKPREEQYNSTYRVVSVLTVLHQD WLNGKEYKCKVSNKALPAPIEKTISKAKGQPREPQVYTLPPSRDELTKN QVSLTCLVKGFYPSDIAVEWESNGQPENNYKTTPPVLDSDGSFFLYSKL TVDKSRWQQGNVFSCSVMHEALHNHYTQKSLSLSPGK |
| 341 | IgG1 | WT human IgG1 nucleic acid sequence | GCCAGCACCAAGGGCCCCTCTGTGTTCCCTCTGGCCCCTTCCAGCAA GTCCACCTCTGGCGGAACAGCCGCTCTGGGCTGCCTGGTCAAGGAC TACTTCCCCGAGCCTGTGACCGTGTCCTGGAACTCTGGCGCTCTGAC CAGCGGAGTGCACACCTTCCCTGCTGTGCTGCAGTCCTCCGGCCTGT ACTCCCTGTCCTCCGTGGTGACCGTGCCTTCCAGCTCTCTGGGCACC CAGACCTACATCTGCAACGTGAACCACAAGCCCTCCAACACCAAGG TGGACAAGAAGGTGGAACCCAAGTCTTGCGACAAGACCCACACCTG TCCCCCCTGTCCTGCCCCTGAACCTCTGGGCGGACCTTCCGTGTTCCT GTTCCCCCCAAAGCCCAAGGACACCCTGATGATCTCCCGGACCCCC GAAGTGACCTGCGTGGTGGTACGGCCGTGAAGTGCACAACGCCAA GAAGTTCAATTGGTACGTGGACGGCGTGGAAGTGCACAATGCCAAG ACAAAGCCTAGAGAGGAACAGTACAACTCCACCTACCGGGTGGTG TCCGTGCTGACCGTGCTGCACCAGGATTGGCTGAACGGCAAAGAGT ACAAGTGCAAGGTCTCCAACAAGGCCCTGCCTGCCCCCATCGAAAA GACCATCTCCAAGGCCAAGGGCCAGCCCCGGGAACCCCAGTGTAC ACACTGCCCCCTAGCAGGGACGAGCTGACCAAGAACCAGGTGTCC TGACCTGTCTCGTGAAAGGCTTCTACCCCTCCGATATCGCCGTGGAA TGGGAGTCCAATGGCCAGCCTGAGAACAACTACAAGACCACCCCC CTGTGCTGGACTCCGACGGCTCATTCTTCCTGTACAGCAAGCTGACA GTGGACAAGTCCCGGTGGCAGGAGGGCAACGTGTTCTCTTGCTCCG TGATGCACGAGGCCCTGCACAACCACTACACCCAGAAGTCCCTGTC CCTGAGCCCCGGCAAGTGATGA |
| 342 | Mutated 1D05 – HC mutant 2 | Amino acid sequence of 1D05 heavy chain with V to A and F to S back-mutation in framework region to germline highlighted with IgG1 disabled (LAGA) constant region | EVQLVESGGGLVQPGRSLRLSCAASGFTFDDYAMHWVRQAPGKGLEW VSGISWIRTGIGYADSVKGRFTISRDNAKNSLYLQMNSLRAEDTALYYC AKDMKSGTYGGWFDTWGQGTLVTVSSASTKGPSVFPLAPCSRSTSES TAALGCLVKDYFPEPVTVSWNSGALTSGVHTFPAVLQSSGLYSLSSVV TVPSSSLGTKTYTCNVDHKPSNTKVDKRVESKYGPPCPPCPAPELAGAP SVFLFPPKPKDTLMISRTPEVTCVVVDVSQEDPEVQFNWYDGVEVHN AKTKPREEQFNSTYRVVSVLTVLHQDWLNGKEYKCKVSNKGLPSSIEK TISKAKGQPREPQVYTLPPSQEEMTKNQVSLTCLVKGFYPSDIAVEWES NGQPENNYKTTPPVLDSDGSFFLYSRLTVDKSRWQEGNVFSCSVMHEA LHNHYTQKSLSLSLGK |

We claim:

1. An antibody or a fragment thereof which specifically binds to hPD-L1, wherein the antibody or fragment thereof comprises a $V_H$ domain which comprises a CDRH3 sequence of SEQ ID NO: 9 or 12 and competes for binding to said hPD-L1 with the antibody 84G09, which antibody 84G09 comprises the $V_H$ amino acid sequence of SEQ ID NO:13 and the $V_L$ amino acid sequence of SEQ ID NO:23.

2. The antibody or fragment thereof according to claim 1, wherein the $V_H$ domain comprises the CDRH1 amino acid sequence of SEQ ID NO:7 or 10.

3. The antibody or fragment thereof according to claim 1, wherein the $V_H$ domain comprises the CDRH1 amino acid sequence of SEQ ID NO:7 or 10 and the CDRH2 amino acid sequence of SEQ ID NO:8 or 11.

4. The antibody or fragment thereof according to claim 1, wherein the $V_H$ domain comprises the amino acid sequence of SEQ ID NO:13.

5. The antibody or fragment thereof according to claim 1, wherein the $V_H$ domain comprises the CDRH1 amino acid sequence of SEQ ID NO:7 or 10 and the CDRH2 amino acid sequence of SEQ ID NO:8 or 11, and further comprising a $V_L$ domain, which comprises the CDRL1 amino acid sequence of SEQ ID NO:17 or 20.

6. The antibody or fragment thereof according to claim 1, wherein the $V_H$ domain comprises the CDRH1 amino acid sequence of SEQ ID NO:7 or 10 and the CDRH2 amino acid sequence of SEQ ID NO:8 or 11, and further comprising a $V_L$ domain, which comprises the CDRL1 amino acid sequence of SEQ ID NO:17 or 20, and the CDRL2 amino acid sequence of SEQ ID NO:18 or 21.

7. The antibody or fragment thereof according to claim 1, wherein the $V_H$ domain comprises the CDRH1 amino acid sequence of SEQ ID NO:7 or 10 and the CDRH2 amino acid sequence of SEQ ID NO:8 or 11, and further comprising a $V_L$ domain, which comprises the CDRL1 amino acid sequence of SEQ ID NO:17 or 20, the CDRL2 amino acid sequence of SEQ ID NO:18 or 21, and the CDRL3 amino acid sequence of SEQ ID NO:19 or 22.

8. The antibody or fragment thereof according to claim 1, wherein the $V_H$ domain comprises the amino acid sequence of SEQ ID NO:13, and further comprising a $V_L$ domain which comprises the amino acid sequence of SEQ ID NO:23.

9. The antibody or fragment thereof according to claim 1, comprising two copies of said $V_H$ domain.

10. The antibody or fragment thereof according to claim 1, further comprising a second antibody or fragment thereof that specifically binds to a target antigen other than hPD-L1.

11. The antibody or fragment thereof according to claim 10, wherein the first antibody or fragment thereof specifically binds to hPD-L1 and the second antibody or fragment thereof specifically binds another target antigen selected from the group consisting of: PD-1, CTLA-4, TIGIT, TIM-3, LAG-3 VISTA, BTLA, HVEM, CSF1R, CCR4, CD39, CD40, CD73, CD96, CXCR2, CXCR4, CD200, GARP, SIRPα, CXCL9, CXCL10, CD155, CD137, CSF1R, CD137, GITR, OX40, CXCR3, CD3, and ICOS.

12. The antibody or fragment thereof according to claim 1, comprising two copies of said VH domain and said VL domain.

13. The antibody or a fragment thereof according to claim 1, comprised within a bispecific antibody which comprises specificity for hPDL-1 and a target antigen other than hPDL-1.

14. The antibody or a fragment thereof according to claim 1, wherein said antibody is comprised within an immunocytokine and wherein said antibody is fused to a cytokine molecule.

15. A composition comprising the antibody of claim 1, and a pharmaceutically acceptable excipient, diluent, or carrier.

16. A method of treating a malignant tumour in a human in need thereof, the method comprising administering to the human the antibody or fragment thereof according to any one of claim 15.

17. The method of claim 16, wherein the malignant tumour is selected from the group consisting of: melanoma, Merkel cell carcinoma, squamous non-small cell lung cancer, non-squamous non-small cell lung cancer, renal cell cancer, bladder cancer, head and neck squamous cell carcinoma, mesothelioma, virally induced cancers, cervical cancer, nasopharyngeal cancer, soft tissue sarcomas, haematological malignancies, Hodgkin's and non-Hodgkin's disease, and diffuse large B-cell lymphoma.

18. The method of claim 17, wherein the malignant tumour is melanoma.

19. The method of claim 17, wherein the malignant tumour is non-small cell lung cancer.

20. The method of claim 17, wherein the malignant tumour is bladder cancer.

* * * * *

UNITED STATES PATENT AND TRADEMARK OFFICE
CERTIFICATE OF CORRECTION

PATENT NO. : 9,617,338 B1  
APPLICATION NO. : 15/354971  
DATED : April 11, 2017  
INVENTOR(S) : Jamie Campbell et al.

It is certified that error appears in the above-identified patent and that said Letters Patent is hereby corrected as shown below:

In the Specification

In the Table found at Columns 147 and 148, SEQ ID NO: 13, please replace the following:
"EVQLVESGGGLVQPGRSLRLSCAASGFTFDDYAMHWVRQtPGKGLEWVSGISWkSnilGYAD SVKGRFTISRDNAKNSLYLQMNSLRAEDTALYYCARDITGSGSYGWFDPWGQGTLVTVSS"

With:
--EVQLVESGGGLVQPGRSLRLSCAASGFTFDDYAMHWVRQtPGKGLEWVSGISWkSnilGYA DSVKGRFTISRDNAKNSLYLQMNSLRAEDTALYYCARDITGSGSYGWFDPWGQGTLVT VSS--

Signed and Sealed this  
Sixth Day of June, 2017

Michelle K. Lee  
*Director of the United States Patent and Trademark Office*